US005688808A

United States Patent [19]
Jones et al.

[11] Patent Number: 5,688,808
[45] Date of Patent: Nov. 18, 1997

[54] STEROID RECEPTOR MODULATOR COMPOUNDS AND METHODS

[75] Inventors: Todd K. Jones, Solana Beach; David T. Winn, San Diego; Lin Zhi, San Diego; Lawrence G. Hamann, San Diego; Christopher M. Tegley, San Diego; Charlotte L. F. Pooley, San Diego, all of Calif.

[73] Assignee: Ligand Pharmaceuticals Incorporated, San Diego, Calif.

[21] Appl. No.: 463,231

[22] Filed: Jun. 5, 1995

Related U.S. Application Data

[63] Continuation-in-part of Ser. No. 363,529, Dec. 22, 1994, abandoned.

[51] Int. Cl.[6] .................. A61K 31/47; C07D 471/04; C07D 221/16; C07D 491/48; C07D 491/52
[52] U.S. Cl. .................. 514/285; 514/242; 514/243; 514/246; 514/247; 514/248; 514/249; 514/250; 514/255; 514/256; 514/259; 514/267; 544/179; 544/180; 544/183; 544/233; 544/234; 544/235; 544/238; 544/245; 544/246; 544/249; 544/284; 544/333; 544/342; 544/343; 544/344; 544/353; 546/62; 546/70; 546/77; 546/78
[58] Field of Search .................. 546/62, 70, 77, 546/78; 514/285, 242, 243, 246, 247, 248, 249, 250, 255, 256, 259, 267; 544/179, 180, 183, 233, 234, 235, 238, 245, 246, 249, 284, 338, 342, 343, 344, 353

[56] References Cited

U.S. PATENT DOCUMENTS

| | | | |
|---|---|---|---|
| 3,798,031 | 3/1974 | Janssens et al. | 96/1.8 |
| 3,830,647 | 8/1974 | Janssens et al. | 96/1.5 |
| 3,832,171 | 8/1974 | Janssens et al. | 96/1.5 |
| 3,928,686 | 12/1975 | Poot et al. | 428/457 |
| 3,979,394 | 9/1976 | Janssens et al. | 260/283 |
| 4,380,634 | 4/1983 | Atkins | 546/89 |
| 4,943,502 | 7/1990 | Terrell et al. | 430/58 |
| 5,147,844 | 9/1992 | Weber et al. | 503/227 |
| 5,272,146 | 12/1993 | Haugwitz | 514/232.8 |

FOREIGN PATENT DOCUMENTS

| | | |
|---|---|---|
| 0260744 | 3/1988 | European Pat. Off. . |
| 555119 | 3/1977 | U.S.S.R. . |

OTHER PUBLICATIONS

Atkins, R. and Bliss, D., "Substituted Coumarins and Azacoumarins. Synthesis and Fluorescent Properties," *J. Org. Chem.*, vol. 43, No. 10 (1978).

Bissell, E., Mitchell, A., and Smith, R., "Synthesis and Chemistry of 7-Amino-4-(trifluoromethyl)coumarin and Its Amino Acid and Peptide Derivatives," *J. Org. Chem.*, vol. 45, N. 12 (1980).

G.N. Gromova and K.B. Piotrovskii, "Relative Volatility of Stabilizers for Polymer Materials," *Khim. Prom-st.*, 43:97 (Moscow 1967).

Database Crossfire, Beilstein Informationssysteme GmbH, BRN=880905, Sheinkman, et al., *J. Org. Chem.* USSR, vol. 9, 1973, pp. 2571–2576.

Database Crossfire, Beilstein, BRN=143474, Topsom, *Journal of Organic Chemistry*, vol. 30, 1965, Easton US, pp. 3560–3561.

Database Crossfire, Beilstein, BRN=18052, Ueda, *Yakugaku Zasshi*, vol. 57, 1937, pp. 312–316.

Database Crossfire, Beilstein, BRN=185528, Hively, et al., *Anal. Chem.*, vol. 27, 1955, pp. 100–101.

Database Crossfire, Beilstein, BRN=384096, Diels, *Chemische Berichte*, vol. 35, 1902, Weinheim de, p. 3278.

Database Crossfire, Beilstein, BRN=193508, 211894, Mosettig, *Journal of the American Chemical Society*, vol. 57, 1935, DC US, p. 902.

Database Crossfire, Beilstein, BRN=1129121, Atkins, R.L., *Journal of Organic Chemistry*, vol. 43, 1978, Easton US, pp. 1975–1980.

Database Crossfire, Beilstein, BRN=1241334, 1682456, Ivanov, et al., *Bull. Acad. Sci. USSR Div. Chem. Sci.* (Engl. Transl.), vol. 25, 1976, pp. 2069–2071.

Database Crossfire, Beilstein, BRN=4800533, 4800630, Ashwood, V.A., et al., *Journal of Medicinal Chemistry*, vol. 34, No. 11, 1991, Washington US, pp. 3261–3267.

Database Crossfire, Beilstein, BRN=424721, Eastman Kodak, *Chem. Abstr.*, 1970, vol. 74, p. 32685.

Database Crossfire, Beilstein, BRN=140265, Heliodoro, *Chem. Abstr.*, 1975, vol. 84, p. 74121.

Database Crossfire, Beilstein, BRN=640834, Brown, *Journal of the Chemical Society*, 1964, Letchworth GB, pp. 3132–3140.

Database Crossfire, Beilstein, BRN=390257, Liska, *Journal of Medicinal Chemistry*, vol. 15, 1972, Washington US, p. 1177.

Database Crossfire, Beilstein, BRN=1565891, Jolidon, *Helvetica Chimica Acta*, vol. 60, 1977, Basel CH, pp. 978–1021.

Database Crossfire, Beilstein, BRN=269284, Cavallito, *Journal of the American Chemical Society*, vol. 66, 1944, DC US, p. 1927.

Mosettig E, Robinson RA. J. Amer. Chem. Soc. 57, pp. 902–905, 1935.

Teutsch. G. and Philibert D. (1994) Human Reproduction vol. 9, Supplement 1, pp. 12–31.

Cook CE, Waui MC, Lee YW, Fail Pa, Petrow V. (1992) Life Sci. 52, 155–162.

Martin DW. Mayes PA, Rodwell VW. (1983) Harper's Review of Biochemistry. Lange Medical Publications, California, p. 499.

*Primary Examiner*—C. Warren Ivy
*Assistant Examiner*—Evelyn Huang
*Attorney, Agent, or Firm*—Thomas E. Jurgensen; William L. Respess; James Scott Elmer

[57] ABSTRACT

Non-steroidal compounds which are high affinity, high selectivity modulators for steroid receptors are disclosed. Also disclosed are pharmaceutical compositions incorporating such compounds, methods for employing the disclosed compounds and compositions for treating patients requiring steroid receptor agonist or antagonist therapy, intermediates useful in the preparation of the compounds and processes for the preparation of the steroid receptor modulator compounds.

27 Claims, No Drawings

STEROID RECEPTOR MODULATOR COMPOUNDS AND METHODS

RELATED PATENT APPLICATIONS

This application is a Continuation-In-Part of U.S. patent application Ser. No. 08/363,529, filed Dec. 22, 1994, abandoned the entire disclosure of which is herein incorporated by reference.

FIELD OF THE INVENTION

This invention relates to non-steroidal compounds that are modulators (i.e. agonists and antagonists) of steroid receptors (e.g., progesterone receptor, androgen receptor, estrogen receptor, glucocorticoid receptor and mineralocorticoid receptor), and to methods for the making and use of such compounds.

BACKGROUND OF THE INVENTION

Intracellular receptors (IRs) form a class of structurally-related genetic regulators scientists have named "ligand dependent transcription factors." R. M. Evans, 240 *Science*, 889 (1988). Steroid receptors are a recognized subset of the IRs, including the progesterone receptor (PR), androgen receptor (AR), estrogen receptor (ER), glucocorticoid receptor (GR) and mineralocorticoid receptor (MR). Regulation of a gene by such factors requires both the IR itself and a corresponding ligand which has the ability to selectively bind to the IR in a way that affects gene transcription.

Ligands to the IRs can include low molecular weight native molecules, such as the hormones progesterone, estrogen and testosterone, as well as synthetic derivative compounds such as medroxyprogesterone acetate, diethylstilbesterol and 19-nortestosterone. These ligands, when present in the fluid surrounding a cell, pass through the outer cell membrane by passive diffusion and bind to specific IR proteins to create a ligand/receptor complex. This complex then translocates to the cell's nucleus, where it binds to a specific gene or genes present in the cell's DNA. Once bound to DNA, the complex modulates the production of the protein encoded by that gene. In this regard, a compound which binds an IR and mimics the effect of the native ligand is referred to as an "agonist", while a compound that inhibits the effect of the native ligand is called an "antagonist."

Ligands to the steroid receptors are known to play an important role in health of both women and men. For example, the native female ligand, progesterone, as well as synthetic analogues, such as norgestrel (18-homonorethisterone) and norethisterone (17α-ethinyl-19-nortestosterone), are used in birth control formulations, typically in combination with the female hormone estrogen or synthetic estrogen analogues, as effective modulators of both PR and ER. On the other hand, antagonists to PR are potentially useful in treating chronic disorders, such as certain hormone dependent cancers of the breast, ovaries, and uterus, and in treating non-malignant conditions such as uterine fibroids and endometriosis, a leading cause of infertility in women. Similarly, AR antagonists, such as cyproterone acetate and flutamide have proved useful in the treatment of hyperplasia and cancer of the prostate.

The effectiveness of known modulators of steroid receptors is often tempered by their undesired side-effect profile, particularly during long-term administration. For example, the effectiveness of progesterone and estrogen agonists, such as norgestrel and diethylstilbesterol respectively, as female birth control agents must be weighed against the increased risk of breast cancer and heart disease to women taking such agents. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a GR antagonist. Accordingly, identification of compounds which have good specificity for one or more steroid receptors, but which have reduced or no cross-reactivity for other steroid or intracellular receptors, would be of significant value in the treatment of male and female hormone responsive diseases.

A group of quinoline analogs having an adjacent polynucleic ring system of the indene or fluorene series or an adjacent polynucleic heterocyclic ring system with substituents having a nonionic character have been described as photoconductive reducing agents, stabilizers, laser dyes and antioxidants. See e.g., U.S. Pat. Nos. 3,798,031; 3,830,647; 3,832,171; 3,928,686; 3,979,394; 4,943,502 and 5,147,844 as well as Soviet Patent No. 555,119; R. L. Atkins and D. E. Bliss, "Substituted Coumarins and Azacoumarins: Synthesis and Fluorescent Properties", 43 *J. Org. Chem.*, 1975 (1978), E. R. Bissell et al., "Synthesis and Chemistry of 7-Amino-4-(trifluoromethyl)coumarin and Its Amino Acid and Peptide Derivatives", 45 *J. Org. Chem.*, 2283 (1980) and G. N. Gromova and K. B. Piotrovskii, "Relative Volatility of Stabilizers for Polymer Materials," 43 *Khim. Prom-st.*, 97 (Moscow, 1967). However, no biological activity of any kind has been ascribed to these compounds.

SUMMARY OF THE INVENTION

The present invention is directed to compounds, pharmaceutical compositions, and methods for modulating processes mediated by steroid receptors. More particularly, the invention relates to non-steroidal compounds and compositions which are high affinity, high specificity agonists, partial agonists and antagonists for the PR, AR, ER, GR and MR steroid receptors, as well as to compounds with combined activity on one or more of these receptors. Also provided are methods of making such compounds and pharmaceutical compositions, as well as critical intermediates used in their synthesis.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

DEFINITIONS AND NOMENCLATURE

As used herein, the following terms are defined with the following meanings, unless explicitly stated otherwise. Furthermore, in an effort to maintain consistency in the naming of compounds of similar structure but differing substituents, the compounds described herein are named according to the following general guidelines. The numbering system for the location of substituents on such compounds is also provided.

The term alkyl, alkenyl, alkynyl and allyl includes straight-chain, branched-chain, cyclic, saturated and/or unsaturated structures, and combinations thereof.

The term aryl refers to an optionally substituted six-membered aromatic ting, including polyaromatic rings.

The term heteroaryl refers to an optionally substituted five-membered heterocyclic ting containing one or more heteroatoms selected from the group consisting of carbon, oxygen, nitrogen and sulfur, including polycyclic rings, or a six-membered heterocyclic ring containing one or more heteroatoms selected from the group consisting of carbon and nitrogen, including polycyclic rings.

A quinoline is defined by the following structure, and may be recognized as a benzannulated pyridine. Compounds of structures 4, 5, 13, 79, 83 and 86 herein are named as quinolines.

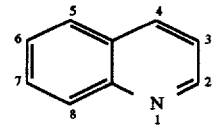

An indeno[1,2-g]quinoline is defined by the following structure. Compounds of structures 16 (X=C) and 20 herein are named as indeno[1,2-g]quinolines.

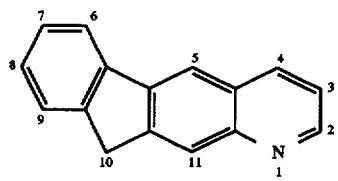

An indeno[2,1-f]quinoline is defined by the following structure. Compounds of structure 17 (X=C) herein are named as indeno[1,2-f]quinolines.

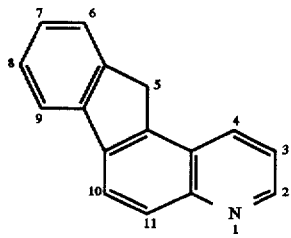

A benzo[b]furano[3,2-g]quinoline is defined by the following structure. Compounds of structure 16 (X=O) herein are named as benzo[b]furano[3,2-g]quinolines.

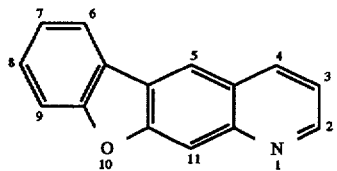

A benzo[b]furano[2,3-f]quinoline is defined by the following structure. Compounds of structure 17 (X=O) herein are named as benzo[b]furano[2,3-f]quinolines.

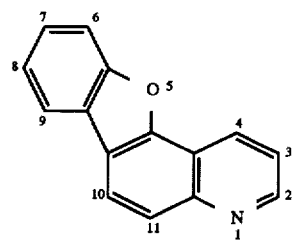

An indolo[3,2-g]quinoline is defined by the following structure. Compounds of structure 16 (X=N) herein are named as indolo[3,2-g]quinolines.

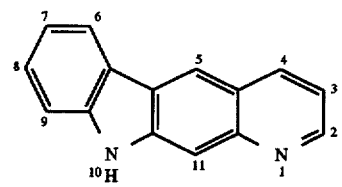

An indolo[2,3-f]quinoline is defined by the following structure. Compounds of structures 17 (X=N) and 29 herein are named as indolo[2,3-f]quinolines.

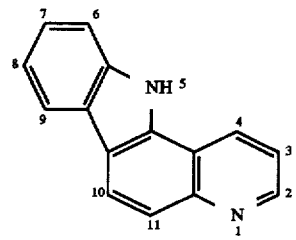

A coumarino[3,4-f]quinoline is defined by the following structure. Compound 159 and compounds of structures 41 and 88 herein are named as coumarino[3,4-f]quinolines.

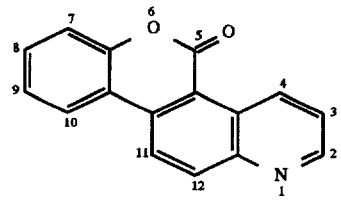

A 5H-chromeno[3,4-f]quinoline is defined by the following structure. Compounds of structures 34, 35, 42, 45 to 54, 93, 95, 97 to 99, 1A, 4A, 7A to 11A, 17A to 19A and 25A to 27A herein are named as coumarino[3,4-f]quinolines.

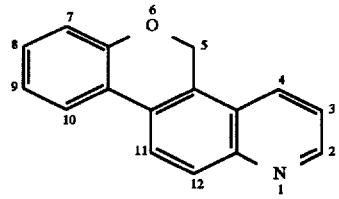

An 8-pyranono[5,6-g]quinoline is defined by the following structure. Compounds of structures 57 (Y=O), 60 (Y=O), 63 (Y=O), 69 (Y=O), 73 (Y=O), 28A (Y=O), 33A, 34A, 37A (X=O), 38A (X=O), 40A (X=O), 41A (X=O), 45A, 65A (X=O) and 67A (X=O) herein are named as 8-pyranono[5,6-g]quinolines.

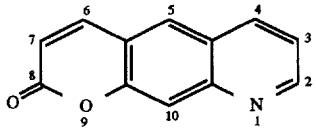

A 10-isocoumarino[4,3-g]quinoline is defined by the following structure. Compounds of structures 57 ($R^2=R^3=$ benzo, Y=O), 60 ($R^2=R^3=$benzo, Y=O), and 63 ($R^2=R^3=$benzo, Y=O) herein are named as 10-isocoumarino[4,3-g]quinolines.

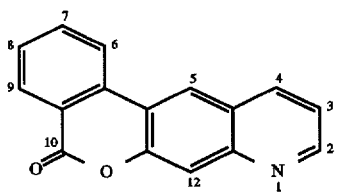

A 10-isoquinolino[4,3-g]quinoline is defined by the following structure. Compounds of structures 57 ($R^2=R^3=$ benzo, Y=NH), 60 ($R^2=R^3=$benzo, Y=NH), and 63 ($R^2=R^3=$benzo, Y=NH) herein are named as 10-isoquinolino[4,3-g]quinolines.

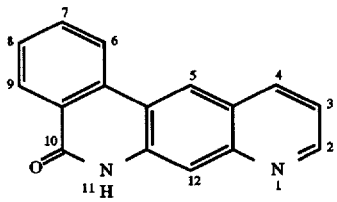

An 8-pyridono[5,6-g]quinoline is defined by the following structure. Compounds of structures 57 (Y=N), 60 (Y=N), 63 (Y=N), 69 (Y=N), 73 (Y=N), 28A (Y=N), 37A (X=N), 38A (X=N), 40A (X=N), 41A (X=N), 47A, 53A, 62A, 63A, 65A (X=N), 67A (X=N), 70A, 72A, 74A, 79A, 80A, 81A and 84A herein are named as 8-pyridono[5,6-g]quinolines.

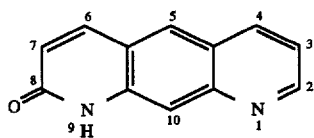

A 10H-isochromeno[4,3-g]quinoline is defined by the following structure. Compounds of structures 61 ($R^2=R^3=$ benzo, Y=O) and 62 ($R^2=R^3=$benzo, Y=O) herein are named as 10H-isochromeno[4,3-g]quinolines.

An 8H-pyrano[3,2-g]quinoline is defined by the following structure. Compounds of structures 61 (Y=O) and 62 (Y=O) herein are named as 8H-pyrano[3,2-g]quinolines.

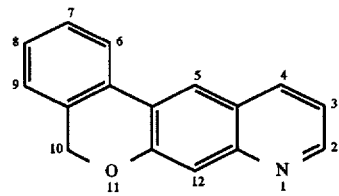

A 10-thioisoquinolino[4,3-g]quinoline is defined by the following structure. Compounds of structures 58 ($R^2=R^3=$ benzo, Y=NH) and 76 ($R^2=R^3=$benzo, Y=NH) herein are named as 10-thioisoquinolino[4,3-g]quinolines.

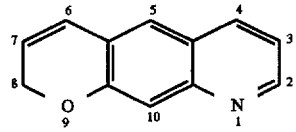

A 9-pyrido[3,2-g]quinoline is defined by the following structure. Compounds of structures 71 (Y=N) and 75 (Y=N) herein are named as 9-pyrido[3,2-g]quinolines.

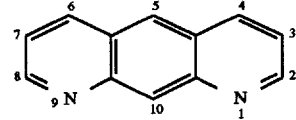

An 8-thiopyranono[5,6-g]quinoline is defined by the following structure. Compounds of structures 58 (Y=O), 76 (Y=O) and 29A (Y=O) herein are named as 8-thiopyranono[5,6-g]quinolines.

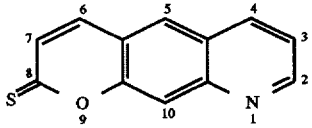

An 6-pyridono[5,6-g]quinoline is defined by the following structure. Compounds of structures 70 (Y=N) and 74 (Y=N) herein are named as 6-pyridono[5,6-g]quinolines.

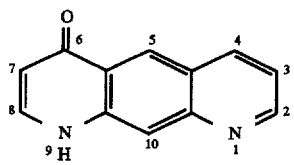

A 9-thiopyran-8-ono[5,6-g]quinoline is defined by the following structure. Compounds of structure 57 (Y=S), 28A (Y=S), 37A (X=S), 38A (X=S), 40A (X=S), 41A (X=S), 65A (X=S) and 67A (X=S) herein are named as 9-thiopyran-8-ono[5,6-g]quinolines.

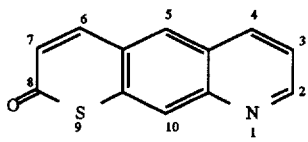

An 7-pyridono[5,6-f]indoline is defined by the following structure. Compounds of structures 49A, 50A, 57A, and 83A are named as 7-pyridono[5,6-f]indolines.

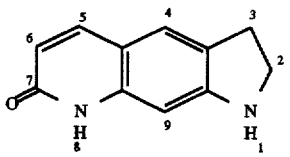

An 5H-isochromeno[3,4-f]quinoline is defined by the following structure. Compounds of structures 22A, 23A and 24A are named as 5H-isochromeno[3,4-f]quinolines.

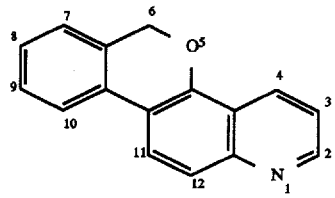

DETAILED DESCRIPTION OF EMBODIMENTS OF THE INVENTION

Compounds of the present invention are defined as those having the formulae:

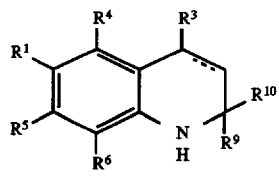
(I)

OR

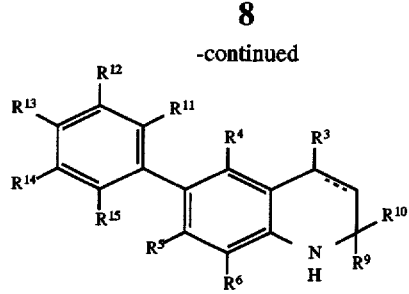
(II)

OR

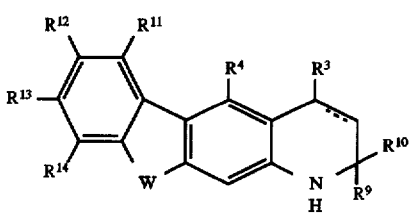
(III)

OR

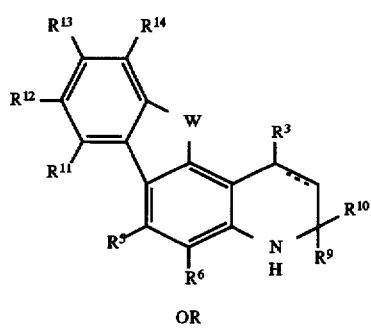
(IV)

OR

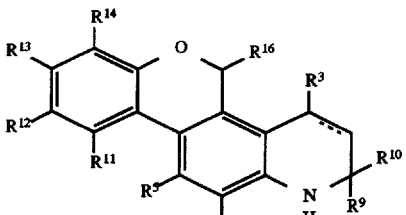
(V)

OR

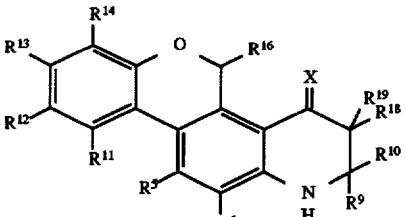
(VI)

OR

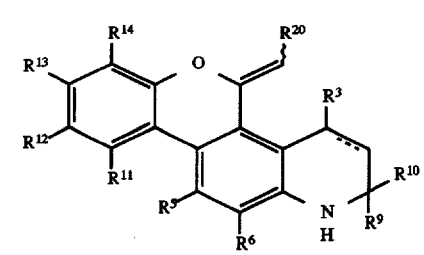
(VII)

-continued

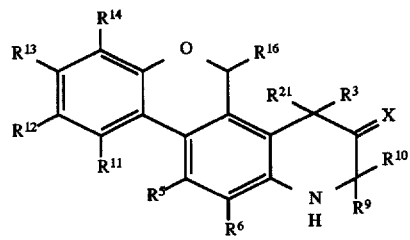
(VIII)

OR

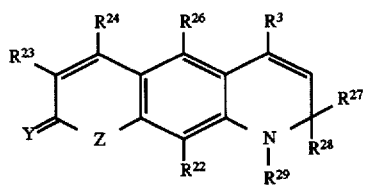
(IX)

OR

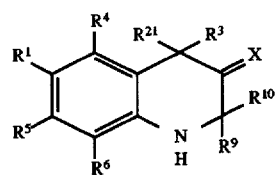
(X)

OR

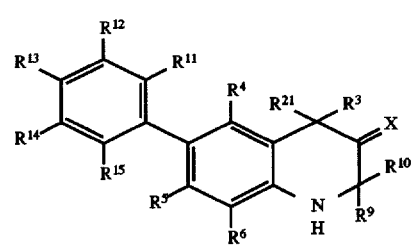
(XI)

OR

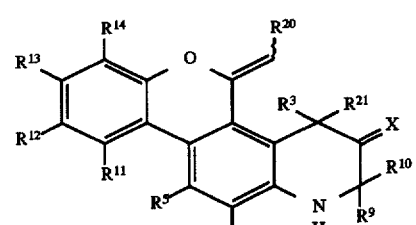
(XII)

OR

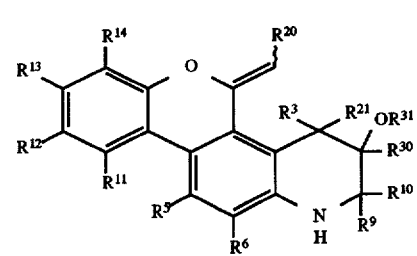
(XIII)

OR

-continued

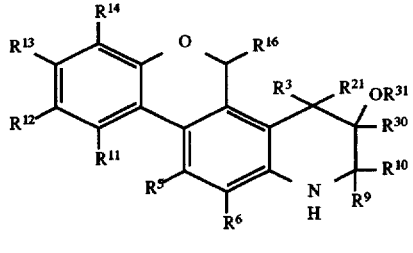
(XIV)

OR

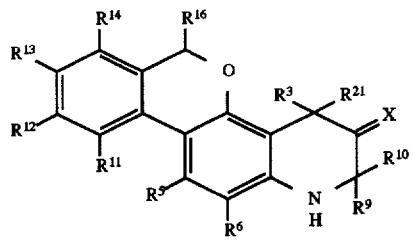
(XV)

OR

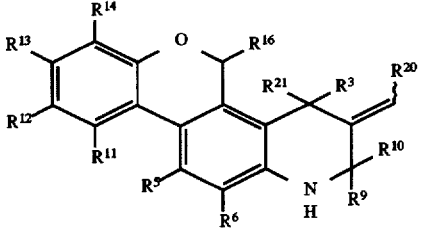
(XVI)

OR

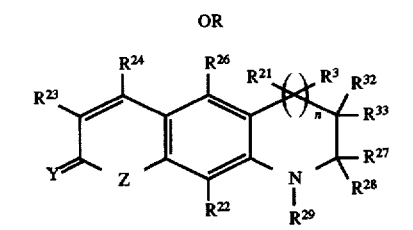
(XVII)

OR

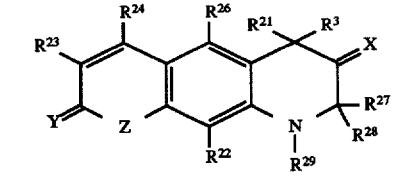
(XVIII)

wherein:

$R^1$ is a heteroaryl optionally substituted with a $C_1$–$C_4$ alkyl, F, Cl, Br, $NO_2$, $CO_2H$, $CO_2R^2$, CHO, CN, $CF_3$, $CH_2OH$ or $COCH_3$, where $R^2$ is hydrogen, a $C_1$–$C_4$ alkyl or perfluoroalkyl, aryl, heteroaryl or optionally substituted allyl, arylmethyl, alkynyl or alkenyl, and where said $R^1$ heteroaryl is attached to compounds of formulas I and X through a carbon or nitrogen atom;

$R^3$ is hydrogen, a $C_1$–$C_4$ alkyl or perfluoroalkyl, hydroxymethyl, aryl, heteroaryl or optionally substituted allyl, arylmethyl, alkynyl or alkenyl;

$R^4$ through $R^6$ each independently are hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$ has the definition given above, $R^7$ is hydrogen, a $C_1$–$C_4$ alkyl or perfluoroalkyl, aryl, heteroaryl, optionally substituted allyl or arylmethyl, $OR^8$ or $NHR^8$, where $R^8$ is hydrogen, a $C_1$–$C_6$ alkyl or perfluoroalkyl, aryl, heteroaryl, optionally substituted allyl or arylmethyl, $SO_2R^2$ or $S(O)R^2$;

$R^9$ and $R^{10}$ each independently are hydrogen, a $C_1$–$C_6$ alkyl or perfluoroalkyl, aryl, heteroaryl or optionally substituted allyl, arylmethyl, alkynyl or alkenyl, or $R^9$ and $R^{10}$ taken together can form a three- to seven-membered ring optionally substituted with hydrogen, F, $OR^2$, or $NR^2R^7$, where $R^2$ and $R^7$ have the definitions given above;

$R^{11}$ through $R^{15}$ each independently are hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$, $R^7$ and $R^8$ have the definitions given above;

W is O, NH, $NR^7$, $CH_2$, CHOH, C=O, OC=O, O=CO, $NR^7C$=O, NHC=O, O=$CNR^7$, O=CNH, SC=O, O=CS, or $CHOCOR^7$, where $R^7$ has the definition given above, except that when W is NH, $CH_2$ or O in the compounds of formula III, then $R^{11}$ through $R^{14}$ and $R^4$ cannot all be hydrogen when $R^3$, $R^9$ and $R^{10}$ are all $CH_3$, nor can they be a single F, Cl or Br substituent with the remaining substituents all being hydrogen when $R^3$, $R^9$ and $R^{10}$ are all $CH_3$, and further except that when W is O or NH in the compounds of formula IV, then $R^5$ through $R^6$ and $R^{11}$ through $R^{14}$ cannot all be hydrogen when $R^3$, $R^9$ and $R^{10}$ are all $CH_3$;

X is $CH_2$, O, S or where $R^7$ has the definition given above;

$R^{16}$ is hydrogen, OH, $OR^{17}$, $SR^{17}$, $NR^2R^7$, optionally substituted allyl, arylmethyl, alkynyl, alkenyl, aryl, heteroaryl or $C_1$–$C_{10}$ alkyl, where $R^{17}$ is a $C_1$–$C_{10}$ alkyl or perfluoroalkyl, or is an optionally substituted allyl, arylmethyl, aryl or heteroaryl, and where $R^2$ and $R^7$ have the definitions given above;

$R^{18}$ and $R^{19}$ each independently are hydrogen, a $C_1$–$C_6$ alkyl or perfluoroalkyl, aryl, heteroaryl or optionally substituted allyl, arylmethyl, alkynyl or alkenyl, or $R^{18}$ and $R^{19}$ taken together can form a three- to seven-membered ring optionally substituted with hydrogen, F, $OR^2$, or $NR^7R^8$, where $R^2$, $R^7$ and $R^8$ have the definitions given above;

$R^{20}$ is a $C_1$–$C_6$ alkyl or an optionally substituted allyl, arylmethyl, alkenyl, aryl or heteroaryl;

$R^{21}$ is hydrogen, a $C_1$–$C_4$ alkyl or optionally substituted allyl, arylmethyl, aryl or heteroaryl;

$R^{22}$ is hydrogen, a $C_1$–$C_4$ alkyl, F, Cl, Br, I, $OR^2$, $NR^2R^7$ or $SR^2$, where $R^2$ and $R^7$ have the definitions given above;

$R^{23}$ is hydrogen, Cl, Br, $OR^8$, $NR^2R^7$, a $C_1$–$C_4$ alkyl or perhaloalkyl, or is an optionally substituted allyl, arylmethyl, alkynyl, alkenyl, aryl or heteroaryl, where $R^2$, $R^7$ and $R^8$ have the definitions given above;

$R^{24}$ is hydrogen, F, Br, Cl, a $C_1$–$C_4$ alkyl or perhaloalkyl, aryl, heteroaryl, $CF_3$, $CF_2OR^{25}$, $CH_2OR^{25}$, or $OR^{25}$, where $R^{25}$ is a $C_1$–$C_4$ alkyl, except that $R^{24}$ cannot be $CH_3$ when Z is O, $R^{22}$, $R^{23}$, $R^{26}$ and $R^{29}$ are all hydrogen and $R^3$, $R^{27}$ and $R^{28}$ all are $CH_3$;

$R^{26}$ is hydrogen, a $C_1$–$C_4$ alkyl, F, Cl, Br, I, $OR^2$, $NR^2R^7$ or $SR^2$, where $R^2$ and $R^7$ have the definitions given above;

$R^{27}$ and $R^{28}$ each independently are hydrogen, a $C_1$–$C_4$ alkyl or perfluoroalkyl, heteroaryl, optionally substituted allyl, arylmethyl, alkynyl or alkenyl, or an aryl optionally substituted with hydrogen, F, Cl, Br, $OR^2$ or $NR^2R^7$, or $R^{27}$ and $R^{28}$ taken together can form a three- to seven-membered ring optionally substituted with hydrogen, F, Cl, Br, $OR^2$ or $NR^2R^7$, where $R^2$ and $R^7$ have the definitions given above;

$R^{29}$ is hydrogen, a $C_1$–$C_6$ alkyl or an optionally substituted allyl, arylmethyl, aryl or heteroaryl;

$R^{30}$ and $R^{31}$ each independently are hydrogen, a $C_1$–$C_6$ alkyl or an optionally substituted allyl, arylmethyl, aryl or heteroaryl, or $R^{30}$ and $R^{31}$ taken together can form a three- to seven-membered ring optionally substituted with hydrogen, F, Cl, $OR^2$ or $NR^2R^7$, where $R^2$ and $R^7$ have the definitions given above;

$R^{32}$ and $R^{33}$ each independently are hydrogen, a $C_1$–$C_4$ alkyl or an aryl optionally substituted with hydrogen, F, Cl, Br, $OR^2$ or $NR^2R^7$, or $R^{32}$ and $R^{33}$ taken together can form a three- to seven-membered ring optionally substituted with hydrogen, F, Cl, Br, $OR^2$ or $NR^2R^7$, where $R^2$ and $R^7$ have the definitions given above;

n is 0 or 1;

Y is O or S;

Z is O, S, NH, $NR^2$ or $NCOR^2$, where $R^2$ has the same definition given above;

the wavy line in the compounds of formulas VII, XII, XIII and XVI represent an olefin bond in either the cis or trans configuration; and the dotted lines in the structures depict optional double bonds, except that when there is a $C_3$–$C_4$ double bond in the nitrogen bearing ring of compounds of formula II, then $R^{11}$ through $R^{15}$ cannot all be hydrogen and $R^3$, $R^9$ and $R^{10}$ cannot all be methyl, and further except when $R^{23}$ is an aryl, $R^{22}$, $R^{24}$ and $R^{29}$ are all hydrogen, $R^3$ is $CH_3$ and Z is $NR^2$, then $R^2$ cannot be a $C_1$–$C_4$ alkyl.

Preferably, the compounds of formulae I, II, III, IV, X and XI comprise PR antagonists, the compounds of formulae V and VI comprise PR modulators (i.e. both PR agonists and antagonists), the compounds of formulae VII, VIII, XII, XIII, XIV, XV and XVI comprise PR agonists, and the compounds of formulae IX, XVII and XVIII comprise AR modulators (i.e., both AR agonists and antagonists). More preferably, the compounds of formulae IX and XVII comprise AR antagonists.

The present invention also provides a pharmaceutical composition comprising an effective amount of steroid receptor modulating compounds of the formulae:

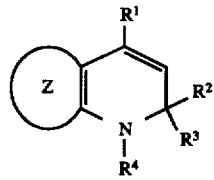

OR

-continued

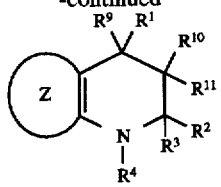

OR

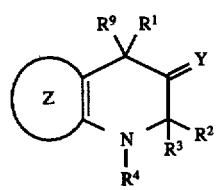

wherein:

R[1] through R[3] each independently are hydrogen, a $C_1$–$C_6$ alkyl, optionally substituted allyl, arylmethyl, alkynyl, alkenyl, aryl, or heteroaryl;

R[4] is hydrogen, a $C_1$–$C_6$ alkyl, or R[5]C=O, OR[6], or NR[6]R[7], where R[5] is hydrogen, a $C_1$–$C_6$ alkyl, optionally substituted allyl, arylmethyl, alkynyl, alkenyl, aryl, or heteroaryl, and wherein R[6] and R[7] each independently are hydrogen, a $C_1$–$C_6$ alkyl, optionally substituted allyl, arylmethyl, aryl, or heteroaryl;

R[9] through R[10] each independently are hydrogen, a $C_1$–$C_6$ alkyl, optionally substituted allyl, arylmethyl, alkynyl, alkenyl, aryl, or heteroaryl;

R[11] is hydrogen, a $C_1$–$C_6$ alkyl, OR[6] or optionally substituted allyl, arylmethyl, alkynyl, alkenyl, aryl, or heteroaryl, where R[6] has the same definition given above, or R[1] and R[2], R[2] and R[3], R[1] and R[9], R[10] and R[11], R[1] and R[10] and/or R[11] and R[2] when taken together can form a three- to seven-membered ring optionally substituted with hydrogen, F, OR[6] or NR[6]R[7], where R[6] through R[7] have the definitions given above, provided, however, that R[1], R[2], R[10] and R[11] cannot form more than two three- to seven-membered rings at a time;

Y is O, CHR[6] or NR[6], where R[6] has the same definition given above; and

Z is an aryl or heteroaryl group, including mono- and poly-cyclic structures, optionally substituted at one or more positions with hydrogen, a $C_1$–$C_6$ alkyl, optionally substituted allyl, arylmethyl, alkynyl, alkenyl, aryl, heteroaryl, F, Cl, Br, I, CN, R[5]C=O, R[6]R[7]NC=O, R[6]OC=O, perfluoroalkyl, haloalkyl, a $C_1$–$C_6$ straight-chain hydroxy alkyl, HOCR[5]R[8], nitro, R[6]OCH$_2$, R[6]O, NH$_2$, or R[6]R[7]N, where R[5] through R[7] have the definitions given above and where R[8] is hydrogen, a $C_1$–$C_6$ alkyl or optionally substituted allyl, arylmethyl, alkynyl, alkenyl, aryl, or heteroaryl; and a pharmaceutically acceptable carrier.

Preferred Z groups, wherein the dashed lines indicate the preferred mode of attachment to the nitrogen-bearing ring, include the following:

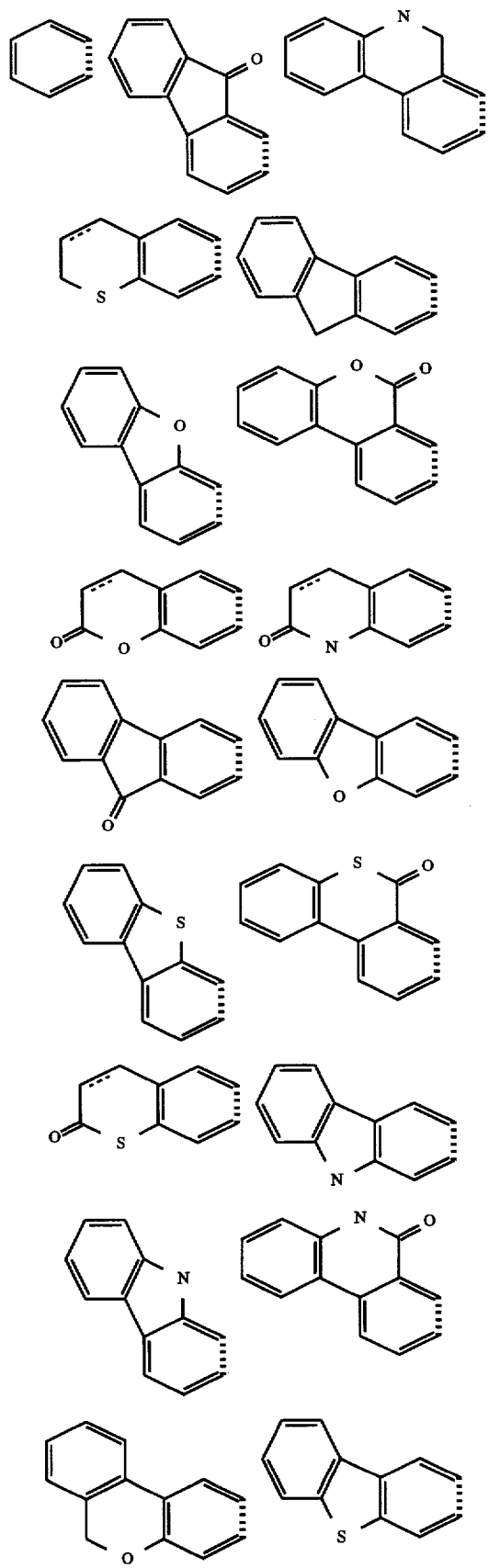

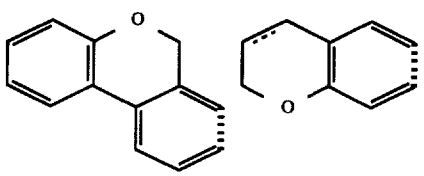
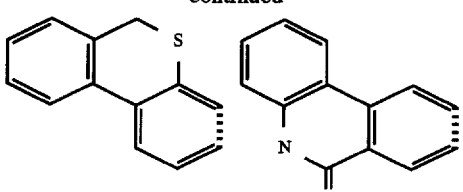
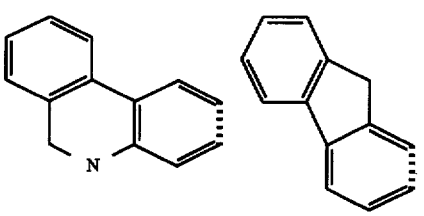
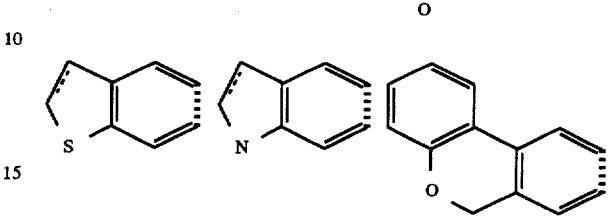
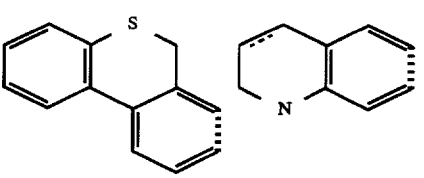
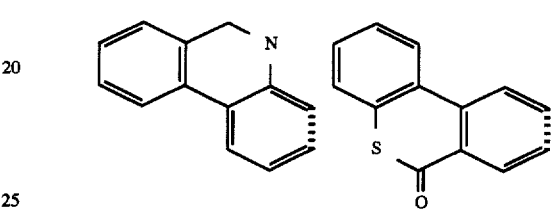
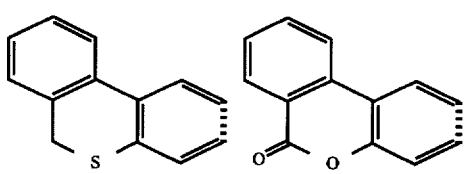
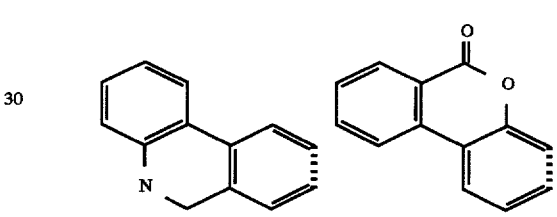
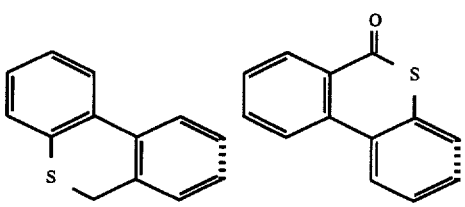
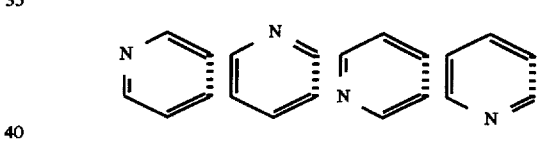
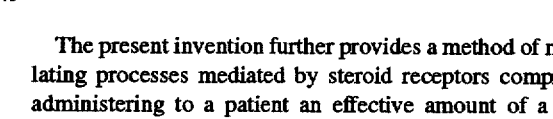
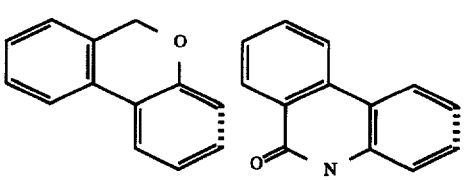
The present invention further provides a method of modulating processes mediated by steroid receptors comprising administering to a patient an effective amount of a compound of the formula:
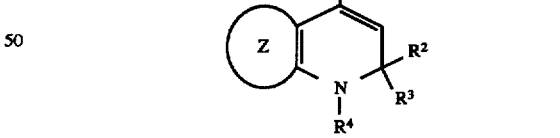
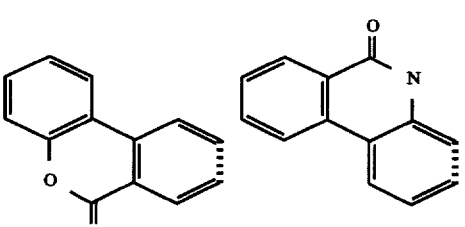
OR
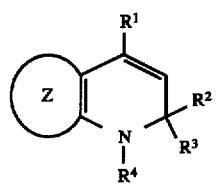
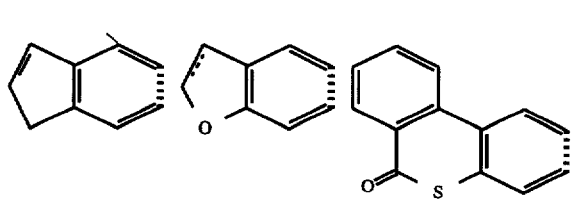
OR

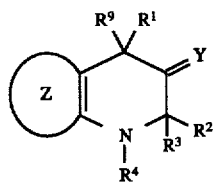
wherein $R^1$ through $R^{11}$ and Z have the same definitions as given above.
In a preferred aspect, the present invention provides a pharmaceutical composition comprising an effective amount of asteroid receptor modulating compound of the formulae:
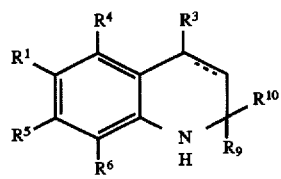 (I)
OR
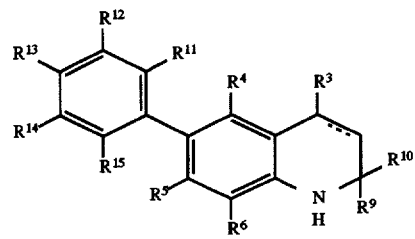 (II)
OR
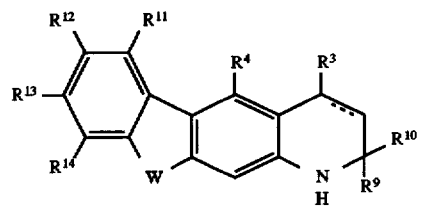 (III)
OR
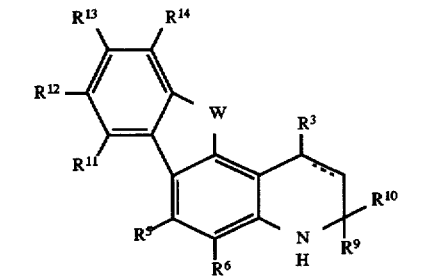 (IV)
OR
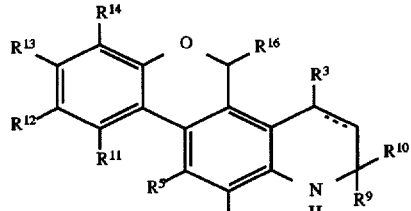 (V)
OR
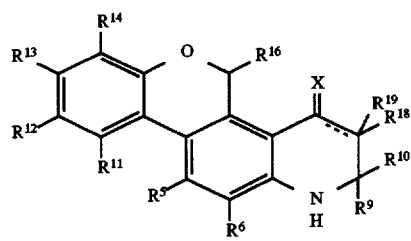 (VI)
OR
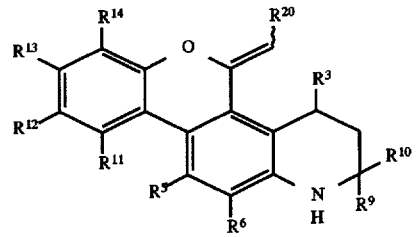 (VII)
OR
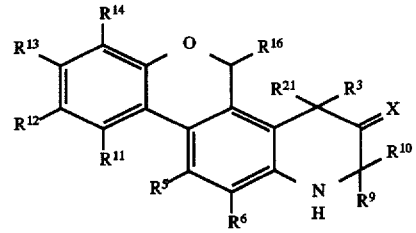 (VIII)
OR
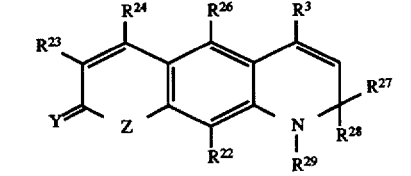 (IX)
OR
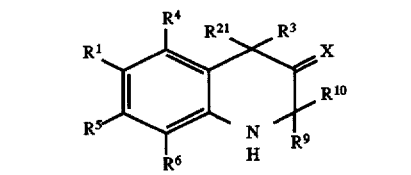 (X)
OR

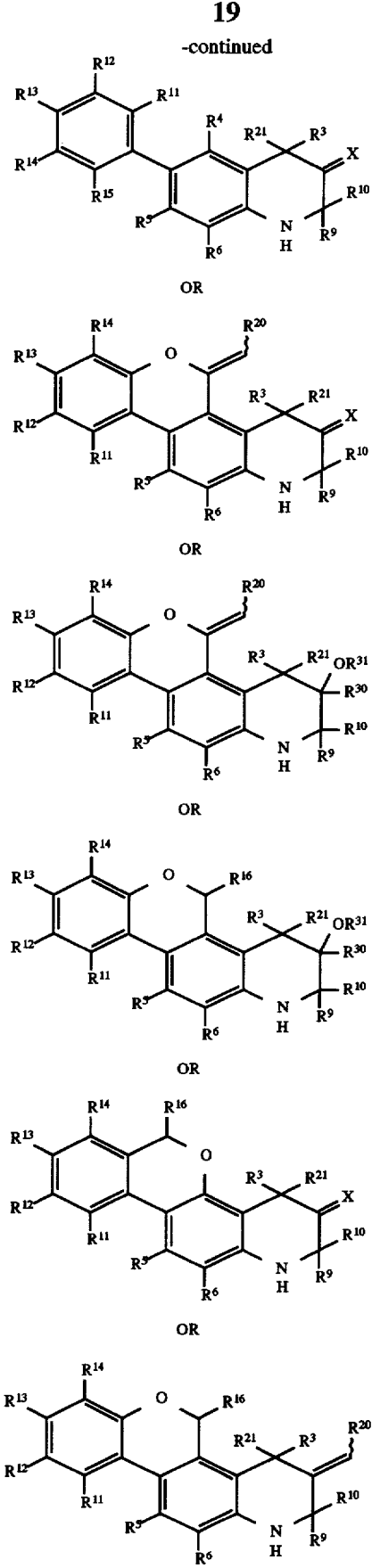

wherein:

R¹ is a heteroaryl optionally substituted with a $C_1$–$C_4$ alkyl, F, Cl, Br, $NO_2$, $CO_2H$, $CO_2R^2$, CHO, CN, $CF_3$, $CH_2OH$ or $COCH_3$, where $R^2$ is hydrogen, a $C_1$–$C_4$ alkyl or perfluoroalkyl, aryl, heteroaryl or optionally substituted allyl, arylmethyl, alkynyl or alkenyl, and where said R¹ heteroaryl is attached to compounds of formulas I and X through a carbon or nitrogen atom;

R³ is hydrogen, a $C_1$–$C_4$ alkyl or perfluoroalkyl, hydroxymethyl, aryl, heteroaryl or optionally substituted allyl, arylmethyl, alkynyl or alkenyl;

R⁴ through R⁶ each independently are hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where R² has the definition given above, R⁷ is hydrogen, a $C_1$–$C_4$ alkyl or perfluoroalkyl, aryl, heteroaryl, optionally substituted allyl or arylmethyl, $OR^8$ or $NHR^8$, where R⁸ is hydrogen, a $C_1$–$C_6$ alkyl or perfluoroalkyl, aryl, heteroaryl or optionally substituted allyl, arylmethyl, $SO_2R^2$ or $S(O)R^2$;

R⁹ and R¹⁰ each independently are hydrogen, a $C_1$–$C_6$ alkyl or perfluoroalkyl, aryl, heteroaryl or optionally substituted allyl, arylmethyl, alkynyl or alkenyl, or and taken R⁹ and R¹⁰ taken together can form a three- to seven-membered ring optionally substituted with hydrogen, F, $OR^2$, or $NR^2R^7$, where R² and R⁷ have the definitions given above;

R¹¹ through R¹⁵ each independently are hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where R², R⁷ and R⁸ have the definitions given above;

W is O, NH, $NR^7$, $CH_2$, CHOH, C=O, OC=O, O=CO, $NR^7C$=O, NHC=O, O=$CNR^7$, O=CNH, SC=O, O=CS, or $CHOCOR^7$, where R⁷ has the definition given above;

X is $CH_2$, O, S or $NR^7$, where R⁷ has the definition given above;

R¹⁶ is hydrogen, OH, $OR^{17}$, $SR^{17}$, $NR^2R^7$, optionally substituted allyl, arylmethyl, alkynyl, alkenyl, aryl, heteroaryl or $C_1$–$C_{10}$ alkyl, where $R^{17}$ is a $C_1$–$C_{10}$ alkyl or perfluoroalkyl, or is an optionally substituted allyl, arylmethyl, aryl or heteroaryl, and where $R^2$ and $R^7$ have the definitions given above;

$R^{18}$ and $R^{19}$ each independently are hydrogen, a $C_1$-$C_6$ alkyl or perfluoroalkyl, aryl, heteroaryl or optionally substituted allyl, arylmethyl, alkynyl or alkenyl, or $R^{18}$ and $R^{19}$ taken together can form a three- to seven-membered ring optionally substituted with hydrogen, F, $OR^2$, or $NR^7R^8$, where $R^2$, $R^7$ and $R^8$ have the definitions given above;

$R^{20}$ is a $C_1$-$C_6$ alkyl or an optionally substituted allyl, arylmethyl, alkenyl, aryl or heteroaryl;

$R^{21}$ is hydrogen, a $C_1$-$C_4$ alkyl or optionally substituted allyl, arylmethyl, aryl or heteroaryl;

$R^{22}$ is hydrogen, a $C_1$-$C_4$ alkyl, F, Cl, Br, I, $OR^2$, $NR^2R^7$ or $SR^2$, where $R^2$ and $R^7$ have the definitions given above;

$R^{23}$ is hydrogen, Cl, Br, $OR^8$, $NR^2R^7$, a $C_1$-$C_4$ alkyl or perhaloalkyl, or is an optionally substituted allyl, arylmethyl, alkynyl, alkenyl, aryl or heteroaryl, where $R^2$, $R^7$ and $R^8$ have the definitions given above;

$R^{24}$ is hydrogen, F, Br, Cl, a $C_1$-$C_4$ alkyl or perhaloalkyl, aryl, heteroaryl, $CF_3$, $CF_2OR^{25}$, $CH_2OR^{25}$, or $OR^{25}$, where $R^{25}$ is a $C_1$-$C_4$ alkyl;

$R^{26}$ is hydrogen, a $C_1$-$C_4$ alkyl, F, Cl, Br, I, $OR^2$, $NR^2R^7$ or $SR^2$, where $R^2$ and $R^7$ have the definitions given above;

$R^{27}$ and $R^{28}$ each independently are hydrogen, a $C_1$-$C_4$ alkyl or perfluoroalkyl, heteroaryl, optionally substituted allyl, arylmethyl, alkynyl or alkenyl, or an aryl optionally substituted with hydrogen, F, Cl, Br, $OR^2$ or $NR^2R^7$, or $R^{27}$ and $R^{28}$ taken together can form a three- to seven-membered ring optionally substituted with hydrogen, F, Cl, Br, $OR^2$ or $NR^2R^7$, where $R^2$ and $R^7$ have the definitions given above;

$R^{29}$ is hydrogen, a $C_1$-$C_6$ alkyl or an optionally substituted allyl, arylmethyl, aryl or heteroaryl;

$R^{30}$ and $R^{31}$ each independently are hydrogen, a $C_1$-$C_6$ alkyl or an optionally substituted allyl, arylmethyl, aryl or heteroaryl, or $R^{30}$ and $R^{31}$ taken together can form a three- to seven-membered ring optionally substituted with hydrogen, F, Cl, $OR^2$ or $NR^2R^7$, where $R^2$ and $R^7$ have the definitions given above;

$R^{32}$ and $R^{33}$ each independently are hydrogen, a $C_1$-$C_4$ alkyl or an aryl optionally substituted with hydrogen, F, Cl, Br, $OR^2$ or $NR^2R^7$, or $R^{32}$ and $R^{33}$ taken together can form a three- to seven-membered ring optionally substituted with hydrogen, F, Cl, Br, $OR^2$ or $NR^2R^7$, where $R^2$ and $R^7$ have the definitions given above;

n is 0 or 1;

Y is O or S;

Z is O, S, NH, $NR^2$ or $NCOR^2$, where $R^2$ has the same definition given above;

the wavy line in the compounds of formulas VII, XII, XIII and XVI represent an olefin bond in either the cis or trans configuration;

the dotted lines in the structures depict optional double bonds; and a pharmaceutically acceptable carrier.

Preferably, the compounds of formulae I, II, III, IV, X and XI comprise PR antagonism, the compounds of formulae V and VI comprise PR modulators (i.e. both PR agonists and antagonists), the compounds of formulae VII, VIII, XII, XIII, XIV, XV and XVI comprise PR agonists, and the compounds of formulae IX, XVII and XVIII comprise AR modulators (i.e., both AR agonists and antagonists). More preferably, the compounds of formulae IX and XVII comprise AR antagonists.

In a further preferred aspect, the present invention comprises a method of modulating processes mediated by steroid receptors comprising administering to a patient an effective amount of a compound of the formulae I through XVIII shown above, wherein $R^1$ through $R^{35}$, W, X, Y and Z all have the same definitions as those given above for the preferred pharmaceutical composition of the present invention.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl) aminomethane. Additional pharmaceutically acceptable salts are known to those skilled in the art.

The PR agonist, partial agonist and antagonist compounds of the present invention are particularly useful for female hormone replacement therapy and as modulators of fertility (e.g., as contraceptives, contragestational agents or abortifacients), either alone or in conjunction with ER modulators. The PR active compounds are also useful in the treatment of dysfunctional uterine bleeding, dysmenorrhea, endometriosis, leiomyomas (uterine fibroids), hot flashes, mood disorders, meningiomas as well as in various hormone-dependent cancers, including, without limitation, cancers of the ovaries, breast, endometrium and prostate.

AR agonist, partial agonist and antagonist compounds of the present invention will prove useful in the treatment of acne, male-pattern baldness, male hormone replacement therapy, wasting diseases, hirsutism, stimulation of hematopoiesis, hypogonadism, prostatic hyperplasia, various hormone-dependent cancers, including, without limitation, prostate and breast cancer and as anabolic agents.

ER agonists, partial agonists and antagonists compounds of the present invention are useful in female hormone replacement therapy and as fertility modulators, typically in combination with a PR modulator (i.e., a progestin, such as Premarin®). ER modulator compounds are also useful to treat atrophic vaginitis, kraurosis vulvae, osteoporosis, hirsutism, hot flashes, vasomotor symptoms, mood disorders, neuroendocrine effects, acne, dysmenorrhea and hormonally dependent cancers, including, without limitation, breast and prostate cancer.

GR and MR agonists, partial agonists and antagonists of the present invention can be used to influence the basic, life sustaining systems of the body, including carbohydrate, protein and lipid metabolism, electrolyte and water balance, and the functions of the cardiovascular, kidney, central nervous, immune, skeletal muscle and other organ and tissue systems. In this regard, GR and MR modulators have proved useful in the treatment of inflammation, tissue rejection, auto-immunity, hypertension, various malignancies, such as leukemias, lymphomas and breast and prostate cancers, Cushing's syndrome, glaucoma, obesity, rheumatoid arthritis, acute adrenal insufficiency, congenital adrenal hyperplasia, osteoarthritis, rheumatic fever, systemic lupus erythematosus, polymyositis, polyarteritis nodosa, granulomatous polyarteritis, allergic diseases such as urticaria, drag reactions and hay fever, asthma, a variety of skin diseases, inflammatory bowel disease, hepatitis and cirrhosis. Accordingly, GR and MR active compounds have been used as immuno stimulants and repressors, wound healing—tissue repair agents, catabolic/antianabolic activators and as anti-viral agents, particularly in the treatment of exacerbated herpes simplex virus.

It will be understood by those skilled in the art that while the compounds of the present invention will typically be employed as a selective agonists, partial agonists or antagonists, that there may be instances where a compound with a mixed steroid receptor profile is preferred. For example, use of a PR agonist (i.e., progestin) in female contraception often leads to the undesired effects of increased water retention and acne flare ups. In this instance, a compound that is primarily a PR agonist, but also displays some AR and MR modulating activity, may prove useful. Specifically, the mixed MR effects would be useful to control water balance in the body, while the AR effects would help to control any acne flare ups that occur.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative PR antagonist compounds according to the present invention include: 1,2,3,4-Tetrahydro-2,2,4-trimethyl-6-phenylquinoline (Compound 100); 1,2-Dihydro-2,2,4-trimethyl-6-(1,2,3-thiadiazol-5-yl)quinoline (Compound 101); 1,2-Dihydro-2,2,4-trimethyl-6-(1,3-oxazol-5-yl)quinoline (Compound 102); 6-(4,5-Dichloroimidazol-1-yl)-1,2-dihydro-2,2,4-trimethylquinoline (Compound 103); 6-(4-Bromo-1-methylpyrazol-3-yl)-1,2-dihydro-2,2,4-trimethylquinoline (Compound 104); 1,2-Dihydro-2,2,4-trimethyl-6-(3-pyridyl)quinoline (Compound 105); 6-(4-Fluorophenyl)-1,2,-dihydro-2,2,4-trimethylquinoline (Compound 106); 1,2-Dihydro-6-(3-trifluoromethylphenyl)-2,2,4-trimethylquinoline (Compound 107); 1,2-Dihydro-2,2,4-trimethyl-6-(4-nitrophenyl)quinoline (Compound 108); 6-(2,3-Dichlorophenyl)-1,2-dihydro-2,2,4-trimethylquinoline (Compound 109); 1,2-Dihydro-6-(2-hydroxycarbonyl-4-nitrophenyl)-2,2,4-trimethylquinoline (Compound 110); 6-(3,4-Dichlorophenyl)-1,2-dihydro-2,2,4-trimethylquinoline (Compound 111); 4-Ethyl-1,2-dihydro-2,2-dimethyl-6-phenylquinoline (Compound 112); 1,2-Dihydro-2,2-dimethyl-6-phenyl-4-propylquinoline (Compound 113); 6-(2-Chlorophenyl)1,2-dihydro-2,2,4-trimethylquinoline (Compound 114); 1,2-Dihydro-2,2,4-trimethylindenol[1,2-g]quinoline (Compound 115); 1,2-Dihydro-2,2,4-trimethylindeno[2,1-f]quinoline (Compound 116); 8-Bromo-1,2-dihydro-2,2,4-trimethylindeno[1,2-g]quinoline (Compound 117); 1,2-Dihydro-2,2,4-trimethylbenzo[b]furano[3,2,g]quinoline (Compound 118); 1,2-Dihydro-2,2,4-trimethylbenzo[b]furano[2,3-f]quinoline (Compound 119); 6-Fluoro-1,2-dihydro-2,2,4-trimethylindeno[2,1-f]quinoline (Compound 120); 9-Fluoro-1,2-dihydro-2,2,4-trimethylindeno[1,2-g]quinoline (Compound 121); 1,2-Dihydro-9-hydroxylmethyl-2,2,4-trimethylindeno[1,2-g]quinoline (Compound 122); 8-Chloro-1,2-dihydro-2,2,4-trimethylindeno[1,2-g]quinoline (Compound 123); 8-Fluoro-1,2-dihydro-2,2,4-trimethylindeno[1,2-g]quinoline (Compound 124); 8-Acetyl-1,2-dihydro-2,2,4-trimethylindeno[1,2-g]quinoline (Compound 125); 6-Fluoro-1,2-dihydro-2,2,4-trimethylindeno[1,2-g]quinoline (Compound 126); 7-Bromo-1,2-dihydro-2,2,4-trimethylindeno[2,1-f]quinoline (Compound 127); 1,2-Dihydro-2,2,4-trimethyl-7-nitroindeno[2,1-f]quinoline (Compound 128); 1,2-Dihydro-2,2,4-trimethyl-8-nitroindeno[1,2-g]quinoline (Compound 129); 6,9-Difluoro-1,2-dihydro-2,2,4-trimethylindeno[1,2-g]quinoline (Compound 130); 7-Fluoro-1,2-dihydro-2,2,4-trimethyl-11-(thiomethyl)indeno[2,1-f]quinoline (Compound 131); 5,8-Difluoro-1,2-dihydro-10-hydroxy-2,2,4-trimethylindeno[1,2-g]quinoline (Compound 132); 7,9-Difluoro-1,2-dihydro-10-hydroxy-2,2,4-trimethylindeno[1,2-g]quinoline (Compound 133); 7,10-Difluoro-1,2-dihydro-2,2,4-trimethyl-5-oxoindeno[3,2-f]quinoline (Compound 134); 7,9-Difluoro-1,2-dihydro-2,2,4-trimethyl-10-oxoindeno[1,2-g]quinoline (Compound 135); 8-Fluoro-1,2-dihydro-10-hydroxy-2,2,4-trimethylindeno[1,2-g]quinoline (Compound 136); 8-Fluoro-1,2-dihydro-2,2,4-trimethyl-10-oxoindeno[1,2-g]quinoline (Compound 137); 7-Fluoro-1,2-dihydro-2,2,4-trimethyl-8-nitroindeno[1,2-g]quinoline (Compound 138); 5-Chloro-1,2-dihydro-10-hydroxy-2,2,4-trimethylindeno[1,2-g]quinoline (Compound 139); 6-Fluoro-1,2-dihydro-2,2,4-trimethyl-10-oxoindeno[1,2-g]quinoline (Compound 140); 6-Fluoro-1,2-dihydro-10-hydroxy-2,2,4-trimethylindeno[1,2-g]quinoline (Compound 141); 5,8-Difluoro-1,2-dihydro-2,2,4-trimethyl-10-(trifluoroacetoxy)indeno[1,2-g]quinoline (Compound 142); 6-(3,5-Difluorophenyl)-1,2,3,4-tetrahydro-2,2,4-trimethylquinoline (Compound 143); 1,2-Dihydro-2,2,4-trimethylindolo[3,2-g]quinoline (Compound 144); 5-Ethyl-1,2-dihydro-2,2,4-trimethylindolo[2,3-f]quinoline (Compound 145); 6-(3-Chlorophenyl)-1,2-dihydro-2,2,4-trimethylquinoline (Compound 146); 6-(3,5-Difluorophenyl)-1,2-dihydro-2,2,4-trimethylquinoline (Compound 147); 6-(3-Fluorophenyl)-1,2-dihydro-2,2,4-trimethylquinoline (Compound 148); 1,2-Dihydro-2,2,4-trimethyl-6-(4-pyridyl)quinoline (Compound 149); 6-(3-Cyanophenyl)-1,2-dihydro-2,2,4-trimethylquinoline (Compound 150); 6-(3,5-Dichlorophenyl)-1,2-dihydro-2,2,4-trimethylquinoline (Compound 151); 6-(2,3-Difluorophenyl)-1,2-dihydro-2,2,4-trimethylquinoline (Compound 152); 1,2-Dihydro-2,2,4-trimethyl-6-(pentafluorophenyl)quinoline (Compound 153); 1,2-Dihydro-2,2,4-trimethyl-6-[4-(trifluoroacetyl)phenyl]quinoline (Compound 154); 1,2-Dihydro-2,2,4-trimethyl-6-(1,3-pyrimid-5-yl)quinoline (Compound 155); 6-(3-Cyanophenyl)-1,2,3,4-tetrahydro-2,2,4-trimethylquinoline (Compound 156); 5,8-Difluoro-1,2-dihydro-2,2,4-trimethylindeno[1,2-g]quinoline (Compound 157); 7,10-Difluoro-1,2-dihydro-2,2,4-trimethylindeno[2,1-f]quinoline (Compound 158); 8-Cyano-1,2-dihydro-2,2,4-trimethylindeno[3,2-e]quinoline (Compound 270); 6-(3-Cyano-5-fluorophenyl)-1,2-dihydro-2,2,4-trimethylquinoline (Compound 271); 6-(3-Cyano-4-fluorophenyl)-1,2-dihydro-2,2,4-trimethylquinoline (Compound 272); 6-(3-Cyano-6-fluorophenyl)-1,2-dihydro-2,2,4-trimethylquinoline (Compound 273); 6-[5-fluoro-3-(trifluoromethyl)phenyl]-1,2-dihydro-2,2,4-trimethylquinoline (Compound 274); 6-(3-chloro-2-methylphenyl)-1,2-dihydro-2,2,4-trimethylquinoline (Compound 275); 1,2-Dihydro-2,2,4-trimethyl-6-(3- nitrophenyl)quinoline (Compound 276); 6-(3-Acetylphenyl)-1,2-dihydro-2,2,4-trimethylquinoline (Compound 277); 6-(3-cyano-2-methylphenyl)-1,2-dihydro-2,2,4-trimethylquinoline (Compound 278); 1,2-Dihydro-2,2,4-trimethyl-6-(3-methylphenyl)quinoline (Compound 279); 6-(5-Fluoro-3-nitrophenyl)-1,2-dihydro-2,2,4-trimethylquinoline (Compound 280); 1,2-Dihydro-6-(3-methoxyphenyl)-2,2,4-trimethylquinoline (Compound 281); 6-(5-Cyano-3-pyridyl)-1,2-dihydro-2,2,4-trimethylquinoline (Compound 282); 1,2-Dihydro-2,2,4-trimethyl-6-(2-methyl-3-nitrophenyl)quinoline (Compound 283); 6-(2-Amino-3,5-difluorophenyl)-1,2-dihydro-2,2,4-trimethylquinoline (Compound 284); 6-(3-Bromo-2-chloro-5-fluorophenyl)-1,2-dihydro-2,2,4-trimethylquinoline (Compound 285); 6-(3-Cyano-5-fluorophenyl)-1,2-dihydro-2,2,4-trimethyl-3-quinolone (Compound 286); 6-(3-Fluoro-2-methylphenyl)-1,2-dihydro-2,2,4-trimethylquinoline (Compound 287); 1,2-Dihydro-2,2,4-trimethyl-6-(3-methylthiophenyl)quinoline (Compound 288); 6-(5-Chloro-2-thienyl)-1,2-dihydro-2,2,4-trimethylquinoline (Compound 289); 1,2-Dihydro-2,2,4-trimethyl-6-(3-methyl-2-thienyl)quinoline (Compound 290); 8-Fluoro-1,2-dihydro-2,2,4-trimethyl-6-(3-nitrophenyl)quinoline (Compound 291); 1,2-Dihydro-6-(3-nitrophenyl)-2,2,4,8-tetramethylquinoline (Compound 292); 6-(5-Bromo-3-pyridyl)-1,2-dihydro-2,2,4-trimethylquinoline (Compound 293); 6-(3-Bromo-2-pyridyl)-1,2-dihydro-2,2,4-trimethylquinoline (Compound 294); 6-(3-Bromo-2-thienyl)-1,2-dihydro-2,2,4-trimethylquinoline (Compound 295); 1,2-Dihydro-6-(2,3,5,6-tetrafluoro-4-pyridyl)-2,2,4-trimethylquinoline (Compound 296); 5,8-Difluoro-1,2-dihydro-6-(3-nitrophenyl)-2,2,4-trimethylquinoline (Compound 297); 2,4-Diethyl-8-fluoro-1,2-dihydro-2-methyl-6-(3-nitrophenyl)quinoline (Compound 298); 6-(3-Bromophenyl)-1,2-dihydro-2,2,4-trimethylquinoline (Compound 299); 1,2-Dihydro-2,2,4-trimethyl-6-(5-nitro-2-thienyl)quinoline (Compound 300); 1,2-Dihydro-6-(2,4,5-trifluorophenyl)-2,2,4-trimethylquinoline (Compound 301); 6-(3-Bromo-5-fluorophenyl)-1,2-dihydro-2,2,4-trimethylquinoline (Compound 302); 6-(5-Carboxaldehyde-3-thienyl)-1,2-dihydro-2,2,4-trimethylquinoline (Compound 303); 1,2-Dihydro-2,2,4,7-tetramethyl-6-(3-nitrophenyl)quinoline (Compound 304); 6-(5-Fluoro-2-methoxy-3-nitrophenyl)-1,2-dihydro-2,2,4-trimethylquinoline (Compound 305); 6-(3-Chloro-2-methoxyphenyl)-1,2-dihydro-2,2,4-trimethylquinoline (Compound 306); 1,2-Dihydro-2,2,4-trimethyl-6-(2,3,4-trifluorophenyl)quinoline (Compound 307); 6-(3-Bromo-2-methylphenyl)-1,2-dihydro-2,2,4-trimethylquinoline (Compound 308); 7-Chloro-1,2-dihydro-2,2,4-trimethyl-6-(3-nitrophenyl)quinoline (Compound 309); 5-Chloro-1,2-dihydro-2,2,4-trimethyl-6-(3-nitrophenyl)quinoline (Compound 310); 8-Chloro-1,2-dihydro-2,2,4-trimethyl-6-(3-nitrophenyl)quinoline (Compound 311); 8-Ethyl-1,2-dihydro-2,2,4-trimethyl-6-(3-nitrophenyl)quinoline (Compound 312); 9-Chloro-1,2-dihydro-2,2-dimethyl-5-coumarino[3,4-f]quinoline (Compound 313); 1,2-Dihydro-9-methoxy-2,2,4-trimethyl-5-coumarino[3,4-f]quinoline (Compound 314); 9-Fluoro-1,2-dihydro-2,2,4,11-tetramethyl-5-coumarino[3,4-f]quinoline (Compound 315); 1,2-Dihydro-2,2,4,9-tetramethyl-5-coumarino[3,4-f]quinoline (Compound 316); 7-Chloro-1,2-dihydro-2,2,4-trimethyl-5-coumarino[3,4-f]quinoline (Compound 317); (R/S)-9-Chloro-1,2-dihydro-5-methoxy-2,2,4-trimethyl-5H-chromeno[3,4-f]quinoline (Compound 319); (R/S)-9-Fluoro-1,2-dihydro-2,2,4-trimethyl-5H-chromeno[3,4-f]quinoline (Compound 328); 6-(5-Cyano-2-thienyl)-1,2-dihydro-2,2,4-trimethylquinoline (Compound 451); 6-(5-Cyano-3-thienyl)-1,2-dihydro-2,2,4-trimethylquinoline (Compound 452); 6-(3-Formylphenyl)-1,2-dihydro-2,2,4-trimethylquinoline (Compound 453); 1,2-Dihydro-2,2,4-trimethyl-6-[3-(methylsulfonyl)phenyl]quinoline (Compound 454); (R/S)-6-(3-Cyano-5-fluorophenyl)-1,2,3,4-Tetrahydro-2,2,4-trimethylquinoline (Compound 455); and (R/S)-9-Chloro-1,2-dihydro-2,2,4-trimethyl-5-phenyl-5H-chromeno[3,4-f]quinoline (Compound 456).

Representative PR modulator compounds (i.e., agonists and antagonists) according to the present invention include: (R/S)-5-Butyl-1,2-dihydro-2,2,4-trimethyl-5H-chromeno[3,4-f]quinoline (Compound 160); (R/S)-1,2-Dihydro-2,2,4-trimethyl-5-phenyl-5H-chromeno[3,4-f]quinoline (Compound 161); (R/S)-1,2,3,4-Tetrahydro-2,2-dimethyl-4-methylidene-5-phenyl-5H-chromeno[3,4-f]quinoline (Compound 162); (R/S)-5-(4-Chlorophenyl)-1,2-dihydro-2,2,4-trimethyl-5H-chromeno[3,4-f]quinoline (Compound 163); (R/S)-5-(4-Chlorophenyl)-1,2,3,4-tetrahydro-2,2-dimethyl-4-methylidene-5H-chromeno[3,4-f]quinoline (Compound 104); (R/S)-5-(4-Fluorophenyl)-1,2-dihydro-2,2,4-trimethyl-5H-chromeno[3,4-f]quinoline (Compound 165); (R/S)-5-(4-Acetylphenyl)-1,2-dihydro-2,2,4-trimethyl-5H-chromeno[3,4-f]quinoline (Compound 166); (R/S)-1,2-Dihydro-2,2,4-trimethyl-5-(4-methylphenyl)-5H-chromeno[3,4-f]quinoline (Compound 167); (R/S)-1,2-Dihydro-5-(4-methoxyphenyl)-2,2,4-trimethyl-5H-chromeno[3,4-f]quinoline (Compound 168); (R/S)-1,2-Dihydro-2,2,4-trimethyl-5-[4-(trifluoromethyl)phenyl]-5H-chromeno[3,4-f]quinoline (Compound 169); (R/S)-1,2-Dihydro-2,2,4-trimethyl-5-(thiophen-3-yl)-5H-chromeno[3,4-f]quinoline (Compound 170); (−)-1,2-Dihydro-2,2,4-trimethyl-5-(4-methylphenyl)-5H-chromeno[3,4-f]quinoline (Compound 171); (−)-5-(4-Chlorophenyl)-1,2-dihydro-2,2,4-trimethyl-5H-chromeno[3,4-f]quinoline (Compound 172); (R/S)-1,2-Dihydro-2,2,4-trimethyl-5-(3-methylphenyl)-5H-chromeno[3,4-f]quinoline (Compound 173); (+)-(4I,5I)- 5-(4-Chlorophenyl)-1,2,3,4-tetrahydro-2,2,4-trimethyl-5H-chromeno[3,4-f]quinoline (Compound 174); (−)-(4I,5I)-5-(4-Chlorophenyl)-1,2,3,4-tetrahydro-2,2,4-trimethyl-5H-chromeno[3,4-f]quinoline (Compound 175); (R/S-4I,5u)-5-(4-Chlorophenyl)-1,2,3,4-tetrahydro-2,2,4-trimethyl-5H-chromeno[3,4-f]quinoline (Compound 176); (R/S)-5-(3-Chlorophenyl)-1,2-dihydro-2,2,4-trimethyl-5H-chromeno[3,4-f]quinoline (Compound 177); (R/S)-5-(3-Chlorophenyl)-1,2,3,4-tetrahydro-2,2-dimethyl-4-methylidene-5H-chromeno[3,4-f]quinoline (Compound 178); (R/S)-5-(4-Bromophenyl)-1,2-dihydro-2,2,4-trimethyl-5H-chromeno[3,4-f]quinoline (Compound 179); (R/S)-5-(4-Bromophenyl)-1,2,3,4-tetrahydro-2,2-dimethyl-4-methylidene-5H-chromeno[3,4-f]quinoline (Compound 180); (R/S)-5-(3-Bromophenyl)-1,2-dihydro-2,2,4-trimethyl-5H-chromeno[3,4-f]quinoline (Compound 181); (R/S)-5-(3-Bromophenyl)-1,2,3,4-tetrahydro-2,2-dimethyl-4-methylidene-5H-chromeno[3,4-f]quinoline (Compound 182); (R/S)-5-(3,4-Dichlorophenyl)-1,2-dihydro-2,2,4-trimethyl-5H-chromeno[3,4-f]quinoline (Compound 183); (R/S)-5-(3-Bromo-2-pyridyl)-1,2-dihydro-2,2,4-trimethyl-5H-chromeno[3,4-f]quinoline (Compound 184); (R/S)-1,2-Dihydro-5-hydroxy-2,2,4-trimethyl-5H-chromeno[3,4-f]quinoline (Compound 185); (R/S)-1,2-Dihydro-2,2,4-trimethyl-5-methoxy-5H-chromeno[3,4-f]quinoline (Compound 186); (R/S)-1,2-Dihydro-2,2,4-trimethyl-5-propoxy-H-chromeno[3,4-f]quinoline (Compound 187); (R/S)-5-Allyl-1,2-dihydro-2,2,4-trimethyl-5H-chromeno[3,4-f]quinoline (Compound 188); (R/S)-1,2-Dihydro-2,2,4-trimethyl-5-propyl-5H-chromeno[3,4-f]quinoline (Compound 189); (R/S)-1,2-Dihydro-2,2,4-trimethyl-5-(2-pyridyl)-5H-chromeno[3,4-f]quinoline (Compound 190); (R/S)-5-(3-Fluorophenyl)-1,2-dihydro-2,2,4-trimethyl-5H-chromeno[3,4-f]quinoline (Compound 191); (R/S)-5-(3-Fluorophenyl)-1,2,3,4-tetrahydro-2,2-dimethyl-4-methylidene-5H-chromeno[3,4-f]quinoline (Compound 192); (R/S)-1,2-Dihydro-2,2,4-trimethyl-5-propylthio-5H-chromeno[3,4-f]quinoline (Compound 193); (R/S)-1,2-Dihydro-5-(3-methoxyphenyl)-2,2,4-trimethyl-5H-chromeno[3,4-f]quinoline (Compound 194); (R/S) 1,2-Dihydro-2,2,4-trimethyl-5-[3 (trifluoromethyl)phenyl]-5H-chromeno[3,4-f]quinoline (Compound 195); (R/S)-5-(3-Fluoro-4-methylphenyl)-1,2-dihydro-2,2,4-trimethyl-5H-chromeno[3,4-f]quinoline (Compound 196); (R/S)-5-(4-Bromo-3-pyridyl)-1,2-dihydro-2,2,4-trimethyl-5H-chromeno[3,4-f]quinoline (Compound 197); (R/S)-1,2-Dihydro-2,2,4-trimethyl-5-(3-pyridyl)-5H-chromeno[3,4-f]quinoline (Compound 198); (R/S)-5-(4-Chloro-3-fluorophenyl)-1,2-dihydro-2,2,4-trimethyl-5H-chromeno[3,4-f]quinoline (Compound 199); (R/S)-1,2-Dihydro-2,2,4,5-tetramethyl-5H-chromeno[3,4-f]quinoline (Compound 200); (R/S)-1,2-Dihydro-5-hexyl-2,2,4-trimethyl-5H-chromeno[3,4-f]quinoline (Compound 201); 1,2-Dihydro-2,2,4-trimethyl-5H-chromeno[3,4-f]quinoline (Compound 202); (R/S)-1,2-Dihydro-5-(3-methylbutyl)-2,2,4-trimethyl-5H-chromeno[3,4-f]quinoline (Compound 203); (R/S)-5-(4-Chlorobutyl)-1,2-dihydro-2,2,4-trimethyl-5H-chromeno[3,4-f]quinoline (Compound 204); (R/S)-5-Benzyl-1,2-dihydro-2,2,4-trimethyl-5H-chromeno[3,4-f]quinoline (Compound 205); (R/S)-5-(4-Bromobutyl)-1,2-dihydro-2,2,4-trimethyl-5H-chromeno[3,4-f]quinoline (Compound 206); (R/S)-5-Butyl-9-fluoro-1,2-dihydro-2,2,4-trimethyl-5H-chromeno[3,4-f]quinoline (Compound 210); (R/S)-5-Butyl-8-fluoro-1,2-dihydro-2,2,4-trimethyl-5H-chromeno[3,4-f]quinoline (Compound 211); (R/S)-5-(3-Chlorophenyl)- 9-fluoro-1,2-dihydro-2,2,4-trimethyl-5H-chromeno[3,4-f]quinoline (Compound 212); (R/S)-5-(4-Chloro-3-methylphenyl)-9-fluoro-1,2-dihydro-2,2,4-trimethyl-5H-chromeno[3,4-f]quinoline (Compound 213); (R/S)-5-(4-Chlorophenyl)-9-fluoro-1,2-dihydro-2,2,4-trimethyl-5H-chromeno[3,4-f]quinoline (Compound 214); (R/S)-9-Fluoro-1,2-dihydro-5-(4-methoxyphenyl)-2,2,4-trimethyl-5H-chromeno[3,4-f]quinoline (Compound 215); (R/S)-8-Fluoro-1,2-dihydro-5-methoxyl-2,2,4-trimethyl-5H-chromeno[3,4-f]quinoline (Compound 216); (R/S)-5-(4-Chlorophenyl)-8-fluoro-1,2-dihydro-2,2,4-trimethyl-5H-chromeno[3,4-f]quinoline (Compound 217); and (R/S)-9-Chloro-5-(4-chlorophenyl)-1,2-dihydro-2,2,4-trimethyl-5H-chromeno[3,4-f]quinoline (Compound 218); 9-Chloro-1,2-dihydro-2,2,4-trimethyl-5H-chromeno[3,4-f]quinoline (Compound 320); (R/S)-9-Fluoro-1,2-dihydro-5-methoxy-2,2,4-trimethyl-5H-chromeno[3,4-f]quinoline (Compound 322); (R/S)-9-Fluoro-1,2-dihydro-2,2,4-trimethyl-5-thiopropoxy-5H-chromeno[3,4-f]quinoline (Compound 323); (R/S)-9-Fluoro-1,2-dihydro-2,2,4-trimethyl-5-propoxy-5H-chromeno[3,4-f]quinoline (Compound 324); (R/S)-1,2-Dihydro-9-methoxy-2,2,4-trimethyl-5H-chromeno[3,4-f]quinoline (Compound 329); (R/S)-1,2-Dihydro-2,2,4,9-tetramethyl-5H-chromeno[3,4-f]quinoline (Compound 330); (R/S)-7-Chloro-1,2-dihydro-2,2,4-trimethyl-5H-chromeno[3,4-f]quinoline (Compound 331); (R/S)-5-(4-Bromo-3-pyridyl)-1,2,3,4-tetrahydro-2,2-dimethyl-4-methylidene-5H-chromeno[3,4-f]quinoline (Compound 347); (R/S)-5-(3,5-Difluorophenyl)-1,2-dihydro-2,2,4-trimethyl-5H-chromeno[3,4-f]quinoline (Compound 348); (R/S)-5-(3-Bromo-5-fluorophenyl)-1,2,3,4-tetrahydro-2,2-dimethyl-4-methylidene-5H-chromeno[3,4-f]quinoline (Compound 352); (Z)-1,2,-Dihydro-5-(2,4,6-trimethylbenzylidene)-2,2,4-trimethyl-5H-chromeno[3,4-f]quinoline (Compound 364); (Z)-5-Benzylidene-9-fluoro-1,2-dihydro-2,2,4,11-tetramethyl-5H-chromeno[3,4-f]quinoline (Compound 377); (R/S)-5-(4-Chlorophenyl)-1,2,3,4-tetrahydro-2,2-dimethyl-5H-chromeno[3,4-f]-4-quinolinone (Compound 378); (R/S)-5-(4-Chlorophenyl)-1,2,3,4-tetrahydro-2,2,3,3-tetramethyl-5H-chromeno[3,4-f]4-quinolinone (Compound 379); (R/S)-5-(4-Chlorophenyl)-1,2-dihydro-2,2-dimethyl-5H-chromeno[3,4-f]4-quinoline (Compound 380); (+)-(R*-4l,5l)-5-(4-Chlorophenyl)-1,2,3,4-tetrahydro-2,2,4-trimethyl-5H-chromeno[3,4-f]-3-quinolinone (Compound 381); (−)-(R*-4l,5l)-5-(4-Chlorophenyl)-1,2,3,4-tetrahydro-2,2,4-trimethyl-5H-chromeno[3,4-f]-3-quinolinone (Compound 382); (R/S)-5-(4-Chlorophenyl)-1,2,3,4-tetrahydro-2,2-dimethyl-5H-chromeno[3,4-f]-3-quinolinone (Compound 383); (R/S)-3-(3-Fluorobenzyl)-5-(3-fluorobenzylidene)-1,2,3,4-tetrahydro-3-hydroxy-2,2,4-trimethyl-5H-chromeno[3,4-f]quinoline (Compound 384); (R/S)-3,5-Dibutyl-1,2,3,4-tetrahydro-3-hydroxy-2,2,4-trimethyl-5H-chromeno[3,4-f]quinoline (Compound 385); (R/S)-5-Butyl-1,2,3,4-tetrahydro-2,2,4-trimethyl-5H-chromeno[3,4-f]-3-quinolinone (Compound 386); (R/S-4l,5l)-1,2,3,4-Tetrahydro-2,2,4-trimethyl-5-phenyl-5H-chromeno[3,4-f]-3-quinolinone (Compound 387); (R/S-4l,5u)-1,2,3,4-Tetrahydro-2,2,4-trimethyl-5-phenyl-5H-chromeno[3,4-f]-3-quinolinone (Compound 388); (R/S-4l,6u)-1,2,3,4-Tetrahydro-2,2,4-trimethyl-6-phenyl-5H-isochromeno[3,4-f]-3-quinolinone (Compound 390); (R/S-4l,6l)-1,2,3,4-Tetrahydro-2,2,4-trimethyl-6-phenyl-5H-isochromeno[3,4-f]-3-quinolinone (Compound 391); (R/S-3l,4u,5u)-5-(4-Chlorophenyl)-1,2,3,4-tetrahydro-3-methoxy- 2,2,4-trimethyl-5H-chromeno[3,4-f]quinoline (Compound 397); (R/S-3l,4u,5l)-5-(4-Chlorophenyl)-1,2,3,4-tetrahydro-3-methoxy-2,2,4-trimethyl-5H-chromeno[3,4-f]quinoline (Compound 398); (R/S-3l,4u,5l)-5-(4-Chlorophenyl)-1,2,3,4-tetrahydro-3-propyloxy-2,2,4-trimethyl-5H-chromeno[3,4-f]quinoline (Compound 399); (R/S-3l,4u,5u)-5-(4-Chlorophenyl)-1,2,3,4-tetrahydro-3-propyloxy-2,2,4-trimethyl-5H-chromeno[3,4-f]quinoline (Compound 400); and (R/S-4l,5l)-3-Benzenzylidene-5-(4-chlorophenyl)-1,2,3,4-tetrahydro-2,2,4-trimethyl-5H-chromeno[3,4-f]quinoline (Compound 401).

Representative PR agonists according to the present invention include: (Z)-5-Butylidene-1,2-dihydro-2,2,4-trimethyl-5H-chromeno[3,4-f]quinoline (Compound 219); (Z)-5-Benzylidene-1,2-dihydro-2,2,4-trimethyl-5H-chromeno[3,4-f]quinoline (Compound 220); (Z)-5-(4-Fluorobenzylidene)-1,2-dihydro-2,2,4-trimethyl-5H-chromeno[3,4-f]quinoline (Compound 221); (Z)-5-(4-Bromobenzylidene)-1,2-dihydro-2,2,4-trimethyl-5H-chromeno[3,4-f]quinoline (Compound 222); (Z)-5-(3-Bromobenzylidene)-1,2-dihydro-2,2,4-trimethyl-5H-chromeno[3,4-f]quinoline (Compound 223); (Z)-5-(3-Chlorobenzylidene)-1,2-dihydro-2,2,4-trimethyl-5H-chromeno[3,4-f]quinoline (Compound 224); (Z)-5-(3-Fluorobenzylidene)-1,2-dihydro-2,2,4-trimethyl-5H-chromeno[3,4-f]quinoline (Compound 225); (Z)-5-(2-Chlorobenzylidene)-1,2-dihydro-2,2,4-trimethyl-5H-chromeno[3,4-f]quinoline (Compound 226); (Z)-5-(2-Bromobenzylidene)-1,2-dihydro-2,2,4-trimethyl-5H-chromeno[3,4-f]quinoline (Compound 227); (Z)-5-(2-Fluorobenzylidene)-1,2-dihydro-2,2,4-trimethyl-5H-chromeno[3,4-f]quinoline (Compound 228); (Z)-5-(2,3-Difluorobenzylidene)-1,2-dihydro-2,2,4-trimethyl-5H-chromeno[3,4-f]quinoline (Compound 229); (Z)-5-(2,5-

Difluorobenzylidene)-1,2-dihydro-2,2,4-trimethyl-5H-chromeno[3,4-f]quinoline (Compound 230); (Z)-9-Fluoro-5-(3-fluorobenzylidene)-1,2-dihydro-2,2,4-trimethyl-5H-chromeno[3,4-f]quinoline (Compound 231); (Z)-9-Fluoro-5-(3-methoxybenzylidene)-1,2-dihydro-2,2,4-trimethyl-5H-chromeno[3,4-f]quinoline (Compound 232); (Z)-8-Fluoro-5-(3-fluorobenzylidene)-1,2-dihydro-2,2,4-trimethyl-5H-chromeno[3,4-f]quinoline (Compound 233); (R/S-4l, 5u)-5-(4-Chlorophenyl)-1,2,3,4-tetrahydro-2,2,4-trimethyl-5H-chromeno[3,4-f]-3-quinolinone (Compound 234); (R/S-4l, 5l)-5-(4-Chlorophenyl)-1,2,3,4-tetrahydro-2,2,4-trimethyl-5H-chromeno[3,4-f]-3-quinolinone (Compound 235); and (R/S)-5-(4-Chlorophenyl)-1,2,3,4-tetrahydro-2,2,4,4-tetramethyl-5H-chromeno[3,4-f]-3-quinolinone (Compound 236); 5-(3-Fluorobenzyl)-1,2-dihydro-2,2,4-trimethyl-5H-chromeno[3,4-f]quinoline (Compound 318); (R/S)-9-Chloro-1,2-dihydro-2,2,4-trimethyl-5-propyloxy-5H-chromeno[3,4-f]quinoline (Compound 321); (R/S)-5-Butyl-9-chloro-1,2-dihydro-2,2,4-trimethyl-5H-chromeno[3,4-f]quinoline (Compound 325); (R/S)-5-Butyl-1,2-dihydro-9-methoxy-2,2,4-trimethyl-5H-chromeno[3,4-f]quinoline (Compound 326); (R/S)-9-Fluoro-1,2-dihydro-2,2,4,5-tetramethyl-5H-chromeno[3,4-f]quinoline (Compound 327); (R/S)-9-Chloro-1,2-dihydro-2,2,4,5-tetramethyl-5H-chromeno[3,4-f]quinoline (Compound 332); (R/S)-5-(4-Bromophenyl)-9-chloro-1,2-dihydro-2,2,4-trimethyl-5H-chromeno[3,4-f]quinoline (Compound 333); (R/S)-9-Chloro-5-(3-chlorophenyl)-1,2-dihydro-2,2,4-trimethyl-5H-chromeno[3,4-f]quinoline (Compound 334); (R/S)-9-Chloro-1,2-dihydro-2,2,4-trimethyl-5-(3-methylphenyl)-5H-chromeno[3,4-f]quinoline (Compound 335); (R/S)-9-Chloro-5-(4-chloro-3-methylphenyl)-1,2-dihydro-2,2,4-trimethyl-5H-chromeno[3,4-f]quinoline (Compound 336); (R/S)-9-Chloro-1,2-dihydro-5-[3-(trifluoromethyl)phenyl]-2,2,4-trimethyl-5H-chromeno[3,4-f]quinoline (Compound 337); (R/S)-9-Chloro-5-(3,5-dichlorophenyl)-1,2-dihydro-2,2,4-trimethyl-5H-chromeno[3,4-f]quinoline (Compound 338); (R/S)-9-Chloro-1,2-dihydro-5-(4-methoxyphenyl)-2,2,4-trimethyl-5H-chromeno[3,4-f]quinoline (Compound 339); (R/S)-9-Chloro-5-(3-fluoro-4-methoxyphenyl)-1,2-dihydro-2,2,4-trimethyl-5H-chromeno[3,4-f]quinoline (Compound 340); (R/S)-9-Chloro-5-(4-fluorophenyl)-1,2-dihydro-2,2,4-trimethyl-5H-chromeno[3,4-f]quinoline (Compound 341); (R/S)-9-Chloro-5-(3-chloro-4-methoxy-5-methylphenyl)-1,2-dihydro-2,2,4-trimethyl-5H-chromeno[3,4-f]quinoline (Compound 342); (R/S)-9-Chloro-5-(4-fluoro-3-methylphenyl)-1,2-dihydro-2,2,4-trimethyl-5H-chromeno[3,4-f]quinoline (Compound 343); (R/S)-9-Chloro-5-(3-fluorophenyl)-1,2-dihydro-2,2,4-trimethyl-5H-chromeno[3,4-f]quinoline (Compound 344); (R/S)-1,2-Dihydro-2,2,4-trimethyl-5[(3,4-methylenedioxy)phenyl]-5H-chromeno[3,4]-fquinoline (Compound 345); (R/S)-5-(4-Chloro-3-methylphenyl)-1,2-dihydro-2,2,4-trimethyl-5H-chromeno[3,4]-fquinoline (Compound 346); (R/S)-5-(3,5-Dichlorophenyl)-1,2-dihydro-2,2,4-trimethyl-5H-chromeno[3,4-f]quinoline (Compound 349); (R/S)-5-(3-Bromo-5-methylphenyl)-1,2-dihydro-2,2,4-trimethyl-5H-chromeno[3,4-f]quinoline (Compound 350); (R/S)-5-(3-Bromo-5-fluorophenyl)-1,2-dihydro-2,2,4-trimethyl-5H-chromeno[3,4-f]quinoline (Compound 351); (R/S)-5-[4-Fluoro-3-(trifluoromethyl)phenyl]-1,2-dihydro-2,2,4-trimethyl-5H-chromeno[3,4-f]quinoline (Compound 353); (R/S)-9-Fluoro-1,2-dihydro-2,2,4-trimethyl-5-(3-methylphenyl)-5H-chromeno[3,4-f]quinoline (Compound 354); (R/S)-1,2-Dihydro-9-methoxy-2,2,4-trimethyl-5-(3-methylphenyl)-5H-chromeno[3,4-f]quinoline (Compound 355); (R/S)-9-Fluoro-5-(3-fluoro-4-methoxyphenyl)-1,2-dihydro-2,2,4-trimethyl-5H-chromeno[3,4-f]quinoline (Compound 356); (R/S)-9-Fluoro-1,2-dihydro-2,2,4-trimethyl-5-[3-(trifluoromethyl)phenyl]-5H-chromeno[3,4-f]quinoline (Compound 357); (R/S)-9-Fluoro-5-(4-fluoro-3-methylphenyl)-1,2-dihydro-2,2,4-trimethyl-5H-chromeno[3,4-f]quinoline (Compound 358); (Z)-5-(2,4-Difluorobenzylidene)-1,2-dihydro-2,2,4-trimethyl-5H-chromeno[3,4-f]quinoline (Compound 359); (Z)-5-(3,4-Difluorobenzylidene)-1,2-dihydro-2,2,4-trimethyl-5H-chromeno[3,4-f]quinoline (Compound 360); (Z)-5-(3-Fluorobenzylidene)-1,2,3,4-tetrahydro-2,2,4-trimethyl-5H-chromeno[3,4-f]quinoline (Compound 361); (Z)-5-(2,6-Difluorobenzylidene)-1,2-dihydro-2,2,4-trimethyl-5H-chromeno[3,4-f]quinoline (Compound 362); (Z)-1,2,-Dihydro-5-(2-methylbenzylidene)-2,2,4-trimethyl-5H-chromeno[3,4-f]quinoline (Compound 363); (Z)-9-Chloro-5-(2,5-difluorobenzylidene)-1,2-dihydro-2,2,4-trimethyl-5H-chromeno[3,4-f]quinoline (Compound 365); (Z)-5-Benzylidene-9-chloro-1,2-dihydro-2,2,4-trimethyl-5H-chromeno[3,4-f]quinoline (Compound 366); (Z)-9-Chloro-1,2-dihydro-2,2,4-trimethyl-5-(2-methylbenzylidene)-5H-chromeno[3,4-f]quinoline (Compound 367); (Z)-5-Benzylidene-9-chloro-1,2-dihydro-2,2-dimethyl-5H-chromeno[3,4-f]quinoline (Compound 368); (Z)-9-Chloro-5-(2-fluorobenzylidene)-1,2-dihydro-2,2,4-trimethyl-5H-chromeno[3,4-f]quinoline (Compound 369); (Z)-9-Chloro-5-(3-fluorobenzylidene)-1,2-dihydro-2,2,4-trimethyl-5H-chromeno[3,4-f]quinoline (Compound 370); (E/Z)-5-Benzylidene-9-fluoro-1,2-dihydro-2,2,4-trimethyl-5H-chromeno[3,4-f]quinoline (Compound 371); (Z)-5-Benzylidene-8-fluoro-1,2-dihydro-2,2,4-trimethyl-5H-chromeno[3,4-f]quinoline (Compound 372); (Z)-5-Benzylidene-1,2-dihydro-9-methoxy-2,2,4-trimethyl-5H-chromeno[3,4-f]quinoline (Compound 373); (Z)-9-Fluoro-1,2-dihydro-2,2,4-trimethyl-5-(2-methylbenzylidene)-5H-chromeno[3,4-f]quinoline (Compound 374); (Z)-8-Fluoro-1,2-dihydro-2,2,4-trimethyl-5-(2-methylbenzylidene)-5H-chromeno[3,4-f]quinoline (Compound 375); (Z)-1,2-Dihydro-9-methoxy-2,2,4-trimethyl-5-(2-methylbenzylidene)-5H-chromeno[3,4-f]quinoline (Compound 376); (Z)-(R/S)-5-(3-Fluorobenzylidene)-1,2,3,4-tetrahydro-2,2,4-trimethyl-5H-chromeno[3,4-f]-3-quinolinone (Compound 389); (Z)-(R/S)-5-(Benzylidene)-1,2,3,4-tetrahydro-2,2,4-trimethyl-5H-chromeno[3,4-f]-3-quinolinone (Compound 392); (R/S-4l,5u)-5-(3-Fluorophenyl)-1,2,3,4-tetrahydro-2,2,4-trimethyl-5H-chromeno[3,4-f]-3-quinolinone (Compound 393); (R/S-4l, 5l)-5-(3-Fluorophenyl)-1,2,3,4-tetrahydro-2,2,4-trimethyl-5H-chromeno[3,4-f]-3-quinolinone (Compound 394); (R/S-4l,5l)-1,2,3,4-Tetrahydro-2,2,4-trimethyl-5-[3-(trifluoromethyl)phenyl]-5H-chromeno[3,4-f]-3-quinolinone (Compound 395); (R/S-4l,5u)-1,2,3,4-Tetrahydro-2,2,4-trimethyl-5-[3-(trifluoromethyl)phenyl]-5H-chromeno[3,4-f]-3-quinolinone (Compound 396); (R/S-4l,5u)-5-(4-Chlorophenyl)-1,2,3,4-tetrahydro-2,2,4-trimethyl-5H-chromeno[3,4-f]-3-quinolinone (Compound 402); (R/S-4l,5l)-5-(4-Chlorophenyl)-1,2,3,4-tetrahydro-2,2,4-trimethyl-5H-chromeno[3,4-f]-3-quinolinone (Compound 403); and (R/S)-5-Butyl-1,2-dihydro-2,2,4,9-tetramethyl-5H-chromeno[3,4-f]quinoline (Compound 457).

Representative AR modulator compounds (i.e., agonists and antagonists) according to the present invention include: 1,2-Dihydro-2,2,4-trimethyl-6-methoxymethyl-8-pyranono[5,6-g]quinoline (Compound 237); 1,2-Dihydro-2,2,4-trimethyl-6-trifluoromethyl-8-pyranono[5,6-g]quinoline (Compound 238); 1,2-Dihydro-2,2,4-trimethyl-10- isocoumarino[4,3-g]quinoline (Compound 239); 1,2-Dihydro-2,2,4-trimethyl-10-isoquinolono[4,3-g]quinoline (Compound 240); 1,2-Dihydro-2,2,4,6-tetramethyl-8-pyridono[5,6-g]quinoline (Compound 241); 1,2-Dihydro-10-hydroxy-2,2,4-trimethyl-10H-isochromeno[4,3-g] quinoline (Compound 242); 1,2-Dihydro-2,2,4,6-tetramethyl-8H-pyrano[3,2-g]quinoline (Compound 243); (R/S)-1,2,3,4-Tetrahydro-2,2,4-trimethyl-10-isoquinolono [4,3-g]quinoline (Compound 244); 1,2-Dihydro-2,2,4-trimethyl-10-thioisoquinolono[4,3-g]quinoline (Compound 245); (+)-1,2,3,4-Tetrahydro-2,2,4-trimethyl-10-isoquinolono[4,3-g]quinoline (Compound 246); 1,2-Dihydro-2,2,4-trimethyl-6-trifluoromethyl-8-pyridono[5,6-g]quinoline (Compound 247); (R/S)-1,2,3,4-Tetrahydro-2,2,4-trimethyl-6-trifluoromethyl-8-pyranono[5,6-g]quinoline (Compound 250); 1,2-Dihydro-2,2,4-trimethyl-6-trifluoromethyl-8-thiopyranono[5,6-g]quinoline (Compound 251); (R/S)-1,2,3,4-Tetrahydro-2,2,4-trimethyl-6-trifluoromethyl-8-thiopyranono[5,6-g]quinoline (Compound 252); 6-Chloro(difluoro)methyl-1,2-dihydro-2,2,4-trimethyl-8-pyranono[5,6-g]quinoline (Compound 253); 9-Acetyl-1,2-dihydro-2,2,4-trimethyl-6-trifluoromethyl-8-pyridono[5,6g]quinoline (Compound 254); 1,2-Dihydro-2,2,4,10-tetramethyl-6-trifluoromethyl-8-pyridono[5,6-g]quinoline (Compound 255); 1,2-Dihydro-2,2,4-trimethyl-6-(1,1,2,2,2-pentafluoroethyl)-8-pyranono [5,6-g]quinoline (Compound 256); (R/S)-6-Chloro (difluoro)methyl-1,2,3,4-tetrahydro- 2,2,4-trimethyl-8-pyranono[5,6-g]quinoline (Compound 257); 7-Chloro-1,2-dihydro-2,2,4-trimethyl-6-trifluoromethyl-8-pyranono[5,6-g]quinoline (Compound 258); (R/S)-7-Chloro-1,2,3,4-tetrahydro-2,2,4-trimethyl-6-trifluoromethyl-8-pyranono[5,6-g]quinoline (Compound 259); 1,2,3,4-Tetrahydro-2,2,4-trimethyl-6-trifluoromethyl-8-pyridono[5,6-g]quinoline (Compound 260); 1,2-Dihydro-2,2,4,9-tetramethyl-6-trifluoromethyl-8-pyridono[5,6-g]quinoline (Compound 261); 1,2-Dihydro-2,2,4-trimethyl-8-trifluoromethyl-6-pyridono[5,6-g]quinoline (Compound 262); 6-[Dichloro (ethoxy)methyl]-1,2-dihydro-2,2,4-trimethyl-8-pyranono[5,6-g]quinoline (Compound 263); 5-(3-Furyl)-1,2-dihydro-2,2,4-trimethyl-8-pyranono[5,6-g]quinoline (Compound 264); 1,2-Dihydro-1,2,2,4-tetramethyl-6-trifluoromethyl-8-pyranono[5,6-g]quinoline (Compound 265); 1,2-Dihydro-6-trifluoromethyl-2,2,4-trimethyl-9-thiopyran-8-ono[5,6-g] quinoline (Compound 266); 1,2-Dihydro-1,2,2,4,9-pentamethyl-6-trifluoromethyl-8-pyridono[5,6-g]quinoline (Compound 267); 7-Chloro-1,2-dihydro-2,2,4-trimethyl-6-trifluoromethyl-8-pyridono[5,6-g]quinoline (Compound 268); and 6-Chloro(difluoro)methyl-1,2-dihydro-2,2,4-trimethyl-8-pyridono[5,6-g]quinoline (Compound 269); (R/S)-1,2,3,4-Tetrahydro-1,2,2,4-tetramethyl-6-trifluoromethyl-8-pyranono[5,6-g]quinoline (Compound 404); (R/S)-5-(3-Furyl)-1,2,3,4-tetrahydro-2,2,4-trimethyl-8-pyranono[5,6-g]quinoline (Compound 405); 5-(3-Furyl)-1,2-dihydro-1,2,2,4-tetramethyl-8-pyranono[5,6-g] quinoline (Compound 406); 5-(3-Furyl)-1,2-dihydro-1,2,2,4-tetramethyl-8-thiopyranono[5,6-g]quinoline (Compound 407); 6-Chloro-5-(3-furyl)-1,2-dihydro-1,2,2,4-tetramethyl-8-pyranono[5,6-g]quinoline (Compound 408); 1,2,3,4-Tetrahydro-2,2,4,10-tetramethyl-6-trifluoromethyl-8-pyridono[5,6-g]quinoline (Compound 409); (R/S)-1,2,3,4-Tetrahydro-4-methyl-6-trifluoromethyl-8-pyranono[5,6-g] quinoline (Compound 410); 1,2-Dihydro-2,2-dimethyl-6-trifluoromethyl-8-pyranono[5,6-g]quinoline (Compound 411); 1,2,3,4-Tetrahydro-2,2-dimethyl-6-trifluoromethyl-8-pyranono[5,6-g]quinoline (Compound 412); 1,2,3,4-Tetrahydro-6-trifluoromethyl-8-pyranono[5,6-g]quinoline (Compound 413); (R/S)-4-Ethyl-1,2,3,4-tetrahydro-6-trifluoromethyl-8-pyranono[5,6-g]quinoline (Compound 414); (R/S)-1,2,3,4-Tetrahydro-1,4-dimethyl-8-pyranono[5,6-g]quinoline (Compound 415); (R/S)-4-Ethyl-1,2,3,4-tetrahydro-1-methyl-8-pyranono[5,6-g]quinoline (Compound 416); 2,2-Dimethyl-1,2,3,4-tetrahydro-6-trifluoromethyl-8-pyridono[5,6-f]quinoline (Compound 417); (R/S)-1,2,3,4-tetrahydro-6-trifluoromethyl-2,2,4-trimethyl-8-pyridono[5,6-f]-3-quinolinone (Compound 418); 5-Trifluoromethyl-7-pyridono[5,6-e]indoline (Compound 419); 8-(4-Chlorobenzoyl)-5-trifluoromethyl-7-pyridono[5,6-e]indoline (Compound 420); 7-tert-Butyloxycarbamoyl-1,2-dihydro-2,2,8-trimethylquinoline (Compound 421); 1,2,3,4-Tetrahydro-6-trifluoromethyl-8-pyridono[5,6-f]quinoline (Compound 422); 1,2-Dihydro-6-trifluoromethyl-1,2,2,4-tetramethyl-8-pyridono[5,6-f] quinoline (Compound 423); 3,3-Dimethyl-5-trifluoromethyl-7-pyridono[5,6-e]indoline (Compound 424); (R/S)-1,2,3,4-Tetrahydro-4-methyl-6-(trifluoromethyl)-8-pyridono[5,6-g]quinoline (Compound 425); (R/S)-1,2,3,4-Tetrahydro-4-methyl-6-(trifluoromethyl)-8-pyridono[5,6-g]quinoline (Compound 426); 1,2,2,-Trimethyl-1,2,3,4-tetrahydro-6-trifluoromethyl-8-pyranono[5,6-g]quinoline (Compound 427); (R/S)-1,2,3,4-Tetrahydro- 4-propyl-6-trifluoromethyl-8-pyranono[5,6-g]quinoline (Compound 428); 1,2,3,4-Tetrahydro-2,2,4-trimethyl-6-trifluoromethyl-9-thiopyran-8-ono[5,6-g] quinoline (Compound 429); 1,2-Dihydro-1,2,2,4-tetramethyl-6-trifluoromethyl-9-thiopyran-8-ono[5,6-g] quinoline (Compound 430); 1,2,3,4-Tetrahydro-1,2,2-trimethyl-6-trifluoromethyl-8-pyridono[5,6-g]quinoline (Compound 431); 1,2,3,4-Tetrahydro-1-methyl-4-propyl-6-trifluoromethyl-8-pyranono[5,6-g]quinoline (Compound 432); 1,2,3,4-Tetrahydro-10-hydroxymethyl-2,2,4-trimethyl-6-trifluoromethyl-8-pyridono[5,6-g]quinoline (Compound 433); 1,2,3,4-Tetrahydro-1,2,2,4-tetramethyl-6-trifluoromethyl-9-thiopyran-8-ono[5,6-g]quinoline (Compound 434); 1,2,3,4-Tetrahydro-2,2,9-trimethyl-6-trifluoromethyl-8-pyridono[5,6-g]quinoline (Compound 435); (R/S)-1,2,3,4-Tetrahydro-3-methyl-6-trifluoromethyl-8-pyridono[5,6-g]quinoline (Compound 436); 1,2,3,4-Tetrahydro-3,3-dimethyl-6-trifluoromethyl-8-pyridono[5,6-g]quinoline (Compound 437); (R/S) 1,2,3,4-Tetrahydro-2,2,3-trimethyl-6-trifluoromethyl-8-pyridono[5,6-g]quinoline (Compound 438); (R/S-2l,4u)-1,2,3,4-Tetrahydro-2,4-dimethyl-6-trifluoromethyl-8-pyridono[5,6-g]quinoline (Compound 439); (R/S-2l,4u)-4-Ethyl-1,2,3,4-tetrahydro-2-methyl-6-trifluoromethyl-8-pyranono[5,6-g]quinoline (Compound 440); (R/S-2l,3u)-1,2,3,4-Tetrahydro-2,3-dimethyl-6-trifluoromethyl-8-pyridono[5,6-g]quinoline (Compound 441); (R/S-2l,3l)-1,2,3,4-Tetrahydro-2,3-dimethyl-6-trifluoromethyl-8-pyridono[5,6-g]quinoline (Compound 442); (R/S)-1,2,3,4-Tetrahydro-2,3,3-trimethyl-6-trifluoromethyl-8-pyridono[5,6-g]quinoline (Compound 443); (R/S)-1,2,3,4-Tetrahydro-2-methyl-6-trifluoromethyl-8-pyridono[5,6-g]quinoline (Compound 444); (R/S)-4-Ethyl-1,2,3,4-tetrahydro-6-trifluoromethyl-8-pyridono[5,6-g]quinoline (Compound 445); (R/S-2l,3u)-1,2,3,4-Tetrahydro-2,3,9-trimethyl-6-trifluoromethyl-8-pyridono[5,6-g]quinoline (Compound 446); (R/S)-1,2,3,4-Tetrahydro-4-propyl-6-trifluoromethyl-8-pyridono[5,6-g]quinoline (Compound 447); (R/S)-3-Ethyl-1,2,3,4-tetrahydro-2,2-dimethyl-6-trifluoromethyl-8-pyridono[5,6-g]quinoline (Compound 448); (R/S)-1,2,3,4-Tetrahydro-2,2-dimethyl-6-trifluoromethyl-3-propyl-8-pyridono[5,6-g]quinoline (Compound 449); and 1-Methyl-5-trifluoromethyl-7-pyridono[5,6-f]indoline (Compound 450).

Compounds of the present invention, comprising classes of quinoline compounds and their derivatives, that can be obtained by routine chemical synthesis by those skilled in the art, e.g., by modification of the quinoline compounds disclosed or by a total synthesis approach.

The sequence of steps for several general schemes to synthesize the compounds of the present invention are shown below. In each of the Schemes the R groups (e.g., $R^1$, $R^2$, etc . . . ) correspond to the specific substitution patterns noted in the Examples. However, it will be understood by those skilled in the art that other functionalities disclosed herein at the indicated positions of compounds of formulas I through XVIII also comprise potential substituents for the analogous positions on the structures within the Schemes.

Scheme I

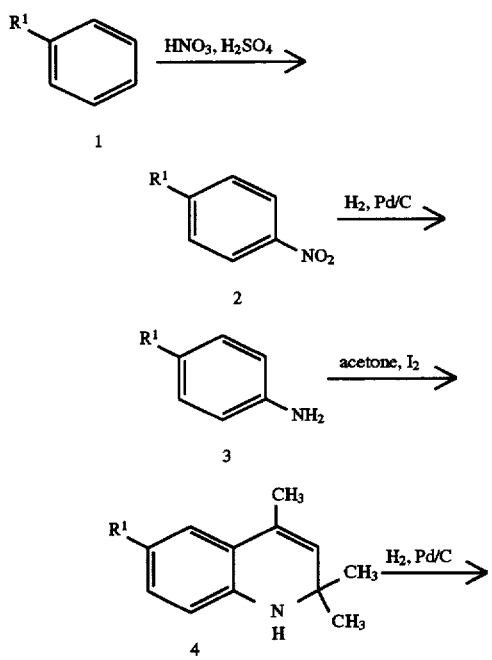

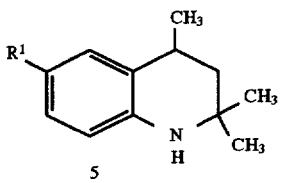

The process of Scheme I begins with the nitration of an arene (structure 1) with, for example, nitric acid in combination with sulfuric acid. The nitro compound (structure 2) is then reduced to the corresponding aniline (structure 3) with, for example, hydrogen over a metal catalyst such as palladium on carbon. The aniline is converted to a 1,2-dihydro-2,2,4-trimethylquinoline (structure 4) by treatment with acetone and a catalyst in a process known as the Skraup reaction. See R. H. F. Manske and M. Kulka, "The Skraup Synthesis of Quinolines", *Organic Reactions* 1953, 7, 59, the disclosure of which is herein incorporated by reference. The catalyst may be an acid, such as p-toluenesulfonic acid, hydrochloric acid, sulfuric acid, or trifluoroacetic acid, or preferably the catalyst may be iodine. The dihydroquinoline may be reduced with, for example, hydrogen catalyzed by a metal catalyst such as palladium on carbon, to afford a 1,2,3,4-tetrahydro-2,2,4-trimethylquinoline (structure 5). Note that many nitro compounds (structure 2) and anilines (structure 3) are commercially available, and the synthesis of compound of structure 4 would thus start with the commercially available material.

Scheme II

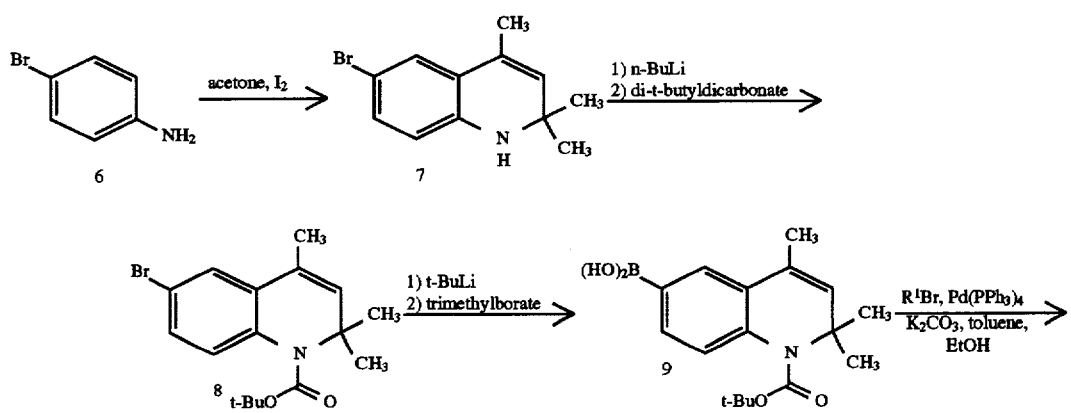

-continued
Scheme II

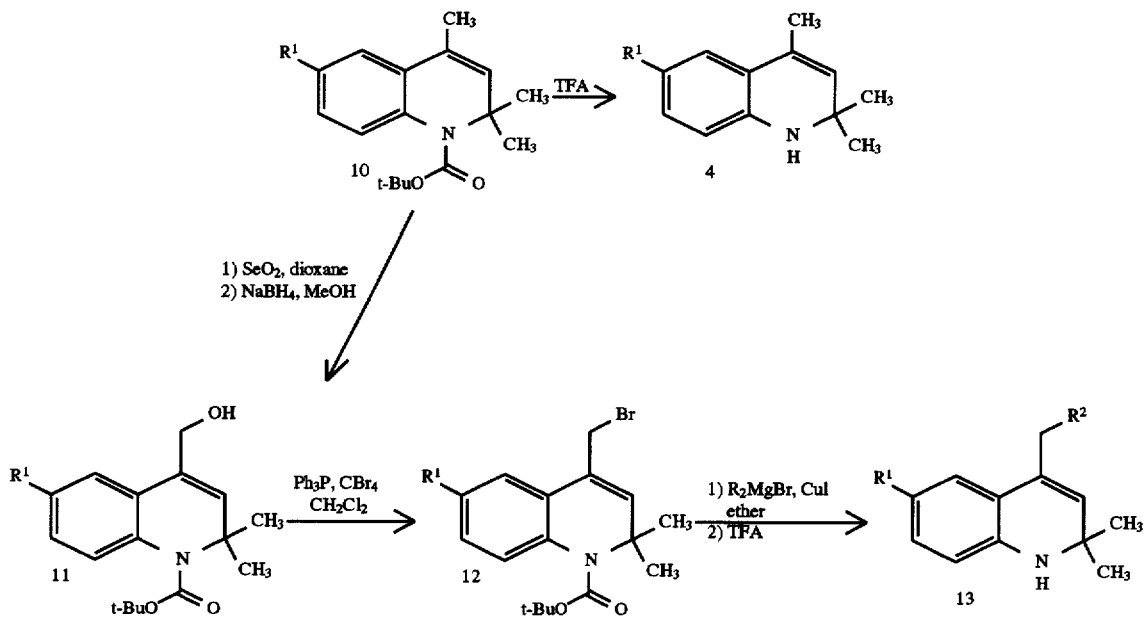

The process of Scheme II begins with the conversion of 4-bromoaniline (Compound 6) to 6-bromo-1,2-dihydro-2,2, 4-trimethylquinoline (Compound 7) by treatment with acetone and a catalyst as described above (the Skraup reaction). The aniline nitrogen is then protected. For example, protection as the t-butyl carbamate requires deprotonation with a strong base, for example, n-butyllithium, followed by reaction with di-t-butyldicarbonate to afford the protected quinoline (Compound 8). The bromine of Compound 8 is then replaced with lithium by a lithium-halogen exchange reaction with an alkyllithium, for example, t-butyllithium. The organolithium intermediate is then allowed to react with a trialkylborate such as trimethylborate to afford, after mild acid hydrolysis, the boronic acid (Compound 9). Treatment of Compound 9 with an aryl, heteroaryl, or vinylbromide compound in the presence of a catalytic amount of a palladium species, for example, tetrakis(triphenylphosphine) palladium, and aqueous base affords a 6-substituted quinoline (structure 10), via a so-called Suzuki crossed-coupling. See A. Suzuki, "Synthetic Studies via the Cross-Coupling Reaction of Organoboron Derivatives with Organic Halides", Pure Appl. Chem. 1991, 63, 419, the disclosure of which is herein incorporated by reference. Deprotection of a compound of structure 10 with acid, for example, trifluoroacetic acid affords the 6-substituted-1,2-dihydro-2,2,4-trimethylquinoline (structure 4).

Alternatively, the C(4) methyl group of a compound of structure 10 may be oxidized with, for example, selenium dioxide to afford the 4-(hydroxymethyl)quinoline (structure 11), which may in turn be converted to the corresponding bromo compound (structure 12), for example with triphenylphosphine and carbon tetrachloride. The bromine atom of a compound of structure 12 may be replaced with an alkyl, aryl, or heteroaryl group by treatment with the corresponding organomagnesium compound in the presence of a copper salt such as copper(I) iodide. Removal of the protecting group with acid, for example, trifluoroacetic acid affords the 4,6-disubstituted-1,2-dihydro-2,2,-dimethylquinoline (structure 13).

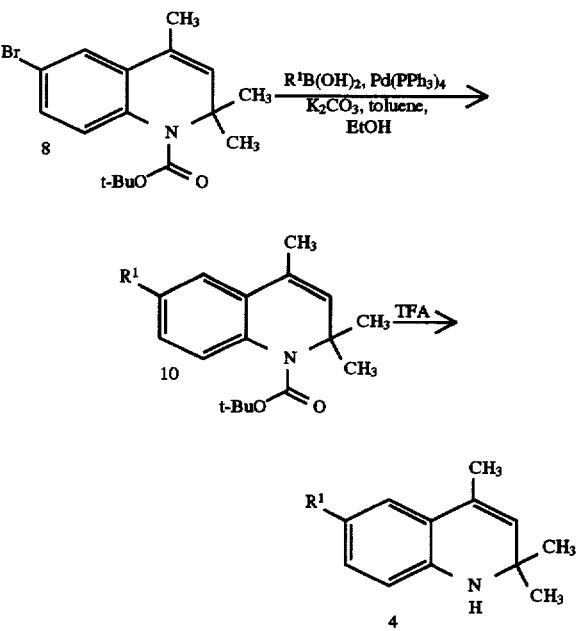

Scheme III

The process of Scheme III involves the direct coupling of Compound 8 with an organoboron species, for example phenylboronic acid, in the presence of a palladium catalyst such as tetrakis(triphenylphosphine)palladium and a base such as potassium carbonate. The coupled product (structure 10) is then deprotected with acid, for example, trifluoroacetic acid, to afford the dihydroquinoline 4.

Scheme IV

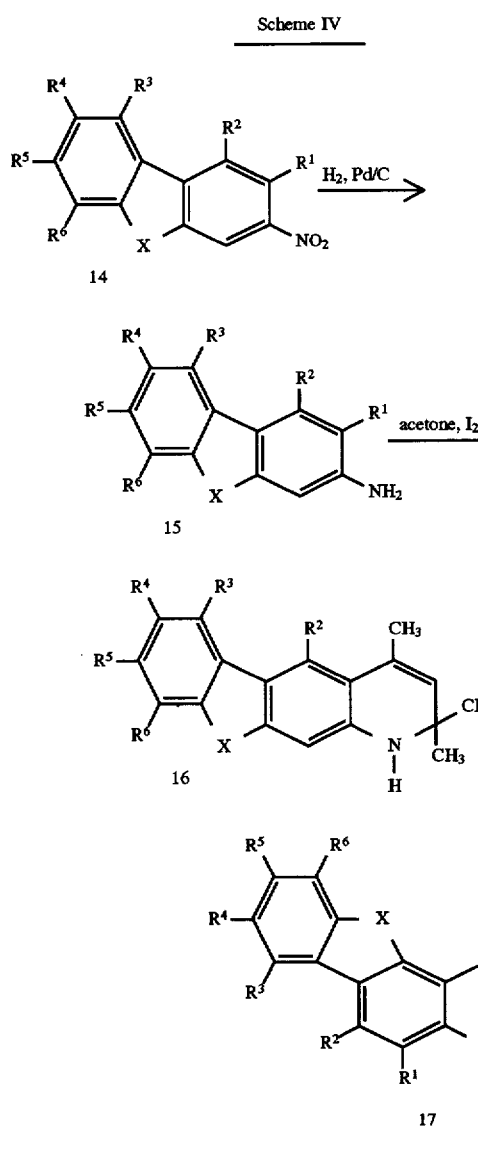

The process of Scheme IV begins with a polycyclic aromatic nitro compound (structure 14) and is similar to the conversion of compounds of structure 2 to compounds of structure 4 (Scheme I). Thus, reduction of the nitro group with, for example, hydrogen over a metal catalyst such as palladium on carbon, followed by cyclization with acetone in the presence of a catalyst such as iodine affords two regioisomeric dihydroquinolines (structures 16 and 17).

Scheme V

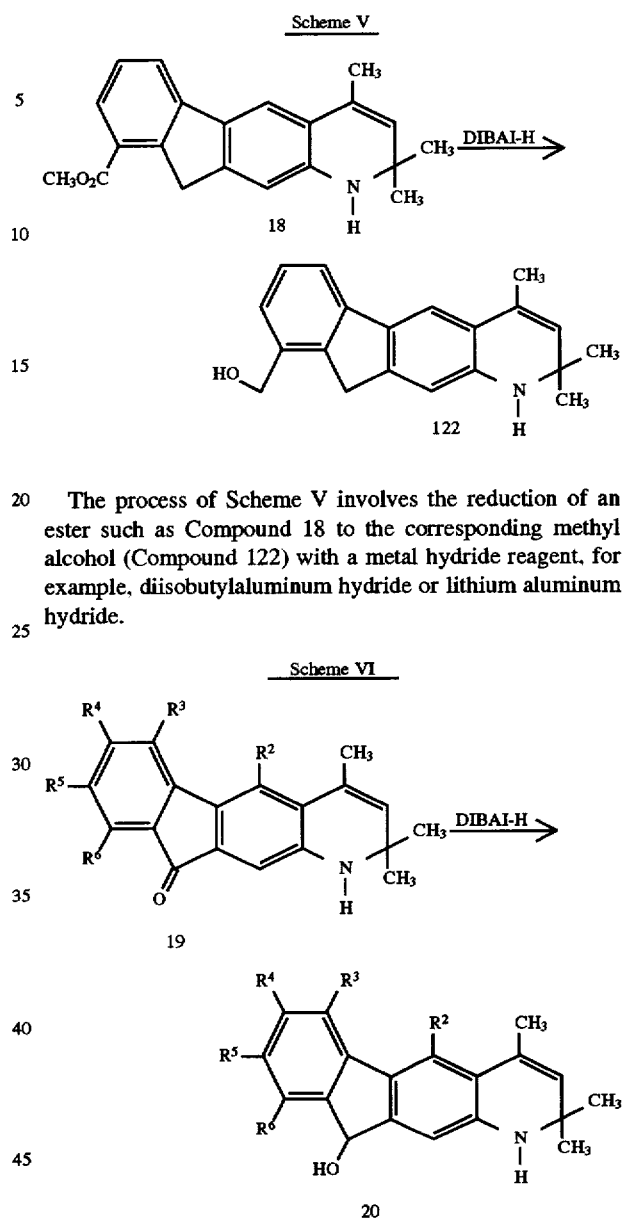

The process of Scheme V involves the reduction of an ester such as Compound 18 to the corresponding methyl alcohol (Compound 122) with a metal hydride reagent, for example, diisobutylaluminum hydride or lithium aluminum hydride.

The process of Scheme VI involves the reduction of the fluorenone (structure 19) to a fluorenol (structure 20) with a reducing agent, for example a metal hydride such as diisobutylaluminum hydride, sodium borohydride, or lithium aluminum hydride.

Scheme VII

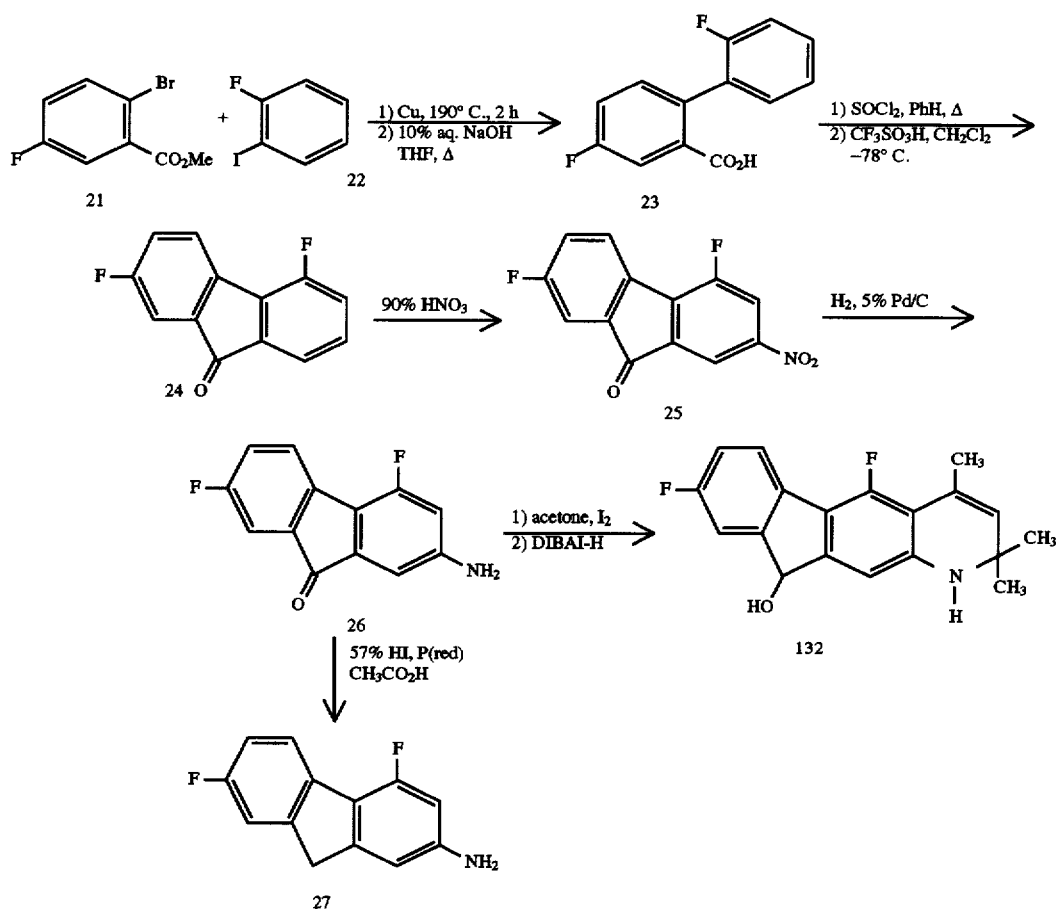

The process of Scheme VII involves the preparation of a fluorene from acyclic precursors. The process of Scheme VII begins with the copper-mediated coupling of methyl-2-bromo-5-fluorobenzoate (Compound 21) with 2-fluoroiodobenzene (Compound 22) with, for example, copper powder at elevated temperatures, a process known as an Ullman coupling reaction. See M. Sainsbury, "Modem Methods of Aryl-Aryl Bond Formation", Tetrahedron 1980, 36, 3327, the disclosure of which is herein incorporated by reference. Hydrolysis of the methyl ester with base, for example, potassium hydroxide, affords the corresponding 2-biphenylcarboxylic acid (Compound 23). Intramolecular Freidel-Crafts acylation of the corresponding mixed anhydride, prepared by treatment of Compound 23 with, for example, thionyl chloride followed by a strong acid such as trifluoromethanesulfonic acid (See B. Hulin and M. Koreeda, "A Convenient, Mild Method for the Cyclization of 3- and 4-Arylalkanoic Acids via Their Trifluoromethane-sulfonic Anhydride Derivatives", J. Org. Chem. 1984, 49, 207, the disclosure of which is herein incorporated by reference), affords 2,5-difluorofluorenone (Compound 24). Nitration of Compound 24 with, for example, concentrated nitric acid affords 4,7-difluoro-2-nitrofluorenone (Compound 25). Reduction of Compound 25 with, for example, hydrogen over a metal catalyst such as palladium on carbon, affords the corresponding aniline (Compound 26). Conversion to the dihydroquinoline with acetone and a catalyst such as iodine, followed by reduction of the ketone with a reducing agent such as diisobutylaluminum hydride, affords Compound 132.

Alternatively, the ketone functionality of Compound 26 may be exhaustively reduced to the methylene compound (Compound 27) with, for example, hydroiodic acid, red phosphorous, and acetic acid. See M. J. Namkung, T. L. Fletcher and W. H. Wetzel, "Derivatives of Fluorene. XX. Fluorofluorenes. V. New Difluoro-2-acetamidofluorenes for the Study of Carcinogenic Mechanisms", J. Med. Chem. 1965, 8, 551, the disclosure of which is herein incorporated by reference.

Scheme VIII

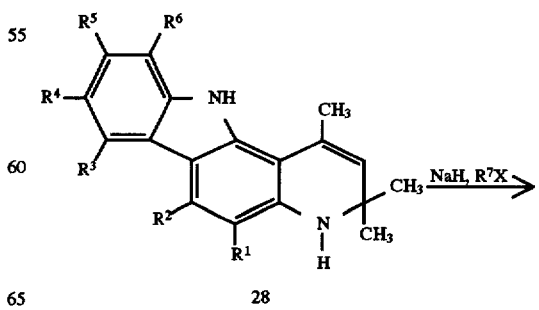

-continued
Scheme VIII

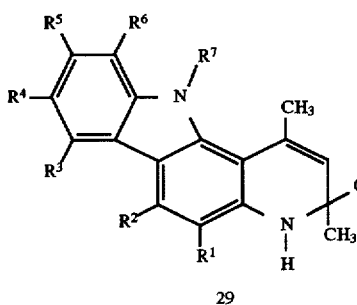

29

The process of Scheme VIII involves the alkylation of N(5) of an indolo[2,3-f]quinoline (structure 28) by deprotonation with a strong base, for example, sodium hydride, followed by alkylation with an alkylating agent such as iodomethane.

The process of Scheme IX begins with the nitration of 2-biphenylcarboxylic acid with, for example, concentrated nitric acid, to afford a mixture of nitro compounds, including 4,2'-dinitro-2-biphenylcarboxylic acid. The crude material is heated to 150°–170° C. in a high-boiling solvent such as dimethylacetamide to effect cyclization of 4,2'-dinitro-2-biphenylcarboxylic acid to the corresponding benzocoumarin. See G. I. Migachev, "Investigations in the Series of Ortho-Substituted Bi-phenyls. I. Nitration of 2-Biphenylcarboxylic Acid and the Chemical Properties of its Nitro Derivatives", Zh. Organich. Khim. 1979, 15, 567, the disclosure of which is herein incorporated by reference. Reduction of the nitro group with, for example, hydrogen over a metal catalyst, affords Compound 31. Treatment of Compound 31 with acetone in the presence of a catalyst, for example, iodine, affords Compound 159. The addition of an organometallic reagent, such as an organolithium or organomagnesium reagent, to Compound 159, affords an intermediate which may be reduced by a trialkylsilane, such as triethylsilane, in the presence of a strong protic acid such as trifluoroacetic acid or a Lewis acid such as boron trifluoride. One or both of two regioisomeric products, structures 32 and 33, are thus obtained.

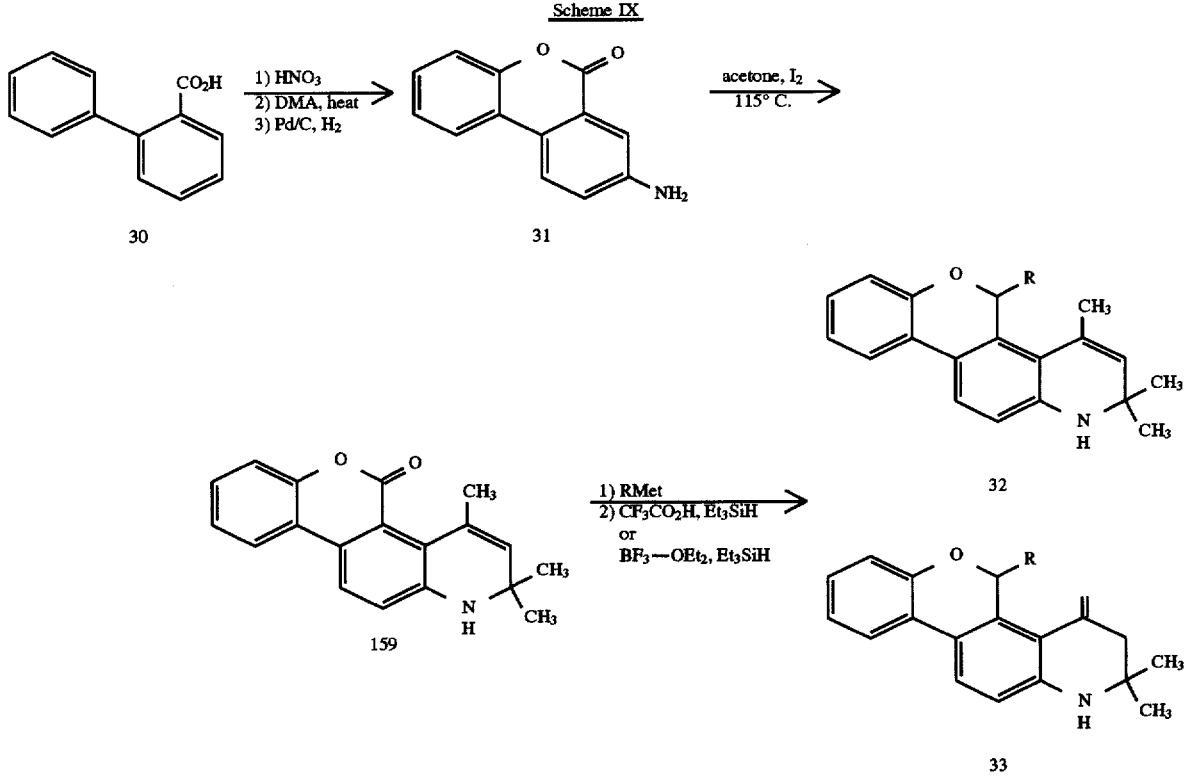

Scheme X

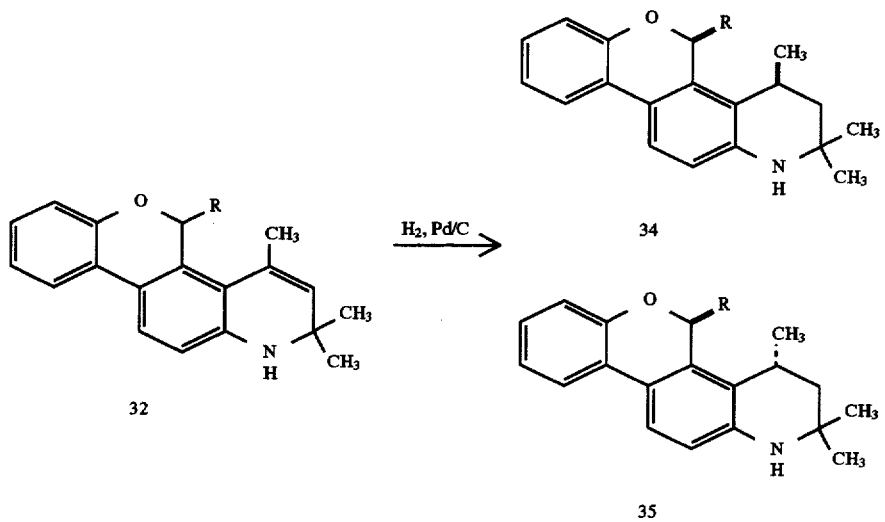

The process of Scheme X involves the reduction of a dihydroquinoline (structure 32) to a mixture of two diastereomeric 1,2,3,4-tetrahydroquinolines (structures 34 and 35) with, for example, hydrogen over a metal catalyst such as palladium on carbon.

Scheme XI

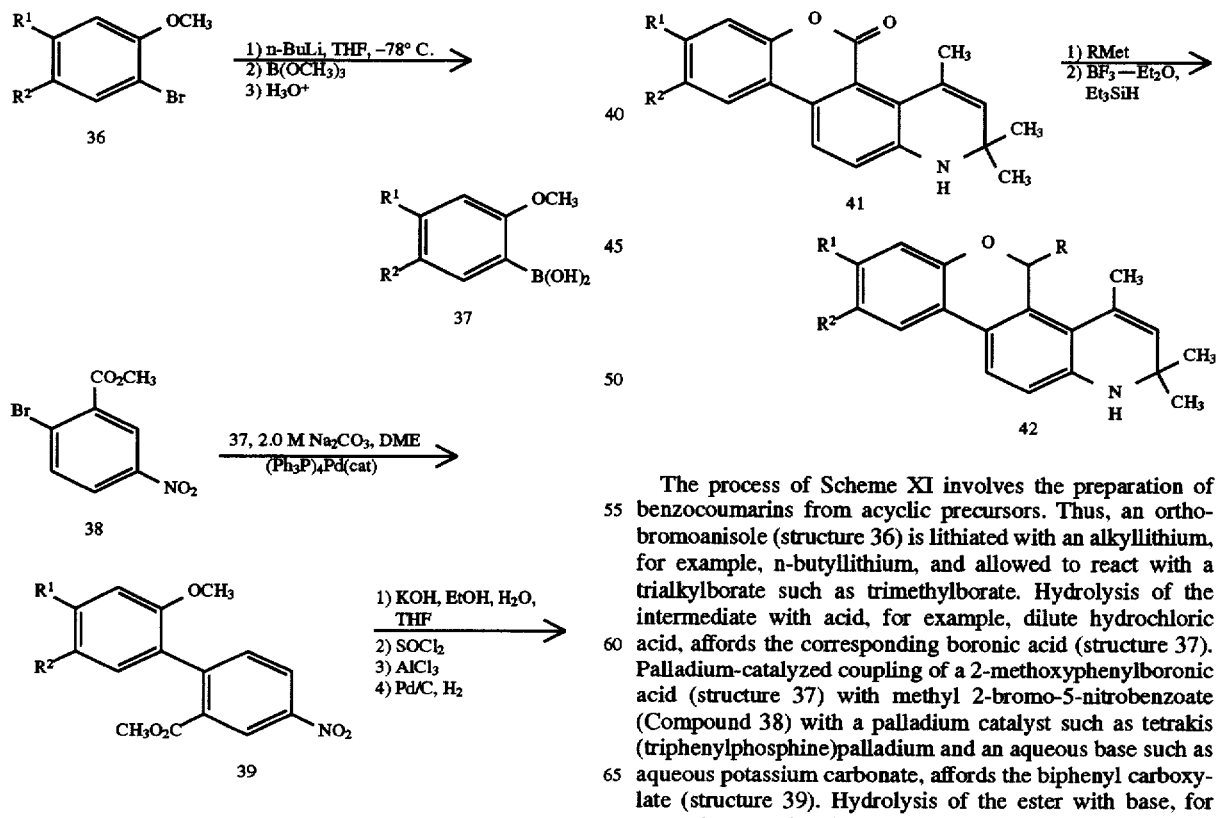

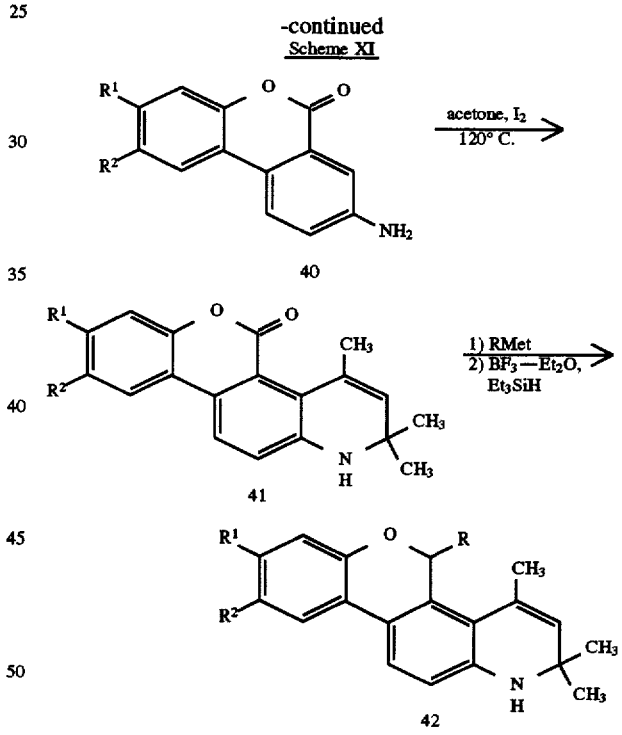

The process of Scheme XI involves the preparation of benzocoumarins from acyclic precursors. Thus, an ortho-bromoanisole (structure 36) is lithiated with an alkyllithium, for example, n-butyllithium, and allowed to react with a trialkylborate such as trimethylborate. Hydrolysis of the intermediate with acid, for example, dilute hydrochloric acid, affords the corresponding boronic acid (structure 37). Palladium-catalyzed coupling of a 2-methoxyphenylboronic acid (structure 37) with methyl 2-bromo-5-nitrobenzoate (Compound 38) with a palladium catalyst such as tetrakis(triphenylphosphine)palladium and an aqueous base such as aqueous potassium carbonate, affords the biphenyl carboxylate (structure 39). Hydrolysis of the ester with base, for example, potassium hydroxide, is followed by conversion of the acid to the acid chloride with, for example, thionyl chloride. Intramolecular acylation is then effected by a Lewis acid such as aluminum trichloride. Reduction of the nitro group with, for example, hydrogen over a metal catalyst, affords the desired aniline (structure 40). Treatment of compounds of structure 40 with acetone and a catalyst such as iodine affords the dihydroquinoline (structure 41). The addition of an organometallic reagent, for example an organolithium or organomagnesium reagent, to a compound of structure 41, followed by treatment of the intermediate with a strong protic or Lewis acid and a trialkylsilane, for example, boron trifluoride and triethylsilane, affords a compound of structure 42.

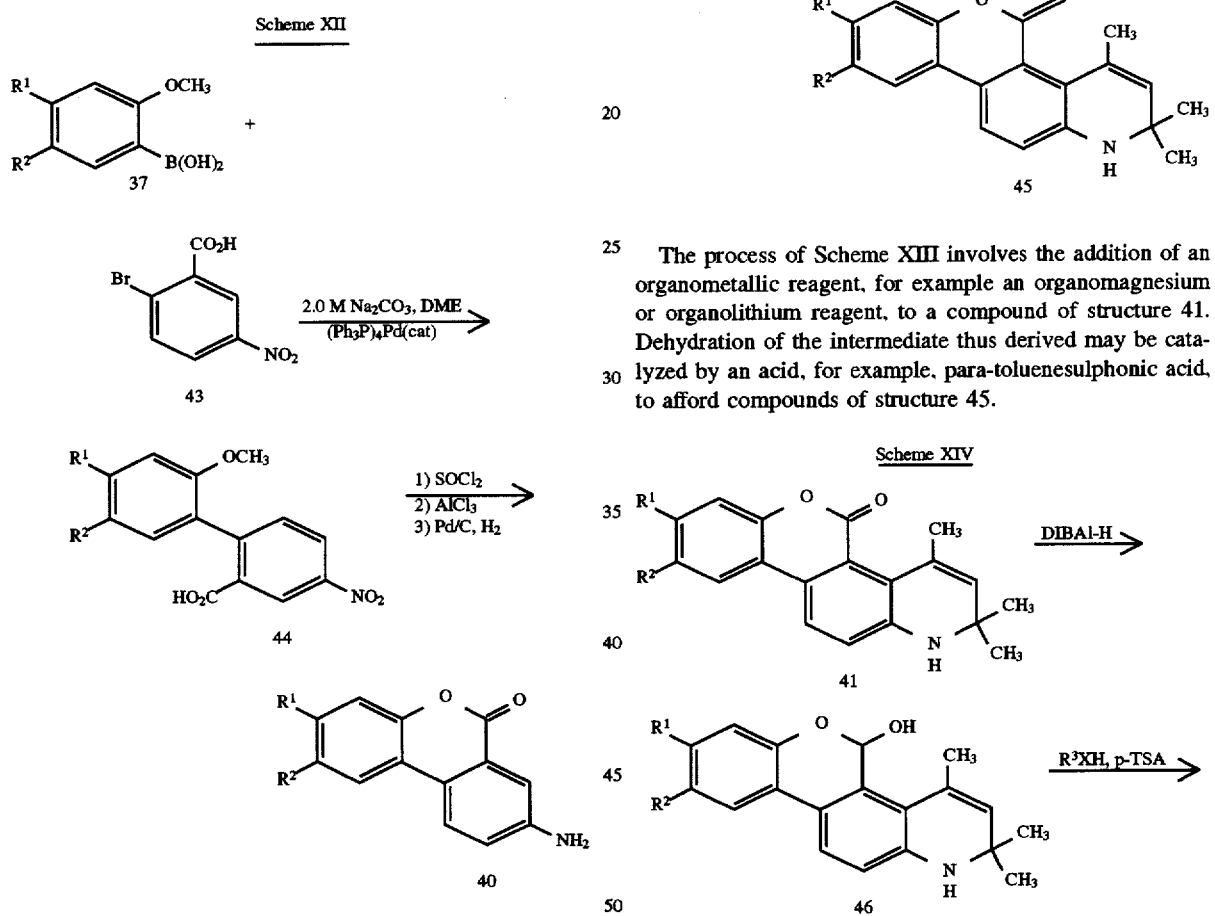

Scheme XII

Scheme XIII

The process of Scheme XIII involves the addition of an organometallic reagent, for example an organomagnesium or organolithium reagent, to a compound of structure 41. Dehydration of the intermediate thus derived may be catalyzed by an acid, for example, para-toluenesulphonic acid, to afford compounds of structure 45.

Scheme XIV

The process of Scheme XII is an alternative synthesis of compounds of structure 40. Thus, direct coupling of a 2-methoxyphenylboronic acid (structure 37) with 2-bromo-5-nitrobenzoic acid (Compound 43) affords the biphenyl-carboxylic acid (structure 44). Treatment of a compound of structure 44 with, for example, thionyl chloride, followed by the addition of a Lewis acid, for example aluminum trichloride, and reduction with, for example hydrogen over palladium on carbon, affords compounds of structure 40. Compounds of structure 40 may be converted to compounds of structure 42 as described in Scheme XI.

-continued
Scheme XIV

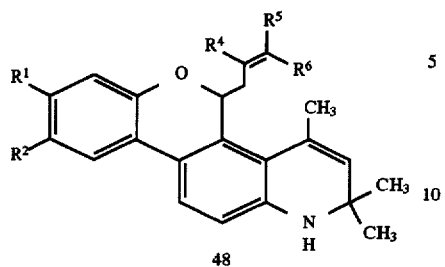

The process of Scheme XIV involves the reduction of a compound of structure 41 with a metal hydride, for example, diisobutylaluminum hydride, to afford a compound of structure 46. Treatment of a compound of structure 46 with an alcohol such as methanol or a thiol such as propanethiol in the presence of an acid such as para-toluenesulphonic acid affords a compound of structure 47 (X=O or S). Treatment of a ketal of structure 47 (X=O) with an allyl silane and a Lewis acid such as trimethylsilyl trifluoromethanesulfonate affords a compound of structure 48.

The process of Scheme XV begins with the protection of the nitrogen atom of a compound of structure 42, which involves deprotonation with a strong base, for example, n-butyllithium, followed by reaction with an anhydride, for example, di-tert-butyl dicarbonate. Hydroboration of a compound of structure 49 with a borane species, for example, borane-tetrahydrofuran, followed by an oxidative work-up using, for example, basic hydrogen peroxide, affords a mixture of two diastereomeric 3-hydroxyltetrahydroquinolines (structures 50 and 51). Separation of the isomers followed by oxidation with typical oxidant, for example, pyridinium chlorochromate, and deprotection with a strong acid, for example, trifluoroacetic acid, affords compounds of structures 52 and 53.

Alternatively, a compound of structure 50 or 51 may be oxidized with, for example, pyridinium chlorochromate, deprotonated at the C(4) position with a strong base such as sodium hydride, and alkylated with an alkylating agent such as iodomethane. Deprotection with strong acid, for example, trifluoroacetic acid then affords a compound of structure 54.

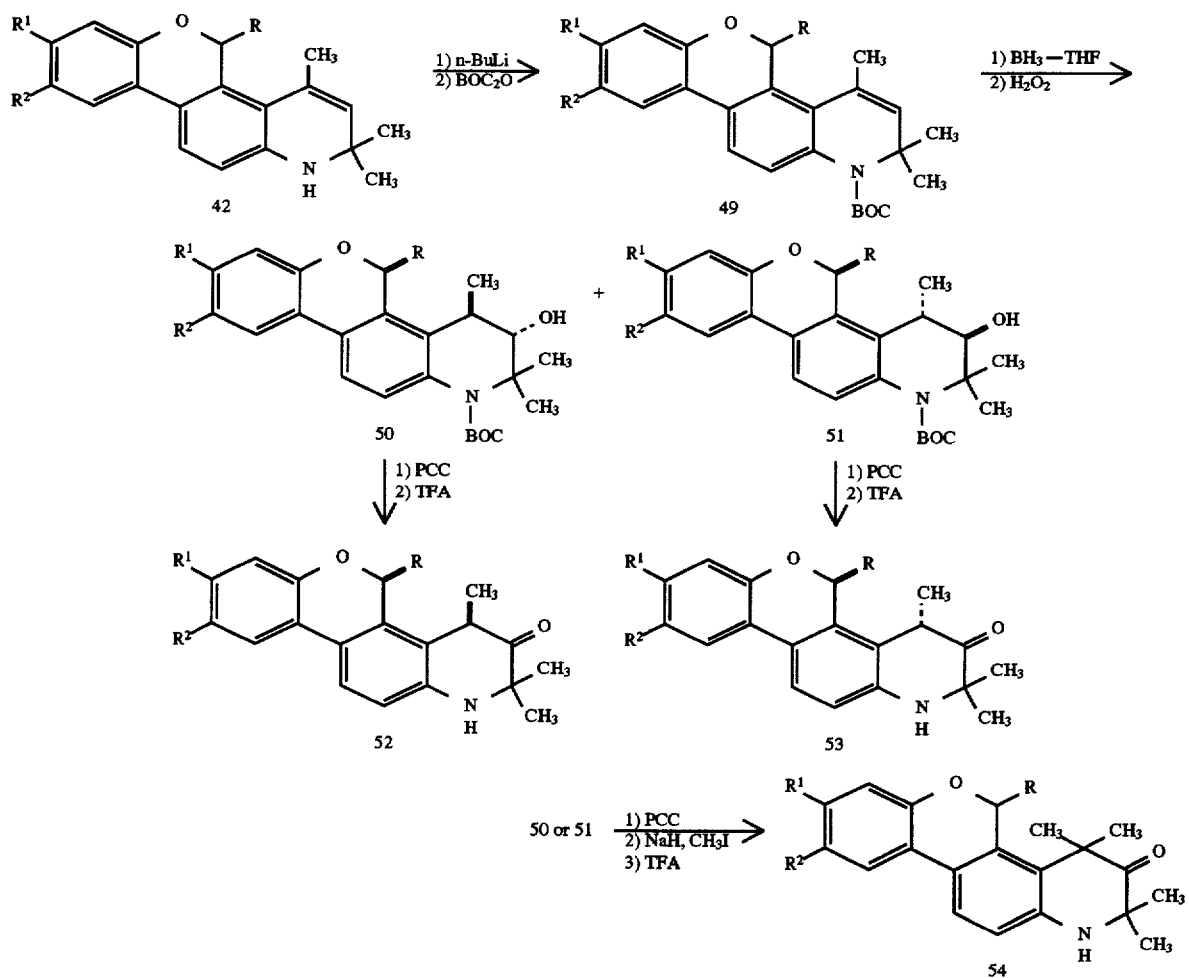

Scheme XVI

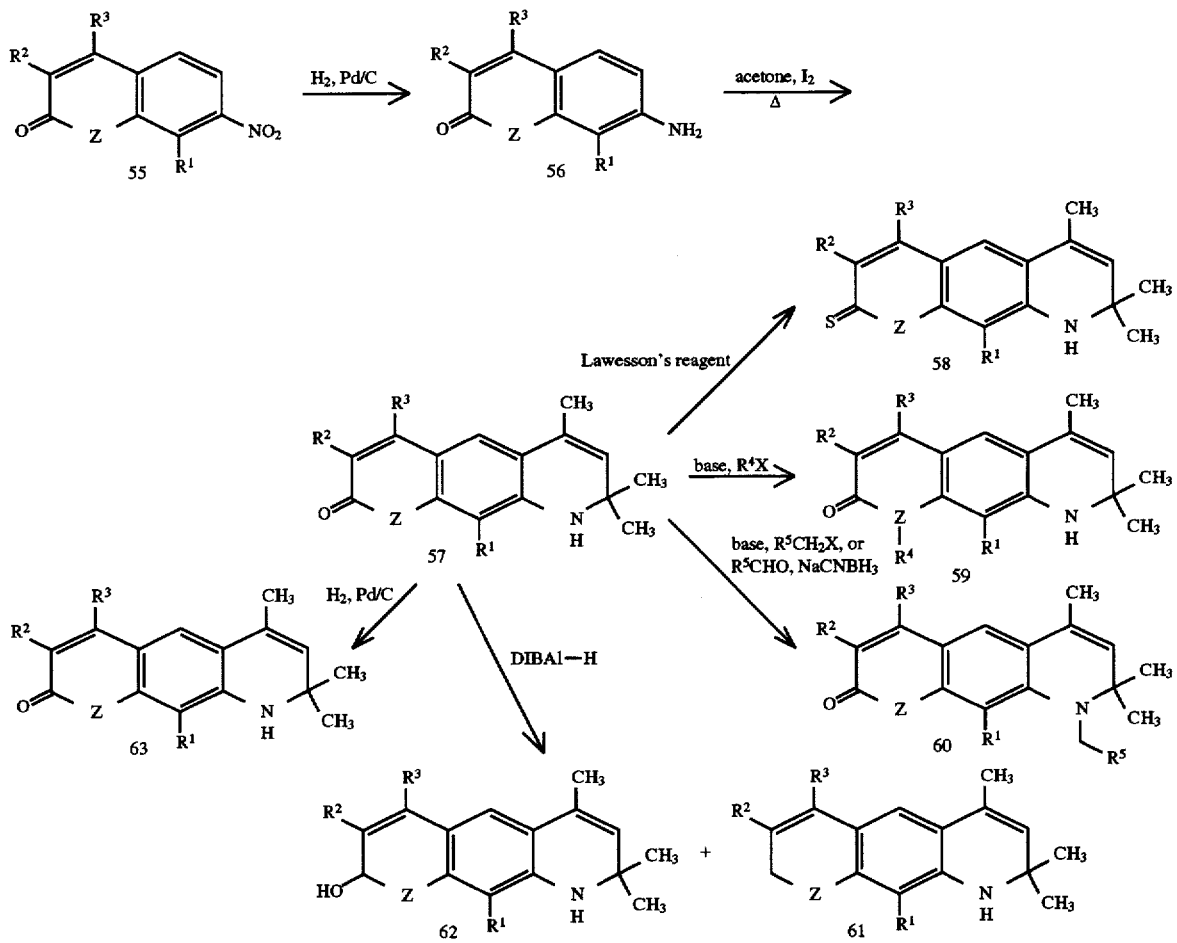

The process of Scheme XVI begins with the reduction of a nitro aromatic compound of structure 55 with, for example, hydrogen over a metal catalyst such as palladium on carbon. Treatment of an aniline of structure 56 with acetone and a catalyst such as iodine affords a compound of structure 57. A compound of structure 57 may be converted to the corresponding thio-compound (structure 58) by treatment with Lawesson's reagent [2,4-bis(4-methoxyphenyl)-1,3-dithia-2,4-diphosphetane-2,4-disulfide]. See B. S. Pedersen, S. Scheibye, K. Clausen and S. O. Lawesson, "Studies on Organophosphorus Compounds. XXII. The Dimer of p-Methoxyphenylthionophosphine sulfide as Thiation Reagent. A New Route to O-Substituted Thioesters and Dithioesters", Bull Soc. Chim. Belg. 1978, 87, 293, the disclosure of which is herein incorporated by reference.

Alternatively, N(9) of a compound of structure 57 (Y=N) may be alkylated by deprotonation with a strong base, for example, sodium hydride, followed by alkylation with an alkylating agent such as iodomethane.

Alternatively, N(1) of a compound of structure 57 (Y=O) may be alkylated by deprotonation with a strong base, for example, sodium hydride, followed by alkylation with an alkylating agent, for example, iodomethane, to afford a compound of structure 60. In addition, N(1) of a compound of structure 57 (Y=O) may be alkylated by treatment with an aldehyde or paraformaldehyde in the presence of sodium cyanoborohydride and acetic acid. See R. O. Hutchins and N. R. Natale, "Cyanoborohydride. Utility and Applications in Organic Synthesis. A Review", Org. Prep. Proced. Int. 1979, 11, 201, the disclosure of which is herein incorporated by reference.

Alternatively, the C(8) ester group of a compound of structure 57 (Y=O) may be reduced with a metal hydride, for example, diisobutylaluminum hydride, to afford one or both of two compounds (structures 61 and 62).

Alternatively, the C(3)–C(4) olefin of a compound of structure 57 may be reduced with, for example, hydrogen over a metal catalyst such as palladium on carbon, to afford the 1,2,3,4-tetrahydroquinoline (structure 63).

Scheme XVII

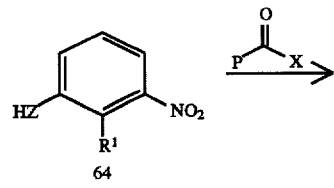

Scheme XVII -continued

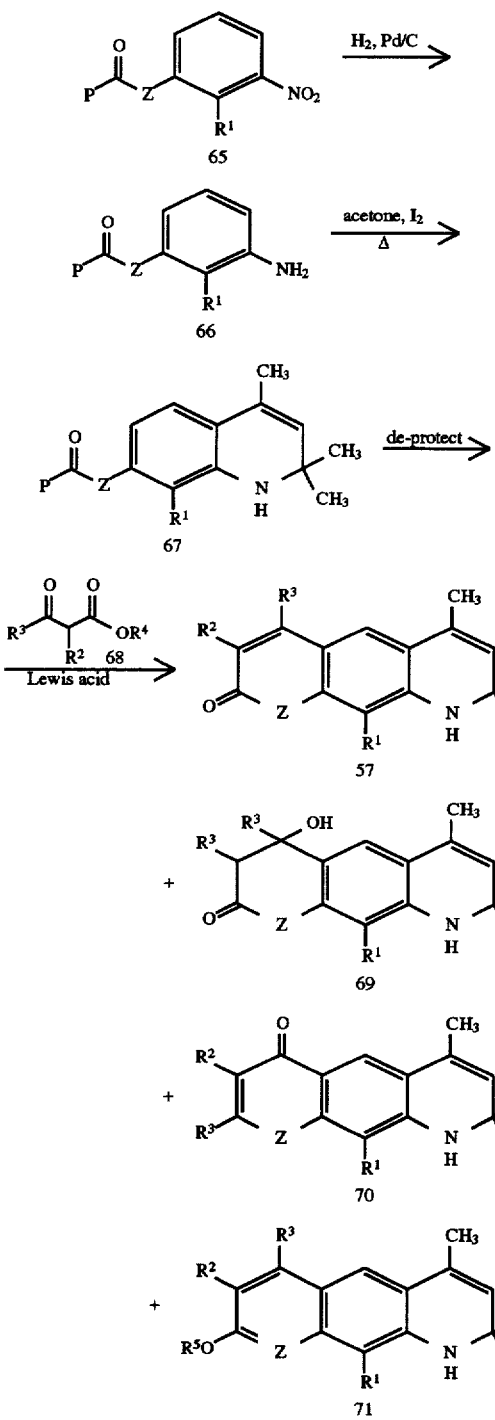

The process of Scheme XVII begins with the acylation of a 3-nitrophenol (structure 64, Y=O) or 3-nitroaniline (structure 64, Y=NH) with an acylating agent, for example, di-tert-butyl dicarbonate or trimethylacetyl chloride, to afford a compound of structure 65. Reduction of the nitro group with, for example, hydrogen over a metal catalyst such as palladium on carbon, affords the corresponding aniline (structure 66). Treatment of a compound of structure 66 with acetone and a catalyst such as iodine affords a compound of structure 67. Deprotection by either acid or base, followed by treatment of the corresponding aniline or phenol with a β-keto ester (structure 68) in the presence of a Lewis acid such as zinc chloride, affords one or more of four compounds (structures 57, 69, 70, and 71). The cyclization of a phenol as described above is known as a Pechmann reaction. See S. Sethna and R. Phadke, "The Pechmann Reaction", *Organic Reactions* 1953, 7, 1, the disclosure of which is herein incorporated by reference. The cyclization of an aniline as described above is known as a Knorr cylization. See G. Jones, "Pyridines and their Benzo Derivatives: (v) Synthesis". In *Comprehensive Heterocyclic Chemistry*, Katritzky, A. R.; Rees, C. W., eds. Pergamon, New York, 1984. Vol. 2, chap. 2.08, pp 421–426, the disclosure of which is herein incorporated by reference. A compound of structure 69 may be converted to a compound of structure 57 by treatment with an acid, for example, para-toluenesulphonic acid. In addition, a compound of structure 71 may be converted to a compound of structure 57 by treatment with, for example, para-chlorophenol.

Scheme XVIII

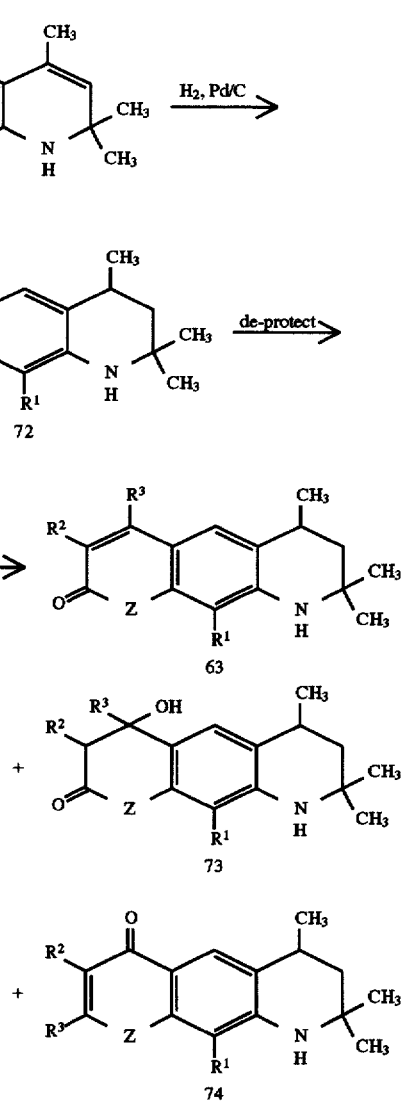

Scheme XVIII (continued)

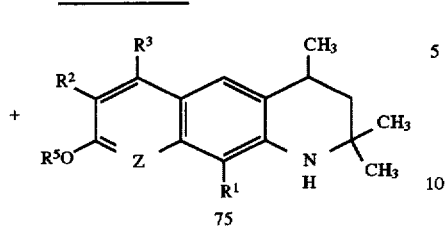

The process of Scheme XVIII begins with the reduction of a compound of structure 67 with, for example, hydrogen over a metal catalyst such as palladium on carbon. Deprotection by either acid or base, followed by treatment of the corresponding aniline or phenol with a β-keto ester (structure 68) in the presence of a Lewis acid such as zinc chloride, as described above in Scheme XVII, affords one or more of four compounds (structures 63, 73, 74, and 75).

Scheme XIX

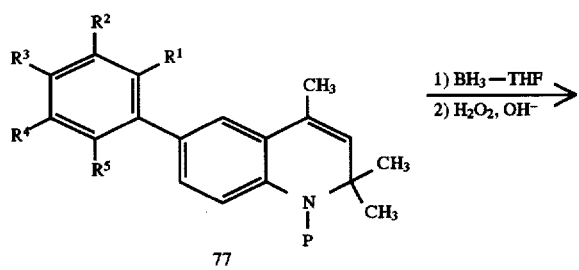

The process of Scheme XIX involves the conversion of a compound of structure 63 to the corresponding thiocompound (structure 78) by treatment with Lawesson's reagent [2,4-bis(4-methoxyphenyl)-1,3-dithia-2,4-diphosphetane-2,4-disulfide].

Scheme XX

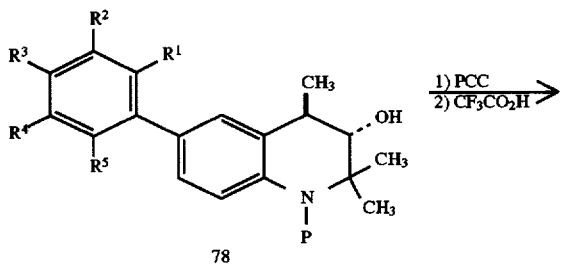

Scheme XX (continued)

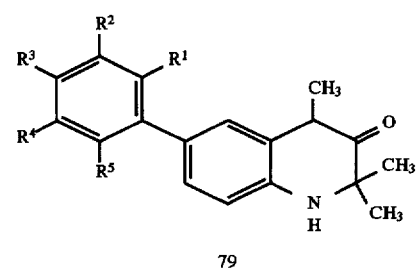

The process of Scheme XX begins with a protected 6-aryl-1,2-dihydro-2,2,4-trimethylquinoline (structure 77), which can be prepared as described in Scheme II. Hydroboration of a compound of structure 77 with a borane species, for example, borane-tetrahydrofuran, followed by an oxidative work-up using, for example, basic hydrogen peroxide, affords a 3-hydroxyltetrahydroquinoline (structure 78). Oxidation of the alcohol with a typical oxidant, for example pyridinium chlorochromate, and deprotection with a strong acid such as trifluoroacetic acid affords a compound of structure 79.

Scheme XXI

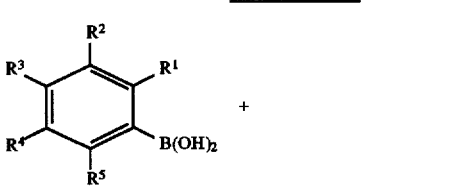

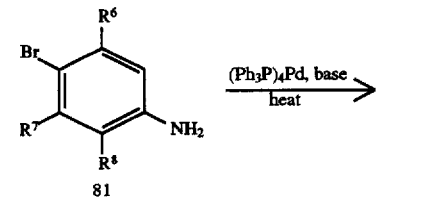

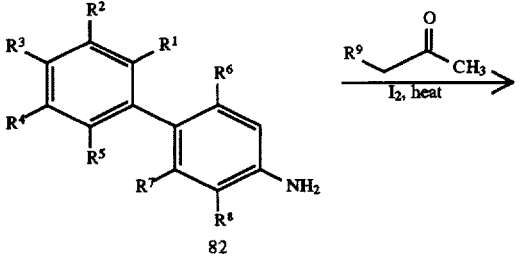

55
-continued
Scheme XXI

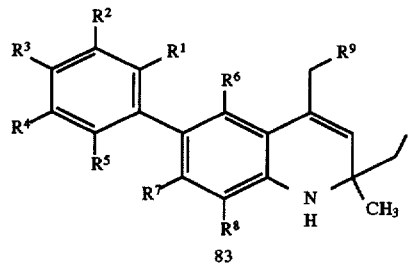
83

The process of Scheme XXI begins with a palladium-catalyzed cross-coupling reaction of an aryl boronic acid (a compound of structure 80) and a 4-bromoaniline (a compound of structure 81) using, for example, tetrakis (triphenylphosphine)palladium as the catalyst, to afford a substituted 4-aminobiphenyl (a compound of structure 82). A Skraup reaction using an alkyl methyl ketone, for example acetone or 2-butanone, affords a compound of structure 83.

Scheme XXII

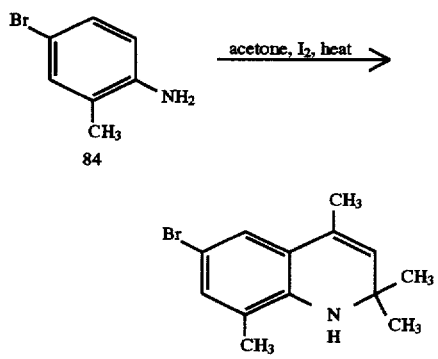

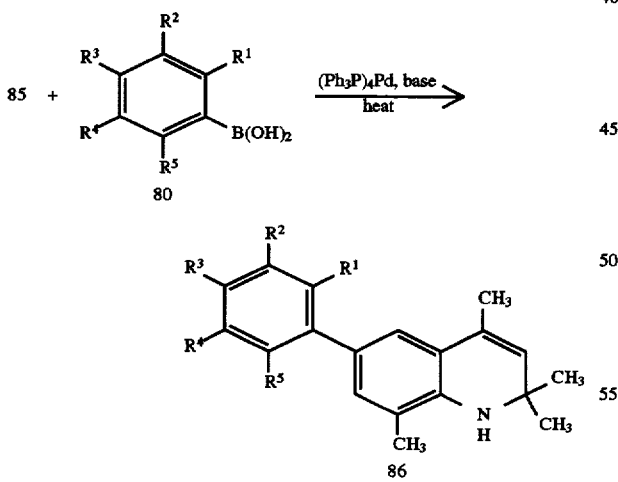

The process of Scheme XXII begins with a Skraup reaction using 4-bromo-2-methylaniline (Compound 84) and acetone to afford Compound 85. A palladium-catalyzed cross-coupling reaction using, for example, tetrakis (triphenylphosphine) palladium as the catalyst, between an aryl boronic acid (a compound of structure 80) and Compound 85 affords a compound of structure 86.

56
Scheme XXIII

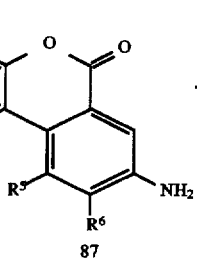
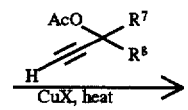
87

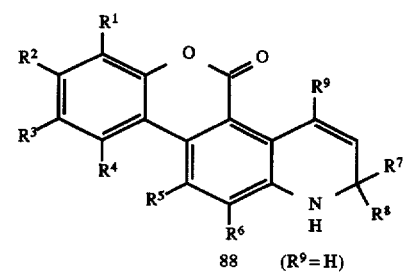
88   ($R^9 = H$)

The process of Scheme XXIII involves the reaction of an aminobenzocoumarin (a compound of structure 87) with a propargyl acetate in the presence of a copper salt, such as copper(I) chloride, to afford a compound of structure 88. See N. R. Easton and D. R. Cassady, "A Novel Synthesis of Quinolines and Dihydroquinolines.", *J. Org. Chem.* 1962, 27, 4713, and N. R. Easton and G. F. Hennion, "Metal Catalyst Process for Converting α-Amino-Acetylenes to Dihydroquinoline", U.S. Pat. No. 3,331,846 (1967), the disclosure of which is herein incorporated by reference.

Scheme XXIV

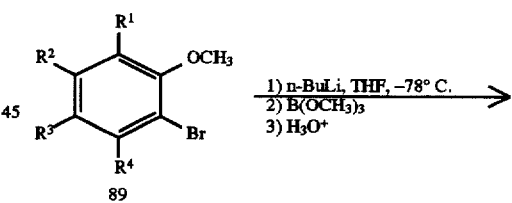
89

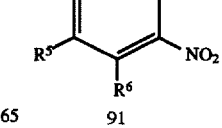
90

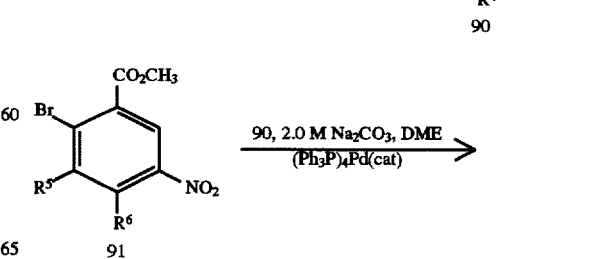
91

Scheme XXIV

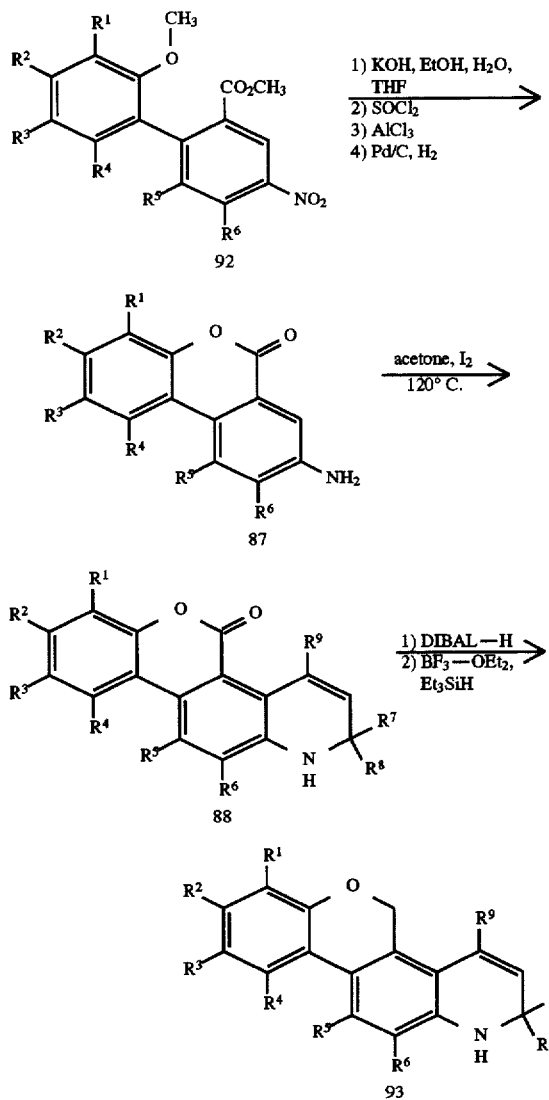

The process of Scheme XXIV involves the preparation of benzocoumarins from acyclic precursors. Thus, an ortho-bromoanisole (structure 89) is lithiated with, for example, n-butyllithium and allowed to react with a trialkylborate such as trimethylborate. Hydrolysis of the intermediate with, for example, dilute hydrochloric acid affords the corresponding boronic acid (structure 90). Palladium-catalyzed coupling of a 2-methoxyphenylboronic acid (structure 90) with a methyl 2-bromo-5-nitrobenzoate (structure 91) with, for example, tetrakis(triphenylphosphine)palladium and potassium carbonate, affords the biphenyl carboxylate (structure 92). Hydrolysis of the ester with, for example, potassium hydroxide, is followed by conversion of the acid to the acid chloride with, for example, thionyl chloride. Intramolecular Friedel-Crafts acylation is then effected by a Lewis acid such as aluminum trichloride. Reduction of the nitro group with, for example, hydrogen over palladium on carbon, affords the desired aniline (structure 87). Treatment of compounds of structure 87 with acetone and iodine affords the dihydroquinoline (structure 88). The reduction of a compound of structure 88 with, for example, diisobutyla-luminum hydride, followed by treatment of the intermediate with, for example, boron trifluoride and triethylsilane, affords a compound of structure 93.

Scheme XXV

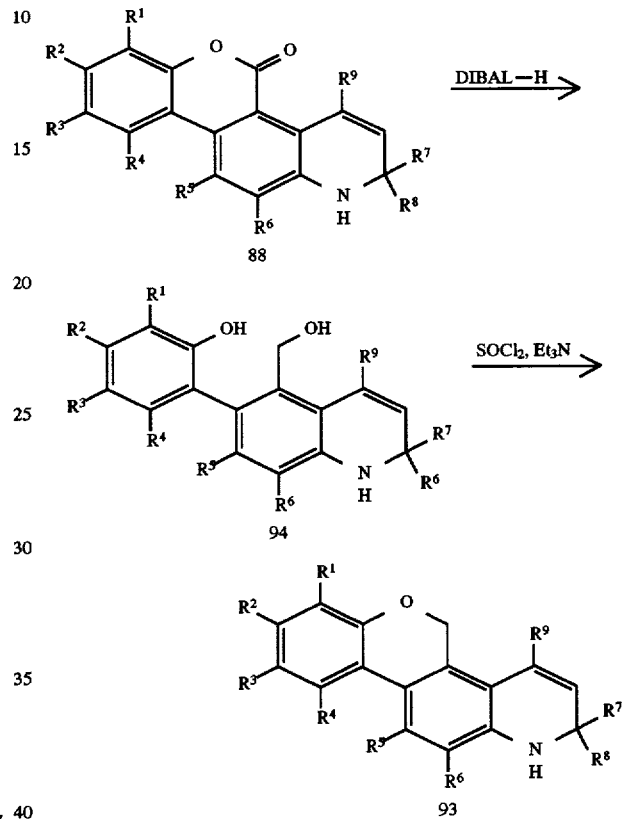

The process of Scheme XXV involves the reduction of a compound of structure 88 with a reducing agent, for example, diisobutylaluminum hydride, to a compound of structure 94. Conversion of the benzyl alcohol to a leaving group by treatment with, for example, thionyl chloride, in the presence of a base such as triethylamine, effects ring closure to a compound of structure 93.

Scheme XXVI

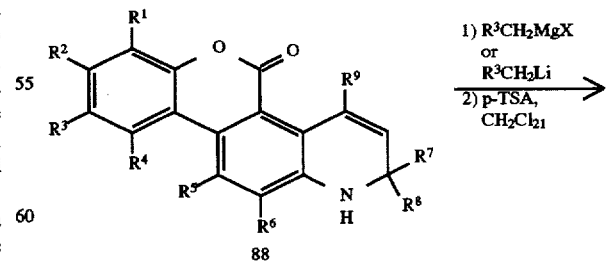

Scheme XXVI (continued)

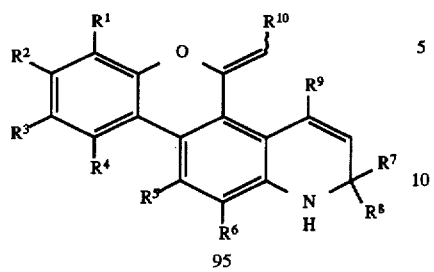

The process of Scheme XXVI begins with the addition of an organolithium or organomagnesium reagent to a compound of structure 88, followed by treatment of the intermediate thus obtained with an acid such as para-toluenesulfonic acid, to afford a compound of structure 95.

Scheme XXVII (continued)

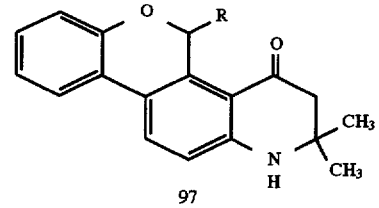

The process of Scheme XXVII begins with the protection of the nitrogen atom of a compound of structure 33 by treatment with a base, for example n-butyllithium, followed by the addition of an acylating agent such as di-tert-butyldicarbonate. Ozonolysis of the olefin affords a compound of structure 96. Subsequent removal of the protecting group with, for example, trifluoroacetic acid, affords a compound of structure 97.

Scheme XXVIII

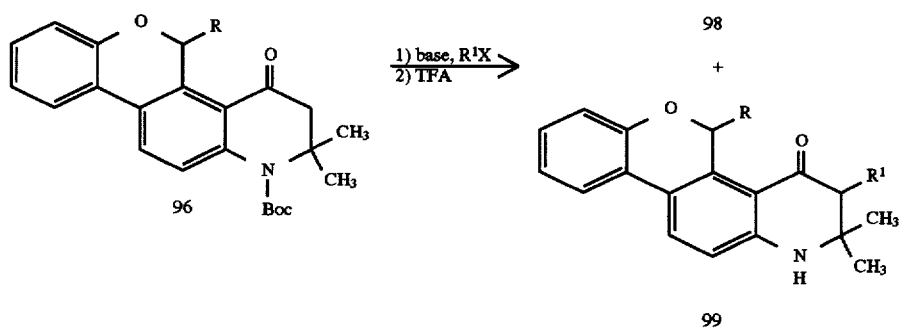

The process of Scheme XXVIII begins with the deprotonation of a compound of structure 96 with, for example, sodium hydride or lithium diisopropylamide, followed by the addition of an alkylating agent such as iodomethane, to afford a mono-alkylated product, or a mixture of mono- and di-alkylated products. Subsequent removal of the protecting group with, for example, trifluoroacetic acid, affords either one or both compounds of structures 98 and 99.

Scheme XXVII

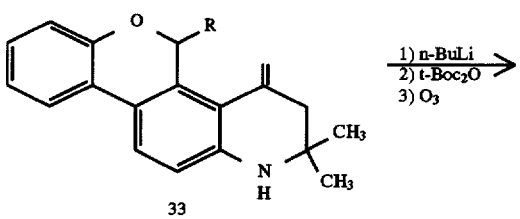

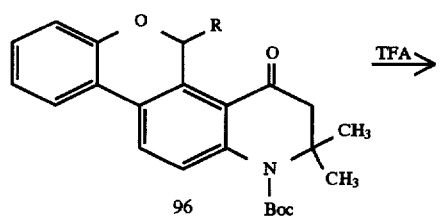

Scheme XXIX

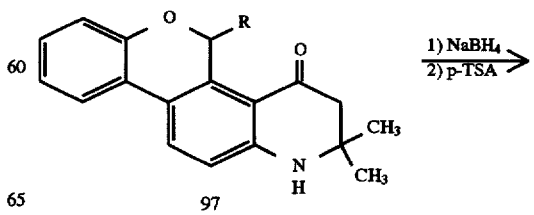

61
-continued
Scheme XXIX

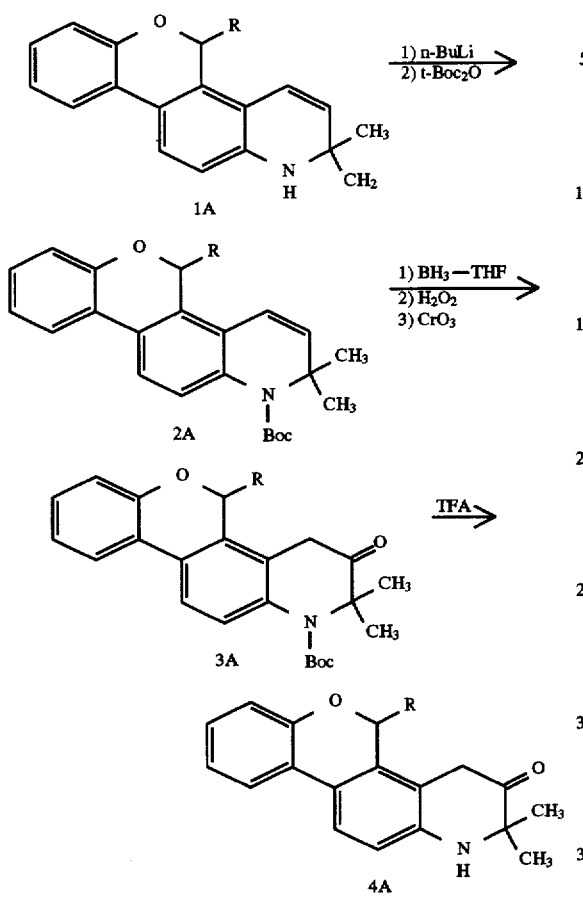

The process of Scheme XXIX begins with the reduction of a compound of structure 97 with, for example sodium borohydride, followed by dehydration of the resulting alcohol by treatment with an acid such as para-toluenesulfonic acid, to afford a compound of structure 1A. The nitrogen atom of a compound of structure 1A is then protected by treatment with a base, for example n-butyllithium, followed by the addition of an acylating agent such as di-tert-butyldicarbonate, to afford a compound of structure 2A. Hydroboration of a compound of structure 2A with a borane species, for example, borane-tetrahydrofuran, followed by an oxidative work-up using, for example, basic hydrogen peroxide, affords a 3-hydroxyltetrahydroquinoline. Oxidation of the alcohol with a typical oxidant, for example chromium trioxide, affords a compound of structure 3A, and deprotection with a strong acid such as trifluoroacetic acid affords a compound of structure 4A.

Scheme XXX

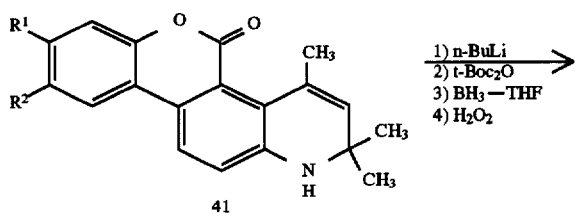

62
-continued
Scheme XXX

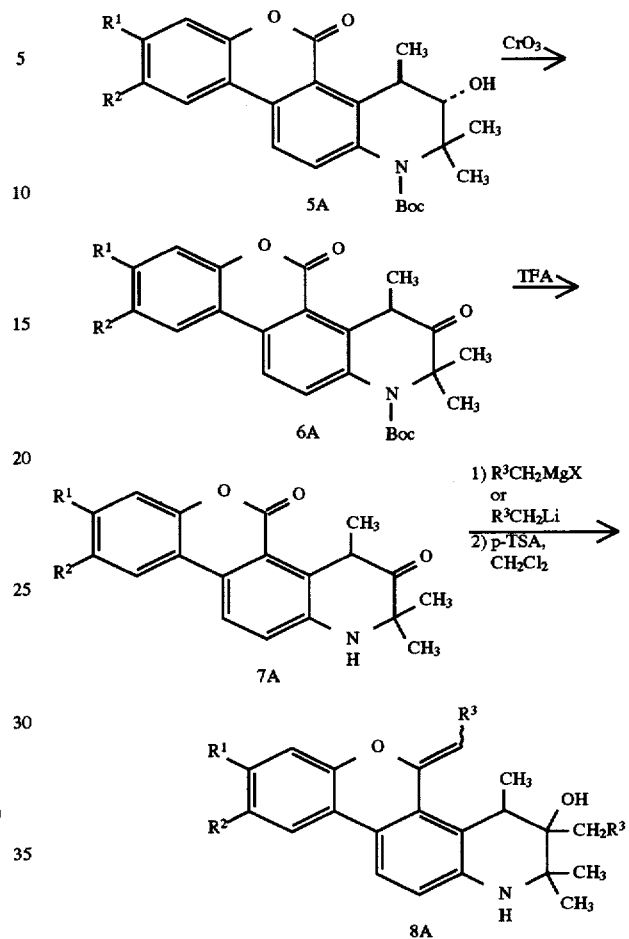

The process of Scheme XXX begins with the protection of the nitrogen atom of a compound of structure 41 by treatment with a base, for example n-butyllithium, followed by the addition of an acylating agent such as di-tert-butyldicarbonate. Hydroboration with a borane species, for example, borane-tetrahydrofuran, followed by an oxidative work-up using, for example, basic hydrogen peroxide, affords a 3-hydroxyltetrahydroquinoline of structure 5A. Oxidation of the alcohol with, for example, chromium trioxide, affords a compound of structure 6A. Removal of the protecting group with, for example, trifluoroacetic acid, affords a compound of structure 7A. The addition of an organolithium or organomagnesium reagent to a compound of structure 7A, followed by dehydration of the intermediate hemiketal with, for example, para-toluenesulfonic acid, affords a compound of structure 8A.

Scheme XXXI

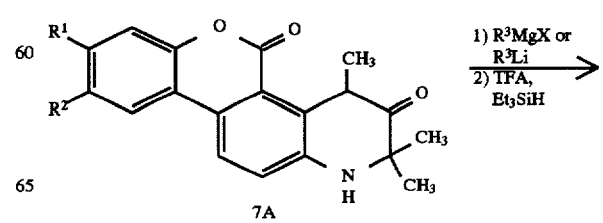

-continued
Scheme XXXI

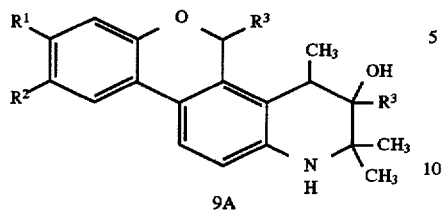

The process of Scheme XXXI begins with the addition of an organolithium or organomagnesium reagent to a compound of structure 7A, followed by reduction of the intermediate hemiketal with, for example, trifluoroacetic acid and triethylsilane, to afford a compound of structure 9A.

The process of Scheme XXXII begins with the addition of an organolithium or organomagnesium reagent to a compound of structure 6A, followed by reduction of the intermediate hemiketal with, for example, trifluoroacetic acid and triethylsilane, to afford a diastereomeric mixture of compounds of structures 10A and 11A.

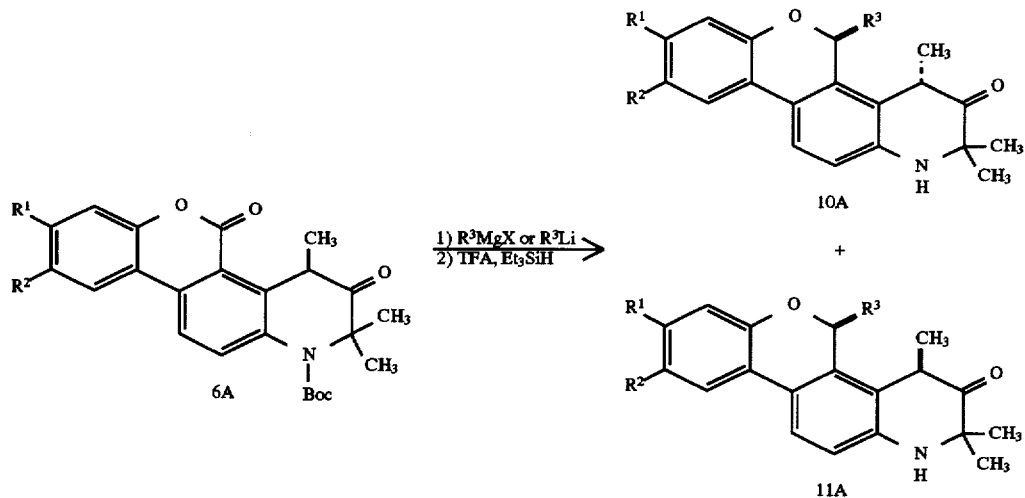

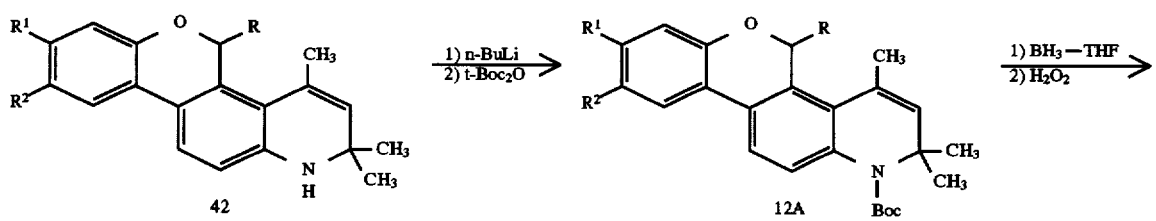

-continued
Scheme XXXIII

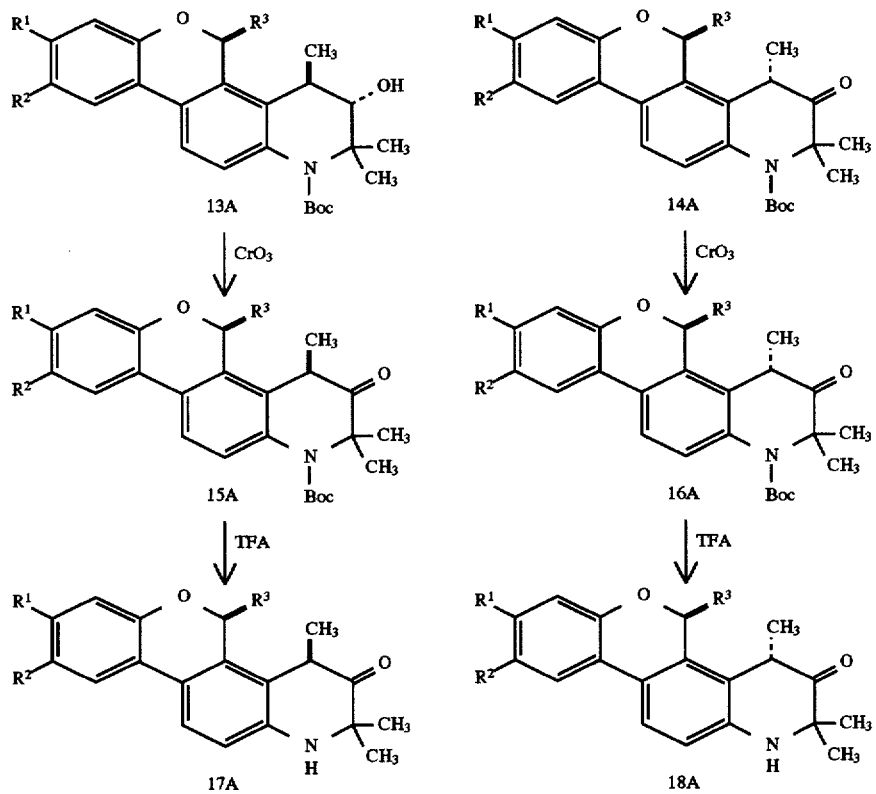

The process of Scheme XXXIII begins with the protection of the nitrogen atom of a compound of structure 42 by treatment with a base, for example n-butyllithium, followed by the addition of an acylating agent such as di-tert-butyldicarbonate. Hydroboration with a borane species, for example, borane-tetrahydrofuran, followed by an oxidative work-up using, for example, basic hydrogen peroxide, affords two diastereomeric 3-hydroxyltetrahydroquinolines of structures 13A and 14A. Independently, each diastereomer may be oxidized with, for example, chromium trioxide, to afford the 3-ketotetrahydroquinolines 15A and 16A, which may subsequently be deprotected with, for example, trifluroacetic acid, to afford compounds of structures 17A and 18A.

Scheme XXXIV

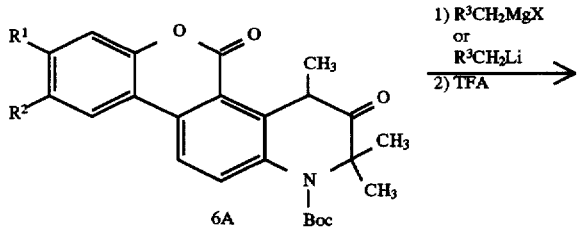

-continued
Scheme XXXIV

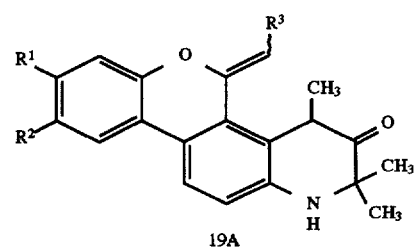

The process of Scheme XXXIV begins with the addition of an organolithium or organomagnesium reagent to a compound of structure 6A. Deprotection of the nitrogen atom and dehydration of the hemiketal with, for example, trifluoroacetic acid, affords a compound of structure 19A.

Scheme XXXV

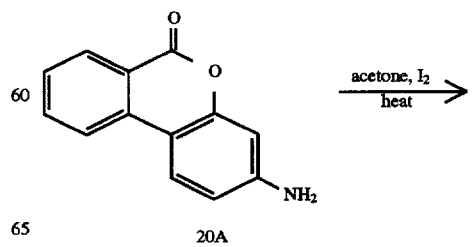

Scheme XXXV

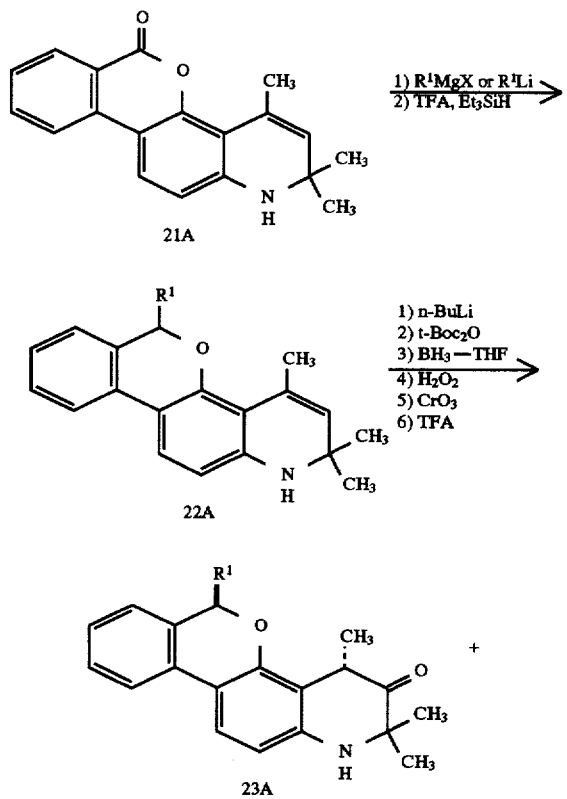

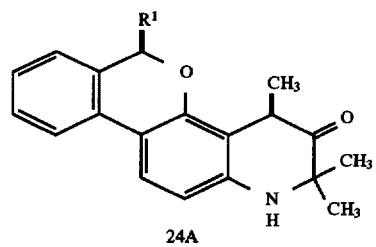

The process of Scheme XXXV begins with a Skraup reaction using Compound 20A and acetone to afford Compound 21A. The addition of an organolithium or organomagnesium reagent to a compound of structure 21A, followed by reduction of the intermediate hemiketal with, for example, trifluoroacetic acid and triethylsilane, affords a compound of structure 22A. Protection of the nitrogen atom of a compound of structure 22A is accomplished by treatment with a base, for example n-butyllithium, followed by the addition of an acylating agent such as di-tert-butyldicarbonate. Hydroboration with a borane species, for example, borane-tetrahydrofuran, followed by an oxidative work-up using, for example, basic hydrogen peroxide, affords a mixture of two diastereomeric 3-hydroxyltetrahydroquinolines, which is oxidized with, for example, chromium trioxide, to afford the 3-ketotetrahydroquinolines. The mixture of 3-ketotetrahydroquinolines may subsequently be deprotected with, for example, trifluroacetic acid, to afford compounds of structures 23A and 24A.

Scheme XXXVI

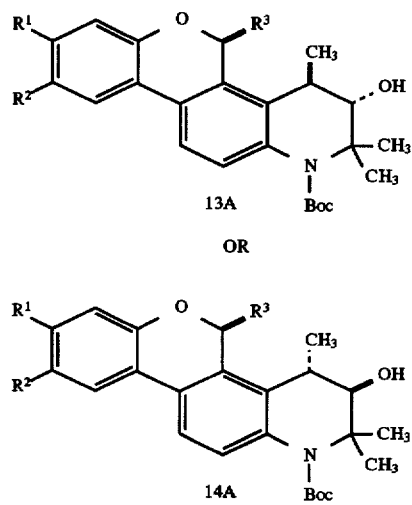

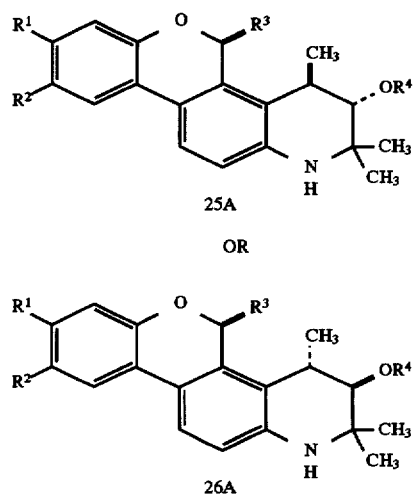

The process of Scheme XXXVI involves the alkylation of the oxygen atom of a compound of structure 13A or 14A. The addition of a base such as sodium hydride and an alkylating agent such as iodomethane, followed by deprotection of the nitrogen atom with, for example, trifluoroacetic acid, affords a compound of structure 25A (from a compound of structure 13A) or structure 26A (from a compound of structure 14A).

Scheme XXXVII

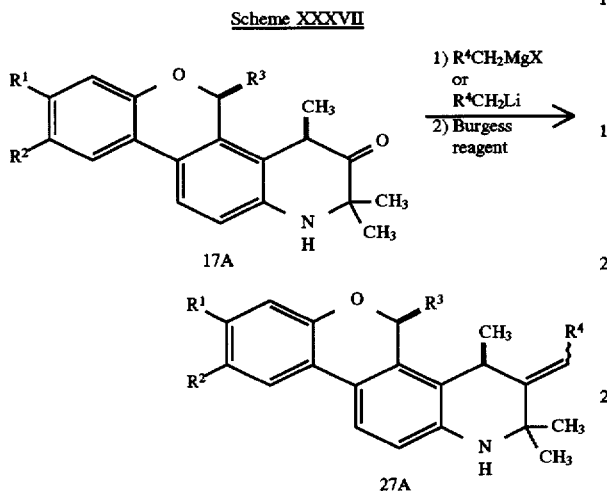

The process of Scheme XXXVII begins with the addition of an organolithium or organomagnesium reagent to a compound of structure 17A, followed by dehydration of tertiary alcohol with, for example, the Burgess reagent [(methoxycarbonylsulfamoyl)triethylammonium hydroxide, inner salt], to afford a compound of structure 27A.

Scheme XXXVIII

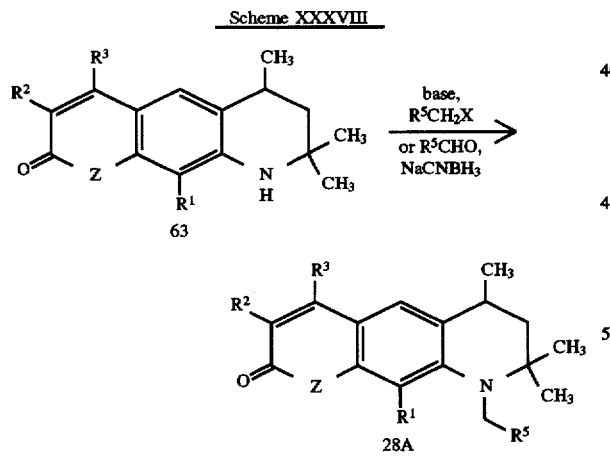

The process of Scheme XXXVIII involves the alkylation of N(1) of a compound of structure 63, which can be accomplished in one of two ways. Treatment of a compound of structure 63 with a base, such as sodium hydride, and an alkylating agent, such as benzyl bromide, affords a compound of structure 28A. Alternatively, treatment of a compound of structure 63 with an aldehyde, for example acetaldehyde or paraformaldehyde, in the presence of a reducing agent, for example sodium cyanoborohydride or sodium (triacetoxy)borohydride, affords a compound of structure 28A.

Scheme XXXIX

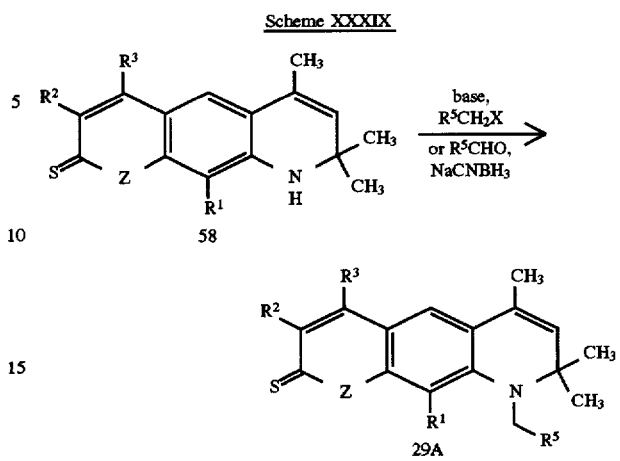

The process of Scheme XXXIX involves the alkylation of N(1) of a compound of structure 58, which can be accomplished in one of two ways. Treatment of a compound of structure 58 with a base, such as sodium hydride, and an alkylating agent, such as benzyl bromide, affords a compound of structure 29A. Alternatively, treatment of a compound of structure 58 with an aldehyde, for example acetaldehyde or paraformaldehyde, in the presence of a reducing agent, for example sodium cyanoborohydride or sodium (triacetoxy)borohydride, affords a compound of structure 29A.

Scheme XL

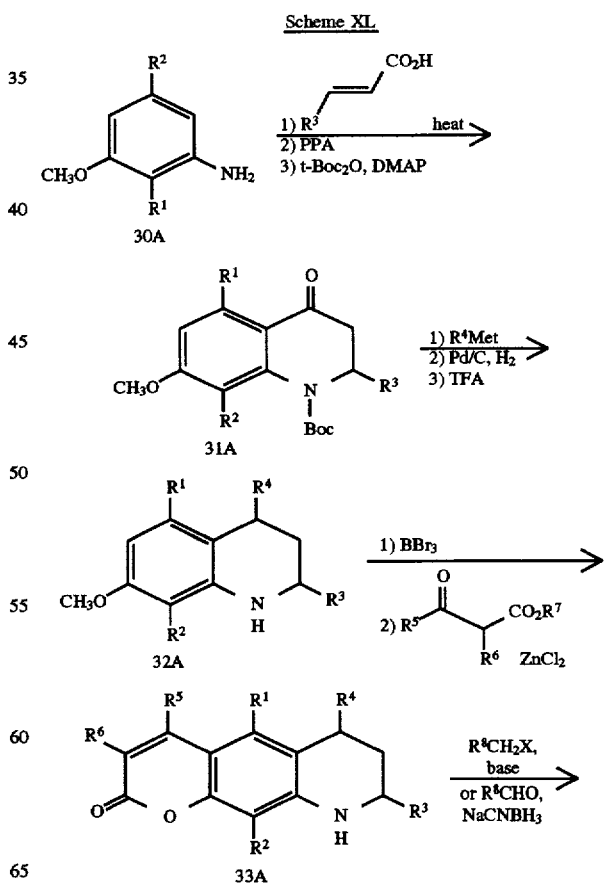

-continued
Scheme XL

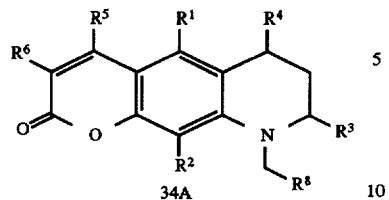
34A

The process of Scheme XL begins with reaction of a 3-methoxyaniline (a compound of structure 30A) with an acrylic acid, for example, crotonic acid, followed by treatment with an acid such as polyphosphoric acid to afford a 4-quinolone. Protection of the nitrogen atom by treatment with a base, for example n-butyllithium, followed by the addition of an acylating agent such as di-tert-butyldicarbonate, affords a compound of structure 31A. Addition of an organomagnesium or organolithium reagent ($R^4$=alkyl, aryl, etc.), or a reducing agent such as sodium borohydride ($R^4$=hydrogen), affords an alcohol. Reduction of the alcohol with, for example hydrogen over palladium on carbon, followed by deprotection of the nitrogen atom, affords a compound of structure 32A. Demethylation of the methyl ether with, for example, boron tribromide, followed by a Pechman cyclization with a β-keto ester effected by, for example, zinc chloride, affords a compound of structure 33A. A compound of structure 33A may further be transformed to a compound of structure 34A by alkylation of the nitrogen atom, which can be accomplished in one of two ways. Treatment of a compound of structure 33A with a base, such as sodium hydride, and an alkylating agent, such as benzyl bromide, affords a compound of structure 34A. Alternatively, treatment of a compound of structure 33A with an aldehyde, for example acetaldehyde or paraformaldehyde, in the presence of a reducing agent, for example sodium cyanoborohydride or sodium (triacetoxy) borohydride, affords a compound of structure 34A.

-continued
Scheme XLI

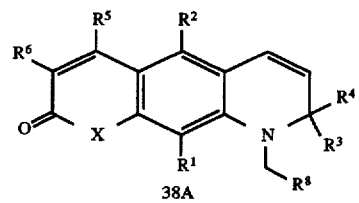
38A

The process of Scheme XLI begins with the reaction of an aniline of structure 35A with a propargyl acetate in the presence of a copper salt such as copper(I) chloride to afford a compound of structure 36A. Deprotection of the heteroatom with, for example ethanolic potassium hydroxide, followed by a Pechman cyclization (X=O or S) or Knorr cyclization (X=NH) with a β-keto ester effected by, for example, zinc chloride, affords a compound of structure 37A. A compound of structure 37A may further be transformed to a compound of structure 38A by alkylation of the nitrogen atom, which can be accomplished in one of two ways. Treatment of a compound of structure 37A with a base, such as sodium hydride, and an alkylating agent, such as benzyl bromide, affords a compound of structure 38A. Alternatively, treatment of a compound of structure 37A with an aldehyde, for example acetaldehyde or paraformaldehyde, in the presence of a reducing agent, for example sodium cyanoborohydride or sodium (triacetoxy) borohydride, affords a compound of structure 38A.

Scheme XLI

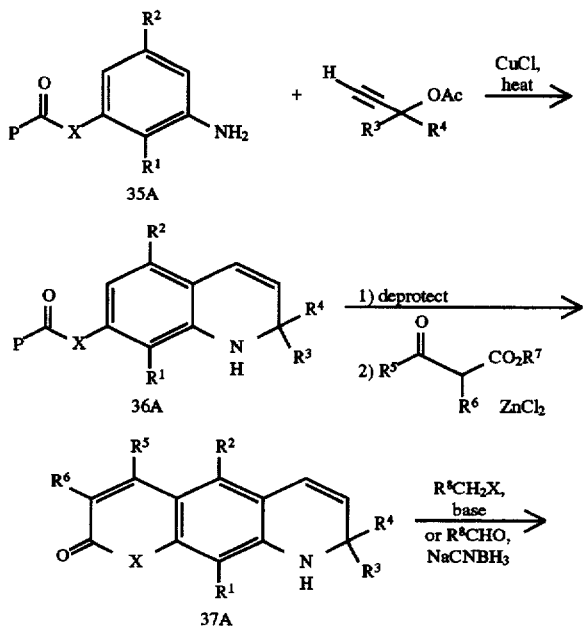

Scheme XLII

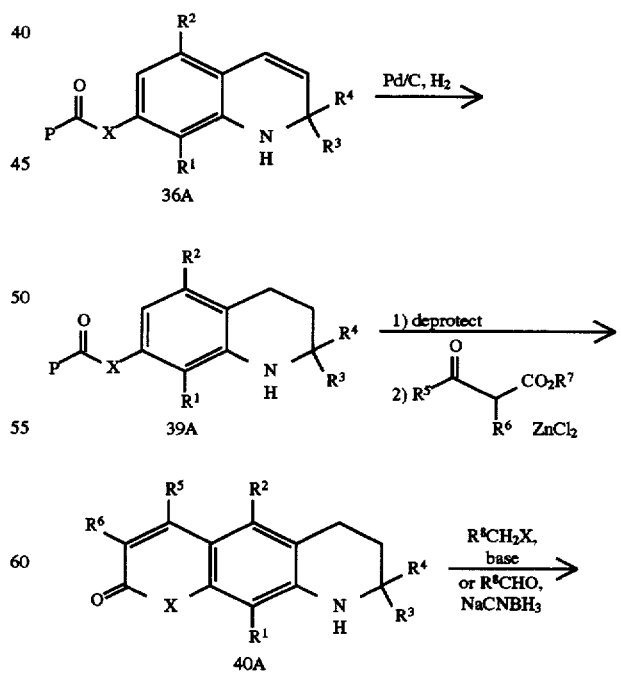

-continued

Scheme XLII

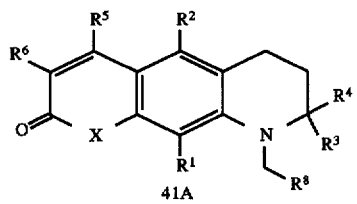

41A

The process of Scheme XLII begins with the reduction of a compound of structure 36A with, for example, hydrogen over palladium on carbon. Deprotection of the heteroatom with, for example ethanolic potassium hydroxide, followed by a Pechman cyclization (X=O or S) or Knorr cyclization (X=NH) with a β-keto ester effected by, for example, zinc chloride, affords a compound of structure 39A. A compound of structure 39A may further be transformed to a compound of structure 40A by alkylation of the nitrogen atom, which can be accomplished in one of two ways. Treatment of a compound of structure 39A with a base, such as sodium hydride, and an alkylating agent, such as benzyl bromide, affords a compound of structure 40A. Alternatively, treatment of a compound of structure 39A with an aldehyde, for example acetaldehyde or paraformaldehyde, in the presence of a reducing agent, for example sodium cyanoborohydride or sodium (triacetoxy)borohydride, affords a compound of structure 40A.

Scheme XLIII

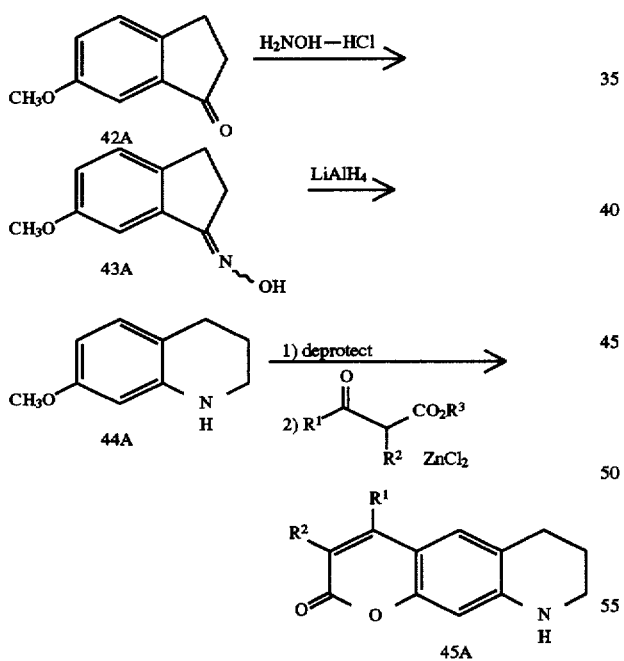

The process of Scheme XLIII begins with 6-methoxy-1-tetralone (Compound 42A) which is treated with hydroxylamine hydrochloride to afford the corresponding oxime, Compound 43A. A reductive Beckman rearrangement effected by, for example, lithium aluminum hydride, affords Compound 44A. Demethylation of the methyl ether with, for example, boron tribromide, followed by a Pechman cyclization with a β-keto ester effected by, for example, zinc chloride, affords a compound of structure 45A.

Scheme XLIV

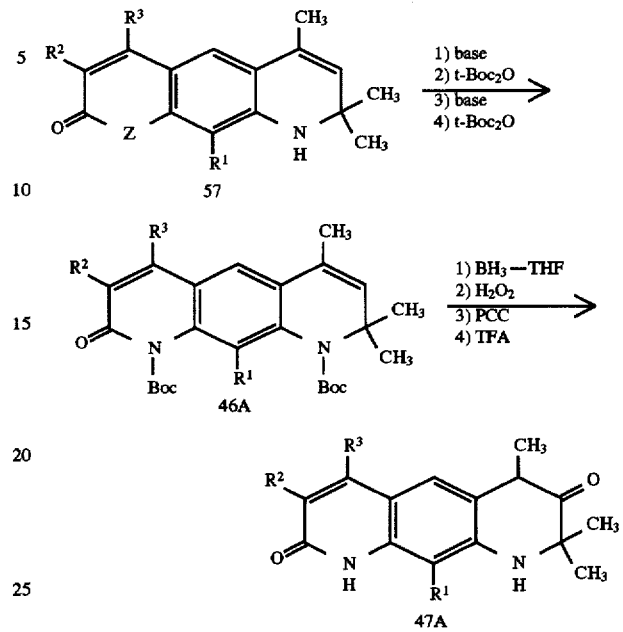

The process of Scheme XLIV begins with the protection of both nitrogen atoms of a compound of structure 57 (Z=NH) by two sequential treatments with a base, for example n-butyllithium, followed by an acylating agent, for example di-tert-butyldicarbonate, to afford a compound of structure 46A. Hydroboration with a borane species, for example, borane-tetrahydrofuran, followed by an oxidative work-up using, for example, basic hydrogen peroxide, affords a 3-hydroxyltetrahydroquinoline, which is oxidized with, for example, pyridinium chlorochromate, to afford the 3-ketotetrahydroquinoline. The 3-ketotetrahydroquinoline may subsequently be deprotected with, for example, trifluoroacetic acid, to afford a compound of structure 47A.

Scheme XLV

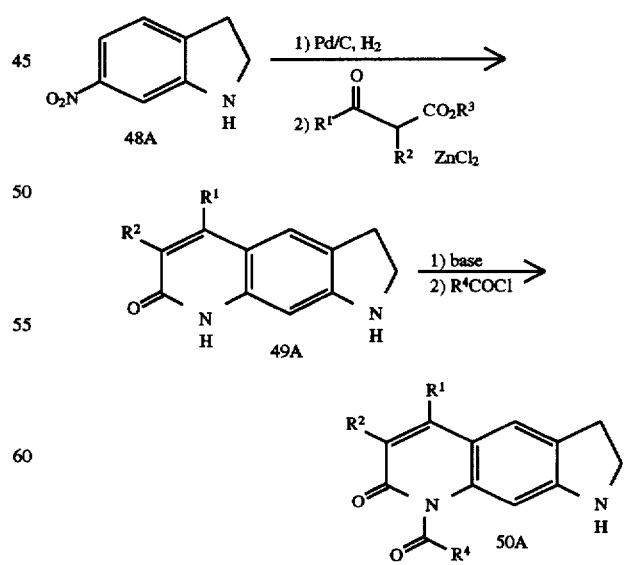

The process of Scheme XLV begins with the reduction of 6-nitroindoline (Compound 48A) with, for example, hydrogen over palladium on carbon. A Pechman cyclization with a β-keto ester effected by, for example, zinc chloride, affords a compound of structure 49A. A compound of structure 49A may further be transformed to a compound of structure 50A by acylation of the quinolone nitrogen atom, which may be effected by deprotonation with, for example, sodium hydride, followed by the addition of an acylating agent, such as 3-nitrobenzoyl chloride.

Scheme XLVI

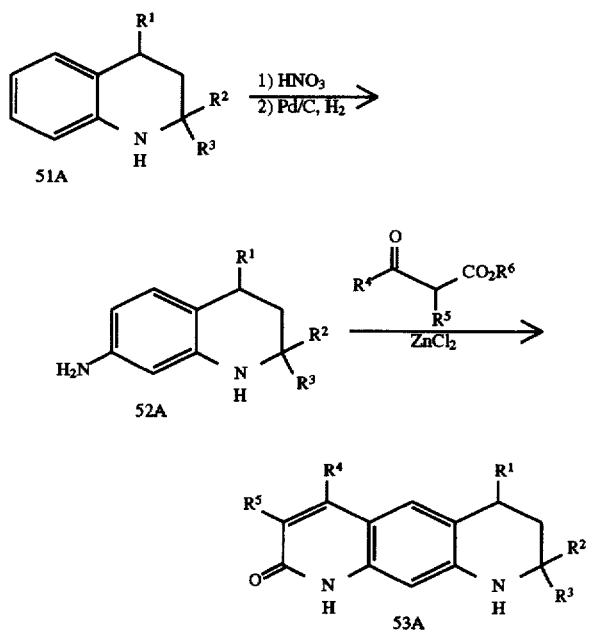

The process of Scheme XLVI begins with the nitration of a 1,2,3,4-tetrahydroquinoline (a compound of structure 51A) by the action of nitric acid in the presence of, for example, sulfuric acid. Reduction of the nitro group with, for example, hydrogen over palladium on carbon, affords a 7-amino-1,2, 3,4-tetrahydroquinoline of structure 52A. A Knorr cyclization with a β-keto ester effected by, for example, zinc chloride, affords a compound of structure 53A.

Scheme XLVII

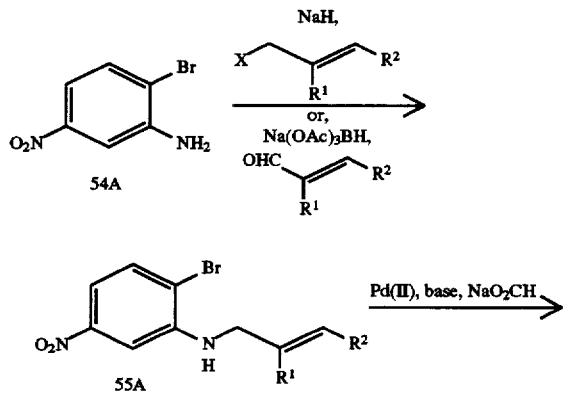

-continued
Scheme XLVII

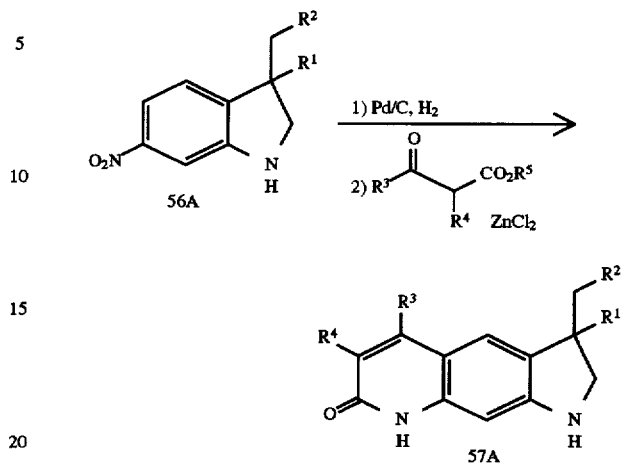

The process of Scheme XLVII begins with the alkylation of 2-bromo-5-nitroaniline (Compound 54A) which may be accomplished in one of two ways. Treatment of Compound 54A with a base such as sodium hydride and an allylating agent, for example, 1-bromo-3-methyl-2-butene, affords a compound of structure 55A. Alternatively, Compound 54A may be treated with an α,β-unsaturated aldehyde, for example, cinnamaldehyde, in the presence of a reducing agent such as sodium triacetoxyborohydride to afford a compound of structure 55A. A palladium-catalyzed cyclization reaction catalyzed by, for example, palladium(II) acetate, affords a compound of structure 56A. Reduction of the nitro group with, for example, hydrogen over palladium on carbon, affords the aniline, and a Knorr cyclization with a β-keto ester effected by, for example, zinc chloride, affords a compound of structure 57A.

Scheme XLVII

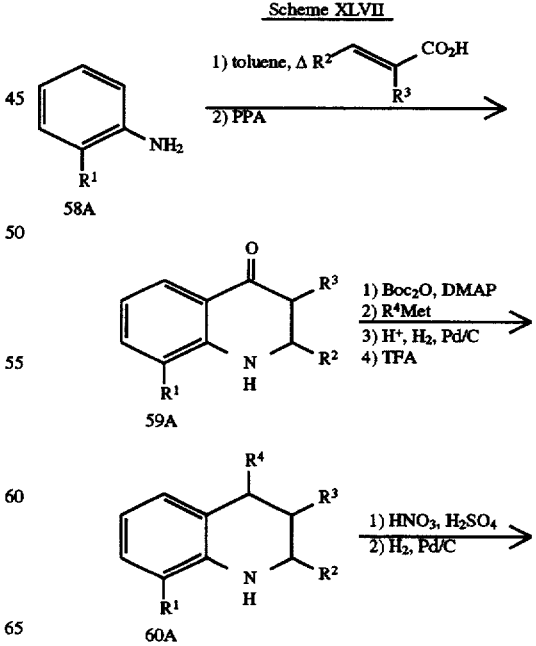

-continued
Scheme XLVII

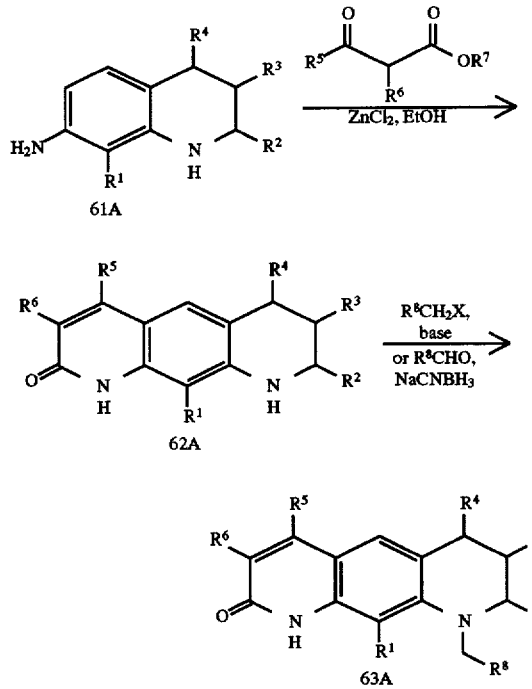

The process of Scheme XLVIII begins with the reaction of an aniline (structure 58A) with an acrylic acid, for example crotonic acid, followed by a cyclization reaction mediated by, for example, polyphosphoric acid to afford a 4-quinolinone of structure 59A. The nitrogen atom is then protected by treatment with a base, for example n-butyllithium, followed by the addition of an acylating agent such as di-tert-butyldicarbonate. Addition of an organomagnesium or organolithium reagent ($R^4$=alkyl, aryl, etc.), or a reducing agent such as sodium borohydride ($R^4$=hydrogen), affords an alcohol. Reduction of the alcohol with, for example hydrogen over palladium on carbon, followed by deprotection of the nitrogen atom, affords a compound of structure 60A. Nitration of a compound of structure 60A by the action of nitric acid in the presence of, for example, sulfuric acid, followed by reduction of the nitro group with, for example, hydrogen over palladium on carbon, affords a 7-amino-1,2,3,4-tetrahydroquinoline of structure 61A. A Knorr cyclization with a β-keto ester effected by, for example, zinc chloride, affords a compound of structure 62A. A compound of structure 62A may be further transformed into a compound of structure 63A by alkylation of the nitrogen atom, which can be accomplished in one of two ways. Treatment of a compound of structure 62A with a base, such as sodium hydride, and an alkylating agent, such as benzyl bromide, affords a compound of structure 63A. Alternatively, treatment of a compound of structure 62A with an aldehyde, for example acetaldehyde or paraformaldehyde, in the presence of a reducing agent, for example sodium cyanoborohydride or sodium (triacetoxy) borohydride, affords a compound of structure 63A.

Scheme XLIX

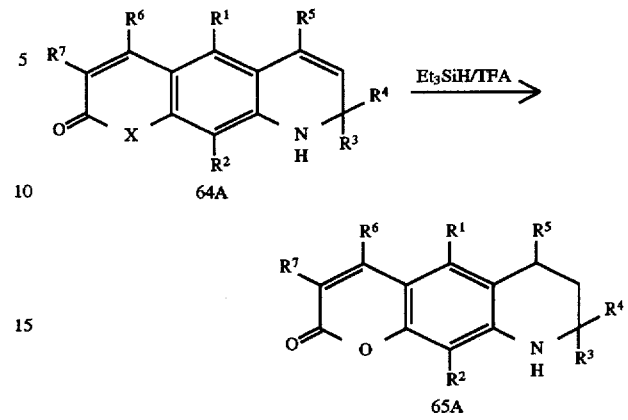

The process of Scheme XLIX involves the reduction of a compound of structure 64A by treatment with, for example, triethylsilane in the presence of trifluoroacetic acid, to afford a compound of structure 65A.

Scheme L

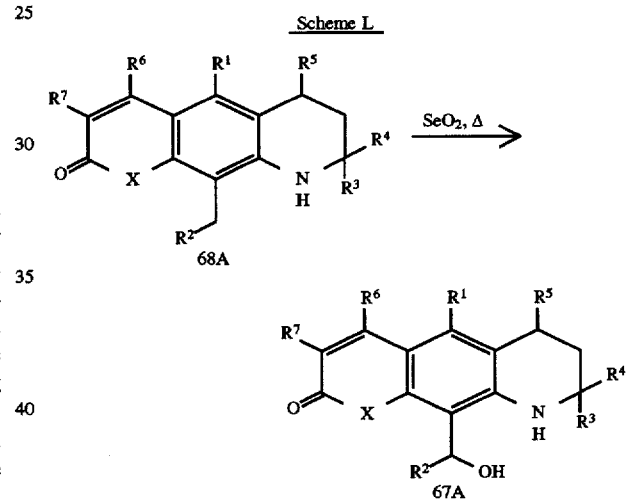

The process of Scheme L involves the oxidation of benzylic substituent of a compound of structure 66A by treatment with, for example, selenium dioxide, to afford a compound of structure 67A.

Scheme LI

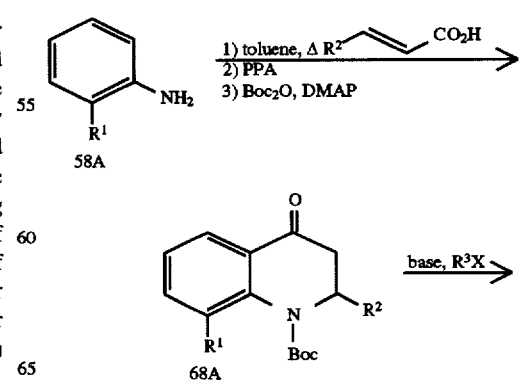

-continued
Scheme LI

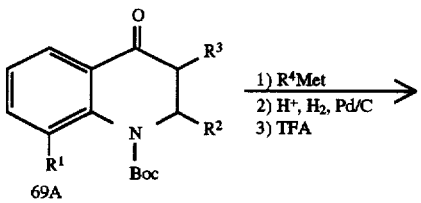
69A

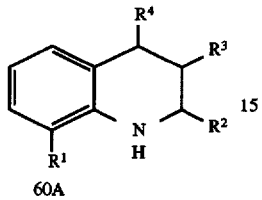
60A

The process of Scheme LI begins with the reaction of an aniline (structure 58A) with an acrylic acid, for example crotonic acid, followed by a cyclization reaction mediated by, for example, polyphosphoric acid to afford a 4-quinolinone. The nitrogen atom is then protected by treatment with a base, for example, 4-dimethylaminopyridine, followed by the addition of an acylating agent such as di-tert-butyldicarbonate to afford a compound of structure 68A. The 4-quinolone is then deprotonated with a base, for example, sodium hydride, and treated with an alkylating agent such as iodomethane, to afford a compound of structure 69A. Addition of an organomagnesium or organolithium reagent ($R^4$=alkyl, aryl, etc.), or a reducing agent such as sodium borohydride ($R^4$=hydrogen), affords an alcohol. Reduction of the alcohol with, for example hydrogen over palladium on carbon, followed by deprotection of the nitrogen atom, affords a compound of structure 60A. Compounds of structure 60A may be transformed into compounds of structure 62A as described in Scheme XLVIII.

Scheme LII

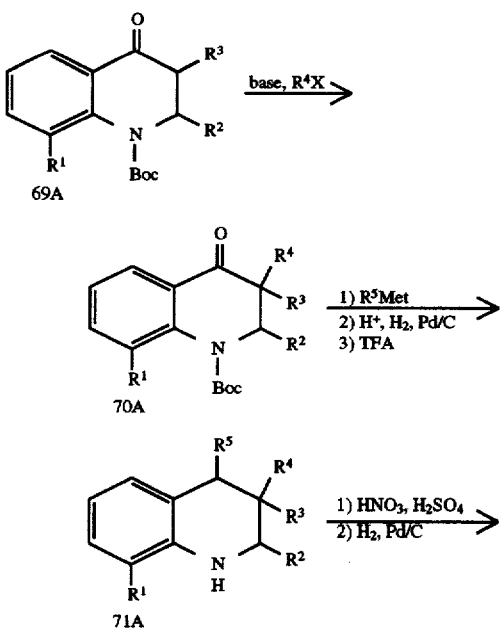

-continued
Scheme LII

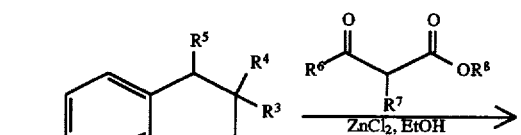
72A

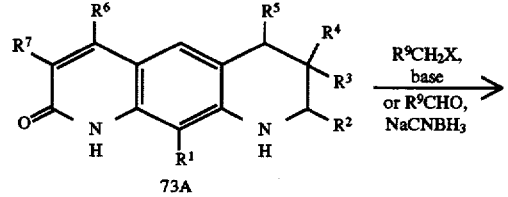
73A

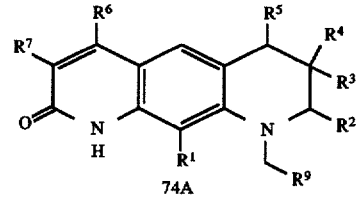
74A

The process of Scheme LII begins with the deprotonation of a compound of structure 69A with a base, for example, sodium hydride, and treatment with an alkylating agent such as iodomethane, to afford a compound of structure 70A. Addition of an organomagnesium or organolithium reagent ($R^5$=alkyl, aryl, etc.), or a reducing agent such as sodium borohydride ($R^5$=hydrogen), affords an alcohol. Reduction of the alcohol with, for example, hydrogen over palladium on carbon, followed by deprotection of the nitrogen atom, affords a compound of structure 71A. Nitration of a compound of structure 71A by the action of nitric acid in the presence of, for example, sulfuric acid, followed by reduction of the nitro group with, for example, hydrogen over palladium on carbon, affords a 7-amino-1,2,3,4-tetrahydroquinoline of structure 72A. A Knorr cyclization with a β-keto ester effected by, for example, zinc chloride, affords a compound of structure 73A. A compound of structure 73A may be further transformed into a compound of structure 74A by alkylation of the nitrogen atom, which can be accomplished in one of two ways. Treatment of a compound of structure 73A with a base, such as sodium hydride, and an alkylating agent, such as benzyl bromide, affords a compound of structure 74A. Alternatively, treatment of a compound of structure 73A with an aldehyde, for example acetaldehyde or paraformaldehyde, in the presence of a reducing agent, for example sodium cyanoborohydride or sodium (triacetoxy)borohydride, affords a compound of structure 74A.

Scheme LIII

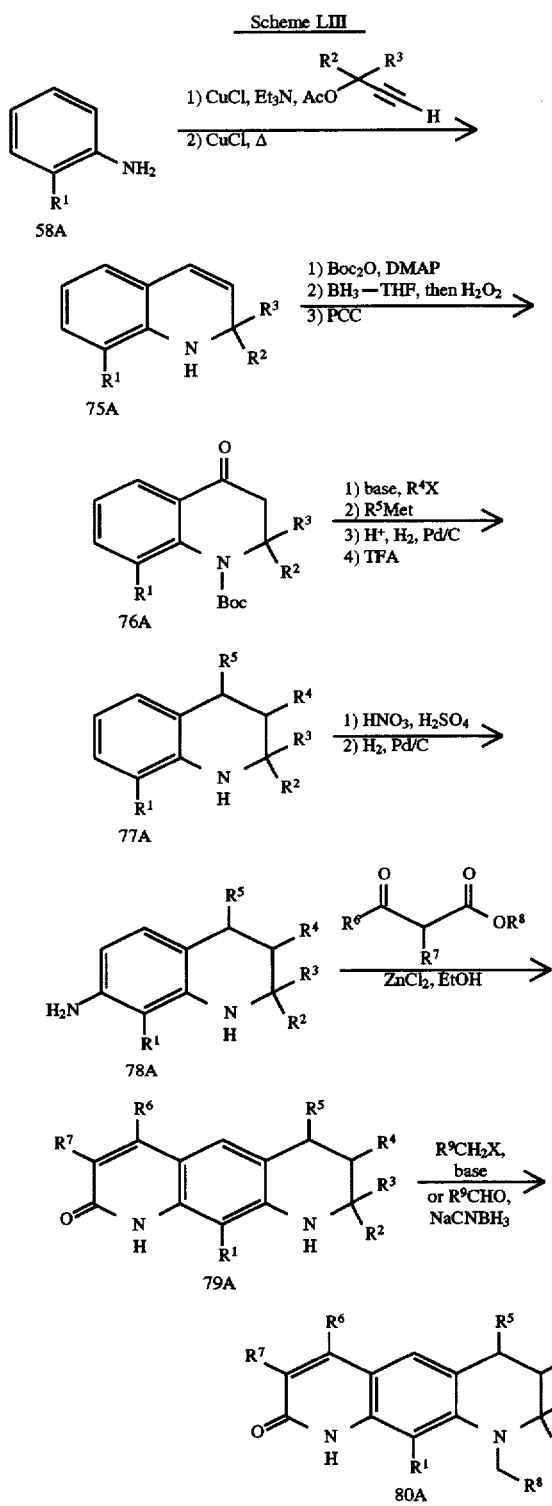

example, basic hydrogen peroxide, affords the 4-hydroxytetrahydroquinoline, which may be oxidized with, for example, pyridinium chlorochromate, to afford a compound of structure 76A. A compound of structure 76A may then be deprotonated with a base, for example, sodium hydride, and treated with an alkylating agent such as iodomethane. Addition of an organomagnesium or organolithium reagent ($R^5$=alkyl, aryl, etc.), or a reducing agent such as sodium borohydride ($R^5$=hydrogen), affords an alcohol. Reduction of the alcohol with, for example, hydrogen over palladium on carbon, followed by deprotection of the nitrogen atom, affords a compound of structure 77A. Nitration of a compound of structure 77A by the action of nitric acid in the presence of, for example, sulfuric acid, followed by reduction of the nitro group with, for example, hydrogen over palladium on carbon, affords 7-amino-1,2,3,4-tetrahydroquinolines of structure 78A. A Knorr cyclization with a β-keto ester effected by, for example, zinc chloride, affords a compound of structure 79A. A compound of structure 79A may be further transformed into a compound of structure 80A by alkylation of the nitrogen atom, which can be accomplished in one of two ways. Treatment of a compound of structure 79A with a base, such as sodium hydride, and an alkylating agent, such as benzyl bromide, affords a compound of structure 80A. Alternatively, treatment of a compound of structure 79A with an aldehyde, for example acetaldehyde or paraformaldehyde, in the presence of a reducing agent, for example sodium cyanoborohydride or sodium (triacetoxy)borohydride, affords a compound of structure 80A.

Scheme LIV

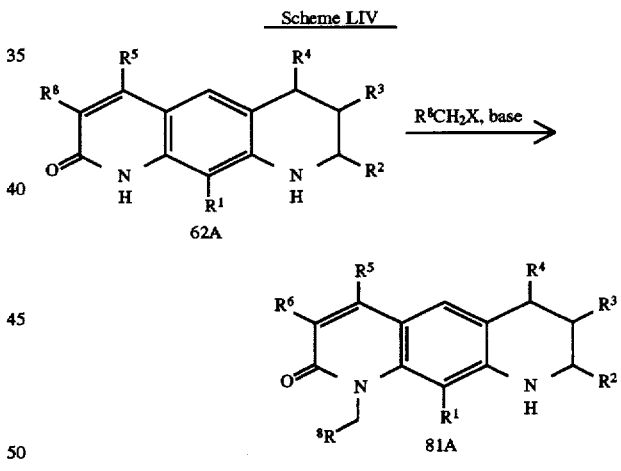

The process of Scheme LIV involves the deprotonation of a compound of structure 62A with, for example, sodium hydride, followed by treatment with an alkylating agent such as iodomethane to afford a compound of structure 81A.

Scheme LV

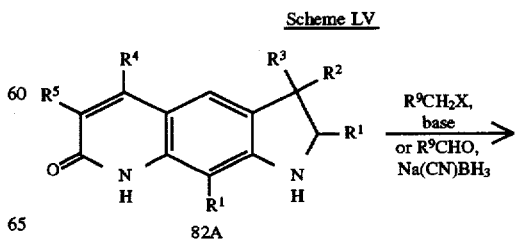

The process of Scheme LIII begins with the reaction of an aniline (structure 58A) with a propargyl acetate in the presence of a copper salt such as copper(I) chloride to afford a compound of structure 75A. The nitrogen atom is then protected by treatment with a base, for example 4-dimethylaminopyridine, followed by the addition of an acylating agent such as di-tert-butyldicarbonate. Hydroboration of the olefin with, for example, borane-tetrahydrofuran, followed by an oxidative work-up with, for -continued
Scheme LV

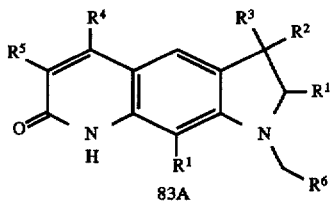

The process of Scheme LV involves the conversion of a compound of structure 82A into a compound of structure 83A by alkylation of the nitrogen atom, which can be accomplished in one of two ways. Treatment of a compound of structure 82A with a base, such as sodium hydride, and an alkylating agent, such as benzyl bromide, affords a compound of structure 83A. Alternatively, treatment of a compound of structure 82A with an aldehyde, for example acetaldehyde or paraformaldehyde, in the presence of a reducing agent, for example sodium cyanoborohydride or sodium (triacetoxy)borohydride, affords a compound of structure 83A.

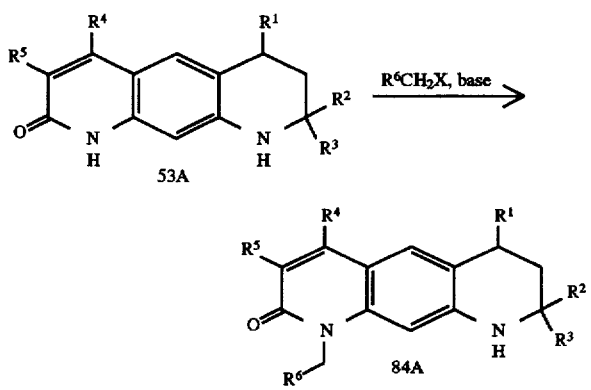

The process of Scheme LVI involves the deprotonation of a compound of structure 53A with, for example, sodium hydride, followed by treatment with an alkylating agent such as iodomethane to afford a compound of structure 84A.

It will be understood by those skilled in the art that certain modifications can be made to the above-described methods that remain within the scope of the present invention.

In a further aspect, the present invention provides several novel processes for the preparation of the compounds of the present invention. Each of these processes is illustrated in one or more of the Schemes shown above, and is described with particularity as follows.

Process 1 is depicted in Scheme II and begins with the conversion of a 4-bromoaniline (Compound 6) to 6-bromo-1,2-dihydro-2,2,4-trimethylquinoline (Compound 7) by treatment with acetone (0.01M to 10M) and 0.01–100 mol % of one or more catalysts (for example, para-toluenesulfonic acid, sulfuric acid, hydrochloric acid, boron trifluoride etherate, magnesium sulfate, or iodine) at –20° C. to 300° C. Additives that inhibit polymerization (for example, 4-tert-butylcatechol) can also be used in addition to the catalyst(s). The aniline nitrogen is then protected. For example, protection as the t-butyl carbamate requires treatment of a solution (typical solvents include toluene, ether, THF) of Compound 7 with a strong base (for example, n-butyllithium, sodium hydride, potassium hydride) at –100° C. to 100° C., followed by reaction with di-t-butyldicarbonate at –100° C. to 100° C. to afford the 6-substituted-1,2-dihydro N-1 protected quinoline (Compound 8). The important steps of process I then begins when the halogen (e.g., bromine) of Compound 8 is replaced with either lithium by a lithium-halogen exchange reaction by treatment of a solution (typical solvents include toluene, ether, THF) of Compound 8 with an alkyllithium (for example, t-butyllithium, n-butyllithium) at –100° C. to 100° C., or with a reactive metal(s), such as magnesium by treatment with magnesium metals (turnings or powder) or zinc, and either iodine or ethylene dibromide in an inert solvent (typical solvents include ether, THF, pentane) at –20° C. to 200° C. The organolithium or organomagnesium intermediate is then allowed to react with a trialkylborate (for example, trimethylborate, triisopropylborate) at –100° C. to 100° C. The organoborate intermediate is hydrolyzed with acid (for example, dilute aqueous hydrochloric acid or sulfuric acid) at –40° C. to 100° C. to afford the boronic acid (e.g., 6-boro-1,2-dihydro N-1 protected quinoline: Compound 9). Alternatively, the organolithium or organomagnesium intermediate may be treated with an organotin species (for example, trimethyltin chloride, tributyltin chloride, etc.) at –100° C. to 200° C. to afford a trialkyltin quinolinoyl compound, a species useful in the coupling processes described in J. K. Stille et al., "4-Methoxy4'-nitrobiphenyl", Organic Syntheses 1992, 71, 97, and T. N. Mitchell, "Palladium-Catalyzed Reactions of Organotin Compounds" Synthesis 1992, 803, the disclosures of which are herein incorporated by reference. Treatment of a solution (typical solvents include toluene, DME, DMF) of Compound 9 with a coupling partner (an aryl, heteroaryl, or vinylbromide; an aryl, heteroaryl, or vinyliodide; or an aryl, heteroaryl, or vinyl triflate) in the presence of a catalytic amount of a palladium species (for example, tetrakis (triphenylphosphine)-palladium, allylpalladium chloride dimer, bis(triphenylphosphine)palladium dichloride), and aqueous base (for example, sodium carbonate, potassium carbonate) at –40° C. to 200° C. affords a 6-substituted-1, 2-dihydro N-1 protected quinoline (structure 10). Deprotection of a compound of structure 10, for example, with acid (for example, trifluoroacetic acid) at –80° C. to 200° C., affords the corresponding 6-substituted-1,2-dihydroquinoline (e.g., structure 4).

Process 2 is depicted in Scheme III and involves the treatment of a solution (typical solvents include toluene, DME, DMF) of 6-halo-1,2-dihydro N-1 protected quinoline Compound 8) with an organoboron species (for example, phenylboronic acid, 3-nitrophenylboronic acid) or an organotin species (such as tributylphenyl tin or trimethyl(4-methoxyphenyl) tin) in the presence of a coupling partner and a catalytic amount of a palladium species (for example, tetrakis (triphenylphosphine)palladium, allylpalladium chloride dimer, bis(triphenylphosphine)palladium dichloride), and aqueous base (for example, sodium carbonate, potassium carbonate) at –40° C. to 200° C. to afford a 6-substituted-1,2-dihydro N-1 protected quinoline (structure 10). Deprotection of a compound of structure 10 with acid (for example, trifluoroacetic acid) at –80° C. to 200° C. affords the 6-substituted-1,2-dihydroquinoline (structure 4).

Process 3 is depicted in Scheme XI and involves the preparation of benzocoumarins from acyclic precursors. Thus, an ortho-bromoanisole (structure 36) is lithiated with an alkyllithium (for example, n-butyllithium, t-butyllithium) at –100° C. to 80° C. in an inert solvent (typical solvents include toluene, ether, THF), and allowed to react with a trialkylborate (for example, trimethylborate, triisopropylborate) at −100° C. to 100° C. Hydrolysis of the intermediate with acid (for example, dilute hydrochloric acid or sulfuric acid) at −40° C. to 100° C., affords the corresponding 2-methoxyphenyl boronic acid (structure 37). Alternatively, the organolithium or organomagnesium intermediate may be treated with a trialkyltin halide (for example, trimethyltin chloride, tributyltin chloride, etc.) at −100° C. to 200° C. to afford a trialkyltin aryl compound, a species useful in the coupling processes described above in Process 1. The important steps of process 3 begin with the palladium-catalyzed coupling of a 2-methoxyphenyl boronic acid (structure 37) with a 2-halo-5-nitrobenzoic acid derivative (typical derivatives include the acid; any one of a number of esters, including methyl, ethyl, allyl, t-butyl, phenyl; or any one of a number of amides, including dimethyl, methyl, diallyl, allyl, dibenzyl) with a palladium catalyst (for example, tetrakis(triphenylphosphine) palladium, allylpalladium chloride dimer, bis (triphenylphosphine)palladium dichloride), and aqueous base (for example, sodium carbonate, potassium carbonate) at −40° C. to 200° C. affords the biaryl carboxylate (structure 39). The product obtained from use of the acid as a coupling partner may be used directly; alternatively, deprotection by hydrolysis of the ester or the amide is accomplished with aqueous base (for example, potassium hydroxide or sodium hydroxide) or aqueous acid (for example, trifluoroacetic acid, hydrochloric acid, sulfuric acid) at −60° C. to 300° C. The acid is converted to the acid chloride with, for example, thionyl chloride in an inert solvent (typical solvents include methylene dichloride, toluene, or 1,2-dichloroethane) at −80° C. to 300° C. Intramolecular cyclization (acylation) is then effected by treatment of a solution of the acid chloride in an inert solvent (typical solvents include methylene dichloride, toluene, or 1,2-dichloroethane) with a Lewis acid (for example, aluminum trichloride, boron trifluoride) at −80° C. to 300° C. to yield the nitrobenzocoumarin. Reduction of the nitro group of the nitrobenzocoumarin with, for example, 1–200 atmospheres of hydrogen over a metal catalyst (for example, Pd/C, PtO$_2$), affords the desired aminobenzocoumarin (structure 40). Treatment of compounds of structure 40 with acetone and a catalyst such as iodine affords the coumarino[3,4-f]quinoline (structure 41), as described above in Process 1. The addition of an organometallic reagent, for example an organolithium or organomagnesium reagent, to a solution of a compound of structure 41 in an inert solvent at −100° C. to 100° C. affords an adduct. This adduct may be reduced by treatment of a solution of the adduct in an inert solvent (such as dichloromethane or toluene) with a strong protic or Lewis acid and a trialkylsilane, (for example, boron trifluoride or trifluoroacetic acid and triethylsilane or methyldiphenylsilane) at −80° C. to 200° C., to afford a 5H-chromeno[3,4-f]quinoline (Compound of structure 42).

Process 4 is depicted in Scheme XIII and involves the addition of an organometallic reagent, for example an organomagnesium or organolithium reagent, to a solution of a compound of structure 41 (i.e., a coumarino[3,4-f]quinoline) in an inert solvent (typical solvents include ether, THF, toluene) at −100° C. to 100° C. Dehydration of the intermediate thus derived may be effect by treatment of a solution of the intermediate (typical solvents include in dichloromethane, ethanol, or toluene) with an acid (for example, para-toluenesulphonic acid, methanesulphonic acid), to afford compounds of structure 45 (i.e., 5H-chromeno[3,4-f]quinolines).

Process 5 is depicted in Scheme XVII and begins with the acylation of a 3-nitroaryl, e.g., a 3-nitrophenol (structure 64, Y=O), 3-nitroaniline (structure 64, Y=NH), or 3-nitrothiophenol (structure 64, Y=S), with an acylating agent (for example, di-tert-butyl dicarbonate or trimethylacetyl chloride), either with or without the addition of a base (for example, 4-dimethylaminopyridine, triethylamine, pyridine) in an inert solvent (typical solvents include dichloromethane, THF, toluene) at −100° C. to 200° C., to afford the 5-protected 3-nitroaryl compound of structure 65. Reduction of the nitro group with, for example, 1-200 atmospheres of hydrogen over a metal catalyst (for example, Pd/C, PtO$_2$), affords the corresponding 5-protected 3-aminoaryl (structure 66). Treatment of a compound of structure 66 with acetone and a catalyst such as iodine and addition of a 1,2-dihydroquinoline affords the 5-protected 1,2-dihydroquinoline compound of structure 67, as described above in Process 1. Deprotection, for example, by either acid (for example, hydrochloric acid, trifluoroacetic acid, sulfuric acid) or base (for example, sodium hydroxide) at −40° C. to 300° C., followed by treatment of a solution (typical solvents include ethanol, toluene, methanol) of the corresponding aniline or phenol with a β-keto ester (structure 68) in the presence of a Lewis acid (for example, zinc chloride, boron trifluoride, aluminum trichloride) at −40° C. to 300° C., affords one or more of the four linear tricyclic 1,2-dihydroquinoline compounds (structures 57, 69, 70, and 71). A compound of structure 69 may be converted to a compound of structure 57 by treatment of a solution (typical solvents include toluene, dichloromethane) of a compound of structure 69 with an acid (for example, para-toluenesulphonic acid, hydrochloric acid) at −40° C. to 300° C. In addition, a compound of structure 71 may be converted to a compound of structure 57 by treatment of a solution (typical solvents include toluene, dichloromethane) of a compound of structure 71 with, for example, para-chlorophenol.

Process 6 is a modification of Process 5. Thus, a solution (typical solvents include ether, THF, toluene) of a 3-aminoaryl, preferably 3-amino thioaryl, is treated with a strong base (for example, sodium hydride, n-butyllithium) at −100° C. to 100° C., followed by the addition of an acylating agent (typical acylating agents include di-t-butyl dicarbonate, trimethylacetyl chloride, acetic anhydride) at −100° C. to 200° C., to afford the corresponding the corresponding 5-protected 3-aminoaryl compound of structure 66 (Y=S). The conversion of a compound of structure 66 (Y=S) to the linear tricyclic 1,2-dihydroquinoline compounds of structures 57, 69, 70 and 71 (Y=S) is accomplished as described above in Process 5.

Process 7 is depicted in Scheme XLVI, and also is included as parts of Schemes XLVIII, LII, and LIII. Process 7 begins with the nitration of a 1,2,3,4-tetrahydroquinoline (for example, a compound of structure 51A in Scheme XLVI, or of structure 60A in Scheme XLVIII, etc) with a nitrating agent. For example a mixture of sulfuric acid and nitric acid is added to a solution of the tetrahydroquinoline in sulfuric acid or sulfuric acid and a second, inert solvent such as nitromethane, at −80° C. to +40° C. The nitro group of the resulting 7-nitro-1,2,3,4-tetrahydroquinoline is then reduced by hydrogenation over a metal catalyst (for example, Pd/C, PtO$_2$) under 1–200 atmospheres of hydrogen, to afford the corresponding aniline (a compound of structure 52A in Scheme XLVI or of structure 72A in Scheme LII, for example). Treatment of a solution (typical solvents include ethanol, toluene, methanol) of the aniline with a b-keto ester (structure 68) in the presence of a Lewis acid (for example, zinc chloride, boron trifluoride, aluminum trichloride) at −40° C. to +300° C., affords the desired quinoline, a compound of structure 53A in Scheme XLVI, or of structure 73A in Scheme LII, etc.

In yet another aspect, the present invention provides novel intermediates useful in the preparation of the steroid modulator compounds of the present invention. The intermediates of the present invention are defined as those having the formulae:

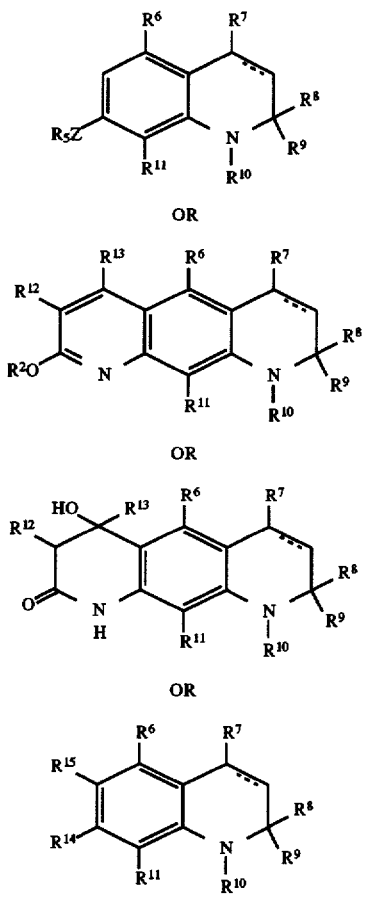

wherein:

Z is O, S, or $NR^1$, where $R^1$ is hydrogen, $R^2C=O$, $R^2C=S$, $R^3OC=O$, $R^3SC=O$, $R^3OC=S$, $R^3SC=S$ or $R^3R^4NC=O$, where $R^2$ is hydrogen, a $C_1-C_6$ alkyl or perfluoroalkyl, optionally substituted allyl or aryl methyl alkenyl, alkynyl, aryl or heteroaryl, and where $R^3$ and $R^4$ each independently are hydrogen, a $C_1-C_6$ alkyl, optionally substituted allyl, arylmethyl, aryl or heteroaryl;

$R^5$ is hydrogen, $R^2C=O$, $R^2C=S$, $R^3OC=O$, $R^3SC=O$, $R^3OC=S$, $R^3SC=S$, or $R^3R^4NC=O$, where $R^2$, $R^3$ and $R^4$ have the same definitions as given above;

$R^6$ is hydrogen, a $C_1-C_6$ alkyl, optionally substituted allyl, aryl methyl, alkenyl, alkynyl, aryl, heteroaryl, $R^3O$, $HOCH_2$, $R^3OCH_2$, F, Cl, Br, I, cyano, $R^3R^4N$ or perfluoroalkyl, where $R^3$ and $R^4$ have the same definitions as given above;

$R^7$ through $R^9$ each independently are hydrogen, a $C_1-C_6$ alkyl, allyl or optionally substituted allyl, arylmethyl, alkynyl, alkenyl, aryl, or heteroaryl, or $R^8$ and $R^9$ taken together form a three- to seven-membered carbocyclic or heterocyclic ring;

$R^{10}$ is hydrogen, a $C_1-C_6$ alkyl, optionally substituted allyl, arylmethyl, aryl, or heteroaryl, $R^2C=O$, $R^2C=S$, $R^3OC=O$, $R^3SC=O$, $R^3OC=S$, $R^3SC=S$ or $R^3R^4NC=O$, where $R^2$ through $R^4$ have the same definitions as given above;

$R^{11}$ and $R^{12}$ each independently represent hydrogen, a $C_1-C_6$ alkyl, substitute substituted allyl, aryl methyl, alkenyl, alkynyl, aryl, heteroaryl, $R^3O$, $HOCH_2$, $R^3OCH_2$, F, Cl, Br, I, cyano, $R^3R^4N$ or perfluoroalkyl, where $R^3$ and $R^4$ have the same definitions as given above;

$R^{13}$ is hydrogen, a $C_1-C_6$ alkyl, optionally substituted allyl, aryl methyl, alkenyl, alkynyl, aryl, heteroaryl, $R^3O$, $HOCH_2$, $R^3OCH_2$, $R^3R^4N$, $CF_2Cl$, $CF_2OR^3$ or perfluoroalkyl where $R^3$ and $R^4$ have the same definitions as given above;

$R^{14}$ is hydrogen, a $C_1-C_6$ alkyl, optionally substituted allyl, aryl methyl, alkenyl, alkynyl, aryl, heteroaryl, $R^3O$, $HOCH_2$, $R^3OCH_2$, F, Cl, Br, I, cyano, $R^3R^4N$ or perfluoroalkyl where $R^3$ and $R^4$ have the same definitions as given above; and $R^{15}$ is F, Cl, Br, I, $B(OR^{16})_2$, $SnR^{17}R^{18}R^{19}$ or $OSO_2R^{20}$, where $R^{16}$ is hydrogen or a $C_1-C_6$ alkyl, $R^{17}$ through $R^{19}$ each independently represent a $C_1-C_6$ alkyl, $R^{20}$ or heteroaryl, $R^{20}$ is a $C_1-C_6$ alkyl, perfluoroalkyl, aryl, or heteroaryl, and $R^2$ has the same definition as given above.

Representative intermediate compounds useful in the preparation of the steroid modulator compounds of the present invention include: 1,2-Dihydro-2,2,4-trimethyl-5-coumarino[3,4-f]quinoline (Compound 159); 9-Fluoro-1,2-dihydro-2,2,4-trimethyl-5-coumarino[3,4-f]quinoline (Compound 207); 8-Fluoro-1,2-dihydro-2,2,4-trimethyl-5-coumarino[3,4-f]quinoline (Compound 208); 9-Chloro-1,2-dihydro-2,2,4-trimethyl-5-coumarino[3,4-f]quinoline (Compound 209); 8-Ethoxy-1,2-dihydro-2,2,4-trimethyl-6-trifluoromethyl-8-pyrido[5,6-g]quinoline (Compound 248); and 1,2,6,7-Tetrahydro-6-hydroxy-2,2,4-trimethyl-6-trifluoromethyl-8-pyridono[5,6-g]quinoline (Compound 249).

The compounds of the present invention also includes racemate, stereoisomers and mixtures of said compounds, including isotopically-labeled and radio-labeled compounds. Such isomers can be isolated by standard resolution techniques, including fractional crystallization and chiral column chromatography.

As noted above, any of the steroid modulator compounds of the present invention can be combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson) hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when radio- or isotopically-labeled as ligands for use in assays to determine the presence of PR, AR, ER, GR or MR in a cell background or extract. They are particularly useful due to their ability to selectively activate progesterone and androgen receptors, and can therefore be used to determine the presence of such receptors in the presence of other steroid receptors or related intracellular receptors.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice, and then separating out the bound ligand/receptor combination by separation techniques which are known to those of skill in the art. These techniques include column separation, filtration, centrifugation, tagging and physical separation, and antibody complexing, among others.

The compounds and pharmaceutical compositions of the present invention can advantageously be used in the treatment of the diseases and conditions described herein. In this regard, the compounds and compositions of the present invention will prove particularly useful as modulators of human fertility, and in the treatment of female and male sex steroid-dependent diseases and conditions such as hormone replacement therapy, dysfunctional uterine bleeding, endometriosis, leiomyomas, acne, male-pattern baldness, osteoporosis, prostatic hyperplasia and various hormone-dependent cancers, such as cancers of the breast, ovaries, endometrium and prostate. The GR and MR active compounds and compositions of the present invention will also prove useful as affectors of carbohydrate, protein and lipid metabolism, electrolyte and water balance, as well as modulators of the functions of the cardiovascular, kidney, central nervous, immune, skeletal muscle and other organ and tissue systems.

The compounds and pharmaceutical compositions of the present invention possess a number of advantages over previously identified steroidal and non-steroidal compounds.

Furthermore, the compounds and pharmaceutical compositions of the present invention possess a number of advantages over previously identified steroid modulator compounds. For example, the compounds are extremely potent activators of PR and AR, preferably displaying 50% maximal activation of PR and/or AR at a concentration of less than 100 nM, more preferably at a concentration of less than 50 nM, more preferably yet at a concentration of less than 20 nM, and most preferably at a concentration of 10 nM or less. Also, the selective compounds of the present invention generally do not display undesired cross-reactivity with other steroid receptors, as is seen with the compound mifepristone (RU486; Roussel Uclaf), a known PR antagonist that displays an undesirable cross reactivity on GR and AR, thereby limiting its use in long-term, chronic administration. In addition, the compounds of the present invention, as small organic molecules, are easier to synthesize, provide greater stability and can be more easily administered in oral dosage forms than other known steroidal compounds.

The invention will be further illustrated by reference to the following non-limiting Examples.

EXAMPLE 1

1,2,3,4-Tetrahydro-2,2,4-trimethyl-6-phenylquinoline Compound 100, structure 5 of Scheme I, where $R^1$=phenyl)

In a flame-dried round bottom (r.b.) flask equipped with a magnetic stir bar was dissolved 1,2-dihydro-2,2,4-trimethyl-6-phenylquinoline (15 mg, 60 μmol) and 10% Pd on C (10 mg) in anhydrous $CH_2Cl_2$ (3 mL). The flask was repeatedly evacuated and filled with $N_2$ to remove any residual $O_2$ and then $H_2$ gas was introduced. The solution was stirred at room temperature for 18 h, filtered though a Celite™ plug, and concentrated in vacuo to afford 7.8 mg (52%) of Compound 100 as an off white solid. Data for Compound 100: $R_f$=0.71 (silica gel, hexane/EtOAc, 3:1). $^1$H NMR (400 MHz, $CDCl_3$): 7.53 (d, J=4.0, 1H), 7.47 (m, 2H), 7.35 (m, 2H), 6.53 (d, J=4.1, 1H), 3.71 (bs, 1H), 2.98 (m, 1H), 1.79 (dd, J=4.0, 8.0, 1H), 1.41 (d, J=4.0, 3H), 1.23 (d, J=8.0, 6H)

EXAMPLE 2

12-Dihydro-2,2,4-trimethyl-6-(1,2,3-thiadiazol-5-yl) quinoline (Compound 101, structure 4 of Scheme I, where $R^1$=2,3,4-thiadiazolyl)

To a dry 250-mL r.b. flask equipped with a magnetic stirring bar and a water cooled reflux condenser was added 4-(1,2,3-thiadiazolyl)aniline (0.990 g, 5.59 mmol) along with a catalytic amount of $I_2$ (~50 mg) dissolved in acetone (HPLC grade, 70 mL). The resulting red solution was heated at reflux with constant stirring for 60 h. The reaction was followed by TLC (hexane/EtOAc, 3:1, visualized by short wave UV, the product appearing as a bright blue spot). After cooling to room temperature (rt), Celite™ (2.0 g) was added and the mixture was concentrated under reduced pressure to give a free flowing powder which was purified by silica gel chromatography (70 g silica gel 60, 240 mesh, hexane/EtOAc, 5:1) to afford 258 mg (18%) of Compound 101 as a light yellow solid: $R_f$=0.35 (hexane/ethyl acetate, 3:1). Data for Compound 101: $^1$H NMR (400 MHz, $C_6D_6$): 7.86 (d, J=2.0, 1H), 7.70 (dd, J=8.4, 2.1, 1H), 7.34 (s, 1H), 6.19 (d, J=8.4, 1H), 5.09 (s, 1H), 3.29 (br s, 1H), 1.87 (d, J=1.2, 3H), 1.02 (s, 6H).

EXAMPLE 3

1,2-Dihydro-2,2,4-trimethyl-6-(1,3-oxazol-5-yl)quinoline Compound 102 structure 4 of Scheme I, where $R^1$=5-oxazolyl)

This compound was prepared using the procedure for EXAMPLE 2 from 4-(1,3-oxazol-5-yl)aniline (460 mg, 2.87 mmol) to afford Compound 102 (299 mg, 1.22 mmol, 43%) as a light brown solid: $R_f$=0.23 (silica gel, hexane/EtOAc, 3:1). Data for Compound 102: $^1$H NMR (400 MHz, $C_6D_6$): 7.40 (d, J=1.99, 1H), 7.32 (s, 1H), 7.26 (dd, J=8.2, 2.0, 1H), 7.14 (s, 1H), 6.10 (d, J=8.4, 1H), 5.06 (s, 1H), 3.23 (br s, 1H), 1.79 (d, J=1.2, 3H), 1.00 (s, 6H),

EXAMPLE 4

6-(4,5-Dichloroimidazol-1-yl)-1,2-dihydro-2,2,4-trimethylquinoline (Compound 103, structure 4 of Scheme I, where $R^1$=4,5-dichloroimidazol-1-yl)

This compound was prepared using the procedure for EXAMPLE 2 from 4-(4,5-dichloroimidazol-1-yl)aniline (1.0 g, 44 mmol) to afford Compound 103 (234 mg, 17%) as an off-white solid: $R_f$=0.26 (silica gel, hexane/ethyl acetate, 3:1). Data for Compound 103: $^1$H NMR (400 MHz, $C_6D_6$) 7.12 (s, 1H), 6.66 (d, J=2.3, 1H), 6.44 (dd, J=8.4, 2.3, 1H), 6.44 (dd, J=8.4, 2.4, 1H), 5.90 (d, J=8.4, 1H), 5.05 (s, 1H), 3.20 (br s, 1H), 1.66 (d, J=1.4, 3H), 0.99 (s, 6H),

EXAMPLE 5

6-(4-Bromo-1-methylpyrazol-3-yl)-1,2-dihydro-2,2,4-trimethylquinoline (Compound 104, structure 4 of Scheme I, where $R^1$=4-bromo-1-methylpyrazol-3-yl)

This compound was prepared using the procedure of EXAMPLE 2 from 4-(4-bromo-1-methylpyrazol-3-yl)aniline (1.0 g, 44 mmol) to afford Compound 104 (540 mg, 41%) as an off-white solid. Data for Compound 104: $R_f$=0.23 (silica gel, hexane/EtOAc, 3:1). $^1$H NMR (400 MHz, $C_6D_6$) 7.64 (s, 1H), 7.01 (d, J=1.8, 1H), 6.90 (dd, J=8.0, 1.8, 1H) 6.10 (d, J=7.9, 1H), 5.04 (s, 1H), 3.37 (s, 3H), 3.23 (br s, 1H), 1.75 (d, J=1.2, 3H), 0.99 (s, 6H).

EXAMPLE 6

1,2-Dihydro-2,2,4-trimethyl-6-(3-pyridyl)quinoline (Compound 105, structure 4 of Scheme I, where $R^1$=3-pyridyl)

3-(4-Nitrophenyl)pyridine (structure 2, where $R^1$=3-pyridyl)

To a solution of $H_2SO_4$ (6 mL) cooled in an ice bath to 0° C. was added 3-phenylpyridine (1.0 g, 6.4 mmol). The orange-red solution was vigorously stirred while $HNO_3$ (1 mL) was slowly added dropwise to give a cloudy light yellow solution. After stirring at room temperature for 20 min the solution was carefully poured into a beaker filled with ice (200 g). The solution was neutralized with 20% NaOH to give a cloudy white suspension which was extracted with EtOAc (3×150 mL). The organic layers were combined, washed with brine (2×50 mL), dried ($NaSO_4$) and concentrated in vacuo to give the desired product (1.2 g, 99%) as a light yellow solid. Data for 3-(4-nitrophenyl) pyridine: $R_f$=0.47 (silica gel, methanol/$CHCl_3$, 5/95); $^1$H NMR (400 MHz, acetone-$d_6$) 8.99 (s, 1H), 8.67 (s, 1H), 8.37 (d, J=7.0, 2H), 8.18 (m, 1H), 8.02 (d, J=7.0, 2H), 7.53 (m, 1H).

3-(4-Aminophenyl)pyridine (structure 3, where $R^1$=3-pyridyl)

In a flame-dried r.b. flask equipped with a magnetic stirring bar was dissolved 3-(4-nitrophenyl)pyridine (131 mg, 0.655 mmol) and 10% Pd on C (10 mg) in anhydrous $CH_2Cl_2$ (3 mL) was added. The flask was repeatedly evacuated and filled with $N_2$ to remove any residual $O_2$, and then $H_2$ gas was introduced. The solution was stirred at rt for 18 h, filtered though a Celite™ plug and concentrated in vacuo to give the desired amine (105 mg, 95%) as an off-white solid. Data for 3-(4-aminophenyl)pyridine: $R_f$=0.17 (silica gel, methanol/$CHCl_3$, 5/95); $^1$H NMR (400 MHz, acetone-$d_6$) 8.77 (d, J=2.3, 1H), 8.42 (dd, J=6.4, 1.6, 1H), 7.88 (m, 1H), 7.41 (d, J=8.5, 2H), 7.33 (m, 1H), 6.78 (d, J=8.5, 2H), 4.86 (br s, 2H).

1,2-Dihydro-2,2,4-trimethyl-6-(3-pyridyl)quinoline (Compound 105, structure 4, where $R^1$=pyridyl)

This compound was prepared using the procedure of EXAMPLE 2 from 3-(4-aminophenyl)pyridine (105 mg, 0.62 mmol) to afford Compound 105 (0.5 mg, 0.3%) as an off-white solid. Data for Compound 105: $R_f$=0.44 (silica gel, hexane/EtOAc, 3:1); $^1$H NMR (400 MHz, $CDCl_3$) 9.13 (s, 1H), 8.58 (d, J=2.5, 1H), 7.48 (m, 1H), 7.36 (s, 1H), 7.26 (s, 1H), 6.96 (s, 1H), 6.82 (m, 1H), 6.26 (d, J=4.0, 1H), 5.12 (s, 1H), 1.80 (s, 3H), 1.06 (s, 6H),

EXAMPLE 7

6-(4-Fluorophenyl)-1,2,-dihydro-2,2,4-trimethylquinoline (Compound 106, structure 4 of Scheme II, where $R^1$=4-fluorophenyl)

6-Bromo-1,2-dihydro-2,2,4-trimethylquinoline (Compound 7)

A dry 500 mL r.b. flask equipped with a magnetic stir bar and a reflux condenser was charged with 4-bromoaniline (35.7g, 0.208 mol) and acetone (250 mL, Aldrich reagent grade). To this solution, $I_2$ (2.637 g, 0.05 equiv) was added turning the solution bright red. The mixture was heated to reflux with constant stirring for 4 days (approximately 90 hours). The reaction was monitored by TLC (20% ethyl acetate/methylene chloride; observed starting material and product under short wave UV). As judged by TLC, 50% of the starting material was consumed during the course of the reaction. The reaction mixture was cooled to room temperature and quenched with saturated $Na_2S_2O_3$ (200 mL). The aqueous mixture was partitioned into 2 phases using ethyl acetate (200 mL). The organic layer was rinsed with saturated $Na_2S_2O_3$ (3×75–100 mL) and brine (100 mL). The combined aqueous layers were extracted with ethyl acetate (100 mL). The organic layers were combined and dried over anhydrous sodium sulfate. The crude dark material was purified by flash chromatography (800 mL silica, 50% ethyl acetate/methylene chloride) followed by re, crystallization of isolated quinoline (hexane) yielding 8.22 g (15%) of Compound 7 (white crystals). Data for Compound 7: $^1$H NMR (400 MHz, acetone-$d_6$) 7.06 (d, J=2, 1H), 6.99 (dd, J=8, 2, 1H), 6.42 (d, J=8, 1H), 5.36 (s, 1H), 5.28 (br s, 1H) 1.92 (d, J=2, 3H), 1.24 (s, 6H).

6-Bromo-1-tert-butyloxycarbonyl-1,2-dihydro-2,2,4-trimethylquinoline (Compound 8)

An oven dried 250 mL r.b. flask equipped with a magnetic stirrer and a nitrogen inlet was charged with Compound 7 (4.04 g, 16.0 mmol). The white crystals were dissolved in 40 mL THF. The clear solution was cooled to −78° C. with constant stirring. A thermocouple was used to monitor the reaction temperature. n-Butyllithium (11.2 mL, 16.8 mmol, 1.50M) was added slowly by syringe over a period of 15 min (temperature maintained between −70° C. and −65° C.) turning the reaction mixture bright yellow. The reaction was allowed to continue stirring at −75° C. for an additional 15 min. The reaction was warmed to 0° C. and the di-tert-butyl-dicarbonate (3.846 g, 17.62 mmol) was added in one portion. NOTE: a significant exotherm was observed with the addition of the dicarbonate from 0° C. to 12° C. The reaction was monitored by TLC as it warmed to rt (50% ethyl acetate/methylene chloride) (3–5 hours). The reaction mixture was quenched with 1.0M $Na_2S_2O_3$ (100 mL) and partitioned with ethyl acetate (100 mL). The organic layer was rinsed with 1.0M $Na_2S_2O_3$ (2×50 mL) and brine (100 mL). The aqueous layers were combined and back extracted with methylene chloride (75 mL). The organic layers were combined and dried ($Na_2SO_4$). The crude mixture was purified by flash chromatography (400 mL silica, 2% ethyl acetate/hexane) to provide Compound 8 (3.765 g, 66.7%) as an oil. Data for Compound 8: $^1H$ NMR (400 MHz, acetone-$d_6$) 7.30 ppm (s, 1H), 7.28 (d, J=8, 1H), 7.11 (d, J=8, 1H), 5.60 (s, 1H), 2.00 (s, 3H), 1.49 (s, 9H), 1.48 (s, 6H).

General Method 1: biaryl coupling of an aryl boronic acid with 6-Bromo-1,2-dihydro-2,2,4-trimethylquinoline (Compound 8)

A 25 mL recovery flask equipped with a magnetic stir bar was charged with Compound 8 (1.0 equiv) in toluene (0.1M). Tetrakis(triphenylphosphine)palladium (0.03 equiv), boronic acid ($R^1B(OH)_2$) (1.3 equiv, 0.1M in ethanol) and potassium carbonate (2.0 equiv, 2.0M) were added to the reaction flask sequentially under a nitrogen atmosphere. A reflux condenser was fitted to the flask and the cloudy reddish solution was stirred rapidly and heated to reflux for about 4 h until the starting material had been completely consumed as judged by TLC (15% ethyl acetate/ hexane). The product mixture was then cooled to room temperature and quenched with saturated $NH_4Cl$ (4–5 mL). Ethyl acetate (5 mL) was used to partition the mixture. The organic layer was rinsed with saturated $NH_4Cl$ (2×5 mL). The aqueous layers were extracted with ethyl acetate (5 mL). The organic layers were combined, dried ($Na_2SO_4$), and purified as indicated.

6-(4-Fluorophenyl)-1,2-dihydro-2,2,4-trimethylquinoline (Compound 106, structure 4, where $R^1$=4-fluorophenyl)

This compound was prepared according to General Method 1 from Compound 8 (119.3 mg, 0.472 mmol) and commercially available 4-fluorobenzeneboronic acid (84.1 mg, 0.601 mmol, Lancaster). The product, Compound 106 (5.0 mg, <1%), was isolated and purified by reverse phase HPLC (ODS, 80% methanol/water, 3.0 mL/min). Data for Compound 106: $^1H$ NMR (400 MHz, acetone-$d_6$) 7.57 ppm (m, 2H), 7.27 (d, J=2, 1H), 7.20 (dd, J=12, 2, 1H), 7.13 (dd, J=16, 8, 2H), 6.57 (d, J=8, 1H), 5.38 (s, 1H), 5.26 (br s, 1H), 2.03 (d, J=1.6, 3H), 1.28 (s, 6H).

EXAMPLE 8

1,2-Dihydro-6-(3-trifluoromethylphenyl)-2,2,4-trimethylquinoline (Compound 107, structure 4 of Scheme II, where $R^1$=3-trifluoromethylphenyl)

This compound was prepared according to General Method 1 (EXAMPLE 7) from Compound 8 (100.0 mg, 0.396 mmol) and commercially available 3-trifluoromethylbenzeneboronic acid (97.8 mg, 0.515 mmol, Lancaster), Compound 107 (2.0 mg, <1%) was isolated and purified by reverse phase high pressure liquid chromatography (HPLC) (ODS, 80% methanol/water, 3.0 mL/min). Data for Compound 107: $^1H$ NMR (400 MHz, acetone-$d_6$) 7.86 (d, J=8, 1H), 7.85 (s, 1H), 7.60 (dd, J=16, 8, 1H), 7.54 (d, J=8, 1H), 7.38 (d, J=2, 1H), 7.32 (dd, J=8, 2, 1H), 6.61 (d, J=8, 1H), 5.40 (s, 1H), 5.40 (s, 1H), 2.78 (s, 3H), 1.30 (s, 6H).

EXAMPLE 9

1,2-Dihydro-2,2,4-trimethyl-6-(4-nitrophenyl)quinoline (Compound 108, structure 4 of Scheme II, R=4-nitrophenyl) (1-tert-Butyloxycarbonyl-1,2-dihydro-2,2,4-trimethyl-6-quinolinyl)boronic acid (Compound 9)

A 25 mL r.b. flask, equipped with a magnetic stirring bar, was charged with Compound 8 (3.765 g, 10.67 mmol) under $N_2$. The oil was dissolved in 11 mL THF (anhydrous) and cooled to −78° C. tert-Butyllithium (12.6 mL, 21.4 mmol, 1.70M) was added by syringe over a period of 10 min (maintaining temperature below −70° C.) turning the reaction mixture from pale yellow to bright yellow. The reaction was allowed to continue at −75° C. until all of the starting material had been consumed as judged by TLC (15% ethyl acetate/hexane). Trimethyl borate (1.22 g, 1.33 mL, 11.7 mmol, 1.1 equiv) was added by syringe over 5–10 minutes (temperature between −70° C. and −65° C.). The reaction was monitored by TLC. Upon completion, the product mixture was quenched with saturated $NH_4Cl$ (200 mL). Addition of ethyl acetate (200 mL) partitioned the mixture into 2 phases. The organic phase was washed with saturated $NH_4Cl$ (100 mL) and brine (100 mL). The combined aqueous layers were extracted with ethyl acetate (100 mL). The organic layers were combined and dried ($Na_2SO_4$). The crude mixture was applied to a small column containing 200 mL silica and 15% ethyl acetate/hexane. The higher $R_f$ impurities were eluted with 2 L of 10% ethyl acetate/hexane. The boronic acid, Compound 9, was eluted with 500 mL ethyl acetate followed by 750 mL ethanol to provide 1.483 g (44%) of Compound 9. Data for Compound 9: $^1H$ NMR (400 MHz, acetone-$d_6$) 7.73 (d, J=1.2, 1H), 7.66 (dd, J=8, 1.2, 1H), 7.13 (d, J=8, 1H), 5.49 (s, 1H), 2.01 (d, J=1.6, 3H), 1.50 (s, 9H), 1.46 (s, 6H).

General Method 2: biaryl coupling of an arylbromide and (1-tert-butyloxycarbonyl-1,2-dihydro-2,2,4-trimethyl-6-quinolinyl)boronic acid (Compound 9)

A 25 mL recovery flask equipped with a magnetic stirring bar, was charged with aryl bromide (1.0 equiv, 0.1M in toluene). Tetrakis(triphenylphosphine)palladium (0.03–0.1 equiv), Compound 9 (1.0 equiv, 0.1M in ethanol) and $K_2CO_3$ (2.0 equiv, 2.0M) were added to the reaction flask sequentially under a nitrogen atmosphere. A reflux condenser was fitted to the flask and the cloudy reddish solution was stirred rapidly and heated to reflux for about 4 h until the starting material had been completely consumed as judged by TLC (15% ethyl acetate/hexane). The product mixture was then cooled to room temperature and quenched with saturated ammonium chloride (4–5 mL). Ethyl acetate (5 mL) was used to partition the mixture. The organic layer was rinsed with saturated ammonium chloride (2×5 mL). The aqueous layers were back extracted with ethyl acetate (5 mL). The organic layers were combined, dried ($Na_2SO_4$), and concentrated. A solution of the crude product in dichloromethane (0.1–0.3M) was cooled to −20° C. (ice/acetone) and treated with trifluoroacetic acid (10–40 equiv). Stirring was continued for 5–15 min and the reaction mixture was treated with excess saturated $NaHCO_3$. The product was extracted with ethyl acetate (3×). The extracts were washed with saturated $NaHCO_3$ (3×), combined, dried ($Na_2SO_4$), concentrated, and purified as indicated.

1,2-Dihydro-trimethyl-6-(4-nitrophenyl)quinoline (Compound 108, structure 4 of Scheme II, where $R^1$=4-nitrophenyl)

This compound was prepared according to General Method 2 from Compound 9 (36.6 mg, 0.115 mmol) and commercially available bromonitrobenzene (19.4 mg, 0.96 mmol, Aldrich). Compound 108 was isolated and purified by recrystallization from hexane to afford 9.4 mg (38%) of Compound 108. Data for Compound 108: $^1H$ NMR (400 MHz, $CDCl_3$) 8.23 (dd, J=8, 1.6, 2H), 7.65 (dd, J=8, 2, 2H), 7.33 (d, J=2, 1H), 7.31 (dd, J=8, 2.4, 1H), 6.51 (d, J=8, 1H), 5.38 (s, 1H), 3.94 (br s, 1H), 2.06 (d, J=1.2, 3H), 1.33 (s, 6H).

EXAMPLE 10

6-(2,3-Dichlorophenyl)-1,2-dihydro-2,2,4-trimethylquinoline (Compound 109, structure 4 of Scheme II, where $R^1$=2,3-dichlorophenyl)

This compound was prepared according to General Method 2 (EXAMPLE 9). From Compound 9 (68.0 mg, 0.21 mmol) and commercially available 2,3-dichlorobromobenzene (40.1 mg, 0.18 mmol, Lancaster) was obtained a crude product which was isolated and purified by reverse phase HPLC (ODS column, 97% methanol/water, 3.0 mL/min) to afford 20 mg (29%) of Compound 109. Data for Compound 109: $^1$H NMR (400 MHz, CDCl$_3$) 7.39 (dd, J=8, 1.6, 1H), 7.19 (dd, J=16, 8, 1H), 7.23 (dd, J=4, 1.6, 1H), 7.11 (d, J=1.6, 1H), 7.05 (dd, J=8, 1.6, 1H), 6.46 (d, J=8, 1H), 5.34 (s, 1H), 3.82 (br s, 1H), 1.99 (s, 3H), 1.32 (s, 6H).

EXAMPLE 11

1,2-Dihydro-6-(2-hydroxycarbonyl-4-nitrophenyl)-2,2,4-trimethylquinoline Compound 110, structure 4 of Scheme II where R$^1$=2-hydroxycarbonyl-4-nitrophenyl)

This compound was prepared according to the General Method 2 (EXAMPLE 9). From Compound 9 (68.0 mg, 0.21 mmol) and methyl 2-bromo-5-nitrobenzoate (446.6 mg, 1.72 mmol), 712 mg (92%) of the coupled quinolinylmethylester was obtained. A portion, 481 mg (1.06 mmol), of this intermediate was hydrolyzed using potassium hydroxide (149 mg, 2.6 mmol) in refluxing 4:1 methanol/water over a period of 3 h. The hydrolyzed product was isolated by extraction with ethyl acetate. The crude product was purified by SGC (200 mL silica, 30% ethyl acetate/hexane to 50% ethyl acetate/hexane) to afford 490 mg (guant) of N-tert-butyloxycarbonyl-1,2-dihydro-6-(2-hydroxycarbonyl-4-nitrophenyl)-2,2,4-trimethylquinoline. N-tert-butyloxycarbonyl-1,2-dihydro-6-(2-hydroxycarbonyl-4-nitrophenyl)-2,2,4-trimethylquinoline (49.0 mg, 0.11 mmol) was then treated with trifluoroacetic acid (0.34 mL, 4.5 mmol) to remove the tert-butyl carbonate group (1–5 minutes, 0° C.). The quenched reaction mixture was purified by silica gel chromatography (SGC) (50 mL silica, 40% ethyl acetate/hexane) to afford 1.2 mg (<1%) of Compound 110. Data for Compound 110: $^1$H NMR (400 MHz, acetone-d$_6$) 8.43 (d, J=2.4, 1H), 8.33 (dd, J=8, 2.4, 1H), 7.72 (d, J=8, 1H), 7.08 (d, J=2, 1H), 7.02 (dd, J=8, 2, 1H), 6.57 (d, J=8, 1H), 5.62 (br s, 1H), 5.41 (s, 1H), 1.96 (d, J=2.4, 3H), 1.28 (s, 6H).

EXAMPLE 12

6-(3,4-Dichlorophenyl)-1,2-dihydro-2,2,4-trimethylquinoline (Compound 111, structure 4 of Scheme II where R$^1$=3,4-dichlorophenyl)

This compound was prepared according to General Method 2 (EXAMPLE 9). From Compound 9 (78.4 mg, 0.25 mmol) and commercially available 3,4-dichlorobromobenzene (56.7 mg, 0.25 mmol, Lancaster) was obtained a crude product which was isolated and purified by preparative thin layer chromatography (PTLC) (1000 µm, 10% ethyl acetate/hexane) to afford 22 mg (28%) of Compound 111. Data for Compound 111: $^1$H NMR (400 MHz, acetone-d$_6$) 7.73 (s, 1H), 7.52 (d, J=1.2, 2H), 7.32 (d, J=2, 1H), 7.26 (dd, J=8, 2, 1H), 6.57 (d, J=8, 1H), 5.42 (br s, 1H), 5.37 (s, 1H), 2.03 (d, J=1.2, 3H), 1.27 (s, 6H).

EXAMPLE 13

4-Ethyl-1,2-dihydro-2,2-dimethyl-6-phenylquinoline (Compound 112, structure 13 of Scheme II, where R$^1$=phenyl, R$^2$methyl)
N-tert-Butyloxycarbonyl-1,2-dihydro-2,2-dimethyl-4-hydroxymethyl-6-phenyl quinoline (structure 11, where R$^1$=phenyl)

A solution of N-tert-butyloxycarbonyl-1,2-dihydro-2,2,4-trimethyl- 6-phenyl quinoline (structure 10, where R$^1$=phenyl) (310 mg, 0.888 mmol) and selenium dioxide (345 mg, 3.11 mmol) in 17 mL of dioxane was heated to reflux for 3 h. The reaction mixture was quenched with 1:1 NaS$_2$O$_3$ (10%) / Na2HCO$_3$ (10%), extracted with dichloromethane, dried (MgSO$_4$), and the organic phase was concentrated in vacuo. Purification by flash chromatography (silica gel, hexane/ethyl acetate, 4:1) gave 212 mg of the intermediate aldehyde along with 75 mg of the desired alcohol of structure 11, where R$^1$=phenyl. The aldehyde was treated with sodium borohydride in 25 mL of methanol at 0° C. After 1 h at 0° C., the reaction mixture was quenched with water, extracted with ethyl acetate and concentrated in vacuo to give an oil that was purified by flash chromatography (silica gel, hexane/ethyl acetate, 4:1) providing structure 11, where R$^1$=phenyl (240 mg, 84%). $^1$H NMR (acetone d$_6$) 7.68 (d, J=9, 2H), 7.61 (d, J=1.8, 1H), 7.47 (dd, J=6.2, 1.8, 1H), 7.41 (d, J=6.4, 2H), 7.29 (m, 2H), 5.80 (s, 1H), 4.51 (d, J=6.8, 2H), 4.12 (t, J=6.8, 1H), 1.52 (br s, 15H).
N-tert-Butyloxycarbonyl-4-bromomethyl-1,2-dihydro-2,2-dimethyl-6-phenyl quinoline (structure 12, where R$^1$=phenyl)

To a solution of N-tert-butyloxycarbonyl-1,2-dihydro-2,2-dimethyl-4-hydroxymethyl-6-phenylquinoline (structure 11, where R$^1$=phenyl) (230 mg, 0.630 mmol) and carbon tetrabromide (220 mg, 0.662 mmol) in 5 mL of dichloromethane at 0° C. was added triphenylphosphine (174 mg, 0.662 mmol) in 2 mL of dichloromethane. The reaction mixture was allowed to warm to rt and stirred for 1 h. The mixture was concentrated in vacuo to a residue that was subjected to flash chromatography (silica gel, hexane/ethyl acetate, 9:1) to give structure 12, where R$^1$=phenyl (72 mg, 27%). $^1$H NMR (acetone d$_6$) 7.67 (m, 3H), 7.52 (dd, J=8.7, 2.1, 1H), 7.45 (t, 2H), 7.32 (m, 2H), 6.07 (s, 1H), 4.60 (s, 2H), 1.55 (s, 6H), 1.53 (s, 9H).

4-Ethyl-1,2-dihydro-2,2-dimethyl-6-phenylquinoline (Compound 112, structure 13 of Scheme II, where R$^1$=phenyl, R$^2$=methyl)

To a solution of N-tert-butyloxycarbonyl-4-bromomethyl-1,2-dihydro-2,2-dimethyl-6-phenylquinoline (structure 12, where R$^1$=phenyl) (20 mg, 0.047 mmol) and copper (I) iodide (4 mg, 0.02 mmol) in 1 mL of anhydrous ether at 0° C. was added MeMgBr (0.060 mL, 3M in ether). After 30 min of stirring at 0° C., the reaction mixture was quenched with saturated NH$_4$Cl and extracted with ethyl acetate. The organic layers were combined, dried (Na$_2$SO$_4$) and concentrated in vacuo to provide an oil which was purified by SGC (silica gel, hexane/ethyl acetate, 9:1) giving N-tert-butyloxycarbonyl-4-ethyl-1,2-dihydro-2,2-dimethyl-6-phenylquinoline (16 mg, 91%). $^1$H NMR (acetone-d$_6$) 7.65 (d, J=8.7, 2H), 7.51 (dd, J=8.0, 1.7, 1H), 7.29 (m, 2H), 7.43 (m, 3H), 5.56 (s, 1H), 2.55 (q, J=8.9, 2H), 1.5 (s, 6H), 1.57 (s, 9H), 1.19 (t, J=8.9, 3H). To a solution of N-tert-butyloxycarbonyl-4-ethyl-1,2-dihydro-2,2-dimethyl-6-phenylquinoline (16 mg, 0.044 mmol) in 1 mL of dichloromethane at 0° C. was added 0.3 mL of trifluoroacetic acid. After 10 min of stirring, the reaction was quenched with saturated NaHCO$_3$, and extracted with dichloromethane. The organic layers were combined, dried (Na$_2$SO$_4$) and concentrated in vacuo to provide an oil that was purified by SGC (silica gel, hexane/ethyl acetate, 7:3) to provide 3 mg (25%) of Compound 112. Data for Compound 112: $^1$H NMR (acetone-d$_6$) 7.55 (d, J=8.6, 2H), 7.37 (m, 3H), 7.23 (m, 2H), 6.59 (d, J=8.26, 1H), 5.38 (s, 1H), 3.76 (s, 1H), 2.48 (q, J=7.4, 2H), 1.29 (s, 6H), 1.17 (t, J=7.4, 3H).

EXAMPLE 14

1,2-Dihydro-2,2-dimethyl-6-phenyl-4-propylquinoline (Compound 113, structure 13 of Scheme II, where R$^1$=phenyl, R$^2$=ethyl)

To a solution of N-tert-butyloxycarbonyl-4-bromomethyl-1,2-dihydro-2,2-dimethyl-6-phenyl quinoline (structure 12, where $R^1$=phenyl) (20 mg, 0.047 mmol) and copper (I) iodide (4 mg, 0.019 mmol) in 1 mL of anhydrous ether at 0° C. was added EtMgBr (0.06 mL, 3M in ether). After 30 min of stirring at 0° C., the reaction mixture was quenched with saturated $NH_4Cl$ and extracted with ethyl acetate. The organic layers were combined, dried ($Na_2SO_4$), and concentrated in vacuo to provide an oil that was used directly in the next step. To the crude quinoline (20 mg, 0.053 mmol) in 1 mL of dichloromethane at 0° C. was added 0.3 mL of trifluoroacetic acid. After 10 min of stirring, the reaction was quenched with aqueous saturated solution of $NaHCO_3$ and extracted with dichloromethane. The organic layers were combined, dried ($Na_2SO_4$) and concentrated in vacuo to provide an oil that was chromatographed (silica gel, hexane/ethyl acetate, 7:3) to give Compound 113 (9 mg, 61%). Data for Compound 113: $^1H$ NMR (acetone-$d_6$) 7.53 (m, 2H), 7.40 (m, 3H), 7.24 (m, 2H), 6.58 (d, J=8.14, 1H), 5.38 (s, 1H), 3.76 (s, 1H), 2.45 (t, J=7.40, 2H), 1.60 (sx, J=7.39, 2H), 1.29 (s, 6H), 0.99 (t, J=7.27, 3H).

EXAMPLE 15

6-(2-Chlorophenyl)-1,2-dihydro-2,2,4-trimethylquinoline (Compound 114, structure 4 of Scheme 11, where $R^1$=2-chlorophenyl)

This compound was prepared according to General Method 2 (EXAMPLE 9). From Compound 9 (48.5 mg, 0.15 mmol) and commercially available 2-chlorobromobenzene (17.8 mL, 0.15 mmol, Lancaster) 15 mg (34%) of Compound 114 was isolated. Data for Compound 114: $^1H$ NMR (400 MHz, acetone-$d_6$) 7.45 (dd, J=8, 1.2, 1H), 7.36 (dd, J=8, 2, 1H), 7.33 (ddd, J=16, 8, 1.2, 1H), 7.23 (ddd, J=16, 8, 2, 1H), 7.11 (d, J=2, 1H), 7.03 (dd, J=8, 2, 1H), 6.53 (d, J=8, 1H), 5.35 (s, 1H), 5.31 (br s, 1H), 1.97 (d, J=1.6, 3H), 1.28 (s, 6H).

EXAMPLE 16

1,2-Dihydro-2,2,4-trimethylindeno[2,1-f]quinoline (Compound 116, structure 17 of Scheme IV, where $R^{1-6}$=H, X=$CH_2$)

General Method 3: 1,2-dihydroquinoline formation from an aniline

To a dry 500-mL r.b. flask equipped with a magnetic stirring bar and a water cooled reflux condenser was added structure 15 along with $I_2$ (0.05–0.2 equiv) dissolved in acetone (0.1–0.5M). The resulting red solution was heated at reflux with constant stirring for 60 h. The reaction was followed by TLC (hexane/EtOAc, 3:1, visualized by short wave UV, the product appearing as a bright blue spot). After cooling to room temperature, Celite™ (2.0 g) was added and the mixture was concentrated under reduced pressure to give a free flowing powder which was purified by flash column chromatography (70 g silica gel 60, 240 mesh, hexane/EtOAc, 5:1) to afford a mixture of isomers of structures 16 and 17.

1,2-Dihydro-2,2,4-trimethylindeno[2,1-f]quinoline (Compound 116, structure 17 of Scheme IV, where $R^{1-6}$=H, X=$CH_2$)

This compound was prepared according to General Method 3 from structure 15 (where $R^{1-6}$=H, X=$CH_2$) (5.0 g, 27 mmol) to afford a mixture of Compound 115 (structure 16 of Scheme IV, where $R^{1-6}$=H, X=$CH_2$)(1.64 g, 22.7%) and Compound 116 (336 mg, 4.65%) in an 85:15 ratio (as determined by $^1H$ NMR). Data for Compound 116: $R_f$=0.57 (silica gel, hexane/EtOAc, 3:1). $^1H$ NMR (400 MHz, $C_6D_6$) 7.62 (d, J=8.0, 1H), 7.45 (d, J=8.0, 1H), 7.28 (d, J=7.3, 1H), 6.31 (d, J=8.0, 1H), 5.19 (s, 1H), 3.74 (s, 2H), 3.28 (br s, 1H), 1.98 (d, J=1.2, 3H), 1.08 (s, 6H).

EXAMPLE 17

8-Bromo-1,2-dihydro-2,2,4-trimethylindeno[1,2-g]quinoline (Compound 117, structure 16 of Scheme IV, where $R^{2-4}$, $R^6$=H, $R^5$=Br, X=$CH_2$)

This compound was prepared according to General Method 3 (EXAMPLE 16) from structure 15 (where $R^{1-4}$, $R^6$=H, $R^5$=Br, X=$CH_2$) (2.0 g, 7.7 mmol) to afford 376 mg (49%) of Compound 117 as a rose colored solid (along with Compound 127, Example 18). Data for Compound 117: $R_f$=0.53 (silica gel, hexane/EtOAc; 3:1). $^1H$ NMR (400 MHz, $C_6D_6$) 7.38 (m, 3H), 6.17 (s, 1H), 5.15 (s, 1H), 3.34 (s, 2H), 3.27 (br s, 1H), 1.93 (d, J=1.0, 3H), 1.08 (s, 6H).

EXAMPLE 18

7-Bromo-1,2-dihydro-2,2,4-trimethylindeno[2,1-f]quinoline (Compound 127, structure 17 of Scheme IV, where $R^{1-4}$, $R^6$=H, $R^5$=Br, X=$CH_2$)

This compound was prepared according to General Method 3 (EXAMPLE 16) from structure 15 (where $R^{1-4}$, $R^6$=H, $R^5$=Br, X=$CH_2$) (2.0 g, 7.7 mmol) to afford of Compounds 117 and 127. Purification by silica gel chromatography afforded pure 117 (376 mg, 49%) (EXAMPLE 17) and mixed fractions containing 117 and 127. Compound 127 was purified by reverse phase HPLC (ODS column, 95% methanol/water, 3.0 mL/min). Data for Compound 127: $R_f$=0.53 (silica gel, hexane/EtOAc, 3:1); $^1H$ NMR (400 MHz, $C_6D_6$) 7.38 (d, J=8.3, 1H), 7.31 (s, 1H), 7.29 (d, J=8.0, 1H), 7.19 (d, J=8.0, 1H), 6.25 (d, J=8.1, 1H), 5.16 (s, 1H), 3.52 (s, 2H), 3.32 (br s, 1H), 1.91 (d, J=1.4, 3H), 1.05 (s, 6H).

EXAMPLE 19

1,2-Dihydro-2,2,4-trimethylbenzo[b]furano[3,2-g]quinoline (Compound 118, structure 16 of Scheme IV, where $R^{2-6}$=H, X=O)

This compound was prepared according to General Method 3 (EXAMPLE 16) from structure 15 (where $R^{1-6}$=H, X=O) (1.0 g, 5.5 mmol) to afford Compound 118 (264 mg, 18.4%) as a yellow solid, and Compound 119 (936 mg, 65%) as a clear colorless oil. Data for Compound 118: $R_f$=0.44 (hexane/EtOAc, 3:1); $^1H$ NMR (400 MHZ, $C_6D_6$) 7.61 (d, J=6.9, 1H), 7.56 (s, 1H), 7.41 (d, J=8.0, 1H), 7.13 (m, 2H), 6.38 (s, 1H), 5.12 (s, 1H), 3.28 (br s, 1H), 1.91 (s, 3H), 1.05 (s, 6H).

EXAMPLE 20

1,2-Dihydro-2,2,4-trimethylbenzo[b]furano[2,3-f]quinoline (Compound 119, structure 17 of Scheme IV, where $R^{1-6}$=H, X=O)

This compound was prepared according to General Method 3 (EXAMPLE 16) from structure 15 (where $R^{1-6}$=H, X=O) to afford Compound 118 (264 mg, 1.00 mmol, 18.4%) as a yellow solid and Compound 119 (936 mg, 3.55 mmol, 65.1%) as a clear colorless oil. Data for Compound 119: $R_f$=0.44 (silca gel, hexane/EtOAc, 3:1); $^1H$ NMR (400 MHz, $C_6D_6$) 7.63 (dd, J=7.4, 1.5, 1H), 7.41 (d, J=8.2, 1H), 7.35 (d, J=7.3, 1H), 7.11 (m, 2H), 6.19 (d, J=8.4, 1H), 5.11 (s, 1H), 3.38 (br s, 1H), 2.49 (d, J=1.2, 3H), 1.06 (s, 6H).

EXAMPLE 21

6-Fluoro-1,2-dihydro-2,2,4-trimethylindeno[2,1-f]quinoline (Compound 120, structure 17 of Scheme IV, where $R^{1-5}$=H, $R^6$=F, X=$CH_2$)

This compound was prepared according to General Method 3 (EXAMPLE 16) from structure 15 (where $R^{1-5}$=H, $R^6$=F, X=$CH_2$) (1.0 g, 5.0 mmol) to afford 248 mg (18%) of a mixture Compounds 120 and 121. Pure samples of Compounds 120 and 121 were obtained by preparative thin layer chromatography (PTLC) (1000 μm, hexane/EtOAc, 9:1). Data for Compound 120: $R_f$=0.70 (hexane/EtOAc 3:1); $^1$H NMR (400 MHz, $C_6D_6$) 7.38 (d, J=8.0, 1H), 7.29 (d, J=7.5, 1H), 7.09 (dd, J=8.1, 5.3, 1H), 6.8 (dd, J=8.6, 8.6, 1H), 6.26 (d, J=8.0, 1H), 5.13 (s, 1H), 3.81 (s, 2H), 3.32 (br s, 1H), 1.88 (d, J=1.2, 3H) 1.05 (s, 6H).

EXAMPLE 22

9-Fluoro-1,2-dihydro-2,2,4-trimethylindeno[1,2-g]quinoline (Compound 121, structure 16 of Scheme IV, where $R^{2-5}$=H, $R^6$=F, X=$CH_2$)

This compound was obtained as described above for Compound 120 (EXAMPLE 21). Data for Compound 121: $R_f$0.71 (silica gel, hexane/EtOAc, 3:1); $^1$H NMR (400 MHz, $C_6D_6$) 7.48 (s, 1H), 7.25 (d, J=7.4, 1H), 7.07 (dd, J=7.8, 5.4, 1H), 6.80 (dd, J=8.7, 8.7, 1H), 6.13 (s, 1H), 5.15 (s, 1H), 3.63 (s, 2H), 3.28, (br s, 1H), 1.93 (d, J=1.2, 3H) 1.09 (s, 6H).

EXAMPLE 23

1,2-Dihydro-9-hydroxymethyl-2,2,4-trimethylindeno[1,2-g]quinoline (Compound 122, Scheme V).

Methyl 1,2-dihydro-2,2,4-trimethylindeno[1,2-g]quinoline-9-carboxylate (structure 16 of Scheme IV where $R^{2-5}$=H, $R^6$=$CO_2CH_3$, X=$CH_2$)

This compound was prepared according to General Procedure 1 from methyl 2-aminofluoreno-8-carboxylate to afford 872 mg (65%) of methyl 1,2-dihydro-2,2,4-trimethylindeno[1,2-g]quinoline-8-carboxylate (structure 16 of Scheme IV where $R^{2-5}$=H, $R^6$=$CO_2CH_3$, X=$CH_2$) as an off white solid. Data for methyl 1,2-dihydro-2,2,4-trimethylindeno[1,2-g]quinoline-9-carboxylate: $^1$H NMR (400 mHz, $C_6D_6$) 8.03 (d, J=7.8, 1H), 7.56 (d, J=7.4, 1H,), 7.50 (s, 1H,), 7.20 (dd, J=15, 7.5, 1H), 6.32 (s, 1H), 5.17 (s, 1H), 4.28 (s, 2H), 3.55 (s, 3H), 1.97 (d, J=1.3, 3H), 1.10 (s, 6H).

1,2-Dihydro-9-hydroxylmethyl-2,2,4-trimethylindeno[1,2-g]quinoline (Compound 122, Scheme V)

In a r.b. flask equipped with a magnetic stirring bar was dissolved methyl 1,2-dihydro-2,2,4-trimethylindeno[1,2-g]quinoline-9-carboxylate (23 mg, 72.1 μmol) in 10 mL dry THF. The solution was stirred at −78° C. for 10 min and DIBAl-H (1.0M in hexanes; 0.43 mL, 6 equiv) was slowly added. After stirring for 20 min the reaction was quenched with $Na_2SO_4.10H_2O$ (100 mg) and the solution was warmed to rt, at which time the reaction mixture became a white gelatinous suspension. The suspension was filtered and washed repeatedly with EtOAc. The washings and filtrate were combined and concentrated in vacuo to give 10 mg (49%) of Compound 122 as a white solid. Data for Compound 122: $R_f$=0.23 (silica gel, hexane/EtOAc, 3:1). $^1$H NMR (400 MHz, acetone-$d_6$) 7.55 (d, J=7.4, 1H), 7.50 (s, 1H); 7.26 (dd, J=15, 7.5, 1H); 7.18 (d, J=7.4, 1H); 6.73 (s, 1H); 5.36 (s, 1H); 5.21 (s, 1H); 4.72 (d, J=5.8, 2H); 4.06 (dd, J=11.4, 5.7, 1H); 3.20 (s, 2H); 2.78 (s, 3H); 1.28 (s, 6H).

EXAMPLE 24

8-Chloro-1,2-dihydro-2,2,4-trimethylindeno[1,2-g]quinoline (Compound 123, structure 16, Scheme IV, where $R^{2-4}$, $R^6$=H, $R^5$=Cl, X=$CH_2$)

2-Amino-7-chlorofluorene (structure 15, Scheme IV, where $R^{1-4}$, $R^6$=H, $R^5$=Cl, X=$CH_2$)

A 100 mL round-bottom flask was charged with structure 14 (where, $R^{2-4}$, $R^6$=H, $R^5$=Cl, X=$CH_2$) (496 mg, 2.02 mmol) and methylene chloride (20 mL) and 10% Pd/C (0.5 g) was added to the solution. The reaction vessel was flushed with nitrogen and stirred under an atmosphere of hydrogen overnight (~15 hours), at which time the starting material was completely consumed as judged by TLC (50% ethyl acetate/hexane). The flask was flushed with nitrogen before exposing the mixture to air. The product mixture was diluted with ethyl acetate (50 mL) and washed with brine (3×30 mL). The organic layers were combined, dried ($Na_2SO_4$), and concentrated. The crude product, structure 15 (where $R^{1-4}$, $R^6$=H, $R^5$=Cl, X=$CH_2$)(400 mg, 92%), was used in the next step without purification.

8-Chloro-1,2-dihydro-2,2,4-trimethylindeno[1,2-g]quinoline (Compound 123, structure 16, Scheme IV, where $R^{2-4}$, $R^6$=H, $R^5$=Cl, X=$CH_2$)

This compound was prepared according to General Method 3 (EXAMPLE 16) from structure 15 (where $R^{1-4}$, $R^6$=H, $R^5$=Cl, X=$CH_2$)(400 mg, 1.85 mmol) and acetone (60 mL, Aldrich reagent grade) to afford Compound 123 and structure 17, where $R^{2-4}$, $R^6$=H, $R^5$=Cl, X=$CH_2$. Purification by PTLC (reverse phase, 80% methanol/water) provided 1.8 mg (<1%) of Compound 123. Data for Compound 123: $^1$H NMR: (400 MHz, acetone-$d_6$) 7.59 (d, J=8, 1H), 7.46 (s, 1H), 7.39 (d, J=2, 1H), 7.24 (dd J=8, 2, 1H), 6.67 (s, 1H), 5.35 (s, 1H), 5.26 (br s, 1H), 3.71 (s, 2H), 1.98 (s 3H, 1.24 (s, 6H).

EXAMPLE 25

8-Fluoro-1,2-dihydro-2,2,4-trimethylindeno[1,2-g]quinoline (Compound 124, structure 16, Scheme IV, where $R^{2-4}$, $R^6$=H, $R^5$=F, X=$CH_2$)

This compound was prepared according to General Method 3 (EXAMPLE 16) from 2-amino-7-fluorofluorene (structure 15, where $R^{1-4}$, $R^6$=H, $R^5$=F, X=$CH_2$) (100 mg, 500 μmol) to afford 43 mg (31%) of a mixture of Compound 124 and structure 17, where $R^{1-4}$, $R^6$=H, $R^5$=F, X=$CH_2$, in a 9:1 ratio. A small aliquot of this mixture was dissolved in acetone and purified by reverse phase preparative TLC (C-18, 20×20 cm, 1000 μm, MeOH/$H_2O$, 5:1) to give Compound 124 as a brown solid. Data for Compound 124: $R_f$=0.59 (silca gel, hexane/EtOAc, 3:1). $^1$H NMR(400 MHz, $C_6D_6$) 7.43 (s, 1H), 7.24 (m, 1H), 6.96 (m, 2H), 6.21 (s, 1H), 5.18 (s, 1H), 3.38 (s, 2H), 1.96 (s, 3H), 1.11 (s, 6H).

EXAMPLE 26

8-Acetyl-1,2-dihydro-2,2,4-trimethylindeno[1,2-g]quinoline (Compound 125, structure 16, Scheme IV, where $R^{2-4}$, $R^6$=H, $R^5$=$ COCH_3$, X=$CH_2$)

In a r.b. flask equipped with a magnetic stir bar was dissolved Compound 115 (EXAMPLE 16) (54 mg, 0.021 mmol) in $CH_2Cl_2$ (3 mL). To this solution was added freshly distilled acetyl chloride (20 μL, 1.3 equiv). The reaction mixture was stirred for 10 min, and $AlCl_3$ (≈30 mg) was added. The reaction was followed by TLC (hexane/EtOAc, 3:1, visualized by short wave UV). After 30 min, the black solution was quenched with $H_2O$ (10 mL), stirred for 2 h, then extracted with EtOAc (2×20 mL), washed with brine (2×20 mL), dried ($Na_2SO_4$), and concentrated on Celite™. Purification by flash column chromotography (20 g silica gel 60, 240 mesh, hexane/EtOAc, 5:1) provided 3.7 mg (6%) of Compound 125 as a light yellow solid. Data for Compound 125: $R_f$=0.59 (silca gel, hexane/EtOAc, 3:1); $^1$H NMR (400 MHz, $C_6D_6$) 8.06 (s, 1H), 7.94 (d, J=8.0, 1H), 7.53 (s, 1H), 7.46 (d, J=8.0, 1H), 6.22 (s, 1H), 5.16 (s, 1H), 3.50 (s, 2H), 2.28 (s, 3H), 1.94 (d, J=1.4, 3H), 1.10 (s, 6H).

EXAMPLE 27

6-Fluoro-1,2-dihydro-2,2,4-trimethylindeno[1,2-g] quinoline Compound 126, structure 16, Scheme IV, where $R^2$, $R^{4-6}$=H $R^3$=F, X=$CH_2$)

This compound was prepared according to General Method 3 (EXAMPLE 16) from 2-amino-5-fluorofluorene (structure 15, where $R^2$, $R^{4-6}$=H, $R^3$=F, X=$CH_2$) (360 mg, 1.72 mmol) to afford 125 mg (26%) of Compound 126 as a light brown solid. Data for Compound 126: $R_f$=0.63 (silca gel, hexane/EtOAc, 3:1); $^1$H NMR (400 MHz, acetone-$d_6$): 7.55 (s, 1H), 7.25 (d, J=7.3, 1H), 7.12 (m, 1H), 7.02 (d, J=10, 10, 1H) 6.73 (s, 1H), 5.39 (s, 1H), 3.81 (s, 2H) 2.87 (s, 3H), 1.28 (s, 6H).

EXAMPLE 28

1,2-Dihydro-2,2,4-trimethyl-7-nitroindeno[2,1-f]quinoline Compound 128 structure 17, Scheme IV, where $R^{1-4}$, $R^6$=H, $R^5$=$NO_2$, X=$CH_2$)

This compound was prepared according to General Method 3 (EXAMPLE 16) from 2-amino-7-nitrofluorene (100 mg, 0.44 mmol) to afford 2 mg (2%) of Compound 128 as a red solid. Data for Compound 128: $R_f$=0.46 (silica gel, 25% EtOAc:hexane); $^1$H NMR (400 MHz, acetone-$d_6$) 8.25 (s, 1H), 8.19 (d, J=7.8, 1H), 7.80 (d, J=7.7, 1H), 7.65 (s, 1H), 6.77 (s, 1H), 5.70 (br s, 1H), 5.45 (s, 1H), 3.88 (s, 2H), 2.10 (s, 3H), 1.31 (s, 6H).

EXAMPLE 29

2-Dihydro-2,2,4-trimethyl-8-nitroindeno[1,2-g]quinoline Compound 129 structure 16, Scheme IV, where $R^{2-4}$, $R^6$=H, $R^5$=$NO_2$, X=$CH_2$)

This compound was prepared according to General Method 1 from 2-amino-7-nitrofluorene (100 mg, 0.44 mmol) to afford 1.0 mg (<1%) of Compound 129 as a red solid. Data for Compound 129: $R_f$=0.46 (silica gel, 25% EtOAc:hexane); $^1$H NMR (400 MHz, acetone-$d_6$) 8.30 (s, 1H), 8.19 (d, J=8.0, 1H), 7.78 (d, J=7.7, 1H), 7.59 (d, J=7.8, 1H), 6.70 (d, J=7.8, 1H), 5.70 (br s, 1H), 5.43 (s, 1H), 4.26 (s, 2H), 2.30 (s, 3H), 1.31 (s, 6H).

EXAMPLE 30

6,9-Difluoro-1,2-dihydro-2,2,4-trimethylindeno[1,2-g] quinoline (Compound 130, structure 16, Scheme IV, where $R^2$, $R^{4-5}$=H, $R^3$, $R^6$=F, X=$CH_2$)

This compound was prepared according to General Method 3 (EXAMPLE 16) from 2-amino-5,8-difluorofluorene (structure 15, where $R^2$, $R^{4-5}$=H, $R^3$, $R^6$=F, X=$CH_2$) (460 mg, 2.03 mmol) to afford 94 mg (15%) of Compound 130 as a light brown solid. Data for Compound 130: $R_f$=0.56 (silica gel, hexane/EtOAc, 3:1); $^1$H NMR (400 MHz, $C_6D_6$) 7.92 (s, 1H), 6.68 (ddd, J=9.1, 6.3, 3.6, 1H), 6.49 (ddd, J=8.5, 6.0, 3.5, 1H), 6.07 (s, 1H), 5.09 (s, 1H), 3.55 (s, 2H), 1.88 (d, J=1.1, 1H), 1.06 (s, 6H).

EXAMPLE 31

7-Fluoro-1,2-dihydro-2,2,4-trimethyl-11-(thiomethyl) indeno[2,1-f]quinoline (Compound 131, structure 17 of Scheme IV, where, $R^1$=$SCH_3$, $R^{2-4}$, $R^6$=H, $R^5$=F, X=$CH_2$)

This compound was prepared according to General Method 3 (EXAMPLE 16) from 2-amino-7-fluoro-3-methylthiofluorene (structure 15, where $R^1$=$SCH_2$, $R^{2-4}$, $R^6$=H, $R^5$=F) (250 mg, 1.17 mmol) to afford 29 mg (7.5%) of Compound 131 (28.6 mg, 81 μmol, 7.5%) as a white solid.

Data for compound 131: $R_f$=0.55 (silica gel, hexane/EtOAc, 3:1); $^1$H NMR (400 mHz, $C_6D_6$) 7.78 (s, 1H), 7.19 (m, 1H), 6.90 (s, 1H,), 6.88 (s, 1H), 5.44 (s, 1H), 5.22 (s, 1H), 3.54 (s, 2H), 2.05 (s, 3H), 1.92 (d, J=1.2, 3H), 1.68 (s, 6H).

EXAMPLE 32

5,8-Difluoro-1,2-dihydro-10-hydroxy-2,2,4-trimethylindeno[1,2-g]quinoline (Compound 132, Scheme VII).

3,2'-Difluoro-2-biphenic acid (Compound 23, Scheme VII):

A flame-dried 50 mL r.b. flask fitted with an air-cooled condenser containing methyl 2-bromo-5-fluorobenzoate (Compound 21, Scheme VII) (4.00 g, 17.16 mmol) and 2-iodofluorobenzene (Compound 22, Scheme VII) (19.05 g, 85.82 mmol, 5.00 equiv) was heated to 176° C., at which time unactivated copper powder (15.0 g, 236 mmol, 13.8 equiv) was added portion-wise over 40 min as the temperature was gradually raised to 190° C. After an additional 40 min at 190° C., the mixture was allowed to cool to rt and was filtered through a bed of Celite™ on a fritted-glass funnel, rinsing with 250 mL ethyl acetate. Concentration under reduced pressure afforded an oil which was shown by $^1$H NMR to be composed of the desired Ullmann heterocoupling product, along with some 2,2'-difluorobiphenyl, and a small amount of uncoupled methyl 2-bromo-5-fluorobenzoate. This crude product mixture was then dissolved in 60 mL THF, and the ester was hydrolyzed by treatment with a large excess of 10% aqueous NaOH at reflux. After 24 h, thin layer chromatography (TLC) analysis indicated complete consumption of starting material, and the crude reaction mixture was neutralized to pH 4 with 1N aqueous HCl. The reaction mixture was then extracted with ethyl acetate (150 mL), and the organic phase was washed with brine (50 mL), dried ($Na_2SO_4$), and concentrated. Purification by silica gel chromatography (silica gel, hexanes/ethyl acetate, gradient elution) afforded 2.64 g (62%) of Compound 23 as a colorless, oily solid. Data for 23: $^1$H NMR (400 MHz, $CDCl_3$) 7.76 (dd, J=9.1, 2.2, 1H), 7.32 (m, 3H), 7.26 (ddd, J=9.5, 7.8, 1.8, 1H), 7.18 (ddd, J=8.1, 7.4, 0.9, 1H), 7.06 (dd, J=9.5, 8.8, 1H).

2,5-Difluorofluorenone (Compound 24, Scheme VII)

To a flame-dried 100 mL flask containing 3,2'-difluoro-2-biphenic acid (Compound 23, Scheme VII) (2.00 g, 8.54 mmol) in 12 mL benzene was added $SOCl_2$ (1.25 mL, 17.1 mmol, 2.00 equiv) and the mixture was heated to reflux for 90 min. The excess $SOCl_2$ and benzene were removed by distillation at ambient pressure. Benzene (6 mL) and $CH_2Cl_2$ (5 mL) were then sequentially added and removed by distillation. Anhydrous $CH_2Cl_2$ (30 mL) was added and the mixture was cooled to −78° C. Trifluoroacetic acid (0.76 mL, 8.54 mmol, 1.00 equiv) was then added and the mixture was allowed to warm to rt overnight. The reaction mixture was poured into 100 mL ice-water, rinsing with 50 mL $CH_2Cl_2$. The layers were separated and the aqueous phase was extracted with an additional 100 mL $CH_2Cl_2$. The combined organic extracts were washed successively with sat'd aqueous $NaHCO_3$, water, and brine, dried ($Na_2SO_4$), and concentrated under reduced pressure to give 1.85 g (quantitative) of Compound 24 as a pale yellow solid. Recrystallization (ethanol) afforded Compound 24 as feathery pale yellow needles (mp 149°–150° C., literature mp 147.5° C. [Namkung et at., "Derivatives of Fluorene XX, Fluorofluorenes, V, New Difluoro-2-acetamidofluorenes for the Study of Carcinogenic Mechanisms", *J. Med. Chem.* 1965, 8, 551–554.]).

4,7-Difluoro-2-nitrofluorenone (Compound 25, Scheme VII):

2,5-Difluorofluorenone (Compound 24, Scheme VII) (0.200 g, 0.925 mmol) was added portion-wise to 0.40 mL fuming nitric acid at 0° C. in a 5 mL round-bottomed flask. The ice bath was removed and the reaction mixture was gently heated to 50° C. for 2 min with a water bath. The reaction mixture was then cooled to rt before the addition of 3.5 mL ice-water. The precipitated product was collected by vacuum filtration, yielding 232 mg (96%) of Compound 25 as a bright yellow solid (top 207° C., literature mp 207°–208° C. [Id.]), which was carried on to the next step without further purification.

2-Amino-4,7-difluorofluorenone (Compound 132, Scheme VII)

4,7-Difluoro-2-nitrofluorenone (Compound 25, Scheme VII) (1.00 g, 3.83 mmol) was dissolved in 175 mL ethyl acetate and 10% palladium on carbon was added (10 mol %). The mixture was stirred under an atmosphere of hydrogen gas maintained by a balloon for 105 min, and was then filtered to remove the catalyst, rinsing with an additional 150 mL ethyl acetate. Removal of the solvent under diminished pressure yielded 885 mg (quantitative) of Compound 132 as a dark purple-red solid (mp 236° C., literature mp 234°–235° C. [Id.]). Data for Compound 132: $^1$H NMR (400 MHz, CDCl$_3$) 7.46 (dd, J=8.1, 4.5, 1H), 7.29 (d, J=1.5, 1H), 7.11 (dd, J=8.5, 6.0, 1H), 6.79 (d, J=1.9, 1H), 6.42 dd, J=10.9, 1.9, 1H), 3.99 (br s, 2H).

5,8-Difluoro-1,2-dihydro-2,2,4-trimethyl-10-oxoindeno[1,2g]quinoline (structure 19 of Scheme VI where $R^2$, $R^5$=F, $R^{3-4}$, $R^6$=H, X=C=O)

This compound was prepared according to General Method 3 (EXAMPLE 16) from Compound 132 (1.0 g, 4.6 mmol) to afford 5,8-difluoro-1,2-dihydro-2,2,4-trimethyl-10-oxoindeno[1,2-g]quinoline (structure 19 of Scheme VI, where $R^2$, $R^5$=F, $R^{3-4}$, $R^6$=H). Data for 5,8-difluoro-1,2-dihydro-2,2,4-trimethyl-10-oxoindeno[1,2-g]quinoline: $R_f$=0.49 (silica gel, hexane/EtOAc, 3:1), $^1$H NMR (400 MHz, acetone-d$_6$) 7.50 (dd, J=8.1, 4.6, 1H), 7.27 (m, 2H), 6.73 (s, 1H), 6.03 (br s, 1H), 5.47 (s, 1H), 2.16 (dd, J=7.1, 1.5, 3H), 1.29 (s, 6H).

General Method 4: Reduction of a fluorenone (structure 19 of Scheme VI) to a 10-hydroxy-2,24-trimethylindeno[1,2-g]quinoline (structure 20 of Scheme VI)

To a flame dried 25-mL r.b flask equipped with a magnetic stir bar was added structure 19 dissolved in anhydrous CH$_2$Cl$_2$ (0.05–0.1M). The resulting purple solution was cooled to −78° C. and to it was added DIBAl-H (1.0M in hexane, 3–4 equiv) under a blanket of N$_2$. The resulting light yellow solution was stirred at −78° C. for 30 min and to it was then added an excess of NaSO$_4$.10 H$_2$O (10–20 equiv). The resulting suspension was warmed to rt during which time the solution became a thick white gel. After stirring for 45 min, the gel was partially dissolved with EtOAc, filtered, and washed repeatedly with EtOAc. The ethyl acetate washes and filtrate were combined and concentrated under reduced pressure to afford structure 20.

5,8-Difluoro-1,2-dihydro-10-hydroxyl-2,2,4-trimethylindeno[1,2-g]quinoline Compound 132, Scheme VII)

Compound 132 was prepared according to General Method 4 from structure 19 (where $R^2$, $R^5$=F, $R^{3-4}$, $R^6$=H) (46 mg, 0.15 mmol) and DIBAl-H (1.0M in hexane, 0.5 mL, 3.2 equiv) to afford 29 mg (62%) of Compound 132 as an off-white solid. Data for Compound 132: $R_f$=0.10 (hexane/EtOAc, 3:1); $^1$H NMR (400 MHz, acetone-d$_6$) 7.54 (dd, J=8.3, 5.0, 1H), 7.24 (dd, J=8.6, 2.3, 1H), 7.06 (ddd, J=11.3, 9.3, 2.5, 1H), 6.68 (s, 1H), 5.63 (br s, 1H), 5.44 (d, J=7.9, 1H), 5.34 (s, 1H), 4.79 (d, J=8.0, 1H), 2.16 (dd, J=6.7, 1.2, 3H), 1.27 (s 3H), 1.25 (s, 3H).

EXAMPLE 33

7,9-Difluoro-1,2-dihydro-2,2,4-trimethyl-10-oxoindeno[1,2-g]quinoline Compound 135, structure 19, Scheme VI, where $R^{2-3}$, $R^5$=H, $R^4$, $R^6$=F, X=CO This compound was prepared according to General Method 3 (EXAMPLE 16) from 2-amino-6,8-difluoro-9-fluorenone (750 mg, 3.2 mmol) to afford 29 mg (2.9%) of Compound 135 as a bright purple solid. Data for Compound 135: $R_f$=0.57 (silica gel, hexane/EtOAc, 3:1). $^1$H NMR (400 MHz, acetone-d$_6$) 7.46 (s, 1H), 7.22 (dd, J=8.5, 1.9, 1H), 6.76 (s, 1H), 6.68 (ddd, J=9.6, 5.8, 2.3, 1H), 5.89 (br s, 1H), 5.52 (s, 1H), 2.06 (s, 3H), 1.30 (s, 6H).

EXAMPLE 34

7,9-Difluoro-1,2-dihydro-10-hydroxy-2,2,4-trimethylindeno[1,2-g]quinoline (Compound 133, structure 20, Scheme IV, where $R^{2-3}$, $R^5$=H, $R^4$, $R^6$=F, X=CHOH)

In a 25 mL r.b. flask equipped with a magnetic stirring bar was dissolved Compound 135 (EXAMPLE 33) (10 mg, 32 µmol) in 6 mL anhydrous CH$_2$Cl$_2$. The solution was cooled to −78° C. and then DIBALH (0.5 mL, 1.0M in hexanes) was added. The solution was stirred for 30 min, and then Na$_2$SO$_4$.10H$_2$O (150 mg) was added. Upon warming to rt, the suspension congealed to a viscous white gel which was washed with ethyl acetate 4×30 mL) and concentrated to afford 9.3 mg (92%) of Compound 133 as an off-white solid. Data for Compound 133: $^1$H NMR (400 MHz, C$_6$D$_6$) 7.40 (s, 1H), 7.09 (dd, J=8.7, 2.1, 1H), 6.84 (s, 1H), 6.55 (ddd, J=10, 5.7, 2.0, 1H), 5.65 (s, 1H), 5.31 (s, 1H), 4.54 (d, J=8.5, 1H), 2.00 (d, J=1.0, 3H), 1.28 (s, 3H), 1.26 (s, 3H).

EXAMPLE 35

7,10-Difluoro-1,2-dihydro-2,2,4-trimethyl-5-oxoindeno[2,1-f]quinoline (Compound 134, structure 17 of Scheme IV, where $R^2$, $R^5$=F, $R^1$, $R^{2-4}$, $R^6$=H, X=C=O)

This compound was prepared according to General Method 3 (EXAMPLE 16) from 2-amino-4,7-difluoro-9-fluorenone (Compound 132, Scheme VII) (1.0 g, 4.6 mmol) to afford 22 mg (1.6%) of Compound 134 as a purple solid. Data for Compound 134: $R_f$=048 (silica gel, hexane/EtOAc, 3:1); $^1$H NMR (400 MHz, acetone-d$_6$) 7.47 (m, 1H), 7.24 (m, 2H), 6.52 (d, J=11, 1H), 6.12 (br s, 1H), 5.66 (s, 1H), 2.25 (d, J=1.5, 3H), 1.27 (s, 6H).

EXAMPLE 36

8-Fluoro-1,2-dihydro-2,2,4-trimethyl-10-oxoindeno[1,2-g]quinoline (Compound 137, structure 16 of Scheme IV, where $R^{2-4}$, $R^6$=H, $R^5$=F, X=C=O)

To a dry 250-mL r.b. flask equipped with a magnetic stir bar and a water-cooled condenser was added 2-amino-7-fluorofluorenone (5.00 g, 23.5 mmol), along with iodine (~15 mg) and mesityl oxide (20 mL, 0.175 mol). The resulting red solution was heated at reflux with constant stirring for 2 days. The reaction was followed by TLC (20% ethyl acetate/hexane). After cooling to rt, the crude product mixture was concentrated and purified by silica gel chromatography (400 mL silica, hexane) which afforded an impure sample of Compound 137. Repurification by silica gel chromatography (hexanes) afforded 64 mg(1%) of Compound 137. Data for Compound 137: $^1$H NMR (400 MHz, acetone-d$_6$) 7.53 (m, 1H), 7.36 (s, 1H), 7.21 (dd, J=10, 8, 1H), 7.16 (dd, J=10, 8, 1H), 6.78 (s, 1H), 5.66 (br s, 1H), 5.51 (s, 1H), 2.04 (s, 3H), 1.29 (s, 6H).

EXAMPLE 37

8-Fluoro-1,2-dihydro-10-hydroxy-2,2,4-trimethylindeno[1,2-g]quinoline (Compound 136, structure 16 of Scheme IV, where $R^{2-4}$, $R^6$=H, $R^5$=F, X=CHOH)

This compound was prepared according to General Method 4 (EXAMPLE 34) from Compound 137 (18.2 mg, 0.05 mmol) and DIBALH (1.0M in hexanes, 0.2 mL) to afford, after purification by PTLC (1000 μm silica, 19/1 hexane/EA) 0.9 mg (5%) of Compound 136 as a white solid. Data for Compound 136: $^1$H NMR (400 MHz, acetone-$d_6$) 7.52 (m, 1H), 7.37 (s, 1H,), 7.21 (dd, J=8, 2.4, 1H), 7.02 (ddd, J=16, 8, 2.4, 1H), 6.77 (s, 1H), 5.38 (d, J=12, 1H), 5.37 (s, 1H,), 5.31 (br s, 1H), 4.59 (d, J=8, 1H), 2.03 (d, J=1.2, 3H), 1.28 (s, 3H), 1.26 (s, 3H).

EXAMPLE 38

7-Fluoro-1,2-dihydro-2,2,4-trimethyl-8-nitroindeno[1,2-g]quinoline (Compound 138, structure 16, Scheme IV, where $R^{2-3}$, $R^6$=H, $R^4$=F, $R^5$=NO$_2$, X=CH$_2$)

This compound was prepared according to General Method 3 (EXAMPLE 16) from 2-amino-6-fluoro-7-nitrofluorene (1.00 g, 4.00 mmol) to afford 98 mg (8%) of Compound 138 as a bright purple solid. Data for Compound 138: $R_f$=0.23 (silica gel, hexane/EtOAc, 3:1); $^1$H NMR (400 MHz, acetone-$d_6$) 8.13 (d, J=8.3, 1H), 7.66 (d, J=12, 1H), 6.64 (s, 1H), 5.47 (s, 1H), 3.85 (s, 2H), 2.77 (d, J=1.0, 3H), 1.36 (s, 6H).

EXAMPLE 39

5-Chloro-1,2-dihydro-10-hydroxy-2,2,4-trimethylindeno[1,2-g]quinoline (Compound 139, structure 20, Scheme VI, where $R^2$=Cl, $R^{3-6}$=H, X=CHOH)

A solution of 2-amino-4-chloro-9-fluorenol (300 mg, 1.30 mmol), I2 (~1 mg) and acetone (20 mL) was heated in a sealed tube at 100° C. for 16 h. To the cooled reaction mixture was added Celite™ (0.5 g), and the slurry was concentrated in vacuo to afford a free-flowing powder which was purified by SGC (230–400 mesh, 2.5×15 cm) using a 10–100% EtOAc:hexane gradient to afford 2.6 mg (1%) of Compound 139 as a white solid. Data for Compound 139: $R_f$=0.14 (silica gel, 25% EtOAc:hexane); $^1$H NMR (400 MHz, acetone-$d_6$) 8.18 (d, J=7.7, 1H), 7.78 (t, J=7.9, 1H), 7.52 (d, J=7.8, 1H), 7.19 (t, J=7.8, 1H), 6.90 (s, 1H), 5.70 (br s, 1H), 5.50 (s, 1H), 5.40 (s, 1H), 4.59 (d, J=8.5, 1H), 2.35 (s, 3H), 1.32 (s, 3H) and 1.21 (s, 3H).

EXAMPLE 40

6-Fluoro-1,2-dihydro-2,2,4-trimethyl-10-oxoindeno[1,2-g]quinoline (Compound 140, structure 19, Scheme VI, where $R^2$, $R^{4-6}$=H, $R^3$=F, X=CO)

This compound was prepared from 5-fluoro-2-nitrofluorenone (1.0 g, 4.1 mmol) in two steps in the manner previously described for Compound 123 (EXAMPLE 24), affording 0.74 g (61%) of Compound 140 as a dark purple solid. Data for Compound 140: $^1$H NMR (400 MHz, CDCl$_3$) 7.33 (s, 1H), 7.26 (m, 3H), 6.75 (s, 1H), 5.45 (s, 1H), 3.96 (br s, 1H), 2.05 (d, J=1.5, 3H), 1.31 (s, 6H).

EXAMPLE 41

6-Fluoro-1,2-dihydro-10-hydroxy-2,2,4-trimethylindeno[1,2-g]quinoline (Compound 141, structure 20, Scheme VI, where $R^2$, $R^{4-6}$=H, $R^3$=F, X=CHOH)

This compound was prepared by General Method 4 from Compound 140 (0.30 g, 1.0 mmol) to afford 0.25 g (84%) of Compound 141 as a pale reddish-purple solid. Data for Compound 141: $^1$H NMR (400 MHz, CDCl$_3$) 7.49 (s, 1H), 7.32 (d, J=7.3, 1H), 7.12 (dt, J=7.8, 4.8, 1H), 7.00 (dd, J=9.8, 8.3, 1H), 6.71 (s, 1H), 5.47 (s, 1H), 5.37 (d, J=1.2, 1H), 3.88 (br s, 1H), 2.06 (d, J=1.2, 3H), 1.31 (s, 3H), 1.30 (s, 3H).

EXAMPLE 42

5,8-1,2-dihydro-2,2,4-trimethyl-10-(trifluoroacetoxy)indeno[1,2-g]quinoline (Compound 142, structure 16, Scheme IV, where $R^2$, $R^5$=F, $R^3$, $R^4$, $R^6$=H, X=CHOCOCF$_3$)

To a flame-dried 25 mL r.b. flask containing 5,8-difluoro-1,2-dihydro-10-hydroxy-2,2,4-trimethylindeno[1,2-g]quinoline, Compound 132, EXAMPLE 32, (15.0 mg,) 0.048 mmol) in 2 mL dichloromethane at 0° C. was added trifluoroacetic anhydride (10 mL, 0.071 mmol, 1.5 equiv) and 4-N,N-dimethylaminopyridine (18.0 mg, 0.147 mmol, 3.0 equiv), and the mixture was allowed to stir for 10 min. The reaction mixture was then transferred to a separatory funnel with ethyl acetate (20 mL), pH 7 potassium phosphate buffer (10 mL) was added and the layers were separated. The organic phase was dried (Na$_2$SO$_4$) and concentrated under diminished pressure. Purification by flash column chromatography (silica gel, hexanes/ethyl acetate, gradient elution) afforded 14.1 mg (76%) of Compound 142 as a light yellow oily solid. Data for Compound 142: $^1$H NMR (400 MHz, CDCl$_3$) 7.59 (dd, J=8.4, 5.0, 1H), 7.15 (dd, J=8.2, 2.4, 1H), 7.09 (dt, J=8.8, 2.5, 1H), 6.64 (s, 1H), 6.47 (s, 1H), 2.19 (dd, J=6.7, 1.2, 3H), 1.29 (s, 3H), 1.28 (s, 3H).

EXAMPLE 43

6-(3,5-Difluorophenyl)-1,2,3,4-tetrahydro-2,2,4-trimethylquinoline (Compound 143, structure 5 of Scheme 1 where $R^1$=3,5-difluorophenyl)

A dry 10 mL r.b. flask was charged with Compound 147 (EXAMPLE 47) (17.4 mg, 0.06 mmol) and 0.3 mL ethyl acetate. To this solution was added 10% Pd/C (20 mg). The reaction mixture was stirred under an atmosphere of hydrogen for 1 h. The reaction was purged with nitrogen until all of the hydrogen had been removed from the flask. The product mixture was filtered through a plug of cotton and Celite™ to remove the solids, rinsed with ethyl acetate (50 mL) and concentrated. The crude material was purified by HPLC (reverse phase, ODS semi-preparatory column, 85% methanol/water, 3.0 mL/min). The major peak was isolated and identified as Compound 143 (3.5 mg, 20%) by NMR. Data for Compound 143: $^1$H NMR (400 MHz, methanol-$d_4$) 7.38 (d, J=2.3, 1H); 7.20 (dd, J=8.5, 1.6, 1H); 7.09 (m, 2H); 6.72 (m, 1H); 6.56 (d, J=8.2, 1H); 2.96 (m, 1H); 1.79 (dd, J=12.9, 5.8, 1H); 1.39 (m, 4H); 1.24 (s, 3H); 1.17 (s, 3H).

EXAMPLE 44

1,2-Dihydro-2,2,4-trimethylindolo[3,2-g]quinoline (Compound 144, structure 16 of Scheme IV, where $R^{1-6}$=H, X=NH)

2-Aminocarbazole (structure 15 of Scheme IV, where $R^{1-6}$=H, X=NH):

2-Nitrocarbazole [Mendenhall, G. D.; Smith, P. A. S. *Org. Syn. Coll.* Vol. 5 1973, 829, the disclosure of which is herein incorporated by reference](structure 14 of Scheme IV, where $R^{1-6}$=H, X=NH) (1.0 g, 4.7 mmol) in 50 mL of ethyl acetate was hydrogenated over 10% Pd/C (50 mg) under an atmosphere of hydrogen for 1.5 h at rt giving, after filtration through Celite™, 840 mg (100%) of 2-aminocarbazole. Data for 2-aminocarbazole: $^1$H NMR (400 MHz, CDCl$_3$) 7.94 (d, J=9.0, 1H), 7.83 (d, J=8.0, 1H), 7.80 (br s, 1H), 7.35 (m, 2H), 7.15 (dd, J=8.2, 1H), 6.67 (d, J=1.8, 1H), 6.58 (dd, J=9.0, 1.8, 1H), 3.73 (br s, 2H).

1,2-Dihydro-2,2,4-trimethylindolo[3,2-g]quinoline (Compound 144, structure 16 of Scheme IV, where $R^{1-6}$=H, X=NH)

A solution of 2-aminocarbazole (structure 15 of Scheme IV, where $R^{1-6}$=H, X=NH) (840 mg, 4.7 mmol) in 10 mL of acetone and one crystal (10 mg) of iodine was heated at 100° C. for 14 h in a sealed tube. The acetone was removed in vacuo to afford a dark oil which was purified by silica gel chromatography (silica gel, hexane/ethyl acetate, 8:2) to afford 738 mg of Compound 144 and 121 mg of 1,2-dihydro-2,2,4-trimethylindolo[2,3-f]quinoline (structure 17 of Scheme IV, where $R^{1-6}$=H, X=NH) (71% combined yield). Data for Compound 144: $^1$H NMR (400 MHz, $CDCl_3$) 7.90 (d, J=8.0, 1H); 7.80 (br s, 1H), 7.66 (br s, 1H), 7.23 (br s, 2H), 7.12 (m, 1H), 6.30 (br s, 1H), 5.32 (br s, 1H), 3.75 (br s, 1H), 2.13 (s, 3H), 1.39 (s, 1H).

EXAMPLE 45

5-Ethyl-1,2-dihydro-2,2,4-trimethylindolo[2,3-f]quinoline (Compound 145, structure 29 of Scheme VIII, where $R^{1-6}$=H, $R^7$=Et)

To a suspension of sodium hydride (60% in mineral oil, 16 mg, 0.405 mmol) in 1 mL of THF at 0° C. was slowly added 1,2-dihydro-2,2,4-trimethylindolo[2,3-f]quinoline (structure 28 of Scheme VIII, where $R^{1-6}$=H) (30 mg, 0.116 mmol) in 1 mL of THF and the resulting mixture was stirred at 0° C. for 30 minutes. Iodoethane (9.3 mL, 0.116 mmol) was added dropwise via a microsyringe and the reaction mixture was brought to rt and stirred for 16 h. The reaction was quenched with 1 mL of water and extracted with 10 mL of ethyl acetate. The organic phase was dried ($Na_2SO_4$) and concentrated in vacuo to a residue that was purified by flash chromatography (silica gel, hexane/ethyl acetate, 9:1) which gave 27 mg (81%) of Compound 145. Data for Compound 145: $^1$H NMR (400 MHz, $CDCl_3$) 7.81 (d, J=7.1, 1H), 7.63 (d, J=8.1; 1H); 7.34 (d, J=8.0, 1H); 7.25 (br s, 1H); 7.12 (apparent t, J=7.4, 1H); 6.51 (br s, 1H); 5.38 (br s, 1H); 4.25 (q, J=7.0, 2H); 4.22 (br s, 1H); 2.16 (s, 3H); 1.26 (s, 6H); 0.91 (t, J=7.0, 3H).

EXAMPLE 46

(3-Chlorophenyl)-1,2-dihydro-2,2,4-trimethylquinoline (Compound 146, structure 4 of Scheme II, where $R^1$=3-chlorophenyl)

This compound was prepared according to General Method 2 (EXAMPLE 9) from Compound 9 (91 mg, 0.29 mmol) and 3-bromochlorobenzene (33.6 mg, 0.29 mmol). The crude product was isolated and purified by silica gel chromatography (50 mL silica, 5% ethyl acetate/hexane) and PTLC (reverse phase, 1000 μm plate, 95% methanol/water) to yield 54 mg (81%) of Compound 146. Data for Compound 146: $^1$H NMR (400 MHz, acetone-$d_6$) 7.56 (d, J=4.0, 1H); 7.50 (d, J=8.0, 1H); 7.34 (apparent t, J=8.0, 1H); 7.31 (d, J=4.0, 1H); 7.24 (dd, J=8.0, 4.0, 1H); 7.23 (dd, J=8.0, 4.0, 1H); 6.57 (d, J=8.0, 1H); 5.60 (s, 1H); 2.03 (s, 3H); 1.27 (s, 6H).

EXAMPLE 47

6-(3,5-Difluorophenyl)-1,2-dihydro-2,2,4-trimethylquinoline (Compound 147, structure 4 of Scheme II, where $R^1$=3,5-difluorophenyl)

This compound was prepared according to General Method 2 (EXAMPLE 9). From Compound 9 (59.7 mg, 0.19 mmol) and 1-bromo-3,5-difluorobenzene (21.6 mL, 0.19 mmol, Lancaster) a crude reaction mixture was isolated and purified by HPLC (reverse phase, semi-preparative column, 85% methanol/water) to yield 5.6 mg of Compound 147 and 0.9 mg of Compound 148 (EXAMPLE 48) (8% combined yield). Data for Compound 147: $^1$H NMR (400 MHz, acetone-$d_6$) 7.34 (d, J=2.2, 1H); 7.28 (dd, J=8.4, 2.3, 1H); 7.19 (m, 2H); 6.80 (m, 1H); 6.57 (d, J=8.3, 1H); 5.47 (s, 1H); 5.38 (s, 1H); 2.04 (s, 3H); 1.28 (s, 6H).

EXAMPLE 48

6-(3-Fluorophenyl)-1,2-dihydro-2,2,4-trimethylquinoline (Compound 148, structure 4 of Scheme II, where $R^1$=3-fluorophenyl)

This compound was obtained along with Compound 147 as described above (EXAMPLE 47). Data for Compound 148: $^1$H NMR (400 MHz, acetone-$d_6$) 7.45 (d, J=8.0, 1H); 7.35 (m, 2H); 7.26 (dd, J=7.7, 2.2, 1H); 7.10 (d, J=2.0, 1H); 7.03 (dd, J=8.1,2.0, 1H); 6.54 (d, J=8.2, 1H); 5.35 (s, 1H); 5.29 (s, 1H); 1.97 (s, 3H); 1.28 (s, 6H).

EXAMPLE 49

1,2-Dihydro-2,2,4-trimethyl-6-(4-pyridyl)quinoline (Compound 149, structure 4 of Scheme II, where $R^1$=4-pyridyl)

This compound was prepared according to General Method 2 (EXAMPLE 9) from Compound 9 (23.8 mg, 0.07 mmol) and 4-bromopyridine hydrochloride (14.5 mg, 0.07 mmol, Aldrich). The crude product was isolated and purified by silica gel chromatography (75 mL silica, 5% ethyl acetate/hexane) and recrystallized twice (hexane/$CH_2Cl_2$, then $Et_2O$) to afford 7.3 mg (40%) of Compound 149. Data for Compound 149: $^1$H NMR (400 MHz, acetone-$d_6$) 8.59 (d, J=6.0, 2H); 7.55 (m, 2H); 7.45 (d, J=2.2, 1H); 7.40 (dd, J=8.3, 2.1, 1H); 6.60 (d, J=8.2, 1H); 5.40 (s, 1H); 2.06 (s, 3H); 1.30 (s, 6H).

EXAMPLE 50

6-(3-Cyanophenyl)-1,2-dihydro-2,2,4-trimethylquinoline (Compound 150, structure 4 of Scheme II, where $R^1$=3-cyanophenyl)

This compound was prepared according to General Method 2 (EXAMPLE 9) from Compound 9 (81.4 mg, 0.26 mmol) and 3-bromobenzonitrile (46.6 mg, 0.26 mmol, Lancaster). The crude product was isolated and purified by silica gel chromatography (75 mL silica, 5% ethyl acetate/hexane) to afford 51.6 mg (74%) of Compound 150 as pale yellow crystals. Data for Compound 150: $^1$H NMR (400 MHz, acetone-$d_6$) 7.94 (d, J=1.1, 1H); 7.88 (m, 1H); 7.56 (m, 2H); 7.38 (d, J=2.2, 1H,); 7.31 (dd, J=8.3, 2.2, 2H); 6.59 (d, J=8.3, 1H); 5.42 (s, 1H); 5.38 (s, 1H); 2.01 (s, 3H); 1.28 (s, 6H).

EXAMPLE 51

6-(3,5-Dichlorophenyl)-1,2-dihydro-2,2,4-trimethylquinoline (Compound 151, structure 4 of Scheme II, where $R^1$=3,5-dichlorophenyl)

This compound was prepared according to General Method 2 (EXAMPLE 9) from Compound 9 (40.4 mg, 0.13 mmol) and 1-bromo-3,5-dichlorobenzene (28.7 mg, 0.13 mmol, Aldrich). The crude product was isolated and purified by silica gel chromatography (75 mL silica, 5% ethyl acetate/hexane) to afford 32 mg (79%) of Compound 151. Data for Compound 151: $^1$H NMR (400 MHz, acetone-$d_6$) 7.53 (d, J=1.8, 2H); 7.34 (d, J=1.8, 1H); 7.27 (m, 2H); 6.57 (d, J=8.3, 1H); 5.38 (s, 1H); 2.04 (s, 3H); 1.28 (s, 6H).

EXAMPLE 52

6-(2,3-Difluorophenyl)-1,2-dihydro-2,2,4-trimethylquinoline (Compound 152, structure 4 of Scheme II, where $R^1$=2,3-difluorophenyl)

This compound was prepared according to General Method 2 (EXAMPLE 9) from Compound 9 (28.7 mg, 0.09 mmol) and 1-bromo-2,3-difluorobenzene (10 µL, 0.09 mmol, Aldrich). The crude product was isolated and purified by silica gel chromatography (75 mL silica, 5% ethyl acetate/hexane) to afford 16 mg (62%) of Compound 152. Data for Compound 152: $^1$H NMR (400 MHz, acetone-$d_6$) 7.21 (m, 5H); 6.57 (d, J=8.3, 1H); 5.37 (s, 1H); 1.99 (s, 3H); 1.28 (s, 6H).

EXAMPLE 53

1,2-Dihydro-2,2,4-trimethyl-6-(pentafluorophenyl) quinoline (Compound 153, structure 4 of Scheme II, where $R^1$=pentafluorophenyl)

This compound was prepared according to General Method 2 (EXAMPLE 9) from Compound 9 (55.3 mg, 0.17 mmol) and 1-bromopentafluorobenzene (21.7 mL, 0.17 mmol, Lancaster). The crude product was isolated and purified by silica gel chromatography (75 mL silica, 5% ethyl acetate/hexane) to afford 2.5 mg (5%) of Compound 153. Data for Compound 153: $^1$H NMR (400 MHz, acetone-$d_6$) 7.11 (d, J=1.2, 1H); 7.03 (dd, J=8.0, 1.6, 1H); 6.60 (d, J=8.3, 1H); 5.57 (s, 1H); 1.95 (s, 3H); 1.29 (s, 6H).

EXAMPLE 54

1,2-Dihydro-2,2,4-trimethyl-6-[4-(trifluoroacetyl)phenyl] quinoline (Compound 154, structure 4 of Scheme II, where $R^1$=4-(trifluoroacetyl)phenyl)

This compound was prepared according to General Method 2 (EXAMPLE 9) from Compound 9 (49.1 mg, 0.15 mmol) and 4'-bromo-2,2,2-trifluoroacetophenone (23.5 µL, 0.15 mmol, Aldrich). The crude product was isolated and purified by silica gel chromatography (75 mL silica, hexane) to afford 50 mg (94%) of Compound 154. Data for Compound 154: $^1$H NMR (400 MHz, acetone-$d_6$) 8.06 (dd, J=8.5, 0.8, 2H,); 7.80 (dd, J=8.6, 1.7, 2H); 7.41 (m, 2H); 5.41 (s, 1H); 4.97 (s, 1H); 2.04 (s, 3H); 1.27 (s, 6H).

EXAMPLE 55

1,2-Dihydro-2,2,4-trimethyl-6-(1,3-pyrimid-5-yl)quinoline (Compound 155, structure 4 of Scheme II, where $R^1$=3,5-pyrimidyl)

This compound was prepared according to General Method 2 (EXAMPLE 9) from Compound 9 (74.4 mg, 0.23 mmol) and 5-bromopyrimidine (37.1 mg, 0.23 mmol, Aldrich). The crude product was isolated and purified by recrystallization ($Et_2O$ hexanes) to afford 2.1 mg (4%) of Compound 155. Data for Compound 155: $^1$H NMR (400 MHz, acetone-$d_6$) 8.97 (s, 1H); 8.94 (s, 2H); 7.39 (d, J=1.9, 1H); 7.32 (dd, J=8.4, 2.2, 1H); 6.63 (d, J=8.3, 1H); 5.39 (s, 1H); 2.05 (s, 3H); 1.29 (s, 6H).

EXAMPLE 56

6-(3-Cyanophenyl)-1,2,3,4-tetrahydro-2,2,4-trimethylquinoline (Compound 156, structure 5 of Scheme I where $R^1$=3-cyanophenyl)

A dry 10 mL r.b. flask was charged with Compound 150 (EXAMPLE 50) (16.7 mg, 0.06 mmol) and 0.5 mL ethyl acetate. To this solution 10% Pd/C (20 mg) was added. The flask was stirred under an atmosphere of hydrogen for 1 h. The reaction was then purged with nitrogen until all of the hydrogen had been removed from the flask. The product mixture was filtered through a plug of cotton and Celite™ to remove the solids, rinsing with ethyl acetate (50 mL). The crude material was purified by HPLC (reverse phase, ODS semi-preparatory column, 85% methanol/water, 3.0 mL/min). The major peak was isolated and identified as Compound 156 (1.8 mg, 11%) by NMR. Data for Compound 156: $^1$H NMR (400 MHz, acetone-$d_6$) 7.93 (d, J=1.3, 1H); 7.88 (m, 1H); 7.55 (m, 2H); 7.51 (d, J=1.4, 1H); 7.28 (dd, J=8.7, 1.4, 1H); 6.59 (d, J=8.4, 1H); 2.95 (m, 1H); 1.80 (dd, J=12.8, 5.4, 1H); 1.39 (m, 4H); 1.25 (s, 3H); 1.19 (s, 3H).

EXAMPLE 57

5,8-Difluoro-1,2-dihydro2,2,4-trimethylindeno[1,2-g] quinoline (Compound 157, structure 16 of Scheme IV, where $R^2$=$R^5$=F, $R^3$=$R^4$=$R^6$=H, X=$CH_2$)

4,7-Difluoro-2-fluorenamine (Namkung, M. J.; Fletcher, T. L.; Wetzel, W. H. Derivatives of Fluorene. XX. Fluorofluorenes. V. New Difluoro-2-acetamidofluorenes for the Study of Carcinogenic Mechanisms. *J. Med. Chem.* 1965, 8, 551–554, the disclosure of which is herein incorporated by reference). To a 25 mL round-bottomed flask containing 4,7-difluoro-9-oxo-2-fluorenamine (EXAMPLE 32) (158.5 mg, 0.686 mmol) in 4.25 mL glacial acetic acid was added red phosphorous (425 mg, 13.7 mmol, 20 equiv) and 57% aqueous HI (0.51 mL). The mixture was heated to reflux for 40 h, then evaporated to near-dryness by distillation. Boiling water (5 mL) was added, and the hot mixture was filtered. Upon addition of 10% $NH_4OH$ (20 mL), a white precipitate formed, and was filtered, washed with water, and dried under vacuum to afford 127 mg (85%) of 4,7-difluoro-2-fluorenamine as a white solid, mp 119°–120° C. (lit. mp 119.5°–121° C.). Data for 4,7-difluoro-2-fluorenamine: $^1$H NMR (400 MHz, $CDCl_3$) 7.70 (dd, J=8.4, 5.2, 1H), 7.15 (dd, J=9.0, 2.0, 1H), 7.03 (app dt, J=9.0, 2.0, 1H), 6.63 (s, 1H), 6.39 (dd, J=11.6, 1.7, 1H), 3.83 (s, 2H), 3.80 (br s, 2H).

5,8-Difluoro-1,2-dihydro-2,2,4-trimethylindeno[1,2-g] quinoline (Compound 157, structure 16 of Scheme IV, where $R^2$=$R^5$=F, $R^3$=$R^4$=$R^6$=H, X=$CH_2$)

This compound was prepared by General Method 3 from 4,7-difluoro-2-fluorenamine (127 mg, 0.58 mmol). Purification by flash column chromatography (silica gel, hexanes/ethyl acetate, gradient elution) afforded 42 mg (24%) of the less polar angular Compound 158 (EXAMPLE 58) as a yellow oil, along with 63 mg (36%) of the more polar Compound 157 as a white solid. Data for Compound 157: $^1$H NMR (400 MHz, $CDCl_3$) 7.68 (dd, J=8.4, 5.3 1H, 9-H), 7.12 (dd, J=8.8, 2.3, 1H, 6-H), 7.00 (apparent dt, J=9.1, 2.3, 1H, 7-H), 6.44 (s, 1H, 11-H), 5.30 (s, 1H, 3-H), 3.86 (br s, 1H, NH), 3.78 (s, 2H, 10-H), 2.22 (dd, J=6.7, 1.5, 3H, 4-$CH_3$), 1.28 [s, 6H, 2-$(CH_3)_2$].

EXAMPLE 58

7,10-Difluoro-1,2-dihydro-2,2,4-trimethylindeno[2,1-f] quinoline (Compound 158, structure 17 of Scheme IV, where $R^2$=$R^5$=F, $R^3$=$R^4$=$R^6$=H, X=$CH_2$)

Compound 158 was obtained along with Compound 157 as described above (EXAMPLE 57). Data for Compound 158: $^1$H NMR (400 MHz, $CDCl_3$) 7.69 (dd, J=8.3, 5.3, 1H, 6-H), 7.11 (dd, J=8.7, 2.4, 1H, 9-H), 7.09 (apparent dt, J=9.1, 2.4, 1H, 7-H), 6.23 (d, J=11.0, 1H, 11-H), 5.34 (s, 1H, 3-H), 4.08 (s, 2H, 5-H), 3.84 (br s, 1H, NH), 2.23 (s, 3H, 4-$CH_3$), 1.26 [s, 6H, 2-$(CH_3)_2$].

EXAMPLE 59

1,2-Dihydro-2,2,4-trimethyl-5-coumarino[3,4-f]quinoline (Compound 159, Scheme IX)

The intermediate 2-nitro-3,4-benzocoumarin was prepared by a modified literature procedure. See *J. Org. Chem.*, U.S.S.R., 15 (3), 503 (1979), the disclosure of which is herein incorporated by reference. To a flask charged with 2-biphenylcarboxylic acid (5 g, 25 mmol) was added 7 mL of 70% nitric acid and the resulting yellow slurry was stirred at rt for 30 min. To this slurry 20 mL of fuming nitric acid was introduced dropwise, giving rise to a clear yellow solution. The reaction mixture was stirred at rt for 15 h, and was then poured into ice water (100 mL). The crude mixture was extracted with ethyl acetate (3×60 mL) and the combined extracts were washed with water (2×20 mL) and brine (2×20 mL). Removal of solvent under reduced pressure afforded a crude yellow solid, which was a 2:1 mixture of two regioisomers. The mixture of the dinitrobiphenylcarboxylic acids was dissolved in 80 mL of DMA and the solution was heated at reflux for 12 hours. The reaction was cooled to rt and diluted with 20 mL of water. The desired product precipitated from the solution upon standing at rt overnight. Filtration of the mixture afforded 2.9 g (50%) of 2-nitro-3,4-benzocoumarin, which was used directly in next reaction without further purification. 2-Nitro-3,4-benzocoumarin (2.9 g, 12 mmol) was dissolved in 600 mL of ethyl acetate and treated with 10% Pd/C (1.0 g, 0.94 mmol) and stirred under a hydrogen balloon for 24 h. Filtration of the catalyst and removal of solvent afforded 2.2 g (86%) of 2-amino-3,4-benzocoumarin as a yellowish solid. An Ace-Thred pressure tube charged with 2-amino-3,4-benzocoumarin (2.2 g, 10.4 mmol), iodine (0.8 g, 3.1 mmol) and acetone (150 mL) was sealed. The tube was heated in an oil bath at 80°–120° C. for 24 h and then cooled to rt. The dark reaction mixture was concentrated under reduced pressure and the crude residue was purified by silica gel chromatography (hexane/EtOAc, 4/1) to give 1.5 g (50%) of Compound 159 as a yellow solid. Data for Compound 159: mp 190°–191° C.; IR (KBr) 3352, 2966, 2924, 1712, 1626, 1450, 1356, 1251, 1205; $^1$H NMR (400 MHz, CDCl$_3$) 7.90 (d, J=7.8, 1H), 7.78 (d, J=8.4, 1H), 7.38–7.22 (m, 3H), 7.01 (d, J=8.4, 1H), 5.58 (s, 1H), 4.31 (br s, 1H), 2.12 (s, 3H), 1.33 (s, 6H); $^{13}$C NMR (100 MHz, CDCl$_3$) 160.3, 150.5, 145.7, 132.4, 131.6, 128.4, 124.2, 122.0, 121.4, 121.2, 119.3, 118.4, 117.2, 50.8, 29.9, 28.6; Anal. Calcd for C$_{19}$H$_{17}$NO$_2$: C, 78.33; H, 5.88; N, 4.81. Found: C, 78.19;H, 6.12; N, 4.52.

EXAMPLE 60

(R/S)-5-Butyl-1,2-dihydro-2,2,4-trimethyl-5H-chromeno[3, 4-f]quinoline Compound 160, structure 32 of Scheme IX where R=n-butyl)
GENERAL METHOD 5: Preparation of compounds of structures 32 and 33 from Compound 159

This transformation involved a two step sequence: addition of a nucleophile (either a commercial reagent or prepared in situ from a metal-halogen exchange reaction), followed by reduction of the resulting cyclic hemiacetal. To a solution of an aryl bromide compound in THF (0.1–0.3M) at −78° C. was slowly added 1.1 equiv. of n-BuLi (as a hexane solution) and the resulting reaction mixture was allowed to stir at −78° C. until the anion was formed. A yellow solution (0.2–0.5M) of Compound 159 in THF was cannulated into the above solution and the resulting dark red mixture was slowly allowed to warm. As soon as the red color faded (around −30° C.), the reaction was quenched with water to give a light yellow solution. The reaction mixture was extracted with ethyl acetate and the combined extracts were washed with brine. Removal of solvent under reduced pressure and purification of the crude residue on a silica gel column using a 1:3 mixture of ethyl acetate and hexane as eluents afforded the hemiacetal intermediate as a yellow oil. To a solution of the hemiacetal intermediate in dichloromethane (0.1M) at −78° C. was added 5–10 equiv of trifluoroacetic acid and triethylsilane (or, alternatively, 2–3 equiv of boron trifluoride etherate and 5–6 equiv of triethylsilane) and the resulting slurry was allowed to warm to rt, giving rise to a dark green solution. The mixture was allowed to stir at rt or reflux in some cases, until the reaction went to completion. The reaction was then quenched with 5% NaOH (aq) and was extracted with ethyl acetate. The combined extracts were washed with brine and concentrated. The crude mixture was purified on a silica gel column using a 1:5 mixture of ethyl acetate and hexane as eluents, affording the desired product in moderate yield. A second silica gel chromatography was needed in several cases to remove the silane oxide and/or separate the isomers of structures 32 and 33 using a 1:2 mixture of dichloromethane and hexane as eluents.

(R/S)-5-Butyl-1,2-dihydro-2,2,4-trimethyl-5H-chromeno[3, 4-f]quinoline (Compound 160, structure 32 of Scheme IX where R=n-butyl)

This compound was prepared by General Method 5 from n-BuLi (1.6M, 0.2 mL) and Compound 159 (50 mg, 0.17 mmol) to afford 40 mg (71%) of Compound 160 as a colorless oil. Data for Compound 160: IR (neat) 3388, 2980, 1593, 1468 and 1435 cm$^{-1}$; $^1$H NMR (400 MHz, CDCl$_3$) 7.62 (d, J=7.8, 1H), 7.44 (d, J=8.3, 1H), 7.14 (t, J=7.8, 1H), 6.98 (t, J=7.8, 1H), 6.92 (d, J=7.8, 1H), 6.59 (d, J=8.3, 1H), 5.88 (dd, J=9.8, 3.1, 1H), 5.49 (s, 1H), 3.88 (br s, 1H), 2.25 (s, 3H), 1.90–1.79 (m, 1H), 1.55–1.25 (m, 5H), 1.28 (s, 3H), 1.20 (s, 3H), 0.84 (t, J=7.3, 3H).

EXAMPLE 61

(R/S)-1,2-Dihydro-2,2,4-trimethyl-5-phenyl-5H-chromeno [3,4-f]quinoline (Compound 161, structure 32 of Scheme IX, where R=phenyl)

This compound was prepared by General Method 5 (EXAMPLE 60) from bromobenzene (0.15 mL, 1.4 mmol) and Compound 159 (50 mg, 0.17 mmol) to afford 15 mg (25%) of Compound 161 as a colorless oil, along with 6 mg (10%) of Compound 162 (EXAMPLE 62). Data for Compound 161: $^1$H NMR (400 MHz, CDCl$_3$) 7.53 (d, J=7.8, 1H), 7.50 (d, J=8.2, 1H), 7.22–7.12 (m, 5H), 7.00 (t, J=7.8, 1H), 6.92 (s, 1H), 6.88(t, J=7.8, 1H), 6.83 (d, J=7.8, 1H), 6.69 (d, J=8.2, 1H), 5.46 (s, 1H), 3.92 (br s, 1H), 1.99 (s, 3H), 1.29 (s, 3H), 1.26 (s, 3H).

EXAMPLE 62

(R/S)-1,2,3,4-Tetrahydro-2,2-dimethyl-4-methylidene-5-phenyl-5H-chromeno[3,4-f]quinoline (Compound 162, structure 33 of Scheme IX, where R=phenyl)

This compound (6 mg, 10%) was obtained along with Compound 161 as described above (EXAMPLE 61). Data for Compound 162: $^1$H NMR (400 MHz, CDCl$_3$) 7.53 (d, J=7.3, 1H), 7.51 (d, J=8.4, 1H), 7.24–7.12 (m, 5H), 6.97 (t, J=7.3, 1H), 6.87 (t, J=7.3, 1H), 6.80 (d, J=7.3, 1H), 6.64 (s, 1H), 6.59 (d, J=8.4, 1H), 4.93 (s, 1H), 4.64 (s, 1H), 4.09 (br s, 1H), 2.44 (d, J=12.1, 1H), 2.18 (d, J=12.1, 1H), 1.34 (s, 3H)and 1.13 (s, 3H).

EXAMPLE 63

(R/S)-5-(4-Chlorophenyl)-1,2-dihydro-2,2,4-trimethyl-5H-chromeno[3,4-f]quinoline (Compound 163, structure 32 of Scheme IX, where R=4-chlorophenyl)

This compound was prepared by General Method 5 (EXAMPLE 60) from 4-bromochlorobenzene (1.4 g, 7 mmol) and Compound 159 (0.5 g, 1.7 mmol) to afford 0.27 g (40%) of Compound 163 as a white solid, in addition to 60 mg (9%) of Compound 164 (EXAMPLE 64). Data for Compound 163: mp 139°–140° C.; IR (KBr) 3371, 2964, 1593, 1469, 1435 cm$^{-1}$; $^1$H NMR (400 MHz, acetone-d$_6$) 7.59 (d, J=7.8, 1H), 7.56 (d, J=8.4, 1H), 7.24(d, J=9.1, 2H), 7.21 (d, J=9.1, 2H), 6.98 (t, J=7.8, 1H), 6.92 (s, 1H), 6.86 (t, J=7.81, 1H), 6.83 (d, J=8.4, 1H), 6.77 (d, J=7.8, 1H), 5.54 (br s, 1H), 5.48 (s, 1H), 1.99 (s, 3H), (1.26 (s, 3H), 1.24 (s, 3H).

EXAMPLE 64

(R/S)-5-(4-Chlorophenyl)-1,2,3,4-tetrahydro-2,2-dimethyl-4-methylidene-5H-chromeno[3,4-f]quinoline (Compound 164, structure 33 of Scheme IX, where R=4-chlorophenyl)

This compound (60 mg, 9%) was obtained along with Compound 163 as described above (EXAMPLE 63). Data for Compound 164: $^1$H NMR (400 MHz, CDCl$_3$) 7.53 (d, J=7.7, 1H), 7.51 (d, J=8.3, 1H), 7.18 (d, J=8.7, 2H), 7.15 (d, J=8.7, 2H), 6.99 (t, J=7.7, 1H), 6.79 (d, J=7.7, 1H), 6.59 (s, 1H), 6.58 (d, J=8.3, 1H), 4.93 (s, 1H), 4.59 (s, 1H), 4.09 (br s, 1H), 2.43 (d, J=12.3, 1H), 2.18 (d, J=12.3, 1H), 1.34 (s, 3H) 1.13 (s, 3H).

EXAMPLE 65

(R/S)-5-(4-Fluorophenyl)-1,2-dihydro-2,2,4-trimethyl-5H-chromeno[3,4-f]quinoline (Compound 165, structure 32 of Scheme IX, where R=4-fluorophenyl)

This compound was prepared by General Method 5 (EXAMPLE 60) from 4-fluorophenylmagnesium bromide (1.0M in THF, 1 mL) and Compound 159 (30 mg, 0.1 mmol) to afford 15 mg (38%) of Compound 165 as a colorless oil. Data for Compound 165: IR (KBr) 3360, 2962, 1707, 1601, 1506, 1469, 1221, 1157 cm$^{31}$ $^1$; $^1$H NMR (400 MHz, acetone-d$_6$) 7.60 (d, J=7.8, 1H), 7.56 (d, J=8.3, 1H), 7.26 (dd, J=8.7, 5.7, 2H), 6.98 (t, J=8.7, 2H), 6.97 (t, J=7.8, 1H), 6.92 (s, 1H), 6.87 (t, J=7.8, 1H), 6.83 (d, J=8.3, 1H), 6.76 (d, J=7.8, 1H), 5.54 (br s, 1H), 5.47 (s, 1H), 1.99 (s, 3H), 1.26 (s, 3H), 1.24 (s, 3H).

EXAMPLE 66

(R/S)-5-(4-Acetylphenyl)-1,2-dihydro-2,2,4-trimethyl-5H-chromeno[3,4-f]quinoline (Compound 166, structure 32 of Scheme IX, where R=4-acetylphenyl)

This compound was prepared by General Method 5 (EXAMPLE 60) from 2-(4-bromophenyl)-2-methyl-1,3-dioxane (219 mg, 1.0 mmol) and Compound 159 (30 mg, 0.1 mmol) to afford 4.5 mg (10%) of Compound 166 as a colorless oil. Data for Compound 166: $^1$H NMR (400 MHz, acetone-d$_6$) 7.83 (d, J=8.3, 2H), 7.60 (d, J=7.6, 1H), 7.57 (d, J=8.4, 1H), 7.36 (d, J=8.3, 2H), 6.99 (s, 1H), 6.98 (t, J=7.6, 1H), 6.89–6.79 (m, 3H), 5.56 (br s, 1H), 550 (s, 1H), 2.49 (s, 3H), 2.00 (s, 3H), 1.28 (s, 3H), 1.25 (s, 3H).

EXAMPLE 67

(R/S)-1,2-Dihydro-2,2,4-trimethyl-5-(4-methylphenyl)-5H-chromeno[3,4-f]quinoline (Compound 167, structure 32 of Scheme IX, where R=4-methylphenyl)

This compound was prepared by General Method 5 (EXAMPLE 60) from 4-bromotoluene (171 mg, 1.0 mmol) and Compound 159 (20 mg, 0.07 mmol) to afford 15 mg (58%) of Compound 167 as a colorless oil. Data for Compound 167: IR (KBr) 3362, 2964, 1707, 1593, 1469, 1437, 1259, 1169 cm$^{-1}$; $^1$H NMR (400 MHz, acetone-d$_6$) 7.58 (d, J=7.9, 1H), 7.54 (d, J=8.5, 1H), 7.10 (d, J=8.0, 2H), 7.00 (d, J=8.0, 2H), 6.97 (t, J=7.9, 1H), 6.89 (s, 1H), 6.84 (d, J=7.9, 1H), 6.81 (d, J=8.5, 1H), 6.75 (d, J=7.9, 1H), 5.47 (bs, 1H), 5.45 (s, 1H), 2.19 (s, 3H), 1.99 (s, 3H ), 1.25 (s, 3H), 1.23 (s, 3H).

EXAMPLE 68

(R/S)-1,2-Dihydro-5-(4-methoxyphenyl)-2,2,4-trimethyl-5H-chromeno[3,4-f]quinoline (Compound 168, structure 32 of Scheme IX, where R=4-methoxyphenyl)

This compound was prepared by General Method 5 (EXAMPLE 60) from 4-bromoanisole (187 mg, 1.0 mmol) and Compound 159 (10 mg, 0.03 mmol) to afford 2.5 mg (10%) of Compound 168 as a colorless oil. Data for Compound 168: $^1$H NMR (400 MHz, acetone-d$_6$) 7.59 (d, J=7.7, 1H), 7.54 (d, J=8.4, 1H), 7.13 (d, J=8.7, 2H), 6.95 (t, J=7.7, 1H), 6.87 (s, 1H), 6.86 (d, J=7.7, 1H), 6.81 (d, J=8.4, 1H), 6.75 (d, J=8.7, 2H), 6.74 (t, J=7.7, 1H), 5.47 (br s, 1H), 5.45 (s, 1H), 3.69 (s, 3H), 1.99 (s, 3H ), 1.25 (s, 3H), 1.23 (s, 3H).

EXAMPLE 69

(R/S)-1,2-Dihydro-2,2,4-trimethyl-5-[4-(trifluoromethyl)phenyl]-5H-chromeno[3-f]quinoline (Compound 169, structure 32 of Scheme IX, where R=4-(trifluoromethyl)phenyl)

This compound was prepared by General Method 5 (EXAMPLE 60) from 4-bromobenzotrifluoride (130 mg, 1.0 mmol) and Compound 159 (20 mg, 0.07 mmol) to afford 10 mg (35%) of Compound 169 as a colorless oil. Data for Compound 169: $^1$H NMR (400 MHz, acetone-d$_6$) 7.61–7.56 (m, 4H), 7.45 (d, J=8.3, 2H), 7.01 (s, 1H), 6.97 (d, J=7.7, 1H), 6.86 (t, J=7.7, 1H), 6.85 (d, J=8.4, 1H), 6.81 (d, J=7.7, 1H), 5.57 (br s, 1H), 5.49 (s, 1H), 1.99 (s, 3H ), 1.27 (s, 3H), 1.25 (s, 3H).

EXAMPLE 70

(R/S)-1,2-Dihydro-2,2,4-trimethyl-5-(thiophen-3-yl)-5H-chromeno[3,4-f]quinoline (Compound 170, structure 30 of Scheme IX, where R=thiophen-3-yl)

This compound was prepared by General Method 5 (EXAMPLE 60) from 3-bromothiophene (163 mg, 1.0 mmol) and Compound 159 (8 mg, 0.03 mmol) to afford 1.1 mg (11%) of Compound 170 as a colorless oil. Data for Compound 170: $^1$H NMR (400 MHz, acetone-d$_6$) 7.60 (d, J=7.3, 1H), 7.54 (d, J=8.4, 1H), 7.31 (dd, J=5.0, 3.0, 1H), 7.08 (d, J=5.0, 1H), 6.98 (t, J=7.3, 1H), 6.93 (s, 1H), 6.89 (t, J=7.3, 1H), 6.88 (d, J=3.0, 1H), 6.79 (d, J=8.1, 2H), 5.48 (br s, 1H), 2.06 (s, 3H), 1.25 (s, 3H), 1.24 (s, 3H).

EXAMPLE 71

(–)-1,2-Dihydro-2,2,4-trimethyl-5-(4-methylphenyl)-5H-chromeno[3,4-f]quinoline (Compound 171, structure 32 of Scheme IX, where R=4-methylphenyl)

This compound was prepared by optical resolution of Compound 167 via HPLC using a chiral column, Chiracel OD-R, using a 9:1 mixture of methanol and water as the mobile phase. The optical purity of Compound 171 was determined by HPLC to be >99% e.e.; $[\alpha]^{20}_D$=–246 (MeOH).

EXAMPLE 72

(–)-5-(4-Chlorophenyl)-1,2-dihydro-2,2,4-trimethyl-5H-chromeno[3,4-f]quinoline (Compound 172, structure 32 of Scheme IX, where R=4-chlorophenyl)

This compound was prepared by optical resolution of Compound 163 via HPLC using a chiral column, Chiracel OD-R, using a 9:1 mixture of methanol and water as mobile phase. The optical purity of Compound 172 was determined by HPLC to be >99% e.e.; $[\alpha]^{20}{}_D$=−254 (MeOH).

EXAMPLE 73

(R/S)-1,2-Dihydro-2,2,4-trimethyl-5-(3-methylphenyl)-5H-chromeno[3,4-f]quinoline (Compound 173, structure 32 of Scheme IX, where R=3-methylphenyl)

This compound was prepared by General Method 5 (EXAMPLE 60) from 3-bromotoluene (171 mg, 1.0 mmol) and Compound 159 (15 mg, 0.05 mmol) to afford 3.6 mg (19%) of Compound 173 as a colorless oil. Data for Compound 173: $^1$H NMR (400 MHz, acetone-$d_6$) 7.59 (d, J=7.8, 1H), 7.54 (d, J=8.4, 1H), 7.10–6.94 (m, 5H), 6.89 (s, 1H), 6.85 (d, J=7.8, 1H), 6.82 (d, J=8.4, 1H), 6.77 (d, J=8.0, 1H), 5.49 (br s, 1H), 5.46 (s, 1H), 2.19 (s, 3H), 2.00 (s, 3H), 1.26 (s, 3H), 1.24 (s, 3H).

EXAMPLE 74

(+)-(4I,5I)-5-(4-Chlorophenyl)-1,2,3,4-tetrahydro-2,2,4-trimethyl-5H-chromeno[3,4-f]quinoline (Compound 174, structure 34 of Scheme X, where R=4-chlorophenyl)

Hydrogenation of Compound 163 (15 mg, 0.04 mmol) in the presence of 10% Pd/C (10%) afforded 12 mg (80%) of (R/S-4I,5I)-5-(4-chlorophenyl)-1,2,3,4-tetrahydro-2,2,4-trimethyl-5H-chromeno[3,4-f]quinoline as a white solid in addition to 1.1 mg (7%) of Compound 176 (EXAMPLE 76) as a white solid. The enantiomers of (R/S-4I,5I)-5-(4-chlorophenyl)-1,2,3,4-tetrahydro-2,2,4-trimethyl-5H-chromeno[3,4-f]quinoline were resolved via HPLC using a chiral column, Chiracel OD-R, using a 9:1 mixture of methanol and water as mobile phase (0.55 mL/min). A 10 mg sample of (R/S4I,5I)-5-(4-chlorophenyl)-1,2,3,4-tetrahydro-2,2,4-trimethyl-5H-chromeno[3,4-f]quinoline afforded 3.1 mg of the first eluting, (+) enantiomer (Compound 174) (24 min), and 3.0 mg of the second eluting, (−) enantiomer (Compound 175, EXAMPLE 75) (30 min). The optical purity of Compound 174 was determined by HPLC to be >99% e.e. Data for Compound 174: mp 158°–159° C.; $^1$H NMR (400 MHz, acetone-$d_6$) 7.63 (d, J=7.8, 1H), 7.53 (d, J=1H), 7.24 (s, 4H), 6.94 (t, J=7.8, 1H), 6.87 (t, J=7.8, 1H), 6.76 (d, J=8.5, 1H), 6.68 (d, J=7.8, 1H), 6.51 (s, 1H), 5.10 (br s, 1H), 3.25 (m, 1H), 1.89 (dd, J=13.5, 6.4, 1H), 1.76 (dd, J=13.5, 4.4, 1H), 1.30 (s, 3H ), 1.21 (s, 3H), 0.83 (d, J=7.3, 3H); $^{13}$C NMR (100 MHz, CDCl$_3$) 150.6, 144.5, 138.6, 134.0, 130.9, 130.5, 128.4, 127.6, 124.9, 123.2, 122.2, 121.9, 120.2, 118.0, 115.8, 74.5, 50.0, 44.3, 31.6, 31.3, 27.5, 22.8. $[\alpha]^{20}{}_D$=+287 (MeOH).

EXAMPLE 75

(−)-(4I,5I)-5-(4-Chlorophenyl)-1,2,3,4-tetraahydro-2,2,4-trimethyl-5-H-chromeno[3,4-f]quinoline (Compound 175, structure 34 of Scheme X where R=4-chlorophenyl)

This compound was prepared by resolution of (R/S-4I,5I) -5-(4-chlorophenyl)-1,2,3,4-tetrahydro-2,2,4-trimethyl-5H-chromeno[3,4-f]quinoline as described above (EXAMPLE 74) via HPLC using a chiral column, Chiracel OD-R, using a 9:1 mixture of methanol and water as mobile phase. The optical purity of Compound 175 was determined by HPLC to be >95% e.e.; $[\alpha]^{20}{}_D$=−260 (MeOH).

EXAMPLE 76

R/S-4I,5u)-5-(4-Chlorophenyl)-1,2,3,4-tetrahydro-2,2,4-trimethyl-5H-chromeno[3,4-f]quinoline (Compound 176, structure 35 of Scheme X where R=4-chlorophenyl)

This compound (1.1 mg, 7%) was obtained along with (R/S-4I,5I)-5-(4-chlorophenyl)-1,2,3,4-tetrahydro-2,2,4-trimethyl-5H-chromeno[3,4-f]quinoline as described above (EXAMPLE 75). Data for Compound 176: $^1$H NMR (400 MHz, CDCl$_3$) 7.54 (d, J=7.6, 1H), 7.47 (d, J=8.4, 1H), 7.15 (d, J=6.5, 2H), 7.10 (d, J=6.5, 2H), 7.01 (t, J=7.6, 1H), 6.89 (t, J=7.6, 1H), 6.83 (d, J=7.6, 1H), 6.59 (d, J=8.4, 1H), 6.47 (s, 1H), 3.73 (br s, 1H), 2.82 (m, 1H), 1.76 (dd, J=13.5, 7.0, 1H), 1.73 (dd, J=13.5, 4.5, 1H), 1.46 (d, J=7.1, 3H), 1.36 (s, 3H), 1.19 (s, 3H); $^{13}$C NMR (100 MHz, CDCl$_3$) 150.5, 143.9, 138.4, 134.0, 130.3, 129.4, 128.6, 127.6, 124.2, 122.6, 122.1, 119.6, 118.0, 115.4, 74.4, 50.1, 42.9, 32.2, 31.8, 27.3, 22.3.

EXAMPLE 77

(R/S)-5-(3-Chlorophenyl-1,2-dihydro-2,2,4-trimethyl-5H-chromeno[3,4-f]quinoline (Compound) 177 structure 32 of Scheme IX where R=3-chlorophenyl)

This compound was prepared by General Method 5 (EXAMPLE 60) from 3-bromochlorobenzene (195 mg, 1.0 mmol) and Compound 159 (20 mg, 0.07 mmol) to afford 14 mg (52%) of Compound 177 as a colorless oil, along with 2.3 mg (7%) of Compound 178 (EXAMPLE 78) as a colorless oil. Data for Compound 177: $^1$H NMR (400 MHz, acetone-$d_6$) 7.61 (d, J=7.8, 1H), 7.57 (d, J=8.4, 1H), 7.28–7.18 (m, 4H), 7.00 (t, J=7.8, 1H), 6.95 (s, 1H), 6.89 (d, J=7.8, 1H), 6.84 (d, J=8.4, 1H), 6.82 (d, J=8.1, 1H), 5.58 (br s, 1H), 5.49 (s, 1H), 2.01 (s, 3H), 1.27 (s, 3H), 1.25 (s, 3H).

EXAMPLE 78

(R/S)-5-(3-Chlorophenyl)-1,2,3,4-tetrahydro-2,2-dimethyl-4-methylidene-5H-chromeno[3,4-f]quinoline (Compound 178, structure 33 of Scheme IX, where R=3-chlorophenyl)

This compound (2.3 mg, 7%) was obtained along with Compound 177 as described above (EXAMPLE 77). Data for Compound 178: $^1$H NMR (400 MHz, acetone-$d_6$) 7.61 (d, J=6.7, 1H), 7.59 (d, J=8.6, 1H), 7.29–7.20 (m, 4H), 6.98 (t, J=6.7, 1H), 6.88 (t, J=6.7, 1H), 6.79 (d, J=6.7, 1H), 6.77 (d, J=8.6, 1H), 6.62 (s, 1H), 4.99 (s, 1H), 4.59 (s, 1H), 2.41 (d, J=12.2, 1H), 2.27 (d, J=12.2, 1H), 1.35 (s, 3H), 1.13 (s, 3H).

EXAMPLE 79

(R/S)-5-(4-Bromophenyl)-1,2-dihydro-2,2,4-trimethyl-5H-chromeno[3,4-f]quinoline (Compound 179, structure 32 of Scheme IX, where R=4-bromophenyl)

This compound was prepared by General Method 5 (EXAMPLE 60) from 1,4-dibromobenzene (250 mg, 1.0 mmol) and Compound 159 (20 mg, 0.07 mmol) to afford 16 mg (54%) of Compound 179 as a colorless oil, along with 2.5 mg (8%) of Compound 180 (EXAMPLE 80) as a colorless oil. Data for Compound 179: $^1$H NMR (400 MHz, acetone-$d_6$) 7.58 (d, J=7.8, 1H), 7.55 (d, J=8.4, 1H), 7.39 (d, J=8.5, 2H), 7.16 (d, J=8.5, 2H), 6.98 (t, J=7.8, 1H), 6.90 (s, 1H), 6.86 (t, J=7.8, 1H), 6.83 (d, J=8.4, 1H), 6.77 (d, J=7.8, 1H), 5.54 (br s, 1H), 5.47 (s, 1H), 1.99 (s, 3H), 1.26 (s, 3H), 1.23 (s, 3H).

EXAMPLE 80

(R/S)-5-(4-Bromophenyl)-1,2,3,4-tetrahydro-2,2-dimethyl-4-methylidene-5H-chromeno[3,4-f]quinoline (Compound 180, structure 33 of Scheme IX, where R=4-bromophenyl)

This compound (2.5 mg, 8%) was obtained along with Compound 179 as described above (EXAMPLE 79). Data for Compound 180: $^1$H NMR (400 MHz, acetone-$d_6$) 7.61

(d, J=6.3, 1H), 7.59 (d, J=8.7, 1H), 7.41 (d, J=8.5, 2H), 7.19 (d, J=8.5, 2H), 6.95 (t, J=6.3, 1H), 6.86 (t, J=6.3, 1H), 6.75 (d, J=8.7, 1H), 6.57 (s, 1H), 4.97 (s, 1H), 4.80 (s, 1H), 2.40 (d, J=12.2, 1H), 2.26 (d, J=12.2, 1H), 1.34 (s, 3H), 1.11 (s, 3H).

EXAMPLE 81

(R/S)-5-(3-Bromophenyl-1,2-dihydro-2,2,4-trimethyl-5H-chromeno[3,4-f]quinoline (Compound) 181, structure 32 of Scheme IX, where R=3-bromophenyl)

This compound was prepared by General Method 5 (EXAMPLE 60) from 1,3-dibromobenzene (250 mg, 1.0 mmol) and Compound 159 (15 mg, 0.05 mmol) to afford 13 mg (60%) of Compound 181 as a colorless oil, along with 2.0 mg (9%) of Compound 182 (EXAMPLE 82) as a colorless oil. Data for Compound 181: IR (neat) 3364, 2962, 1699, 1591, 1469, 143 cm$^{-1}$; $^1$H NMR (400 MHz, acetone-d$_6$) 7.61 (d, J=7.8, 1H), 7.57 (d, J=8.4, 1H), 7.38 (s, 1H), 7.36 (d, J=8.5, 1H), 7.26 (d, J=6.6, 1H), 7.19 (t, J=7.8, 1H), 7.00 (t, J=8.3, 1H), 6.98 (s, 1H), 6.81–6.90 m, 3H), 5.60 (br s, 1H), 5.50 (s, 1H), 2.01 (s, 3H), 1.27 (s, 3H), 1.25 (s, 3H).

EXAMPLE 82

(R/S)-5-(3-Bromophenyl)-1,2,3,4-tetrahydro-2,2-dimethyl-4-methylidene-5H-chromeno[3,4-f]quinoline (Compound) 182, structure 33 of Scheme IX, where R=3-bromophenyl.

This compound (2.0 mg, 9%) was obtained along with Compound 181 as described above (EXAMPLE 81). Data for Compound 182: $^1$H NMR (400 MHz, CDCl$_3$) 7.55 (d, J=7.9, 1H), 7.51 (d, J=8.4, 1H), 7.28 (d, J=8.0,1H), 7.12 (d, J=7.9, 1H), 7.05 (d, J=7.8, 1H), 7.01 (t, J=7.8, 1H), 6.92 (t, J=7.4, 1H), 6.82 (d, J=8.0, 1H), 6.60 (d, J=8.5, 1H), 6.59 (s, 1H), 4.95 (s, 1H), 4.58 (s, 1H), 2.43 (d, J=12.3, 1H), 2.19 (d, J=12.3, 1H), 1.32 (s, 3H), 1.14 (s, 3H).

EXAMPLE 83

(R/S)-5 (3,4-Dichlorophenyl-1,2-dihydro-2,2,4-trimethyl-5H-chromeno[3,4f]quinoline (Compound 183, structure 32 of Scheme IX, where R=3,4-dichlorophenyl This compound was prepared by General Method 5 (EXAMPLE 60) from 1-bromo-3,4-dichlorobenzene (226 mg, 1.0 mmol) and Compound 159 (20 mg, 0.07 mmol) to afford 8.7 mg (30%) of Compound 183 as a colorless oil. Data for Compound 183: $^1$H NMR (400 MHz, CDCl$_3$) 7.53 (d, J=7.8, 1H), 7.50 (d, J=8.3, 1H), 7.28–7.22 (m, 2H), 7.20–7.12 (m, 2H), 6.92 (t, J=7.5, 1H), 6.85 (d, J=8.2, 1H), 6.83 (s, 1H), 6.71 (d, J=8.4, 1H), 5.48 (s, 1H), 4.0 (br s, 1H), 1.97 (s, 3H), 1.30 (s, 3H), 1.26 (s, 3H).

EXAMPLE 84

(R/S)-5-(3-Bromo-2-pyridyl-1,2-dihydro-2,2,4-trimethyl-5H-choromeno[3,4f]quinoline (Compound 184, structure 32 of Scheme IX, where R=3-bromo-2-pyridyl This compound was prepared by General Method 5 (EXAMPLE 60) from 2,6-dibromopyridine (237 mg, 1.0 mmol) and Compound 159 (20 mg, 0.07 mmol) to afford 20 mg (67%) of Compound 184 as a colorless oil. Data for Compound 184: $^1$H NMR (400 MHz, acetone-d$_6$) 7.63 (dd, J=7.8, 1.5, 1H), 7.54 (d, J=8.5, 1H), 7.52 (d, J=7.8, 1H), 7.39 (d, J=7.9, 1H), 7.13 (d, J=7.6, 1H), 7.03 (t, J=7.6, 1H), 6.92–6.80 (m, 4H), 5.52 (s, 1H), 5.48 (s, 1H), 2.03 (s, 3H), 1.25 (s, 3H), 1.24 (s, 3H).

EXAMPLE 85

(R/S)-1,2-Dihydro-5-hydroxy-2,2,4-trimethyl-5H-chromeno[3,4-f]quinoline (Compound 185, structure 46 of Scheme XIV, where R$^1$=R$^2$=H)

To a yellow solution of Compound 159 (20 mg, 0.07 mmol) in 1 mL toluene at −78° C. was added 0.10 mL of DIBALH (1.5M in toluene, 0.075 mmol) and the resulting solution was stirred at −50°±10° C. for 20 min. The reaction was quenched with water (1 mL) and was extracted with ethyl acetate (2×5 mL). Removal of solvent and chromatography of the crude residue on a silica gel column using 20% ethyl acetate/hexane as eluents provided 6 mg (30%) of Compound 185 as a colorless oil. Data for Compound 185: $^1$H NMR (400 MHz, CDCl$_3$) 7.71 (d, J=7.5, 1H), 7.53 (d, J=8.4, 1H), 7.19 (t, J=7.5, 1H), 7.08 (t, J=7.5, 1H), 7.07 (d, J=8.4, 1H), 6.85 (d, J=5.8, 1H), 6.70 (d, J=7.5, 1H), 5.52 (s, 1H), 3.92 (br s, 1H), 2.94 (d, J=5.8, 1H), 2.37 (s, 3H), 1.32 (s, 3H), 1.20 (s, 3H).

EXAMPLE 86

(R/S)-1,2-Dihydro-2,2,4-trimethyl-5-methoxy-5H-chromeno[3,4-f]quinoline (Compound 186, structure 47 of Scheme XIV, where R$^1$=R$^2$=H, X=O, R$^3$=methyl)

To a solution of Compound 185 (25 mg, 0.085 mmol) in MeOH (7 mL) was added a catalytic amount of p-toluenesulphonic acid (~0.25 mg) and the solution was allowed to stir at rt for 5 min. The reaction mixture was quenched with a 10% NaOH solution (0.1 mL) then partitioned between EtOAc (10 mL) and water (3 mL). The organic layer was separated and washed with water (3×1 mL) and brine (3×1 mL) then dried (Na$_2$SO$_4$) and concentrated in vacuo. The crude product was purified on a 20×20 cm, 250 µm. TLC plate, eluting with 25% EtOAc:hexane to afford 8.2 mg (32%) of Compound 186 as a colorless oil. Data for Compound 186: R$_f$=0.28 (silica gel, 25% EtOAc:Hexane); $^1$H NMR (400 MHz, CDCl$_3$) 7.69 (d, J=7.7, 1H), 7.48 (d, J=8.3, 1H), 7.15 (t, J=7.7, 1H), 7.05 (m, 2H), 6.65 (d, J=8.3, 1H), 6.35 (s, 1H), 5.50 (s, 1H), 3.90 (br s, 1H), 3.49 (s, 3H), 2.28 (s, 3H), 1.33 (s, 3H), 1.28 (s, 3H).

EXAMPLE 87

(R/S)-1,2-Dihydro-2,2,4-trimethyl-5-propoxy-5H-chromeno[3,4-f]quinoline (Compound 187, structure 47 of Scheme XIV, where R$^1$=R$^2$=H, X=O, R$^3$=n-propyl)

This compound was prepared in a manner similar to that of Compound 186 (EXAMPLE 86) from Compound 185 (12 mg) and n-propanol to afford 7.2 mg (57%) of Compound 187 as a colorless oil. Data for Compound 187: R$_f$=0.43 (silica gel, 25% EtOAc:hexane); $^1$H NMR (400 MHz, CDCl$_3$) 7.68 (d, J=7.7, 1H), 7.49 (d, J=8.3, 1H), 7.17 (t , J=7.6, 1H), 7.05 (m, 2H), 6.65 (d, J=8.4, 1H), 6.42 (s, 1H), 5.50 (s, 1H), 3.90 (br s, 1H), 3.84 (dt, J=9.2, 6.7, 1H), 3.54 (dt, J=9.3, 6.8, 1H), 2.28 (s, 3H), 1.49 (m, 2H), 1.33 (s, 3H), 1.18 (s, 3H), 0.77 (t, J=7.4, 3H).

EXAMPLE 88

(R/S)-5-Allyl-1,2-dihydro-2,2,4-trimethyl-5H-chromeno[3,4-f]quinoline (Compound 188, structure 48 of Scheme XIV, where R$^1$=R$^2$=R$^4$=R$^5$=R$^6$=H)

To a solution of Compound 186 (12 mg, 0.04 mmol) in dichloromethane (1.5 mL) at 0° C. was added allyltrimethylsilane (0.005 mL, 0.062 mmol) and TMSOTf (0.01 mL, 0.057 mmol) under nitrogen. The reaction was stirred 5 h at rt. The reaction mixture was concentrated in vacuo and purified on a 5×20 cm, 250 µM, TLC plate, eluting with 25% EtOAc in hexane to afford 2.3 mg (18%) of Compound 188 as a colorless oil. Data for Compound 188: R$_f$=0.50 (silica gel, 25% EtOAc:Hexane); $^1$H NMR (400 MHz, acetone-d$_6$) 7.67 (d, J=7.4, 1H), 7.49 (d, J=8.3, 1H), 7.12 (t, J=7.4, 1H), 6.98 (t, J=7.4, 1H), 6.87 (d, J=7.4, 1H), 6.70 (d, J=8.3, 1H), 5.96–5.85 (m, 2H), 5.52 (s, 1H), 5.04 (s, 1H), 5.00 (d, J=8.6, 1H), 2.54 (m, 1H), 2.25 (m, 4H), 1.27 (s, 3H), 1.18 (s, 3H).

EXAMPLE 89

(R/S)-1,2-Dihydro-2,2,4-trimethyl-5-propyl-5H-chromeno[3,4-f]quinoline (Compound 189, structure 32 of Scheme IX, where R=n-propyl)

This compound was prepared by General Method 5 (EXAMPLE 60) from a 2.0M solution of allylmagnesium chloride (0.2 mL, 0.4 mmol) in THF and Compound 159 (25 mg, 0.086 mmol) to afford 5.0 mg(18%) of Compound 189 as a yellow oil. Data for Compound 189: $R_f$=0.27 (silica gel, 25% EtOAc:Hexane); $^1$H NMR (400 MHz, CDCl$_3$) 7.59 (d, J=7.7, 1H), 7.43 (d, J=8.4, 1H), 7.13 (t, J=7.7, 1H), 6.98 (t, J=7.7, 1H), 6.91 (d, J=7.7, 1H), 6.57 (d, J=8.4, 1H), 5.89 (d, J=10.4, 1H), 5.49 (s, 1H), 3.90 (br s, 1H), 2.25 (s, 3H), 1.84 (m, 2H), 1.49–1.35 (m, 2H), 1.29 (s, 3H), 1.20 (s, 3H), 0.89 (t, J=7.4, 3H).

EXAMPLE 90

(R/S)-1,2-Dihydro-2,2,4-trimethyl-5-(2-pyridyl)-5H-chromeno[3,4-f]quinoline (Compound 190, structure 32 of Scheme IX, where R=2-pyridyl)

To a solution of Compound 184 (10 mg, 0.023 mmol) in 1 mL of THF at –78° C. was added a 1.0M hexane solution of n-BuLi (0.05 mL, 0.07 mmol), giving rise to a yellow then dark red solution. The mixture was allowed to stir for 15 min and was quenched with water (1 mL). The mixture was extracted with ethyl acetate (2×10 mL) and the combined extracts were concentrated. Chromatography of the crude mixture on a silica gel column using 10–30% ethyl acetate/hexane as eluents afforded 7 mg (86%) of Compound 190 as a colorless oil. Data for Compound 190: $^1$H NMR (400 MHz, acetone-d$_6$) 8.48 (dd, J=5.4, 1.8, 1H), 7.61 (dd, J=7.8, 1.6, 1H), 7.57 (td, J=7.8, 1.8, 1H), 7.54 (d, J=8.3, 1H), 7.16–7.13 (m, 2H), 6.99 (td, J=7.8, 1.6, 1H), 6.93 (s, 1H), 6.88 (td, J=7.9, 1.0, 1H), 6.80 (d, J=8.5, 1H), 6.77 (dd, J=7.9, 1.1, 1H), 5.48 (bs, 1H), 5.44 (s, 1H), 1.98 (s, 3H), 1.23 (s, 3H), 1.22 (s, 3H).

EXAMPLE 91

(R/S)-5-(3-Fluorophenyl)-1,2-dihydro-2,2,4-trimethyl-5H-chromeno[3,4f]quinoline (Compound 191, structure 32 of Scheme IX, where R=3-fluorophenyl)

This compound was prepared by General Method 5 (EXAMPLE 60) from 1-bromo-3-fluorobenzene (175 mg, 1.0 mmol) and Compound 159 (20 mg, 0.07 mmol) to afford 12 mg (47%) of Compound 191 as a colorless oil, along with 1.5 mg (6%) of Compound 192 (EXAMPLE 92) as a colorless oil. Data for Compound 191: $^1$H NMR (400 MHz, acetone-d$_6$) 7.60 (d, J=7.9, 1H), 7.57 (d, J=8.4, 1H), 7.26 (td, J=7.9, 5.9, 1H), 7.06 (d, J=7.1, 1H), 7.01–6.81 (m, 8H), 5.58 (br s, 1H), 5.49 (s, 1H), 2.02 (s, 3H), 1.27 (s, 3H).

EXAMPLE 92

(R/S)-5-(3-Fluorophenyl-1,2,3,4-tetrahydro-2,2-dimethyl-4-methylidene-5H-chromeno[3,4-f]quinoline Compound 192 structure 33 of Scheme IX, where R=3-fluorophenyl)

This compound (1.5 mg, 6%) was obtained along with Compound 191 as described above (EXAMPLE 91). Data for Compound 192: $^1$H NMR (400 MHz, CDCl$_3$) 7.54 (d, J=8.0, 1H), 7.51 (d, J=8.5, 1H), 7.15 (td, J=7.9, 5.9, 1H), 7.06–6.81 (m, 6H), 6.61 (s, 1H0, 6.59 (d, J=8.0, 1H), 4.94 (s, 1H), 4.61 (s, 1H), 2.43 (d, J=12.3, 1H), 2.19 (d, J=12.3, 1H), (s, 3H), 1.14 (s, 3H).

EXAMPLE 93

(R/S)-1,2-Dihydro-2,2,4-trimethyl-5-propylthio-5H-chromeno3-f]quinoline (Compound 193, structure 47 of Scheme XIV, where R$^1$=R$^2$=H X=S R$^3$=n-propyl)

To a solution of Compound 185 (12 mg, 0.04 mmol) in a 1:1 mixture of 1-propanethiol and methylene chloride (2 mL) was added 2 mg of p-TsOH at rt. The reaction was complete after 1 hour by TLC and was quenched with saturated aqueous NaHCO$_3$. The reaction mixture was extracted with EtOAc (2×10 mL) and the combined organic layers were washed with water and brine then dried over Na$_2$SO$_4$. Removal of solvent in vacuo followed by purification on a 5×20 cm, 250 µm, TLC plate, eluting with 25% EtOAc:hexane, afforded 14 mg (99%) of Compound 193 as a yellow oil. Data for Compound 193: $R_f$=0.43 (silica gel, 25% EtOAc:Hexane); $^1$H NMR (400 MHz, acetone-d$_6$) 7.69 (d, J=7.6, 1H), 7.49 (d, J=8.4, 1H), 7.16 (t, J=7.6, 1H), 7.05 (t, J=7.6, 1H), 6.93 (d, J=7.6, 1H), 6.72 (d, J=8.4, 1H), 5.51 (s, 1H), 2.79–2.73 (m, 1H), 2.62–2.57 (m, 1H), 2.47 (s, 3H), 1.70 (m, 2H), 1.25 (s, 3H), 1.20 (s, 3H), 0.99 (t, J=7.3, 3H).

EXAMPLE 94

(R/S)-1,2-Dihydro-5-(3-methoxyphenyl)-2,2,4-trimethyl-5H-chromeno[3,4-f]quinoline (Compound 194, structure 32 of Scheme IX, where R=3-methoxyphenyl)

This compound was prepared by General Method 5 (EXAMPLE 60) from 3-bromoanisole (187 mg, 1.0 mmol) and Compound 159 (20 mg, 0.07 mmol) to afford 2.6 mg (10%) of Compound 194 as a colorless oil. Data for Compound 194: $^1$H NMR (400 MHz, acetone-d$_6$) 7.59 (d, J=7.8, 1H), 7.55 (d, J=8.4, 1H), 7.12 (t, J=7.9, 1H), 6.98 (t, J=7.2, 1H), 6.91 (s, 1H), 6.88–6.71 (m, 6H), 5.52 (br s, 1H), 5.47 (s, 1H), 3.67 (s, 3H), 2.03 (s, 3H), 1.25 (s, 3H).

EXAMPLE 95

(R/S)1,2-Dihydro-2,2,4-trimethyl -5-3-trifluoromethyl)-5H-chromeno[3,4-f]quinoline (Compound 195, structure 32 of Scheme IX, where R=3-(trifluoromethyl)phenyl).

This compound was prepared by General Method 5 (EXAMPLE 60) from 3-bromobenzotrifluoride (225 mg, 1.0 mmol) and Compound 159 (20 mg, 0.07 mmol) to afford 10 mg (34%) of Compound 195 as a colorless oil. Data for Compound 195: $^1$H NMR (400 MHz, acetone-d$_6$) 7.61 (d, J=7.6, 1H), 7.60 (d, J=9.0, 1H), 7.56–7.45 (m, 4H), 7.04 (s, 1H), 6.98 (t, J=7.6, 1H), 6.89–6.83 (m, 3H), 5.60 (s, 1H), 5.55 (s, 1H), 2.02 (s, 3H), 1.27 (s, 6H).

EXAMPLE 96

(R/S)-5-(3-Fluoro-4-methylphenyl)-1,2-dihydro-2,2,4-trimethyl-5H-chromeno[3,4f]quinoline (Compound 196, structure 32 of Scheme IX, where R=3-fluoro-4-methylphenyl)

This compound was prepared by General Method 5 (EXAMPLE 60) from 4-bromo-2-fluorotoluene (189 mg, 1.0 mmol) and Compound 159 (20 mg, 0.07 mmol) to afford 15 mg (56%) of Compound 196 as a colorless oil. Data for Compound 196: $^1$H NMR (400 MHz, acetone-d$_6$) 7.60 (d, J=7.8, 1H), 7.56 (d, J=8.4, 1H), 7.08 (t, J=7.9, 1H), 6.98 (t, J=7.9, 1H), 6.94 (d, J=8.0, 1H), 6.91 (s, 1H), 6.90–6.80 (m, 4H), 5.55 (br s, 1H), 2.12 (s, 3H), 2.01 (s, 3H), 1.26 (s, 3H), 1.24 (s, 3H).

EXAMPLE 97

(R/S)-5-(4Bromo-3-pyridyl)-1,2-dihydro-2,2,4-trimethyl-5H-chromeno[3,4-f]quinoline (Compound 197, structure 32 of Scheme IX, where R=4-bromo-3-pyridyl)

This compound was prepared by General Method 5 (EXAMPLE 60) from 2,5-dibromopyridine (237 mg, 1.0 mmol) and Compound 159 (20 mg, 0.07 mmol) to afford 7 mg (23%) of Compound 197 as a colorless oil. Data for Compound 197: $^1$H NMR (400 MHz, acetone-$d_6$) 8.24 (d, J=5.2, 1H), 7.62 (dd, J=8.0, 1.3, 1H), 7.57 (d, J=8.4, 1H), 7.34 (s, 1H), 7.27 (d, J=6.5, 1H), 7.06 (td, J=7.4, 1.3, 1H), 6.97 (s, 1H), 6.94–6.88 (m, 1H), 6.86 (d, J=8.4, 1H), 5.68 (br s, 1H), 5.55 (s, 1H), 2.06 (s, 3H), 1.29 (s, 3H), 1.28 (s, 3H).

EXAMPLE 98

(R/S)-1,2-Dihydro-2,2,4-trimethyl-5-(3-pyridyl)-5H-chromeno[3,4-f]quinoline (Compound 198, structure 32 of Scheme IX, where R=3-pyridyl)

This compound was prepared in a manner similar to that of Compound 190 (EXAMPLE 90), from Compound 197 (5 mg, 0.06 mmol) to afford 4 mg (quant) of Compound 198 as a colorless oil. Data for Compound 198: $^1$H NMR (400 MHz, acetone-$d_6$) 8.42 (m, 2H), 7.58 (dd, J=7.7, 1.3, 1H), 7.56 (d, J=8.4, 1H), 7.18 (d, J=5.9, 2H), 7.01 (t,J=7.8, 1H), 6.95 (s, 1H), 6.89–6.83 (m, 3H), 5.61 (br s, 1H), 5.52 (s, 1H), 2.03 (s, 3H), 1.28 (s, 3H).

EXAMPLE 99

(R/S)-5-(4-Chloro-3-fluorophenyl)-1,2-dihydro-2,2,4-trimethyl-5H-chromeno[3,4-f]quinoline (Compound 199, structure 32 of Scheme IX, where R=4-chloro-3-fluorophenyl)

This compound was prepared by General Method 5 (EXAMPLE 60) from 2-chloro-5-bromofluorobenzene (209 mg, 1.0 mmol) and Compound 159 (15 mg, 0.05 mmol) to afford 13 mg (64%) of Compound 199 as a colorless oil. Data for Compound 199: $^1$H NMR (400 MHz, acetone-$d_6$) 7.61 (dd, J=7.7, 1.4, 1H), 7.57 (d, J=8.3, 1H), 7.38 (t, J=7.9, 1H), 7.13 (dd, J=10.3, 1.8, 1H), 7.05 (t, J=7.8, 1H), 7.00 (dd, J=7.7, 1.3, 1H), 6.93 (s, 1H), 6.91–6.81 (m, 3H), 5.62 (br s, 1H), 5.50 (s, 1H), 2.02 (s, 3H), 1.27 (s, 3H), 1.25 (s, 3H).

EXAMPLE 100

(R/S)-1,2-Dihydro-2,2,4,5-tetramethyl-5H-chromeno[3,4-f]quinoline (Compound 200, structure 32 of Scheme IX, where R=methyl)

This compound was prepared by General Method 5 (EXAMPLE 60) from Compound 159 (8 mg) to afford 4.8 mg (63%) of Compound 200 as a yellow oil. Data for Compound 200: $R_f$=0.44 (silica gel, 25% EtOAc:hexane); $^1$H NMR (400 MHz, CDCl$_3$) 7.60 (d, J=7.8, 1H), 7.43 (d, J=8.4, 1H), 7.15 (t, J=8.0, 1H), 7.00 (t, J=8.0, 1H), 6.91 (d, J=8.1, 1H), 6.57 (d, J=8.1, 1H), 6.60 (d, J=6.1, 1H), 5.49 (s, 1H), 3.85 (br s, 1H), 2.26 (s, 3H), 1.38 (d, J=6.6, 3H), 1.27 (s, 3H), 1.22 (s, 3H).

EXAMPLE 101

(R/S)-1,2-Dihydro-5-hexyl-2,2,4-trimethyl-5H-chromeno[3,4-f]quinoline (Compound 201, structure 32 of Scheme IX, where R=n-hexyl)

This compound was prepared by General Method 5 (EXAMPLE 60) from Compound 159 (8 mg) and 1-iodohexane to afford 4.8 mg (63%) of Compound 201 as a yellow oil. Data for Compound 201: $R_f$=0.33 (silica gel, 25% EtOAc:Hexane); $^1$H NMR (400 MHz, CDCl$_3$) 7.59 (d, J=7.8, 1H), 7.43 (d, J=8.3, 1H), 7.12 (t, J=7.6, 1H), 6.98 (t,J=7.4, 1H), 6.91 (d, J=7.7, 1H), 6.56 (d, J=8.1, 1H), 5.86 (d, J=7.4, 1H), 5.49 (s, 1H), 2.25 (s, 3H), 1.83 (m, 2H), 1.41 (m, 3H), 1.28 (s, 3H), 1.20 (s, 3H), 0.84 (t, J=6.7, 3H).

EXAMPLE 102

1,2-Dihydro-2,2,4-trimethyl-5H-chromeno[3,4-f]quinoline (Compound 202, structure 32 of Scheme IX, where R=H)

To a solution of Compound 185 (EXAMPLE 85) (9.5 mg, 0.03 mmol) in methylene chloride (5 mL) maintained at –78 °C was added trifluoroacetic acid (10 mL) and triethylsilane (25 mL). The reaction mixture was allowed to warm to rt, quenched with 1N NaOH (3 mL), and partitioned between EtOAc (10 mL) and water (5 mL). The organic layer was washed with brine (3×3 mL), dried (Na$_2$SO$_4$), filtered, and concentrated. Purification by PTLC (250 µm, 10/1 hexane/EtOAc) afforded 4.6 mg (52%) of Compound 202. Data for Compound 202: $R_f$=0.36 (silica gel, 25% EtOAc:Hexane); $^1$H NMR (400 MHz, CDCl$_3$) 7.58 (d, J=8.0, 1H), 7.38 (d, J=8.3, 1H), 7.15 (t, J=8.0, 1H), 7.02 (t, J=8.0, 1H), 6.94 (d, J=8.0, 1H), 6.58 (d, J=8.3, 1H), 5.47 (s, 1H), 5.32 (s, 2H), 3.90 (br s, 1H ), 2.10 (s, 3H), 1.27 (s, 6H).

EXAMPLE 103

(R/S)-1,2-Dihydro-5-(3-methylbutyl)-2,2,4-trimethyl-5H-chromeno[3,4-f]quinoline (Compound 203, structure 32 of Scheme IX, where R=3-methylbutyl)

This compound was prepared by General Method 5 (EXAMPLE 60) from Compound 159 (13 mg) and 1-bromo-3-methylbutane to afford 1 mg (16%) of Compound 203 as a yellow oil. Data for Compound 203: TLC. $R_f$=0.29 (silica gel, 25% EtOAc:hexane); $^1$H NMR (400 MHz, CDCl$_3$) 7.58 (d, J=8.0, 1H), 7.43 (d, J=8.3, 1H), 7.17 (t,J=8.1, 1H), 6.98 (t, J=8.1, 1H), 6.91 (d, J=7.9, 1H), 6.58 (d, J=8.0, 1H), 5.81 (d, J=8.9, 1H), 5.49 (s, 1H), 3.90 (br s, 1H), 2.24 (s, 3H), 1.80 (m, 1H), 1.44 (m, 2H), 1.28 (m, 5H), 1.21 (s, 3H), 0.79 (d, J=6.2, 3H), 0.70 (d, J=6.2, 3H).

EXAMPLE 104

(R/S)-5-(4-Chlorobutyl)-1,2-dihydro-2,2,4-trimethyl-5H-chromeno[3,4-f]quinoline (Compound 204, structure 32 of Scheme IX, where R=4-chlorobutyl)

This compound was prepared by General Method 5 (EXAMPLE 60) from Compound 159 (8.3 mg) and 1-bromo-4-chlorobutane to afford 2.2 mg (27%) of Compound 204 as a yellow oil. Data for Compound 204: $R_f$=0.38 (silica gel, 25% EtOAc:Hexane); $^1$H NMR (400 MHz, CDCl$_3$) 7.59 (d, J=8.0, 1H), 7.43 (d, J=8.3, 1H), 7.13 (t,J=7.7, 1H), 7.00 (t,J=8.4, 1H), 6.91 (d, J=7.8, 1H), 6.57 (d, J=8.3, 1H), 5.86 (d, J=10.4, 1H), 5.49 (s, 1H), 3.90 (br s, 1H), 2.25 (s, 3H), 1.83 (m, 2H), 1.41 (m, 4H), 1.29 (s, 3H), 1.20 (s, 3H), 0.84 (t, J=7.3, 2H).

EXAMPLE 105

(R/S)-5-Benzyl-1,2-dihydro-2,2,4-trimethyl-5H-chromeno[3,4-f]quinoline (Compound 205, structure 32 of Scheme IX, where R=benzyl)

This compound was prepared by General Method 5 (EXAMPLE 60) from Compound 159 (16.8 mg) and benzylmagnesium chloride to afford 2.6 mg (16%) of Compound 205 as a yellow oil. Data for Compound 205: TLC: $R_f$=0.20 (silica gel, 25% EtOAc:Hexane); $^1$H NMR (400 MHz, CDCl$_3$) 7.66 (d, J=7.8, 1H), 7.48 (d, J=8.4, 1H), 7.30–7.15 (m, 6H), 7.10 (t, J=7.8, 1H), 6.89 (d, J=8.4, 1H), 6.61 (d, J=8.4, 1H), 6.13 (dd, J=10.2, 3.4, 1H), 5.49 (s, 1H), 3.92 (brs, 1H), 3.11 (dd, J=14.6, 10.2, 1H), 2.73 (dd, J=14.6, 3.4, 1H), 2.31 (s, 3), 1.54 (s, 3H), 1.29 (s, 3H).

EXAMPLE 106

(R/S)-5-(4-Bromobutyl)-1,2-dihydro-2,2,4-trimethyl-5H-chromeno[3,4-f]quinoline (Compound 206, structure 32 of Scheme IX, where R=4-bromobutyl)

This compound was prepared by General Method 5 (EXAMPLE 60) from Compound 159 (13.7 mg) and 1,4-dibromobutane to afford 6.0 mg (45%) of Compound 206 as a yellow oil. Data for Compound 206: R$_f$=0.22 (silica gel, 1:1 CH$_2$Cl$_2$/hexane); $^1$H NMR (400 MHz, CDCl$_3$) 7.59 (d, J=8.0, 1H), 7.44 (d, J=8.3, 1H), 7.12 (t, J=7.7, 1H), 6.98 (t, J=8.0, 1H), 6.93 (d, J=8.0, 1H), 6.57 (d, J=8.3, 1H), 5.85 (d, J=10.4, 1H), 5.49 (s, 1H), 3.90 (s, 1H), 2.25 (s, 3H), 1.83 (m, 2H), 1.41 (m, 4H), 1.29 (s, 3H), 1.20 (s, 3H), 0.84 (t, J=7.3, 2H).

EXAMPLE 107

9-Fluoro-1,2-dihydro-2,2,4-trimethyl-5-coumarino[3,4-f] quinoline (Compound 207, structure 41 of Scheme XI, where R$^1$=H, R$^2$=F)

5-Fluoro-2-methoxyphenylboronic acid (structure 37 of Scheme XI, where R$^1$=H, R$^2$=F)

In a 200-mL flask, a solution of 2-bromo-4-fluoroanisole (Aldrich: 4.00 mL, 30.8 mmol) in THF (50 mL) was cooled to −78° C. (CO$_2$/IPA). To this solution n-BuLi (Aldrich: 2.5M in hexanes; 12.4 mL, 31 mmol, 1.0 equivuiv) was added dropwise over a 30 min period. The reaction mixture was stirred at −78° C. for 60 min and treated with trimethylborate (Aldrich: 10.5 mL, 92.4 mmol, 3.0 equivuiv). The reaction mixture was allowed to slowly warm to rt, stirred overnight (12 h), and cooled to 0° C. (ice/HO$_2$). The solution was treated with 5% HCl until the pH reached 6. The reaction mixture was poured into sat'd NH$_4$CI (80 mL) and extracted with CH$_2$Cl$_2$ (3×100 mL). The extracts were washed with sat'd NH$_4$CI (1×80 mL), combined, dried (MgSO$_4$), filtered through a pad of Celite™, and concentrated to afford 4.90 g (94%) of a white semi-solid. Data for 5-fluoro-2-methoxyphenylboronic acid: $^1$H NMR (400 MHz, acetone-d$_6$): 7.47 (dd, J=8.8, 3.3, 1H); 7.17 (m, 1H); 7.05 (dd, J=9.0, 3.9, 1H); 3.93 (s, 3H).

Methyl (5'-fluoro-2'-methoxy-4-nitro-2-biphenyl) carboxylate (structure 39 of Scheme XI, where R$^1$=H, R$^2$=F)

In a 250-mL flask, a solution of methyl (2-bromo-5-nitro) benzoate (Compound 38, Scheme XI) (Aldrich: 5.00 g, 19.2 mmol) in DME (60 mL) was treated with tetrakis (triphenylphosphine)palladium (Aldrich: 0.67 g, 0.58 mmol, 3.0 mol%). The reaction mixture was stirred at rt for 10 min. A solution of 5-fluoro-2-methoxyphenylboronic acid (4.90 g, 29 mmol, 1.5 equivuiv) in EtOH (8 mL) was added, followed by 2.0M Na$_2$CO$_3$ (29 mL, 58 mmol, 3 equivuiv). The reaction mixture was heated to 80° C. for 6 h, cooled to rt, poured into 2.0M Na$_2$CO$_3$ (100 mL), and extracted with EtOAc (3×100 mL). The extracts were washed with brine (1×100 mL), combined, dried (MgSO$_4$), filtered, and concentrated to an orange oil. Purification by SGC (hexane/EtOAc, 10/1) afforded 4.25 g (72%) of methyl (5'-fluoro-2'-methoxy-4-nitro-2-biphenyl)carboxylate as a yellow-orange solid. Data for methyl-(5'-fluoro-2'-methoxy-4-nitro-2-biphenyl)carboxylate: $^1$H NMR (400 MHz, CDCl$_3$) 8.73 (d, J=2.4, 1H); 8.39 (dd, J=8.3, 2.4, 1H); 7.49 (d, J=8.3, 1H); 7.09 (td, J=8.5, 3.1, 1H); 7.00 (dd, J=8.5, 3.1, 1H); 6.85 (dd, J=8.9, 3.2, 1H); 3.76 (s, 3H); 3.70 (s, 3H).

5'-Fluoro-2'-methoxy-4-nitro-2-biphenylcarboxylic acid

In a 200-mL flask, a solution of methyl (5'-fluoro-2'-methoxy-4-nitro-2-biphenyl)carboxylate (4.24 g, 13.9 mmol) in THF (50 mL) was cooled to 0° C. (ice/H$_2$O) and treated with EtOH (10 mL) and 20% KOH (10 mL). The reaction mixture was allowed to warm to rt and stirred overnight, acidified to pH 10 (pH paper) with 10% HCl, and extracted with EtOAc (3×75 mL). The extracts were washed with brine (1×80 mL), combined, dried (MgSO$_4$), filtered, and concentrated to afford 3.68 g (91%) of 5'-fluoro-2'-methoxy-4-nitro-2-biphenylcarboxylic acid as a yellow solid. Data for 5'-fluoro-2'-methoxy-4-nitro-2-biphenylcarboxylic acid: $^1$H NMR (400 MHz, acetone-d$_6$): 8.68 (d, J=2.6, 1H); 8.46 (dd, J=8.5, 2.6, 1H); 7.68 (d, J=8.5, 1H); 7.16 (m, 2H);7.05 (dd, J=8.8, 4.4, 1H); 3.73 (s, 3H).

6-Fluoro-2-nitro-3,4-benzocoumarin

In a 250-mL flask, a suspension of 5'-fluoro-2'-methoxy-4-nitro-2-biphenylcarboxylic acid (3.60 g, 12.3 mmol) in dichloroethane (30 mL) was treated with SOCl$_2$ (0.92 mL, 12.6 mmol, 1.0 equivuiv) and heated to a gentle reflux for 90 min. The reaction vessel was cooled to 0° C. (ice/H$_2$O) and AlCl$_3$ (0.91 g, 6.8 mmol, 0.55 equivuiv) was added portionwise. The reaction mixture was allowed to slowly warm to rt, stirred 5 h, and quenched with 5% HCl (100 mL). The crude product was extracted with EtOAc (4×150 mL). The extracts were washed with sat'd NH$_4$Cl (1×100 mL), combined, dried (MgSO$_4$), filtered, and concentrated to afford 3.19 g (quant) of 6-fluoro-2-nitro-3,4-benzocoumarin as a yellow solid. Data for 6-fluoro-2-nitro-3,4-benzocoumarin: $^1$H NMR (400 MHz, DMSO-d$_6$): 8.84 (d, J=2.3, 1H); 8.67 (m, 2H); 8.40 (d, J=9.2, 1H); 7.55 (m, 2H).

2-Amino-6-fluoro-3,4-benzocoumarin (structure 40 of Scheme XI, where R$^1$=H, R$^2$=F)

In a 500-mL flask, a suspension of 6-fluoro-2-nitro-3,4-benzocoumarin (3.18 g, 12.2 mmol) in EtOAc (300 mL) was treated with 10% Pd/C (2.0 g) and AcOH (0.2 mL), and stirred under an atmosphere of H$_2$ for 1 h. The reaction mixture was filtered and the solids rinsed with acetone (200 mL). Concentration of the filtrate afforded 2.19 g (78%) of 2-amino-6-fluoro-3,4-benzocoumarin as a yellow solid. Data for 2-amino-6-fluoro-3,4-benzocoumarin: $^1$H NMR (400 MHz, acetone-d$_6$): 8.09 (d, J=8.6, 1H); 7.86 (dd, J=9.8, 3.0, 1H); 7.55 (d, J=2.6, 1H); 7.33 (dd, J=9.2, 4.9, 1H); 7.28 (dd, J=9.2, 2.6, 1H); 7.17 (dt, J=3.0, 9.0).

9-Fluoro-1,2-dihydro-2,2,4-trimethyl-5-isocoumarino[3,4-f]quinoline (Compound 207, structure 41 of Scheme XI, where R$^1$=H, R$^2$=F)

In a 200-mL resealable pressure tube, a suspension of 2-amino-6-fluoro-3,4-benzocoumarin (1.10 g) in acetone (100 mL) was treated with iodine (Aldrich: 0.50 g) and heated to 110° C. for 32 h. The reaction mixture was cooled to rt, concentrated to remove the bulk of the acetone, and dissolved in CH$_2$Cl$_2$ (200 mL). The organic layer was washed with 0.5N Na$_2$S$_2$O$_3$ (2×200 mL) and sat'd NaHCO$_3$ (1×100 mL). The aqueous layers were extracted with CH$_2$Cl$_2$ (2×100 mL). The combined organic layers were dried (K$_2$CO$_3$), filtered, and concentrated to afforded an orange solid. Purification by SGC (hexane/EtOAc, 5/1) afforded 0.51 g (34%) of Compound 207 as a bright yellow solid. Data for Compound 207: $^1$H NMR (400 MHz, acetone-d$_6$) 7.96 (d, J=8.6, 1H); 7.83 (dd, J=10.0, 2.9, 1H); 7.30 (dd, J=9.0, 4.9, 1H); 7.22 (d, J=8.6, 1H); 7.17 (m, 1H); 6.25 (br s, 1H); 5.54 (s, 1H); 1.30 (s, 6H). The acetone multiplet obscures the C(4) methyl group.

EXAMPLE 108

8-Fluoro-1,2-dihydro-2,2,4-trimethyl-5-coumarino[3,4-f] quinoline (Compound 208, structure 41 of Scheme XI, where R$^1$=F, R$^2$=H)

2-Bromo-5-fluoroanisole (structure 36 of Scheme XI, where R$^1$=F, R$^2$=H)

In a 250 mL r.b. flask, a solution of 2-bromo-5-fluorophenol (Lancaster: 7.0 mL, 64 mmol, 1.0 equivuiv) in acetone (140 mL) was treated with iodomethane (Aldrich: 4.8 mL, 77 mmol, 1.2 equivuiv), potassium carbonate (8 g), and water (1 mL). The reaction mixture was heated at reflux for 6 h, cooled to rt, clarified with H$_2$O (40 mL), and the bulk of the volatiles was removed under reduced pressure. The reaction mixture was extracted with EtOAc (3×120 mL); the extracts were washed with brine (1×80 mL), combined, dried (K$_2$CO$_3$), filtered, and concentrated to a clear oil. Bulb-to-bulb distillation (60°–65° C., 0.7 Torr) afforded 13.22 g (quant) of 2-bromo-5-fluoroanisole as a colorless liquid. Data for 2-bromo5-fluoroanisole: $^1$H NMR (400 MHz, CDCl$_3$): 7.46 (dd, J=10.6, 8.7, 1H); 6.64 (dd, J=10.4, 2.8, 1H); 5.58 (dt, J=10.4, 2.4, 1H); 3.88 (s, 3H).

4-Fluoro-2-methoxyphenylboronic acid (structure 37 of Scheme XI, where R$^1$=F, R$^2$=H)

In a 100 mL r.b. flask, a solution of 2-bromo-5-fluoroanisole (5.50 g, 26.8 mmol, 1.0 equivuiv) in THF (30 mL) was cooled to –78° C. (CO$_2$/IPA) and n-BuLi (2.5M in hexanes; 10.7 mL, 27 mmol, 1.0 equivuiv) was added via syringe over a 15 min period. The reaction mixture was stirred at –78° C. for 45 min. Trimethylborate (Aldrich: 9:1 mL, 80 mmol, 3.0 equivuiv) was added slowly via syringe. The reaction mixture was allowed to warm to rt, stirred an additional 10 h, and cooled to 0° C. The reaction mixture was brought to pH6 with 5% HCl, poured into sat'd NH$_4$Cl (60 mL), and extracted with methylene chloride (3×80 mL). The extracts were washed with sat'd NH$_4$Cl (1×50 mL), combined, dried (MgSO$_4$), filtered, and concentrated to afford 4.22 g (93%) of crude 4-fluoro-2-methoxyboronic acid as a white solid, which was used without further purification.

7-Fluoro-2-nitro-3,4-benzocoumarin

In a 200 mL r.b. flask, a solution of 2-bromo-5-nitrobenzoic acid (Compound 43, Scheme XII) (Aldrich: 4.10 g, 16.7 mmol, 1.9 equivuiv) in DME (65 mL) was treated with tetrakis(triphenylphosphine) palladium (Aldrich: 0.58 g, 0.50 mmol, 3.0 mol %). The reaction mixture was stirred at rt for 10 min. A solution of 4-fluoro-2-methoxyphenylboronic acid (4.20 g, 25 mmol, 1.5 equivuiv) in EtOH (10 mL) was added, followed by 2.0M Na$_2$CO$_3$ (30 mL). The reaction mixture was heated to 80° C. for 6 h, cooled to rt, poured into 5% HCl (100 mL), and extracted with EtoAc (3×100 mL). The extracts were washed with sat'd NH$_4$Cl (1×100 mL) and brine (1×100 mL), combined, dried (MgSO$_4$), filtered, and concentrated to an orange solid. This crude material, consisting of impure 4'-fluoro-2'-methoxy-4-nitro-2-biphenylcarboxylic acid (structure 44 of Scheme XII, where R$^1$=F, R$^2$=H), was suspended in 1,2-dichloroethane (80 mL), treated with thionyl chloride (1.2 mL), and heated at reflux for 90 min. The reaction mixture was cooled to rt, treated with aluminum trichloride (0.4 g), and allowed to react overnight (11 h). The reaction mixture was poured into 20% KOH (80 mL) and extracted with methylene chloride (3×80 mL). The extracts were combined, dried (MgSO$_4$), filtered, and concentrated to an orange oil. The crude material was dissolved in methylene chloride (50 mL), adsorbed onto Celite™ (1 g), and concentrated to a fluffy orange powder. This powder was applied to a pad of silica gel in a 250 mL Buchner funnel (50×50 mm). The pad was rinsed with 100 mL of 2:1 hexane:EtOAc, which was discarded, and then 400 mL of 1:1 hexane:EtOAc. The filtrate was concentrated to afford 2.08 g (48%) of 7-fluoro-2-nitro-3,4-benzocoumarin as an orange solid. Data for 7-fluoro-2-nitro-3,4-benzocoumarin: $^1$H NMR (400 MHz, acetone-d$_6$) 9.02 (d, J=2.4, 1H); 8.71 (dd, J=8.8, 2.4, 1H); 8.65 (d, J=8.8, 1H); 8.53 (dd, J=9.6, 6.1, 1H); 7.34 (m, 2H).

2-Amino-7-fluoro-3,4-benzocoumarin (structure 40 of Scheme XII, where R$^1$=F, R$^2$=H)

In a 250-mL flask, a suspension of 7-fluoro-2-nitro-3,4-benzocoumarin (2.04 g, 7.9 mmol) in EtOAc (150 mL) was treated with 10% Pd/C (1.2 g) and AcOH (0.2 mL), and stirred under an atmosphere of H$_2$ for 1 h. The reaction mixture was filtered and the solids rinsed with acetone (200 mL). Concentration of the filtrate afforded 1.6 1 g (89%) of 2-amino-7-fluoro-3,4-benzocoumarin as a yellow solid. Data for 2-amino-7-fluoro-3,4-benzocoumarin: $^1$H NMR (400 MHz, acetone-d$_6$) 8.15 (dd, J=9.6, 6.1, 1H); 8.05 (d, J=8.6, 1H); 7.55 (d, J=2.5, 1H); 7.28 (dd, J=8.6, 2.5, 1H); 7.14 (m, 1H); 7.12 (d, J=9.6, 1H); 5.4 (br s, 2H).

8-Fluoro-1,2-dihydro-2,2,4-trimethyl-5-coumarino[3,4-f] quinoline (Compound 208, structure 39 of Scheme XI, where R$^1$=F, R$^2$=H)

In a 200-mL resealable pressure tube, a suspension of 2-amino-7-fluoro-3,4-benzocoumarin (1.61 g) in acetone (100 mL) was treated with iodine (Aldrich: 0.50 g) and heated to 110° C. for 32 h. The reaction mixture was cooled to rt, concentrated to remove the bulk of the acetone, and dissolved in CH$_2$Cl$_2$ (200 mL). The organic layer was washed with 0.5N Na$_2$S$_2$O$_3$ (2×200 mL) and sat'd NaHCO$_3$ (1×100 mL). The aqueous layers were extracted with CH$_2$Cl$_2$ (2×100 mL). The combined organic layers were dried (K$_2$CO$_3$), filtered, and concentrated to afford an orange solid. Purification by SGC (hexane/EtOAc, 5/1) afforded 0.46 g (21%) of Compound 208 as a bright yellow solid. Data for Compound 208: $^1$H NMR (400 MHz, acetone-d$_6$) 8.12 (dd, J=9.6, 5.9, 1H); 7.92 (d, J=9.6, 1H); 7.22 (d, J=8.6, 1H); 7.11 (m, 2H); 6.1 (br s, 1H); 5.53 (d, J=1.29 (s, 6H). The acetone multiplet obscures the C(4) methyl group.

EXAMPLE 109

9-Chloro-1,2-dihydro-2,2,4-trimethyl-5-coumarino[3,4-f] quinoline (Compound 209, structure 41 of Scheme XI, where R$^1$=H, R$^2$=Cl)

2-Bromo-4-chloroanisole (structure 36 of Scheme XI, where R$^1$=H, R$^2$=Cl) In a 250 mL r.b. flask, a solution of 2-bromo-4-chlorophenol (Lancaster: 16.94 g, 81.6 mmol, 1.0 equivuiv) in acetone (160 mL) was treated sequivuentially with iodomethane (6.10 mL, 98 mmol, 1.2 equivuiv), potassium carbonate (12 g), and water (4 mL). The reaction mixture was heated at reflux for 3 h, cooled to rt, and the bulk of the volatiles was removed under reduced pressure. The residue was poured into water (140 mL) and extracted with EtOAc (3×150 mL). The extracts were washed with brine (1×100 mL), combined, dried (K$_2$CO$_3$), filtered through a pad of Celite™, and concentrated to a clear oil. Short-path distillation (80°–85° C., 1 Torr) afforded 17.74 g (98%) of 2-bromo-4-chloroanisole as a clear liquid. Data for 2-bromo-4-chloroanisole: $^1$H NMR (400 MHz, acetone-d$_6$) 7.53 (d, J=2.5, 1H); 7.24 (dd, J=9.7, 2.5, 1H); 6.81 (d, J=9.7, 1H); 3.88 (s, 3H).

5-Chloro-2-methoxyphenylboronic acid (structure 37 of Scheme XI, where R$^1$=H, R$^2$=Cl)

This compound was prepared in a manner similar to that of 5-fluoro-2-methoxyphenylboronic acid (EXAMPLE 107) from 2-bromo-4-chloroanisole (2.00 g, 9.0 mmol, 1.0 equivuiv), n-BuLi (2.5M in hexanes; 3.62 mL, 9.0 mmol, 1.0 equivuiv), and trimethylborate (3.0 mL, 26 mmol, 2.9 equivuiv) to afford 1.30 g (77%) of crude 5-chloro-2-methoxyphenylboronic acid as a white semi-solid. This compound was used in the next reaction with no further purification.

Methyl (5'-chloro-2'-methoxy-4-nitro-2-biphenyl) carboxylate (structure 39 of Scheme XI, where R$^1$=H, R$^2$=Cl)

This compound was prepared in a manner similar to that of methyl-(5'-fluoro-2'-methoxy-4-nitro-2-biphenyl) carboxylate (EXAMPLE 107) from methyl 2-bromo-5- nitrobenzoate (1.25 g, 4.8 mmol, 1.0 equivuiv), tetrakis (triphenylphosphine)palladium (Aldrich: 0.16 g, 0.14 mmol, 2.9 mol %), and 5-chloro-2-methoxyphenylboronic acid (1.30 g, 6.9 mmol, 1.5 equivuiv) to afford 0.85 g (55%) of methyl-5'-chloro-2'-methoxy-4-nitro-2-biphenylcarboxylate as a yellow-orange solid. Data for methyl-5'-chloro-2'-methoxy-4-nitro-2-biphenylcarboxylate: $^1$H NMR (400 MHz, CDCl$_3$): 8.73 (d, J=2.4, 1H); 8.38 (dd, J=8.5, 2.5, 1H); 7.49 (d, J=8.5, 1H); 7.36 (dd, J=8.7, 2.5, 1H); 7.23 (d, J=2.5, 1H); 6.85 (d, J=8.7, 1H); 3.76 (s, 3H); 3.70 (s, 3H).

5'-Chloro-2'-methoxy-4-nitro-2-biphenylcarboxylic acid

This compound was prepared in a manner similar to that of 5'-fluoro-2'-methoxy-4-nitro-2-biphenylcarboxylic acid (EXAMPLE 107) from methyl-5'-chloro-2'-methoxy-4-nitro-2-biphenylcarboxylate (0.83 g, 2.6 mmol) to afford 0.75 g (95%) of 5'-chloro-2'-methoxy-4-nitro-2-biphenylcarboxylic acid as a yellow solid. Data for (5'-chloro-2'-methoxy-4-nitro-2-biphenyl)carboxylic acid: $^1$H NMR (400 MHz, acetone-d$_6$) 8.69 (d, J=2.5, 1H); 8.46 (dd, J=8.3, 2.6, 1H); 7.68 (d, J=8.5, 1H); 7.41 (dd, J=8.9, 2.7, 1H); 7.33 (d, J=2.8, 1H); 7.08 (d, J=8.6, 1H); 3.75 (s, 3H).

6-Chloro-2-nitro-3,4-benzocoumarin

This compound was prepared in a manner similar to that of 6-fluoro-2-nitro-3,4-benzocoumarin (EXAMPLE 107) from 5'-chloro-2'-methoxy-4-nitro-2-biphenylcarboxylic acid (0.74 g, 2.3 mmol), SOCl$_2$ (0.17 mL, 2.3 mmol), and AlCl$_3$ (0.30 g, 2.5 mmol) to afford 0.64 g (quant) of 6-chloro-2-nitro-3,4-benzocoumarin as a yellow solid. Data for 6-chloro-2-nitro-3,4-benzocoumarin: $^1$H NMR (400 MHz, acetone-d$_6$) 9.04 (d, J=2.3, 1H); 8.73 (m, 2H); 8.51 (d, J=2.4, 1H); 7.72 (dd, J=8.6, 2.4, 1H); 7.50 (d, J=8.7, 1H).

2-Amino-6-chloro-3,4-benzocoumarin (structure 40 of Scheme XI, where R$^1$=H, R$^2$=Cl)

This compound was prepared in manner similar to that of 2-amino-6-fluoro-3,4-benzocoumarin from 6-chloro-2-nitro-3,4-benzocoumarin (0.64 g, 2.3 mmol) to afford 0.50 g (88%) of 2-amino-6-chloro-3,4-benzocoumarin as a yellow solid. Data for 2-amino-6-chloro-3,4-benzocoumarin: $^1$H NMR (400 MHz, acetone-d$_6$) 8.11 (m, 2H); 7.55 (d, J=2.5, 1H); 7.39 (dd, J=8.6, 2.5, 1H); 7.28 (m, 2H).

9-Chloro-1,2-dihydro-2,2,4-trimethyl-5-coumarino[3,4-f]quinoline (Compound 209, structure 41 of Scheme XI, where R$^1$=H, R$^2$=Cl)

This compound was prepared in a manner similar to that of Compound 207 from 2-amino-6-chloro-3,4-benzocoumarin (0.50 g) to afford 0.14 g (21%) of Compound 209 as a bright yellow solid. Data for Compound 209: $^1$H NMR (400 MHz, acetone-d$_6$): 8.10 (d, J=2.4, 1H); 8.00 (d, J=8.7, 1H); 7.39 (dd, J=8.7, 2.3, 1H); 7.26 (d, J=8.8, 1H); 7.23 (d, J=8.6, 1H); 5.55 (s, 1H); 1.30 (s, 6H). The acetone multiplet obscures the C(4) methyl group.

EXAMPLE 110

(R/S)-5-Butyl-9-fluoro-1,2-dihydro-2,2,4-trimethyl-5H-chromeno[3,4-f]quinoline (Compound 210, structure 42 of Scheme XI, where R=n-butyl, R$^1$=H, R$^2$=F)

This compound was prepared by General Method 5 (EXAMPLE 60) from Compound 207 (0.53 g, 1.7 mmol) and n-BuLi (2.5M in hexanes, 2.7 mL, 6.8 mmol, 4.0 equivuiv) to afford 0.34 g (57%) of Compound 210 as a yellow foam. Data for Compound 210: $^1$H NMR (400 MHz, acetone-d$_6$): 7.54 (d, J=8.5, 1H); 7.49 (dd, J=10.2, 2.9, 1H); 7.03 (dd, J=8.8, 4.9, 1H); 6.88 (dt, J=2.9, 8.8, 1H); 6.75 (d, J=8.5, 1H); 5.80 (br s, 1H); 5.49 (s, 1H); 4.83 (t, J=7.6, 1H); 2.36 (q, J=7.5, 2H); 2.05 (s, 3H); 1.46 (sextet, J=7.4, 2H); 1.10 (br s, 8H); 0.93 (t, J=7.4, 3H).

EXAMPLE 111

(R/S)-5-Butyl-8-fluoro-1,2-dihydro-2,2,4-trimethyl-5H-chromeno[3,4-f]quinoline (Compound 211, structure 42 of Scheme XI, where R=n-butyl, R$^1$=F, R$^2$=H)

This compound was prepared by General Method 5 (EXAMPLE 60) from Compound 208 (29 mg, 0.09 mmol) and n-BuLi (2.5M in hexanes, 0.16 mL, 0.40 mmol) to afford 6.5 mg (20%) of Compound 211 as a yellow foam. Data for Compound 211: $^1$H NMR (400 MHz, acetone-d$_6$): 7.77 (dd, J=8.7, 6.3, 1H); 7.51 (d, J=8.5, 1H); 6.85 (m, 3H); 5.80 (br s, 1H); 4.84 (t, J=7.5, 1H); 2.37 (q, J=7.5, 2H); 2.07 (s, 3H); 1.47 (sextet, J=7.4, 2H); 1.10 (br s, 8H); 0.93 (t, J=7.4, 3H).

EXAMPLE 112

(R/S)-5-(3-Chlorophenyl)-9-fluoro-1,2-dihydro-2,2,4-trimethyl-5H-chromeno[3,4-f]quinoline (Compound 212, structure 42 of Scheme XI, where R=3-chlorophenyl, R$^1$=H, R$^2$=F)

This compound was prepared by General Method 5 (EXAMPLE 60) from Compound 207 (50 mg, 0.16 mmol) and 3-bromochlorobenzene (120 mL) to afford 46 mg (70%) of Compound 212 as a colorless solid. Data for Compound 212: $^1$H NMR (400 MHz, acetone-d$_6$): 7.56 (d, J=8.4, 1H); 7.36 (dd, J=9.8, 2.9, 1H); 7.25 (m, 4H); 6.95 (s, 1H); 6.85 (d, J=8.5, 1H); 6.81 (m, 1H); 6.74 (td, J=8.5, 2.9, 1H); 5.51 (s, 1H); 2.00 (d, J=1.0, 3H); 1.28 (s, 3H); 1.26 (s, 3H).

EXAMPLE 113

(R/S)-5-(4-Chloro-3-methylphenyl)-9-fluoro-1,2-dihydro-2,2,4-trimethyl-5H-chromeno[3,4-f]quinoline (Compound 213, structure 42 of Scheme XI, where R=4-chloro-3-3-methylphenyl, R$^1$=H, R$^2$=F)

This compound was prepared by General Method 5 (EXAMPLE 60) from Compound 207 (50 mg, 0.16 mmol) and 5-bromo-2-chlorotoluene (0.21 g) to afford 42 mg (62%) of Compound 213 as a colorless solid. Data for Compound 213: $^1$H NMR (400 MHz, acetone-d$_6$): 7.55 (d, J=8.4, 1H); 7.34 (dd, J=10.0, 2.8, 1H); 7.22 (m, 2H); 7.00 (br d, J=10.3, 1H); 6.89 (s, 1H); 6.84 (d, J=8.4, 1H); 6.75 (m, 2H); 5.49 (s, 1H); 2.24 (s, 3H); 1.99 (d, J=1.2, 3H); 1.27 (s, 3H); 1.25 (s, 3H).

EXAMPLE 114

(R/S)-5-(4-Chlorophenyl)-9-fluoro-1,2-dihydro-2,2,4-trimethyl-5H-chromeno[3,4-f]quinoline (Compound 214, structure 42 of Scheme XI, where R=4-chlorophenyl, R$^1$=H, R$^2$=F)

This compound was prepared by General Method 5 (EXAMPLE 60) from Compound 207 (50 mg, 0.16 mmol) and 4-bromochlorobenzene (0.19 g) to afford 33 mg (50%) of Compound 214 as a pale yellow oil. Data for Compound 214: $^1$H NMR (400 MHz, acetone-d$_6$) 7.55 (d, J=8.4, 1H); 7.34 (dd, J=10.0, 2.8, 1H); 7.27 (d, J=8.6, 2H); 7.22 (d, J=8.6, 2H); 6.92 (s, 1H); 6.84 (d, J=8.5, 1H); 6.75 (m, 2H); 5.60 (br s, 1H); 5.48 (d, J=1.3, 1H); 1.99 (d, J=1.3, 3H); 1.27 (s, 3H); 1.24 (s, 3H).

EXAMPLE 115

(R/S)-9-Fluoro-1,2-dihydro-5-(4-methoxyphenyl)-2,2,4-trimethyl-5H-chromeno[3,4-f]quinoline (Compound 215, structure 42 of Scheme XI, where R=4-methoxyphenyl, R$^1$=H, R$^2$=F)

This compound was prepared by General Method 5 (EXAMPLE 60) from Compound 207 (50 mg, 0.16 mmol) and 4-bromoanisole (0.13 mL) to afford 8 mg(12%) of Compound 215 as a pale yellow oil. Data for Compound 215: $^1$H NMR (400 MHz, acetone-d$_6$) 7.53 (d, J=8.4, 1H); 7.34 (dd, J=10.0, 2.8, 1H); 7.11 (d, J=8.8, 2H); 6.86 (s, 1H);

6.82 (d, J=8.4, 1H); 6.76 (d, J=8.6, 2H); 6.70 (m, 2H); 5.6 (br s, 1H); 5.46 (s, 1H); 3.70 (s, 3H); 1.99 (s, 3H); 1.26 (s, 3H); 1.23 (s, 3H).

EXAMPLE 116

(R/S)-8-Fluoro-1,2-dihydro-5-methoxy-2,2,4-trimethyl-5H-chromeno[3,4-f]quinoline (Compound 216, structure 47 of Scheme XIV, where $R^1$=F, $R^2$=H, $R^3$=methyl, X=O)
(R/S)-8-Fluoro-1,2-dihydro-5-hydroxy-2,2,4-trimethyl-5H-chromeno[3,4-f]quinoline (structure 46 of Scheme XIV, where $R^1$=F, $R^2$=H)

This compound was prepared in a manner similar to that of Compound 185 (EXAMPLE 85) from Compound 208 (170 mg) and DIBALH (1.0M in hexane; 1.25 mL) to afford 27 mg (16%) of (R/S)-8-fluoro-1,2-dihydro-5-hydroxyl-2,2,4-trimethyl-5H-chromeno[3,4-f]quinoline as a white solid. Data for (R/S)-8-fluoro-1,2-dihydro-5-hydroxy-2,2,4-trimethyl-5H-chromeno[3,4f]quinoline: $^1$H NMR (400 MHz, acetone-$d_6$): 7.74 (dd, J=8.6, 6.3, 1H); 7.50 (d, J=8.4, 1H); 6.85 (s, 1H); 6.79 (m, 2H); 6.72 (dd, J=9.9, 2.7, 1H); 5.51 (d, J=1.2, 1H); 2.82 (s, 3H); 1.30 (s, 3H); 1.17 (s, 3H). (R/S)-8-Fluoro-1,2-dihydro-5-methoxy-2,2,4-trimethyl-5H-chromeno[3,4-f]quinoline (Compound 216, structure 47 of Scheme XIV, where $R^1$=F, $R^2$=H, $R^3$=methyl, X=O)

This compound was prepared in a manner similar to that of Compound 186 (EXAMPLE 86) from (R/S)-8-fluoro-1,2-dihydro-5-hydroxy-2,2,4-trimethyl-5H-chromeno[3,4-f]quinoline (24 mg) to afford 25 mg (quant) of Compound 216 as a white solid. Data for Compound 216: $^1$H NMR (400 MHz, acetone-$d_6$) 7.74 (dd, J=8.5, 6.2, 1H); 7.50 (d, J=8.4, 1H); 6.85 (m, 2H); 6.79 (d, J=8.4, 1H); 6.38 (s, 1H); 5.52 (t, J=1.0, 1H); 3.46 (s, 3H); 2.26 (d, J=1.2, 3H); 1.31 (s, 3H); 1.15 (s, 3H).

EXAMPLE 117

(R/S)-5-(4-Chlorophenyl)-8-fluoro-1,2-dihydro-2,2,4-trimethyl-5H-chromeno[3,4-f]quinoline (Compound 217, structure 42 of Scheme XI, where R=4-chlorophenyl, $R^1$=F, $R^2$=H)

This compound was prepared by General Method 5 (EXAMPLE 60) from Compound 208 (42 mg, 0.13 mmol) and 4-bromochlorobenzene (0.19 g) to afford 10 mg (18%) of Compound 217 as a pale yellow oil. Data for Compound 217: $^1$H NMR (400 MHz, acetone-$d_6$) 7.62 (dd, J=8.6, 6.3, 1H); 7.53 (d, J=8.4, 1H); 7.27 (d, J=8.7, 2H); 7.23 (d, J=8.7, 2H); 6.96 (s, 1H); 6.83 (d, J=8.2, 1H); 6.67 (m, 1H); 6.58 (dd, J=8.7, 2.5, 1H); 5.48 (d, J=1.3, 1H); 1.99 (d, J=1.2, 3H); 1.26 (s, 3H); 1.23 (s, 3H).

EXAMPLE 118

(R/S)-9-Chloro-5-(4-chlorophenyl)-1,2-dihydro-2,2,4-trimethyl-5H-chromeno[3,4-f]quinoline (Compound 218, structure 42 of Scheme XI, where R=4-chlorophenyl, $R^1$=H, $R^2$=Cl)

This compound was prepared by General Method 5 (EXAMPLE 60) from Compound 209 (40 mg, 0.12 mmol) and 4-bromochlorobenzene (0.19 g) to afford 23 mg (44%) of Compound 218 as an off-white oil. Data for Compound 218: $^1$H NMR (400 MHz, acetone-$d_6$) 7.59 (d, J=2.5, 1H); 7.58 (d, J=8.4, 1H); 7.27 (d, J=8.6, 2H); 7.22 (d, J=8.6, 2H); 6.96 (dd, J=8.5, 2.4, 1H); 6.94 (s, 1H); 6.84 (d, J=8.4, 1H); 6.78 (d, J=8.5, 1H); 5.7 (br s, 1H); 5.49 (d, J=1.1, 1H); 1.99 (d, J=1.1, 3H); 1.27 (s, 3H); 1.24 (s, 3H).

EXAMPLE 119

(Z)-5-Butylidene-1,2-dihydro-2,2,4-trimethyl-5H-chromeno[3,4-f]quinoline Compound 219, structure 45 of Scheme XIII, where $R^1$=$R^2$=H, $R^3$=n-propyl)

General Method 6: Preparation of compounds of structure 43 from Compound 159 or compounds of structure 39.

This transformation involves the addition of a Grignard reagent (or, alternatively, an organolithium reagent) to Compound 159 or compounds of structure 41 followed by an acid catalyzed dehydration reaction. To a flame-dried flask charged with magnesium powder (8–10 equivuiv) and iodine (1–5%) under nitrogen was added one fourth of a solution of the corresponding benzyl bromide (or chloride) (8–10 equivuiv) in 2–3 mL of THF or ether. The mixture was allowed to stir for 5–10 min until the reaction initiated (a few drops of 1,2-dibromoethane might be necessary to initiate the reaction), and then the rest of the benzyl bromide (chloride) solution was added and the reaction went to completion in several min to give a colorless solution. The Grignard reagent solution was cannulated into a yellow solution of Compound 159 or a compound of structure 41 in 1–2 mL of THF and the resulting dark red mixture was allowed to stir at rt for 20–66 min until the red color faded. The reaction was quenched with water (5 mL) and extracted with ethyl acetate (2×15 mL). Removal of the solvent under reduced pressure afforded the crude lactol as a yellow oil, which was dissolved in 5 mL of methylene chloride and was treated with p-toluenesulfonic acid (5–10 mol %). The reaction was stirred at rt for 30 min and was quenched with a 2% NaOH aqueous solution (2 mL). The mixture was extracted with ethyl acetate (20 mL) and was washed with brine (5 mL), and was then concentrated. Chromatography of the crude mixture on a silica gel column using 10% ethyl acetate/hexane as the eluent afforded the compound of structure 45 as a bright yellow oil or solid in good yield.
(Z)-5Butylidene-1,2-dihydro-2,2,4-trimethyl-5H-chromeno[3,4-f]quinoline Compound 219, structure 45 of Scheme XIII where $R^1$=$R^2$=H, $R^3$=n-propyl)

This compound was prepared by General Method 6 from 1.6M hexane solution of n-butyllithium (0.2 mL, 0.32 mmol) and Compound 159 (20 mg, 0.07 mmol) to afford 4.8 mg (21%) of Compound 219 as a bright yellow oil. Data for Compound 219: $R_f$=0.62 (silica gel, 25% EtOAc: hexane); $^1$H NMR (400 MHz, acetone-$d_6$) 7.74 (d, J=7.5, 1H), 7.54 (d, J=8.4, 1H), 7.14 (t, J=7.5, 1H), 7.03–6.98 (m, 2 H), 6.74 (d, J=8.4, 1H), 5.48 (s, 1H), 4.81 (t, J=7.5, 1H), 2.40–2.35 (m, 2H), 2.09 (s, 3H), 1.49–1.44 (m, 2H), 1.27 (br s, 6H), 0.93 (t, J=7.3, 3H).

EXAMPLE 120

(Z)-5-Benzylidene-1,2-dihydro-2,2,4-trimethyl-5H-chromeno[3,4-f]quinoline Compound 220, structure 45 of Scheme XIII where $R^1$=$R^2$=H, $R^3$=phenyl)

This compound was prepared by General Method 6 (EXAMPLE 119) from benzyl bromide (171 mg, 1.0 mmol) and Compound 159 (20 mg, 0.07 mmol) to afford 6.3 mg (25%) of Compound 220 as a bright yellow oil. Data for Compound 220: $R_f$=0.50 (silica gel, 25% EtOAc: hexane); $^1$H NMR (400 MHz, acetone-$d_6$) 7.82 (t, J=7.6, 3H), 7.64 (d, J=8.4, 1H), 7.38 (t, J=7.6, 2H), 7.24–7.20 (m, 3H), (7.09–7.06) (m, 1H), 6.84 (d, J=8.4, 1H), 5.68 (s, 1H), 5.55 (s 1H), 2.11 (s, 3H), 1.29 (br s, 6H).

EXAMPLE 121

(Z)-5-(4-Fluorobenzylidene-1,2-dihydro-2,2,4-trimethyl-5H-chromeno[3,4-f]quinoline (Compound structure 45 of Scheme XIII where $R^1$=$R^2$=H, $R^3$=4-fluorophenyl This compound was prepared by General Method 6 (EXAMPLE 119) from 4-fluorobenzyl chloride (145 mg, 1.0 mmol) and Compound 159 (20 mg, 0.07 mmol) to afford 17 mg (63%) of Compound 221 as a bright yellow oil. Data for Compound 221: $R_f$=0.56 (silica gel, 25% EtOAc: hexane); $^1$H NMR (400 MHz, acetone-$d_6$) 7.87–7.82 (m, 3H), 7.64 (d, J=8.4, 1H), 7.22–7.05 (m, 5H), 6.82 (d, J=8.4, 1H), 5.68 (s, 1H), 5.54 (s, 1H), 2.10 (s, 3H), 1.32) br s, 6H).

EXAMPLE 122

(Z)-5-(4-Bromobenzylidene-1,2-dihydro-2,2,4-trimethyl-5H-chromeno[3,4-f]quinoline (Compound 222, structure 45 of Scheme XIII where $R^1$=$R^2$=H, $R^3$=4-bromophenyl)

This compound was prepared by General Method 6 (EXAMPLE 119) from 4-bromobenzyl bromide (250 mg, 1.0 mmol) and Compound 159 (20 mg, 0.07 mmol) to afford 24 mg (82%) of Compound 222 as a bright yellow oil. Data for Compound 222: $^1$H NMR (400 MHz, acetone-$d_6$) 7.83 (d, J=8.4, 1H), 7.77 (d, J=8.6, 2H), 7.65 (d, J=8.4, 1H), 7.55 (d, J=8.6, 2H), 7.26–7.17 (m, 2H), 7.11–7.06 (m, 1H), 6.84 (d, J=8.3, 1H), 5.66 (s, 1H), 5.55 (s, 1H), 2.09 (s, 3H), 1.34 (br s, 6H).

EXAMPLE 123

(Z)-5-Bromobenzylidene)-1,2-dihydro-2,2,4-trimethyl-5H-chromeno[3,4-f]quinoline (Compound 223, structure 45 of Scheme XIII, where $R^1$=$R^2$=H, $R^3$=3-bromophenyl)

This compound was prepared by General Method 6 (EXAMPLE 119) from 3-bromobenzyl bromide (250 mg, 1.0 mmol) and Compound 159 (15 mg, 0.05 mmol) to afford 22 mg (98%) of Compound 223 as a bright yellow oil. Data for Compound 223: $^1$H NMR (400 MHz, acetone-$d_6$) 8.03 (s, 1H), 7.85 (d, J=7.9, 1H), 7.66 (d, J=8.4, 1H), 7.41–7.17 (m, 4H), 7.09 (t, J=7.9, 1H), 6.85 (d, J=8.3, 1H), 5.67 (s, 1H), 5.55 (s, 1H), 2.10 (s, 3H), 1.33 (br s, 6H).

EXAMPLE 124

(Z)-5-(3-Chlorobenzylidene)-1,2-dihydro-2,2,4-trimethyl-5H-chromeno[3,4]quinoline (Compound 224, structure 45 of Scheme XIII, where $R^1$=$R^2$=H, $R^3$=3-chlorophenyl)

This compound was prepared by General Method 6 (EXAMPLE 119) from 3-chlorobenzyl chloride (161 mg, 1.0 mmol) and Compound 159 (10 mg, 0.035 mmol) to afford 6.3 mg (45%) of Compound 224 as a bright yellow oil. Data for Compound 224: $R_f$=0.33 (silica gel, 25% EtOAc: hexane); $^1$H NMR (400 MHz, acetone-$d_6$) 7.88–7.85 (m, 2H), 7.72 (d, J=8.0, 1H), 7.67 (d, J=8.4, 1H), 7.40 (t, J=8.0, 1H), 7.26–7.20 (m, 3H), 7.12–7.08 (m, 1H), 6.85 (d, J=8.4, 1H), 5.68 (s, 1H), 5.56 (s, 1H), 2.10 (s, 3H), 1.29 (br s, 6H).

EXAMPLE 125

(Z)-5-(3-Fluorobenzylidene-1,2-dihydro-2,2,4-trimethyl-5H-chromeno[3,4-f]quinoline (Compound 225, structure 45 of Scheme XIII, where $R^1$=$R^2$=H, $R^3$=3-fluorophenyl)

This compound was prepared by General Method 6 (EXAMPLE 119) from 3-fluorobenzyl bromide (189 mg, 1.0 mmol) and Compound 159 (20 mg, 0.07 mmol) to afford 5.4 mg (20%) of Compound 225 as a bright yellow oil. Data for Compound 225: $R_f$=0.50 (silica gel, 25% EtOAc: hexane); $^1$H NMR (400 MHz, acetone-$d_6$) 7.85 (d, J=7.9, 1H), 7.66 (d, J=8.6, 2H), 7.52 (d, J=7.9, 1H), 7.43–7.38 (m, 1H), 7.25–7.23 (m, 2H), 7.11–7.07 (m, 1H), 6.85 (d, J=8.6, 1H), 5.70 (s, 1H), 5.55 (s, 1H), 2.10 (s, 3H), 1.29 (br s, 6H).

EXAMPLE 126

(Z)-5-(2-Chlorobenzylidene)-1,2-dihydro-2,2,4-trimethyl-5H-chromeno[3,4-f]quinoline (Compound 226, structure 45 of Scheme XIII, where $R^1$=$R^2$=H, $R^3$=2-chlorophenyl)

This compound was prepared by General Method 6 (EXAMPLE 119) from 2-chlorobenzyl chloride (161 mg, 1.0 mmol) and Compound 159 (20 mg, 0.07 mmol) to afford 8.4 mg (30%) of Compound 226 as a bright yellow oil. Data for Compound 226: $R_f$=0.44 (silica gel, 25% EtOAc: hexane); $^1$H NMR (400 MHz, acetone-$d_6$) 8.44 (d, J=7.9, 1H), 7.85 (d, J=7.9, 1H), 7.67 (d, J=8.5, 1H), 7.45–7.37 (m, 2H), 7.25–7.21 (m, 3H), 7.20–7.11 (m, 1H), 6.86 (d, J=8.5, 1H), 6.20 (s, 1H), 5.55 (s, 1H), 2.15 (s, 3H), 1.29 (br s, 6H).

EXAMPLE 127

(Z)-5-(2-Bromobenzylidene)-1,2-dihydro-2,2,4-trimethyl-5H-chromeno[3,4-f]quinoline (Compound 227, structure 45 of Scheme XIII, where $R^1$=$R^2$=H, $R^3$=2-bromophenyl)

This compound was prepared by General Method 6 (EXAMPLE 119) from 2-bromobenzyl bromide (250 mg, 1.0 mmol) and Compound 159 (20 mg, 0.07 mmol) to afford 2.8 mg (10%) of Compound 227 as a bright yellow oil. Data for Compound 227: $R_f$=0.44 (silica gel, 25% EtOAc: hexane); $^1$H NMR (400 MHz, acetone-$d_6$) 8.45 (d, J=7.9, 1H), 7.85 (d, J=7.9, 1H), 7.67 (d, J=8.5, 1H), 7.64 (d, J=7.9, 1H), 7.45 (t, J=8.5, 1H), 7.23–7.07 (m, 4H), 6.87 (d, J=8.5, 1H), 6.19 (s, 1H), 5.55 (s, 1H), 2.15 (s, 3H), 1.29 (br s, 6H).

EXAMPLE 128

(Z)-5-(2-Fluorobenzylidene)-1,2-dihydro-2,2,4-trimethyl-5H-chromeno[3,4-f]quinoline (Compound 228, structure 45 of Scheme XIII, where $R^1$=$R^2$=H, $R^3$=2-fluorophenyl)

This compound was prepared by General Method 6 (EXAMPLE 119) from 2-fluorobenzyl bromide (189 mg, 1.0 mmol) and Compound 159 (10 mg, 0.034 mmol) to afford 2.1 mg (16%) of Compound 228 as a bright yellow oil. Data for Compound 228: $^1$H NMR (400 MHz, acetone-$d_6$) 8.39 (m, 1H), 7.85 (d, J=7.4, 1H), 7.67 (d, J=8.5, 1H), 7.30–7.06 (m, 6H), 6.86 (d, J=8.5, 1H), 5.96 (s, 1H), 5.90 (s, 1H), 5.55 (s, 1H), 2.13 (s, 3H), 1.32 (br s, 6H).

EXAMPLE 129

(Z)-5-(2,3-Difluorobenzylidene)-1,2-dihydro-2,2,4-trimethyl-5H-chromeno[3,4-f]quinoline (Compound 229, structure 45 of Scheme XIII, where $R^1$=$R^2$=H, $R^3$=2,3-difluorophenyl)

This compound was prepared by General Method 6 (EXAMPLE 119) from 2,3-difluorobenzyl bromide (207 mg, 1.0 mmol) and Compound 159 (10 mg, 0.034 mmol) to afford 4.8 mg (35%) of Compound 229 as a bright yellow oil. Data for Compound 229: $^1$H NMR (400 MHz, acetone-$d_6$) 8.18 (dd, J=8.0, 6.6, 1H), 7.87 (d, J=7.5, 1H), 7.69 (d, J=8.5, 1H), 7.30–7.08 (m, 5H), 6.89 (d, J=8.4, 1H), 5.94 (s, 1H), 5.57 (s, 1H), 2.12 (s, 3H), 1.31 (br s, 6H).

EXAMPLE 130

(Z)-5-(2,5-Difluorobenzylidene)-1,2-dihydro-2,2,4-trimethyl-5H-chromeno[3,4-f-]quinoline (Compound 230, structure 45 of Scheme XII, where $R^1$=$R^2$=H, $R^3$=2,5-difluorophenyl)

This compound was prepared by General Method 6 (EXAMPLE 119) from 2,5-difluorobenzyl bromide (207 mg, 1.0 mmol) and Compound 159 (15 mg, 0.05 mmol) to afford 17 mg (82%) of Compound 230 as a bright yellow oil. Data for Compound 230: $^1$H NMR (400 MHz, acetone-$d_6$) 8.12 (m, 1H), 7.88 (d, J=8.31, 1H), 7.69 (d, J=8.5, 1H), 7.30–7.00 (m, 5H), 6.89 (d, J=8.4, 1H), 5.93 (s, 1H), 5.94 (s, 1H), 5.56 (s, 1H), 2.11 (s, 3H), 1.32 (br s, 6H).

EXAMPLE 131

(Z)-9-Fluoro-5-(3-fluorobenzylidene)-1,2-dihydro-2,2,4-trimethyl-5H-chromeno[3,4-f]quinoline (Compound 231, structure 45 of Scheme XIII, where $R^1$=H, $R^2$=F, $R^3$=3-fluorophenyl)

This compound was prepared by General Method 6 (EXAMPLE 119) from 3-fluorobenzyl chloride (0.17 g) and Compound 207 (31 mg) to afford 7.5 mg (19%) of Compound 231 as a yellow oil. Data for Compound 231: $^1$H NMR (400 MHz, acetone-$d_6$) 7.65 (d, J=8.4, 1H), 7.64 (m, 1H); 7.60 (dd, J=10.0, 3.0, 1H); 7.52 (d, J=7.6, 1H); 7.40 (m, 1H); 7.26 (dd, J=8.9, 4.8, 1H); 7.00 (m, 2H); 6.86 (d, J=8.3, 1H); 5.72 (s, 1H); 5.57 (d, J=1.2, 1H); 2.10 (s, 3H), 1.40 (br s, 6H).

EXAMPLE 132

(Z)-9-Fluoro-5-(3-methoxybenzylidene)-1,2-dihydro-2,2,4-trimethyl-5H-chromeno[3,4-f]quinoline (Compound 232, structure 45 of Scheme XIII, where $R^1$=H, $R^2$=F, $R^3$=3-methoxylphenyl)

This compound was prepared by General Method 6 (EXAMPLE 119) from 3-methoxylbenzyl chloride (0.18 g) and Compound 207 (31 mg) to afford 11 mg (27%) of Compound 232 as a yellow oil. Data for Compound 232: $^1$H NMR (400 MHz, acetone-$d_6$) 7.63 (d, J=5, 1H); 7.58 (dd, J=10.0, 2.9, 1H); 7.48 (br s, 1H); 7.28 (d, J=5.1, 2H); 7.22 (m, 1H); 6.98 (m, 1H); 6.83 (d, J=9.6, 1H); 6.82 (m, 1H); 5.68 (s, 1H); 5.56 (s, 1H); 3.86 (s, 3H); 2.10 (s, 3H); 1.35 (br s, 6H).

EXAMPLE 133

(Z)-8-Fluoro-5-(3-fluororbenzylidene)-1,2-dihydro-2,2,4-trimethyl-5H-chromeno[3,4-f]quinoline (Compound 233, structure 45 of Scheme XIII, where $R^1$=F, $R^2$=H, $R^3$=3-fluorophenyl)

This compound was prepared by General Method 6 (EXAMPLE 119) from 3-fluorobenzyl chloride (0.17 g) and Compound 208 (31 mg) to afford 7.5 mg (19%) of Compound 233 as a yellow oil. Data for Compound 233: $^1$H NMR (400 MHz, acetone-$d_6$) 7.88 (dd, J=9.7, 6.2, 1H); 7.63 (d, J=8.5, 1H); 7.58 (m, 2H); 7.42 (dd, J=8.0, 6.4, 1H); 7.09 (dd, J=9.5, 2.7, 1H); 7.00 (m, 1H); 6.92 (m, 1H); 6.85 (d, J=8.2, 1H); 5.73 (s, 1H); 5.63 (s, 1H); 2.10 (s, 3H); 1.35 (br s, 6H).

EXAMPLE 134

(R/S-4l, 5u)-5-(4-Chlorophenyl)-1,2,3,4-tetrahydro-2,2,4-trimethyl-5H-chromeno[3,4-f]-3-quinolinone (Compound 234, structure 52 of Scheme XV, where R=4-chlorophenyl, $R^1$=$R^2$=H)

This compound was prepared by a four step procedure as depicted in Scheme XV. To a yellow solution of Compound 163 (EXAMPLE 63) (120 mg, 0.3 mmol) in THF (6 mL) at −78° C. was added 0.3 mL of n-BuLi (1.6M in hexane, 0.48 mmol), and the resulting solution was stirred for 15 min before a solution of di-t-butyl dicarbonate (150 mg, 0.7 mmol) in 2 mL of THF was introduced. The reaction mixture was allowed to warm up to rt and was stirred for 5 h. The mixture was quenched with water and was extracted with ethyl acetate (2×20 mL). Removal of solvent and chromatography of the crude mixture on a silica gel column using 10–30% mixture of ethyl acetate and hexane afforded 50 mg (34%) of the t-Boc protected quinoline (structure 49 of Scheme XV where R=4-chlorophenyl, $R^1$=$R^2$=H) and 80 mg (66%) of Compound 163. The t-Boc protected Compound 163 (structure 49 of Scheme XV where R=4-chlorophenyl, $R^1$=$R^2$=H) (40 mg, 0.08 mmol) in THF (4 mL) was treated with 0.3 mL of BH$_3$.THF (1.0M in THF, 0.3 mmol) at rt for 3 h and was then quenched with 0.2 mL of KOH (3M aqueous). To the above solution 0.2 mL of H$_2$O$_2$ (30% in water) was added and the mixture was stirred for 30 min, then 5 mL of water was introduced. The mixture was extracted with EtOAc, washed with brine and concentrated. Chromatography of the crude mixture on a silica gel column (10–30% EtOAc/hexane gradient) afforded two major isomers. The first fraction (20 mg, 50%) was assigned as (R/S-31, 4u, 5l)-1-t-butyloxycarbonyl-5-(4-chlorophenyl)-1,2,3,4-tetrahydro-3-hydroxy-2,2,4-trimethyl-5H-chromeno [3,4-f]quinoline (structure 50 of Scheme XV where R=4-chlorophenyl, $R^1$=$R^2$=H). The second fraction (12 mg, 30%) was assigned as (R/S-31, 4u, 5u)-1-t-butyloxylcarbonyl-5-(4-chlorophenyl)-1,2,3,4-tetrahydro-3-hydroxy-2,2,4-trimethyl-5H-chromeno[3,4,f-]quinoline (structure 51 of Scheme XV where R=4-chlorophenyl, $R^1$=$R^2$=H).

(R/S-31, 4u, 5l)-1-t-Butyloxylcarbonyl-5-(4-chlorophenyl)-1,2,3,4-tetrahydro-3-hydroxy-2,2,4-trimethyl-5H-chromeno[3,4-f]quinoline (structure 50 of Scheme XV where R=4-chlorophenyl, $R^1$=$R^2$=H) (20 mg, 0.04 mmol) was oxidized with PCC (100 mg, 0.46 mmol) in 5 mL of methylene chloride at rt for 60 min to yield (R/S-4l, 5u)-1-t-butyloxylcarbonyl-5-(4-chlorophenyl)-1,2,3,4-tetrahydro-2,2,4-trimethyl-5H-chromeno[3,4-f]-3-quinoline as a colorless oil after chromatography. This compound was then treated with 0.2 mL of TFA in 0.5 mL of methylene chloride for 30 min and was quenched with 5 mL of KOH (2%). The reaction mixture was extracted with EtOAc, washed with brine and was concentrated. Chromatography of the crude residue on a silica gel column (10–30% EtOAc/hexane gradient) afforded 15 mg (93%) of Compound 234 as a white solid. Data for Compound 234: $^1$H NMR (400 MHz, CDCl$_3$) 7.64 (d, J=8.2,2H), 7.18 (d, J=8.6, 2H), 7.13 (d, J=8.6, 2H), 7.05 (t, J=7.9, 1H), 6.96 (t, J=7.8, 1H), 6.84 (d, J=8.3, 1H), 6.76 (d, J=7.9, 1H), 6.37 (s, 1H), 3.73 (s, 1H), 3.56 (q, J=7.4, 1H), 1.44 (s, 3H), 1.26 (s, 3H), 0.87 (d, J=7.4, 3H).

EXAMPLE 135

(R/S-4l, 5l)-5-(4-Chlorophenyl)-1,2,3,4-tetrahydro-2,2,4-trimethyl-5H-chromeno[3,4-f]-3-quinolinone (Compound 235, structure 53 of Scheme XV, where R=4-chlorophenyl, $R^1$=$R^2$=H)

(R/S-31, 4u, 5u)-1-t-Butyloxylcarbonyl-5-(4-chlorophenyl)-1,2,3,4-tetrahydro-3-hydroxy-2,2,4-trimethyl-5H-chromeno[3,4-f]quinoline (structure 51 of Scheme XV where R=4-chlorophenyl, $R^1$=$R^2$=H) (EXAMPLE 134) (12 mg, 0.024 mmol) was oxidized and deprotected by methods similar to that described for Compound 234 (EXAMPLE 134) to yield 8 mg (84%) of Compound 235 as a white solid. Data for Compound 235: $^1$H NMR (400 MHz, CDCl$_3$) 7.59 (d, J=8.4, 1H), 7.57 (d, J=8.0, 1H), 7.15 (d, J=8.5, 2H), 7.06 (d, J=8.5, 2H), 7.04 (m, 1H), 6.94 (t, J=7.8, 1H), 6.85 (d, J=7.6, 1H), 6.83 (d, J=8.3, 1H), 3.73 (s, 1H), 3.35 (d, J=7.5, 1H), 1.50 (d, J=7.5, 3H), 1.46 (s, 3H), 1.17 (s, 3H).

EXAMPLE 136

(R/S)-5-(4-Chlorophenyl)-1,2,3,4-tetrahydro-2,2,4,4-tetramethyl-5H-chromeno[3,4-f]-3-quinoline (Compound 236, structure 54 of Scheme XV where R=4-chlorophenyl, $R^1$=$R^2$=H)

To a solution of (R/S-4l, 5u)-1-t-butyloxylcarbonyl-5-(4-chlorophenyl)-1,2,3,4-tetrahydro-2,2,4-trimethyl-5H-chromeno[3,4f-]-3-quinoline (EXAMPLE 234) (5 mg, 0.01 mmol) in 2 mL of THF was added 10 mg of NaH (40% in mineral oil, 0.25 mmol) and the resulting slurry was stirred at rt for 20 min before MeI (0.1 g, 0.7 mmol) was introduced. The mixture was stirred at rt for 2 h and was then quenched with water (5 mL). The mixture was extracted with EtOAc and purified by silica gel chromatography to provide 1.5 mg (36%) of Compound 236 as a colorless oil. Data for Compound 236: $^1$H NMR (400 MHz, CDCl$_3$) 7.59 (d, J=8.2, 1H), 7.56 (d, J=7.8, 1H), 7.13 (d, J=8.7, 2H), 7.09 (d, J=8.7, 2H), 7.01 (t, J=7.9, 1H), 6.91 (t, J=7.9, 1H), 6.85 (s, 1H), 6.83–6.78 (m, 2H), 3.83 (s, 1H), 1.63 (s, 3H), 1.38 (s, 3H), 1.38 (s, 3H), 1.33 (s, 3H), 1.28 (s, 3H).

EXAMPLE 137

1,2-Dihydro-2,2,4-trimethyl-6-methoxymethyl-8-pyranono[5,6-g]quinoline (Compound 237, structure 57 of Scheme XVI, where $R^1$=$R^2$=H, $R^3$=methoxylmethyl, Y=O)

General Method 7: 1,2-Dihydro-2,2,4-trimethylquinolines (Compounds of structure 57 or 67) from anilines (Compounds of structure 56 or 66); ambient pressure version In an r.b. flask equivuipped with a reflux condensor, a solution of the aniline (a compound of structure 56 or 66) in acetone (0.05–0.20M) was treated with iodine (5–20 mol %) and heated to reflux for 1–3 days. Addition of Celite™ followed by concentration afforded a fluffy orange powder which was purified by silica gel chromatography to afford the desired dihydroquinoline (compound of structure 57 or 67).

1,2-Dihydro-2,2,4-trimethyl-6-methoxymethyl-8-pyranono[5,6-g]quinoline (Compound 237, structure 57 of Scheme XVI, where $R^1$=$R^2$=H, $R^3$=methoxylmethyl, Y=O)

This compound was prepared by General Method 7 from 7-amino-4-methoxymethylcoumarin (structure 56 of Scheme XVI, where $R^1$=$R^2$=H, $R^3$=methoxymethyl) (1.0 g, 4.87 mmol) to afford 82 mg (6%) of Compound 237 as a light yellow solid in addition to 487 mg (35%) of 1,2-dihydro-2,2,4-trimethyl-8-methoxymethyl-6-pyranono[6,5-f]quinoline. Data for Compound 237: R$_f$=0.23 (silica gel, hexanes/EtOAc, 2:1); $^1$H NMR (400 MHz, C$_6$D$_6$) 7.01 (s, 1H), 6.24 (s, 1H), 6.18 (s, 1H), 5.02 (s, 1H), 3.97 (s, 2H), 3.74 (br s, 1H), 2.92 (s, 3H), 1.78 (d, J=1.0, 3H), 0.98 (s, 6H).

EXAMPLE 138

1,2-Dihydro-2,2,4-trimethyl-6-trifluoromethyl-8-pyranono[5,6-g]quinoline (Compound 238, structure 57 of Scheme XVII, where $R^1$=$R^2$=H, $R^3$=trifluoromethyl, Y=O)

This compound was prepared as depicted in Scheme XVII and as described below.

O-Pivaloyl-3-nitrophenol (structure 65 of Scheme XVII, where $R^1$=H, P=t-butyl, Y=O)

To 300 mL of CH$_2$Cl$_2$ was added 3-nitrophenol (structure 64 of Scheme XVII, where $R^1$=H, Y=O) (15 g, 0.11 mol), pyridine (20 mL) and DMAP (10 mg). To this cooled solution (0° C.) was slowly added trimethylacetyl chloride (18 mL, 146 mmol, 1.4 equivuiv). The solution was allowed to warm to rt and stirred for 3 h. To the amber colored solution was added sat'd NH$_4$Cl (300 mL). The organic layer was washed with 1N HCl (2×150 mL), 10% CuSO$_4$.5 H$_2$O (2×100 mL), and brine (2×100 mL). The extract was dried (Na$_2$SO$_4$) and concentrated in vacuo to give 22.5 g (94%) of O-pivaloyl-3-nitrophenol as a white solid. Data for O-pivaloyl-3-nitrophenol: R$_f$0.55 (silica gel, hexanes/EtOAc, 3:1); $^1$H NMR (400 MHz, CDCl$_3$) 8.11 (dd, J=4.2, 1.3, 1H), 7.96 (t, J=2.2, 1H), 7.56 (dd, J=8.4, 8.2, 1H), 7.42 (dd, J=6.5, 1.3, 1H), 1.35 (s, 9H).

O-Pivaloyl-3-aminophenol (structure 66 of Scheme XVII, where $R^1$=H, P=t-butyl, Y=O)

To 60 mL anhydrous CH$_2$Cl$_2$ was added O-pivaloyl-3-nitrophenol (5.0 g, 22.4 mmol) and a catalytic amount (50 mg) of 10% Pd on C. The flask was repeatedly evacuated and flushed with N$_2$. The reaction flask was again evacuated and H$_2$ was introduced by balloon. After stirring under an atmosphere of H$_2$ for 3 h, the reaction flask was flushed twice with N2. The suspension was then filtered through a bed of Celite™ and concentrated to give 4.15 g (96%) of O-pivaloyl-3-aminophenol as a viscous amber oil. Data for O-pivaloyl-3-aminophenol: R$_f$0.21 (silica gel, hexanes/EtOAc, 3:1); $^1$H NMR (400 MHz, CDCl$_3$) 7.12 (dd, J=8.0, 8.0, 1H), 6.52 (dd, J=7.8, 2.7, 1H), 6.44 (ddd, J=8.0, 2.4, 1.4, 1H), 6.38 (t, J=2.2, 1H), 3.81 (br s, 2H), 1.34 (s, 9H).

General Method 8. 1,2-Dihydro-2,2,4-trimethylquinolines (Compounds of structure 57 or 67) from anilines (Compounds of structure 56 or 66); pressure tube version In a threaded resealable pressure tube, a solution of the aniline (a compound of structure 56 or 66) in acetone (0.05–0.20M) was treated with iodine (5–20 mol %) and heated to 100°–120° C. for 1–3 days. The reaction vessel was allowed to cool to rt and transferred to a r.b. flask. Addition of Celite™ followed by concentration afforded a fluffy orange powder which was purified by silica gel chromatography to afford the desired dihydroquinoline (Compound of structure 57 or 67).

1,2-Dihydro-2,2,4-trimethyl-7-(1,1,1-trimethylacetoxy)quinoline (structure 67 of Scheme XVII, where $R^1$=H, P=t-butyl, Y=O)

This compound was prepared by General Method 8 from O-pivaloyl-3-aminophenol (structure 66 of Scheme XVII, where $R^1$=H, P=t-butyl, Y=O) (1.26 g, 6.53 mmol) to afford 1.06 g (60%) of 1,2-dihydro-2,2,4-trimethyl-7-(1,1,1-trimethylacetoxy)quinoline as a light brown solid. Data for 1,2-dihydro-2,2,4-trimethyl-7-(1,1,1-trimethylacetoxy)quinoline: R$_f$0.23 (silica gel, hexanes/EtOAc, 3:1); $^1$H NMR (400 MHz, CDCl$_3$) 7.00 (d, J=8.3, 1H), 6.28 (dd, J=5.2, 2.3, 1H), 5.25 (s, 1H), 3.69 (s, 1H), 1.96 (d, J=1.2, 3H), 1.32 (s, 9H), 1.26 (s, 6H).

1,2-Dihydro-7-hydroxy-2,2,4-trimethylquinoline

To 70 mL 85% ethanol was added 1,2-dihydro-2,2,4-trimethyl-7-(1,1,1-trimethylacetoxy)quinoline (1.03 g, 3.77 mmol) and 20% NaOH(aq) (3 mL) to give a clear colorless solution. The reaction was followed by TLC (hexanes/EtOAc, 3:1). After 3 h the resulting purple solution was quenched with sat'd NH$_4$Cl (200 mL) and extracted with ethyl acetate (2×100 mL). The combined organic layers were washed with brine (2×75 mL), dried (Na$_2$SO$_4$), and concentrated in vacuo to give a dark purple oil. The oil was dissolved in a minimal amount of hexanes/ethyl acetate (3:1), and filtered though a plug of silica rinsing with a solution of hexanes/ethyl acetate (3:1). The washes were concentrated in vacuo to afford 710 mg (99%) of 1,2-dihydro-7-hydroxy-2,2,4-trimethylquinoline as a dark yellow oil. Data for 1,2-dihydro-7-hydroxy-2,2,4-trimethylquinoline: R$_f$0.30 (silica gel, hexanes/EtOAc, 3:1); $^1$H NMR (400 MHz, DMSO-d$_6$) 8.90 (s, 1H), 6.70 (d, J=8.2, 1H), 5.89 (d, J=2.3, 1H), 5.85 (dd, J=8.3, 2.4, 1H), 5.65 (s, 1H), 5.04 (s, 1H), 1.8 (d, J=1.1, 3H), 1.14 (s, 6H).

1,2-Dihydro-2,2,4-trimethyl-6-trifluoromethyl-8-pyranono[5,6-g]quinoline (Compound 238, structure 57 of Scheme XVII, where $R^1$=$R^2$=H, $R^3$=trifluoromethyl, Y=O)

General Method 9: Preparation of Compounds of structure 56 or 57 from phenols.

To a solution of 1,2-dihydro-7-hydroxy-2,2,4-trimethylquinoline (0.1–0.5M) in absolute EtOH was added a β-keto ester (a compound of structure 68) (1–3 equivuiv) in a 4×13.5 cm pressure tube equivuipped with a magnetic stir bar and a threaded Teflon stopcock. To this solution was added ZnCl$_2$ (1–6 equivuiv). The sealed pressure tube was heated in a oil bath at 80°–120° C. for 6–72 h. The cooled solution was diluted with sat'd NH$_4$Cl and extracted with ethyl acetate. The combined organics were concentrated on Celite™ under reduced pressure to give a free flowing powder, which was purified by flash column chromatography (silica gel 60, hexanes/ethyl acetate, 5:1) to give the desired product. Further purification could be effected by recrystallization from hexanes/toluene.

1,2Dihydro-2,2,4-trimethyl-6-trifluoromethyl-8-pyranono[5,6-g]quinoline (Compound 238, structure 55 of Scheme XVII, where R$^1$=R$^2$=H, R$^3$=trifluoromethyl, Y=O)

This compound was prepared by General Method 9 from 1,2-dihydro-7-hydroxy-2,2,4-trimethylquinoline (1.58 g, 8.5 mmol) and ethyl 4,4,4-trifluoroacetoacetate (3.00 g, 16.8 mmol, 2.0 equivuiv) to afford 1.7 g (66%) of Compound 238 as a light yellow powder. Data for Compound 238: R$_f$ 0.32 (silica gel, hexanes/EtOAc, 3:1); $^1$H NMR (400 MHz, C$_6$D$_6$) 7.22 (s, 1H), 6.15 (s, 1H), 5.97 (s, 1H), 4.93 (s, 1H), 3.23 (br s, 1H), 1.66 (d, J=1.1, 3H), 0.98 (s, 6H).

EXAMPLE 139

1,2-Dihydro-2,2,4-trimethyl-10-isocoumarino[4,3-g]quinoline (Compound 239, structure 57 of Scheme XVI, where R$^1$H, R$^2$=R$^3$=benzo, Y=O)

This compound was prepared by General Method 8 (EXAMPLE 138) from 7-amino-3,4-benzocoumarin (structure 56 of Scheme XVI, where R$^1$=H, R$^2$=R$^3$=benzo, Y=O) (180 mg, 0.85 mmol) to afford 75 mg (30%) of Compound 239 along with 150 mg (60%) of 1,2-dihydro-2,2,4-trimethyl-10-isocoumarino[3,4-f]quinoline as yellow solids. Data for Compound 239: mp 246°–248° C.; $^1$H NMR (400 MHz, CDCl$_3$) 8.18 (d, J=7.6, 1H), 8.16 (d, J=7.6, 1H), 7.80 (s, 1H), 7.78 (t, J=7.6, 1H), 7.43 (t, J=7.6, 1H), 6.39 (s, 1H), 5.45 (s, 1H), 2.11 (s, 3H), 1.33 (s, 6H), $^{13}$C NMR (100 MHz, CDCl$_3$) 162.2, 152.7, 146.1, 136.4, 134.9, 130.7, 129.1, 127.2, 126.5, 120.5, 119.4, 119.0, 117.8, 107.6, 99.8, 52.7, 31.8, 19.0; Anal. Calcd for C$_{19}$H$_{17}$NO$_2$: C, 78.33; H, 5.88; N, 4.81. Found: C, 77.99; H, 5.79; N, 4.72.

EXAMPLE 140

1,2-Dihydro-2,2,4-trimethyl-10-isoquinolono[4,3-g]quinoline (Compound 240, structure 57 of Scheme XVI, where R$^1$=H, R$^2$=R$^3$=benzo, Y=NH)

3-Amino-6 (5H)-phenanthridinone (structure 56 of Scheme XVI, where R$^1$=H, R$^2$=R$^3$=benzo, Y=NH)

A mixture of 3-nitro-6 (5H)-phenanthridinone (structure 55 of Scheme XVI, where R$^1$=H, R$^2$=R$^3$=benzo, Y=NH) (480 mg, 1.5 mmol) and 50 mg of 10% Pd/C in 60 mL of DMF was stirred under an atomsphere of H$_2$ for 2 h. The mixture was filtered through a Celite™ pad and the filtrate was concentrated to give 0.4 g of the crude aniline as a yellow solid. This material was used without further purification.

1,2-Dihydro-2,2,4-trimethyl-10-isoquinolono[4,3-g]quinoline (Compound 240, structure 57 of Scheme XVI, where R$^1$=H, R$^2$=R$^3$=benzo, Y=NH)

This compound was prepared by General Method 8 (EXAMPLE 238) from 3-amino-6 (5H)-phenanthridinone (0.4 g), iodine (150 mg, 0.6 mmol), acetone (16 mL) and DMF (14 mL) to afford 220 mg (51%) of Compound 240 as a yellow solid. Data for Compound 240: mp 301°–302° C.; IR (KBr, cm$^{-1}$) 3300, 3010, 1670, 1450, 1300; $^1$H NMR (400 MHz, CDCl$_3$) 8.28 (d, J=7.6, 1H), 8.25 (d, J=7.6, 1H), 7.90 (s, 1H), 7.70 (t, J=7.6, 1H), 7.39 (t, J=7.6, 1H), 6.48 (s, 1H), 5.78 (br s, 1H), 5.42 (s, 1H), 2.13 (s, 3H), 1.33 (s, 6H); $^{13}$C NMR (100 MHz, acetone-d$_6$) 162.4, 147.1, 139.2, 137.0, 133.3, 129.2, 128.7, 128.6, 125.8, 125.0, 121.8, 118.9, 118.4 108.5, 98.1, 52.8, 31.6, 19.0.

EXAMPLE 141

1,2-Dihydro-2,2,4,6-tetramethyl-8-pyridono[5,6-g]quinoline (Compound 241, structure 57 of Scheme XVI, where R$^1$=R$^2$=H, R$^3$=methyl, Y=NH)

This compound was prepared by General Method 8 (EXAMPLE 238) from Carbostyril 124 (structure 56 of Scheme XVI, where R$^1$=R$^2$=H, R$^3$=methyl, Y=NH) (500 mg, 2.8 mmol) to afford 175 mg (25%) of Compound 241 as a pale yellow solid. Data for Compound 241: mp 282°–284° C.; IR (KBr, cm$^{-1}$) 2966, 2918, 1658, 1641, 1425, 1257; $^1$H NMR (400 MHz, CDCl$_3$) 7.24 (s, 1H), 6.34 (s, 1H), 6.23 (s, 1H), 5.37 (s, 1H), 2.41 (s, 3H), 2.04 (s, 3H), 1.29 (s, 6H); $^{13}$C NMR (100 MHz, CDCl$_3$) 165.0, 149.8, 146.5, 140.3, 129.2, 127.6, 119.1, 118.5, 114.9, 112.5, 97.2, 52.4, 31.8, 19.3, 18.9.

EXAMPLE 142

1,2-Dihydro-10-hydroxy-2,2,4-trimethyl-10H-isochromeno[4,3-g]quinoline (Compound 242, structure 62 of Scheme XVI, where R$^1$=H, R$^2$=R$^3$=benzo, Y=O)

To a yellow solution of Compound 239 (EXAMPLE 139) (10 mg, 0.033 mmol) in 0.5 mL of toluene at –78° C. was added 0.050 mL of DIBALH (1.5M in toluene, 0.075 mmol), and the resulting solution was stirred at –50°±10° C. for 20 min. The reaction was quenched with water (1 mL) and extracted with ethyl acetate (2×5 mL). Removal of solvent and chromatography of the crude residue (silica gel, 20% ethyl acetate/hexanes) afforded 6 mg (63%) of Compound 242 as a colorless oil. Data for Compound 242: $^1$H NMR (400 MHz, acetone-d$_6$) 7.74 (d, J=7.8, 1H), 7.52 (s, 1H), 7.37 (t, J=7.8, 1H), 7.31 (d, J=7.8, 1H), 7.19 (t, J=7.8, 1H), 6.26 (d, J=6.5, 1H), 6.17 (s, 1H), 5.97 (d, J=6.5, 1H), 5.40 (br s, 1H), 5.29 (s, 1H), 2.05 (s, 3H), 1.27 (s, 6H).

EXAMPLE 143

1,2-Dihydro-2,2,4,6-tetramethyl-8H-pyrano[3,2-g]quinoline (Compound 243, structure 61 of Scheme XVI, where R$^1$=R$^2$=H, R$^3$=methyl, Y=O)

1,2-Dihydro-2,2,4,6-tetramethyl-8-pyranono[5,6-g]quinoline (structure 57 of Scheme XVI, where R$^1$=R$^2$=H, R$^3$=methyl, Y=O)

To a solution of 7-nitro-4-methylcoumarin (structure 55 of Scheme XVI, where R$^1$=R$^2$=H, R$^3$=methyl, Y=O) (0.61 g, 1.75 mmol) was added 50 mg of 10% Pd/C. The reaction mixture was stirred under an atmosphere of H$_2$ for 2 h. The mixture was filtered through a pad of Celite™ and the filtrate was concentrated to give 0.5 g of the crude amino compound as a yellow solid. This material was used without further purification, and was submitted to General Method 3 to afford 90 mg (20%) of 1,2-dihydro-2,2,4,6-tetramethyl-8-pyranono[5,6-g]quinoline as a yellow solid. Data for 1,2-dihydro-2,2,4,6-tetramethyl-8-pyranono[5,6-g]quinoline: mp 258°–260° C.; IR (KBr) 3300, 2955, 1720, 1630, 1505, 1390, 1250; $^1$H NMR (400 MHz, CDCl$_3$) 7.27 (s, 1H), 6.30 (s, 1H), 6.12 (br s, 1H), 5.84 (s, 1H), 5.44 (s, 1H), 2.37 (s, 3H), 2.05 (s, 3H), 1.32 (s, 6H); $^{13}$C NMR (100 MHz, CDCl$_3$) 161.9, 155.4, 153.1, 147.1, 128.8, 127.0, 119.2, 110.3, 109.0, 98.6, 52.6, 31.8, 18.6.

1,2-Dihydro-2,2,4,6-tetramethyl-8H-quinoline (Compound 243, structure 61 of Scheme XVI, where R$^1$=R$^2$=H R$^3$=methyl, Y=O)

To a solution of 1,2-dihydro-2,2,4,6-tetramethyl-8-pyranono[5,6-g]quinoline (15 mg, 0.06 mmol) in 1 mL of toluene at −78° C. was added DIBAl-H (0.5M in toluene, 0.24 mL, 0.12 mmol) and the resulting mixture was allowed to stir at −50° C. for 60 min, generating a clear brown solution. The reaction was quenched with water (1 mL) and was extracted with ethyl acetate (2×10 mL). The organic extract was concentrated and was chromatographed (silica gel, 4:1 hexanes/ethyl acetate) to afford 1 mg (5%) of Compound 243 as a colorless oil. Data for Compound 243: $^1$H NMR (400 MHz, acetone-$d_6$) 6.84 (s, 1H), 5.96 (s, 1H), 5.33 (t, J=3.5, 1H), 5.26 (s, 1H), 5.21 (s, 1H), 4.59 (d, J=3.5, 2H), 1.96 (s, 3H), 1.93 (s, 3H), 1.24 (s, 6H).

EXAMPLE 144

(R/S)-1,2,3,4-Tetrahydro-2,2,4-trimethyl-10-isoquinolono[4,3-g]quinoline (Compound 244, structure 63 of Scheme XVI, where $R^1$=H, $R^2$=$R^3$=benzo, Y=O)

Hydrogenation of Compound 240 (550 mg, 1.9 mmol) over 10% Pd/C (200 mg) in 250 mL of ethyl acetate for 14 h at rt afforded 510 mg (92%) of Compound 244 as a yellow solid. Data for Compound 244: mp 263°–264° C.; IR (KBr) 3304, 2960, 2928, 1658, 1606, 1467, 1267 cm$^{-1}$; $^1$H NMR (400 MHz, CDCl$_3$) 9.67 (br s, 1H), 8.45 (d, J=8.0, 1H), 8.11 (d, J=8.0, 1H), 7.94 (s, 1H), 7.69 (t, J=8.0, 1H), 7.41 (t, J=8.0, 1H), 6.25 (s, 1H), 4.08 (br s, 1H), 3.02 (m, 1H), 1.81 (dd, J=12.8, 5.2, 1H), 1.49 (t, J=12.8, 1H), 1.46 (d, J=6.7, 3H), 1.29 (s, 3H) and 1.23 (s, 3H).

EXAMPLE 145

1,2-Dihydro-2,2,4-trimethyl-10-thioisoquinolono[4,3g]quinoline (Compound 245, structure 58 of Scheme XVI, where $R^1$=H, $R^2$=$R^3$=benzo, Y=O)

A mixture of Compound 240 (9 mg, 0.03 mmol) and Lawesson's reagent (41 mg, 0.1 mmol) in 2 mL of THF was stirred at 80° C. for 3 h, generating a bright yellow solution. Removal of the solvent and chromatography of the crude mixture (silica gel, 1:1 ethyl acetate/hexanes) afforded 8.2 mg (90%) of Compound 245 as a yellow oil. Data for Compound 245: $^1$H NMR (400 MHz, acetone-$d_6$) 8.93 (d, J=8.1, 1H), 8.33 (d, J=8.1, 1H), 8.01 (s, 1H), 7.75 (t, J=8.1, 1H), 7.44 (t, J=8.1, 1H), 6.73 (s, 1H), 5.97 (br s, 1H), 5.51 (s, 1H), 2.15 (s, 3H), 1.35 (s, 6H).

EXAMPLE 146

(+)-1,2,3,4-Tetrahydro-2,2,4-trimethyl-10-isoquinolono[4,3-g]quinoline (Compound 246, structure 63 of Scheme XVI, where $R^1$=H, $R^2$=$R^3$=benzo, Y=O)

This compound was prepared by a HPLC separation of the enantiomers of Compound 244 using a Chiracel OD-R column, using a 4:1 mixture of methanol and water as the mobile phase. The optical purity of Compound 246 was determined by HPLC to be >99% e.e.; $[\alpha]^{20}$D=+106 (MeOH).

EXAMPLE 147

1,2-Dihydro-2,2,4-trimethyl-6-trifluoromethyl-8-pyridono[5,6-g]quinoline (Compound 247, structure 57 of Scheme XVII, where $R^1$=$R^2$=H, $R^3$=trifluoromethyl, Y=NH)

This compound was prepared as depicted in Scheme XVII and as described below.

1-tert-Butyloxycarbamoyl-3-nitrobenzene (structure 65 of Scheme XVII, where $R^1$=H, P=t-butyloxycarbonyl, Y=NH). General Method 10. N-Boc-Protection of Nitroanilines To a flame-dried 500 mL r.b. flask containing 3-nitroaniline (structure 64 of Scheme XVII, where $R^1$=H, Y=NH) (20.0 g, 144.8 mmol) in 150 mL THF was added di-tert-butyl dicarbonate (31.60 g, 144.8 mmol, 1.00 equiv/iv), and the mixture was cooled to 0° C. 4-N,N-Dimethylaminopyridine (19.46 g, 159.3 mmol, 1.10 equiv/iv) was added portion-wise, and the mixture was allowed to warm to rt overnight. Ethyl acetate (400 mL) was added, and the mixture was washed with 1M NaHSO$_4$ (aq) (2×200 mL) and brine (200 mL), dried (Na$_2$SO$_4$), and concentrated under reduced pressure. Purification by flash column chromatography (silica gel, hexanes/ethyl acetate, 9:1) afforded 31.4 g (91%) of 1-tert-butyloxycarbamoyl-3-nitrobenzene as a white solid. Data for 1-tert-butyloxycarbamoyl-3-nitrobenzene: $^1$H NMR (400 MHz, CDCl$_3$) 8.31 (dd, 1H, J=2.2, 2.2, 1H, 2-H), 7.88 (dd, J=7.9, 1.5, 1H, 4-H), 7.69 (br d, J~7.8, 1H, 6-H), 7.44 (dd, J=22, 8.1, 1H, 5-H), 6.74 (br s, 1H, NH), 1.54 [s, 9H, (CH$_3$)$_3$CO)].

3-tert-Butyloxycarbamoylaniline (structure 66 of Scheme XVII, where $R^1$=H, P=t-butyloxycarbonyl, Y=NH To an oven-dried 1-L r.b. flask containing 1-tert-butyloxycarbamoyl-3-nitrobenzene (20.0 g, 83.9 mmol) in 500 mL 1:1 ethyl acetate/ethanol at rt was added 10% Pd on C (approx 1 mol %), and the mixture was stirred under an atmosphere of H$_2$ gas for 6 h. The reaction mixture was then filtered, and concentrated under diminished pressure to give 17.4 g (quant of 3-tert-butyloxycarbamoylaniline as a white oily solid. Data for 3-tert-butyloxycarbamoylaniline: $^1$H NMR (400 MHz, CDCl$_3$) 7.04 (t, J=8.0, 8.0, 1H, 5-H), 6.98 (br s, 1H, NH), 6.53 (dd, J=7.9, 1.8, 1H, 4-H), 6.36 (m, 2H, 6,2-H), 3.66 (br s, 2H, NH$_2$), 1.51 [s, 9H, (CH$_3$)$_3$CO)].

7-tert-Butyloxycarbamoyl-1,2-dihydro-2,2,4-trimethylquinoline (structure 67 of Scheme XVII, where $R^1$=H, P=t-butyloxycarbonyl, Y=NH) General Method 11: Skraup Cyclization of tert-Butyloxycarbamoylanilines To an oven-dried 1 L r.b. flask containing 3-tert-butyloxycarbamoylaniline (17.4 g, 83.5 mmol), MgSO$_4$ (50 g, 5 equiv/iv), and 4-tert-butylcatechol (420 mg, 3 mol %) in 120 mL acetone (approx 0.75M in the aniline) was added iodine (1.07 g, 5 mol %), and the mixture was heated to reflux for 8 h. The crude reaction mixture was then cooled to rt, filtered through a bed of Celite™ on a fritted-glass funnel, rinsing with ethyl acetate, dried (Na$_2$SO$_4$), and concentrated under reduced pressure. Purification by flash column chromatography (silica gel, hexanes/ethyl acetate, gradient elution) afforded 19.9 g (82%) of 7-tert-butyloxycarbamoyl-1,2-dihydro-2,2,4-trimethylquinoline as a white solid, which was further purified by recrystallization from acetonitrile to give white needles. Data for 7-tert-butyloxycarbamoyl-1,2-dihydro-2,2,4-trimethylquinoline: $^1$H NMR (400 MHz, CDCl$_3$) 6.93 (d, J=8.3, 1H, 5-H), 6.81 (br s, 1H, HNBoc), 6.34 (m, 2H, 6,8-H), 5.21 (d, J=0.9, 1H, 3-H), 3.71 (br s, 1H, NH), 1.94 (d, J=1.0, 3H, 4-CH$_3$), 1.50 [s, 9H, (CH$_3$)$_3$CO)], 1.24 [s, 6H, 2-(CH$_3$)$_2$].

7-Amino-1,2-dihydro-2,2,4-trimethylquinoline General Method 12: Removal of Boc Protective Group from Compounds of structure 67 of Scheme XVII, where P=t-butyloxycarbonyl, Y=NH)

To an oven-dried 25 mL r.b. flask containing 7-tert-butyloxycarbamoyl-1,2-dihydro-2,2,4-trimethylquinoline (400 mg, 1.38 mmol) in 2 mL dichloromethane at 0° C. was added trifluoroacetic acid (1.06 mL, 10 equiv/iv), and the mixture was allowed to warm to rt. After 3 h at rt, the reaction mixture was diluted with 50 mL dichloromethane, transferring to a 125 mL erlynmeyer flask, and cooled to 0° C. before neutralization to pH 8 with sat'd aqueous NaHCO$_3$. The biphasic mixture was transferred to a separatory funnel, the layers were separated, and the organic phase was dried (Na$_2$SO$_4$), and concentrated under reduced pressure to afford a light reddish oil. The crude material thus obtained was of greater than 98% purity by $^1$H NMR, and was carried on to the next step without further purification. While the 7-amino-quinoline obtained decomposed appreciably within a few hours upon standing at rt, ethanolic solutions could be stored at −20° C. for 2–3 days without substantial adverse effect on the subsequivuent reaction outcome. Typically however, the material was stored in bulk as the crystalline Boc-protected amine, and portions were hydrolysed as needed. Data for 7-amino-1,2-dihydro-2,2,4-trimethylquinoline: $^1$H NMR (400 MHz, CDCl$_3$) 6.86 (d, J=8.2, 1H, 5-H), 5.99 (dd, J=8.0, 2.3, 1H, 6-H), 5.79 (d, J=2.0, 1H, 8-H), 5.12 (d, J=1.4, 1H, 3-H), 3.53 (br s, 3H, NH$_2$, NH), 1.93 (d, J=1.2, 3H, 4-CH$_3$), 1.24 [s, 6H, 2-(CH$_3$)$_2$].

1,2-Dihydro-2,2,4-trimethyl-6-trifluoromethyl-8-pyridono [5,6-g]quinoline (Compound 247, structure 57 of Scheme XVII, where R$^1$=R$^2$=H, R$^3$=trifluoromethyl, Y=NH) General Method 13: Knorr Cyclization of 7-amino-1,2-dihydro-2,2,4-trimethylquinolines with a β-Keto Ester To an oven-dried 10 mL r.b. flask containing 7-amino-1,2-dihydro-2,2,4-trimethylquinoline (100 mg, 0.53 mmol) and ethyl 4,4,4-trifluoroacetoacetate (85.4 mL, 0.58 mmol, 1.1 equivuiv) in 2.5 mL absolute ethanol was added ZnCl$_2$ (110 mg, 0.81 mmol, 1.5 equivuiv) and the mixture was heated to reflux for 3 h. Upon cooling to rt, the reaction mixture was diluted with 40 mL ethyl acetate, and the organic solution was washed with sat'd aqueous NH$_4$Cl, dried (Na$_2$SO$_4$), and concentrated under reduced pressure. Purification by flash column chromatography (silica gel, hexanes/ethyl acetate, gradient elution) afforded 72 mg (44%) of Compound 247 as a bright fluorescent-yellow solid, in addition to 70 mg (40%) of Compound 248 (EXAMPLE 148) as a pale yellow crystalline solid, and 10.4 mg (6%) of Compound 249 (EXAMPLE 149) as a white solid. Data for Compound 247: $^1$H NMR (400 MHz, CDCl$_3$) 11.45 (br s, 1H, CONH), 7.38 (s, 1H, 5-H), 6.66 (s, 1H, 7-H), 6.27 (s, 1H, 10-H), 5.42 (s, 1H, 3-H), 4.35 [br s, 1H, (CH$_3$)$_2$CNH], 2.03 (s, 3H, 4-CH$_3$), 1.33 [s, 6H, 2-(CH$_3$)$_2$].

EXAMPLE 148

8-Ethoxy-1,2-dihydro-2,2,4-trimethyl-6-trifluoromethyl-8-pyrido[5,6-g]quinoline (Compound 248, structure 71 of Scheme XVII, where R$^1$=R$^2$=H, R$^3$=trifluoromethyl, R$^5$=ethyl, Y=N)

This compound was obtained along with Compounds 247 and 249 as described above (EXAMPLE 147). Data for Compound 248: $^1$H NMR (400 MHz, CDCl$_3$) 7.56 (d, 1H, J=1.8, 5-H), 6.84 (s, 1H, 7-H), 6.74 (s, 1H, 10-H), 5.52 (s, 1H, 3-H), 4.47 (q, 2H, J=7.0, CH$_3$CH$_2$O), 4.12 [br s, 1H, (CH$_3$)$_2$CNH], 2.09 (d, 3H, J=1.3, 4-CH$_3$), 1.42 (t, 3H, J=7.0, CH$_3$CH$_2$O), 1.34 [s, 6H, 2-(CH$_3$)$_2$]. This product was readily converted to the 2-quinolone isomer Compound 247 by heating neat with 10 equivuiv p-chlorophenol at 180° C. for 3 h, giving Compound 247 in >80% yield.

EXAMPLE 149

(R,S)-1,2,6,7-Tetrahydro-6-hydroxy-2,2,4-trimethyl-6-trifluoromethyl-8-pyridono[5,6-g]quinoline (Compound 249, structure 69 of Scheme XVII, where R$^1$=R$^2$=H, R$^3$=trifluoromethyl, Y=NH)

This compound was obtained along with Compounds 247 and 248 as described above (EXAMPLE 147). Data for Compound 249: $^1$H NMR (400 MHz, DMSO-d$_6$) 10.16 (s, 1H, CONH), 7.09 (s, 1H, 5-H), 6.61 (s, 1H, OH), 6.24 (s, 1H, 10-H), 6.01 [s, 1H, (CH$_3$)$_2$CNH], 5.21 (s, 1H, 3-H), 2.80 and 2.72 (ABq, 2H, J$_{AB}$=16.4, 7-H), 1.86 (s, 3H, 4-CH$_3$), 1.19 and 1.17 [2s, 2×3H, 2-(CH$_3$)$_2$]. This product was readily converted to the 2-quinolone isomer Compound 247 by heating to 60° C. in benzene or toluene with a catalytic amount of p-TsOH for 2 h, giving Compound 247 in >95% yield.

EXAMPLE 150

(R/S)-1,2,3,4-Tetrahydro-2,2,4-trimethyl-6-trifluoromethyl-8-pyranono[5,6-g]quinoline (Compound 250, structure 63 of Scheme XVIII, where R$^1$=R$^2$=H, R$^3$=trifluoromethyl, Y=O)

(R/S)-1,2,3,4-Tetrahydro-2,2,4-trimethyl-7-(1,1,1-trimethylacetoxy)quinoline (structure 72 of Scheme XVIII, where R$^1$=H, P=t-butyl, Y=O)

In a dry r.b. flask equivuipped with a magnetic stir bar was suspended 1,2-dihydro-2,2,4-trimethyl-7-(1,1,1-trimethylacetoxy)quinoline (structure 67 of Scheme XVIII, where R$^1$=H, P=t-butyl, Y=O; EXAMPLE 138) (1.01 g, 3.37 mmol) and 10% Pd/C (200 mg) in CH$_2$Cl$_2$. The flask was charged with H$_2$ gas and allowed to react for 12 h with constant stirring. The suspension was filtered though a bed of Celite™, washed with EtOAc (2×50 mL) and concentrated in vacuo to afford 996 mg (98%) of (R/S)-1,2,3,4-tetrahydro-2,2,4-trimethyl-7-(1,1,1-trimethylacetoxy) quinoline as a light brownish-red solid. Data for (R/S)-1,2,3,4-tetrahydro-2,2,4-trimethyl-7-(1,1,1-trimethylacetoxy) quinoline: $^1$H NMR (400 MHz, CDCl$_3$) 7.10 (dd, J=8.5, 0.9, 1H), 6.30 (dd, J=8.4, 2.4, 1H), 6.13 (d, J=2.2, 1H), 3.62 (br s, 1H), 2.87 (m, 1H), 1.71 (dd, J=13, 5.4, 1H), 1.41 (apparent t, J=13, 1H), 1.31 (m, 10H), 1.22 (s, 3H), 1.16 (s, 3H).

(R/S)-1,2,3,4-Tetrahydro-7-hydroxy-2,2,4-trimethylquinoline

This compound was prepared as described above for 1,2-dihydro-7-hydroxy-2,2,4-trimethylquinoline (EXAMPLE 138) from (R/S)-1,2,3,4-tetrahydro-2,2,4-trimethyl-7-(1,1,1-trimethylacetoxy)quinoline (230 mg, 0.845 mmol) to afford (R/S)-1,2,3,4-tetrahydro-7-hydroxy-2,2,4-trimethylquinoline, which was used in the following reaction without further purification.

(R/S)-1,2,3,4-Tetrahydro-2,2,4-trimethyl-6-trifluoromethyl-8-pyranono[5,6-g]quinoline (Compound 250, structure 63 of Scheme XVIII, where R$^1$=R$^2$=H, R$^3$=trifluoromethyl, Y=O)

This compound was prepared by General Method 9 (EXAMPLE 238) from crude (R/S)-1,2,3,4-tetrahydro-7-hydroxy-2,2,4-trimethylquinoline and ethyl 4,4,4-trifluoroacetoacetate (310 mg, 1.69 mmol, 2 equivuiv) to afford 160 mg (61% overall) of Compound 250 as a yellow solid. Data for Compound 250: R$_f$ 0.4 (hex/EtOAc, 3:1); $^1$H NMR (400 MHz, CDCl$_3$) 7.41 (s, 1H), 6.37 (s, 1H), 6.33 (s, 1H), 4.46 (s, 1H), 2.92 (m, 1H), 1.80 (dd, J=13, 5.0, 1H), 1.42 (dd, J=13, 13, 1H), 1.38 (d, J=6.0, 3H), 1.31 (s, 3H), 1.25 (s, 3H).

EXAMPLE 151

1,2-Dihydro-2,2,4-trimethyl-6-trifluoromethyl-8-thiopyranono[5,6-g]quinoline (Compound 251, structure 58 of Scheme XVI, where R$^1$=R$^2$=H, R$^3$=trifluoromethyl, Y=O)

In a dry pressure tube equivuipped with a magnetic stir bar was dissolved Compound 238 (EXAMPLE 138) (50 mg, 0.159 mmol) and Lawesson's reagent (320 mg, 0.79 mmol, 5 equivuiv) in 15 mL toluene. The resulting solution was heated at 100° C. for 20 h. The cooled solution was concentrated on Celite™ to give a free flowing powder which was purified by flash column chromotography (silica gel, hexanes/EtOAc, 5:1) to give 40 mg (78%) of Compound 251 as a bright red solid. Data for Compound 251: $R_f$ 0.36 (silica gel, hex/EtOAc, 3:1); $^1$H NMR (400 MHz, acetone-$d_6$) 7.25 (s, 1H,), 4.03 (s, 1H), 6.89 (br s, 1H), 6.53 (s, 1H), 5.62 (s, 1H), 2.77 (d, J=1.1, 3H), 1.39 (s, 6H).

EXAMPLE 152

(R/S)-1,2,3,4-Tetrahydro-2,2,4-trimethyl-6-trifluoromethyl-8-thiopyranonol[5,6-g]quinoline (Compound 252, structure 76 of Scheme XIX, where $R^1=R^2=H$, $R^3$=trifluoromethyl, Y=O)

In a dry pressure tube equivuipped with a magnetic stir bar was dissolved Compound 250 (EXAMPLE 150) (26 mg, 0.0836 mmol) and Lawesson's reagent (60 mg, 0.41 mmol, 5 equivuiv) in 15 mL toluene. The resulting solution was heated at 100° C. for 20 h. The cooled solution was concentrated on Celite™ to give a free flowing powder which was purified by flash column chromotography (silica gel, hexanes/EtOAc, 5:1) to afford 19.2 mg (71%) of Compound 252 as a bright orange solid. Data for Compound 252: Rf 0.37 (silica gel, hex/EtOAc, 3:1); $^1$H NMR (400 MHz, CDCl$_3$) 7.43 (s, 1H), 7.16 (s, 1H), 6.45 (s, 1H), 4.59 (br s, 1H), 2.93 (m, 1H), 1.82 (dd, J=13, 5.1, 1H), 1.45 (app t, J=13, 1H), 1.39 (d, J=6.6, 3H), 1.34 (s, 3H), 1.27 (s, 3H).

EXAMPLE 153

6-Chloro(difluoro)methyl-1,2-dihydro-2,2,4-trimethyl-8-pyranono[5,6-g]quinoline (Compound 253, structure 57 of Scheme XVII, where $R^1=R^2=H$, $R^3$=chlorodifluoromethyl, Y=O)

This compound was prepared by General Method 9 (EXAMPLE 238) from 1,2-dihydro-7-hydroxy-2,2,4-trimethyiquinoline (EXAMPLE 138) (71 mg, 0.37 mmol) and methyl 4-chloro-4,4-difluoroacetoacetate (150 mg, 1.62 mmol, 2.2 equivuiv) to afford 17.6 mg (15%) of Compound 253 as a light yellow solid. Data for Compound 253: $R_f$ 0.35 (hex/EtOAc, 3:1); $^1$H NMR (400 MHz, CDCl$_3$) 7.40 (s, 1H), 6.33 (s, 1H), 6.31 (s, 1H), 5.41 (s, 1H), 4.42 (br s, 1H), 2.02 (s, 3H), 1.36 (s, 6H).

EXAMPLE 154

9-Acetyl-1,2-dihydro-2,2,4-trimethyl-6-trifluoromethyl-8-pyridono[5,6-g]quinoline (Compound 254, structure 59 of Scheme XVI, where $R^1=R^2=H$, $R^3$=trifluoromethyl, $R^4$=acetyl, Y=N)

To an oven-dried 10-mL r.b. flask containing Compound 247 (15 mg, 0.049 mmol) in 1 mL dichloromethane at rt was added acetic anhydride (0.10 mL, xs) and 4-N,N-dimethylaminopyridine (6.5 mg, 0.054 mmol, 1.1 equivuiv), and the mixture was stirred 10 min. Dichloromethane (20 mL) was added, and the solution was washed with 1M pH 7 potassium phosphate buffer, dried (Na$_2$SO$_4$), and concentrated under reduced pressure. Purification by flash column chromatography (silica gel, hexanes/ethyl acetate, gradient elution) afforded 16 mg (92%) of Compound 254 as a yellow oily solid. Data for Compound 254: $^1$H NMR (400 MHz, CDCl$_3$) 7.66 (s, 1H, 5-H), 7.08 (s, 1H, 7-H), 6.83 (s, 1H, 10-H), 5.63 (s 1H, 3-H), 4.31 [br s, 1H, (CH$_3$)$_2$CNH], 2.38 (s, 3H, CH$_3$CON), 2.12 (s, 3H, 4-CH$_3$), 1.48 [s, 6H, 2-(CH$_3$)$_2$)].

EXAMPLE 155

1,2-Dihydro-2,2,4,10-tetramethyl-6-trifluoromethyl-8-pyridono[5,6-g]quinoline (Compound 255, structure 57 of Scheme XVII, where $R^1$=methyl, $R^2$=H, $R^3$=trifluoromethyl, Y=NH) 6-tert-Butyloxycarbamoyl-2-nitrotoluene (structure 65 of Scheme XVII, where $R^1$=methyl, P=t-butyloxycarbonyl, Y=NH)

This intermediate was prepared from 2-methyl-3-nitroaniline (5.00 g, 32.8 mmol) by General Method 10 (EXAMPLE 147), affording 7.44 g (90%) of 6-tert-butyloxycarbamoyl-2-nitrotoluene as an off-white solid. Data for 6-tert-butyloxycarbamoyl-2-nitrotoluene: $^1$H NMR (400 MHz, CDCl$_3$) 7.98 (br d, J=8.0, 1H, 5-H), 7.51 (br d, J=8.1, 1H, 3-H), 7.28 (dd, J=7.6, 3.4, 1H, 4-H), 6.58 (br s, 1H, NH), 2.34 (s, 3H, 1-CH$_3$), 1.53 [s, 9H, (CH$_3$)$_3$CO)].

2-Amino-6-tert-butyloxycarbamoyltoluene (structure 66 of Scheme XVII, where $R^1$=methyl, P=t-butyloxycarbonyl, Y=NH)

This compound was prepared from 6-tert-butyloxycarbamoyl-2-nitrotoluene (4.60 g, 18.2 mmol) in a manner similar to that described for 3-tert-butyloxycarbamoylaniline (EXAMPLE 147), affording 4.00 g (99%) of 2-amino-6-tert-butyloxycarbamoyltoluene as a colorless oil. Data for 2-amino-6-tert-butyloxycarbamoyltoluene: $^1$H NMR (400 MHz, CDCl$_3$) 7.04 (br d of ABq, J$_{AB}$=8.0, J$_A$=0, J$_B$=7.9, 2H, 5,4-H), 6.49 (d, J=8.3, 1H, 3-H), 6.26 (br s, 1H, NH), 3.61 (br s, 2H, NH$_2$), 2.02 (s, 3H, 1-CH$_3$), 1.51 [s, 9H, (CH$_3$)$_3$CO)].

7-tert-Butyloxycarbamoyl-1,2-dihydro-2,2,4,8-tetramethylquinoline (structure 67 of Scheme XVII, where $R^1$=methyl, P=t-butyloxycarbonyl, Y=NH)

This compound was prepared from 2-amino-6-tert-butyloxycarbamoyltoluene (4.00 g, 18.0 mmol) according to General Method 11 (EXAMPLE 147), affording 4.56 g (84%) of 7-tert-butyloxycarbamoyl-1,2-dihydro-2,2,4,8-tetramethylquinoline as a white solid. Data for 7-tert-butyloxycarbamoyl-1,2-dihydro-2,2,4,8-tetramethylquinoline: $^1$H NMR (400 MHz, CDCl$_3$) 6.94 and 6.88 (br ABq, J$_{AB}$=8.3, 2H, 6.5-H), 6.16 (br s, 1H, HNBoc), 5.27 (s, 1H, 3-H), 3.61 (br s, 1H, (CH$_3$)$_2$CNH]) 2.04 (s, 3H, 8-CH$_3$), 1.97 (s, 3H, 4-CH$_3$), 1.50 (s, 9H, (CH$_3$)$_3$CO)]), 1.28 (s, 6H, 2-(CH$_3$)$_2$).

7-Amino-1,2-dihydro-2,2,4,8-tetramethyiquinoline

This compound was prepared by General Method 12 (EXAMPLE 147) from 7-tert-butyloxycarbamoyl-1,2-dihydro-2,2,4,8-tetramethylquinoline (400 mg, 1.32 mmol) affording 267 mg (quant) of 7-amino-1,2-dihydro-2,2,4,8-tetramethylquinoline as a light reddish oil. Data for 7-amino-1,2-dihydro-2,2,4,8-tetramethylquinoline: $^1$H NMR (400 MHz, CDCl$_3$) 6.82 (d, J=8.2, 1H, 5-H), 6.08 (d, J=8.1, 1H, 6-H), 5.15 (d, J=1.2, 1H, 3-H), 3.56 (br s, 3H, NH$_2$, NH), 1.95 (d, J=1.2, 3H, 4-CH$_3$), 1.91 (s, 3H, 8-CH$_3$), 1.27 [s, 6H, 2-(CH$_3$)$_2$].

1,2-Dihydro-2,2,4,10-tetramethyl-6-trifluoromethyl-8-pyridono[5,6-g]quinoline (Compound 255, structure 57 of Scheme XVII, where $R^1$=methyl, $R^2$=H, $R^3$=trifluoromethyl, Y=NH)

This compound was prepared by General Method 13 (EXAMPLE 147) from 7-amino-1,2-dihydro-2,2,4,8-tetramethylquinoline (100 mg, 0.49 mmol) and ethyl 4,4,4-trifluoroacetoacetate (107 mL, 0.73 mmol, 1.5 equivuiv) affording 75 mg (47%) of Compound 255 as a fluorescent-yellow solid. Data for Compound 255: $^1$H NMR (400 MHz, CDCl$_3$) 9.23 (br s, 1H, CONH), 7.37 (s, 1H, 5-H), 6.67 (s, 1H, 7-H), 5.45 (s, 1H, 3-H), 4.14 [br s, 1H, (CH$_3$)$_2$CNH], 2.12 (s, 3H, 10-CH$_3$), 2.04 (d, J=1.1, 3H, 4-CH$_3$), 1.37 [s, 6H, 2-(CH$_3$)$_2$].

EXAMPLE 156

1,2-Dihydro-2,2,4-trimethyl-6-(1,1,2,2,2-pentafluoroethyl)-8-pyranono[5,6-g]quinoline (Compound 256, structure 57 of Scheme XVII, where $R^1=R^2=H$, $R^3$=pentafluoroethyl, Y=O)

This compound was prepared by General Method 9 (EXAMPLE 238) from 1,2-dihydro-7-hydroxy-2,2,4-trimethylquinoline (EXAMPLE 138) (67 mg, 0.35 mmol) and ethyl 4,4,5,5,5-pentafluoropropionylacetate (179 mg, 0.76 mmol, 2.2 equivuiv) to afford 11.8 mg (10%) of Compound 256 as a light yellow solid. Data for Compound 256: $^1$H NMR (400 MHz, CDCl$_3$) 7.31 (s, 1H), 6.35 (s, 1H), 6.33 (s, 1H), 5.40 (s, 1H), 4.54 (s, 1H), 1.99 (d, J=1.1, 3H), 1.35 (s, 6H).

EXAMPLE 157

(R/S)-6-Chloro(difluoro)methyl-1,2,3,4-tetrahydro-2,2,4-trimethyl-8-pyranono[5,6-g]quinoline (Compound 257, structure 63 of Scheme XVIII, where R$^1$=R$^2$=H, R$^3$=chlorodifluoromethyl, Y=O)

This compound was prepared by General Method 9 (EXAMPLE 238) from (R/S)-1,2,3,4-tetrahydro-7-hydroxy-2,2,4-trimethylquinoline (EXAMPLE 150) (57 mg, 0.29 mmol) and methyl 4-chloro-4,4-difluoroacetoacetate (120 mg, 0.645 mmol, 2.2 equivuiv) to afford 35.6 mg (38%) of Compound 257 as a light yellow solid. Data for Compound 257: R$_f$ 0.37 (hex/EtOAc, 3:1); $^1$H NMR (400 MHz, CDCl$_3$) 7.55 (s, 1H), 6.36 (s, 1H), 6.32 (s, 1H), 4.53 (br s, 1H), 2.95 (m, 1H), 1.80 (ddd, J=13, 5.1, 1.5, 1H), 1.45 (apparent t, J=13, 1H), 1.39 (d, J=6.7, 3H), 1.32 (s, 3H), 1.27 (s, 3H).

EXAMPLE 158

7-Chloro-1,2-dihydro-2,2,4-trimethyl-6-trifluoromethyl-8-pyranono[5,6-g]quinoline (Compound 258, structure 57 of Scheme XVII, where R$^1$=H, R$^2$=Cl, R$^3$=trifluoromethyl, Y=O)

This compound was prepared by General Method 9 (EXAMPLE 238) from 1,2-dihydro-7-hydroxy-2,2,4-trimethylquinoline (EXAMPLE 138) (78 mg, 0.41 mmol) and ethyl 2-chloro-4,4,4-trifluoroacetoacetate (195 mg, 0.898 mmol, 2.2 equivuiv) to afford 7.2 mg (6%) of Compound 258 as a red solid. Data for Compound 258: Rf 0.33 (hex/EtOAc, 3:1); $^1$H NMR (400 MHz, CDCl$_3$) 7.37 (s, 1H), 6.32 (s, 1H), 5.42 (s, 1H), 4.54 (br s, 1H), 2.01 (d, J=1.0, 3H), 1.31 (s, 6H).

EXAMPLE 159

(R/S)-7-Chloro-1,2,3,4-tetrahydro-2,2,4-trimethyl-6-trifluoromethyl-8-pyranono[5,6-g]quinoline (Compound 259, structure 63 of Scheme XVIII, where R$^1$=H, R$^2$=Cl, R$^3$=trifluoromethyl, Y=O)

This compound was prepared by General Method 9 (EXAMPLE 238) from (R/S)-1,2,3,4-tetrahydro-7-hydroxy-2,2,4-trimethylquinoline (EXAMPLE 150) (57 mg 0.29 mmol) and ethyl 2-chloro-4,4,4-trifluoroacetoacetate (140 mg, 0.645 mmol, 2.2 equivuiv) to afford 6.8 mg (7%) of Compound 259 as a yellow solid. Data for Compound 259: R$_f$ 0.35 (hex/EtOAc, 3:1); $^1$H NMR (400 MHz, CDCl$_3$) 7.53 (s, 1H), 6.32 (s, 1H), 4.51 (br s, 1H), 2.93 (m, 1H), 1.81 (dd, J=13, 3.7, 1H), 1.44 (apparent t, J=13, 3H), 1.31 (s, 3H), 1.25 (s, 3H).

EXAMPLE 160

(R/S)-1,2,3,4-Tetrahydro-2,2,4-trimethyl-6-trifluoromethyl-8-pyridono[5,6-g]quinoline (Compound 260, structure 63 of Scheme XVIII, where R$^1$=R$^2$=H, R$^3$=trifluoromethyl, Y=NH)
(R/S)-7-tert-Butyloxycarbamoyl-1,2,3,4-tetrahydro-2,2,4-trimethylquinoline (structure 72 of Scheme XVIII, where R$^1$=H, P=t-butyloxycarbonyl, Y=NH)

To an oven-dried 100 mL round-bottomed flask containing 7-tert-butyloxycarbamoyl-1,2-dihydro-2,2,4-trimethylquinoline (EXAMPLE 147) (200 mg, 0.69 mmol) in 50 mL 2:1 ethyl acetate/ethanol at rt was added 10% Pd on C (approx 1 mol %), and the mixture was stirred under an atmosphere of H$_2$ for 4 h. The reaction mixture was then filtered, and concentrated under diminished pressure to give 201 mg (quant) of 7-tert-butyloxycarbamoyl-1,2,3,4-tetrahydro-2,2,4-trimethylquinoline as a white oily solid. Data for (R/S)-7-tert-butyloxycarbamoyl-1,2,3,4-tetrahydro-2,2,4-trimethylquinoline: $^1$H NMR (400 MHz, CDCl$_3$) 7.02 (d, J=8.7, 1H, 5-H), 6.73 (br s, 1H, HNBoc), 6.39 (dd, J=8.3, 2.2, 1H, 6-H), 6.29 (br s, 1H, 8-H), 3.62 (br s, 1H, NH), 2.85 (ddq, J=12.5, 12.3, 6.4, 1H, 4-H), 1.70 and 1.39 [d of ABq, J$_{AB}$=12.8, J$_A$=5.5 Hz (3-H$_{equiv}$), J$_B$=12.6 Hz 3-H$_{ax}$)2H], 1.49 [s, 9H, (CH$_3$)$_3$CO)], 1.29 (d, J=6.7, 3H, 4-CH$_3$), 1.21 (s, 3H, 2-CH$_3$), 1-14 (s, 3H, 2-CH$_3$).

(R/S)-7-Amino-1,2,3,4-tetrahydro-2,2,4-trimethylquinoline

This compound was prepared by General Method 12 (EXAMPLE 147) from 7-tert-butyloxycarbamoyl-1,2,3,4-tetrahydro-2,2,4-trimethylquinoline (150 mg, 0.51 mmol) to afford 98 mg (quant) of (R/S)-7-amino-1,2,3,4-tetrahydro-2,2,4-trimethylquinoline as a light reddish oil. Data for 7-amino-1,2,3,4-tetrahydro-2,2,4-trimethylquinoline: $^1$H NMR (400 MHz, CDCl$_3$) 6.92 (dd, J=8.0, 0.8, 1H, 5-H), 6.02 (dd, J=8.2, 2.3, 1H, 6-H), 5.77 (d, J=2.3, 1H, 8-H), 3.39 (br s, 3H, NH$_2$, NH), 2.81 (ddq, J=12.6, 12.3, 6.4, 1H, 4-H), 1.68 and 1.38 [d of ABq, J$_{AB}$=12.8, J$_A$=5.5 Hz (3-H$_{equiv}$), J$_B$=12.5 Hz (3-H$_{ax}$)2H], 1.26 (d, J=6.7, 3H, 4-CH$_3$), 1.19 (s, 3H, 2-CH$_3$), 1.19 (s, 3H, 2-CH$_3$), 1.14 (s, 3H, 2-CH$_3$).

1,2,3,4-Tetrahydro-2,2,4-trimethyl-6-trifluoromethyl-8-pyridono[5,6-g]quinoline (Compound 260, structure 63 of Scheme XVIII, where R$^1$=R$^2$=H, R$^3$=trifluoromethyl, Y=NH)

This compound was prepared by General Method 13 (EXAMPLE 147) from (R/S)-7-amino-1,2,3,4-tetrahydro-2,2,4-trimethylquinoline (98 mg, 0.51 mmol) and ethyl 4,4,4-trifluoroacetoacetate (82 mL, 0.56 mmol, 1.1 equivuiv) to afford 66 mg (42%) of Compound 260 as a fluorescent-yellow solid. Data for Compound 260: $^1$H NMR (400 MHz, CDCl$_3$) 11.32 (br s, 1H, CONH), 7.50 (s, 1H, 5-H), 6.64 (s, 1H, 7-H), 6.41 (s, 1H, 10-H), 4.55 [br s, 1H, (CH$_3$)$_2$CNH], 2.91 (ddq, J=12.6, 12.4, 6.3, 1H, 4-H), 1.76 and 1.41 [d of ABq, J$_{AB}$=12.8, J$_A$=5.5 Hz (3-H$_{equiv}$), J$_B$=12.4 Hz (3-H$_{ax}$) 2H], 1.37 (d, J=6.8, 3H, 4-CH$_3$), 1.22 (s, 3H, 2-CH$_3$), 1.18 (s, 3H, 2-CH$_3$).

EXAMPLE 161

1,2-Dihydro-2,2,4,9-tetramethyl-6-trifluoromethyl-8-pyridono[5,6-g]quinoline (Compound 261, structure 57 of Scheme XVI, where R$^1$=R$^2$=H, R$^3$=trifluoromethyl, R$^4$=methyl)

To an oven-dried 50-mL r.b. flask containing Compound 247 (500.0 mg, 1.62 mmol) in 5 mL THF at 0° C. was added portion-wise sodium hydride (7 1.4 mg of a 60% dispersion in mineral oil, 1.78 mmol, 1.10 equivuiv). After 30 rain, iodomethane (101 mL, 1.62 mmol, 1.00 equivuiv) was added, and the mixture was allowed to warm to rt, and after 4 h, the reaction mixture was cooled to 0° C., and water (5 mL) was added. The reaction mixture was then diluted with 100 mL ethyl acetate, and the organic solution was washed with 50 mL brine, dried (Na$_2$SO$_4$), and concentrated under reduced pressure. Purification by flash column chromatography (silica gel, hexanes/ethyl acetate, gradient elution) afforded 497 mg (95%) of Compound 261 as a bright fluorescent-yellow solid. Data for Compound 261: $^1$H NMR (400 MHz, CDCl$_3$) 7.41 (d, J=1.7, 1H, 5-H), 6.73 (s, 1H, 7-H), 6.28 (s, 1H, 10-H), 5.42 (s, 1H, 3-H), 4.36 [br s, 1H, (CH$_3$)$_2$CNH], 3.62 (s, 3H, NCH$_3$), 2.04 (d, J=1.2, 3H, 4-CH$_3$), 1.33 [s, 6H, 2-(Ch$_3$)$_2$].

EXAMPLE 162

1,2-Dihydro-2,2,4-trimethyl-8-trifluoromethyl-6-pyridono [5,6-g]quinoline (Compound 262, structure 70 of Scheme XVII, where R$^1$=R$^2$=H, R$^3$=trifluoromethyl, Y=NH)

An alternative procedure for the Knorr reaction combined 7-amino-1,2-dihydro-2,2,4-trimethylquinoline (EXAMPLE 147) (131 mg, 0.70 mmol) and ethyl 4,4,4-trifluoroacetoacetate (154 mL, 1.05 mmol, 1.5 equivuiv) with 0.5 mL polyphosphoric acid (PPA) in a 10-mL r.b. flask and the mixture was heated to 100° C. for 2 h. The cooled reaction mixture was diluted with 140 mL ethyl acetate, and the solution was washed with neutralized to pH 8 with 50 mL sat'd aqueous NaHCO$_3$. The layers were separated, and the organic phase was washed with 50 mL brine, dried (Na$_2$SO$_4$), and concentrated under reduced pressure. Purification by flash column chromatography (silica gel, hexanes/ethyl acetate, gradient elution) afforded 79 mg (37%) of Compound 247 along with 8 mg (4%) of Compound 262 as a fluorescent-yellow solid. Data for Compound 262: $^1$H NMR (400 MHz, CDCl$_3$) 10.50 (br s, 1H, C=CCF$_3$NH), 7.33 (s, 1H, 5-H), 6.62 (s, 1H, 7-H), 6.17 (s, 1H, 10-H), 5.33 (s, 1H, 3-H), 4.21 [br s, 1H, (CH$_3$)$_2$CNH], 2.04 (s, 3H, 4-CH$_3$), 1.36 [s, 6H, 2-(CH$_3$)$_2$].

EXAMPLE 163

6-[Dichloro(ethoxy)methyl]-1,2-dihydro-2,2,4-trimethyl-8-pyranono[5,6-g]quinoline (Compound 263, structure 57 of Scheme XVII, where R$^1$=R$^2$=H, R$^3$=dichloro(ethoxy)methyl, Y=O)

This compound was prepared by General Method 9 (EXAMPLE 238) from 1,2-dihydro-7-hydroxy-2,2,4-trimethylquinoline (EXAMPLE 138) (67 mg, 0.35 mmol) and ethyl 4,4,4-trichloroacetoacetate (179 mg, 0.77 mmol, 2.2 equivuiv) to afford 30 mg (24%) of Compound 263 as a light orange solid. Data for Compound 263: Rf 0.28 (hex/EtOAc, 3:1); $^1$H NMR (400 MHz, CDCl$_3$) 7.97 (s, 1H), 6.51 (s, 1H), 6.32 (s, 1H), 4.42 (q, J=7.2, 2H), 2.92 (m, 1H), 1.79 (dd, J=13, 5.1, 1H), 1.40 (m, 4H), 1.38 (d, J=6.6, 3H), 1.30 (s, 3H), 1.25 (s, 3H).

EXAMPLE 164

5-(3-Furyl)-1,2-dihydro-2,2,4-trimethyl-8-pyranono[5,6-g]quinoline (Compound 264, structure 57 of Scheme XVII, where R$^1$=R$^2$=H, R$^3$=3-furyl, Y=O)

This compound was prepared by General Method 9 (EXAMPLE 238) from 1,2-dihydro-7-hydroxy-2,2,4-trimethylquinoline (EXAMPLE 138) (120 mg, 0.62 mmol) and ethyl β-oxo-3-furanpropionate (227 mg, 1.25 mmol, 2 equivuiv) to afford 6.4 mg (3%) of Compound 264 as a light yellow solid. Data for Compound 264: R$_f$ 0.30 (hex/EtOAc, 3:1); $^1$H NMR (400 MHz, CDCl$_3$) 7.76 (s, 1H), 7.76 (dd, J=3.5, 1.8, 1H), 7.34 (s, 1H), 6.66 (d, J=1.7, 1H), 6.35 (s, 1H), 6.06 (s, 1H), 5.36 (s, 1H), 4.34 (s, 1H), 1.95 (d, J=1.1, 3H), 1.34 (s, 6H).

EXAMPLE 165

1,2-Dihydro-1,2,2,4-tetramethyl-6-trifluoromethyl-8-pyranono[5,6-g]quinoline (Compound 265, structure 60 of Scheme XVI where R$^1$=R$^2$=R$^5$=H R$^3$=trifluoromethyl, Y=O)

In a dry r.b. flask equivuipped with a magnetic stir bar was dissolved Compound 238 (50 mg, 0.162 mmol) and paraformaldehyde (48 mg, 1.62 mmol, 10 equivuiv) in glacial acetic acid (10 mL). To this bright yellow solution was added NaCNBH$_3$ (50 mg, 0.81 mmol, 5 equivuiv). The solution stirred for 18 h under an atmosphere of N$_2$. In a separate flask was prepared a suspension of 100 g ice and 20 mL of 20% NaOH(aq). The reaction mixture was slowly poured over the NaOH solution, extracted with EtOAc (3×50 mL), washed with brine, dried (Na$_2$SO$_4$) and concentrated in vacuo to afford 50.6 mg (97%) of Compound 265 as a bright yellow solid. Data for Compound 265: Rf 0.39 (hex/EtOAc, 3:1); $^1$H NMR (400 MHz, CDCl$_3$) 7.20 (d, J=1.8, 1H), 6.36 (s, 2H), 5.36 (d, J=1.0, 1H), 2.88 (s, 3H), 2.00 (d, J=1.1, 3H), 1.39 (s, 6H).

EXAMPLE 166

1,2-Dihydro-6-trifluoromethyl-2,2,4-trimethyl-9-thiopyran-8-ono[5,6-g]quinoline (Compound 266 structure 57 of Scheme XVII, where R$^1$=R$^2$=H, R$^3$=trifluoromethyl, Y=S)

3-Amino-S-t-butyloxycarbonyl thiophenol structure 66 of Scheme XVII where R$^1$=H, P=t-butyloxycarbonyl, Y=S)

To a solution of 3-aminothiophenol (500 mg, 4.0 mmol) and di-t-butyl dicarbonate (872 mg, 4.0 mmol) in 10 mL of dry dichloromethane at 0° C. was added dropwise, triethylamine (557 mL, 4.0 mmol). When the addition was complete, the reaction was allowed to warm to rt and the resulting mixture was stirred for 16 h. The reaction mixture was concentrated in vacuo and the residue was then diluted with 20 mL of ethyl acetate and washed with water (2×10 mL), dried (Na$_2$SO$_4$) and concentrated in vacuo to an oil that was subjected to flash chromatography (silica gel, hexanes/ethyl acetate, 7:3) which gave 274 mg (30%) of 3-amino-S-t-butyloxycarbonyl thiophenol as a clear oil. Data for 3-amino-S-t-butyloxycarbonyl thiophenol: $^1$H NMR (400 MHz, CDCl$_3$) 7.12 (apparent t, J=8.2, 1H), 6.90 (d, J=8.2, 1H), 6.84 (d, J=2.2, 1H), 6.68 (dd, J=8.2, 2.2, 1H), 3.68 (br s, 2H), 1.56 (s, 9H).

7-t-Butyloxycarbonylthio-1,2-dihydro-2,2,4-trimethylquinoline (structure 67 of Scheme XVII, where R$^1$=H P=t-butyloxycarbonyl, Y=S This compound was prepared by General Method 13 (EXAMPLE 147) from 3-amino-S-t-butyloxycarbonyl thiophenol (274 mg, 1.2 mmol) to afford 148 mg (40%) of 7-t-butyloxycarbonylthio-1,2-dihydro-2,2,4-trimethylquinoline as a yellowish oil. Data for 7-t-butyloxycarbonylthio-1,2-dihydro-2,2,4-trimethylquinoline: $^1$H NMR (400 MHz, CDCl$_3$) 7.02 (d, J=7.9, 1H), 6.74 (dd, J=7.9, 1.6, 1H), 6.57 (d, J=1.6, 1H), 5.31 (s, 1H), 3.73 (br s, 1H), 1.95 (s, 3H), 1.50 (s, 9H), 1.26 (s, 6H).

1,2-Dihydro-6-trifluoromethyl-2,2,4-trimethyl-9-thiopyran-8-ono[5,6-g]quinoline (Compound 266 structure 57 of Scheme XVII where R$^1$=R$^2$=H R$^3$=trifluoromethyl, Y=S)

Trifluoroacetic acid (744 mL, 0.0096 mol) was added all at once via a syringe to a solution of 7-t-butyloxycarbonylthio-1,2-dihydro-2,2,4-trimethylquinoline (0.14 g) in 1 mL of dry dichloromethane at 0° C. After 10 min the ice bath was removed and the mixture was allowed to stir at rt for 45 minutes. It was then cooled to 0° C. and neutralized with sat'd NaHCO$_3$, extracted with dichloromethane (3×10 mL). The combined organic phases were washed with water (10 mL), dried (Na$_2$SO$_4$) and concentrated in vacuo to a crude product (50 mg) that was used directly in the next step. A solution of the crude material obtained above (50 mg) and zinc chloride (100 mg, 0.724 mmol) in 0.5 mL of absolute ethanol was heated in a sealed tube for 16 h at 80° C. The reaction was quenched with sat'd NH₄Cl (2 mL) and extracted with ethyl acetate (2×5 mL), dried (Na₂SO₄) and concentrated in vacuo to an orange solid residue that was subjected to flash chromatography (silica gel, hexanes/ethyl acetate, 7:3), followed by preparative TLC (500 µm, hexanes/ethyl acetate, 7:3) to afford 2.2 mg (3%) of Compound 266 as a yellow oil. Data for Compound 266: ¹H NMR (400 MHz, CDCl₃) 7.54 (s, 1H), 6.62 (s, 1H), 6.43 (s, 1H), 5.44 (s, 1H), 4.32 (br s, 1H), 2.03 (s, 3H), 1.29 (s, 6H).

EXAMPLE 167

1,2-Dihydro-1,2,2,4,9-pentamethyl-6-trifluoromethyl-8-pyridono[5,6-g]quinoline (Compound 267 structure 60 of Scheme XVI, where R¹=R²=R⁵=H, R³=trifluoromethyl, Y=N-methyl)

To a 25-mL r.b. flask containing Compound 247 (EXAMPLE 147) (125.8 mg, 0.41 mmol) in 5 mL DMF at rt was added 200 mg (approx 10 equivuiv) solid KOH. After 30 min, iodomethane (129 ML, 2.04 mmol, 5.0 equivuiv) was then added, and the mixture was allowed to stir at rt overnight. Ethyl acetate (50 mL) was then added, the biphasic mixture was neutralized to pH 6 with sat'd aqueous NH₄Cl, and the layers were separated. The organic phase was washed with brine, dried over Na₂SO₄, and concentrated under reduced pressure. Purification by flash column chromatography (silica gel, hexanes/ethyl acetate, gradient elution) afforded 111 mg (81%) of Compound 267 as a bright fluorescent-yellow solid. Data for Compound 267: ¹H NMR (400 MHz, CDCl₃) 7.37 (s, 1H, 5-H), 6.74 (s, 1H, 7-H), 6.21 (s, 1H, 10-H), 5.38 (s, 1H, 3-H), 3.69 [s, 3H, CONCH₃], 2.94 [s, 3H, (CH₃)₂CNCH₃], 2.03 (s, 3H, 4-CH₃), 1.40 [s, 6H, 2-(CH₃)₂].

EXAMPLE 168

7-Chloro-1,2-dihydro-2,2,4-trimethyl-6-trifluoromethyl-8-pyridono[5,6-g]quinoline (Compound 268, structure 57 of Scheme XVII where R¹=H, R²=Cl, R³=trifluoromethyl, Y=NH)

This compound was prepared by General Method 13 (EXAMPLE 147) from 7-amino-1,2-dihydro-2,2,4-trimethylquinoline (EXAMPLE 147) (64 mg, 0.34 mmol) and ethyl 2-chloro-4,4,4-trifluoroacetoacetate (147 mg, 0.68 mmol, 2.0 equivuiv) to afford 36 mg (31%) of Compound 268 as a fluorescent-yellow solid. Data for Compound 268: ¹H NMR (400 MHz, CDCl₃) 7.52 (s, 1H, 5-H), 6.31 (s, 1H, 10-H), 5.43 (s, 1H, 3-H), 4.47 [br s, 1H, (CH₃)₂CNH], 2.03 (s, 3H, 4-CH₃), 1.33 [s, 6H, 2-(CH₃)₂].

EXAMPLE 169

6-Chloro(difluoro)methyl-1,2-dihydro-2,2,4-trimethyl-8-pyridono[5,6-g]quinoline (Compound 269, structure 57 of Scheme XVII, where R¹=R²=H, R³=chloro(difluoromethyl), Y=NH)

This compound was prepared by General Method 13 (EXAMPLE 147) from 7-amino-1,2-dihydro-2,2,4-trimethylquinoline (EXAMPLE 147) (60 mg, 0.33 mmol) and methyl 4-chloro-4,4-difluoroacetoacetate (92 mg, 0.49 mmol, 1.5 equivuiv) to afford 17 mg (16%) of Compound 269 as a fluorescent-yellow solid. Data for Compound 269: ¹H NMR (400 MHz, CDCl₃) 12.50 (br s, 1H, CONH), 7.52 (s, 1H, 5-H), 6.62 (s, 1H, 7-H), 6.39 (s, 1H, 10-H), 5.42 (s, 1H, 3-H), 4.48 [br s, 1H, (CH₃)₂CNH], 2.04 (d, J=1.0, 3H, 4-CH₃), 1.31 [s, 6H, 2-(CH₃)₂].

EXAMPLE 170

8-Cyano-1,2-dihydro-2,2,4-trimethylindeno[3,2-e]quinoline (Compound 270, structure 16 of Scheme IV, where R²⁻⁴, R⁶=H, R⁵=cyano, X=CH₂)

To a 25-mL r.b. flask equivuipped with a magnetic stir bar were added Compound 117 (104.7 mg, 0.40 mmol), DMF (1.5 mL), pyridine (0.16 mL), and copper (I) cyanide (43.2 mg, 0.48 mmol). A reflux condenser was attached to the flask. The green cloudy mixture was stirred at reflux for 3 hours, and allowed to cool to room temperature. The reaction mixture was diluted with ether (30 mL) which formed a precipitate in the dark solution. The precipitate was gravity filtered through Celite. The filtrate was rinsed three times with ether (20 mL). The isolated solution was added to a separatory funnel. The organic layer was washed with 2:1 mixture of water and ammonium hydroxide (20 mL) followed by saturated ammonium chloride solution (2×20 mL) and saturated sodium bicarbonate (20 mL). The aqueous layers were extracted with ether (3×10 mL). The organic layers were combined, dried (Na₂SO₄), and concentrated. The product was purified by flash column chromatography (75 mL silica, hexane) to afford 30 mg (26%) of Compound 270. Data for Compound 270: ¹H NMR (400 MHz, acetone-d₆) 7.77 (d, J=7.9, 1H), 7.72 (s, 1H), 7.61 (m, 2H), 6.72 (s, 1H), 5.54 (s, 1H), 5.39 (s, 1H), 3.79 (s, 2H), 2.08 (s, 3H), 1.29 (s, 6H).

EXAMPLE 171

6-(3-Cyano-5-fluorophenyl)-1,2-dihydro-2,2,4-trimethylquinoline (Compound 271, structure 4 of Scheme II where R¹=3-cyano-5-fluorophenyl)

3-Bromo-5-fluorobenzonitrile

To a 1 liter r.b. flask equivuipped with a magnetic stir bar, commercially available 1,3-dibromo-5-fluorobenzene (44.0 g, 173.3 mmol), DMF (268 mL), pyridine (28.0 mL), and copper (I) cyanide (15.5 g, 173.3 mmol) were added under nitrogen. A reflux condenser was attached to the flask. The green cloudy mixture was stirred at reflux for 3 h. The reaction progress was difficult to monitor by TLC, so once lower Rf impurities were observed the reaction was allowed to cool to rt. The reaction mixture was quenched with 200 mL ether which formed a precipitate in the dark solution. The precipitate was gravity filtered through Celite. The filtrate was rinsed three times with ether (100 mL). The isolated solution was added to a separatory funnel. The organic layer was washed with 2 to 1 mixture of water and ammonium hydroxide (200 mL) followed by saturated ammonium chloride solution (2×200 mL) and saturated sodium bicarbonate (200 mL). The aqueous layers were extracted with ether (3×100 mL). The organic layers were combined and dried (Na₂SO₄). The product, 3-bromo-5-fluorobenzonitrile, was purified by flash column chromatography (300 mL silica, hexane) followed by re, crystallization from hexane to afford 22.3 g (65%) of the product as white crystals. Data for 3-bromo-5-fluorobenzonitrile: ¹H NMR (400 MHz, acetone-d₆) 7.81 (s, 1H), 7.73 (dd, J=8.4, 1.9, 1H), 7.65 (dd, J=8.5, 2.0, 1H).

6-(3-Cyano-5-fluorophenyl)-1,2-dihydro-2,2,4-trimethylquinoline (Compound 271, structure 4 of Scheme II, where R¹=3-cyano-5-fluorophenyl)

This compound was prepared according to General Method 2 (EXAMPLE 9) from Compound 9 (46.3 mg, 0.14 mmol) and 3-bromo-5-fluorobenzonitrile (29.1 mg, 0.14 mmol). The crude material was purified by recrystallization from hexane to afford 15.8 mg (37%) of Compound 271. Data for Compound 271: ¹H NMR (400 MHz, acetone-d₆) 7.83 (app t, J=1.3, 1H), 7.68 (dd, J=10.6, 4.0, 1H), 7.43 (d, J=2.0, 1H), 7.41 (dd, J=2.2, 1.2 1H) 7.35 (dd, J=8.3, 2.2, 1H), 6.59 (d, J=8.4, 1H), 5.35 (br s, 1H), 5.39 (s, 1H), 2.04 (s, 3H), 1.28 (s, 6H).

EXAMPLE 172

6-(3-Cyano-4-fluorophenyl)-1,2-dihydro-2,2,4-trimethylquinoline (Compound 272, structure 4 of Scheme II, where R¹=3-cyano-4-fluorophenyl)

This compound was prepared according to General Method 2 (EXAMPLE 9) from Compound 9 (53.8 mg, 0.17 mmoles) and 3-bromo-6-fluoro-benzonitrile (33.9 mg, 0.17 mmol). The crude material was purified by HPLC (reverse phase ODS column, 85% methanol/water, 3.0 mL/min) to afford 3.3 mg (7%) of Compound 272. Data for Compound 272: $^1$H NMR (400 MHz, acetone-d$_6$) 7.97 (dd, J=6.1, 2.2, 1H), 7.93 (m, 1H), 7.39 (t, J=17.9, 9.0, 1H), 7.35 (d, J=1.5, 1H), 7.27 (dd, J=8.3, 1.9, 1H), 6.58 (d, J=8.3, 1H), 5.38 (s, 1H), 5.34 (s, 1H), 2.08 (s, 3H), 1.28 (s, 6H).

EXAMPLE 173

6-(3-Cyano-6-fluorophenyl)-1,2-dihydro-2,2,4-trimethylquinoline (Compound 273, structure 4 of Scheme II, where R$^1$=3-cyano-6-fluorophenyl)

This compound was prepared according to General Method 2 (EXAMPLE 9) from Compound 9 (70.0 mg, 0.22 mmol) and 3-bromo-4-fluorobenzonitrile (44.1 mg, 0.22 mmol). The crude material was purified by HPLC (reverse phase ODS column, 85% methanol/water, 3.0 mL/min) to afford 3.3 mg (5%) of Compound 273. Data for Compound 273: $^1$H NMR (400 MHz, acetone-d$_6$) 7.90 (dd, J=7.5, 2.1, 1H), 7.67 (m, 1H), 7.36 (dd, J=10.9, 8.5, 1H), 7.28 (s, 1H), 7.21 (m, 1H), 6.58 (d, J=8.2, 1H), 5.48 (s, 1H), 5.37 (s, 1H), 2.04 (s, 3H), 1.29 (s, 6H).

EXAMPLE 174

6-[5-fluoro-3-(trifluoromethyl)phenyl]-1,2-dihydro-2,2,4-trimethylquinoline (Compound 274, structure 4 of Scheme II, where R$^1$=5-fluoro-3-(trifluoromethyl)phenyl)

This compound was prepared according to General Method 2 (EXAMPLE 9) from Compound 9 (42.8 mg, 0.13 mmol) and 3-bromo-5-fluorobenzotrifluoride (32.7 mg, 0.13 mmol). The crude material was purified by HPLC (reverse phase ODS column, 90% methanol/water, 3.0 mL/min) to afford 3.1 mg (7%) of Compound 274. Data for Compound 274: $^1$H NMR (400 MHz, acetone-d$_6$) 7.71 (s, 1H), 7.63 (d, J=10.5, 1H), 7.40 (d, J=2.2, 1H), 7.34 (dd, J=8.1, 2.0, 1H), 7.29 (d, J=8.6, 1H), 6.59 (d, J=8.3, 1H), 5.50 (s, 1H), 5.39 (s, 1H), 2.05 (s, 3H), 1.29 (s, 6H).

EXAMPLE 175

6-(3-chloro-2-methylphenyl)-1,2-dihydro-2,2,4-trimethylquinoline (Compound 275, structure 4 of Scheme II, where R$^1$=3-chloro-2-methylphenyl)

This compound was prepared according to General Method 2 (EXAMPLE 9) from Compound 9 (70.0 mg, 0.22 mmol) and 2-bromo-6-chlorotoluene (45.2 mg, 0.22 mmol). The crude material was purified by flash column chromatography (75 ml silica, hexane to 5% ethyl acetate/hexane) to afford 63.1 mg (96%) of Compound 275. Data for Compound 275: $^1$H NMR (400 MHz, acetone-d$_6$) 7.30 (d, J=8.3, 1H), 7.16 (m, 1H), 6.95 (s, 1H), 6.87 (d, J=10.2, 1H), 6.54 (d, J=8.0, 1H), 5.36 (s, 1H), 5.25 (s, 1H), 2.03 (s, 3H), 1.28 (s, 6H).

EXAMPLE 176

1,2-Dihydro-2,2,4-trimethyl-6-(3-nitrophenyl)quinoline (Compound 276, structure 4 of Scheme II, where R$^1$=3-nitrophenyl)

This compound was prepared according to General Method 2 (EXAMPLE 9) from Compound 9 (19.4 mg, 0.06 mmol) and 3-nitrobromobenzene (12.3 mg, 0.06 mmol). The crude material was purified by flash column chromatography (75 ml silica, hexane to 5% ethyl acetate/hexane) followed by reverse phase flash column chromatography (50 mL ODS, 80% methanol/water) to afford 2.9 mg (16%) of Compound 276. Data for Compound 276: $^1$H NMR (400 MHz, acetone-d$_6$) 8.35 (app t, J=4.1, 2.0, 1H), 8.05 (d, J=8.0, 1H), 8.01 (dd, J=8.1, 6.5, 1H), 7.64 (t, J=15.9, 8.0, 1H), 7.40 (d, J=2.1, 1H), 7.34 (dd, J=8.4, 2.3, 1H), 6.61 (d, J=8.4, 1H), 5.40 (d, J=1.4, 1H), 2.05 (s, 3H), 1.29 (s, 6H).

EXAMPLE 177

6-(3-Acetylphenyl)-1,2-dihydro-2,2,4-trimethylquinoline (Compound 277, structure 4 of Scheme II, where R$^1$=3-acetyphenyl)

This compound was prepared according to General Method 2 (EXAMPLE 9) from Compound 9 (66.2 mg, 0.21 mmol) and 3-bromoacetophenone (41.4 mg, 0.21 mmol). The crude material was purified by flash column chromatography (30 ml silica, hexane to 20% acetone/hexane) followed by reverse phase flash column chromatography (50 mL ODS, 70% methanol/water) and a second normal phase flash column chromatography (30 mL silica, hexane to 20% acetone/hexane) to afford 5.0 mg (8%) of Compound 277. Data for Compound 277: $^1$H NMR (400 MHz, acetone-d$_6$) 8.13 (s, 1H), 7.81 (m, 1H), 7.50 (t, J=15.0, 7.8, 1H), 7.33 (m, 2H), 6.59(d, J=8.1, 1H), 5.38 (s, 1H), 5.32 (s, 1H), 2.62 (s, 3H), 2.08 (s, 3H), 1.28 (s, 6H).

EXAMPLE 178

6-(3-cyano-2-methylphenyl)-1,2-dihydro-2,2,4-trimethylquinoline (Compound 278, structure 4 of Scheme II, where R$^1$=3-cyano-2-methylphenyl)

3-Bromo-2-methylbenzonitrile.

This compound was prepared in a manner similar to that described for 3-bromo-5-fluorobenzonitrile from commercially available 2,6-dibromotoluene (1.80 g, 7.20 mmol), DMF (11 mL), pyridine (1.1 mL), and copper (I) cyanide (0.52 g, 5.76 mmol). The crude product was purified by flash column chromatography (100 mL silica, hexane) to afford 50 mg (35%) of 3-bromo-2-methylbenzonitrile. Data for 3-bromo-2-methylbenzonitrile: $^1$H NMR (400 MHz, acetone-d$_6$) 7.88 (d, J=8.0, 1H), 7.73 (d, J=8.0, 1H), 7.32 (t, J=15.8, 7.9, 1H), 2.58 (s, 3H).

6-(3-cyano-2-methylphenyl)-1,2-dihydro-2,2,4-trimethylquinoline (Compound 278, structure 4 of Scheme II, where R$^1$=3-cyano-2-methylphenyl).

This compound was prepared according to General Method 2 (EXAMPLE 9) from Compound 9 (56.5 mg, 0.18 mmol) and 3-bromo-2-methylbenzonitrile (34.8 mg, 0.18 mmol). The crude material was purified by flash column chromatography (50 ml silica, hexane to 20% acetone/hexane) followed by a second flash column chromatography (75 mL silica, hexane to 20% acetone/hexane) to afford 10.5 mg (20%) of Compound 278. Data for Compound 278: $^1$H NMR (400 MHz, acetone-d$_6$) 7.59 (dd, J=7.7, 0.9, 1H), 7.48 (dd, J=7.8, 0.8, 1H), 7.36 (t, J=15.3, 7.7, 1H), 6.99 (d, J=1.8, 1H), 6.91 (dd, J=8.1, 1.9, 1H), 6.58 (d, J=8.1, 1H), 5.37 (s, 1H), 5.30 (s, 1H), 2.48 (s, 3H), 1.97 (s, 3H), 1.30 (s, 6H).

EXAMPLE 179

1,2-Dihydro-2,2,4-trimethyl-6-(3-methylphenyl)quinoline (Compound 279, structure 4 of Scheme II, where R$^1$=3-methylphenyl)

This compound was prepared according to General Method 2 (EXAMPLE 9) from Compound 9 (99.5 mg, 0.31 mmol) and 3-bromotoluene (53.5 mg, 0.31 mmoles). The crude material was purified by HPLC (reverse phase, ODS column, 80% methanol/water, 3.0 mL/min.) to afford 2.7 mg (3%) of Compound 279. Data for Compound 279: $^1$H NMR (400 MHz, acetone-$d_6$) 7.37 (s, 1H), 7.32 (d, J=7.9, 1H), 7.28 (d, J=2.0, 1H), 7.21 (m, 2H), 7.02 (d, J=7.3, 1H), 6.55 (d, J=8.3, 1H), 5.36 (s, 1H), 5.22 (s, 1H), 2.34 (s, 3H), 2.03 (s, 3H), 1.27 (s, 6H).

EXAMPLE 180

6-(5-Fluoro-3-nitrophenyl)-1,2-dihydro-2,2,4-trimethylquinoline (Compound 280, structure 4 of Scheme II, where $R^1$=5-fluoro-3-nitrophenyl)

1-Fluoro-3-nitroiodobenzene

To a 25 mL round-bottom flask equivuipped with a magnetic stir bar 3-iodo-5-nitroaniline (543.3 mg, 2.06 mmol) and methylene chloride (10 mL) were added under nitrogen. Nitrogen was bubbled through the colorless solution for 15 min. The solution was cooled to 0° C. in an ice bath. At that point approximately 500 mg nitrosonium tetrafluoroborate was added in one portion making a cloudy precipitate. The reaction was allowed to continue stirring for 2 hours. The mixture was kept under nitrogen as 10 mL dry, deoxygenated ortho-dichlorobenzene was added. A distillation apparatus was fitted to the reaction flask. The flask was placed in an oil bath and was heated until the material had completely distilled over. The crude product was isolated by washing the residue through a short column (74 mL silica, hexane). Purification by silica gel chromatography (74 mL silica, hexane) afforded 279.4 mg (50%) of 5-fluoro-3-nitroiodobenzene. Data for 5-fluoro-3-nitroiodobenzene: $^1$H NMR (400 MHz, acetone-$d_6$) 8.36 (s, 1H), 8.00 (m, 2H).

6-(5-Fluoro-3-nitrophenyl)-1,2-dihydro-2,2,4-trimethylquinoline (Compound 280, structure 4 of Scheme II, where $R^1$=5-fluoro-3-nitrophenyl)

This compound was prepared according to General Method 2 (EXAMPLE 9) from Compound 9 (140.2 mg, 0.44 mmol) and 5-fluoro-3-nitroiodobenzene (117.6 mg, 0.44 mmol). The crude material was purified by flash column chromatography (150 ml silica, hexane to 20% acetone/hexane) followed by a second flash column chromatography (100 mL silica, hexane to 20% acetone/hexane) to afford 95 mg (69%) of Compound 280. Data for Compound 280: $^1$H NMR (400 MHz, acetone-$d_6$) 8.22 (app t, J=3.0, 1.5, 1H), 7.78 (m, 1H), 7.43 (d, J=2.2, 1H), 7.38 (dd, J=8.4, 2.3, 1H), 6.61 (d, J=8.3, 1H), 5.58 (s, 1H), 5.40 (s, 1H), 2.05 (s, 3H), 1.29 (s, 6H).

EXAMPLE 181

1,2-Dihydro-6-(3-methoxyphenyl)-2,2,4-trimethylquinoline (Compound 281, structure 4 of Scheme II, where $R^1$=3-methoxyphenyl)

This compound was prepared according to General Method 2 (EXAMPLE 9) from Compound 9 (79.1 mg, 0.25 mmol) and 3-bromoanisole (46.5 mg, 0.25 mmol). The crude material was purified by flash column chromatography (75 mL silica, hexane to 10% ethyl acetate/hexane) to afford 2.1 mg (3%) of Compound 281. Data for Compound 281: $^1$H NMR (400 MHz, acetone-$d_6$) 7.25 (m, 2H), 7.11 (d, J=6.9, 1H), 7.07 (app t, J=4.1, 2.2, 1H), 6.78 (dd, J=8.6, 2.2, 1H), 6.55 (d, J=8.3, 1H), 5.36 (s, 1H), 5.26 (s, 1H), 3.82 (s, 3H), 2.03 (s, 3H), 1.27 (s, 6H).

EXAMPLE 182

6-(5-Cyano-3-pyridyl)-1,2-dihydro-2,2,4-trimethylquinoline (Compound 282, structure 4 of Scheme II, where $R^1$=5-cyano-3-pyridyl)

This compound was prepared according to General Method 2 (EXAMPLE 9) from Compound 9 (45.6 mg, 0.14 mmol) and 3-cyano-5-bromopyridine (26.2 mg, 0.14 mmol). The crude material was purified by flash column chromatography (100 mL silica, hexane) to afford 10.4 mg (26%) of Compound 282. Data for Compound 282: $^1$H NMR (400 MHz, acetone-$d_6$) 8.21 (d, J=1.7, 1H), 7.79 (m, 2H), 7.44 (d, J=2.1, 1H), 7.39 (dd, J=8.4, 2.3, 1H), 6.61 (d, J=8.2, 1H), 5.59 (s, 1H), 5.40 (s, 1H), 2.05 (s, 3H), 1.29 (s, 6H).

EXAMPLE 183

1,2-Dihydro-2,2,4-trimethyl-6-(2-methyl-3-nitrophenyl)quinoline (Compound 283, structure 4 of Scheme II, where $R^1$=2-methyl-3-nitrophenyl)

This compound was prepared according to General Method 2 (EXAMPLE 9) from Compound 9 (170.6 mg, 0.54 mmol) and 2-bromo-6-nitrotoluene (115.8 mg, 0.54 mmol). The crude material was purified by flash column chromatography (80 ml silica, hexane to 20% acetone/hexane) followed by a second flash column chromatography (75 mL silica, hexane to 20% acetone/hexane) to afford 68 mg (41%) of Compound 283. Data for Compound 283: $^1$H NMR (400 MHz, acetone-$d_6$) 7.71 (d, J=7.9, 1H), 7.49 (dd, J=7.4, 0.9, 1H), 7.41 (t, J=15.6, 7.9, 1H), 6.99 (d, J=1.8, 1H), 6.91 (dd, J=8.1, 1.9, 1H), 6.57 (d, J=8.2, 1H), 5.37 (s, 1H), 5.32 (s, 1H), 2.35 (s, 3H), 1.97 (s, 3H), 1.29 (s, 6H).

EXAMPLE 184

6-(2-Amino-3,5-difluorophenyl)-1,2-dihydro-2,2,4-trimethylquinoline (Compound 284, structure 4 of Scheme II, where $R^1$=2-amino-3,5-difluorophenyl)

This compound was prepared according to General Method 2 (EXAMPLE 9) from Compound 9 (48.8 mg, 0.15 mmol) and 2-bromo-4,6-difluoroaniline (31.9 mg, 0.15 mmol). The crude material was purified by flash column chromatography (ODS reverse phase, 80% methanol/water) to afford 15 mg (33%) of Compound 284. Data for Compound 284: $^1$H NMR (400 MHz, acetone-$d_6$) 7.10 (d, J=2.0, 1H), 7.02 (dd, J=8.1, 2.0, 1H), 6.80 (m, 1H), 6.69 (m, 1H), 6.56 (d, J=8.1, 1H), 5.36 (s, 1H), 5.34 (s, 1H), 4.22 (br s, 2H), 1.97 (s, 3H), 1.28 (s, 6H).

EXAMPLE 185

6-(3-Bromo-2-chloro-5-fluorophenyl)-1,2-dihydro-2,2,4-trimethylquinoline (Compound 285, structure 4 of Scheme II, where $R^1$=3-bromo-2-chloro-5-fluorophenyl)

This compound was prepared according to General Method 2 (EXAMPLE 9) from Compound 9 (143.3 mg, 0.45 mmol) and 1-chloro-2,6-dibromo-4-fluorobenzene (129.9 mg, 0.45 mmol). The crude material was purified by flash column chromatography (50 mL silica, hexane) followed by reverse phase preparatory TLC (1000 mL ODS, 80% methanol/water) to afford 4.3 mg (3%) of Compound 285. Data for Compound 285: $^1$H NMR (400 MHz, acetone-$d_6$) 7.50 (dd, J=7.8, 3.0, 1H), 7.19 (dd, J=9.2, 3.0, 1H), 7.10 (d, J=2.0, 1H), 7.03 (dd, J=8.1, 2.0, 1H), 6.55 (d, J=8.3, 1H), 5.61 (s, 1H), 5.37 (s, 1H), 1.97 (s, 3H), 1.29 (s, 6H).

EXAMPLE 186

6-(3-Cyano-5-fluorophenyl)-1,2-dihydro-2,2,4-trimethyl-3-quinolone (Compound 286, structure 79 of Scheme XX, where $R^1$=$R^3$=$R^5$=H, $R^2$=cyano, $R^4$=fluoro, P=t-butoxycarbonyl)

In a 100 mL r.b. flask, a solution of 1,2-dihydro-6-(3-cyano-5-fluorophenyl)-2,2,4-trimethyl-1-t-butoxycarbonylquinoline (structure 77 of Scheme XX, where $R^1$=$R^3$=$R^5$=H, $R^2$=cyano, $R^4$=fluoro, P=t- butoxycarbonyl, an intermediate from EXAMPLE 171) (134.8 mg, 0.34 mmol) in THF (17.2 mL) was treated with a 1.0M THF solution of BH$_3$-THF (1.29 mL, 1.3 mmol, 3.9 equivuiv). The reaction mixture was stirred for 20 min, then poured into a cold (0° C.) 10M solution of NaOH (50 mL), ether (50 mL), and 30% hydrogen peroxide (10 mL). The reaction mixture was stirred overnight (16 h). The reaction mixture was extracted with ether (3×20 mL). The extracts were combined, dried (Na$_2$SO$_4$), and concentrated. The crude material was dissolved in CH$_2$Cl$_2$ (2 mL) and treated with PCC (50 mg). The reaction mixture was stirred for 1 h, filtered through a pad of Celite, and concentrated. Purification by flash column chromatography (175 mL silica, hexane) afforded 1.3 mg (1%) of Compound 286 as a white solid. Data for Compound 286: $^1$H NMR (400 MHz, acetone-d$_6$) 7.90 (s, 1H), 7.75 (d, J=10.6, 1H), 7.54 (m, 2H), 7.48 (d, J=8.3, 1H), 6.95 (d, J=8.2, 1H), 5.52 (s, 1H), 3.61 (m, 1H), 1.49 (d, J=7.05, 3H), 1.33 (s, 3H), 1.23 (s, 3H).

EXAMPLE 187

6-(3-Fluoro-2-methylphenyl)-1,2-dihydro-2,2,4-trimethylquinoline (Compound 287, structure 4 of Scheme II, where R$^1$=3-fluoro-2-methylphenyl)

This compound was prepared by General Method 2 (EXAMPLE 9) from Compound 9 (50 mg, 0.158 mmol) and 2-bromo-6-fluorotoluene (60 mg, 0.315 mmol). Purification by flash chromatography on silica gel (20 g) using 5% EtOAc:hexanes afforded 6 mg (14%) of Compound 287 as a yellow oil. Data for Compound 287: $^1$H NMR (400 MHz, acetone-d$_6$) 7.20 (m, 1H), 7.02 (m, 1H), 6.98 (m, 2H), 6.91 (m, 1H), 6.56 (d, J=8.0, 1H), 5.37 (s, 1H), 5.29 (br s, 1H), 2.19 (s, 3H), 1.98 (s, 3H), 1.28 (s, 6H).

EXAMPLE 188

1,2-Dihydro-2,2,4-trimethyl-6-(3-methylthiophenyl)quinoline (Compound 288, structure 4 of Scheme II, where R$^1$=3-methylthiophenyl)

This compound was prepared by General Method 2 (EXAMPLE 9) from Compound 9 (50 mg, 0.158 mmol) and 3-bromothioanisole (64 mg, 0.315 mmol). Purification by flash chromatography on silica gel (20 g) using 5% EtOAc:hexanes afforded 7 mg (15%) of Compound 288 as a yellow oil. Data for Compound 288: $^1$H NMR (400 MHz, acetone-d$_6$) 7.43 (s, 1H), 7.32 (m, 3H), 7.24 (m, 2H), 7.14 (m, 1H), 6.57 (d, J=8.1, 1H), 5.37 (s, 1H), 5.31 (br s, 1H), 2.53 (s, 3H), 1.28 (s, 6H).

EXAMPLE 189

6-(5-Chloro-2-thienyl)-1,2-dihydro-2,2,4-trimethylquinoline (Compound 289, structure 4 of Scheme II, where R$^1$=5-chloro-2-thienyl)

This compound was prepared by General Method 2 (EXAMPLE 9) from Compound 9 (50 mg, 0.158 mmol) and 2-bromo-5-chlorothiophene (63 mg, 0.315 mmol). Purification by flash chromatography on silica gel (20 g) using 5% EtOAc:hexanes afforded 10 mg (22%) of Compound 289 as a yellow oil. Data for Compound 289: $^1$H NMR (400 MHz, acetone-d$_6$) 7.21 (d, J=2.1, 1H), 7.1 (dd, J=8.1, 2.0, 1H), 7.02 (d, J=3.7, 1H), 6.93 (d, J=3.7, 1H), 6.51 (d, 8.3, 1H), 5.42 (br s, 1H), 5.40 (s, 1H), 2.01 (s, 3H), 1.27 (s, 6H).

EXAMPLE 190

1,2-Dihydro-2,2,4-trimethyl-6-(3-methyl-2-thienyl)quinoline (Compound 290, structure 4 of Scheme II, where R$^1$=3-methyl-2-thienyl)

This compound was prepared by General Method 2 (EXAMPLE 9) from Compound 9 (50 mg, 0.158 mmol) and 2-bromo-3-methylthiophene (57 mg, 0.315 mmol). Purification by flash chromatography on silica gel (20 g) using 5% EtOAc:hexanes afforded 5 mg (12%) of Compound 290 as a yellow oil. Data for Compound 290: $^1$H NMR (400 MHz, acetone-d$_6$) 7.18 (d, J=5.2, 1H), 7.09 (d, J=1.9, 1H), 7.03 (dd, J=8.1, 2.0, 1H), 6.88 (d, 5.1, 1H), 6.54 (d, J=8.1, 1H), 5.38 (s, 1H), 5.32 (br s, 1H), 2.26 (s, 3H), 1.99 (s, 3H), 1.29 (s, 6H).

EXAMPLE 191

8-Fluoro-1,2-dihydro-2,2,4-trimethyl-6-(3-nitrophenyl)quinoline (Compound 291, structure 83 of Scheme XXI, where R$^1$=R$^{3-7}$=R$^9$=H, R$^8$=F)

4-Amino-3-fluoro-3'-nitrobiphenyl (structure 82 of Scheme XXI, where R$^1$=R$^{3-7}$=H, R$^8$=F) General Method 14: Suzuki Coupling of a 4-Bromoaniline with an Arylboronic Acid.

A mixture of 3-nitrobenzeneboronic acid (0.70 g, 4.2 mmol), 4-bromo-2-fluoroaniline (730 mg, 4.0 mmol), (PPh$_3$)$_4$Pd (93 mg, 0.08 mmol), and K$_2$CO$_3$ (0.69 g, 5.0 mmol) in toluene (20 mL) and water (2 mL) was heated at 95° C. for 16 h and the mixture was diluted with EtOAc (20 mL). The mixture was washed with water (10 mL) and brine (10 mL), concentrated and purified by silica gel chromatography to afford the 4-amino-3-fluoro-3'-nitrobiphenyl (structure 82 of Scheme XXI, where R$^1$=R$^{3-7}$=H, R$^8$=F) (0.4 g, 41%) as a yellow solid.

8-Fluoro-1,2-dihydro-2,2,4-trimethyl-6-(3-nitrophenyl)quinoline (Compound 291, structure 83 of Scheme XXI, where R$^1$=R$^{3-7}$=R$^9$=H, R$^8$=F).

This compound was prepared by General Method 8 (EXAMPLE 138) from 4-amino-3-fluoro-3'-nitrobiphenyl (0.4 g, 1.7 mmol) to afford 101 mg (19%) of Compound 291 as a red solid, in addition to 0.8 g of the starting aminobiphenyl. Data for Compound 291: IR (neat) 3400, 2968, 1531, 1506, 1346; $^1$H NMR (400 MHz, CDCl$_3$) 8.35 (t, J=2.0, 1H), 8.10 (dd, J=7.8, 2.0, 1H), 7.80 (d, J=7.8, 1H), 7.54 (t, J=7.8, 1H), 7.14 (d, J=11.7, 1H), 7.11 (d, J=1.8, 1H), 5.43 (s, 1H), 4.07 (bs, 1H), 2.07 (s, 3H), 1.35 (s, 6H); $^{13}$C NMR (100 MHz, CDCl$_3$) 150.4 (d, J=237), 149.0, 142.6, 132.2, 132.1, 130.0, 129.8, 128.0, 126.2 (d, J=7.0), 124.0, 121.2, 121.1, 117.8, 113.0 (d, J=20), 52.1, 31.7, 19.1.

EXAMPLE 192

1,2-Dihydro-6-(3-nitrophenyl)-2,2,4,8-tetramethylquinoline (Compound 292, structure 86 of Scheme XXII, where R$^1$=R$^{3-5}$=H, R$^2$=nitro)

4-Bromo-2-methylaniline (5.58 g, 30 mmol) was treated with iodine (0.2 g, 0.9 mmol) and acetone (150 mL) in a sealed tube at 80° C. for 24 h to provide 6-bromo-1,2-dihydro-8-methylquinoline (Compound 85 of Scheme XXII) in 9% yield as a yellow oil (0.70 g). Most of the aniline (>80%) was recovered. A mixture of the 6-bromo-1,2-dihydro-8-methylquinoline (90 mg, 0.33 mmol), 3-nitrobenzeneboronic acid (167 mg, 1.0 mmol), Pd(PPh$_3$)$_4$ (24 mg, 0.02 mmol), K$_2$CO$_3$ (190 mg, 1.38 mmol) in toluene (7 mL) and water (1.5 mL) was heated at 70° C. for 16 h. Standard work-up followed by chromatography afforded 23 mg (23%) of Compound 292 as a yellow oil. Data for Compound 292: IR (neat) 3412, 2966, 1602, 1530, 1348; $^1$H NMR (400 MHz, CDCl$_3$) 8.38 (t, J=2.0, 1H), 8.08 (dd, J=7.8 and 2.0, 1H), 7.85 (d, J=7.8, 1H), 7.52 (t, J=7.8, 1H), 7.24 (d, J=11.7, 1H), 7.21 (d, J=1.9, 1H), 5.39 (s, 1H), 3.72 (bs, 1H), 2.18 (s, 3H), 2.07 (s, 3H), 1.34 (s, 6H); $^{13}$C NMR (100

MHz, CDCl$_3$) 148.9, 143.7, 142.0, 132.2, 129.6, 128.8, 128.7, 128.6, 126.5, 121.3, 121.0, 120.7, 120.6, 120.3, 52.3, 31.9, 19.2, 17.3.

EXAMPLE 193

6-(5-Bromo-3-pyridyl)-1,2-dihydro-2,2,4-trimethylquinoline (Compound 293, structure 4 of Scheme II, where R$^1$=5-bromo-3-pyridyl)

This compound was prepared by General Method 2 (EXAMPLE 9) from 3,5-dibromopyridine (119 mg, 0.5 mmol) and Compound 9 (50 mg, 0.16 mmol) to afford 18 mg (35%) of Compound 290 as a yellow oil. Data for Compound 290: $^1$H NMR (400 MHz, CDCl$_3$) 8.69 (s, 1H), 8.52 (s, 1H), 7.93 (t, J=2.0, 1H), 7.21 (d, J=2.1, 1H), 7.20 (dd, J=8.1,2.1, 1H), 6.50(d, J=8.1 1H), 5.37 (s, 1H), 3.88 (bs, 1H), 2.05 (s, 3H), 1.31 (s, 6H).

EXAMPLE 194

6-(3-Bromo-2-pyridyl)-1,2-dihydro-2,2,4-trimethylquinoline (Compound 294, structure 4 of Scheme II, where R$^1$=3-bromo-2-pyridyl)

This compound was prepared by General Method 2 (EXAMPLE 9) from 2,6-dibromopyridine (237 mg, 1.0 mmol) and Compound 9 (100 mg, 0.32 mmol) to afford 42 mg (40%) of Compound 294 as a yellow oil. Data for Compound 294: IR (neat) 3379, 2966, 1604, 1575, 1433, 1124; $^1$H NMR (400 MHz, CDCl$_3$) 7.68 (d, J=1.9, 1H), 7.66 (dd, J=8.1, 1.9, 1H), 7.54 (d, J=7.8 1H), 7.49 (t, J=7.8, 1H), 7.23 (d, J=7.8, 1H), 6.49 (d, J=8.1, 1H), 5.35 (s, 1H), 3.93 (bs, 1H), 2.08 (s, 3H), 1.30 (s, 6H); $^{13}$C NMR (100 MHz, CDCl$_3$) 159.3, 145.1, 142.1, 138.8, 128.7, 128.6, 127.7, 126.6, 124.6, 122.6, 121.5, 117.6, 113.1, 52.4, 31.6, 18.9.

EXAMPLE 195

6-(3-Bromo-2-thienyl)-1,2-dihydro-2,2,4-trimethylquinoline (Compound 295, structure 4 of Scheme II, where R$^1$=3-bromo-2-thienyl)

This compound was prepared by General Method 2 from 2,5-dibromothiophene (242 mg, 1.0 mmol) and Compound 9 (50 mg, 0.16 mmol) to afford 24 mg (45%) of Compound 295 as a yellow oil. Data for Compound 295: $^1$H NMR (400 MHz, CDCl3) 7.17 (bs, 1H), 7.15 (dd, J=8.1, 1.9, 1H), 6.95 (d, J=3.7, 1H), 6.86 (bs, 1H), 6.42 (bs, 1H), 5.36 (s, 1H), 3.80 (bs, 1H), 2.01 (s, 3H), 1.29 (s, 6H).

EXAMPLE 196

1,2-Dihydro-6-(2,3,5,6-tetrafluoro-4-pyridyl)-2,2,4-trimethylquinoline (Compound 296, structure 4 of Scheme II, where R$^1$=2,3,5,6-tetrafluoro-4-pyridyl)

This compound was prepared by General Method 2 from 4-bromo-2,3,5,6-tetrafluoropyridine (150 mg, 0.63 mmol) and Compound 9 (50 mg, 0.16 mmol) to afford 13.4 mg (26%) of Compound 296 as a white solid. Data for Compound 296: $^1$H NMR (400 MHz, CDCl$_3$) 7.23 (s, 1H), 7.20 (d, J=7.9, 1H), 6.51 (d, J=7.9, 1H), 5.38 (s, 1H), 4.08 (bs, 1H), 2.00 (s, 3H), 1.33 (s, 6H); $^{13}$C NMR (100 MHz, CDCl$_3$) 145.4, 144.5 (dd, J=230, 16), 139.3 (dd, J=256, 33), 130.7 (d, J=17.2), 129.0, 128.6, 125.7, 123.8, 121.1, 113.8, 113.1, 112.6, 52.7, 32.1, 18.7.

EXAMPLE 197

5,8-Difluoro-1,2-dihydro-6-(3-nitrophenyl)-2,2,4-trimethylquinoline (Compound 297, structure 83 of Scheme XXI, where R$^1$=R$^{3-5}$=R$^7$=R$^9$=H, R$^2$=nitro, R$^6$=R$^8$=fluoro)

This compound was prepared by the same procedure as described in the synthesis of Compound 291 (EXAMPLE 191) from 4-bromo-2,5-difluoroaniline (32 mg, 0.13 mmol) and 3-nitrobenzeneboronic acid (167 mg, 1.0 mmol) to afford 3 mg (10%) of Compound 297 as a colorless oil. Data for Compound 297: $^1$H NMR (400 MHz, CDCl$_3$) 8.33 (t, J=1.6, 1H), 8.14 (dd, J=8.0, 1.6, 1H), 7.78 (d, J=8.0, 1H), 7.57 (t, J=8.0, 1H), 6.94 (dd, J=10.8, 6.3, 1H), 5.37 (s, 1H), 4.16 (bs, 1H), 2.17 (dd, J=7.0, 1.3, 3H), 1.34 (s, 6H).

EXAMPLE 198

2,4-Diethyl-8-fluoro-1,2-dihydro-2-methyl-6-(3-nitrophenyl)quinoline (Compound 298, structure 83 of Scheme XXI, where R$^1$=R$^{3-7}$=H, R$^2$=nitro, R$^8$=fluoro, R$^9$=methyl)

A mixture of 2-fluoro-4-(3-nitrophenyl)aniline (100 mg, 0.43 mmol), iodine (10 mg, 0.039 mmol) and 2-butanone (5 mL) was heated at 100° C. in a sealed tube for 16 h. Removal of solvent and chromatography of the crude mixture on a silica gel column afforded 4 mg (3%) of Compound 298 as a yellow oil. Data for Compound 298: $^1$H NMR (400 MHz, CDCl$_3$) 8.33 (t, J=2.0, 1H), 8.10 (dd, J=7.8, 2.0, 1H), 7.81 (d, J=7.8, 1H), 7.54 (t, J=7.8, 1H), 7.14 (s, 1H), 7.12 (d, J=11.0, 1H), 5.30 (s, 1H), 3.96 (bs, 1H), 2.47 (q, J=7.5, 2H), 1.57 (q, J=7.5, 2H), 1.31 (s, 3H), 1.21 (t, J=7.5, 3H), 0.95 (t, J=7.5, 3H).

EXAMPLE 199

6-(3-Bromophenyl)-1,2-dihydro-2,2,4-trimethylquinoline (Compound 299, structure 4 of Scheme II, where R$^1$=3-bromophenyl)

This compound was prepared by General Method 2 (EXAMPLE 9) from Compound 9 (100 mg, 0.32 mmol) and 1,3-dibromobenzene (0.20 mL, 1.60 mmol). The crude product was purified by prep TLC (5×20 cm, 250 mm, 25% EtOAc:hexane) to afford 2.3 mg (2%) of Compound 299 as a white solid. Data for compound 299: Rf=0.43 (silica gel, 25% EtOAc:hexane); 1H NMR (400 MHz, acetone-d$_6$) 7.72 (s, 1H), 7.56 (d, J=8.5, 1H), 7.38 (d, J=8.5, 1H), 7.37 (m, 2H), 7.24 (d, J=8.5, 1H), 6.58 (d, J=8.5, 1H), 5.39 (br m, 2H), 2.04 (s, 3H), 1.29 (s, 6H).

EXAMPLE 200

1,2-Dihydro-2,2,4-trimethyl-6-(5-nitro-2-thienyl)quinoline (Compound 300, structure 4 of Scheme II, where R$^1$=5-nitro-2-thienyl)

This compound was prepared by General Method 2 (EXAMPLE 9) from Compound 9 (50 mg, 0.16 mmol) and 2-bromo-5-nitrothiophene (0.16 g, 0.79 mmol). The crude product was purified by prep TLC (20×20 cm, 1000 mm, 25% EtOAc:hexane) to afford 50 mg (81%) of Compound 300 as a purple solid. Data for compound 300:Rf=0.40 (silica gel, 25% EtOAc:hex); $^1$H NMR (400 MHz, CDCl$_3$) 7.85 (d, J=4.3, 1H), 7.27 (m, 2H), 7.04 (d, J=4.3, 1H), 6.43 (d, J=8.5, 1H), 5.38 (brs, 1H), 4.13 (brs, 1H), 2.03 (s, 3H), 1.32 (s, 6H).

EXAMPLE 201

1,2-Dihydro-6-(2,4,5-trifluorophenyl)-2,2,4-trimethylquinoline (Compound 301, structure 4 of Scheme II, where R$^1$=2,4,5-trifluorophenyl)

This compound was prepared by General Method 2 (EXAMPLE 9) from compound 9 (50 mg, 0.16 mmol) and 2,4,5-trifluorobromobenzene (0.10 mL, 0.79 mmol). The crude product was purified by prep TLC (5×20 cm, 250 mm, 25% EtOAc:hexane) to afford 15 mg (31%) of Compound 301 as a yellow oil. Data for compound 301:Rf=0.40 (silica gel, 25% EtOAc:hex); $^1$H NMR (400 MHz, CDCl$_3$) 7.21 (m, 1H), 7.18 (s, 1H), 7.13 (d, J=8.5, 1H), 6.96 m, 1H), 6.47 (d, J=8.5, 1H), 5.34 (s, 1H), 3.83 (brs, 1H), 2.01 (s, 3H), 1.31 (s, 6H.

EXAMPLE 202

6-(3-Bromo-5-fluorophenyl)-1,2-dihydro-2,2,4-trimethylquinoline (Compound 302, structure 4 of Scheme II, where R$^1$=3-bromo-5-fluorophenyl)

This compound was prepared by General Method 2 (EXAMPLE 9) from compound 9 (50 mg, 0.16 mmol) and 1,3-dibromo-5-fluorobenzene (0.20 mL, 1.60 mmol). The crude product was purified by prep TLC (20×20 cm, 500 mm, 25% EtOAc:hexane) to afford 20 mg (36%) of Compound 302 as a colorless oil. Data for compound 302:Rf= 0.40 (silica gel, 25% EtOAc:hex); $^1$H NMR(400 MHz, CDCl$_3$) 7.44 (s, 1H), 7.21 to 7.09 (m, 4H), 6.46 (d, J=8.5, 1H), 5.35 (s, 1H), 3.80 (brs, 1H), 2.04 (s, 3H), 1.30 (s, 6H).

EXAMPLE 203

6-(5-Carboxaldehyde-3-thienyl)-1,2-dihydro-2,2,4-trimethylquinoline (Compound 303, structure 4 of Scheme II, where R$^1$=3-thienyl-5-carboxaldehyde)

This compound was prepared by General Method 2 (EXAMPLE 9) from compound 9 (50 mg, 0.16 mmol) and 4-bromo-2-thiophenecarboxaldehyde (0.15 g, 0.79 mmol). The crude product was purified by prep TLC (20×20 cm, 1000 mm, 25% EtOAc:hexane) to afford 31 mg (70%) of Compound 303 as a yellow oil. Data for compound 303:Rf= 0.44 (silica gel, 25% EtOAc:hex); $^1$H NMR(400 MHz, CDCl$_3$) 9.95 (s, 1H), 7.96 (s, 1H), 7.66 (s, 1H), 7.25 (s, 1H), 7.22 (d, J=3.8, 1H), 6.47 (d, J=8.5, 1H), 5.37 (s, 1H), 3.84 (brs, 1H), 2.04 (s, 3H), 1.31 (s, 6).

EXAMPLE 204

1,2-Dihydro-2,2,4,7-tetramethyl-6-(3-nitrophenyl)quinoline (Compound 304, structure 83 of Scheme XXI, where R$^1$=R$^{3-5}$=R$^6$=R$^{8-9}$=H, R$^2$=nitro, R$^7$=methyl) 4-Amino-2-methyl-3'-nitrobiphenyl (structure 82 of Scheme XXI, where R$^1$=R$^{3-5}$=R$^6$=R$^8$=H, R$^2$=nitro, R$^7$=methyl).

This compound was made according to the General Method 14 (EXAMPLE 191) from 3-nitrobenzene boronic acid (673.2 mg, 3.82 mmol) and 4-bromo-3-methylaniline (710.2 mg, 3.82 mmol) to afford 540 mg (62%) of 4-amino-2-methyl-3'-nitrobiphenyl (structure 82 of Scheme XXI, where R$^1$=R$^{3-5}$=R$^6$=R$^8$=H, R$^2$=nitro, R$^7$=methyl), Data for 4-amino-2-methyl-3'-nitrobiphenyl: $^1$H NMR (400 MHz, acetone-d$_6$) 8.13 (dd, J=7.5, 1.1, 1H), 8.09 (dd, J=3.9, 1.8, 1H), 7.73 (ddd, J=7.7, 1.6, 1.4, 1H), 7.66 (dd, J=1H), 6.99 (d, J=8.0, 1H), 6.60 (m, 1H), 4.73 (br s, 1H), 2.18 (s, 3H). 1,2-Dihydro-2,2,4,7-tetramethyl-6-(3-nitrophenyl)quinoline (Compound 304, structure 83 of Scheme XXI, where R$^1$=R$^{3-5}$=R$^6$=R$^{8-9}$=H, R$^2$=nitro, R$^7$=methyl.

This compound was prepared according to General Method 8 (EXAMPLE 138) from 540 mg of 4-amino-2-methyl-3'-nitrobiphenyl. Approximately 10% of the reaction mixture was worked up and purified to afford 1.5 mg of Compound 304. Data for Compound 304: $^1$H NMR (400 MHz, acetone-d$_6$) 8.13 (m, 2H), 7.76 (dd, J=8.9, 1.2, 1H), 7.69 (t, J=15.9, 8.0, 1H), 6.93 (s, 1H), 6.43 (s, 1H), 5.32 (s, 1H), 2.14 (s, 3H), 1.95 (s, 3H), 1.27 (s, 6H).

EXAMPLE 205

6-(5-Fluoro-2-methoxy-3-nitrophenyl)-1,2-dihydro-2,2,4-trimethylquinoline (Compound 305, structure 4 of Scheme II, where R$^1$=5-fluoro-2-methoxy-3-nitrophenyl)

This compound was prepared by General Method 2 (EXAMPLE 9) from compound 9 (60 mg, 0.19 mmol) and 2-bromo-4-fluoro-6-nitroanisole (37 mg, 0.15 mmol). The crude product was purified by silica gel chromatography (EtOAc/hexane, 10:1) to afford 5 mg (8%) of Compound 305 as a yellow oil. Data for compound 305: $^1$H NMR (400 MHz, CDCl$_3$) 7.34 (dd, J=7.3, 3.3, 1H), 7.25 (m, 3H), 7.21 (dd, J=8.1, 2.0, 1H), 6.50 (d, J=8.3, 1H ), 5.37 (s, 1H), 3.89 (s, 1H), 3.55 (s, 3H), 2.01 (d, J=1.4, $^1$H ), 1.33 (s, 6H).

EXAMPLE 206

6-(3-Chloro-2-methoxyphenyl)-1,2-dihydro-2,2,4-trimethylquinoline (Compound 306, structure 4 of Scheme II, where R$^1$=3-chloro-2-methoxyphenyl)

This compound was prepared by General Method 2 (EXAMPLE 9) from compound 9 (60 mg, 0.19 mmol) and 2-bromo-6-chloroanisole (33 mg, 0.15 mmol). The crude product was purified by silica gel chromatography (EtOAc/hexane, 10:1) to afford 6 mg (8%) of Compound 306 as a yellow oil. Data for compound 306: $^1$H NMR (400 MHz, CDCl$_3$) 7.30 (m, 2H), 7.20 (m, 2H), 7.05 (t, J=8.0, 1H), 6.51 (d, J=8.3, 1H), 5.34 (s, 1H), 3.75 (s, 1H), 3.52 (s, 3H), 2.01 (s, 3H), 1.34 (s, 6H).

EXAMPLE 207

1,2-Dihydro-2,2,4-trimethyl-6-(2,3,4-trifluorophenyl)quinoline (Compound 307, structure 4 of Scheme II, where R$^1$=2,3,4-trifluorophenyl)

This compound was prepared by General Method 2 (EXAMPLE 9) from compound 9 (60 mg, 0.19 mmol) and 1-bromo-2,3,4-trifluorobenzene (0.11 mL, 0.93 mmol). The crude product was purified by silica gel chromatography (EtOAc/hexane, 10:1) to afford 30 mg (53%) of Compound 307 as white crystals. Data for compound 307: $^1$H NMR (400 MHz, acetone-d$_6$) 7.28 (m, 1H), 7.20 (m, 2H), 7.13 (dt, J=8.2, 1.9, 1H), 6.58 (d, J=8.3, 1H), 5.43 (br s, 1H), 5.39 (s, 1H), 2.00 (d, J=1.3, 3H), 1.30 (s, 6H).

EXAMPLE 208

6-(3-Bromo-2-methylphenyl)-1,2-dihydro-2,2,4-trimethylquinoline (Compound 308, structure 4 of Scheme II, where R$^1$=3-bromo-2-methylphenyl)

This compound was prepared by General Method 2 (EXAMPLE 9) from compound 9 (50 mg, 0.16 mmol) and 2,6-dibromotoluene (0.16 g, 0.64 mmol). The crude product was purified by silica gel chromatography (EtOAc/hexane, 10:1) to afford 27 mg (50%) of Compound 308 as a colorless glass. Data for compound 308: $^1$H NMR (400 MHz, CDCl$_3$) 7.49 (d, J=8.3, 1H), 7.17 (d, J=6.9, 1H), 7.04 (t, J=7.7, 1H), 6.95 (d, J=1.9, 1H ), 6.89 (dd, J=8.0, 19 1H), 646 (d, J=8.0, 1H), 5.35 (s, 1H), 3.77 (br s, 1H), 1.97 (d, J=1.2, 3H), 1.32 (s, 6H).

EXAMPLE 209

7-Chloro-1,2-dihydro-2,2,4-trimethyl-6-(3-nitrophenyl)quinoline (Compound 309, structure 83 of Scheme XXI, where R$^1$=R$^{3-5}$=R$^6$=R$^{8-9}$=H, R$^2$=nitro, R$^7$=chloro) 2-Chloro-4-amino-3'-nitrobiphenyl (structure 82 of Scheme XXI, where R$^1$=R$^{3-5}$=R$^{7-8}$=H, R$^2$=nitro, R$^6$=chloro)

This compound was prepared by General Method 14 (EXAMPLE 191) from 3-nitrobenzeneboronic acid (0.25 g, 1.5 mmol), 4-bromo-3-chloroaniline (0.21 g, 1.0 mmol), and (PPh$_3$)$_4$Pd (35 mg, 0.030 mmol) to afford 0.08 g (32%) of 2-chloro-4-amino-3'-nitrobiphenyl as an orange solid. Data for 2-chloro-4-amino-3'-nitrobiphenyl: 1H NMR (400 MHz, acetone-d$_6$) 8.29 (app t, J=2.0, 1H), 8.18 (dt, J=9.0, 1.2, 1H), 7.76 (dd, J=9.0, 1.2, 1H), 7.56 (t, J=8.0, 1H), 7.14 (d, J=8.2, 1H), 6.82 (d, J=2.2, 1H), 6.65 (dd, J=8.2, 2.2, 1H), 3.86 (br s, 2H).

7-Chloro-1,2-dihydro-2,2,4-trimethyl-6-(3-nitrophenyl) quinoline (Compound 309, structure 83 of Scheme XXI, where R$^1$=R$^{3-6}$=R$^{8-9}$=H, R$^2$=nitro, R$^7$=chloro)

This compound was prepared by General Method 8 (EXAMPLE 138) from 2-chloro-4-amino-3'-nitrobiphenyl (0.08 g, 0.3 mmol) to afford 15 mg (15%) of Compound 309 as an orange solid, in addition to 2 mg (2%) of Compound 310 (EXAMPLE 210) as an orange solid. The structures of Compounds 309 and 310 were secured by n.O.e. experiments. Data for Compound 309: $^1$H NMR (400 MHz, acetone-d$_6$) 8.77 (t, J=2.0, 1H), 8.21 (dt, J=9.0, 1.2, 1H), 7.88 (dd, J=6.6, 1.6, 1H), 7.1, 1H), 7.10 (s, 1H), 6.67 (s, 1H), 5.43 (s, 1H), 1.99 (s, 3H), 1.32 (s, 6H).

EXAMPLE 210

5-Chloro-1,2-dihydro-2,2,4-trimethyl-6-3-nitrophenyl) quinoline (Compound 310, structure 83 of Scheme XXI, where R$^1$=R$^{3-5}$=R$^{7-9}$H, R$^2$=nitro R$^6$=chloro)

This compound (2 mg, 2%) was obtained along with Compound 309 (EXAMPLE 209) as described above. Data for Compound 310: $^1$H NMR (400 MHz, acetone-d$_6$) 8.21 (d, J=1.4, 1H), 8.20 (m, 1H), 7.81 (dt, J=8.8, 1.4, 1H), 7.70 (m, 1H), 7.01 (d, J=8.1, 1H), 6.71 (d, J=8.1, 1H), 5.74 (br s, 1H), 5.55 (d, J=1.3, 1H), 2.31 (d, J=1.3, 3H), 1.28 (s, 6H).

EXAMPLE 211

8-Chloro-1,2-dihydro-2,2,4-trimethyl-6-3-nitrophenyl) quinoline Compound 311 structure 83 of Scheme XXI where R$^1$=R$^{3-7}$=R$^9$=H, R$^2$nitro, R$^8$=chloro)

3-Chloro-4-amino-3'-nitrobiphenyl (structure 82 of Scheme XXI, where R$^1$=R$^{3-7}$=H, R$^2$=nitro, R$^8$=chloro This compound was prepared by General Method 14 (EXAMPLE 191) from 3-nitrobenzeneboronic acid (0.25 g, 1.5 mmol), 4-bromo-2-chloroaniline (0.21 g, 1.0 mmol), and (PPh$_3$)$_4$Pd (35 mg, 0.030 mmol) to afford a crude material which was used directly in the next step.

8-Chloro-1,2-dihydro-2,2,4-trimethyl-6-3-nitrophenyl) quinoline Compound 311, structure 83 of Scheme XXI, where R$^1$=R$^{3-7}$=R$^9$=H, R$^2$=nitro R$^8$=chloro This compound was prepared by General Method 8 (EXAMPLE 138) from the crude biphenyl amine obtained above to afford 2 mg (1%) of Compound 311 as an orange solid. Data for Compound 311: $^1$H NMR (400 MHz, acetone-d$_6$) 8.48 (d, J=2.0, 1H), 8.11 (dd, J=8.0, 2.0, 1H), 8.04 (dd, J=6.6, 1.6, 1H), 7.67 (t, J=8.0, 1H), 7.55 (d, J=2.0, 1H), 7.40 (d, J=2.0, 1H), 5.43 (s, 1H), 1.99 (s, 3H), 1.29 (s, 6H).

EXAMPLE 212

8-Ethyl-1,2-dihydro-2,2,4-trimethyl-6-3-nitrophenyl) quinoline Compound 312, structure 83 of Scheme XXI where R$^1$=R$^{3-7}$=R$^9$=H, R$^2$=nitro R$^8$=ethyl)

4-Amino-3-ethyl-3'-nitrobiphenyl structure 82 of Scheme XXI, where R$^1$=R$^{3-7}$=H, R$^2$=nitro, R$^8$=ethyl This compound was prepared by General Method 14 (EXAMPLE 191) from 3-nitrobenzeneboronic acid (0.47 g, 2.8 mmol), 4-bromo-2-ethylaniline (432 mg, 2.16 mmol), and (PPh$_3$)$_4$Pd (75 mg, 0.065 mmol) to afford 139 mg (20%) of 4-amino-3-ethyl-3'-nitrobiphenyl. Data for 4-amino-3-ethyl-3'-nitrobiphenyl: $^1$H NMR (400 MHz, acetone-d$_6$) 8.38 (t, J=2.1, 1H), 8.08 (m, 1H), 8.00 (m, 1H), 7.66 (t, J=8.0, 1H), 7.45 (d, J=2.3, 1H), 7.39 (dd, J=8.3, 2.3 1H), 6.83 (d, J=8.3, 1H), 4.68 (br s, 2H).

8-Chloro-1,2-dihydro-2,2,4-trimethyl-6-(3-nitrophenyl) quinoline (Compound 311, structure 83 of Scheme XXI, where R$^1$=R$^{3-7}$=R$^9$=H, R$^2$=nitro, R$^8$=chloro)

This compound was prepared by General Method 8 (EXAMPLE 138) from the crude biphenyl amine obtained above to afford 2 mg (1%) of Compound 311 as an orange solid. Data for Compound 311: $^1$H NMR (400 MHz, acetone-d$_6$) 8.38 (t, J=2.1, 1H), 8.06 (m, 2H), 7.66 (t, J=8.0, 1H), 7.34 (m, 1H), 5.44 (s, 1H), 4.88 (br s, 1H), 2.60 (q, J=7.5, 2H), 2.08 (s, 3H), 1.34 (s, 6H), 1.23 (t, J=7.5, 3H).

EXAMPLE 213

9-Chloro-1,2-dihydro-2,2-dimethyl-5-coumarino[3,4-f] quinoline (Compound 313, structure 88 of Scheme XXIII, where R$^{1-2}$=R$^{4-6}$=R$^9$=H, R$^7$=R$^8$=methyl, R$^3$=chloro)

2-Amino-6-chloro-3,4-benzocoumarin (structure 87 of Scheme XXIII, where R$^{1-2}$=R$^{4-6}$=H, R$^3$=chloro, an intermediate from EXAMPLE 109) (100 mg, 0.407 mmol) and 1,1-dimethyl propargyl acetate (52 mg, 0.41 mmol) were dissolved in THF (5 mL) and treated with triethylamine (57 μL, 0.41 mmol). The resulting solution was treated with CuCl (20 mg, 0.20 mmol). The reaction mixture was heated at reflux for 16 h. The reaction was quenched with 1% (v/v) HCl (2 mL) and diluted with EtOAc (20 mL). The mixture was poured into a separatory funnel and the aqueous layer was extracted with EtOAc (2×20 mL). The combined organics were washed with brine (1×20 mL), dried (Na$_2$SO$_4$), filtered, and concentrated onto Celite. The material was purified by flash chromatography on silica gel (50 g) using 15% EtOAc:hexanes as eluent to afford 50 mg of the dimethyl propargyl amine intermediate. This material was dissolved in THF and treated with CuCl (2 mg, 0.02 mmol) and heated at reflux for 16 h. The reaction was quenched with 1% (v/v) HCl (2 mL) and diluted with EtOAc and water. The reaction mixture was poured into a separatory funnel and the aqueous was extracted with EtOAc (2×20 mL). The combined organics were washed with brine (15 mL), dried (Na$_2$SO$_4$), filtered, and concentrated onto Celite. The material was purified by flash chromatography on silica gel (20 g) using 15% EtOAc:hexanes to afford 30 mg (24%) of Compound 313 as a yellow solid. Data for Compound 313: $^1$H NMR (400 MHz, acetone-d$_6$) 8.07 (d, J=2.4, 1H), 7.99 (d, J=8.7, 1H), 7.91 (d, J=10.4, 1H ), 7.38 (dd, J=8.6, 2.4, 1H), 7.26 (d, J=8.7, 1H), 7.10 (d, J=8.5, 1H), 6.04 (br s, 1H), 5.74 (dd, J=10.4, 1.4, 1H), 1.36 (s, 6H).

EXAMPLE 214

1,2-Dihydro-9-methoxy-2,2,4-trimethyl-5-coumarino[3,4-f] quinoline (Compound 314, structure 41 of Scheme XI, where R$^1$=H, R$^2$=methoxy)

2,5-Dimethoxyphenylboronic acid (structure 37 of Scheme XI, where R$^1$=H, R$^2$=methoxy)

This compound was prepared in a manner similar to that of 5-fluoro-2-methoxyphenylboronic acid (EXAMPLE 107) from 1-bromo-2,5-dimethoxybenzene (2.00 mL, 13.3 mmol), n-BuLi (2.5 M in hexanes; 5.34 mL, 13.3 mmol), and trimethylborate (4.5 mL, 40 mmol) to afford 2.43 g (99%) of 2,5-dimethoxyphenylboronic acid which was used without further purification.

Methyl (2',5'-dimethoxy-4-nitro-2-biphenylcarboxylate)

This compound was prepared in a manner similar to that of methyl 5'-fluoro-2'-methoxy-4-nitro-2-biphenylcarboxylate (EXAMPLE 107) from methyl 2-bromo-5-nitrobenzoate (2.46 g, 9.46 mmol), (PPh$_3$)$_4$Pd (0.33 g, 0.28 mmol), and 2,5-dimethoxyphenylboronic acid (2.42 g, 13.3 mmol) to afford 2.08 g (69%) of methyl (2',5'-dimethoxy-4-nitro-2-biphenylcarboxylate) as a white solid. Data for methyl (2',5'-dimethoxy-4-nitro-2-biphenylcarboxylate): $^1$H NMR (400 MHz, CDCl$_3$) 8.70 (d, J=2.4, 1H), 8.37 (dd, J=8.4, 2.5, 1H), 7.52 (d, J=8.5, 1H), 6.92 (dd, J=8.8, 3.0, 1H), 6.84 (m, 1H), 3.82 (s, 3H), 3.75 (s, 3H), 3.67 (s, 3H).

2',5'-Dimethoxy-4-nitro-2-biphenylcarboxylic acid

This compound was prepared in a manner similar to that of 5'-fluoro-2'-methoxy-4-nitro-2-biphenylcarboxylic acid (EXAMPLE 107) from methyl 2',5'-dimethoxy-4-nitro-2-biphenylcarboxylate (2.07 g) to afford 1.93 g (99%) of 2',5'-dimethoxy-4-nitro-2-biphenylcarboxylic acid as a white solid. Data for 2',5'-dimethoxy-4-nitro-2-biphenylcarboxylic acid: $^1$H NMR (400 MHz, acetone-d$_6$) 8.64 (d, J=2.5, 1H), 8.43 (dd, J=8.4, 2.6, 1H), 7.67 (d, J=8.5, 1H), 6.94 (m, 2H), 3.80 (s, 3H), 3.68 (s, 3H).

6-Methoxy-2-nitro-3,4-benzocoumarin

This compound was prepared in a manner similar to that of 6-fluoro-2-nitro-3,4-benzocoumarin (EXAMPLE 107) from 2',5'-dimethoxy-4-nitro-2-biphenylcarboxylic acid (1.93 g, 6.36 mmol), SOCl$_2$ (0.47 mL, 6.4 mmol), and AlCl$_3$ (0.67 g, 5.0 mmol) to afford 1.71 g (99%) of 6-methoxy-2-nitro-3,4-benzocoumarin as an orange powder. Data for 6-methoxy-2-nitro-3,4-benzocoumarin: $^1$H NMR (400 MHz, acetone-d$_6$) 9.04 (d, J=2.4, 1H), 8.74 (d, J=8.9, 1H), 8.69 (dd, J=8.9, 2.4, 1H), 7.92 (d, J=2.9, 1H), 7.41 (d, J=9.0, 1H), 7.30 (dd, J=9.0, 2.9, 1H), 3.97 (s, 3H).

2-Amino-6-methoxy-3,4-benzocoumarin (structure 40 of Scheme XI, where R$^1$=H, R$^2$=methoxy).

This compound was prepared in a manner similar to that of 2-amino-6-fluoro-3,4-benzocoumarin (EXAMPLE 107) from 6-methoxy-2-nitro-3,4-benzocoumarin (1.71 g, 6.3 mmol) to afford 1.27 g (80%) of 2-amino-6-methoxy-3,4-benzocoumarin as a white solid. Data for 2-amino-6-methoxy-3,4-benzocoumarin: $^1$H NMR (400 MHz, acetone-d$_6$) 8.10 (d, J=8.7, 1H), 7.60 (d, J=2.8, 1H), 7.55 (d, J=2.5, 1H), 7.25 (m, 2H), 6.99 (dd, J=8.7, 2.8, 1H), 3.90 (s, 3H).

1,2-Dihydro-9-methoxy-2,2,4-trimethyl-5-coumarino[3,4-f]quinoline (Compound 314, structure 41 of Scheme XI, where R$^1$=H, R$^2$=methoxy)

This compound was prepared in a manner similar to that of Compound 207 from 2-amino-6-methoxy-3,4-benzocoumarin (1.27 g, 5.0 mmol) to afford 0.25 g (15%) of Compound 314 as a yellow solid. Data for Compound 314: $^1$H NMR (400 MHz, CDCl$_3$) 7.73 (d, J=8.6, 1H ), 7.35 (d, J=2.8, 1H), 7.23 (d, J=8.9, 1H), 7.00 (d, J=8.6, 1H), 6.92 (dd, J=8.9, 2.8, 1H), 5.57 (s, 1H), 4.29 (brs, 1H), 3.88 (s, 3H), 2.11 (d, J=1.1, 3H), 1.33 (s, 6H).

EXAMPLE 215

9-Fluoro-1,2-dihydro-2,2,4,11-tetramethyl-5-coumarino[3,4-f]quinoline (Compound 315, structure 88 of Scheme XXIV, where R$^{1-2}$=R$^4$=R$^6$=H, R$^3$=fluoro, R$^5$=R$^{7-9}$=methyl) Methyl 2'-fluoro-5'-methoxy-6-methyl-4-nitro-2-biphenylcarboxylate (structure 92 of Scheme XXIV, where R$^{1-2}$=R$^4$=R$^6$=H, R$^3$=fluoro, R$^5$=methyl)

This compound was prepared in a manner similar to that of methyl 5'-fluoro-2'-methoxy-4-nitro-2-biphenylcarboxylate (EXAMPLE 107) from methyl 2-bromo-3-methyl-5-nitrobenzoate (1.73 g, 6.31 mmol), (PPh$_3$)$_4$Pd (0.22 g, 0.19 mmol), and 5-fluoro-2-methoxyphenylboronic acid (EXAMPLE 107) (1.50 g, 8.8 mmol) to afford 0.77 g (38%) of methyl 2'-fluoro-5'-methoxy-6-methyl-4-nitro-2-biphenylcarboxylate. Data for 2'-fluoro-5'-methoxy-6-methyl-4-nitro-2-biphenylcarboxylate: 8.61 (d, J=2.3, 1H), 8.27 (d, J=2.4, 1H), 7.09 (m, 1H), 6.91 (dd, J=9.0, 4.3, 1H), 6.73 (dd, J=8.2, 3.0, 1H), 3.70 (s, 3H), 3.69 (s, 3H), 2.19 (s, 3H).

2'-Fluoro-5'-methoxy-4-nitro-2-biphenylcarboxylic acid

This compound was prepared in a manner similar to that of 5'-fluoro-2'-methoxy-4-nitro-2-biphenylcarboxylic acid (EXAMPLE 107) from methyl 2'-fluoro-5'-methoxy-6-methyl-4-nitro-2-biphenylcarboxylate (0.77 g) to afford 0.73 g (99%) of 2'-fluoro-5'-methoxy-4-nitro-2-biphenylcarboxylic acid as a white solid, which was used in the next step without further purification.

6-Fluoro-4-methyl-2-nitro-3,4-benzocoumarin

This compound was prepared in a manner similar to that of 6-fluoro-2-nitro-3,4-benzocoumarin (EXAMPLE 107) from 2'-fluoro-5'-methoxy-4-nitro-2-biphenylcarboxylic acid (0.73 g, 2.4 mmol), SOCl$_2$ (0.18 mL, 2.4 mmol), and AlCl$_3$ (0.32 g, 2.4 mmol) to afford 0.63 g (95%) of 6-fluoro-4-methyl-2-nitro-3,4-benzocoumarin as an orange powder. Data for 6-fluoro-4-methyl-2-nitro-3,4-benzocoumarin: $^1$H NMR (400 MHz, acetone-d$_6$) 8.99 (d, J=2.5, 1H), 8.63 (d, J=2.5, 1H ), 8.29 (dd, J=10.9, 2.4, 1H), 7.53 (m, 2H), 3.14 (s, 3H).

2-Amino-6-fluoro-4-methyl-3,4-benzocoumarin (structure 87 of Scheme XXIV, where R$^{1-2}$=R$^4$=R$^6$=H, R$^3$=fluoro, R$^5$=methyl)

This compound was prepared in a manner similar to that of 2-amino-6-fluoro-3,4-benzocoumarin (EXAMPLE 107) from 6-fluoro-4-methyl-2-nitro-3,4-benzocoumarin (0.61 g) to afford 0.54 g (99%) of 2-amino-6-fluoro-4-methyl-3,4-benzocoumarin as a white solid, which was used in the next step without further purification.

9-Fluoro-1,2-dihydro-2,2,4,11-tetramethyl-5-coumarino[3,4-f]quinoline (Compound 315, structure 88 of Scheme XXIV, where R$^{1-2}$=R$^4$=R$^6$=H, R$^3$=fluoro, R$^5$=R$^{7-9}$=methyl)

This compound was prepared in a manner similar to that of Compound 207 from 2-amino-6-fluoro-4-methyl-3,4-benzocoumarin (0.54 g) to afford 0.29 g (40%) of Compound 315 as a yellow solid. Data for Compound 315: $^1$H NMR (400 MHz, acetone-d$_6$) 7.87 (dd, J=11.4, 2.9, 1H), 7.32 (dd, J=9.0, 5.1, 1H), 7.28 (m, 1H), 7.02 (s, 1H), 5.52 (d, J=1.2, 1H), 2.76 (s, 3H), 2.01 (s, 3H), 1.30 (s, 6H).

EXAMPLE 216

1,2-Dihydro-2,2,4,9-tetramethyl-5-coumarino[3,4-f]quinoline (Compound 316, structure 41 of Scheme XI, where R$^1$=H, R$^2$=methyl)

2-Methoxy-5-methylphenylboronic acid (structure 37 of Scheme XI, where R$^1$=H, R$^2$=methyl)

This compound was prepared in a manner similar to that of 5-fluoro-2-methoxyphenylboronic acid (EXAMPLE 107) from 2-bromo-4-methylanisole (2.00 g, 9.94 mmol), n-BuLi (2.5M in hexanes; 4.00 mL, 10 mmol), and trimethylborate (3.4 mL, 30 mmol) to afford 1.60 g (96%) of 2-methoxy-5-methylphenylboronic acid which was used without further purification.

Methyl 2'-methoxy-5'-methyl-4-nitro-2-biphenylcarboxylate

This compound was prepared in a manner similar to that of methyl 5'-fluoro-2'-methoxy-4-nitro-2-biphenylcarboxylate (EXAMPLE 107) from methyl 2-bromo-5-nitrobenzoate (1.80 g, 6.92 mmol), (PPh$_3$)$_4$Pd (0.33 g, 0.28 mmol), and 2-methoxy-5-methylphenylboronic acid (1.58 g, 9.51 mmol) to afford 2.03 g (98%) of methyl 2'-methoxy-5'-methyl-4-nitro-2-biphenylcarboxylate as a white solid. Data for methyl (2'-methoxy-5'-methyl-4-nitro-2-biphenylcarboxylate): $^1$H NMR (400 MHz, CDCl$_3$) 8.69 (d, J=2.5, $^1$H ), 8.36 (dd, J=8.4, 2.5, 1H), 7.51 (d, J=8.5, 1H), 7.20 (m, 1H), 7.07 (d, J=2.1, 1H), 6.81 (d, J=8.4, 1H), 3.75 (s, 3H), 3.69 (s, 3H), 2.35 (s, 3H).

2'-Methoxy-5'-methyl-4-nitro-2-biphenylcarboxylic acid

This compound was prepared in a manner similar to that of 5'-fluoro-2'-methoxy-4-nitro-2-biphenylcarboxylic acid (EXAMPLE 107) from methyl 2'-methoxy-5'-methyl-4-nitro-2-biphenylcarboxylate (2.02 g) to afford 1.93 g (99%) of 2'-methoxy-5'-methyl-4-nitro-2-biphenylcarboxylic acid as a white solid. Data for 2'-methoxy-5'-methyl-4-nitro-2-biphenylcarboxylic acid: $^1$H NMR (400 MHz, acetone-$d_6$) 8.63 (d, J=2.5, 1H), 8.42 (dd, J=8.5, 2.5, 1H), 7.63 (d, J=8.5, 1H), 7.19 (m, 1H), 7.14 (d, J=2.2, 1H), 6.93 (d, J=8.4, 1H), 3.70 (s, 3H), 2.32 (s, 3H).

6-Methyl-2-nitro-3,4-benzocoumarin

This compound was prepared in a manner similar to that of 6-fluoro-2-nitro-3,4-benzocoumarin (EXAMPLE 107) from 2'-methoxy-5'-methyl-4-nitro-2-biphenylcarboxylic acid (1.92 g, 6.68 mmol), SOCl$_2$ (0.49 mL, 6.7 mmol), and AlCl$_3$ (0.89 g, 6.7 mmol) to afford 1.65 g (97%) of 6-methyl-2-nitro-3,4-benzocoumarin as an orange powder. Data for 6-methyl-2-nitro-3,4-benzocoumarin: $^1$H NMR (400 MHz, acetone-$d_6$) 9.04 (d, J=2.5, 1H), 8.69 (m, 2H), 8.26 (s, 1H), 7.53 (d, J=8.6, 1H), 7.35 (d, J=8.6, 1H), 2.49 (s, 3H).

2-Amino-6-methyl-3,4-benzocoumarin (structure 40 of Scheme XI, where R$^1$=H, R$^2$=methyl)

This compound was prepared in a manner similar to that of 2-amino-6-fluoro-3,4-benzocoumarin (EXAMPLE 107) from 6-methyl-2-nitro-3,4-benzocoumarin (1.64 g) to afford 1.40 g (99%) of 2-amino-6-methyl-3,4-benzocoumarin as a white solid, which was used in the next step without further purification.

1,2-Dihydro-2,2,4,9-tetramethyl-5-coumarino[3,4-f]quinoline (Compound 316, structure 41 of Scheme XI, where R$^1$=H, R$^2$=methyl)

This compound was prepared in a manner similar to that of Compound 207 from 2-amino-6-methyl-3,4-benzocoumarin (1.40 g) to afford 0.738 g (38%) of Compound 316 as a yellow solid. Data for Compound 316: $^1$H NMR (400 MHz, acetone-$d_6$) 7.96 (d, J=8.6, 1H), 7.89 (s, 1H), 7.19 (d, J=8.6, 1H), 7.18 (m, 1H), 7.14 (d, J=8.4, 1H), 6.04 (brs, 1H), 5.51 (s, 1H), 2.41 (s, 3H), 1.29 (s, 6H). The C(4) methyl is obscured by the acetone multiplet.

EXAMPLE 217

7-Chloro-1,2-dihydro-2,2,4-trimethyl-5-coumarino[3,4-f]quinoline (Compound 317, structure 88 of Scheme XXIV, where R$^1$=chloro, R$^{2-6}$=H, R$^{7-9}$=methyl)

3-Chloro-2-methoxyphenylboronic acid (structure 90 of Scheme XXIV, where R$^1$=chloro, R$^{2-4}$=H)

This compound was prepared in a manner similar to that of 5-fluoro-2-methoxyphenylboronic acid (EXAMPLE 107) from 2-bromo-6-chloroanisole (0.71 g, 3.2 mmol), n-BuLi (2.5M in hexanes; 1.28 mL, 3.2 mmol), and trimethylborate (1.09 mL, 9.6 mmol) to afford 0.55 g (91%) of 3-chloro-2-methoxyphenylboronic acid which was used without further purification.

Methyl (3'-chloro-2'-methoxy-4-nitro-2-biphenylcarboxylate)

This compound was prepared in a manner similar to that of methyl (5'-fluoro-2'-methoxy-4-nitro-2-biphenylcarboxylate) (EXAMPLE 107) from methyl 2-bromo-5-nitrobenzoate (0.58 g, 2.2 mmol), (PPh$_3$)$_4$Pd (77 mg, 0.066 mmol), and 5-chloro-2-methoxyphenylboronic acid (0.54 g, 2.9 mmol) to afford 245 mg (35%) of methyl (3'-chloro-2'-methoxy-4-nitro-2-biphenylcarboxylate) as a clear oil. Data for methyl (3'-chloro-2'-methoxy-4-nitro-2-biphenylcarboxylate): $^1$H NMR (400 MHz, CDCl$_3$) 8.79 (d, J=2.4, 1H), 8.40 (dd, J=8.4, 2.4, 1H), 7.57 (d, J=8.5, 1H), 7.45 (m, 1H), 7.15 (m, 2H), 3.75 (s, 3H), 3.47 (s, 3H).

3'-Chloro-2'-methoxy-4-nitro-2-biphenylcarboxylic acid

This compound was prepared in a manner similar to that of 5'-fluoro-2'-methoxy-4-nitro-2-biphenylcarboxylic acid (EXAMPLE 107) from methyl (3'-chloro-2'-methoxy-4-nitro-2-biphenylcarboxylate) (230mg) to afford 0.21 g (99%) of 3'-chloro-2'-methoxy-4-nitro-2-biphenylcarboxylic acid as a white solid. Data for 3'-chloro-2'-methoxy-4-nitro-2-biphenylcarboxylic acid: $^1$H NMR (400 MHz, acetone-$d_6$) 8.76 (d, J=2.5, 1H), 8.50 (dd, J=8.4, 2.5, 1H), 7.74 (d, J=8.5, 1H), 7.51 (dd, J=7.9, 1.8, 1H), 7.31 (dd, J=7.4, 1.8, 1H), 7.24 (t, J=7.9), 3.47 (s, 3H).

8-Chloro-2-nitro-3,4-benzocoumarin

This compound was prepared in a manner similar to that of 6-fluoro-2-nitro-3,4-benzocoumarin (EXAMPLE 107) from 3'-chloro-2'-methoxy-4-nitro-2-biphenylcarboxylic acid (0.20 g, 0.65 mmol), SOCl$_2$ (50 mL, 0.69 mmol), and AlCl$_3$ (85 mg, 0.65 mmol) to afford 0.18 g (99%) of 8-chloro-2-nitro-3,4-benzocoumarin as yellow crystals. Data for 8-chloro-2-nitro-3,4-benzocoumarin: $^1$H NMR (400 MHz, acetone-$d_6$) 9.06 (t, J=1.4, 1H), 8.74 (s, 2H), 8.45 (dd, J=8.0, 1.4, 1H), 7.32 (dd, J=8.0, 1.2, 1H), 7.51 (t, J=8.0, 1H).

2-Amino-8-chloro-3,4-benzocoumarin (structure 87 of Scheme XXIV, where R$^1$=chloro, R$^{2-6}$=H)

This compound was prepared in a manner similar to that of 2-amino-6-fluoro-3,4-benzocoumarin (EXAMPLE 107) from 8-chloro-2-nitro-3,4-benzocoumarin (0.18 g, 0.65 mmol) to afford 0.10 g (62%) of 2-amino-8-chloro-3,4-benzocoumarin as a white solid, which was used in the next step without further purification.

7-Chloro-1,2-dihydro-2,2,4-trimethyl-5-coumarino[3,4-f]quinoline (Compound 317, structure 88 of Scheme XXIV, where R$^1$=chloro, R$^{2-6}$=H, R$^{7-9}$=methyl)

This compound was prepared in a manner similar to that of Compound 207 from 2-amino-9-chloro-3,4-benzocoumarin (0.10 g) to afford 24 mg (18%) of Compound 317 as a yellow solid. Data for Compound 317: $^1$H NMR (400 MHz, acetone-$d_6$) 8.04 (dd, J=8.1, 1.1, 1H), 7.98 (d, J=8.7, 1H), 7.48 (dd, J=9.0, 1.1, 1H), 7.28 (t, J=8.8, 1H), 7.23 (d, J=8.6, 1H), 6.24 (br s, 1H), 5.55 (d, J=1.2, 1H), 2.08 (s, 3H), 1.31 (s, 6H).

EXAMPLE 218

5-(3-Fluorobenzyl)-1,2-dihydro-2,2,4-trimethyl-5H-chromeno[3,4-f]quinoline (Compound 318, structure 32 of Scheme IX, where R=3-fluorobenzyl)

To a solution of Compound 225 (EXAMPLE 125) (10 mg, 0.03 mmol) in CH$_2$Cl$_2$ (5 ml) was added triethylsilane (0.05 ml, 0.3 mmol) and trifluoroacetic acid (0.024 ml, 0.3 mmol) at rt. The reaction was monitored by TLC and was found to be complete after 15 hours. The reaction mixture was quenched with an aqueous 10% NaOH solution (5 mL) then extracted with EtOAc (10 mL). The organic layer was washed with brine (3×5 mL), dried (Na$_2$SO$_4$), then concentrated in vacuo to afford a yellow oil. The crude product was purified by prep TLC (5×20 cm, 250 mm, 1:1 CH$_2$Cl$_2$:hexane) to afford 1.0 mg (8%) of Compound 318 as a yellow oil. Data for Compound 318:Rf=0.26 (silica gel, 25% EtOAc:hex); $^1$H NMR (400 MHz, CDCl$_3$) 7.66 (d, J=8.5, 1H), 7.48 (d, J=8.5 1H), 7.23 (m, 2H), 7.03 (m, 1H), 6.89 (m, 3H), 6.61 (d, J=8.5, 1H), 6.10 (m, 1H), 5.49 (s, 1H), 3.98 (brs, 1H), 3.10 (m, 1H), 2.73 (m, 1H), 2.29 (s, 3H), 1.29 (s, 3H), 1.19 (s, 3H).

EXAMPLE 219

(R/S)-9-Chloro-1,2-dihydro-5-methoxy-2,2,4-trimethyl-5H-chromeno[3,4-f]quinoline (Compound 319, structure 47 of Scheme XIV, where R$^1$=H, R$^2$=chloro, R$^3$=methyl, X=O)

(R/S)-9-chloro-1,2-dihydro-5-hydroxy-2,2,4-trimethyl-5H-chromeno[3,4-f]quinoline (structure 46 of Scheme XIV, where R¹=H, R²=chloro) and 6-(5-chloro-2-hydroxyphenyl)-1,2-dihydro-5-hydroxymethyl-2,2,4-trimethylquinoline (structure 94 of Scheme XXV, where $R^{1-2}=R^{4-6}=H$, $R^3$=chloro, $R^{7-9}$=methyl)

Compound 209 (EXAMPLE 109) (100 mg, 0.307 mmol) was dissolved in THF, cooled to –40° C., and treated with DIBAL (614 µL, 0.614 mmol, 1M in THF, Aldrich), warming to –20° C. over 30 min. The reaction mixture was quenched with NH₄Cl (sat) (2 mL) and allowed to warm to rt. The reaction mixture was poured into a separatory funnel containing EtOAc and water. The aqueous was extracted with EtOAc (2×20 mL). The combined organics were washed with NaCl (sat) (1×15 mL), dried (Na₂SO₄), filtered, and concentrated onto Celite. The material was purified by flash chromatography using 25% EtOAc:hexanes to afford 65 mg of (R/S)-9-chloro-1,2-dihydro-5-hydroxy-2,2,4-trimethyl-5H-chromeno[3,4-f]quinoline (structure 46 of Scheme XIV, where R¹=H, R²=chloro) and 20 mg of 6-(5-chloro-2-hydroxyphenyl)-1,2-dihydro-5-hydroxymethyl-2,2,4-trimethylquinoline (structure 94 of Scheme XXV, where $R^{1-2}=R^{4-6}=H$, $R^3$=chloro, $R^{7-9}$=methyl). Data for (R/S)-9-chloro-1,2-dihydro-5-hydroxy-2,2,4-trimethyl-5H-chromeno[3,4-f]quinoline: ¹H NMR (400 MHz, acetone-d₆) 7.71 (d, J=2.4, 1H), 7.55 (d, J=8.4, 1H), 7.11 (dd, J=8.5, 2.4, 1H), 6.94 (d, J=8.4, 1H), 6.84 (d, J=5.9, 1H), 6.78 (d, J=8.2, 1H), 6.01 (d, J=6.0, 1H), 5.56 (bs, 1H), 5.52 (s, 1H), 2.36 (s, 3H), 1.31 (s, 3H), 1.18 (s, 3H). Data for 6-(5-chloro-2-hydroxyphenyl)-1,2-dihydro-5-hydroxymethyl-2,2,4-trimethylquinoline: ¹H NMR (400 MHz, acetone-d₆) 7.18 (dd, J=8.5, 3.0, 1H ), 7.10 (d, J=2.5, 1H), 6.92 (d, J=8.6, 1H), 6.75 (d, J=8.0, 1H), 6.63 (d, J=8.1, 1H), 5.46 (s, 1H), 5.25 (s, 1H), 4.55 (ABq, J=11.4, 2H), 2.35 (s, 3H), 1.27 (s, 6H).

(R/S)-9-Chloro-1,2-dihydro-5-methoxy-2,2,4-trimethyl-5H-chromeno[3,4-f]quinoline (Compound 319, structure 47 of Scheme XIV, where R¹=H, R²=chloro, R³=methyl, X=O)

(R/S)-9-chloro-1,2-dihydro-5-hydroxy-2,2,4-trimethyl-5H-chromeno[3,4-f]quinoline (30 mg, 0.092 mmol) was dissolved in methanol (3 mL) and treated with p-toluenesulfonic acid (10 mg). After 10 min the reaction was quenched with NaHCO₃ (2 mL). The resulting mixture was diluted with water (2 mL), poured into a separatory funnel, and extracted with EtOAc (3×20 mL). The combined organics were washed with NaCl(sat) (1×20 mL), dried (Na₂SO₄), filtered, and concentrated onto Celite. The material was purified by flash chromatography on silica (20 g) using 10% EtOAc:hexanes as eluent to afford 20 mg (64%) of Compound 319 as an opaque oil. Data for Compound 319: ¹H NMR (400 MHz, acetone-d₆) 7.73 (d, J=2.4, 1H), 7.56 (d, J=8.3, 1H), 7.17 (dd, J=8.2, 2.4, 1H), 7.08 (d, J=8.3, 1H), 6.80 (d, J=8.3, 1H), 6.37 (s, 1H), 5.62 (br s, 1H), 5.54 (s, 1H), 3.44 (s, 3H), 2.27 (2, 3H), 1.32 (s, 3H), 1.17 (s, 3H).

EXAMPLE 220

9-Chloro-1,2-dihydro-2,2,4-trimethyl-5H-chromeno3,4-f]quinoline (Compound 320, structure 93 of Scheme XXV, where $R^{1-2}=R^{4-6}=H$, R³=chloro, $R^{7-9}$=methyl)

6-(5-Chloro-2-hydroxyphenyl)-1,2-dihydro-5-hydroxymethyl-2,2,4-trimethylquinoline (EXAMPLE 219; structure 94 of Scheme XXV, where $R^{1-2}=R^{4-6}=H$, R³=chloro, $R^{7-9}$=methyl)(20 mg, 0.061 mmol) was dissolved in CH₂Cl₂ and treated with thionyl chloride (5 µL, 0.067 mmol) and triethylamine (9 µL 0.067 mmol). After 2 h the reaction was quenched with water and poured into a separatory funnel containing CH₂Cl₂ (20 mL) and water (10mL). The aqueous was extracted with CH₂Cl₂ (2×20 mL). The combined organics were washed with NaCl (sat) (1×15 mL), dried (Na₂SO₄), filtered and concentrated. The resulting benzyl chloride intermediate was dissolved in 1,2-dichloroethane (1 mL) and treated with triethylamine (100 mL), then heated to reflux. After 1 h the reaction was quenched with water and poured into a separatory funnel. The pH was adjusted to 6 (1% v/v HCl) and the aqueous was extracted with CH₂Cl₂ (2×20 mL) The combined organics were washed with NaCl(sat) (20 mL), dried (Na₂SO₄), filtered, and concentrated onto Celite. The material was purified by flash chromatography on silica gel (20 g) using 5% EtOAc:hexanes to afford 10 mg (53%) of Compound 320. Data for Compound 320: ¹H NMR (400 MHz, acetone-d₆) 7.60 (d, J=2.4, 1H), 7.43 (d, J=8.4, 1H), 7.08 (dd, J=8.5, 2.4, 1 h), 6.89 (d, J=8.5, 1H), 6.70 (d, J=8.4, 1H), 5.56 (br s, 1H), 5.49 (s, 1H), 5.32 (s, 2H), 2.11 (s, 3H), 1.25 (s, 6H).

EXAMPLE 221

(R/S)-9-Chloro-1,2-dihydro-2,2,4-trimethyl-5-propyloxy-5H-chromeno[3,4-f]quinoline (Compound 321, structure 47 of Scheme XIV, where R¹=H, R²=chloro, R³=propyl, X=O)

(R/S)-9-Chloro-1,2-dihydro-5-hydroxy-2,2,4-trimethyl-5H-chromeno[3,4-f]quinoline (EXAMPLE 219; structure 46 of Scheme XIV, where R¹=H, R²=chloro) (30 mg, 0.092 mmol) was dissolved in 1-propanol (3 mL) and treated with p-toluenesulfonic acid (10 mg). After 10 min the reaction was quenched with NaHCO₃ (2 mL). The resulting mixture was diluted with H₂O (2 mL), poured into a separatory funnel, and extracted with EtOAc (3×20 mL). The combined organics were washed with NaCl(sat) (1×20 mL), dried (Na₂SO₄), filtered, and concentrated onto celite. The material was purified by flash chromatography on silica (20 g) using 10% EtOAc:hexanes as eluent to afford 22 mg (61%) of Compound 321 as an opaque oil. Data for Compound 321: ¹H NMR (400 MHz, acetone-d₆) 7.73 (d, J=2.4, 1H), 7.56 (d, J=8.5, 1H), 7.14 (dd, J=8.3, 2.5, 1H), 7.03 (d, J=8.5, 1H), 6.80 (d, J=8.5, 1H), 6.46 (s, 1H), 5.60 (br s, 1H), 5.53 (s, 1H), 3.81 (m, 1H), 3.59 (m, 1H), 2.29 (s, 3H), 1.46 (m, 2H), 1.32 (s, 3H), 1.17 (s, 3H), 0.75, (m, 3H).

EXAMPLE 222

(R/S)-9-Fluoro-1,2-dihydro-5-methoxy-2,2,4-trimethyl-5H-chromeno[3,4-f]quinoline (Compound 322, structure 47 of Scheme XIV, where R¹=H, R²=fluoro, R³=methyl, X=O)

This compound was prepared in a manner similar to that described for Compound 319 (EXAMPLE 219) from Compound 207 (55 mg) to afford 34 mg (59%) of Compound 322 as a clear oil. Data for Compound 322: ¹H NMR (400 MHz, acetone-d₆) 7.53 (d, J=8.5, 1H), 7.48 (dd, J=9.9, 3.0, 1H), 7.05 (dd, J=8.7, 4.9, 1H), 6.92 (m, 1H), 6.80 (d, J=8.3, 1H ), 6.34 (s, 1H), 5.54 (d, J=1.4, 1H), 3.44 (s, 3H), 2.28 (d, J=1.4, 3H), 1.32 (s, 3H), 1.16 (s, 3H).

EXAMPLE 223

(R/S) -9-Fluoro-1,2-dihydro-2,2,4-trimethyl-5-thiopropoxy-5H-chromeno[3,4-f]quinoline (Compound 323, structure 47 of Scheme XIV, where R¹=H, R²=fluoro, R³=propyl, X=S)

(R/S)-9-Fluoro-1,2-dihydro-5-hydroxy-2,2,4-trimethyl-5H-chromeno[3,4-f]quinoline (structure 46 of Scheme XIV, where R¹=H, R²=fluoro)

This compound was prepared in a manner similar to that of 9-chloro-1,2-dihydro-5-hydroxy-2,2,4-trimethyl-5H- chromeno[3,4-f]quinoline (EXAMPLE 219) from Compound 207 (0.16 g, 0.51 mmol) to afford 80 mg (50%) of 9-fluoro-1,2-dihydro-5-hydroxy-2,2,4-trimethyl-5H-chromeno[3,4-f]quinoline as a white solid. Data for 9-fluoro-1,2-dihydro-5-hydroxy-2,2,4-trimethyl-5H-chromeno[3,4-f]quinoline: $^1$H NMR (400 MHz, acetone-d$_6$) 7.52 (d, J=8.5, 1H), 7.46 (dd, J=9.9, 2.9, 1H), 6.93 (m, 1H), 6.86 (m, 2H), 6.78 (d, J=8.5, 1H), 5.98 (d, J=6.0, 1H), 5.56 (br s, 1H), 5.52 (d, J=1.1, 1H), 2.37 (d, J=1.2, 3H), 1.30 (s, 3H), 1.18 (s, 3H).

(R/S)-9-Fluoro-1,2-dihydro-2,2,4-trimethyl-5-thiopropoxy-5H-chromeno[3,4-f]quinoline (Compound 323, structure 47 of Scheme XIV, where $R^1$=H, $R^2$=fluoro, $R^3$=propyl, X=S)

This compound was prepared in a manner similar to that of Compound 319 (EXAMPLE 219) from 9-fluoro-1,2-dihydro-5-hydroxy-2,2,4-trimethyl-5H-chromeno[3,4-f]quinoline (18 mg) to afford 21 mg (99%) of Compound 323 as a clear oil. Data for Compound 323: $^1$H NMR (400 MHz, acetone-d$_6$) 7.48 (d, J=8.5, 1H), 7.45 (dd, J=10.0, 1.7, 1H), 7.14 (s, 1H), 6.95 (m, 2H), 6.73 (d, J=8.5, 1H), 5.52 (d, J=1.3, 1H), 2.76 (m, 1H), 2.58 (dt, J=12.9, 7.4, 1H), 2.47 (d, J=1.2, 3H), 1.66 (m, 2H), 1.25 (s, 3H), 1.22 (s, 3H), 0.95 (t, J=7.3, 3H).

EXAMPLE 224

(R/S)-9-Fluoro-1,2-dihydro-2,2,4-trimethyl-5-propoxy-5H-chromeno[3,4-f]quinoline (Compound 324, structure 47 of Scheme XIV, where $R^1$=H, $R^2$=fluoro, $R^3$=propyl, X=O)

This compound was prepared in a manner similar to that of Compound 319 (EXAMPLE 219) from 9-fluoro-1,2-dihydro-5-hydroxy-2,2,4-trimethyl-5H-chromeno[3,4-f]quinoline (EXAMPLE 223) (20 mg) to afford 21 mg (95%) of Compound 324 as a white solid. Data for Compound 324: $^1$H NMR (400 MHz, acetone-d$_6$) 7.53 (d, J=8.4, 1H), 7.47 (dd, J=9.9, 2.9, 1H), 7.02 (dd, J=8.8, 5.0, 1H), 6.95 (m, 1H), 6.80 (d, J=8.5, 1H), 5.53 (d, J=1.5, 1H), 3.81 (dt, J=9.2, 6.7, 1H), 3.58 (dt, J=9.2, 6.7, 1H), 2.29 (d, J=1.5, 3H), 1.46 (sext, J=6.9, 2H), 1.32 (s, 3H), 1.16 (s, 3H), 0.75 (t, J=7.4, 3H).

EXAMPLE 225

(R/S)-5-Butyl-9-chloro-1,2-dihydro-2,2,4-trimethyl-5H-chromeno[3,4-f]quinoline (Compound 325, structure 42 of Scheme XI, where $R^1$=H, $R^2$=chloro, R=butyl)

This compound was prepared by General Method 5 (EXAMPLE 60) from Compound 209 (38 mg, 0.12 mmol) and 2.5M n-BuLi in hexanes (0.28 mL, 0.70 mmol) to afford 7 mg (16%) of Compound 325 as a clear oil. Data for Compound 325: $^1$H NMR (400 MHz, acetone-d$_6$) 7.72 (d, J=2.4, 1H), 7.58 (d, J=8.5, 1H), 7.12 (dd, J=8.3, 2.5, 1H), 7.05 (d, J=8.5, 1H), 6.75 (d, J=8.5, 1H), 5.53 (s, 1H), 4.82 (t, J=8.0, 1H), 2.40 (m, 2H), 2.09 (s, 3H), 1.5–1.4 (m, 6H ), 1.25 (br s, 6H), 0.95 (t, J=7.8, 3H).

EXAMPLE 226

(R/S)-5-Butyl-1,2-dihydro-9-methoxy-2,2,4-trimethyl-5H-chromeno[3,4-f]quinoline (Compound 326, structure 42 of Scheme XI, where $R^1$=H, $R^2$=methoxy, R=butyl)

This compound (12 mg, 33%) was obtained as a by-product in the formation of Compound 355 (EXAMPLE 255) as a colorless oil. Data for Compound 326: $^1$H NMR (400 MHz, acetone-d$_6$) 7.47 (d, J=8.4, 1H), 7.20 (d, J=2.8, 1H), 6.80 (d, J=8.5, 1H), 6.69 (m, 2H), 5.79 (dd, J=10.3, 3.2, 1H), 5.51 (d, J=1.2, 1H), 3.80 (s, 3H), 2.24 (d, J=1.0, 1H), 1.74 (m, 1H), 1.5–1.3 (m, 5H), 1.27 (s, 3H), 1.18 (s, 3H), 0.84 (t, J=7.5, 3H).

EXAMPLE 227

(R/S)-9-Fluoro-1,2-dihydro-2,2,4,5-tetramethyl-5H-chromeno[3,4-f]quinoline (Compound 327, structure 42 of Scheme XI, where $R^1$=H, $R^2$=fluoro, R=methyl)

This compound was prepared by General Method 5 (EXAMPLE 60) from Compound 207 (36 mg, 0.12 mmol) and 1.4M MeLi in ether (0.45 mL, 0.63 mmol) to afford 6 mg (16%) of Compound 327 as a clear oil. Data for Compound 327: $^1$H NMR (400 MHz, acetone-d$_6$) 7.46 (d, J=8.4, 1H), 7.41 (dt, J=10.0, 1.5, 1H), 6.84 (m, 2H), 6.80 (d, J=8.5, 1H ), 6.07 (q, J=6.5, 1H), 5.53 (d, J=1.4, 1H), 2.25 (d, J=1.1, 3H), 1.32 (d, J=6.5, 3H), 1.26 (s, 3H), 1.20 (s, 3H).

EXAMPLE 228

(R/S)-9-Fluoro-1,2-dihydro-2,2,4-trimethyl-5H-chromeno[3,4-f]quinoline (Compound 328, structure 42 of Scheme XI, where $R^1$=R=H, $R^2$=fluoro)

This compound was prepared in a manner similar to that described for Compound 202 (EXAMPLE 102) from 9-fluoro-1,2-dihydro-5-hydroxy-2,2,4-trimethyl-5H-chromeno[3,4-f]quinoline (EXAMPLE 223) (15 mg) to afford 14 mg (99%) of Compound 328 as a clear glass. Data for Compound 328: $^1$H NMR (400 MHz, acetone-d$_6$) 7.41 (d, J=8.4, 1H), 7.41 (dt, J=10.0, 1.5, 1H), 6.84 (m, 2H), 6.70 (d, J=8.4, 1H ), 5.49 (d, J=1.2, 1H), 5.29 (s, 2H), 2.11 (d, J=1.6, 3H), 1.26 (s, 6H).

EXAMPLE 229

(R/S)-1,2-Dihydro-9-methoxy-2,2,4-trimethyl-5H-chromeno[3,4-f]quinoline (Compound 329, structure 42 of Scheme XI, where $R^1$=R=H, $R^2$=methoxy)

(R/S)-1,2-Dihydro-5-hydroxy-9-methoxy-2,2,4-trimethyl-5H-chromeno[3,4-f]quinoline (structure 46 of Scheme XIV, where $R^1$=H, $R^2$=methoxy)

This compound was prepared in a manner similar to that of 9-chloro-1,2-dihydro-5-hydroxy-2,2,4-trimethyl-5H-chromeno[3,4-f]quinoline (EXAMPLE 219) from Compound 314 (24 mg, 0.075 mmol) to afford 15 mg (62%) of 1,2-dihydro-5-hydroxy-9-methoxy-2,2,4-trimethyl-5H-chromeno[3,4-f]quinoline as a white solid, which was used directly in the next step.

(R/S)-1,2-Dihydro-9-methoxy-2,2,4-trimethyl-5H-chromeno[3,4-f]quinoline (Compound 329, structure 42 of Scheme XI, where $R^1$=R=H, $R^2$=methoxy)

This compound was prepared in a manner similar to that described for Compound 202 (EXAMPLE 102) from 1,2-dihydro-5-hydroxy-9-methoxy-2,2,4-trimethyl-5H-chromeno[3,4-f]quinoline (15 mg) to afford 12 mg (98%) of Compound 329 as a clear glass. Data for Compound 329: $^1$H NMR (400 MHz, acetone-d$_6$) 7.41 (d, J=8.3, 1H), 7.16 (d, J=3.0, 1H), 6.81 (d, J=8.6, 1H), 6.68 (m, 1H), 5.48 (d, J=1.2, 1H), 5.23 (s, 2H), 3.80 (s, 3H), 2.10 (d, J=1.2, 3H), 1.24 (s, 6H).

EXAMPLE 230

(R/S)-1,2-Dihydro-2,2,4,9-tetramethyl-5H-chromeno[3,4-f]quinoline (Compound 330, structure 42 of Scheme XI, where $R^1$=R=H, $R^2$=methyl)

This compound was prepared in a manner similar to Compound 229 (EXAMPLE 229) from Compound 316 (34 mg, 0.11 mmol), to afford 16 mg (50%) of Compound 330 as a clear oil. Data for Compound 330: $^1$H NMR (400 MHz, acetone-d$_6$) 7.42 (m, 1H), 7.41 (d, J=8.4, 1H), 6.90 (m, 1H), 6.76 (d, J=8.0, 1H), 6.64 (d, J=8.4,H), 5.48 (s, 1H), 5.41 (br s, 1H), 5.25 (s, 2H), 2.30 (s, 3H), 2.11 (d, J=1.4, 3H), 1.24 (s, 6H).

EXAMPLE 231

(R/S)-7-Chloro-1,2-dihydro-2,2,4-trimethyl-5H-chromeno[3,4-f]quinoline (Compound 331, structure 93 of Scheme XXIV, where $R^1$=chloro, $R^{2-6}$=H, $R^{7-9}$=methyl)

This compound was prepared in a manner similar to Compound 229 (EXAMPLE 229) from Compound 317 (20 mg, 0.061 mmol) to afford 11 mg (58%) of Compound 331 as a clear oil. Data for Compound 331: $^1$H NMR (400 MHz, acetone-$d_6$) 7.57 (dd, J=7.9, 1.2, $^1$H ), 7.42 (d, J=8.4, 1H), 7.18 (dd, J=7.9, 1.2, 1H), 6.98 (t, J=7.9, 1H), 6.70 (d, J=8.4, 1H), 5.56 (br s, 1H), 5.50 (d, J=1.2, 1H), 5.40 (s, 2H), 2.14 (d, J=1.3, 3H), 1.25 (s, 6H).

EXAMPLE 232

(R/S)-9-Chloro-1,2-dihydro-2,2,4,5-tetramethyl-5H-chromeno[3,4-f]quinoline (Compound 332, structure 42 of Scheme XI, where $R^1$=H, $R^2$=chloro, R=methyl)

This compound was prepared by General Method 5 (EXAMPLE 60) from Compound 209 (40 mg, 0.123 mmol) and methyllithium (438 μl, 0.614 mmol, 1.4M in ether, Aldrich) to afford 8 mg (20%) of Compound 332 as an opaque oil. Data for Compound 332: $^1$H NMR (400 MHz, acetone-$d_6$) 7.65 (d, J=2.5, 1 h), 7.49 (d, J=8.4, 1H ), 7.08 (dd, J=8.5, 2.4, 1H), 6.85 (d, J=8.5, 1H), 6.70 (d, J=8.5, 1H), 6.09 (s, 1H), 5.52 (s, 1H), 2.25 (s, 3H), 1.32 (d, J=6.5, 3H), 1.26 (s, 3H), 1.20 (s, 3H).

EXAMPLE 233

(R/S)-5-(4-Bromophenyl)-9-chloro-1,2-dihydro-2,2,4-trimethyl-5H-chromeno[3,4-f]quinoline (Compound 333, structure 42 of Scheme XI, where R=4-bromophenyl, $R^1$=H, $R^2$=Cl)

This compound was prepared by General Method 5 (EXAMPLE 60) from Compound 209 (40 mg, 0.123 mmol) and 1,4-dibromobenzene (203 mg, 0.859 mmol) to afford 11 mg (19%) of Compound 333 as a pale cream colored oil. Data for Compound 333: $^1$H NMR (400 MHz, acetone-$d_6$) 7.59 (d, J=2.4, 1H), 7.58 (d, J=6.3, 1H), 7.42 (d, J=8.5, 2H), 7.16 (d, J=8.5, 2H), 6.94 (dd, J=8.2, 4.2, 1H), 6.92 (s, 1H), 6.84 (d, J=8.4, 1H), 6.77 (d, J=8.4, 1H), 5.68 (br s, 1H), 5.48 (s, 1H), 1.98 (s, 3H), 1.27 (s, 3H), 1.24 (s, 3H).

EXAMPLE 234

(R/S)-9-Chloro-5-(3-chlorophenyl)-1,2-dihydro-2,2,4-trimethyl-5H-chromeno[3,4-f]quinoline (Compound 334, structure 42 of Scheme XI, where R=3-chlorophenyl, $R^1$=H, $R^2$=Cl)

This compound was prepared by General Method 5 (EXAMPLE 60) from Compound 209 (40 mg, 0.123 mmol) and 3-bromochlorobenzene (164 mg, 0.856 mmol) to afford 9 mg (17%) of Compound 334 as a pale yellow oil. Data for Compound 334: $^1$H NMR (400 MHz, acetone-$d_6$) 7.61 (d, J=2.3, 1H), 7.59 (d, J=9.0, 1H), 7.25 (m, 4H), 6.95 (m, 2H), 6.85 (d, J=8.3, 1H), 6.83 (d, J=7.3, 1H), 5.72 (br s, 1H), 5.50 (s, 1H), 2.00 (s, 3H), 1.28 (s, 3H), 1.26 (s, 3H).

EXAMPLE 235

(R/S)-9-Chloro-1,2-dihydro-2,2,4-trimethyl-5-(3-methylphenyl)-5H-chromeno3,4-f]quinoline (Compound 335, structure 42 of Scheme XI, where R=3-methylphenyl, $R^1$=H, $R^2$=Cl)

This compound was prepared by General Method 5 (EXAMPLE 60) from Compound 209 (20 mg, 0.061 mmol) and 3-bromotoluene (147 mg, 0.859 mmol) to afford 10 mg (41%) of Compound 335 as a pale white oil. Data for Compound 335: $^1$H NMR (400 MHz, acetone-$d_6$) 7.59 (d, J=2.4, 1H), 7.58 (d, J=9.1, 1H), 7.19 (m, 2H), 6.95 (m, 3H), 6.83 (d, J=8.5, 1H), 6.78 (d, J=8.5, 1H), 5.64 (brs, 1H), 5.81 (s, 1H), 2.20 (s, 3H), 2.05 (s, 3H), 1.27 (s, 3H), 1.24 (s, 3H).

EXAMPLE 236

(R/S)-9-Chloro-5-(4-chloro-3-methylphenyl)-1,2-dihydro-2,2,4-trimethyl-5H-chromeno[3,4-f]quinoline (Compound 336, structure 42 of Scheme XI, where R=4-chloro-3-methylphenyl, $R^1$=H, $R^2$=Cl)

This compound was prepared by General Method 5 (EXAMPLE 60) from Compound 209 (20 mg, 0.061 mmol) and 5-bromo-2-chlorotoluene (177 mg, 0.859 mmol) to afford 9 mg (34%) of Compound 336 as a cream colored oil. Data for Compound 336: $^1$H NMR (400 MHz, acetone-$d_6$) 7.60 (d, J=2.4, 1H), 7.57 (d, J=8.5, $^1$H ), 7.23 (m, 2H), 7.00 (m, 2H), 6.91 (s, 1H), 6.84 (d, J=8.2, 1H), 6.79 (d, J=8.5, 1H), 5.68 (br s, 1H), 5.48 (ds, 1H), 2.23 (s, 3H), 1.99 (s, 3H), 1.27 (s, 3H), 1.25 (s, 3H).

EXAMPLE 237

(R/S)-9-Chloro-1,2-dihydro-5-[3-(trifluoromethyl)phenyl]-2,2,4-trimethyl-5H-chromeno[3,4-f]quinoline (Compound 337, structure 42 of Scheme XI, where R=3-(trifluoromethyl)phenyl, $R^1$=H, $R^2$=Cl)

This compound was prepared by General Method 5 (EXAMPLE 60) from Compound 209 (40 mg, 0.123 mmol) and 3-bromobenzotrifluoride (276 mg, 1.23 mmol) to afford 11 mg (20%) of Compound 337 as a cream colored oil. Data for Compound 337: $^1$H NMR (400 MHz, acetone-$d_6$) 7.61 (d, J=2.3, 1H), 7.52 (m, 4H), 7.07 (s, 1H), 6.99 (dd, J=8.5, 2.4, 1H), 6.87 (d, J=8.3 1H), 6.84 (d, J=8., 1H), 5.73 (br s, 1H), 5.51 (s, 1H), 2.01 (s, 3H), 1.27 (s, 6H).

EXAMPLE 238

(R/S)-9-Chloro-5-(3,5-dichlorophenyl)-1,2-dihydro-2,2,4-trimethyl-5H-chromeno[3,4-f]quinoline (Compound 338, structure 42 of Scheme XI, where R=3,5-dichlorophenyl, $R^1$=H, $R^2$=Cl)

This compound was prepared by General Method 5 (EXAMPLE 60) from Compound 209 (40 mg, 0.123 mmol) and 1-bromo-3,5-dichlorobenzene (277 mg, 1.23 mmol) using diethyl ether for the formation of the aryl lithium in the first step. The final step afforded 11 mg (20%) of Compound 338 as a pale yellow oil. Data for Compound 338: $^1$H NMR (400 MHz, acetone-$d_6$) 7.64 (d, J=2.3, 1H), 7.61 (d, J=8.5, 1H), 7.32 (s, 1H), 7.20 (s, 1H), 7.19 (s, 1H), (dd, J=8.9, 2.4, 1H), 6.91 (s, 1H), 6.89 (d, J=6.7, 1H), 6.88 (d, J=6.7, 1H), 5.78 (br s, 1H), 5.53 (s, 1H), 2.03 (s, 3H), 1.28 (s, 3H), 1.27 (s, 3H).

EXAMPLE 239

(R/S)-9-Chloro-1,2-dihydro-5-(4-methoxyphenyl)-2,2,4-trimethyl-5H-chromeno[3,4-f]quinoline (Compound 339, structure 42 of Scheme XI, where R=4-methoxyphenyl, $R^1$=H, $R^2$=Cl)

This compound was prepared by General Method 5 (EXAMPLE 60) from Compound 209 (40 mg, 0.123 mmol) and 4-bromoanisole (230 mg, 1.23 mmol) to afford 11 mg (21%) of Compound 339 as a pale yellow oil. Data for Compound 339: $^1$H NMR (400 MHz, acetone-$d_6$) 7.59 (d, J=2.5, 1H), 7.56 (d, J=8.5, 1H), 7.11 (d, J=8.7, 2H), 6.94 (dd, J=8.5, 2.4, 1H), 6.89 (s, 1H), 6.82 (d, J=8.5, 1H), 6.75 (m, 3H), 5.61 (br s, 1H), 5.45 (s, 1H), 3.69 (s, 3H), 1.99 (s, 3H), 1.26 (s, 3H), 1.23 (s, 3H).

EXAMPLE 240

(R/S)-9-Chloro-5-(3-fluoro-4-methoxyphenyl)-1,2-dihydro-2,2,4-trimethyl-5H-chromeno[3,4-f]quinoline (Compound 340, structure 42 of Scheme XI, where R=3-fluoro-4-methoxyphenyl, $R^1$=H, $R^2$=Cl)

This compound was prepared by General Method 5 (EXAMPLE 60) from Compound 209 (20 mg, 0.061 mmol) and 4-bromo-2-fluoroanisole (88 mg, 0.429 mmol) to afford 8 mg (29%) of Compound 340 as a pale yellow oil. Data for Compound 340: $^1$H NMR (400 MHz, acetone-$d_6$) 7.60 (d, J=2.4, 1H), 7.58 (d, J=8.5, 1H), 7.02 (dd, J=10.2, 2.4, 1H), 6.97 (dd, J=8.5, 2.3, 1H), 6.94 (d, J=8.5, 1H), 6.90 (s, 1H), 6.89 (m, 1H), 6.84 (d, J=8.5, 1H), 6.79 (d, J=8.5, 1H), 5.68 (br s, 1H), 5.48 (s, 1H), 3.79 (s, 3H), 2.00 (s, 3H), 1.27 (s, 3H), 1.24 (s, 3H).

EXAMPLE 241

(R/S)-9-Chloro-5-(4-fluorophenyl)-1,2-dihydro-2,2,4-trimethyl-5H-chromeno[3,4-f]quinoline (Compound 341, structure 42 of Scheme XI, where R=4-fluorophenyl, $R^1$=H, $R^2$=Cl)

This compound was prepared by General Method 5 (EXAMPLE 60) from Compound 209 (40 mg, 0.123 mmol) and 4-fluorophenyl magnesium bromide (1 ml, 1.03 mmol, 1M, Aldrich) to afford 11 mg (22%) of Compound 341 as a pale yellow oil. Data for Compound 341: $^1$H NMR (400 MHz, acetone-$d_6$) 7.60 (d, J=2.4, 1H), 7.58 (d, J=7.3, 1H), 7.24 (m, 2H), 6.96 (m, 4H), 6.84 (d, J=8.3, 1H), 5.67 (br s, 1H), 5.48 (s, 1H), 1.98 (s, 3H), 1.26 (s, 3H), 1.24 (s, 3H).

EXAMPLE 242

(R/S)-9-Chloro-5-(3-chloro-4-methoxy-5-methylphenyl)-1,2-dihydro-2,2,4-trimethyl-5H-chromeno[3,4-f]quinoline (Compound 342, structure 42 of Scheme XI, where R=3-chloro-4-methoxy-5-methylphenyl, $R^1$=H, $R^2$=Cl)

This compound was prepared by General Method 5 (EXAMPLE 60) from Compound 209 (40 mg, 0.123 mmol) and 4-bromo-2-chloro-5-methylanisole (181 mg, 0.770 mmol) to afford 12 mg (21%) of Compound 342 as a pale yellow oil. Data for Compound 342: $^1$H NMR (400 MHz, acetone-$d_6$) 7.61 (d, J=2.4, 1H), 7.58 (d, J=8.4, 1H), 7.03 (m, 1H), 6.99 (dd, J=8.5, 2.4, 2H), 6.91 (s, 1H), 6.84 (dd, J=8.3, 3.8, 2H), 5.69 (br s, 1H), 5.49 (s, 1H), 3.70 (s, 3H), 2.18 (s, 3H), 2.01 (s, 3H), 1.27 (s, 3H), 1.26 (s, 3H).

EXAMPLE 243

(R/S)-9-Chloro-5-(4-fluoro-3-methylphenyl)-1,2-dihydro-2,2,4-trimethyl-5H-chromeno[3,4-f]quinoline (Compound 343, structure 42 of Scheme XI, where R=4-fluoro-3-methylphenyl, $R^1$=H, $R^2$=Cl)

This compound was prepared by General Method 5 (EXAMPLE 60) from Compound 209 (40 mg, 0.123 mmol) and 4-fluoro-3-phenyl magnesium bromide (1 ml, 1.026 mmol, 1M, Aldrich) to afford 8 mg (16%) of Compound 343 as a pale yellow oil. Data for Compound 343: $^1$H NMR (400 MHz, acetone-$d_6$) 7.59 (d, J=2.6, 1H), 7.57 (d, J=8.6, 1H), 7.12 (d, J=8.1, 1H), 6.99 (m, 1H), 6.96 (dd, J=8.2, 2.4, 1H), 6.90 (m, 1H), 6.84 (d, J=8.3, 1H), 6.77 (d, J=8.5, 1H), 5.68 (br s, 1H), 5.48 (s, 1H), 2.14 (s, 3H), 1.25 (s, 3H), 1.24 (s, 3H).

EXAMPLE 244

(R/S)-9-Chloro-5-(3-fluorophenyl)-1,2-dihydro-2,2,4-trimethyl-5H-chromeno[3,4-f]quinoline (Compound 344, structure 42 of Scheme XI, where R=3-fluorophenyl, $R^1$=H, $R^2$=Cl)

This compound was prepared by General Method 5 (EXAMPLE 60) from Compound 209 (40 mg, 0.123 mmol) and 1-bromo-3-fluorobenzene (150 mg, 0.860 mmol) to afford 11 mg (22%) of Compound 344 as a pale yellow oil. Data for Compound 344: $^1$H NMR (400 MHz, acetone-$d_6$) 7.61 (d, J=2.4, 1H), 7.59 (d, J=8.4, 1H), 7.29 (m, 1H), 7.04 (d, J=7.9, 1H), 6.97 (m, 4H), 6.85 (d, J=8.5, 1H), 6.80 (d, J=8.5, 1H), 5.7 (br s, 1H), 5.50 (s, 1H), 2.01 (s, 3H), 1.27 (s, 3H), 1.25 (s, 3H).

EXAMPLE 245

(R/S)-1,2-Dihydro-2,2,4-trimethyl-5-[(3,4-methylenedioxy)phenyl]-5H-chromeno[3,4]-fquinoline (Compound 345, structure 32 of Scheme IX, where R=3,4-(methylenedioxy)phenyl This compound was prepared by the General Procedure 5 (EXAMPLE 60) from 4-bromo-1,2-(methylenedioxy)benzene (201 mg, 1.0 mmol) and Compound 159 (15 mg, 0.05 mmol) to afford 1.5 mg (8%) of Compound 345 as a colorless oil. Data for Compound 345: $^1$H NMR (400 MHz, acetone-$d_6$) 7.60 (d, J=7.6, 1H), 7.55 (d, J=8.4, 1H), 6.98 (t, J=7.6, 1H), 6.88–6.60 (m, 6H), 5.98 (s, 1H), 5.91 (s, 2H), 5.51 (bs, 1H), 5.46 (s, 1H), 2.02 (s, 3H), 1.25 (s, 3H), 1.23 (s, 3H).

EXAMPLE 246

(R/S)-5-(4-Chloro-3-methylphenyl)-1,2-dihydro-2,2,4-trimethyl-5H-chromeno[3,4]-fquinoline (Compound 346, structure 32 of Scheme IX, where R=4-chloro-3-methylphenyl)

This compound was prepared by the General Method 5 (EXAMPLE 60) from 5-bromo-2-chlorotoluene (206 mg, 1.0 mmol) and Compound 159 (10 mg, 0.03 mmol) to afford 8.0 mg (67%) of Compound 346 as a colorless oil. Data for Compound 346: $^1$H NMR (400 MHz, acetone-$d_6$) 7.60 (d, J=7.6, 1H), 7.55 (d, J=8.4, 1H), 7.23–7.19 (m, 2H), 7.01 (d, J=9.9, 1H), 6.97 (d, J=7.7, 1H), 6.89 (s, 1H), 6.88–6.81 (m, 2H), 6.78 (d, J=8.0, 1H), 5.55 (bs, 1H), 5.48 (s, 1H), 2.22 (s, 3H), 2.00 (s, 3H), 1.26 (s, 3H), 1.24 (s, 3H).

EXAMPLE 247

(R/S)-5-(4-Bromo-3-pyridyl)-1,2,3,4-tetrahydro-2,2-dimethyl-4-methylidene-5H-chromeno[3,4-f]quinoline (Compound 347, structure 33 of Scheme IX, where R=4-bromo-3-pyridyl)

This compound (1.8 mg, 3%) was obtained as a colorless oil along with Compound 197 as described above (EXAMPLE 97). Data for Compound 347: $^1$H NMR (400 MHz, CDCl$_3$) 8.22 (d, J=5.2, 1H), 7.56–7.49 (m, 2H), 7.34 (s, 1H), 7.12 (d, J=6.5, 1H), 7.03 (td, J=7.4, 1.3, 1H), 6.92 (td, J=7.4, 1.3, 1H), 6.86 (d, J=7.5, 1H), 6.61 (d, J=8.2, 1H), 6.58 (s, 1H), 4.98 (s, 1H), 4.52 (s, 1H), 2.43 (d, J=14.5, 1H), 2.22 (d, J=14.5, 1H), 1.34 (s, 3H), 1.17 (s, 3H).

EXAMPLE 248

(R/S)-5-(3,5-Difluorophenyl)-1,2-dihydro-2,2,4-trimethyl-5H-chromeno[3,4-f]quinoline (Compound 348, structure 32 of Scheme IX, where R=3,5-difluorophenyl)

This compound was prepared by the General Method 5 (EXAMPLE 60) from 1-bromo-3,5-difluorobenzene (193 mg, 1.0 mmol) and Compound 159 (20 mg, 0.07 mmol) to afford 14 mg (53%) of Compound 348 as a colorless oil.

Data for Compound 348: $^1$H NMR (400 MHz, acetone-d$_6$) 7.63 (d, J=7.6, 1H), 7.58 (d, J=8.4, 1H), 7.03 (t, J=7.7, 1H), 6.95 (s, 1H), 6.94–6.83 (m, 6H), 5.62 (bs, 1H), 5.11 (s, 1H), 2.04 (s, 3H), 1.27 (s, 3H), 1.26 (s, 3H).

EXAMPLE 249

(R/S)-5-(3,5-Dichlorophenyl)-1,2-dihydro-2,2,4-trimethyl-5H-chromeno[3,4-f]quinoline (Compound 349, structure 32 of Scheme IX, where R=3,5-dichlorophenyl)

This compound was prepared by the General Method 5 (EXAMPLE 60) from 1-bromo-3,5-dichlorobenzene (226 mg, 1.0 mmol) and Compound 159 (15 mg, 0.05 mmol) to afford 20 mg (95%) of Compound 249 as a colorless oil. Data for Compound 349: IR (neat) 3350, 2940, 1690, 1590, 1480, 1070; $^1$H NMR (400 MHz, acetone-d$_6$) 7.63 (d, J=7.7, 1H), 7.58 (d, J=8.4, 1H), 7.29 (t, J=1.9, 1H), 7.20 (d, J=1.9, 2H), 7.03 (t, J=7.7, 1H), 6.97 (s, 1H), 6.93–6.85 (m, 3H), 5.63 (bs, 1H), 5.53 (s, 1H), 2.04 (s, 3H), 1.28 (s, 3H), 1.27 (s, 3H); $^{13}$C NMR (100 MHz, acetone-d$_6$) 151.0, 147.3, 145.7, 135.5, 135.1, 135.0, 129.0, 128.8, 128.6, 128.4, 127.8, 125.3, 124.6, 123.2, 123.0, 120.3, 119.7, 118.3, 116.4, 116.3, 74.9, 51.2, 24.0.

EXAMPLE 250

(R/S) -5-(3-Bromo-5-methylphenyl)-1,2-dihydro-2,2,4-trimethyl-5H-chromeno[3,4-f]quinoline (Compound 350, structure 32 of Scheme IX, where R=3-bromo-5-methylphenyl)

This compound was prepared by the General Method 5 (EXAMPLE 60) from 3,5-dibromotoluene (250 mg, 1.0 mmol) and Compound 159 (10 mg, 0.03 mmol) to afford 6.1 mg (46%) of Compound 350 as a colorless oil. Data for Compound 350: $^1$H NMR (400 MHz, acetone-d$_6$)7.61 (d, J=7.7, 1H), 7.56 (d, J=8.4, 1H), 7.17 (s, 1H), 7.14 (s, 1H), 7.10 (s, 1H), 7.01 (t, J=7.7, 1H), 6.91 (s, 1H), 6.90–6.82 (m, 3H), 5.58 (bs, 1H), 5.50 (s, 1H), 2.21 (s, 3H), 2.02 (s, 3H), 1.27 (s, 3H), 1.26 (s, 3H).

EXAMPLE 251

(R/S)-5-(3-Bromo-5-fluorophenyl)-1,2-dihydro-2,2,4-trimethyl-5H-chromeno[3,4-f]quinoline (Compound 351, structure 32 of Scheme IX, where R=3-bromo-5-fluorophenyl)

This compound was prepared by the General Method 5 (EXAMPLE 60) from 1,3-dibromo-5-fluorobenzene (254 mg, 1.0 mmol) and Compound 159 (10 mg, 0.03 mmol) to afford 6.2 mg (46%) of Compound 351 as a white powder, along with 0.7 mg (5%) of Compound 352 (EXAMPLE 252). Data for Compound 351: mp 82°–84° C.; IR (neat) 3367, 1699, 1595, 1581, 1469, 1435, 1251; $^1$H NMR (400 MHz, acetone-d$_6$) 7.63 (d, J=7.7, 1H), 7.58 (d, J=8.4, 1H), 7.23 (d, J=5.2, 1H), 7.20 (s, 1H), 7.08–7.02 (m, 2H), 6.97 (s, 1H), 6.94–6.85 (m, 3H), 5.64 (bs, 1H), 5.53 (s, 1H), 2.04 (s, 3H), 1.28 (s, 3H), 1.27 (s, 3H); $^{13}$C NMR (100 MHz, acetone-d$_6$) 163.4 (d, J=250 Hz), 151.1, 147.3, 146.4 (d, J=7.0 Hz), 135.0, 129.1, 128.8, 128.4, 128.3, 125.3, 124.6, 123.2, 123.0, 122.9, 120.4, 119.7, 119.2 (d, J=24.8 Hz), 118.3, 116.4, 115.2 (d, J=22.2 Hz), 74.9, 51.2, 29.4, 24.0.

EXAMPLE 252

(R/S)-5-(3-Bromo-5-fluorophenyl)-1,2,3,4-tetrahydro-2,2-dimethyl-4-methylidene-5H-chromeno[3,4-f]quinoline (Compound 352, structure 33 of Scheme IX, where R=3-bromo-5-fluorophenyl)

The compound (0.7 mg, 5%) was obtained along with Compound 351 as described above (EXAMPLE 251) as a colorless oil. Data for Compound 352: $^1$H NMR (400 MHz, CDCl$_3$) 7.54 (d, J=7.7, 1H), 7.51 (d, J=8.4, 1H), 7.24 (d, J=5.5, 1H), 7.06–6.84 (m, 5), 6.60 (d, J=8.4, 1H), 6.57 (s, 1H), 4.96 (s, 1H), 4.56 (s, 1H), 4.01 (bs, 1H), 2.42 (d, J=12.3, 1H), 2.21 (d, J=12.3, 1H), 1.34 (s, 3H), 1.15 (s, 3H).

EXAMPLE 253

(R/S)-5-[4-Fluoro-3-(trifluoromethyl)phenyl]-1,2-dihydro-2,2,4-trimethyl-5H-chromeno[3,4-f]quinoline (Compound 353, structure 32 of Scheme IX, where R=4-fluoro-3-(trifluoromethyl)phenyl)

This compound was prepared by the General Method 5 (EXAMPLE 60) from 5-bromo-2-fluorobenzotrifluoride (243 mg, 1.0 mmol) and Compound 159 (10 mg, 0.03 mmol) to afford 3.5 mg (27%) of Compound 353 as a colorless oil. Data for Compound 353: $^1$H NMR (400 MHz, acetone-d$_6$) 7.62 (d, J=7.7, 1H), 7.61–7.53 (m, 3H), 7.27 (t, J=7.7, 1H), 7.04–6.82 (m, 5H), 5.62 (bs, 1H), 5.51 (s, 1H), 2.02 (s, 3H), 1.26 (s, 6H).

EXAMPLE 254

(R/S)-9-Fluoro-1,2-dihydro-2,2,4-trimethyl-5-(3-methylphenyl)-5H-chromeno[3,4-f]quinoline (Compound 354, structure 42 of Scheme XI, where R=3-methylphenyl, R$^1$=H, R$^2$=F)

This compound was prepared by General Method 5 (EXAMPLE 60) from Compound 207 (31 mg, 0.10 mmol) and 3-bromotoluene (90 mL, 0.74 mmol) to afford 18 mg (46%) of Compound 354 as a colorless glass. Data for Compound 354: $^1$H NMR (400 MHz, acetone-d$_6$) 7.53 (d, J=8.5, 1H), 7.33 (dd, J=9.9, 2.9, 1H), 7.08 (m, 2H), 6.98 (d, J=6.7, 2H), 6.89 (s, 1H), 6.83 (d, J=8.5, 1H), 6.75 (m, 2H), 5.48 (s, 1H), 2.20 (s, 3H), 1.99 (s, 3H), 1.27 (s, 3H), 1.25 (s, 3H).

EXAMPLE 255

(R/S)-1,2-Dihydro-9-methoxy-2,2,4-trimethyl-5-(3-methylphenyl)-5H-chromeno[3,4-f]quinoline (Compound 355, structure 42 of Scheme XI, where R=3-methylphenyl, R$^1$=H, R$^2$=methoxy)

This compound was prepared by General Method 5 (EXAMPLE 60) from Compound 314 (32 mg, 0.10 mmol) and 3-bromotoluene (90 mL, 0.74 mmol) to afford 10 mg (25%) of Compound 355 as a colorless glass. Data for Compound 355: $^1$H NMR (400 MHz, acetone-d$_6$) 7.53 (d, J=8.5, 1H), 7.13 (d, J=2.8, 1H), 7.08 (m, 2H), 6.99 (m, 2H), 6.83 (d, J=6.0, 1H), 6.80 (s, 1H), 6.70 (d, J=8.7, 1H), 6.55 (dd, J=8.7, 2.8, 1H), 5.46 (d, J=1.2, 1H), 3.72 (s, 3H), 2.24 (s, 3H), 1.98 (s, 3H), 1.26 (s, 3H), 1.24 (s, 3H).

EXAMPLE 256

(R/S)-9-Fluoro-5-(3-fluoro-4-methoxyphenyl)-1,2-dihydro-2,2,4-trimethyl-5H-chromeno[3,4-f]f]quinoline (Compound 356, structure 42 of Scheme XI, where R=3-fluoro-4-methoxyphenyl, R$^1$=H, R$^2$=F)

This compound was prepared by General Method 5 (EXAMPLE 60) from Compound 207 (41 mg, 0.12 mmol) and 4-bromo-3-fluoroanisole (0.13 mL, 1.0 mmol) to afford 11 mg (20%) of Compound 356 as a yellow oil. Data for Compound 356: $^1$H NMR (400 MHz, acetone-d$_6$) 7.55 (d, J=8.5, 1H), 7.35 (dd, J=10.0, 2.8, 1H), 7.01 (dd, J=12.5, 1.9, 1H), 6.95 (t, J=6.9, 1H), 6.87 (m, 3H), 6.74 (m, 2H), 5.48 (d, J=1.2, 1H), 3.79 (s, 3H), 1.97 (s, 3H), 1.27 (s, 3H), 1.24 (s, 3H). 3H).

EXAMPLE 257

(R/S)-9-Fluoro-1,2-dihydro-2,2,4-trimethyl-5-[3-(trifluoromethyl)phenyl]-5H-chromeno[3,4-f]quinoline (Compound 357, structure 42 of Scheme XI, where R=3-(trifluoromethyl)phenyl, R$^1$=H, R$^2$=F)

This compound was prepared by General Method 5 (EXAMPLE 60) from Compound 207 (40 mg, 0.12 mmol) and 3-bromobenzotrifluoride (0.14 mL, 1.0 mmol) to afford 11 mg (20%) of Compound 357 as a yellow oil. Data for Compound 357: $^1$H NMR (400 MHz, acetone-d$_6$) 7.54 (d, J=8.5, 1H), 7.35 (dd, J=9.9, 2.9, 1H), 7.10 (m, 2H), 6.98 (d, J=6.7, 2H), 6.89 (s, 1H), 6.85 (d, J=8.5, 1H), 6.75 (m, 2H), 5.48 (s, 1H), 1.99 (s, 3H), 1.27 (s, 3H), 1.25 (s, 3H).

EXAMPLE 258

(R/S)-9-Fluoro-5-(4-fluoro-3-methylphenyl)-1,2-dihydro-2,2,4-trimethyl-5H-chromeno[3,4-f]quinoline (Compound 358, structure 42 of Scheme XI, where R=4-fluoro-3-methylphenyl, R$^1$=H, R$^2$=F)

This compound was prepared by General Method 5 (EXAMPLE 60) from Compound 207 (38 mg, 0.12 mmol) and 1.0M 4-fluoro-3-methylphenyl magnesium chloride in THF (Aldrich) to afford 25 mg (51%) of Compound 358 as a yellow oil. Data for Compound 358: $^1$H NMR (400 MHz, acetone-d$_6$) 7.54 (d, J=8.4, 1H), 7.34 (dd, J=10.0, 2.8, 1H), 7.14 (m, 1H), 7.00 (m, 1H), 6.91 (d, J=9.6, 1H), 6.88 (s, 1H), 6.83 (d, J=8.4, 1H), 6.79–6.68 (m, 2H), 5.48 (s, 1H), 2.13 (s, 3H), 1.99 (s, 3H), 1.27 (s, 3H), 1.24 (s, 3H).

EXAMPLE 259

(Z)-5-(2, 4-Difluorobenzylidene)-1,2-dihydro-2,2,4-trimethyl-5H-chromeno[3,4-f]quinoline (Compound 359, structure 45 of Scheme XIII, where R$^1$=R$^2$=H, R$^3$=2,4-difluorophenyl)

This compound was prepared by General Method 6 (EXAMPLE 119) from 2, 4-difluorobenzyl bromide (0.27 ml, 2.10 mmol) and compound 159 (20 mg, 0.07 mmol) to afford 16 mg (56%) of Compound 359 as a yellow oil. Data for Compound 359: Rf=0.44 (silica gel, 25% EtOAc:hex); $^1$H NMR(400 MHz, acetone-d$_6$) 8.43 (m, 1H), 7.86 (d, J=8.5, 1H), 7.67 (d, J=8.5, 1H), 7.20 (m, 2H), 7.11 to 7.03 (m, 3H), 6.86 (d, J=8.5, 1H), 5.88 (s, 1H), 5.55 (s, 1H), 2.11 (s, 3H), 1.29 (brs, 6H).

EXAMPLE 260

(Z)-5-(3,4-Difluorobenzylidene)-1,2-dihydro-2,2,4-trimethyl-5H-chromeno[3,4-f]quinoline, (Compound 360, structure 45 of Scheme XIII, where R$^1$=R$^2$=H, R$^3$=3,4-difluorophenyl)

This compound was prepared by General Method 6 (EXAMPLE 119) from 3,4-difluorobenzyl bromide (0.27 ml, 2.10 mmol) and Compound 159 (20 mg, 0.07 mmol) to afford 20 mg (70%) of Compound 360 as a yellow oil. Data for Compound 360: Rf=0.44 (silica gel, 25% EtOAc:hex); $^1$H NMR (400 MHz, acetone-d$_6$) 7.83 (m, 2H), 7.66 (d, J=8.5, 1H), 7.55 (m, 1H), 7.31 (m, 1H), 7.24 (m, 2H), 7.10 (m, 1H), 6.85 (d, J=8.5, 1H), 5.67 (s, 1H), 5.55 (s, 1H), 2.08 (s, 3H), 1.28 (brs, 6H).

EXAMPLE 261

(Z)-5-(3-Fluorobenzylidene)-1,2,3,4-tetrahydro-2,2,4-trimethyl-5H-chromeno[3,4-f]quinoline (Compound 361, structure xx of Scheme XXX, where R$^1$=R$^2$=H, R$^3$=3-difluorophenyl)

A solution of Compound 159 (20 mg, 0.07 mmol) in EtOAc (10 ml) was stirred over 10% Pd/C (5 mg) at rt under an atmosphere of H$_2$ (1 atm) for 15 h. The reaction mixture was filtered then concentrated in vacuo to afford 14 mg (70%) of the 1,2,3,4-tetrahydro-2,2,4-trimethyl-5H-coumarino[3,4-e]quinoline as a yellow solid. According to General Method 6 (EXAMPLE 119), from 3-fluorobenzyl chloride (0.17 ml, 1.40 mmol) and 1,2,3,4-tetrahydro-2,2,4-trimethyl-5H-coumarino[3,4-e]quinoline (14 mg, 0.05 mmol) was obtained 8.6 mg (46%) of Compound 361 as a yellow solid. Data for Compound 361: Rf=0.38 (silica gel, 25% EtOAc:hex); $^1$H NMR (400 MHz, acetone-d$_6$) 7.82 (d, J=8.5, 1H), 6.69 (m, 1H), 7.62 (d, J=8.5, 1H), 7.58 (d, J=8.5, 1H), 7.40 (m, 1H), 7.22 (m, 2H), 7.08 (m, 1H), 6.97 (m, 1H), 6.74 (d, J=8.5, 1H), 6.24 (s, 1H), 5.30 (brs, 1H), 3.76 (m, 1H), 1.97 (m, 1H), 1.55 (m, 1H), 1.40 (d, J=6.6, 3H), 1.30 (s, 3H), 1.26 (s, 3H).

EXAMPLE 262

(Z)-5-(2, 6-Difluorobenzylidene)-1,2-dihydro-2,2,4-trimethyl-5H-chromeno[3,4-f]quinoline (Compound 362, structure 45 of Scheme XIII, where R$^1$=R$^2$=H, R$^3$=2, 6-difluorophenyl)

This compound was prepared by General Method 6 (EXAMPLE 119) from α-bromo-2, 3-difluorotoluene (0.43 g, 2.1 mmol) and Compound 159 (20 mg, 0.07 mmol) to afford 4.4 mg (16%) of Compound 362 as a yellow oil. Data for Compound 362: Rf=0.45 (silica gel, 25% EtOAc:hex); $^1$H NMR (400 MHz, acetone-d$_6$) 7.83 (d, J=8.5, 1H), 7.68 (d, J=8.5, 1H), 7.35 (m, 1H), 7.15 (m, 1H), 7.04 (m, 3H), 6.90 (d, J=8.5H, 1H), 6.87 (d, J=8.5, 1H), 5.61 (s, 1H), 5.57 (s, 1H), 2.23 (s, 3H), 1.32 (brs, 6H).

EXAMPLE 263

(Z)-1,2,-Dihydro-5-(2-methylbenzylidene)-2,2,4-trimethyl-5H-chromeno[3,4-f]quinoline (Compound 363, structure 45 of Scheme XIII, where R$^1$=R$^2$=H, R$^3$=2-methylphenyl)

This compound was prepared by General Method 6 (EXAMPLE 119) from α-chloro-o-xylene (0.20 ml, 1.6 mmol) and Compound 159 (15 mg, 0.05 mmol) to afford 15 mg (76%) of Compound 363 as a yellow oil. Data for Compound 363: Rf=0.45 (silica gel, 25% EtOAc:hex); $^1$H NMR (400 MHz, acetone-d$_6$) 8.22 (d, J=8.5, 1H), 7.82 (d, J=8.5, 1H), 7.64 (d, J=8.5, 1H), 7.26 to 7.04 (m, 6H), 6.83 (d, J=8.5, 1H), 5.94 (s, 1H), 5.54 (s, 1H), 2.28 (s, 3H), 2.15 (s, 3H), 1.25 (brs, 6H).

EXAMPLE 264

(Z)-1,2-Dihydro-5-(2, 4, 6-trimethylbenzylidene)-2,2,4-trimethyl-5H-chromeno[3,4fquinoline (Compound 364, structure 45 of Scheme XIII, where R$^1$=R$^2$=H, R$^3$=2,4,6-trimethylphenyl)

This compound was prepared by General Method 6 (EXAMPLE 119) from α-chloroisodurene (0.50 g, 3.0 mmol) and Compound 159 (30 mg, 0.10 mmol) to afford 20 mg (50%) of Compound 364 as a yellow oil. Data for Compound 364: Rf=0.40 (silica gel, 25% EtOAc:hex); $^1$H NMR (400 MHz, CDCl$_3$) 7.65 (d, J=8.5, 1H), 7.51 (d, J=8.5, 1H), 7.15 (t, J=8.5, 1H), 6.93 (t, J=8.5, 1H), 6.88 (s, 2H), 6.80 (d, J=8.5, 1H), 6.65 (d, J=8.5, 1H), 5.69 (s, 1H), 5.50 (s, 1H), 3.73 (brs, 1H), 2.28 (s, 6H), 2.26 (s, 3H), 2.16 (s, 3H), 1.45 (brs, 6H).

EXAMPLE 265

(Z)-9-Chloro-5-(2,5-difluorobenzylidene)-1,2-dihydro-2,2,4-trimethyl-5H-chromeno[3,4-f]quinoline (Compound 365, structure 45 of Scheme XIII, where R$^1$=H, R$^2$=Cl, R$^3$=2, 5-difluorophenyl)

This compound was prepared by General Method 6 (EXAMPLE 119) from Compound 209 (40 mg, 0.123 mmol) and a-bromo-2, 5-difluorotoluene (414 mg, 2.0 mmol) to afford 10 mg (19%) of Compound 365 as a yellow oil. Data for Compound 365: $^1$H NMR (400 MHz, acetone-$d_6$) 8.05 (m, 1H), 7.87 (s, 1H), 7.72 (d, J=8.5, 1H), 7.26 (m, 1H), 7.19 (m, 1H), 7.06 (m, 1H, 6.90 (d, J=8.5, 1H), 5.94 (s, 1H), 5.57 (s, 1H), 2.11 (s, 3H), 1.32 (br s, 6H).

EXAMPLE 266

(Z)-5-Benzylidene-9-chloro-1,2-dihydro-2,2,4-trimethyl-5H-chromeno[3,4-f]quinoline (Compound 366, structure 45 of Scheme XIII, where $R^1$=H, $R^2$=Cl, $R^3$=phenyl)

This compound was prepared by General Method 6 (EXAMPLE 119) from Compound 209 (40 mg, 0.123 mmol) and benzyl magnesium chloride (614 μL, 0.614 mmol, 1M, Aldrich) to afford 10 mg (20%) of Compound 366 as a yellow oil. Data for Compound 366: $^1$H NMR (400 MHz, acetone-$d_6$) 7.83 (d, J=2.3, 1H), 7.81 (m, 2H), 7.67 (d, J=8.4, 1H), 7.39 (m, 2H), 7.21 (m, 3H), 6.84 (d, J=8.5, 1H), 5.71 (s, 1H), 2.10 (s, 3H), 1.34 (br s, 6H).

EXAMPLE 267

(Z)-9-Chloro-1,2-dihydro-2,2,4-trimethyl-5-(2-methylbenzylidene)-5H-chromeno[3,4-f]quinoline (Compound 367, structure 45 of Scheme XIII, where $R^1$=H, $R^2$=Cl, $R^3$=2-methylphenyl)

This compound was prepared by General Method 6 (EXAMPLE 119) from Compound 209 (50 mg, 0.154 mmol) and α-chloro-o-xylene (345 mg, 2.46 mmol) to afford 14 mg (22%) of Compound 366 as a yellow oil. Data for Compound 366: $^1$H NMR (400 MHz, acetone-$d_6$) 7.85 (d, J=2.5, 1H), 7.66 (d, J=8.5, 1H), 7.17 (m, 2H), 7.11 (m, 2H), 6.80 (d, J=8.5, 2H), 6.55 (s, 1H), 5.73 (s, 1H), 4.98 (s, 1H), 2.19 (s, 3H), 1.29 (br s, 3H), 1.21 (s, 3H).

EXAMPLE 268

(Z)-5-Benzylidene-9-chloro-1,2-dihydro-2,2-dimethyl-5H-chromeno[3,4-f]quinoline (Compound 368, structure 95 of Scheme XXVI, where $R^{1-2}$=$R^{4-6}$=$R^9$=H, $R^7$=$R^8$=methyl, $R^{10}$=phenyl)

This compound was prepared by General Method 6 (EXAMPLE 119) from Compound 313 (25 mg, 0.080 mmol) and benzyl magnesium chloride (0.802 mL, 0.802 mmol, 1M solution in ether, Aldrich) to afford 5 mg (16%) of Compound 368 as a yellow oil. Data for Compound 368: $^1$H NMR (400 MHz, acetone-$d_6$) 7.86 (d, J=7.1, 1H), 7.79 (d, J=2.2, 1H), 7.63 (d, J=8.5, 1H), 7.40 (m, 2H), 7.20 (m, 4H), 6.89 (d, J=8.6, 1H), 6.78 (d, J=8.4, 1H), 5.99 (s, 1H), 5.70 (d, J=8.3, 1H), 1.37 (s, 6H).

EXAMPLE 269

(Z)-9-Chloro-5-(2-fluorobenzylidene)-1,2-dihydro-2,2,4-trimethyl-5H-chromeno[3,4-f]quinoline (Compound 369, structure 45 of Scheme XIII, where $R^1$=H, $R^2$=Cl, $R^3$=2-fluorophenyl)

This compound was prepared by General Method 6 (EXAMPLE 119) from Compound 209 (40 mg, 0.123 mmol) and 2-fluorobenzylbromide (160 mg, 0.860 mmol) to afford 9 mg (18%) of Compound 369 as a yellow oil. Data for Compound 369: $^1$H NMR (400 MHz, acetone-$d_6$) 8.32 (m, 1H), 7.84 (d, J=1.7, 1H), 7.69 (d, J=8.5, 1H), 7.26 (m, 2H), 7.20 (d, J=3.0, 1H), 7.18 (m, 2H), 6.87 (d, J=8.5, 1H), 5.97 (s, 1H), 5.57 (s, 1H), 2.11 (s, 3H), 1.33 (br s, 6H).

EXAMPLE 270

(Z)-9-Chloro-5-(3-fluorobenzylidene -1,2-dihydro-2,2,4-trimethyl-5H-chromeno[3,4-f]quinoline (Compound 370 structure 45 of Scheme XIII, where $R^1$-H $R^2$=Cl $R^3$=3-fluorophenyl)

This compound was prepared by General Method 6 (EXAMPLE 119) from Compound 209 (38 mg, 0.12 mmol) and 3-fluorobenzyl chloride (0.23 mL, 1.9 mmol) to afford 20 mg (42%) of Compound 370 as a yellow oil. Data for Compound 370: $^1$H NMR (400 MHz, acetone-$d_6$) 7.85 (d, J=2.3, 1H), 7.69 (d, J=8.5, 1H), 7.66 (m, 1H), 7.52 (d, J=7.7, 1H) 7.41 (m, 1H), 7.25 (m, 2H), 7.01 (m, 1H), 6.87 (d, J=8.4, 1H), 5.73 (s, 1H), 5.57 (d, J=1.2, 1H 6H). The C(4) methyl is obscured by the acetone multiplet.

EXAMPLE 271

(E/Z)-5-Benzylidene-9-fluoro-1,2-dihydro-2,2,4-trimethyl-5H-chromeno[3,4-f]quinoline Compound 371, structure 45 of Scheme XIII where $R^1$=H, $R^2$=F, $R^3$=phenyl)

This compound was prepared by General Method 6 (EXAMPLE 119) from Compound 207 (79 mg, 0.25 mmol) and 1.0M benzylmagnesium chloride in $Et_2O$ (Aldrich) to afford 20 mg (19%) of Compound 371 as a yellow oil, as a 2:1 Z/E mixture. Data for Compound (Z)-371: $^1$H NMR (400 MHz, acetone-$d_6$) 7.80 (d, J=7.7, 1H), 7.6 (m, 2H), 7.39 (t, J=7.8, 1H), 7.23 (m, 2H), 7.15 (m, 1H), 7.08 (m, 1H), 6.95 (m, 1H), 6.83 (dd, J=8.4, 2.8, 1H), 5.70 (s, 1H), 5.55 (d, J=1.2, 1H), 2.10 (s, 3H), 1.35–1.25 (br d, 6H). The characteristic signals for (E)-371 are: 6.53 (s, 1H), 5.04 (s, 1H), 1.94 (d, J=1.2, 3H), 1.33 (s, 3H), 1.00 (s, 3H).

EXAMPLE 272

(Z)-5-Benzylidene-8-fluoro 1-2-dihydro-2,2,4-trimethyl-5H-chromeno[3,4-f]quinoline Compound 372, structure 45 of Scheme XIII where $R^1$=F, $R^2$=H, $R^3$=phenyl This compound was prepared by General Method 6 (EXAMPLE 119) from Compound 208 (55 mg, 0.18 mmol) and 1.0M benzylmagnesium chloride in $Et_2O$ (Aldrich) to afford 11 mg (17%) of Compound 372 as a yellow oil. Data for Compound 372: $^1$H NMR (400 MHz, acetone-$d_6$) 7.86 (dd, J=8.7, 6.2, 1H), 7.80 (d, J=7.6, 2H), 7.61 (d, J=8.4, 1H), 7.40 (app t, J=7.8, 2H), 7.20 (m, 1H), 7.05 (m, 1H), 6.86 (m, 1H), 6.83 (d, J=8.4, 1H), 5.71 (s, 1H), 5.55 (d, J=1.1, 1H), 2.11 (s, 3H), 1.40 (br s, 6H).

EXAMPLE 273

(Z)-5-Benzylidene-1,2-dihydro-9-methoxy-2,2,4-trimethyl-5H-chromeno[3,4-f]quinoline (Compound 373 structure 45 of Scheme XIII where $R^1$=H, $R^2$=methoxy $R^3$=phenyl)

This compound was prepared by General Method 6 (EXAMPLE 119) from Compound 314 (55 mg, 0.18 mmol) and 1.0M benzylmagnesium chloride in $Et_2O$ (Aldrich) to afford 11 mg (17%) of Compound 373 as a yellow oil. Data for Compound 373: $^1$H NMR (400 MHz, acetone-$d_6$) 7.79 (d, J=7.6, 2H), 7.53 (d, J=8.5, 1H), 7.4–7.2 (m, 5H), 6.84 (m, 2H), 5.67 (s, 1H), 5.55 (s, 1H), 3.82 (s, 3H), 2.11 (s, 3H), 1.35–1.30 (br s, 6H).

EXAMPLE 274

(Z)-9-Fluoro-1,2-dihydro-2,2,4-trimethyl-5-(2methylbenzylidene-5H-chromeno[3,4-f]quinoline (Compound 374, structure 45 of Scheme XIII, where $R^1$=H, $R^2$=fluoro, $R^3$=2-methylphenyl)

This compound was prepared by General Method 6 (EXAMPLE 119) from Compound 207 (34 mg, 0.11 mmol) and freshly prepared 1.0M 2-methylbenzyl magnesium chloride in $Et_2O$ to afford 30 mg (70%) of Compound 374 as a yellow oil. Data for Compound 374: $^1$H NMR (400 MHz, acetone-$d_6$) 8.20 (d, J=7.9, 1H), 7.64 (d, J=8.5, 1H), 7.58

(dd, J=10.0, 2.9, 1H), 7.26 (app t, J=7.6, 1H), 7.19 (d, J=7.4, 1H), 7.14 (m, 2H), 6.94 (m, 1H), 6.84 (d, J=8.5, 1H), 5.95 (s, 1H), 5.55 (d, J=1.1, 1H), 2.28 (s, 3H), 2.14 (d, J=1.1, 3H), 1.35–1.30 (br s, 6H).

EXAMPLE 275

(Z)-8-Fluoro-1,2-dihydro-2,2,4-trimethyl-5-(2methylbenzylidene-5H-chromeno[3,4-f]quinoline (Compound 375, structure 45 of Scheme XIII, where $R^1$=H, $R^2$=fluoro, $R^3$=2-methylphenyl)

This compound was prepared by General Method 6 (EXAMPLE 119) from Compound 208 (31 mg, 0.10 mmol) and freshly prepared 1.0M 2-methylbenzyl magnesium chloride in $Et_2O$ to afford 32 mg (80%) of Compound 375 as a yellow oil. Data for Compound 375: $^1H$ NMR (400 MHz, acetone-$d_6$) 8.19 (d, J=7.9, 1H), 7.86 (dd, J=8.8, 4.2, 1H), 7.61 (d, J=8.5, 1H) 7.28 (app t, J=7.6, 1H), 7.20 (d, J=6.9, 1H), 7.15 (m, 1H), 6.94 (dd, J=9.6, 2.7, 1H), 6.86 (m, 2H), 5.97 (s, 1H), 5.55 (d, J=1.2, 1H), 2.28 (s, 3H), 2.14 (s, 3H), 1.35 (br s, 6H).

EXAMPLE 276

(Z)-1,2-Dihydro-9-methoxy-2,2,4-trimethyl-5-(2-methylbenzylidene)-5H-chromeno[3,4-f]quinoline (Compound 376, structure 45 of Scheme XIII, where $R^1$=H, $R^2$=methoxy, $R^3$=2-methylphenyl)

This compound was prepared by General Method 6 (EXAMPLE 119) from Compound 314 (55 mg, 0.18 mmol) and 1.0M benzylmagnesium chloride in $Et_2O$ (Aldrich) to afford 11 mg (17%) of Compound 373 as a yellow oil. Data for Compound 373: $^1H$ NMR (400 MHz, acetone-$d_6$) 8.23 (d, J=7.8, 1H), 7.64 (d, J=8.5, 1H), 7.37 (m, 1H), 7.30 (m, 1H), 7.15 (m, 2H), 7.04 (d, J=8.6, 1H), 6.82 (d, J=8.4, 1H), 6.77 (dd, J=8.6, 3.0, 1H), 5.92 (s, 1H), 5.53 (d, J=1.2, 1H), 3.82 (s, 3H), 2.27 (s, 3H), 2.14 (s, 3H), 1.35 (br s, 6H).

EXAMPLE 277

(Z)-5-Benzylidene-9-fluoro-1,2-dihydro-2,2,4,11-tetramethyl-5H-chromeno[3,4-f]quinoline (Compound 377 structure 95 of Scheme XXVI where $R^{1-2}$=$R^4$=$R^6$=H, $R^3$=F, $R^5$=$R^{7-9}$=methyl, $R^{10}$=phenyl)

This compound was prepared by General Method 6 (EXAMPLE 119) from Compound 315 (28 mg, 0.087 mmol) and 1.0M benzylmagnesium chloride in $Et_2O$ (Aldrich) to afford 19 mg (56%) of Compound 377 as a yellow foam. Data for Compound 377: $^1H$ NMR (400 MHz, acetone-$d_6$) 7.79 (d, J=7.6, 2H), 6.63 (dd, J=11.4, 2.9, 1H), 7.39 (app t, J=7.8, 2H), 7.25 (m, 2H), 6.97 (m, 1H), 6.68 (s, 1H), 5.74 (s, 1H), 5.52 (d, J=1.2, 1H), 2.61 (s, 3H), 1.33 (br s, 6H).

EXAMPLE 278

(R/S)-5-(4-Chlorophenyl)-1,2,3,4-tetrahydro-2,2-dimethyl-5H-chromeno[3,4-f]quinoline (Compound 378, structure 97 of Scheme XXVII, where R=4-chlorophenyl)

To a solution of Compound 164 (EXAMPLE 64) (220 mg, 0.6 mmol) in 6 mL of THF at $-78°$ C. was added 1.6M n-BuLi hexane solution (1 mL, 1.6 mmol), followed by di-t-butyl dicarbonate (0.7 g, 3.2 mmol) in 2 mL of THF. The reaction mixture was warmed to rt and stirred for 15 h, then was quenched with 2% NaOH aqueous solution. The mixture was extracted with EtOAc (2×30 mL) and was concentrated. Chromatography of the crude residue on a silica gel column using 10% EtOAc/hexane as solvent afforded the N-Boc Compound 164 (87 mg) in 30% yield in addition to 60% of the starting material (132 mg). The N-Boc material (40 mg, 0.082 mmol) in methanol (20 mL) at $-78°$ C. was treated with $O_3$ for 3 min and then with methyl sulfide (0.5 mL) for 30 min. Removal of solvent and chromatography of the crude mixture afforded a colorless oil, which was treated with excess TFA (0.5 mL) in 1 mL of $CH_2Cl_2$ for 60 min. The reaction was quenched with 2% NaOH (5 mL) and was extracted with EtOAc (2×30 mL). Removal of the solvent and chromatography again provided 15 mg (47%) of Compound 378 as a yellow oil. Data for Compound 378: $^1H$ NMR (400 MHz, acetone-$d_6$) 7.86 (d, J=8.8, 1H), 7.61 (d, J=7.7, 1H), 7.40 (s, 1H), 7.04 (t, J=7.7, 1H), 6.99 (d, J=8.8, 1H), 6.90 (t, J=7.7, 1H), 6.82 (d, J=7.7, 1H), 6.38 (bs, 1H), 2.65 (d, J=15.2, 1H), 2.44 (d, J=15.2, 1H) 1.97 (s, 3H), 1.37 (s, 3H), 1.27 (s, 3H).

EXAMPLE 279

(R/S)-5-(4-Chlorophenyl)-1,2,3,4-tetrahydro-2,2,3,3-tetramethyl-5H-chromeno[3,4-f]quinoline (Compound 379 structure 98 of Scheme XXVIII where R=4-chlorophenyl, $R^1$=methyl)

To a suspension of 40% NaH in mineral oil (10 mg, 0.25 mmol) in THF (1 mL) was added a solution of (R/S)-1-(t-butoxycarbonyl)-5-(4-chlorophenyl)-1,2,3,4-tetrahydro-2,2-dimethyl-5H-chromeno[3,4-f]quinoline (structure 96 of Scheme XXVIII, where R=4-chlorophenyl, $R^1$=methyl) (10 mg, 0.02 mmol) and excess MeI (0.1 mL). The reaction was stirred at rt for 2 h and was quenched with water (1 mL), and extracted with EtOAc (2×5 mL). Removal of solvent provided the crude mixture, which was treated with TFA (0.2 mL) in dichloromethane (1 mL) for 60 min. Chromatography of the crude mixture on a silica gel column using 15% EtOAc/Hexane as solvent afforded 6.5 mg (78%) of Compound 379 as a colorless oil. Data for Compound 379: $^1H$ NMR (400 MHz, $CDCl_3$) 7.73 (d, J=8.7, 1H), 7.49 (d, J=7.7, 1H), 7.30 (s, 1H), 7.13 (s, 4H), 7.04 (t, J=7.7, 1H), 6.91 (t, J=7.7, 1H), 6.83 (d, J=7.7, 1H), 6.71 (d, J=8.7, 1H), 4.28 (s, 1H), 1.29 (s, 3H), 1.20 (s, 3H), 1.13 (s, 3H), 1.03 (s, 3H).

EXAMPLE 280

(R/S)-5-(4-Chlorophenyl)-1,2-dihydro-2,2-dimethyl-5H-chromeno[3,4-f]quinoline (Compound 380, structure 1A of Scheme XXIX, where R=4-chlorophenyl)

To a solution of Compound 379 (EXAMPLE 279) (10 mg, 0.025 mmol) in toluene (1 mL) at $-78°$ C. was added 0.5M DIBAL toluene solution (0.1 mL, 0.05 mmol) and the resulting mixture was warmed up to rt. The reaction mixture was quenched with water (1 mL) and was extracted with EtOAc (2×5 mL). Removal of solvent and chromatography of the mixture on a silica gel column afforded 6.8 mg (70%) of 5-(4-chlorophenyl)-1,2,3,4-tetrahydro-4-hydroxy-2,2-dimethyl-5H-chromeno[3,4-J]quinoline as a colorless oil, which was treated in dichloromethane (1 mL) with a catalytic amount of TsOH for 3 h to provide 4.1 mg (63%) of Compound 380 as a colorless oil. Data for Compound 380: $^1H$ NMR (400 MHz, acetone-$d_6$) 7.60 (d, J=7.7, 1H), 7.52 (d, J=8.5, 1H), 7.27 (d, J=8.6, 2H), 7.25 (d, J=8.6, 2H), 7.01 (t, J=7.7, 1H), 6.89 (t, J=7.7 Hz, 1H), 6.81 (d, J=7.7, 1H), 6.67 (d, J=8.5, 1H), 6.57 (s, 1H), 6.33 (d, J=10.0, 1H), 5.57 (d, J=10.0, 1H), 5.55 (bs, 1H), 1.32 (s, 3H), 1.30 (s, 3H).

EXAMPLE 281

(+)-R*-4l,5l)-5-(Chlorophenyl)-1,2,3,4-tetrahydro-2,2,4-trimethyl-5H-chromeno[3,4-f]quinoline (Compound 381 structure 53 of Scheme XV where R=4-chlorophenyl, $R^1$=$R^2$=H)

This compound (0.7 mg) was prepared by HPLC separation of the enantiomers of Compound 381 by a chiral column, Chiracel OD-R, using a 9:1 mixture of methanol and water as mobile phase. The optical purity of Compound 381 was determined by HPLC to be >90% e.e.; $[\alpha]^{20}_D$=+101 (MeOH).

EXAMPLE 282

(−)-(R *-4l, 5l)-5-(4-Chlorophenyl)-1,2,3,4-tetrahydro-2,2,4-trimethyl-5H-chromeno[3,4-f]quinoline (Compound 382, structure 53 of Scheme XV, where R=4-chlorophenyl, $R^1$=$R^2$=H)

This compound (1.5 mg) was prepared by HPLC separation of the enantiomers of Compound 235 by a chiral column, Chiracel OD-R, using a 9:1 mixture of methanol and water as mobile phase. The optical purity of Compound 382 was determined by HPLC to be 68% e.e.; $[\alpha]^{20}_D$=−63 (MeOH).

EXAMPLE 283

(R/S)-5-(4-Chlorophenyl)-1,2,3,4-tetrahydro-2,2-dimethyl-5H-chromeno[3,4-f]quinoline (Compound 383, structure 4A of Scheme XXIX, where R=4-chlorophenyl)

This compound (0.63 mg, 3%) was prepared in a manner similar to that described for Compound 234 (EXAMPLE 134) from Compound 380 (EXAMPLE 280) as a colorless oil. The major product (41%) was Compound 378 (EXAMPLE 278). Data for Compound 383: $^1$H NMR (400 MHz, CDCl$_3$) 7.62 (d, J=8.3, 1H), 7.60 (d, J=7.7, 1H), 7.17 (d, J=8.6, 2H), 7.09 (d, J=8.6, 2H), 7.06 (t, J=7.7, 1H), 6.94 (t, J=7.7, 1H), 6.83–6.80 (m, 2H), 6.26 (s, 1H), 3.88 (bs, 1H), 3.55 (d, J=20.0, 1H), 3.11 (d, J=10.0, 1H), 1.33 (s, 3H), 1.32 (s, 3H).

EXAMPLE 284

(R/S)-3-(3-Fluorobenzyl)-5-(3-fluorobenzylidene)-1,2,3,4-tetrahydro-3-hydroxy-2,2,4-trimethyl-5H-chromeno[3,4-f]quinoline (Compound 384, structure 8A of Scheme XXX, where R1=R2=H, R3=3-fluorophenyl)

(R/S)-1,2,3,4-Tetrahydro-2,2,4-trimethylcoumarino[3,4-f]-3-quinolinone (structure 7A of Scheme XXX, where $R^1$=$R^2$=H)

This compound was prepared by the same Boc-protection/hydroboration/oxidation/deprotection procedure as described in the synthesis of Compound 234 (EXAMPLE 134) from Compound 159 (EXAMPLE 59) (440 mg, 2.0 mmol) to afford 98 mg (16%) of (R/S)-1,2,3,4-tetrahydro-2,2,4-trimethylcoumarino[3,4-f]=3-quinolinone as a yellowish oil. Data for (R/S)-1,2,3,4-tetrahydro-2,2,4-trimethylcoumarino[3,4-f]-3-quinolinone: $^1$H NMR (400 MHz, CDCl$_3$) 7.95 (d, J=8.6, 2H), 7.38 (t, J=8.2, 1H), 7.31–7.24 (m, 2H), 7.16 (d, J=8.5, 1H), 5.29 (q, J=7.4, 1H), 3.94 (bs, 1H), 1.56 (s, 3H), 1.48 (d, J=7.4, 3H), 1.22 (s, 3H). (R/S)-3-(3-Fluorobenzyl)-5-(3-fluorobenzylidene )-1,2,3,4-tetrahydro-3-hydroxy-2,2,4-trimethyl-5H-chromeno[3,4-f] quinoline (Compound 384, structure 8A of Scheme XXX, where R1=R2=H, R3=3-fluorophenyl) To a solution of (R/S)-1,2,3,4-tetrahydro-2,2,4-trimethylcoumarino[3,4-f]-3-quinoline (3 mg, 0.01 mmol) in ether (3 mL) at rt was added the freshly prepared a 0.5M 3-fluorobenzylmagnesium chloride ether solution (0.5 mL, 0.25 mmol) and the resulting mixture was stirred at rt for 2 h, then was quenched with water (5 mL). The mixture was extracted with EtOAc (2×5 mL) and was concentrated and purified by silica gel chromatography to afford the intermediate, which was treated with TsOH (5 mg) in dichloromethane (1 mL) for 60 min. The reaction was quenched with 2% NaOH (5 mL) and was extracted with EtOAc (2×5 mL). Removal of solvent and chromatography of the mixture afforded 3.0 mg (59%) of Compound 384 as a colorless oil. Data for Compound 384: $^1$H NMR (400 MHz, CDCl$_3$) 7.71 (d, J=7.8, 1H), 7.63 (d, J=11.0, 1H), 7.51 (d, J=8.4, 1H), 7.40 (d, J=7.8, 1H), 7.33 (td, J=7.8, 6.2, 1H), 7.28–7.18 (m, 3H), 7.13–6.92 (m, 5H), 6.65 (d, J=8.3, 1H), 5.89 (s, 1H), 3.73 (q, J=6.8, 1H), 3.66 (s, 1H), 3.08 (d, J=14.2, 1H), 2.97 (d, J=14.2, 1H), 2.79 (s, 1H), 1.33 (s, 3H), 1.29 (d, J=6.8, 3H), 1.18 (s, 3H).

EXAMPLE 285

(R/S)-3,5-Dibutyl-1,2,3,4-tetrahydro-3-hydroxy-2,2,4-trimethyl-5H-chromeno[3,4-f]quinoline (Compound 385, structure 9A of Scheme XXXI, where $R^1$=$R^2$=H, $R^3$=n-butyl)

To a solution of (R/S)-1,2,3,4-tetrahydro-2,2,4-trimethylcoumarino[3,4-f]-3-quinolinone (EXAMPLE 284) (4 mg, 0.01 mmol) in ether (3 mL) at rt was added 1.6M n-BuLi hexane solution (0.05 mL, 0.08 mmol) and the resulting mixture was stirred at rt for 2 h, then was quenched with water (5 mL). The mixture was extracted with EtOAc (2×5 mL) and was concentrated and purified by silica gel chromatography to afford the intermediate, which was treated with Et$_3$SiH (0.05 mL) and TFA (0.05 mL) in dichloromethane (1 mL) for 60 min. The reaction was quenched with 2% NaOH (5 mL) and was extracted with EtOAc (2×5 mL). Removal of solvent and chromatography of the mixture afforded 0.8 mg (20%) of Compound 385 as a colorless oil. The relative stereochemistry of this compound was not determined. Data for Compound 385: $^1$H NMR (400 MHz, CDCl$_3$) 7.61 (d, J=7.8, 1H), 7.44 (d, J=8.3Hz, 1H), 7.44 J=8.3 Hz, 1H), 7.14 (t, J=7.8, 1H), 6.98 (t, J=7.8, 1H), 6.94 (d, J=7.8, 1H), 6.53 (d, J=8.3, 1H), 5.53 (dd, J=10.3, 3.5, 1H), 3.42 (bs, 1H), 2.94 (q, J=7.0, 1H), 2.65 (s, 1H), 1.88–1.63 (m, 2H), 1.53–1.22 (m, 10H), 1.44 (d, J=7.0, 3H), 1.33 (s, 3H), 1.08 (s, 3H), 0.94 (t, J=7.2, 3H), 0.87 (t, J=7.2, 3H).

EXAMPLE 286

(R/S)-5-Butyl-1,2,3,4-tetrahydro-2,2,4-trimethyl-5H-chromeno[3,4-f]-3-quinolinone (Compound 386, structure 10A or 11A of Scheme XXXII, where $R^1$=$R^2$=H, $R^3$=n-butyl)

To a solution of (R/S)-1-t-butoxycarbonyl-1,2,3,4-tetrahydro-2,2,4-trimethylcoumarino[3,4-f]-3-quinolinone (structure 6A of Scheme XXX, where $R^1$=$R^2$=H, an intermediate from EXAMPLE 284) (4 mg, 0.012 mmol) in THF (1 mL) at −78° C. was added 1.6M n-BuLi hexane solution (0.016 mL, 0.024 mmol) and the resulting mixture was warmed up slowly to −20° C., then was quenched with water (0.5 mL). Removal of solvent provided the crude product, which was treated with TFA (0.05 mL, 0.65 mmol) and Et$_3$SiH (0.1 mL, 0.65 mmol) in dichloromethane (1 mL) for 60 min. The reaction was quenched with 2% NaOH (2 mL) and was extracted with EtOAc (2×5 mL). Removal of solvent and chromatography of the residue afforded 0.7 mg (17%) of Compound 386 as a colorless oil. The relative stereochemistry of Compound 386 was not determined. Data for Compound 386: $^1$H NMR (400 MHz, CDCl$_3$) 7.63 (d, J=7.7, 1H), 7.51 (d, J=8.2, 1H), 7.16 (t, J=7.7, 1H), 7.01 (t, J=7.7, 1H), 6.96 (d, J=7.7, 1H), 6.74 (d, J=8.2, 1H), 5.32 (dd, J=10.1 and 1.0, 1H), 3.66 (q, J=7.2, 1H), 1.98–1.90 (m, 1H), 1.58–1.18 (m, 5H), 1.48 (s, 3H), 1.44 (d, J=7.2, 3H), 1.20 (s, 3H), 0.89 (t, J=7.3, 3H).

EXAMPLE 287

(R/S-4l,5l)-1,2,3,4-Tetrahydro-2,2,4-trimethyl-5-phenyl-5H-chromeno[3,4-f]-3-quinolinone (Compound 387, structure 18A of Scheme XXXIII, where $R^1=R^2=H$, $R^3$=phenyl)

This compound, along with Compound 388 (EXAMPLE 288), was prepared by the same Boc-protection/hydroboration/oxidation/deprotection procedure as described in the synthesis of Compound 234 (EXAMPLE 134) from Compound 161 (EXAMPLE 61) (40 mg, 0.11 mmol). Compound 387 (4.0 mg, 10%) was obtained as a colorless oil. Data for Compound 387: $^1$H NMR (400 MHz, CDCl$_3$) 7.59 (d, J=8.3, 1H), 7.57 (d, J=7.6, 1H), 7.21–7.12 (m, 5H), 7.05 (t, J=7.6, 1H), 6.92 (t, J=7.6, 1H), 6.86 (d, J=7.6, 1H), 6.83 (d, J=8.3, 1H), 6.37 (s, 1H), 3.72 (bs, 1H), 3.41 (q, J=7.5, 1H), 1.50 (d, J=7.5, 3H), 1.45 (s, 3H), 1.17 (s, 3H).

EXAMPLE 288

(R/S-4l,5u)-1,2,3,4-Tetrahydro-2,2,4-trimethyl-5-phenyl-5H-chromeno[3,4-f]-3-quinolinone (Compound 388, structure 17A of Scheme XXXIII, where $R^1=R^2=H$, $R^3$=phenyl)

This compound, along with Compound 387 (EXAMPLE 287), was prepared by the same Boc-protection/hydroboration/oxidation/deprotection procedure as described in the synthesis of Compound 234 (EXAMPLE 134) from Compound 161 (EXAMPLE 61) (40 mg, 0.11 mmol). Compound 388 (7.3 mg, 18%) was obtained as a white powder. Data for Compound 388: mp 108°–110° C.; IR (neat) 3358, 2972, 1720, 1473, 1292, 1213, 752; $^1$H NMR (400 MHz, CDCl$_3$) 7.66 (d, J=7.7, 1H), 7.64 (d, J=8.2, 1H), 7.20 (s, 5H), 7.06 (t, J=7.7, 1H), 6.95 (t, J=7.7, 1H), 6.83 (d, J=8.2, 1H), 6.77 (d, J=7.7, 1H), 6.39 (s, 1H), 3.72 (bs, 1H), 3.58 (q, J=7.4, 1H), 1.44 (s, 3H), 1.23 (s, 3H), 0.80 (d, J=7.4, 3H); $^{13}$C NMR (100 MHz, CDCl$_3$) 214.4, 151.0, 143.2, 139.3, 131.1, 128.9, 128.8, 128.6, 128.5, 123.4, 122.7, 122.2, 122.1, 122.0, 118.3, 116.6, 75.4, 60.2, 43.9, 28.1, 27.3, 16.3. Anal. (C$_{25}$H$_{23}$NO$_2$-3/4H$_2$O) C, H, N.

EXAMPLE 289

(Z)-(R/S)-5-(3-Fluorobenzylidene)-1,2,3,4-tetrahydro-2,2,4-trimethyl-5H-chromeno[3,4-f]-3-quinolinone (Compound 389, structure 19A of Scheme XXXIV, where $R^1=R^2=H$, $R^3$=3-fluorophenyl)

To a solution of (R/S)-1-t-butoxycarbonyl-1,2,3,4-tetrahydro-2,2,4-trimethylcoumarino[3,4-f]-3-quinolinone (structure 6A of Scheme XXX, where $R^1=R^2=H$, an intermediate from EXAMPLE 284) (10 mg, 0.025 mmol) in THF (1 mL) at −78° C. was added freshly prepared 1.0M 3-fluorobenzylmagnesium bromide (0.06 mL, 0.06 mmol) and the reaction was slowly warmed up to rt and was quenched with water (1 mL). The mixture was extracted with EtOAc (2×5 mL) and was concentrated to provide the crude intermediate, which was treated with excess TFA (0.2 mL) in dichloromethane (1 mL) for 30 min and then quenched with 5% NaOH (5 mL). The mixture was extracted with EtOAc (2×10 mL), concentrated and chromatographied to afford 6.0 mg (60%) of Compound 389 as a yellowish oil. Data for Compound 389: IR (neat) 3356, 1716, 1604, 1469, 1251; $^1$H NMR (400 MHz, CDCl$_3$) 7.73 (d, J=7.8, 1H), 7.70 (d, J=11.1, 1H), 7.60 (d, J=8.3, 1H), 7.42 (d, J=7.8, 1H), 7.31 (td, J=8.0 and 6.2, 1H), 7.22 (d, J=8.1, 1H), 7.18 (d, J=7.0, 1H), 7.08 (t, J=7.1, 1H), 6.94 (td, J=8.4 and 2.4, 1H), 6.85 (d, J=8.3, 1H), 5.87 (s, 1H), 4.33 (q, J=7.3, 1H), 3.78 (s, 1H), 1.56 (d, J=7.3, 3H), 1.51 (s, 3H), 1.24 (s, 3H); $^{13}$C NMR (100 MHz, CDCl$_3$) 2.14.0, 162.4 (d, J=244.0 Hz), 152.3, 147.0, 144.2, 137.2 (d, J=8.1 Hz), 129.8 (d, J=8.8 Hz), 128.7, 128.0, 125.4, 124.2, 123.0, 122.6, 122.4, 121.9, 121.8, 118.1, 116.5, 115.8 (d, J=23.1 Hz), 114.1, 113.8 (d, J=21.1 Hz), 60.1, 44.9, 27.7, 27.2, 17.4. A minor 1.0 mg (<10%) product was also isolated and identified as (E)-(R/S)-5-(3-fluorobenzylidene)-1,2,3,4-tetrahydro-2,2,4-trimethyl--5H-chromeno[3,4-f]-3-quinolinone $^1$H NMR (400 MHz, CDCl$_3$) 7.78 (d, J=7.9, 1H), 7.70 (d, J=8.7, 1H), 7.67 (d, J=10.2, 1H), 7.42 (d, J=7.8, 1H), 7.35–7.26 (m, 3H), 7.21 (d, J=8.1, 1H), 7.10 (t, J=8.2, 1H), 6.97 (td, J=8.4 and 2.4, 1H), 5.80 (s, 1H), 4.28 (q, J=7.3, 1H), 3.55 (bs, 1H), 1.88 (s, 3H), 1.76 d, J=7.3, 3H), 1.33 (s, 3H).

EXAMPLE 290

(R/S-4l, 6u)-1,2,3,4-Tetrahydro-2,2,4-trimethyl-6-phenyl-5H-isochromeno[3,4-f]-3-quinolinone (Compound 390, structure 23A of Scheme XXXV, where $R^1$=phenyl)) 1,2-Dihydro-2,2,4-trimethyl-10-isocoumarino[3,4-f]quinoline (Compound 21A, Scheme XXXV)

This compound was prepared by General Method 8 (EXAMPLE 138) from 7-amino-3,4-benzocoumarin to afford 1,2-dihydro-2,2,4-trimethyl-10-isocoumarino[3,4-f] quinoline (150 mg, 0.52 mmol, 60%) as a yellow solid. Data for 1,2-dihydro-2,2,4-trimethyl-10-isocoumarino[3,4-f] quinoline: mp 197°–199° C.; IR (KBr) 3350, 2960, 1711, 1608, 1566, 1468and 1311; $^1$H NMR (400 MHz, CDCl$_3$) 8.20 (d, J=7.6, 1H), 8.10 (d, J=7.6, 1H), 7.83 (d, J=8.6, 1H), 7.77 (t, J=7.6, 1H), 7.44 (t, J=7.6, 1H), 6.64 (d, J=8.6, 1H), 5.88 (bs, 1H), 5.38 (s, 1H), 2.39 (s, 3H), 1.29 (s, 6H); $^{13}$C NMR (100 MHz, CDCl$_3$) 161.5, 149.6, 146.9, 136.6, 134.8, 130.4, 128.3, 126.6, 122.8, 120.8, 119.0, 111.1, 109.6, 108.6, 51.7, 30.4, 23.6.

1,2-Dihydro-2,2,4-trimethyl-6-phenyl-5H-isochromeno[3,4-f]quinoline (structure 22A of Scheme XXXV, where $R^1$=phenyl)

This compound was prepared by General Method 5 (EXAMPLE 60) from 1,2-dihydro-2,2,4-trimethyl-10-isocoumarino[3,4-f]quinoline (60 mg, 0.20 mmol) and bromobenzene (157 mg, 1.0 mmol) to afford 60 mg (85%) as a colorless oil. Data for 1,2-dihydro-2,2,4-trimethyl-6-phenyl-5H-isochromeno[3,4-f]quinoline: $^1$H NMR (400 MHz, CDCl$_3$) 7.60 (d, J=7.7, 1H), 7.44 (d, J=8.3, 1H), 7.43–7.30 (m, 7H), 7.10 (t, J=7.7, 1H), 6.73 (d, J=7.7, 1H), 6.04 (s, 1H), 5.22 (s, 1H), 3.87 (bs, 1H), 2.11 (s, 3H), 1.26 (s, 3H), 1.23 (s, 3H); $^{13}$C NMR (100 MHz, CDCl$_3$) 152.0, 146.3, 145.2, 139.6, 132.9, 131.6, 129.3, 128.6, 128.4, 125.9, 125.6, 123.5, 121.2, 113.9, 111.2, 108.5, 80.1, 51.4, 30.3, 30.1, 23.5.

(R/S-4l,6u)-1,2,3,4-Tetrahydro-2,2,4-trimethyl-6-phenyl-5H-isochromeno[3,4-f]-3-quinolinone This compound was prepared by the same Boc-protection/hydroboration/oxidation/deprotection procedure as described in the synthesis of Compound 234 (EXAMPLE 134) from 1,2-dihydro-2,2,4-trimethyl-6-phenyl-5H-isochromeno[3,4-f]quinoline (30 mg, 0.085 mmol). Compound 390 (2.2 mg, 7%) was obtained as a colorless oil, along with xx mg (14%) of Compound 391 (EXAMPLE 291). Data for Compound 390: $^1$H NMR (400 MHz, CDCl$_3$) 7.65 (d, J=7.8, 1H), 7.49 (d, J=8.4, 1H), 7.37 (t, J=7.8, 1H), 7.30 (s, 5H), 7.19 (t, J=7.8, 1H), 6.89 (d, J=7.8, 1H), 6.38 (d, J=8.4, 1H), 6.14 (s, 1H), 3.83 (q, J=7.5, 1H), 3.67 (bs, 1H), 1.41 (s, 3H), 1.39 (d, J=7.5, 3H), 1.12 (s, 3H).

EXAMPLE 291

(R/S-4l, 6l)-1,2,3,4-Tetrahydro-2,2,4-trimethyl-6-phenyl-5H-isochromeno[3,4-f]-3-quinolinone (Compound 391, structure 24A of Scheme XXXV, where $R^1$=phenyl)

Compound 391 (4.4 mg, 14%) was obtained as a colorless oil along with Compound 390 as described above (EXAMPLE 290). Data for Compound 391: IR (neat) 3358, 1716, 1614, 1471, 1439, 1030; $^1$H NMR (400 MHz, CDCl$_3$) 7.66 (d, J=7.7, 1H), 7.53 (d, J=8.3, 1H), 7.35 (s, 5H), 7.34 (t, J=7.7, 1H), 7.15 (t, J=7.7, 1H), 6.79 (d, J=7.7, 1H), 6.12 (s, 1H), 3.82 (q, J=7.3, 1H), 3.66 (bs, 1H), 1.41 (s, 3H), 1.23 (s, 3H), 1.14 (d, J=7.3, 3H).

EXAMPLE 292

(Z)-(R/S)-5-(Benzylidene)-1,2,3,4-tetrahydro-2,2,4-trimethyl-5H-chromeno[3,4-f]-3-quinolinone (Compound 392, structure 19A of Scheme XXXIV, where $R^1=R^2=H$, $R^3=$phenyl)

To a solution of (R/S)-1-t-butoxycarbonyl-1,2,3,4-tetrahydro-2,2,4-trimethylcoumarino[3,4-f]-3-quinolinone (structure 6A of Scheme XXX, where $R^1=R^2=H$, an intermediate from EXAMPLE 284) (10 mg, 0.025 mmol) in THF (1 mL) at –78° C. was added 1.0M benzylmagnesium bromide (0.06 mL, 0.06 mmol) and the reaction was slowly warmed up to rt and was quenched with water (1 mL). The mixture was extracted with EtOAc (2×5 mL) and was concentrated to provide the crude intermediate, which was treated with excess TFA (0.2 mL) in dichloromethane (1 mL) for 30 min and then quenched with 5% NaOH (5 mL). The mixture was extracted with EtOAc (2×10 mL), concentrated and chromatographied to afford 3.8 mg (40%) of Compound 392 as a colorless oil. Data for Compound 392: IR (neat) 3354, 1716, 1469, 1261, 1045; $^1$H NMR (400 MHz, CDCl$_3$) 7.81 (d, J=7.3, 2H), 7.72 (d, J=7.7, 1H), 7.59 (d, J=8.4, 1H), 7.39 (t, J=7.3, 2H), 7.24–7.18 (m, 2H), 7.17 (d, J=7.7, 1H), 7.08 (t, J=7.7, 1H), 6.83 (d, J=8.4, 1H), 5.91 (s, 1H), 4.37 (q, J=7.3, 1H), 3.76 (s, 1H), 1.57 (d, J=7.3, 3H), 1.51 (s, 3H), 1.24 (s, 3H); $^{13}$C NMR (100 MHz, CDCl$_3$)2.14.1, 152.7, 146.0, 144.2, 135.1, 129.5, 128.6, 128.5, 127.1, 124.2, 122.8, 122.4, 122.2, 121.8, 121.7, 117.8, 116.5, 115.4, 60.1, 44.9, 27.7, 27.2, 17.4.

EXAMPLE 293

(R/S-4l,5u)-5-(3-Fluorophenyl)-1,2,3,4-tetrahydro-2,2,4-trimethyl-5H-chromeno[3,4-f]quinolinone (Compound 393, structure 17A of Scheme XXXIII, where $R^1=R^2=H$, $R^3=$3-fluorophenyl)

This compound, along with Compound 394 (EXAMPLE 294), was prepared by the same Boc-protection/ hydroboration/oxidation/deprotection procedure as described in the synthesis of Compound 234 (EXAMPLE 134) from Compound 191 (EXAMPLE 91) (30 mg, 0.081 mmol). Compound 393 (6.9 mg, 22%) was obtained as a colorless oil. Data for Compound 393: IR (neat) 3356, 1719, 1602, 1487, 1288, 1209, 1028; $^1$H NMR (400 MHz, CDCl$_3$) 7.66 (d, J=7.7, 1H), 7.64 (d, J=8.3, 1H), 7.19 (td, J=7.9, 5.8, 1H), 7.09–6.86 (m, 5H), 6.85 (d, J=8.3, 1H), 6.78 (d, J=7.7, 1H), 6.38 (s, 1H), 3.72 (bs, 1H), 3.58 (q, J=7.4, 1H), 1.44 (s, 3H), 1.23 (s, 3H), 0.87 (d, J=7.4, 3H); $^{13}$C NMR (100 MHz, CDCl$_3$) 214.1, 162.9 (d, J=246.2), 150.7, 143.3, 141.8 (d, J=6.3), 130.4, 130.2, 130.1, 128.6, 124.6, 123.3, 122.7, 122.4, 122.3 (d, J=22.1), 118.3, 116.9, 115.8 (d, J=21.4), 74.5, 60.2, 43.9, 28.1, 27.3, 14.4.

EXAMPLE 294

(R/S-4l,5l)-5-(3-Fluorophenyl)-1,2,3,4-tetrahydro-2,2,4-trimethyl-5H-chromeno[3,4-f]-3-quinolinone (Compound 394, structure 18A of Scheme XXXIII, where $R^1=R^2=H$, $R^3=$3-fluorophenyl)

This compound, along with Compound 393 (EXAMPLE 293), was prepared by the same Boc-protection/ hydroboration/oxidation/deprotection procedure as described in the synthesis of Compound 234 (EXAMPLE 134) from Compound 191 (EXAMPLE 91) (30 mg, 0.081 mmol). Compound 394 (5.0 mg, 16%) was obtained as a colorless oil. Data for Compound 394: IR (neat) 3356, 1719, 1608, 1473, 1288, 1209, 1039; $^1$H NMR (400 MHz, CDCl$_3$) 7.60 (d, J=8.3, 1H), 7.58 (d, J=7.7, 1H), 7.15 (td, J=7.9, 5.8, 1H), 7.09 (t, J=7.7, 1H), 6.97–80 (m, 6H), 6.34 (s, 1H), 3.73 (s, 1H), 3.38 (q, J=7.3, 1H), 1.50 (d, J=7.3, 3H), 1.46 (s, 3H), 1.19 (s, 3H); $^{13}$C NMR (100 MHz, CDCl$_3$) 213.2, 162.9 (d, J=247), 150.8, 142.7, 141.6 (d, J=6.4), 130.2, 130.1, 129.9, 128.5, 123.6, 122.8, 122.7, 122.4, 122.2, 118.3, 116.8, 115.5 (d, J=21.6), 114.9 (d, J=22.6 Hz), 74.2, 60.1, 43.0, 27.3, 26.6, 18.4.

EXAMPLE 295

(R/S-41,5l)-1,2,3,4-Tetrahydro-2,2,4-trimethyl-5-[3-(trifluoromethyl)phenyl]-5H-chromeno[3,4-f]-3-quinolinone (Compound 395, structure 18A of Scheme XXXIII, where $R^1=R^2=H$, $R^3=$3-(trifluoromethyl)phenyl)

This compound, along with Compound 396 (EXAMPLE 396), was prepared by the same Boc-protection/ hydroboration/oxidation/deprotection procedure as described in the synthesis of Compound 234 (EXAMPLE 134) from Compound 195 (EXAMPLE 95) (20 mg, 0.049 mmol). Compound 395 (3.2 mg, 15%) was obtained as a colorless oil. Data for Compound 395: IR (neat) 3354, 2926, 1720, 1607, 1473, 1211, 1126, 1074; $^1$H NMR (400 MHz, CDCl$_3$) 7.61 (d, J=8.3, 1H), 7.57 (d, J=7.7, 1H), 7.42 (t, J=7.7, 1H), 7.39 (s, 1H), 7.38–7.30 (m, 2H), 7.09 (t, J=7.7, 1H), 6.95 (d, J=7.7, 1H), 6.91 (d, J=8.4, 1H), 6.86 (d, J=8.3, 1H), 6.39 (s, 1H), 3.77 (s, 1H), 3.37 (q, J=7.3, 1H), 1.50 (d, J=7.3, 3H), 1.48 (s, 3H), 1.20 (s, 3H); $^{13}$C NMR (100 MHz, CDCl$_3$)213.1, 150.7, 142.8, 131.1, 129.4, 129.1, 128.6, 125.4, 124.6, 123.0, 122.7, 122.6, 122.5, 122.2, 118.3, 117.0, 74.0, 60.2, 43.1, 27.1, 26.5, 18.4.

EXAMPLE 296

(R/S-4l,5u)-1,2,3,4-Tetrahydro-2,2,4-trimethyl-5-[3-(trifluoromethyl)phenyl]-5H-chromeno[3,4-f]-3-quinolinone (Compound 396, structure 17A of Scheme XXXIII, where $R^1=R^2=H$, $R^3=$3-(trifluoromethyl)phenyl)

This compound, along with Compound 395 (EXAMPLE 395), was prepared by the same Boc-protection/ hydroboration/oxidation/deprotection procedure as described in the synthesis of Compound 234 (EXAMPLE 134) from Compound 195 (EXAMPLE 95) (20 mg, 0.049 mmol). Compound 396 (3.2 mg, 15%) was obtained as a colorless oil. Data for Compound 396: IR (neat)3356, 2928, 1718, 1602, 1330, 1126, 1074; $^1$H NMR(400 MHz, CDCl$_3$) 7.67 (d, J=8.3, 1H), 7.65 (d, J=7.7, 1H), 7.52 (s, 1H), 7.48 (m, 1H), 7.35–7.30 (m, 2H), 7.08 (t, J=7.7, 1H), 6.98 (t, J=7.7, 1H), 6.88 (d, J=8.3, 1H), 6.78 (d, J=7.7, 1H), 6.43 (s, 1H), 3.75 (s, 1H), 3.57 (q, J=7.4, 1H), 1.45 (s, 3H), 1.24 (s, 3H), 0.86 (d, J=7.4, 3H); $^{13}$C NMR (100 MHz, CDCl$_3$) 214.0, 150.5, 143.3, 140.3, 132.1, 131.2 (q, J=31.7), 130.0, 129.1, 128.7, 125.7, 123.3, 122.7, 122.6, 122.5, 122.2, 118.3, 117.1, 74.3, 60.2, 43.8, 28.2,27.3, 16.5.

EXAMPLE 297

(R/S-3l,4u,5u)-5-(4-Chlorophenyl)-1,2,3,4-tetrahydro-3-methoxy-2,2,4-trimethyl-5H-chromeno[3,4-f]quinoline (Compound 397, structure 26A of Scheme XXXVI, where $R^1=R^2=H$, $R^3=$4-chlorophenyl, $R^4=$methyl)

To a solution of (R/S-3l,4u,5u)-5-(4-chlorophenyl)-1,2,3, 4-tetrahydro-3-hydroxy-2,2,4-trimethyl-5H-chromeno[3,4- f]quinoline (structure 14A of Scheme XXXIII, where $R^1=R^2=H$, $R^3$=4-chlorophenyl, an intermediate from EXAMPLE 135) (8 mg, 0.016 mmol) in DMF (0.5 mL) and excess MeI (0.5 mL) was added 60% NaH in mineral oil (10 mg, 0.25 mmol). The resulting white slurry was stirred at rt for 2 h and was quenched with water (5 mL). The mixture was extracted with EtOAc (2×10 mL) and was concentrated to give the crude product, which was treated with TFA (0.2 mL) in $CH_2Cl_2$ (1 mL) for 60 min and was quenched with 5% NaOH (5 mL). The mixture was extracted with EtOAc (2×10 mL), concentrated and was purified by silica gel chromatography to afford 5.0 mg (75%) of Compound 397 as a colorless oil. Data for Compound 397: $^1$H NMR (400 MHz, $CDCl_3$) 7.53 (d, J=7.7, 1H), 7.48 (d, J=8.4, 1H), 7.12 (s, 4H), 7.4M(t, J=7.7, 1H), 6.89 (t,J=7.7, 1H), 6.87 (d, J=7.7, 1H), 6.63 (d, J=8.4, 1H), 6.48 (s, 1H), 3.74 (bs, 1H), 3.26 (s, 3H), 3.08 (d, J=3.8, 1H), 2.83 (qd, J=7.3, 3.8, 1H), 1.52 (d, J=7.3, 3H), 1.35 (s, 3H), 1.50 (s, 3H).

EXAMPLE 298

(R/S-3l,4u,5u)-5-(4-Chlorophenyl)-1,2,3,4-tetrahydro-3-methoxy-2,2,4-trimethyl-5H-chromeno[3,4-f]quinoline (Compound 398, structure 25A of Scheme XXXVI, where $R^1=R^2=H$, $R^{3-4}$-chlorophenyl, $R^4$=methyl)

To a solution of (R/S-3l, 4u, 5l)-5-(4-chlorophenyl)-1,2,3,4-tetrahydro-3-hydroxy-2,2,4-trimethyl-5H-chromeno[3,4-f]quinoline (structure 13A of Scheme XXXIII, where $R^1=R^2=H$, $R^3$=4-chlorophenyl, an intermediate from EXAMPLE 135) (8 mg, 0.016 mmol)in DMF (0.5 mL) and excess MeI (0.5 mL) was added 60% NaH in mineral oil (10 mg, 0.25 mmol). The resulting white slurry was stirred at rt for 2 h and was quenched with water (5 mL). The mixture was extracted with EtOAc (2×10 mL) and was concentrated to give the crude product, which was treated with TFA (0.2 mL) in $CH_2Cl_2$ (1 mL) for 60 min and was quenched with 5% NaOH (5 mL). The mixture was extracted with EtOAc (2×10 mL), concentrated and was purified by silica gel chromatography to afford 4.7 mg (70%) of Compound 398 as a colorless oil. Data for Compound 398: $^1$H NMR (400 MHz, $CDCl_3$) 7.55 (d, J=7.7, 1H), 7.47 (d, J=8.4, 1H), 7.16 (d, J=8.7, 2H), 7.12 (d, J=8.7, 2H), 6.97 (t, J=7.7, 1H), 6.89 (t, J=7.7, 1H), 6.73 (d, J=7.7, 1H), 6.68 (d, J=8.4, 1H), 6.34 (s, 1H), 3.65 (bs, 1H), 3.53 (s, 3H), 3.03 (s, 1H), 3.02 (qd, J=7.0, 0.8, 1H), 1.30 (s, 3H), 1.11 (s, 3H), 0.88 (d, J=7.0, 3H).

EXAMPLE 299

(R/S-3l,4u,5l)-5-(4-Chlorophenyl)-1,2,3,4-tetrahydro-3-propyloxy-2,2,4-trimethyl-5H-chromeno[3,4-f]quinoline (Compound 399s structure 25A of Scheme XXXVI, where $R^1=R^2=H$, $R^3$=4-chlorophenyl, $R^4$=propyl)

To a solution of (R/S-3l, 4u, 5l)-5-(4-chlorophenyl)-1,2,3,4-tetrahydro-3-hydroxy-2,2,4-trimethyl-5H-chromeno[3,4-f]quinoline (structure 13A of Scheme XXXIII, where $R^1=R^2=H$, $R^3$=4-chlorophenyl, an intermediate from EXAMPLE 135) (7 mg, 0.014 mmol) in DMF (0.5 mL) and excess PrI (0.5 mL) was added 60% NaH in mineral oil (10 mg, 0.25 mmol). The resulting white slurry was stirred at rt for 2 h and was quenched with water (5 mL). The mixture was extracted with EtOAc (2×10 mL) and was concentrated to give the crude product, which was treated with TFA (0.2 mL) in $CH_2Cl_2$ (1 mL) for 60 min and was quenched with 5% NaOH (5 mL). The mixture was extracted with EtOAc (2×10 mL), concentrated and was purified by silica gel chromatography to afford 2.5 mg (40%) of Compound 399 as a colorless oil. Data for Compound 399: $^1$H NMR (400 MHz, $CDCl_3$) 7.57 (d, J=7.7, 1H), 7.48 (d, J=8.4, 1H), 7.16 (d, J=8.6, 2H), 7.12 (d, J=8.6, 2H), 6.99 (t, J=7.7, 1H), 6.89 (t, J=7.7, 1H), 6.73 (d, J=7.7, 1H), 6.68 (d, J=8.4, 1H), 6.33 (s, 1H), 3.65 (bs, 1H), 3.58 (m, 2H), 3.11 (d, J=5.8, 1H), 3.00 (qd, J=7.0, 5.8, 1H), 1.65–1.50 (m, 2H), 1.30 (s, 3H), 1.10 (s, 3H), 0.93 (t, J=5.8, 1H), 0.88 (d, J=7.0, 3H).

EXAMPLE 300

(R/S-3l,4u,5u)-5-(4-Chlorophenyl)-1,2,3,4-tetrahydro-3-propyloxy-2,2,4-trimethyl-5H-chromeno[3,4-f]quinoline (Compound 400, structure 26A of Scheme XXXVI, where $R^1=R^2=H$, $R^3$=4-chlorophenyl, $R^4$=propyl)

To a solution of (R/S-3l,4u,5u)-5-(4-chlorophenyl)-1,2,3,4-tetrahydro-3-hydroxy-2,2,4-trimethyl-5H-chromeno[3,4-f]quinoline (structure 14A of Scheme XXXIII, where $R^1=R^2=H$, $R^3$=4-chlorophenyl, an intermediate from EXAMPLE 135) (8 mg, 0.016 mmol) in DMF (0.5 mL) and excess PrI (0.5 mL) was added 60% NaH in mineral oil (10 mg, 0.25 mmol). The resulting white slurry was stirred at rt for 2 h and was quenched with water (5 mL). The mixture was extracted with EtOAc (2×10 mL) and was concentrated to give the crude product, which was treated with TFA (0.2 mL) in $CH_2Cl_2$ (1 mL) for 60 min and was quenched with 5% NaOH (5 mL). The mixture was extracted with EtOAc (2×10 mL), concentrated and was purified by silica gel chromatography to afford 2.5 mg (40%) of Compound 400 as a colorless oil. Data for Compound 400: $^1$H NMR (400 MHz, $CDCl_3$) 7.54 (d, J=7.7, 1H), 7.48 (d, J=8.4, 1H), 7.12 (d, J=8.6, 2H), 7.09 (d, J=8.6, 2H), 7.02 (t, J=7.7, 1H), 6.89 (t, J=7.7, 1H), 6.87 (d, J=7.7, 1H), 6.62 (d, J=8.4, 1H), 6.48 (s, 1H), 3.72 (bs, 1H), 3.28 (m, 2H), 3.16 (d, J=4.0, 1H), 2.78 (qd, J=7.2, 4.0, 1H), 1.51 (d, J=7.2, 3H), 1.51–1.36 (m, 2H), 1.34 (s, 3H), 1.14 (s, 3H), 0.80 (t, J=7.4, 3H).

EXAMPLE 301

(R/S-4l,5l)-3-Benzenzylidene-5-(4-chlorophenyl)-1,2,3,4-tetrahydro-2,2,4-trimethyl-5H-chromeno[3,4-f]quinoline (Compound 401, structure 27A of Scheme XXXVII, where $R^1=R^2=H$, $R^{3-4}$-chlorophenyl, $R^4$=phenyl)

To a solution of Compound 234 (EXAMPLE 134) (35 mg, 0.086 mmol) in THF (4 mL) was added a 1.0M ether solution of benzylmagnesium chloride (0.3 mL, 0.3 mmol) and the reaction was stirred at rt for 2 h. The reaction mixture was quenched with water (5 mL) and extracted with EtOAc (2×10 mL). Removal of solvent and chromatography of the crude residue afforded the adduct in 66% yield as a 8:1 mixture of two isomers. The adduct intermediate (8 mg, 0.016 mmol) and Burgess reagent (15 mg, 0.063 mmol) in benzene were heated at reflux for 2 h. Removal of solvent and purification of the mixture on a prep TLC plate using a 25% mixture of EtOAc/Hexane as solvent afforded 0.5 mg (7%) of Compound 401 as a colorless oil. Data for Compound 401: $^1$H NMR (400 MHz, $CDCl_3$) 7.61 (d, J=7.7, 1H), 7.56 (d, J=8.4, 1H), 7.43 (t, J=7.5, 2H), 7.32 (t, J=7.7, 1H), 7.21 (d, J=7.6, 2H), 7.16 (d, J=8.6, 2H), 7.05–6.93 (m, 2H), 6.96 (d, J=8.6, 2H), 6.72 (d, J=8.4, 1H), 6.68 (d, J=7.7, 1H), 6.38 (s, 1H), 6.05 (s, 1H), 4.02 (q, J=7.5, 1H), 3.55 (bs, 1H), 1.52 (s, 3H), 1.41 (s, 3H), 0.84 (d, J=7.5, 3H).

EXAMPLE 302

(R/S-4l,5u)-5-(4-Chlorophenyl)-1,2,3,4-tetrahydro-2,2,4-trimethyl-5H-chromeno[3,4-f]-3-quinolinone (Compound 402, structure 53 of Scheme XV, where $R^1$=H, $R^2$=fluoro, R=4-chlorophenyl)

This compound (2.2 mg, 4%) was prepared in a manner similar to that described for the preparation of Compound 234 (EXAMPLE 134) from Compound 214 (EXAMPLE 114) (50 mg, 0.16 mmol). In addition, 2.2 mg (4%) of Compound 403 (EXAMPLE 303) was also obtained as a clear-colorless oil. Data for compound 402: Rf=0.38 (silica gel, 25% EtOAc:hex); $^1$H NMR (400 MHz, CDCl$_3$) 7.51 (d, J=8.5, 1H), 7.23 (d, J=8.5, 1H), 7.16 (d, J=8.5, 2H), 7.04 (d, J=8.5, 2H), 6.84 (d, J=8.5, 1H), 6.78 (m, 2H), 6.30 (s, 1H), 3.79 (brs, 1H), 3.33 (q, J=7.5, J=7.5, 1H), 1.49 (d, J=7.5, 3H), 1.46 (s, 3H), 1.25 (s, 3H).

EXAMPLE 303

(R/S-4l,5l)-5-(4-Chlorophenyl)-1,2,3,4-tetrahydro-2,2,4-trimethyl -5H-chromeno[3,4-f]-3-quinolinone (Compound 403, structure 52 of Scheme XV, where $R^1$=H, $R^2$=fluoro, R=4-chlorophenyl)

This compound (2.2 mg, 4%) was obtained along with Compound 402 as described above (EXAMPLE 302). Data for compound 403: Rf=0.38 (silica gel, 25% EtOAc:hex); $^1$H NMR (400 MHz, CDCl$_3$) 7.56 (d, J=8.5, 1H), 7.31 (d, J=8.5, 1H), 7.20 (d, J=8.5, 2H), 7.10 (d, J=8.5, 2H), 6.85 (d, J=8.5, 1H), 6.74 (m, 2H), 6.35 (s, 1H), 3.79 (brs, 1H), 3.55 (q, J=7.5, J=7.5, 1H), 1.45 (s, 3H), 1.26 (s, 3H), 0.86 (d, J=7.5, 3H).

EXAMPLE 304

(R/S)-1,2,3,4-Tetrahydro-1,2,2,4-tetramethyl -6-trifluoromethyl-8-pyranono[5,6-g]quinoline (Compound 404, structure 28A of Scheme XXXVIII, where $R^1$=$R^2$=$R^5$=H, $R^3$=trifluoromethyl, Z=O)

In a flame dried r.b. flask was dissolved Compound 250 (EXAMPLE 150) (50 mg, 161 μmol) in glacial acetic acid (10 mL). To the stirred solution was added paraformaldehyde (51 mg, 1.61 mmol, 10 equiv). The cloudy yellow solution stirred for 10 min, then NaCNBH$_3$ (50 mg, 805 μmol, 5 equiv) was added at once. Upon addition the solution emitted gas for approx. 5 min then turned a brilliant fluorescent yellow/green. After stirring at rt under a blanket of N$_2$ for 20 h, the solution was slowly poured over ice and quenched with NaOH (20%), extracted with EtOAc (2×50 mL), washed with brine (2×25 mL), dried over Na$_2$SO$_4$ and concentrated in vacuo to give 51.3 mg (99%) of Compound 404 as a yellow-green solid. Data for Compound 404: $R_f$=0.39 (hexanes/EtOAc; 3:1). $^1$H NMR (400 MHz, CDCl$_3$) 7.31 (dd, J=1.5, 1.5, 1H), 6.44 (s, 1H), 6.35 (s, 1H), 2.90 (s, 3H, N-C$\underline{H}_3$), 2.83 (m, partially obscured by Me, 1H, C4-H), 1.84 (dd, J=4.2, 13.3, 1H, C3-H), 1.53 (dd, J=13.0, 13.0, 1H), 1.36 (d, J=6.6, 3H, C4-C$\underline{H}_3$), 1.35 (s, 3H, C2-C$\underline{H}_3$), 1.29 (s, 3H, C2-C$\underline{H}_3$).

EXAMPLE 305

(R/S)-5-(3-Furyl)-1,2,3,4-tetrahydro-2,2,4-trimethyl-8-pyranono[5,6-g]quinoline (Compound 405, structure 63 of Scheme XVIII, where $R^1$=$R^2$=H, R3=$^3$-furyl, Z=O)

In a oven dried pressure tube equivuipped with a magnetic stir bar was dissolved (R/S)-1,2,3,4-tetrahydro-2,2,4-trimethyl-7-hydroxyquinoline (EXAMPLE 150) (50.8 mg, 292 μmol), ethyl 3-keto-3-(3-furyl)propionate (0.10 mL, 642 μmol, 2.2 equiv) and ZnCl$_2$ (119 mg, 876 μmol, 3 equiv) in absolute ethanol (6 mL). The solution was heated at 105° C. for 19 h. The cooled solution was concentrated on Celite™ to give a free flowing powder which was purified via silica gel flash column chromatography using a solvent system of hexanes/ethyl acetate (4:1) to 14.6 mg (16% ) of Compound 405 as a yellow oil. Data for Compound 405: $R_f$=0.26 (hexanes/EtOAc; 3:1); $^1$H NMR (400 MHz, CDCl$_3$) 7.76 (s, 1H), 7.58 (dd, J=1.4, 3.0, 1H), 7.48 (s, 1H), 6.66 (s, 1H), 6.37 (s, 1H), 6.06 (s, 1H), 4.37 (br s, 1H, NH), 2.91 (m, 1H, C4-H), 1.78 (dd, J=4.1, 13, 1H, C3-H), 1.44 (dd, J=13, 13, 1H, C3-H), 1.33 (d, J=6.7, 3H, C4-CH$_3$), 1.31 (s, 3H, C2-CH$_3$), 1.23 (s, 3H, C2-CH$_3$).

EXAMPLE 306

5-(3-Furyl)-1,2-dihydro-1,2,2,4-tetramethyl-8-pyranono[5,6-g]quinoline (Compound 406, structure 60 of Scheme XVI, where $R^1$=$R^2$=$R^5$=H, $R^3$=3-furyl, Z=O) In a flame dried r.b. flask was dissolved Compound 264 (EXAMPLE 164) (1.1 mg, 3.58 μmol) in glacial acetic acid (3 mL). To the stirred solution was added para-formadehyde (1.2 mg, 36 μmol, 10 equiv). The cloudy yellow solution stirred for 10 min then NaCNBH$_3$ (1.1 mg, 17 μmol, 5 equiv) was added at once. Upon addition the solution emitted gas for approx 5 min then turned bright yellow. After stirring at rt under a blanket of N$_2$ for 20 h the solution was slowly poured over ice and quenched with NaOH (20%), extracted with EtOAc (2×10 mL), washed with brine (2×10 mL), dried over Na$_2$SO$_4$ and concentrated in vacuo to give a impure product that was further purified by preparatory plate chromatography (silica gel, 1000 μm) using a solvent system of 4:1 hexanes/EtOAc to afford 0.8 mg (70% ) of Compound 406 as a yellow-green solid. Data for Compound 406: $R_f$=0.25 (hexanes/EtOAc; 3:1). $^1$H NMR (400 MHz, CDCl$_3$) 7.77 (s, 1H), 7.57 (d, J=1.7, 1H), 7.30 (s, 1H), 6.66 (d, J=1.7, 1H), 6.40 (s, 1H), 6.07 (s, 1H), 5.33 (s, 1H, C3-H), 2.89 (s, 3H, N-C$\underline{H}_3$), 1.95 (d, J=1.1, 3H, C4-C$\underline{H}_3$), 1.38 (s, 6H, (C$\underline{H}_3$)2).

EXAMPLE 307

5-(3-Furyl)-1,2-dihydro-1,2,2,4-tetramethyl-8-thiopyranono[5,6-g]quinoline (Compound 407, structure 29A of Scheme XXXIX, where $R^1$=$R^2$=$R^5$=H, $R^3$=3-furyl, Z=O)

In a dry r.b. flask was dissolved LG12066X (5.2 mg, 16.1 μmol) in glacial acetic acid (5 mL). To the stirred solution was added para-formadehyde (5.4 mg, 160 μmol, 10 equiv). The cloudy red solution stirred for 10 min then NaCNBH$_3$ (5.1 mg, 80 μmol, 5 equiv) was added at once. After stirring under a blanket of N$_2$ for 12 h the solution was slowly poured over ice and quenched with NaOH (20%), extracted with EtOAc (2×20 mL), washed with brine (2×20 mL), dried over Na$_2$SO$_4$ and concentrated in vacuo to give an impure product that was further purified by prep TLC (silica gel, 1000 μm) using a solvent system of 4:1 hexanes/EtOAc to afford 3.2 mg (60%) of Compound 407 as a red solid. Data for Compound 407: $R_f$=0.39 (hexanes/EtOAc; 3:1). $^1$H NMR (400 MHz, CDCl$_3$) 7.21 (d, J=1.7, 1H), 7.16 (s, 1H), 6.51 (s, 1H), 5.42 (s, 1H, C3-$\underline{H}$), 2.90 (s, 3H, N-C$\underline{H}_3$), 2.00 (d, J=1.1, 3H, C4-C$\underline{H}_3$), 1.41 (s, 6H, (CH$_3$)$_2$).

EXAMPLE 308

6-Chloro-5-(3-furyl)-1,2-dihydro-1,2,2,4-tetramethyl-8-pyranono[5,6-g]quinoline (Compound 408, structure 60 of Scheme XVI, where $R^1$=$R^5$=H, R2=chloro, $R^3$=trifluoromethyl, Z=O)

In a dry r.b. flask was dissolved Compound 258 (EXAMPLE 158) (5.9 mg, 17.2 μmol) in glacial acetic acid (5 mL). To the stirred solution was added para-formadehyde (5.5 mg, 172 μmol, 10 equiv). The cloudy yellow solution stirred for 10 min then NaCNBH$_3$ (5.8 mg, 86 μmol, 5 equiv) was added at once. After stirring under a blanket of N$_2$ for 12 h the solution was slowly poured over ice and quenched with NaOH (20%), extracted with EtOAc (2×20 mL), washed with brine (2×20 mL), dried over Na$_2$SO$_4$ and concentrated in vacuo to give an impure product that was further purified by 3 consecutive prep TLC's (silica gel, 1000 gm) using a solvent system of 4:1 hexanes/EtOAc to afford 2.5 mg (40%) of Compound 408 as a orange/yellow solid. Data for Compound 408: R$_f$=0.36 (hexanes/EtOAc; 3:1). $^1$H NMR (400 MHz, CDCl$_3$) 7.32 (d, J=1.7, 1H), 6.33 (s, 1H), 5.38 (s, 1H, C3-H), 2.88 (s, 3H, N-CH$_3$), 1.99 (d, J=1.1, 3H, C4-CH3), 1, 39 (s, 6H, (CH$_3$)$_2$).

EXAMPLE 309

1,2,3,4-Tetrahydro-2,2,4,10-tetramethyl-6-trifluoromethyl-8-pyridono[5,6-g]quinoline (Compound 409, structure 63 of Scheme XVIII, where R$^1$=methyl, R$^2$=H, R$^3$=trifluoromethyl, Z=NH)

7-tert-Butyloxycarbamoyl-1,2,3,4-tetrahydro-2,2,4,8-tetramethylquinoline (structure 72 of Scheme XVIII, where R$^1$=methyl, P=t-butoxy, Z=NH).

This compound was prepared from 7-tert-butyloxycarbamoyl-1,2-dihydro-2,2,4,8-tetramethylquinoline (EXAMPLE 155) (4.50 g, 14.9 mmol) according to the general hydrogenation procedure previously described (EXAMPLE 160), affording 4.48 g (99%) of the desired tetrahydroquinoline as a white solid. Data for 7-tert-butyloxycarbamoyl-1,2,3,4-tetrahydro-2,2,4,8-tetramethylquinoline: $^1$H NMR (400 MHz, CDCl$_3$) 7.03 (d, 1H, J=8.3, 5-H), 6.81 (d, 1H, J=8.2, 6-H), 6.13 (br s, 1H, BOCNH), 3.43 (br s, 2H, NH$_2$), 2.91 (ddq, 1H, J=19.0, 12.8, 6.6, 4-H), 1.96 (s, 3H, 8-CH$_3$), 1.73 and 1.40 (d of ABq, 2H, J$_{AB}$=12.8, J$_A$=5.6, J$_B$=12.6, 3-H), 1.31 (d, 3H, J=6.7, 4-CH$_3$), 1.28 and 1.16 ppm [2s, 2×3H, 2-(CH$_3$)$_2$].

7-Amino-1,2-dihydro-2,2, 4, 8-tetramethylquinoline

This compound was prepared by General Method 12 (EXAMPLE 147) from 7-tert-butyloxycarbamoyl-1,2,3,4-tetrahydro-2,2,4,8-tetramethylquinoline (4.48 g, 14.9 mmol) to afford 2.92 g (96%) of the desired aniline as a light reddish oil. Data for 7-amino-1,2-dihydro-2,2,4,8-tetramethylquinoline: $^1$H NMR (400 MHz, CDCl$_3$) 6.89 (d, 1H, J=8.1, 5-H), 6.14 (d, 1H, J=8.2, 6-H), 3.42 (br s, 3H, NH$_2$, NH), 2.87 (ddq, 1H, J=18.7, 12.7, 6.4, 4-H), 1.90 (s, 3H, 8-CH$_3$), 1.70 and 1.39 (d of ABq, 2H, J$_{AB}$=12.8, J$_A$=5.6, J$_B$=12.5, 3-H), 1.29 (d, 3H, J=6.7, 4-CH$_3$), 1.27 and 1.16 ppm [2s, 2×3H, 2-(CH$_3$)$_2$].

1,2,3,4-Tetrahydro-2,2,4,10-tetramethyl-6-trifluoromethyl-8-pyridono[5,6-g]quinoline This compound was prepared by General Method 13 (EXAMPLE 147) from 7-amino-1,2,3,4-tetrahydro-2,2,4,8-tetramethylquinoline (2.92 g, 14.3 mmol) and ethyl 4,4,4-trifluoroacetoacetate (3.13 mL, 21.4 mmol, 1.5 equivuiv) to afford 2.04 g (44%) of Compound 409 as a pale fluorescent-yellow solid. Data for Compound 409: mp 239–40 ° C; $^1$H NMR (400 MHz, CDCl$_3$) 9.70 (br s, 1H, CON/B, 7.50 (s, 1H, 5-H), 6.68 (s, 1H, 7-H), 4.13 [br s, 1H, (CH$_3$)$_2$CNH], 3.00 (ddq, 1H, J=12.9, 12.4, 6.3,4-H), 2.15 (s, 3H, 10-CH$_3$), 1.83 and 1.46 [dd of ABq, 2H, J$_{AB}$=13.0, J$_A$=5.3, 1.6 Hz (3-H$_{equiv}$), J$_B$=12.9, 0 Hz (3-H$_{ax}$)], 1.40 (d, 3H, J=6.6, 4-CH$_3$), 1.36 and 1.25 ppm [2s, 2×3H, 2-(CH$_3$)$_2$]. $^{13}$C NMR (100 MHz, CDCl$_3$) d 162.5, 144.9, 139.1, 137.1, 124.3, 122.7, 120.9, 113.8, 105.7, 101.6, 50.2, 43.5, 31.8, 28.9, 27.6, 20.1, 9.7 ppm. Anal. Calcd for C$_{17}$H$_{19}$F$_3$N$_2$O: C, 62.95; H, 5.90; N, 8.64. Found: C, 63.02; H, 6.01; N, 8.48.

EXAMPLE 310

(R/S)-1,2,3,4-Tetrahydro-4-methyl-6-trifluoromethyl-8-pyranono[5,6-g]quinoline (Compound 410, structure 33A of Scheme XL, where R$^{1-3}$=R$^6$=H, R$^4$=methyl, R$^5$=trifluoromethyl) 3-(3-Methoxyanilino)propionic acid To a oven dried 500 mL rb flask equivuipped with a magnetic stir bar and a water cooled reflux condenser was dissolved anisidine (5 mL, 44.6 mmol) in toluene (70 mL). The stirred solution was heated to reflux and acrylic acid (3.0 mL, 44.1 mmol, 1 equiv) was dripped in over a 10 min period to give a clear colorless solution. After heating at reflux for 3 h the dark red solution was cooled to rt and concentrated in vacuo to remove both the unreacted acrylic acid and toluene to give a 6.4 g of a 1: 1 mixture of the desired amino acid and anisidine as a red viscous oil. Data for 3-(3-Methoxyanilino)proionic acid: R$_f$=0.1 (hexanes/EtOAc, 3:1); $^1$H NMR (400 MHz, CDCl$_3$) 9.08 (br s, 1H, NH), 7.28 (d, J=4.3, 1H), 7.21 (dd, J=8.1, 8.1, 1H), 7.03 (dd, J=1.3, 7.9, 1H), 6.67 (dd, J=2.3, 8.4, 1H),3.80 (s, 3H), 3.58 (s, 2H), 2.33 (s, 3H).

1,2,3,4-Tetrahydro-7-methoxy-4-quinolone

To a oven dried 500 mL rb flask equivuipped with a magnetic stir bar and a N$_2$ gas inlet, the material obtained above was dissolved in PPA (~150 mL). The resulting red viscous solution was heated at 100° C. with constant stirring under a blanket of N$_2$ for 12 h. The still warm solution was carefully poured over ice (1 L) and while vigorously stirring the iced solution with a metal stir rod the reaction was quenched by slow addition of a sat. K$_2$CO$_3$ solution. The near neutral solution was extracted with CHCl$_3$ (5×150 mL), washed with brine (2×100 mL), dried over Na$_2$SO$_4$ and concentrated in vacuo to give an impure solid. The solid was purified by taking up in EtOAc and concentrating the liquor on Celite™ to give a free flowing powder which was purified via flash column chromatography (silica gel, CH$_2$Cl$_2$/MeOH, 95:5) to give 1.2 g (62%) of 1,2,3,4-tetrahydro-7-methoxy-4-quinolone as a yellow solid. Data for 1,2,3,4-tetrahydro-7-methoxy-4-quinolone: R$_f$=0.43 (CH$_2$Cl$_2$/MeOH, 95:5); $^1$H NMR (400 MHz, CDCl$_3$) 7.79 (d, J=8.8, 1H), 6.31 (dd, J=2.0, 8.9, 1H), 6.08 (d, J=2.0, 1H), 4.54 (br s, 1H, NH), 3.78 (s, 3H, OCH$_3$), 3.54 (td, J=1.7, 8.0, 2H), 2.63 (t, J=7.0, 2H).

1-t-Butoxycarbonyl-1,2,3,4-tetrahydro-7-methoxy-4-quinolone (structure 31A of Scheme XL, where R$^{1-3}$=H)

To a flame dried 250 mL rb flask equivuipped with a magnetic stir bar and a N$_2$ gas inlet was dissolved 1,2,3,4-tetrahydro-7-methoxy-4-quinolone (1.18 g, 6.67 mmol) and BOC anhydride (2.03 g, 9.33 mmol, 1.33 equiv) in anhydrous THF (60 mL). The solution was cooled to 0° C. and N, N-dimethyl-4-aminopyridine (DMAP) (1.30 g, 10.7 mmol, 1.6 equiv) was added with constant stirring. After stirring over N$_2$ for 16 h the reaction was carefully quenched with 10% NaHSO$_4$ solution (20 mL). The biphasic solution was extracted with EtOAc (3×50 mL), washed with brine (2×50 mL), dried over Na$_2$SO$_4$ and concentrated in vacuo to give 1.65 g (90%) of 1-t-butoxycarbonyl-1,2,3,4-tetrahydro-7-methoxy-4-quinolone as an off white solid. Data for 1-t-butoxycarbonyl-1,2,3,4-tetrahydro-7-methoxy-4-quinolone: R$_f$=0.31 (hexanes/EtOAc, 3:1); $^1$H NMR (400 MHz, CDCl$_3$) 7.27 (d, J=1.6, 1H), 7.06 (d, J=8.5, 1H), 6.61 (dd, J=2.4, 8.5, 1H), 3.78 (s, 3H), 3.71 (t,J=6.0,2H), 2.82 (m, 1H), 2.02 (m, 1H), 1.57 (m, 1H), 1.27 (d, J=7.0, 3H).

(R/S)-1-t-Butoxycarbonyl-1,2,3,4-tetrahydro-4-hydroxy-4-methyl-7-methoxyquinoline To a flame dried 250 mL 3-necked rb flask equivuipped with a magnetic stir bar was added Ce(III)Cl.7 H$_2$O (2.74 g, 7.35 mmol., 2 equiv). The flask was heated in a 140° C. oil bath under reduced pressure (~1 ton) for 2.5 h. The flask was cooled to rt and slowly filled with N$_2$ g. The white powder was suspended in dry THF (30 mL), stirred at rt for 1 h and then cooled to −78° C. To the white suspension was added a 1.4M solution of methyl lithium (MeLi) in Et$_2$O (5.25 mL, 7.35 mmol, 2 equiv) by syringe. The dark yellow/brown solution stirred at −78° C. for 1 h and then 1-t-butoxycarbonyl-1,2,3,4-tetrahydro-7-methoxy-4-quinolone dissolved in 3 mL THF was added. The solution stirred at −78° C. for 3 h and was warmed to 0° C. for 2 h. The reaction did not go to completion and staffing material was observed by TLC (silica gel, hexane/EtOAc, 3:1). The reaction was quenched with H$_2$O (1 mL) and allowed to warm to rt. The solution was neutralized with sat NH$_4$Cl solution (5 mL), extracted with EtOAc (3×100 mL), washed with brine (1×100 mL), dried over Na$_2$SO$_4$ and concentrated in vacuo to give a mix of the desired alcohol and starting material. The mixture was taken up in EtOAc and concentrated on Celite™ to give a free flowing powder which was purified via flash column chromatography (silica gel, hexanes/EtOAc, 3:1) to give 796 mg (74%) of the desired product as a vicious clear colorless oil. Data for 1-t-butoxycarbonyl-1,2,3,4-tetrahydro-4-hydroxy-4-methyl-7-methoxy-quinoline: R$_f$=0.20 (hexanes/EtOAc, 3:1); $^1$H NMR (400 MHz, CDCl$_3$) 7.42 (d, J=8.7, 1H), 7.33 (d, J=1H), 6.66 (dd, J=2.5, 8.6, 1H), 3.98 (m, 1H), 3.79 (s, 3H, OCH$_3$), 3.61 (m, 1H), 1.98 (m, 2H), 1.58 (s, 3H), 1.53 (s, 9H).

(R/S)-1-t-Butoxycarbonyl-1,2,3,4-tetrahydro-4-methyl-7-methoxy-quinoline

To a oven dried 250 mL rb flask equivuipped with a magnetic stir bar was dissolved 1-t-butoxycarbonyl-1,2,3,4-tetrahydro-4-hydroxy-4-methyl-7-methoxy-quinoline (44 mg, 150 μmol) in EtOAc (15 mL). The flask was repeatedly evacuated and flushed with N$_2$ then a catalytic amount of 10% Pd on C (∼5 mg) was added. The flask was again evacuated and flushed with N$_2$ several times and then H$_2$ was introduced by balloon. The solution was stirred under H$_2$ for 12 h. The flask was again evacuated and flushed with N$_2$ several times to remove any residual H$_2$ and the solution was filtered through a pad of Celite™ and concentrated in vacuo to give the desired amine (37.0 mg, 133 μmol, 90% yield) as a clear colorless oil. Data for 1-t-butoxycarbonyl-1,2,3,4-tetrahydro-4-methyl-7-methoxy-quinoline: R$_f$=0.59 (hexanes/EtOAc, 3:1); $^1$H NMR (400 MHz, CDCl$_3$) 7.28 (d, J=2.3, 1 H, Ar-8), 7.07 (d, J=8.5, 1H, Ar-5), 6.61 (dd, J=2.5, 8.5, 1H, Ar-6), 3.78 (s, 3H, OMe), 3.71 (dd, J=6.1, 12.2, 2H, C2-H), 2.83 (m, 1H, C4-H), 2.00 (m, 1H, C3-H), 1.58 (m, 1H, C3-H), 1.53, (s, 9H, (CH$_3$)$_3$), 1.27 (d, J=7.0 Hz, 3H, C4-CH$_3$).

(R/S)-1,2,3,4-Tetrahydro-4-methyl-7-methoxyquinoline. To a oven dried 250 mL r.b. flask equivuipped with a magnetic stir bar and a N$_2$ gas inlet was dissolved 1-t-butoxycarbonyl-1,2,3,4-tetrahydro-4-methyl-7-methoxy-quinoline (678 mg, 2.44 mmol) in CH$_2$Cl$_2$ (15 mL). To the stirred solution was added trifluoroacetic acid (TFA) (2 mL) at rt. The solution stirred under N$_2$ for 2 h and then quenched with sat NaHCO3 solution (25 mL), extracted with CH$_2$Cl$_2$ (3×20 mL), washed with brine (1×30 mL), dried over Na$_2$SO$_4$ and concentrated in vacuo to give 370 mg (77%) of the desired quinoline as a clear colorless oil. Data for 1,2,3,4-tetrahydro-4-methyl-7-methoxyquinoline: R$_f$=0.32 (hexanes/EtOAc, 3:1); $^1$H NMR (400 MHz, CDCl$_3$) 6.95 (d, J=8.1, 1H, Ar-5), 6.22 (dd, J=2.5, 8.3, 1H, Ar-6), 6.03 (d, J=2.6, 1H, Ar-8), 3.86 (br s, 1H, NH), 3.73 (s, 3H, OMe), 3.28 (m, 2H, C2-H), 2.85 (m, 1H, C4-H), 1.95 (m, 1H, C3-H), 1.64 (m, 1H, C3-H), 1.25 (d, J=6.9, 3H, C4-Me).

(R/S)-1,2,3,4-Tetrahydro-7-hydroxy-4-methylquinoline

To a flame dried 25 mL rb flask equivuipped with a magnetic stir bar and a N$_2$ gas inlet was dissolved 1,2,3,4-tetrahydro-4-methyl-7-methoxyquinoline (17.7 mg, 100 μmol) in CH$_2$Cl$_2$ (3 mL). The solution was cooled to 0° C. under a blanket of N$_2$ and then 250 μL of a 1.0M solution of BBr3 in hexanes (250 μmol, 2.5 equiv) was added at once by syringe. The stirred solution was warmed to rt and allowed to react for 3 h. The reaction was quenched with H$_2$O (1 mL), neutralized with sat. NaHCO$_3$ (4 mL) and extracted with CH$_2$Cl$_2$ (5×50 mL), dried over Na$_2$SO$_4$ and concentrated to give 12 mg (66%) of the desired phenolic quinoline as a light yellow oil. Data for (R/S)-1,2,3,4-tetrahydro-7-hydroxy-4-methylquinoline: R$_f$=0.15 (hexanes/EtOAc, 3:1); 1H NMR (400 MHz, CDCl$_3$) 6.91 (d, J=8.7, 1H), 6.12 (dd, J=2.5, 8.3, 1H), 5.97 (d, J=2.5, 1H), 3.27 (m, 2H, H, C2-H), 2.84 (m, 1H, C4-H), 1.95 (m, 1H, C3-H), 1.66 (m, 1H, C3-H), 1.25 d, J=6.9, 3H, C4-CH$_3$).

(R/S)-1,2,3,4-Tetrahydro-4-methyl-6-trifluoromethyl-8-pyranono[5,6-g]quinoline (Compound 410, structure 33A of Scheme XL, where R$^{1-3}$=R$^6$=H, R$^4$=methyl, R$^5$=trifluoromethyl)

In an oven dried pressure tube equivuipped with a magnetic stir bar was dissolved (R/S)-1,2,3,4-tetrahydro-7-hydroxy-4-methylquinoline (11.7 mg, 64.6 μmol) and trifluoromethyl ethyl acetoacetate (20 gL, 146 μmol, 2.2 equiv) and ZnCl$_2$ (20 mg) in 0.5 mL absolute ethanol. The light yellow solution was heated at 98° C. for 20 h and cooled to rt. The dark green solution was concentrated on Celite™ to give a free flowing powder which was purified via silica gel flash column chromatography using a solvent system of hexanes/ethyl acetate (4:1) to give 12.4 mg (66%) of Compound 410 as a yellow solid. Data for Compound 410: R$_f$=0.19 (hexanes/EtOAc, 3:1); $^1$H NMR (400 MHz, CDCl$_3$) 7.29 (s, 1H), 6.36 (m, 2H), 4.70 (br s, 1H, NH), 3.43 (m, 2H, C2-H), 2.95 (m, 1H, C4-H), 1.97 (m, 1H, C3-H), 1.72 (m, 1H, C3-H), 1.31 (d, J=7.0, 3H, C4-CH$_3$).

EXAMPLE 311

1,2-Dihydro-2,2-dimethyl-6-trifluoromethyl-8-pyranono[5,6-g]quinoline (Compound 411, structure 37A of Scheme XLI, where R$^{1-2}$=R$^6$=H, R$^3$=R$^4$=methyl, R$^5$=trifluoromethyl, X=O) 1,2-Dihydro-2,2-dimethyl-7-(1,1,1-trimethylacetoxy)quinoline (structure 36A of Scheme XLI, where R$^1$=R$^2$=H, R$^3$=R$^4$=methyl, P=t-butyl, X=O).

In a oven dried pressure tube equivuipped with a magnetic stir bar was dissolved O-pivaloyl-3-aminophenol (EXAMPLE 138) (4.8 g, 25.0 mmol, 1.5 equiv) and 3-methyl-3-acetoxy-1-butyne (2.1 g, 16.7 mmol, 1 equiv) in dry THF (∼5 mL). To the stirred solution was added CuCl (240 mg, 25 mmol, 0.15 equiv). The sealed pressure tube was heated at 98° C. for 5 h, cooled to rt and concentrated on Celite™ to give a free flowing powder which was purified via flash column chromatography (silica gel, hexanes/EtOAc, 5:1) to give 1.2 g (18%) of the desired product as an off white solid. Data for 1,2-dihydro-2,2-dimethyl-7-(1,1,1-trimethylacetoxy)quinoline: R$_f$=0.80 (hexanes/EtOAc, 3:1); $^1$H NMR (400 MHz, CDCl$_3$) 6.83 (d, J=8.0, 1H), 6.23 (m, 2H), 6.12 (d, J=2.1, 1H), 5.42 (d, J=9.7, 1H), 3.67 (br s, 1H), 1.31 (s, 9H), 1.29 (s, 6H). $^{13}$C NMR (100 MHz, CDCl$_3$) 177, 151, 130, 127, 123, 117, 109, 105, 52, 49, 31, 27.

1,2-Dihydro-7-hydroxy-2,2-dimethylquinoline

To a oven dried rb flask was dissolved 1,2-dihydro-2,2-dimethyl-7-(1,1,1-trimethylacetoxy)quinoline (48 mg, 185 mmol) in absolute ethanol (5 mL) and H$_2$O (1 mL). To the stirred solution was added a catalytic amount of 20% aqueous NaOH solution (∼0.2 mL). After 1.5 h the dark purple solution was diluted with H$_2$O (10 mL), EtOAc (15 mL) and quenched with sat. NH$_4$Cl solution (5 mL). The bi-phasic solution was extracted with EtOAc (4×20 mL), washed with brine (2×30 mL), dried (Na2SO4) and concentrated in vacuo to give 31 mg (96%) of the desired phenolic amine, which was used without further purification.

1,2-Dihydro-2,2-dimethyl-6-trifluoromethyl-8-pyranono[5,6-g]quinoline (Compound 411, structure 37A of Scheme XLI, where $R^{1-2}=R^6=H$, $R^3=R^4=$methyl, $R^5=$trifluoromethyl, X=O)

In a oven dried pressure tube equivuipped with a magnetic stir bar was dissolved 1,2-dihydro-7-hydroxy-2,2-dimethylquinoline (31 mg, 177 μmol), ethyl (4, 4, 4-trifluoroacetoacetate) (75 mg, 408 μmol, 2.2 equiv) and $ZnCl_2$ (75 mg, 550 μmol, 3 equiv) in absolute EtOH. Upon addition of the $ZnCl_2$ the solution went a dark brown. The sealed pressure tube was heated at 105° C. for 16 h, cooled to rt and concentrated on Celite™ to give a free flowing powder which was purified via flash column chromatography (silica gel, hexanes/EtOAc, 5:1) to give 2.3 mg (4.4%) of Compound 411 as a bright yellow solid. Data for Compound 411: $R_f$=0.31 (hexanes/EtOAc, 3:1); $^1$H NMR (400 MHz, CDCl$_3$) 7.11 (s, 1H), 6.41 (s, 1H), 6.32 (s, 2H), 5.58 (d, J=8.0, 1H), 4.39 (br s, 1H), 1.55 (s, 6H).

EXAMPLE 312

1,2,3,4-Tetrahydro-2,2-dimethyl-6-trifluoromethyl-8-pyranono[5,6-g]quinoline (Compound 412, structure 40A of Scheme XLII, where $R^{1-2}=R^6=H$, $R^3=R^4=$methyl, $R^5=$trifluoromethyl, X=O) 1,2,3,4-Tetrahydro-2,2-dimethyl-7-(1,1,1-trimethylacetoxy)quinoline (structure 39A of Scheme XLII, where $R^1=R^2=H$, $R^3=R^4=$methyl, P=t-butyl, X=O). To a oven dried 250 mL rb flask equivuipped with a magnetic stir bar and a N$_2$ gas inlet was dissolved 1,2-dihydro-2,2-dimethyl-7-(1,1,1-trimethylacetoxy)quinoline (EXAMPLE 311) (47 mg, 192 μmol) in dry EtOAc (5 mL). The flask was repeatedly evacuated and flushed with N$_2$ then a catalytic amount of 10% Pd on C (~10 mg) was added. The flask was again evacuated and flushed with N$_2$ several times and then H$_2$ was introduced by balloon. The solution was stirred under H$_2$ for 13 h. The flask was again evacuated and flushed with N$_2$ several times to remove any residual H$_2$ and the solution was filtered through a pad of Celite™ and concentrated in vacuo to give the desired amine (38.0 mg, 154 μmol, 81% yield) as an off white solid. Data for 1,2,3,4-tetrahydro-2,2-dimethyl-7-(1,1,1-trimethylacetoxy)quinoline: $R_f$=0.54 (hexanes/EtOAc, 3:1); $^1$H NMR (400 MHz, CDCl$_3$) 6.93 (d, J=8.1, 1H), 6.26 (dd, J=2.3, 8.1, 1H), 6.13 (d, J=2.1, 1H), 3.59 (br s, 1H), 2.73 (t, J=6.7, 2H), 1.67 (t, J=6.7, 2H), 1.32 (s, 9H), 1.18 (s, 6H).

1,2,3,4-Tetrahydro-7-hydroxy-2,2-dimethylquinoline

To a oven dried rb flask was dissolved 1,2,3,4-tetrahydro-2,2-dimethyl-7-(1,1,1-trimethylacetoxy)quinoline (38 mg, 154 μmol) in absolute ethanol (5 mL) and H$_2$O (1 mL). To the stirred solution was added a catalytic amount of 20% aqueous NaOH solution (~0.2 mL) and stirred under N$_2$ at rt. After 3 h the dark purple solution was diluted with H$_2$O (10 mL), EtOAc (15 mL) and quenched with sat. NH$_4$Cl solution (5 mL). The bi-phasic solution was extracted with EtOAc (4×20 mL), washed with brine (2×30 mL), dried (Na$_2$SO$_4$) and concentrated in vacuo to give 25 mg (92%) of the desired phenolic amine as a light yellow oil. Data for 1,2,3,4-tetrahydro-7-hydroxy-2,2-dimethylquinoline: $R_f$=0.22 (hexanes/EtOAc, 3:1); $^1$H NMR (400 MHz, CDCl$_3$) 6.82 (d, J=8.1, 1H), 6.09 (dd, J=2.6, 8.2, 1H), 5.93 (d, J=2.4, 1H), 2.68 (t, J=6.7, 2H), 1.67 (t, J=6.7, 2H), 1.19 (s, 6H).

1,2,3,4-Tetrahydro-2,2-dimethyl-6-trifluoromethyl-8-pyranono[5,6-g]quinoline Compound 412, structure 40A of Scheme XLII, where $R^{1-2}=R^6=R^8=H$, $R^3=R^4=$methyl, $R^5=$trifluoromethyl, X=O,)

In a oven dried pressure tube equivuipped with a magnetic stir bar was dissolved 1,2,3,4-tetrahydro-7-hydroxy-2,2-dimethylquinoline (25.1 mg, 142 μmol), TFEEA (62 mg, 338 μmol, 2.2 equiv) and ZnCl$_2$ (62 mg, 462 μmol, 3 equiv) in absolute EtOH. The sealed pressure tube was heated at 105° C. for 13 h, cooled to rt and concentrated on Celite™ to give a free flowing powder which was purified via flash column chromatography (silica gel, hexanes/EtOAc, 5:1) to 26.3 mg (60%) of Compound 412 as a bright yellow solid. Data for Compound 412: $R_f$=0.31 (hexanes/EtOAc, 3:1); $^1$H NMR (400 MHz, CDCl$_3$) 7.26 (s, 1H), 6.37 (m, 2H), 4.52 (br s, 1H)m, 2.83 (t, J=6.6, 2H), 1.74 (t, J=6.6, 2H), 1.28 (s, 6H).

EXAMPLE 313

1,2,3,4-Tetrahydro-6-triifluoromethyl-8-pyranono[5,6-g]quinoline (Compound 413, structure 45A of Scheme XLIII, where $R^1=H$, $R^2=$-trifluoromethyl).

3-Methoxy-trans indanone oxime (Compound 43A, Scheme XLIII)

To an oven dried 250 mL rb flask equivuipped with a magnetic stir bar, a N$_2$ gas inlet and a water cooled reflux condenser was dissolved 7-methoxyindanone (2.0 g, 12.3 mmol), Et$_3$N (3.0 mL, 21.5 mmol, 1 equiv) and NH$_2$OH.HCl (1,48 g, 21.5 mmol, 1 equiv) in MeOH (50 mL). The clear colorless solution was heated at reflux for 12 h, cooled to rt and partially concentrated under reduced pressure to half the original volume. The liquor was diluted with H$_2$O (25 mL) and extracted with EtOAc (4×50 mL), washed with brine (3×25 mL), dried (Na$_2$SO$_4$) and concentrated in vacuo to afford 2.14 g (99%) of the desired adduct as a white solid. Data for 3-methoxy-trans-indanone oxime: $R_f$=0.23 (hexanes/EtOAc, 3:1); $^1$H NMR (400 MHz, CDCl$_3$) 8.01 (br s, 1H), 7.47 (d, J=2.4, 1H), 6.88 (dd, J=2.4, 8.3, 1H), 6.82 (d, J=8.3, 1H), 3.30 (s, 3H), 2.79 (m, 2H), 2.44 (t, J=6.7, 2H).

1,2,3,4-Tetrahydro-7-methoxyquinoline (Compound 44A Scheme XLIII)

In a flame dried 100 mL rb flask equivuipped with a magnetic stir bar, a N$_2$ gas inlet and a water cooled reflux condenser was dissolved 3-methoxy-trans indanone oxime (280 mg, 1.10 mmol) in dry THF. Under a blanket of N$_2$ the solution was cooled to 0° C. and a 1.0M solution of LAH in pentane (0.5 mL, 5.0 mmol, 4.3 equiv) was added via syringe. The solution was then heated to reflux for 4.5 h. The solution was cooled to rt and quenched with H$_2$O (2 mL), extracted with EtOAc (3×25 mL), washed with brine (50 mL), dried over Na$_2$SO$_4$ and concentrated on Celite™ to give a free flowing powder which was purified via flash column chromatography (silica gel, hexanes/EtOAc, 3:1) to give 14 mg (8%) of the desired adduct as an off white solid. Data for 1,2,3,4-tetrahydro-7-methoxyquinoline: $R_f$=0.35 (hexanes/EtOAc, 3:1); $^1$H NMR (400 MHz, CDCl$_3$) 6.84 (d, J=8.0, 1H), 6.19 (dd, J=2.5, 8.2, 1H), 6.03 (d, J=2.5, 1H), 3.81 (br s, 1H), 3.73 (s, 3H), 3.27 (m, 2H), 2.69 (t, J=6.4, 2H), 1.91 (m, 2H).

1,2,3,4-tetrahydro-7-hydroxyquinoline

In a flame dried 100 mL rb flask equivuipped with a magnetic stir bar and a N$_2$ gas inlet was dissolved 1,2,3,4-tetrahydro-7-methoxyquinoline (14.0 mg, 85.8 μmol) in CH$_2$Cl$_2$ (~3 mL). The solution was cooled to −78° C. under a blanket of N$_2$ and a 1.0M solution of BBr3 in CH$_2$Cl$_2$ (0.25 mL, 250 μmol, 3 equiv) was added via syringe. The solution stirred at −78° C. for 1 h, warmed to 0° C. for 1 h and rt for 2 h. The reaction was quenched with H2O (2 mL), extracted with CH$_2$Cl$_2$ (3×20 mL), washed with brine (2×20 mL), dried (Na$_2$SO$_4$) and concentrated in vacuo to afford 12 mg (88%) of the desired adduct as a yellow oil. Data for 1,2,3,4-tetrahydro-7-hydroxyquinoline: $R_f$=0.21 (hexanes/EtOAc, 3:1); $^1$H NMR (400 MHz, CDCl$_3$) 6.79 (d, J=8.2, 1H), 6.12 (dd, J=2.4, 8.0, 1H), 6.04 (d, J=2.3, 1H), 4.78 (br s, 1H), 3.27 (m, 2H), 2.67 (m, 2H), 1.91 (m, 2H).

1,2,3,4-Tetrahydro-6-trifluoromethyl-8-pyranono[5,6-g]quinoline (Compound 413, structure 45A of Scheme XLIII, where $R^1$=H, $R^2$=trifluoromethyl)

In a oven dried pressure tube equivuipped with a magnetic stir bar was dissolved 1,2,3,4-tetrahydro-7-hydroxyquinoline (11.7 mg, 78.5 µmol), TFEEA (>10 fold excess) and ZnCl$_2$ (>10 fold excess) in absolute EtOH (3 mL). The sealed pressure tube was heated at 110° C. for 16 h, cooled to rt and concentrated on Celite™ to give a free flowing powder which was purified via flash column chromatography (silica gel, hexanes/EtOAc, 4:1) to give 8.6 mg, (41%) of Compound 413 as a bright yellow solid. Data for Compound 413: $R_f$=0.31 (hexanes/EtOAc, 3:1); $^1$H NMR (400 MHz, CDCl$_3$) 7.21 (s, 1H), 6.35 (m, 2H), 4.66 (br s, 1H), 3.40 (m, 2H), 2.80 (t, J=6.3, 2H), 1.95 (m, 2H).

EXAMPLE 314

(R/S)-4-Ethyl-1,2,3,4-tetrahydro-6-trifluoromethyl-8-pyranono[5,6-g]quinoline (Compound 414, structure 33A of Scheme XL, where $R^{1-3}$=$R^6$=H, $R^4$=ethyl, $R^5$=trifluoromethyl)

(R/S)-1-t-Butoxycarbonyl-4-ethyl-1,2,3,4-tetrahydro-4-hydroxy-7-methoxyquinoline To a flame dried 250 mL r.b. flask equivuipped with a magnetic stir bar and a N$_2$ gas inlet was dissolved (R/S)-1-t-Butoxycarbonyl-1,2,3,4-tetrahydro-7-methoxy-4-quinolone (106 mg, 390 µmol) in dry THF (8 mL). The solution was cooled to 0° C. under a blanket of N$_2$ and a 1.0M solution of ethyl magnesium bromide (EtMgBr) in ethyl ether (1.3 mL, 1.36 mmol, 3.5 equiv) was added via syringe. The solution was stirred at 0° C. for 2 h and at rt for 3 h. The reaction did not go to completion and starting material was observed by TLC (silica gel, hexane/EtOAc, 3:1). The reaction was quenched with H$_2$O (2 mL), extracted with EtOAc (4×25 mL), washed with brine (40 mL), dried over Na$_2$SO$_4$ and concentrated in vacuo to give 38 mg (32%) of the desired alcohol as a colorless oil. Data for (R/S)-1-t-butoxycarbonyl-4-ethyl-1,2,3,4-tetrahydro-4-hydroxy-7-methoxyquinoline: $R_f$=0.14 (hexanes/EtOAc, 3:1); $^1$H NMR (400 MHz, CDCl$_3$) 7.36 (d, J=8.7, 1H, Ar-5H), 7.34 (d, J=2.5, 1H, Ar-8H), 6.67 (dd, J=2.5, 8.5, 1H, Ar-6H), 4.08 (m, 1H), 3.86 (br s, 1H, OH), 3.79 (s, 3H, OMe), 3.43 (m, 1H), 1.87 (m, 3H), 1.53 (s, 9H, t-butyl), 0.859 (t, J=7.4, 3H, —CH$_3$).

(R/S)-1-t-Butoxycarbonyl-4-ethyl-1,2,3,4-tetrahydro-7-methoxyquinoline

To an oven dried 250 mL r.b. flask equivuipped with a magnetic stir bar and a N$_2$ gas inlet was dissolved (R/S)-1-t-butoxycarbonyl-4-ethyl-1,2,3,4-tetrahydro-4-hydroxy-7-methoxyquinoline (37.6 mg, 123 µmol) in dry EtOAc (8 mL). The flask was repeatedly evacuated and flushed with N$_2$ then a catalytic amount of 10% Pd on C (~10 mg) was added. The flask was again evacuated and flushed with N$_2$ several times and then H$_2$ was introduced by balloon. The solution was stirred under H$_2$ for 14 h. The flask was again evacuated and flushed with N$_2$ several times to remove any residual H$_2$ and the solution was filtered through a pad of Celite™ and concentrated in vacuo to give 34 mg (95%) of the desired amine as a clear colorless oil. Data for (R/S)-1-t-butoxycarbonyl-4-ethyl-1,2,3,4-tetrahydro-7-methoxyquinoline: $R_f$=0.52 (hexanes/EtOAc, 3:1); $^1$H NMR (400 MHz, CDCl$_3$) 7.27 (d, J=2.3, 1H, Ar-8H), 7.02 (d, J=8.5, 1H, Ar-5H), 6.59 (dd, J=2.7, 8.4, 1H, Ar-6H), 3.78 (s, 3H, OMe), 3.74 (m, partially obscured by OMe, 1H), 3.58 (m, 1H), 2.62 (m, 1H), 1.95 (m, 1H), 1.72 (m, 2H), 1.53 (s, 9H, t-butyl), 1.48 (m, partially obscure by t-butyl, 1H), 0.949 (t, J=7.4, 3H, —CH$_3$).

(R/S)-4-Ethyl-1,2,3,4-tetrahydro-7-methoxyquinoline

In a oven dried 250 mL r.b. flask equivuipped with a magnetic stir bar and a N$_2$ gas inlet was dissolved (R/S)-1-t-butoxycarbonyl-4-ethyl-1,2,3,4-tetrahydro-7-methoxyquinoline (34.0 mg, 117 µmol) in dry CH$_2$Cl$_2$ (1 mL). To the stirred solution was added TFA (1.2 mL) at rt and was allowed to react for 2 h. The dark red solution was quenched with sat NaHCO$_3$ solution (10 mL), extracted with CH$_2$Cl$_2$ (3×25 mL), washed with brine (50 mL), dried (Na$_2$SO$_4$) and concentrated in vacuo to afford 21 mg (95%) of the desired amine as a clear light yellow oil. Data for (R/S)-4-ethyl-1,2,3,4-tetrahydro-7-methoxyquinoline: $R_f$=0.1 (hexanes/EtOAc, 3:1); $^1$H NMR (400 MHz, CDCl$_3$) 6.92 (d, J=8.5, 1H), 6.21 (dd, J=2.5, 8.2, 1H), 6.03 (d, J=2.5, 1H), 3.73 (s, 3H), 3.27 (m, 2H), 2.59 (m, 1H), 1.86 (m, 1H), 1.75 (m, 2H), 1.48 (m, 1H), 0.968 (t, J=7.4, 3H).

(R/S)-4-Ethyl-1,2,3,4-tetrahydro-7-hydroxyquinoline (structure 32A of Scheme XL, where $R^{1-3}$=H, $R^4$=ethyl)

In a flame dried 100 mL rb flask equivuipped with a magnetic stir bar and a N$_2$ gas inlet was dissolved (R/S)-4-ethyl-1,2,3,4-tetrahydro-7-methoxyquinoline (21 mg, 109.9 µmol) in CH$_2$Cl$_2$ (4 mL). The solution was cooled to 0° C. and a 1.0M solution of BBr$_3$ in CH$_2$Cl$_2$ (0.33 mL, 320 µmol, 2.75 equiv) was added slowly by syringe. The solution was warmed to rt and stirred under a blanket of N$_2$ for 9 h. The reaction was quenched by addition of sat. NaHCO$_3$ solution (5 mL), extracted with CH$_2$Cl$_2$ (3×25 mL), washed with brine (2×20 mL), dried (Na$_2$SO$_4$) and concentrated in vacuo to give 19 mg (99%) of the desired phenolic amine as a clear yellow oil. Data for (R/S)-4-ethyl-1,2,3,4-tetrahydro-7-hydroxyquinoline: $^1$H NMR (400 MHz, CDCl$_3$) 6.85 (d, J=8.1, 1H), 6.11 (dd, J=2.4, 8.3, 1H), 5.98 (d, J=2.4, 1H), 3.25 (m, 2H), 2.57 (m, 1H), 1.85 (m, 1H), 1.76 (m, 1H), 1.67 (m, 1H), 1.51 (m, 1H), 0.940 (t, J=7.4, 3H).

(R/S)-4-Ethyl-1,2,3,4-tetrahydro-6-trifluoromethyl-8-pyranono[5,6-g]quinoline (Compound 414, structure 33A of Scheme XL, where $R^{1-3}$=$R^6$=H, $R^4$=ethyl, $R^5$=trifluoromethyl In a oven dried pressure tube equivuipped with a magnetic stir bar was dissolved (R/S)-4-ethyl-1,2,3,4-tetrahydro-7-hydroxyquinoline (19 mg, 109 µmol) and TFEAA (excess) and ZnCl$_2$ (excess) in absolute EtOH (~3 mL). The sealed pressure tube was heated at 101° C. for 10 h, cooled to rt and concentrated on Celite™ to give a free flowing powder which was purified via flash column chromatography (silica gel, hexanes/EtOAc, 3:1) to give 3 mg (47%) of Compound 414 as a bright yellow solid. Data for Compound 414: $R_f$=0.19 (hexanes/EtOAc, 3:1); $^1$H NMR (400 MHz, CDCl$_3$) 7.25 (s, 1H), 6.38 (s, 1H), 6.36 (s, 1H), 4.70 (br s, 1H), 3.40 (m, 2H), 2.70 (m, 1H), 1.89 (m, 2H), 1.67 n(m, 1H), 1.55 (m, 1H), 0.95 (t, J=7.4, 3H).

EXAMPLE 315

(R/S)-1,2,3,4-Tetrahydro-1,4-dimethyl-8-pyranono[5,6-g]quinoline (Compound 415, structure 34A of Scheme XL, where $R^{1-3}$=$R^6$=$R^8$=H, $R^4$=methyl, $R^5$=trifluoromethyl)

In a flame dried 100 mL rb flask equivuipped with a magnetic stir bar was dissolved Compound 410 (EXAMPLE 310) (10.0 mg, 35.6 µmol) in glacial acetic acid (4 mL). To the stirred solution was added para-formadehyde (12 mg, 356 µmol, 10 equiv). The cloudy yellow solution stirred for 10 min then NaCNBH$_3$ (12 mg, 178 µmol, 5 equiv) was added at once. Upon addition the solution emitted gas for approx 5 min then turned bright yellow. After stirring for 12 h the solution was slowly poured over ice and quenched with NaOH (20%), extracted with EtOAc (2×25 mL), washed with brine (50 mL), dried (Na$_2$SO$_4$) and concentrated in vacuo to give 8.9 mg (86%) of Compound 415 as a yellow-green solid. Data for Compound 415: R$_f$=0.22 (hexanes/EtOAc; 3:1); $^1$H NMR (400 MHz, CDCl$_3$) 7.25 (s, 1H), 6.42 (s, 1H), 6.35 (s, 1H), 3.42 (m, 2H), 3.00 (s, 3H), 2.91 (m, 1H), 2.00 (m, 1H), 1.72 (m, 1H), 1.28 (d, J=6.8, 3H).

EXAMPLE 316

(R/S)-4-Ethyl-1,2,3,4-tetrahydro-1-methyl-8-pyranono[5,6-f]quinoline (Compound 416, structure 34A of Scheme XL, where R$^{1-3}$=R$^6$=R$^8$=H, R$^4$=ethyl, R$^5$=trifluoromethyl)

In a flame dried 100 mL rb flask equivuipped with a magnetic stir bar was dissolved Compound 414 (8.0 mg, 27.1 μmol) in glacial acetic acid (3 mL). To the stirred solution was added para-formadehyde (8.0 mg, 271 μmol, 10 equiv). The cloudy yellow solution stirred for 10 min then NaCNBH$_3$ (8.0 mg, 135 μmol, 5 equiv) was added at once. Upon addition the solution emitted gas for approx. 5 min then turned bright yellow. After stirring for 12 h the solution was slowly poured over ice and quenched with NaOH (20%), extracted with EtOAc (2×25 mL), washed with brine (50 mL), dried (Na$_2$SO$_4$) and concentrated in vacuo to give 7.9 mg (94% yield) of Compound 416 as a bright yellow-green solid. Data for Compound 416: R$_f$=0.23 (hexanes/EtOAc; 3:1); $^1$H NMR (400 MHz, CDCl$_3$) 7.20 (s, 1H), 6.43 (s, 1H), 6.35 (s, 1H), 3.47 (m, 1H), 3.30 (m, 1H), 3.00 (s, 3H), 2.68 (m, 1H), 1.89 (m, 2H), 1.56 (m, 4H), 0.980 (d, J=7.4, 3H).

EXAMPLE 317

2,2-Dimethyl-1,2,3,4-tetrahydro-6-trifloromethyl-8-pyridono[5,6-f]quinoline Compound 417, structure 40A of Scheme XLII, where R$^{1-2}$=R$^6$=H, R$^3$=R$^4$=methyl, R$^5$=trifluoromethyl) 7-tert-Butyloxycarbamoyl-1,2-dihydro-2,2-dimethylquinoline (structure 36A of Scheme XLII, where R$^1$=R$^2$=H, R$^3$=R$^4$=methyl)

To a flame-dried 200 mL r.b. flask containing 3-tert-butylcarbamoylaniline (EXAMPLE 147) (7.7 g, 0.037 mol) in 40 mL of anhydrous THF was added CuCl (183 mg, 1.8 mmol), triethylamine (5.15 mL, 0.037 mol) and 3-acetoxy-3-methyl-1-butyne (4.66 g, 0.037 mol). The reaction mixture was brought to reflux for 5 h then cooled to rt and filtered though a short pad of celite. Purification by flash column chromatography (silica gel, hexanes/ethyl acetate, 7:3) afforded 6.83 g (67%) of the desired propargyl intermediate that was used directly for the next step. The propargyl amine (6.5 g, 0.0237 mol) was dissolved in 40 mL of anhydrous THF, CuCl (234 mg, 0.0024 mol) was added and the mixture was heated to reflux for 16 h. The reaction mixture was diluted with ethyl acetate (200 mL), and washed with water and brine. The organic layer was dried (Na$_2$SO$_4$) and concentrated in vacuo to an oil that was subjected to chromatography (silica gel, hexanes/ethyl acetate, 9:1) which afforded 2.24 g (34%) of 7-tert-butyloxycarbamoyl-1,2-dihydro-2,2-dimethylquinoline along with 4.1 g (63%) of the undesired regioisomer. Data for 7-tert-butyloxycarbamoyl-1,2-dihydro-2,2-dimethylquinoline: $^1$H NMR (400 MHz, CDCl$_3$) 6.80 (bs, 1H), 6.77 (d, J=7.4, 1H), 6.33 (bs, 1H), 6.31 (bd, J=7.4, 1H), 6.18 (d, J=9.7, 1H), 5.37 (d, J=9.7, 1H), 3.70 (bs, 1H), 1.49 (s, 9H), 1.27 (s, 6H). 7-Amino-1,2,3,4-tetrahydro-2,2-dimethylquinoline A solution of 7-tert-butyloxycarbamoyl-1,2-dihydro-2,2-dimethylquinoline (3.4 g, 0.012 mol) in 150 mL of ethyl acetate was hydrogenated under an atmosphere of hydrogen with Pd-C 10% (340 mg) at rt for 7 h. Filtration over celite afforded 3.7 g (100%) of pure 7-tert-butyloxycarbamoyl-1,2,3,4-tetrahydro-2,2-dimethylquinoline. The title compound was prepared by General Method 12 (EXAMPLE 147) from 7-tert-butyloxycarbamoyl-1,2,3,4-tetrahydro-2,2-dimethylquinoline (3.7 g, 0.012 mol) to afford 2.35 g (100%) of 7-amino-1,2,3,4-tetrahydro-2,2-dimethylquinoline as a light reddish oil. Data for 7-amino-1,2,3,4-tetrahydro-2,2-dimethylquinoline: $^1$H NMR (400 MHz, CDCl$_3$) 6.77 (d, J=7.9, 1H), 6.00 (dd, J=7.9, 2.2, 1H), 5.81 (d, J=2.2, 1H), 3.47 (bs, 1H), 3.40 (bs, 2H), 2.66 (t, J=6.7, 2H), 1.65 (t, J=6.7, 2H), 1.18 (s, 6H).

2,2-Dimethyl-1,2,3,4-tetrahydro-6-trifloromethyl-8-pyridono[5,6-f]quinoline (Compound 417, structure 40A of Scheme XLII, where R$^{1-2}$=R$^6$=H, R$^3$=R$^4$=methyl, R$^5$=trifluoromethyl)

This compound was prepared by General Method 13 (EXAMPLE 147) from 7-amino-1,2,3,4-tetrahydro-2,2-dimethylquinoline (2.35 g, 0.012 mol), ZnCl$_2$ (2.74 g, 0.02 mol) and ethyl 4,4,4-trifluoroacetoacetate (2.15 mL, 0.013 mol) to afford 1.91 g (48%) of Compound 417. Data for Compound 417: $^1$H NMR (400 MHz, DMSO D$_6$) 11.70 (s, 1H), 7.18 (s, 1H), 6.85 (s, 1H), 6.35 (s, 1H), 2.65 (t, J=6.6, 2H), 1.61 (t, J=6.6, 2H), 1.17 (s, 6H).

EXAMPLE 318

(R/S)-1,2,3,4-tetrahydro-6-trifluoromethyl-2,2,4-trimethyl-8-pyridono[5,6-f-]-3-quinolinone Compound 418 structure 47A of Scheme XLIV, where R$^1$=R$^2$=H, R$^3$=trifluoromethyl) 1,9-di-tert-Butloxcarbamoyl-1,2-dihydro-6-trifluoromethyl-2,2,4-trimethyl-8-pyridono[5,6-f]quinoline structure 46A of Scheme XLIV, where R$^1$=R$^2$=H, R$^3$=trifluoromethyl)

To a suspension of NaH 60% in mineral oil (16 mg, 0.387 mmol) in 1 mL of anhydrous THF at 0° C., was added dropwise, a solution of Compound 247 (EXAMPLE 147) (100 mg, 0.32 mmol) and the resulting mixture was stirred at 0° C. for 10 min. A solution of t-Boc$_2$O (78 mg, 0.355 mmol) in 1 mL of THF was added dropwise and the reaction mixture was stirred at rt for 1 h. The reaction mixture was quenched with water (1 mL), extracted with ethyl acetate (2×5 mL) and concentrated in vacuo to give 148 mg (100%) of a yellow solid that was used directly for the next step. To a solution of 9-tert-butyloxycarbamoyl-1,2-dihydro-2,2,4-trimethyl-8-pyridono[5,6-f]quinoline (130 mg, 0.32mmol) in 10 mL of anhydrous THF at −78° C. was added n-BuLi 2.5M in hexane (121 mL, 0.32 mmol) and the mixture stirred for 10 min. t-Boc$_2$O (73 mg, 0.33 mmol) in 1 mL of THF was added and the reaction mixture stirred at −78° C. for 6.5 h. The temperature was raised to 0° C. and the mixture quenched with water (3 mL), extracted with ethyl acetate (2×10 mL), dried (Na$_2$SO$_4$) and concentrated in vacuo to give a solid residue. Purification by flash column chromatography (silica gel, hexanes/ethyl acetate, 8:2) gave 79 mg (48%) of 1,9-di-tert-butyloxycarbamoyl- 1,2-dihydro-2,2,4-trimethyl-8-pyridono[5,6-f]quinoline (15). $^1$H NMR (400 MHz, CDCl$_3$) 7.76 (s, 1H), 7.72 (s, 1H), 7.38 (s, 1H), 5.67 (s, 1H), 2.13 (s, 3H), 1.62 (s, 9H), 1.57 (s, 9H), 1.50 (s, 9H). 1-tert-butyloxycarbamoyl-1,2,3,4-tetrahydro-3-hydroxy-6-trifluoromethyl-2,2,4-trimethyl-8-pyridono[5,6-f]quinoline A solution of 1,9-di-tert-butyloxycarbamoyl-1,2-dihydro-2,2,4-trimethyl-8-pyridono[5,6-f]quinoline (79 mg, 0.155 mmol) in 2 mL of anhydrous THF at rt was treated with 388 μL of BH$_3$.THF (1.0M in THF, 0.388 mmol) for 3 h and was then quenched with 78 μL of NaHCO$_3$ satd't followed by 30% H$_2$O$_2$ (78 μL). The reaction mixture was stirred for 1 h, then 2 mL of water was added. The mixture was extracted with ethyl acetate (5 mL), dried (Na$_2$SO$_4$) and concentrated in vacuo to an oil that was subjected to flash column chromatography (silica gel, hexanes/ethyl acetate, 7:3) to give 21 mg (32%) of 1-tert-butyloxycarbamoyl-1,2,3,4-tetrahydro-3-hydroxy-2,2,4-trimethyl-8-pyridono [5,6-f] quinoline. Data for 1-tert-butyloxycarbamoyl-1,2,3,4-tetrahydro-3-hydroxy-2,2,4-trimethyl-8-pyridono[5,6-f] quinoline: $^1$H NMR (400 MHz, CDCl$_3$) 12.5 (bs, 1H), 7.51 (s, 1H), 7.28 (s, 1H), 6.85 (s, 1H), 3.19 (dd, J=7.3, 5.2, 1H), 2.91 (m, 1H), 2.14 (d, J=7.0, 1H), 1.65 (s, 3H), 1.55 (s, 9H), (s, 3H), 1.46 (d, J=6.1, 1H).

(R/S)-1,2,3,4-tetrahydro-6-trifluoromethyl-2,2,4-trimethyl-8-pyridono[5,6-f]-3-quinolinone (Compound 418, structure 47A of Scheme XLIV, where R$^1$=R$^2$=H, R$^3$=trifluoromethyl)

To a suspension of PCC (50 mg, 0.23 mmol) in 2 mL of dichloromethane at rt was added 1-tert-butyloxycarbamoyl-1,2,3,4-tetrahydro-3-hydroxy-6-trifluoromethyl-2,2,4-trimethyl-8-pyridono[5,6-f]quinoline (16) (10 mg, 0.023 mmol) in 1 mL of dichloromethane. The reaction mixture was stirred at rt for 1.5 h, then it was filtered over celite and the solvent was removed in vacuo to give a dark oil that was subjected to flash column chromatography (silica gel, hexanes/ethyl acetate, 6:4) to give 5.5 mg (56%) of 1-tert-butyloxycarbamoyl-1,2,3,4-tetrahydro-6-trifluoromethyl-2,2,4-trimethyl-8-pyridono[5,6-.f]-3-quinolinone that was used directly for the next step. The title compound was prepared by General Method 12 (EXAMPLE 147) from 1-tert-butyloxyarbamoyl-1,2,3,4-tetrahydro-6-trifluoromethyl-2,2,4-trimethyl-8-pyridono[5,6-f]-3-quinolinone (5.5 mg, 0.013 mmol) to afford 3 mg (71%) of Compound 418. Data for Compound 418: $^1$H NMR (400 MHz, CDCl$_3$) 12.3 (bs, 1H), 7.51 (s, 1H), 6.85 (s, 1H), 6.71 (s, 1H), 4.27 (s, 1H), 3.61 (q, J=6.3, 1H), 1.55 (d, J=6.3, 3H), 1.40 (s, 3H), 1.31 (s, 3H).

EXAMPLE 319

5-Trifluoromethyl-7-pyridono[5,6-e]indoline (Compound 419, structure 49A of Scheme XLV, where R$^1$=trifluoromethyl, R$^2$=H)
6-Aminoindoline A solution of 6-nitroindoline (1 g, 6.1 mmol) in 50 mL of ethyl acetate was hydrogenated under an atmosphere of hydrogen with Pd-C 10% (100 mg) at rt for 3 h. Filtration over celite afforded 1.0 g (98%) of 6-aminoindoline. Data for 6-aminoindoline: $^1$H NMR (400 MHz, CDCl$_3$) 7.40 (d, J=7.4, 1H), 6.05 (d, J=2.0, 1H), 6.03 (d, J=7.5, 1H), 3.67 (bs, 1H), 3.49 (t, J=8.1, 2H), 3.48 (bs, 2H), 2.90 (t, J=8.2, 2H).
5-Trifluoromethyl-7-pyridono[5,6-e]indoline (Compound 419, structure 49A of Scheme XLV, where R$^1$=trifluoromethyl, R$^2$=H)

This compound was prepared by General Method 13 (EXAMPLE 147) from 6-aminoindoline (200 mg, 1.2 mmol), ZnCl$_2$ (262 mg, 1.93 mmol) and ethyl 4,4,4-trifluoroacetoacetate (194 mL, 1.32 mmol) to afford 100 mg (32%) of Compound 419. Data for Compound 419: $^1$H NMR (400 MHz, DMSO D$_6$) 12.1 (s, 1H), 7.31 (s, 1H), 6.82 (s, 1H), 6.49 (s, 1H), 6.40 (s, 1H), 3.59 (t, J=8.1, 2H), 3.01 (t, J=8.1, 2H).

EXAMPLE 320

8-(4-Chlorobenzoyl)-5-trifluoromethyl-7-pyridono[5,6-e]indoline (Compound 420, structure 50A of Scheme XLV, where R$^1$=trifluromethyl, R$^2$=H, R$^3$=4-chlorophenyl)

To a solution of Compound 419 (EXAMPLE 319) (13 mg, 0.05 mmol) in 2 mL of anhydrous THF at −78° C. was added n-BuLi 2.5M in hexane (21 mL, 0.05 mmol) and the resulting mixture was stirred for 15 min. Then 4-chlorobenzoyl chloride (6.4 mL, 0.05 mmol) was added and the reaction mixture was slowly brough to rt over a period of 30 min. The reaction mixture was quenched with a saturated aqueous solution of NH$_4$Cl (1 mL), extracted with ethyl acetate (5 mL) and concentrated in vacuo to an oil that was subjected to flash column chromatography (silica gel, hexanes/ethyl acetate, 8:2) which afforded 3 mg (15%) of Compound 420. Data for Compound 420: $^1$H NMR (400 MHz, CDCl$_3$) 8.19 (d, J=8.6, 2H), 7.77 (s, 1H), 7.51 (d, J=8.6 2H), 7.25 (s, 1H), 6.99 (s, 1H), 4.45 (s, 1H), 3.77 (t, J=8.0, 2H), 3.28 (t, J=8.0, 2H).

EXAMPLE 321

7-tert-Butyloxycarbamoyl-1,2-dihydro-2,2,8-trimethylquinoline (structure 36A, Scheme XLII, where R$^1$=R$^3$=R$^4$=methyl, R$^2$=H, P=t-butoxy, X=NH)

To a flame-dried 10 mL r.b. flask containing 3-tert-butylcarbamoyl-2-methylaniline (EXAMPLE 155) (490 mg, 0.0022 mol) in 3 mL of anhydrous THF was added CuCl (11 mg, 0.1 mmol), triethylamine (307 mL, 0.0022 mol) and 3-acetoxy-3-methyl-1-butyne (278 mg, 0.0022 mol). The reaction mixture was brought to reflux for 5 h then cooled to rt and filtered through a short pad of celite. Purification by flash column chromatography (silica gel, hexanes/ethyl acetate, 7:3) afforded 290 mg (46%) of the desired propargyl intermediate that was used directly for the next step. The propargyl amine (290 mg, 0.001 mol) was dissolved in 5 mL of anhydrous THF. CuCl (5 mg, 0.05 mmol) was added and the mixture was heated to reflux for 16 h. The reaction mixture was diluted with ethyl acetate (10 mL), and washed with water then brine. The organic layer was dried (Na$_2$SO$_4$) and concentrated in vacuo to an oil that was subjected to chromatography (silica gel, hexanes/ethyl acetate, 9:1) which afforded 114 mg (40%) of 7-tert-butyloxycarbamoyl-1,2-dihydro-2,2,8-trimethylquinoline. Data for 7-tert-butyloxycarbamoyl-1,2-dihydro-2,2,8-trimethylquinoline: $^1$H NMR (400 MHz, CDCl$_3$) 6.85 (d, J=7.4, 1H), 6.75 (d, J=7.4, 1H), 6.23 (d, J=9.5, 1H), 6.18 (bs, 1H), 5.42 (d, J=9.5, 1H), 3.57 (bs, 1H), 1.92 (s, 3H), 1.45 (s, 9H), 1.29 (s, 6H).
7-Amino-1,2,3,4-tetrahydro-2,2,8-trimethylquinoline A solution of 7-tert-butyloxycarbamoyl-1,2-dihydro-2,2,8-trimethylquinoline (114 mg, 0.39 mmol) in 4 mL of ethyl acetate was hydrogenated under an atmosphere of hydrogen with Pd-C 10% (11 mg) at rt for 7 h. Filtration over Celite afforded 60 mg (60%) of 7-tert-butyloxycarbamoyl-1,2,3,4-tetrahydro-2,2,8-trimethylquinoline. The title compound was prepared by General Method 12 (EXAMPLE 147) from 7-tert-butyloxycarbamoyl-1,2,3,4-tetrahydro-2,2,8-trimethylquinoline (60 mg, 0.206 mmol) to afford 30 mg (77%) of 7-amino-1,2,3,4-tetrahydro-2,2,8-trimethylquinoline as a light reddish oil. Data for 7-amino-1,2,3,4-tetrahydro-2,2,8-trimethylquinoline: $^1$H NMR (400 MHz, CDCl$_3$) 6.70 (d, J=7.9, 1H), 6.09 (d, J=7.9, 1H), 3.30 (bs, 3H), 2.71 (t, J=6.7, 2H), 1.89 (s, 3H), 1.65 (t, J=6.7, 2H), 1.21 (s, 6H).
2,2,10-Trimethyl-1,2,3,4-tetrahydro-6-trifloromethyl-8-pyridono[5,6-f]quinoline (Compound 421, structure 40A of Scheme XLII, where R$^1$=R$^3$=R$^4$=methyl, R$^2$=R$^6$=H, R$^5$=trifluoromethyl)

This compound was prepared by General Method 13 (EXAMPLE 147) from 7-amino-1,2,3,4-tetrahydro-2,2,8-trimethylquinoline (30 mg, 0.159 mmol), ZnCl$_2$ (35 mg, 0.255 mmol) and ethyl 4,4,4-trifluoroacetoacetate (26 mL, 0.175 mmol) to afford 21 mg (42%) of Compound 421. Data for Compound 421: $^1$H NMR (400 MHz, CDCl$_3$) 9.13 (s, 1H), 7.34 (s, 1H), 6.67 (s, 1H), 4.10 (s, 1H), 2.88 (t, J=6.7, 2H), 2.10 (s, 3H), 1.75 (t, 6.7, 2H), 1.30 (s, 6H).

EXAMPLE 322

1,2,3,4-Tetrahydro-6-trifluoromethyl-8-pyridono[5,6-f]quinoline (Compound 422, structure 53A of Scheme XLVI, where $R^{1-3}=R^5=H$, $R^4$=trifluoromethyl)

7-Nitro-1,2,3,4-tetrahydroquinoline 1,2,3,4-Tetrahydroquinoline (5 g, 0.0375 mol) was dissolved in 16 mL of sulfuric acid and the temperature lowered to 0° C., then 90% fuming nitric acid (1.67 mL, 0.0375 mol) was added slowly and the mixture stirred at 0° C. for 30 min. It was then poured onto 100 g of ice and extracted with dichloromethane (2×100 mL). The organic phase was washed with saturated aqueous solution of $NaHCO_3$ (75 mL) and concentrated in vacuo to a reddish residue that was subjected to chromatography (silica gel, hexanes/ethyl acetate, 8:2) which afforded 4.1 g (61%) of 7-nitro-1,2,3,4-tetrahydroquinoline. Data for 7-nitro- 1,2,3,4-tetrahydroquinoline: $^1$H NMR (400 MHz, $CDCl_3$) 7.39 (dd, J=8.3, 2.2, 1H), 7.26 (d, J=3.5, 1H), 7.01 (d, J=8.3, 1H), 4.16 (bs, 1H), 3.35 (t, J=5.0, 2H), 2.8 (t, J=6.3, 2H), 1.95 (quintet, J=6.1, 2H).

7-Amino-1,2,3,4-tetrahydroquinoline (structure 52A of Scheme XLVI, where $R^{1-3}=H$)

A solution of 7-nitro-1,2,3,4-tetrahydroquinoline (396 mg, 0.0022 mol) in 4 mL of ethyl acetate was hydrogenated under an atmosphere of hydrogen with PdC 10% (40 mg) at rt for 2 h. Filtration over celite afforded 330 mg (100%) of 7-amino-1,2,3,4-tetrahydroquinoline. Data for 7-amino-1,2,3,4-tetrahydroquinoline: $^1$H NMR (400 MHz, $CDCl_3$) 6.72 (d, J=7.9, 1H), 6.00 (dd, J=7.9, 2.3, 1H), 5.84 (d, J=2.3, 1H), 3.67 (bs, 1H), 3.42 (bs, 2H), 3.24 (t, J=5.0, 2H), 2.65 (t, J=6.4, 2H), 1.91 (quintet, J=6.0 Hz. 2H).

1,2,3,4-Tetrahydro-6-trifluoromethyl-8-pyridono[5,6-f]quinoline (Compound 422, structure 53A of Scheme XLVI, where $R^{1-3}=R^5=H$, $R^4$=trifluoromethyl)

This compound was prepared by General Method 13 (EXAMPLE 147) from 7-amino-1,2,3,4-tetrahydroquinoline (330 mg, 0.0022 mol), $ZnCl_2$ (452 mg, 0.0033 mol) and ethyl 4,4,4-trifluoroacetoacetate (356 mL, 0.0024 mol) to afford 70 mg (11%) of Compound 422. Data for Compound 422: $^1$H NMR (400 MHz, DMSO $D_6$) 11.7 (bs, 1H), 7.11 (s, 1H), 6.92 (s, 1H), 6.35 (s, 2H), 3.22 (bs, 2H), 2.71 (t, J=5.1, 2H), 1.93 (quintet, J=6.1, 2H).

EXAMPLE 323

1,2-Dihydro-6-trifluoromethyl-1,2,2,4-tetramethyl-8-pyridono[5,6-f]quinoline (Compound 423, structure 60 of Scheme XVI, where $R^{1-2}=R^5=H$, $R^3$=trifluoromethyl, Z=NH)

To a stirred solution of Compound 247 (EXAMPLE 147) (100 mg, 0.323 mmol) and paraformaldehyde (98 mg, 3.23 mmol) in 3 mL of acetic acid at rt was added portionwise sodium cyanoborohydride (102 mg, 1.61 mmol). The resulting mixture was stirred at 25° C. for 29 h then carefully poured into 20% aqueous NaOH (10 mL) and ice 10 g and the pH adjusted to ~7. The mixture was extracted with dichloromethane (25mL), dried ($Na_2SO_4$) and concentrated in vacuo to a fluorescent yellow solid that was subjected to flash column chromatography (silica gel, hexanes/ethyl acetate, 8:2) to give 92 mg (71%) of Compound 423. Data for Compound 423: $^1$H NMR (400 MHz, $CDCl_3$) 11.21 (bs, 1H), 7.33 (s, 1H), 6.67 (s, 1H), 6.23 (s, 1H), 5.39 (s, 1H), 2.92 (s, 3H), 2.02 (s, 3H), 1.38 (s, 6H).

EXAMPLE 324

3,3-Dimethyl-5-trifluoromethyl-7-pyridono[5,6-e]indoline (Compound 424, structure 57A of Scheme XLVII, where $R^1$=methyl, $R^2=R^4$=H, $R^3$=trifluoromethyl)

2-bromo-N-(2-methyl-2-propenyl)-5-nitroaniline (structure 55A of Scheme XLVII, where $R^1$=methyl, $R^2$=H)

To a suspension of NaH 60% dispersion in oil (97 mg, 0.0023 mol) in 2 mL of anhydrous THF at 0° C. was added 2-bromo-5-nitroaniline (500 mg, 0.0023 mol) in 2 mL of THF dropwise, the temperature was raised to rt to complete deprotonation then lowered to 0° C. 3-bromo-2-methylpropene (232 mL, 0.0023 mol) was added very slowly and the reaction mixture was stirred at 0° C. for 3 h then neutralized with water (5 mL). The mixture was extracted with ethyl acetate (2×10 mL), dried ($Na_2SO_4$) and concentrated in vacuo to an oil that was subjected to flash column chromatography (silica gel, hexanes/ethyl acetate, 8:2) to give 200 mg (32%) of 2-bromo-N-(2-methyl-2-propenyl)-5-nitroaniline (structure 55A of Scheme XLVII, where $R^1$=methyl, $R^2$=H). Data for 2-bromo-N-(2-methyl-2-propenyl)-5-nitroaniline: $^1$H NMR (400 MHz, $CDCl_3$) 7.55 (d, J=8.5, 1H), 7.40 (dd, J=8.5, 2.8, 1H), 7.39 (d, J=2.8, 1H), 4.96 (s, 2H), 4.95 (bs, 1H), 3.82 (d, J=5.9, 2H), 1.81 (s, 3H).

3,3-Dimethyl-6-nitroindoline (structure 56A of Scheme XLVII, where $R^1$=methyl, $R^2$=H)

A solution of 2-bromo-N-(2-methyl-2-propenyl)-5-nitroaniline (100 mg, 0.369 mmol), Pd(OAc)$_2$ (2 mg, 0.0073 mol), $Bu_4NBr$ (119 mg, 0.369 mmol) and triethylamine (129 mL, 0.922 mmol) in 1 mL of dry DMF under argon atmosphere was heated at 80° C. for 1 h. Then sodium formate (25 mg, 0.369 mmol) was added to the reaction mixture with continued heating at 80° C. for 20 h. Water (2 mL) was added and the mixture was extracted with ethyl acetate (2×5 mL), dried ($Na_2SO_4$) and concentrated in vacuo to an oil that was subjected to flash column chromatography (silica gel, hexanes/ethyl acetate, 8:2) to give 60 mg (80%) of 3, 3-dimethyl-6-nitroindoline. Data for 3, 3-dimethyl-6-nitroindoline: $^1$H NMR (400 MHz, $CDCl_3$) 7.60 (dd, J=8.2, 2.0, 1H), 7.35 (d, J=2.0, 1H), 7.08 (d, J=8.2, 1H), 3.98 (bs, 1H), 3.41 (s, 2H), 1.33 (s, 6H).

6-Amino-3,3-dimethylindoline

A solution of 3,3-dimethyl-6-nitroindoline (60 mg, 0.31 mmol) in 3 mL of ethyl acetate was hydrogenated under an atmosphere of hydrogen with Pd-C 10% (10 mg) at rt for 3 h. Filtration over celite afforded 45 mg (90%) of 6-amino-3,3-dimethylindoline. Data for 6-amino-3,3-dimethylindoline: $^1$H NMR (400 MHz, $CDCl_3$)6.80 (d, J=7.8, 1H), 6.08 (dd, J=7.8, 2.1, 1H), 6.01 (d, J=2.1, 1H), 3.60 (bs, 1H), 3.50 (bs, 2H), 3.26 (s, 2H), 1.25 (s, 6H).

3,3-Dimethyl-5-trifluoromethyl-7-pyridono[5,6-e]indoline (Compound 424, structure 57A of Scheme XLVII, where $R^1$=methyl, $R^2=R^4$=H, $R^3$=trifluoromethyl)

This compound was prepared by General Method 13 (EXAMPLE 147) from 6-amino-3,3-dimethylindoline (45 mg, 0.277 mmol), $ZnCl_2$ (57 mg, 0.416 mmol) and ethyl 4,4,4-trifluoroacetoacetate (45 mL, 0.305 mmol) to afford 7.3 mg (9%) of 3,3-dimethyl-5-trifluoromethyl-7-pyridono [5,6-e]indoline (22). $^1$H NMR (400 MHz, $CDCl_3$) 12.4 (bs, 1H), 7.32 (s, 1H), 6.73 (s, 1H), 6.52 (s, 1H), 4.33 (s, 1H), 3.45 (s, 2H), 1.36 (s, 3H).

EXAMPLE 325

(R/S)-1,2,3,4-Tetrahydro-4-methyl-6-(trifluoromethyl)-8-pyridono[5,6-g]quinoline (Compound 425, structure 62A of Scheme XLVIII, where $R^{1-3}=R^6=H$, $R^4$=methyl, $R^5$=trifluoromethyl) 1,2,3,4-Tetrahydro-4-quinolinone (structure 59A of Scheme XLVIII, where $R^{1-3}=H$)

In a 200 mL r.b. flask was introduced aniline (9.78 mL, 0.107 mol), acrylic acid (7.36 mL, 0.107 mol) and toluene (100 mL). The reaction mixture was stirred and heated at 100° C. for 16 h, cooled to rt and the solvent was removed in vacuo to give 10.34 g (60%) of the desired intermediate carboxylic acid that was used directly without further purification for the next step. In a 500 mL r.b. flask was introduced the acid (10.34 g, 0.064 mol) and polyphosphoric acid (200 mL). The reaction mixture was stirred and heated at 100° C. for 16 h. The reaction mixture was cooled to rt, poured onto 700 mL of a 1:1 mixture of ice/water and neutralized slowly with NaOH. The aqueous phase was extracted with ethyl acetate (3×200 mL), dried ($Na_2SO_4$) and the solvent was removed in vacuo to give a solid residue that was subjected to flash chromatography (silica gel, hexanes/ethyl acetate, 6:1) to afford 6.97 g (76%) of 1,2,3,4-tetrahydro-4-quinolinone. Data for 1,2,3,4-tetrahydro-4-quinolinone: $^1$H NMR (400 MHz, $CDCl_3$) 7.84 (dd, J=7.9, 1.1, 1H), 7.28 (ddd, J=7.9, 7.9, 1.2, 1H), 6.72 (ddd, J=8.1, 8.1, 0.8, 1H), 6.66 (d, J=8.1, 1H), 4.49 (s, 1H), 3.56 (t, J=6.9, 2H), 2.69 (t, J=6.8, 2H).

1-tert-Butyloxycarbonyl-1,2,3,4-tetrahydro-4-quinolinone

To a stirred solution of $Boc_2O$ (10.05 g, 0.046 mol) and 1,2,3,4-tetrahydro-4-quinolinone (6.16 g, 0.042 mol) in THF (100 mL) at 0° C. was added slowly DMAP (5.11 g, 0.042 mol) in 100 mL of THF. The reaction mixture was stirred overnight, then water (75 mL) was added and the mixture was extracted with ethyl acetate (2×200 mL). The organic phase was dried ($Na_2SO_4$) and the solvent was removed in vacuo to give a solid residue that was subjected to flash chromatography (silica gel, hexanes/ethyl acetate, 8:2) which afforded 8.5 g (82%) of 1-tert-butyloxycarbamoyl-1,2,3,4-tetrahydro-4-quinolinone. Data for 1-tert-butyloxycarbonyl-1,2,3,4-tetrahydro-4-quinolinone: $^1$H NMR (400 MHz, $CDCl_3$) 7.98 (dd, J=7.9, 1.7, 1H), 7.76 (d, J=8.4, 1H), 7.49 (ddd, J=7.5, 7.5, 1.7, 1H), 7.15 (ddd, J=8.0, 8.0, 0.9, 1H), 4.15 (t, J=6.3, 2H), 2.76 (t, J=6.6, 2H), 1.55 (s, 9H).

1-tert-Butyloxycarbonyl-1,2,3,4-tetrahydro-4-hydroxy-4-methylquinoline

To a solution of 1-tert-butyloxycarbonyl-1,2,3,4-tetrahydro-4-quinolinone (170 mg, 0.687 mmol) in THF (5 mL) at 0° C. was added 3.0M methylmagnesium bromide in ether (688 mL, 2.1 mmol). The reaction mixture was stirred at 0° C. for 1 h then quenched with water (2 mL), extracted with ethyl acetate (2×10 mL), dried ($Na_2SO_4$) and the solvent was removed in vacuo to give an oil that was subjected to flash chromatography (silica gel, hexanes/ethyl acetate, 7:3) to afford 120 mg (66%) of 1-tert-butyloxycarbonyl-1,2,3,4-tetrahydro-4-hydroxy-4-methylquinoline. Data for 1-tert-butyloxycarbonyl-1,2,3,4-tetrahydro-4-hydroxy-4-methylquinoline: $^1$H NMR (400 MHz, DMSO-$D_6$) 7.54 (d, J=7.7, 1H), 7.50 (dd, J=7.7, 1.5, 1H), 7.14 (ddd, J=7.3, 7.3, 1.7, 1H), 7.04 (ddd, J=7.9, 7.9, 1.0, 1H), 5.14 (s, 1H), 3.69 (m, 2H), 1.87 (t, J=6.5, 2H), 1.46 (s, 9H), 1.37 (s, 3H).

1-tert-Butyloxycarbonyl-1,2,3,4-tetrahydro-4-methylquinoline

A solution of 1-tert-butyloxycarbonyl-1,2,3,4-tetrahydro-4-hydroxy-4-methylquinoline (109 mg, 0.41 mmol) in ethyl acetate (3 mL) was hydrogenated under an atmosphere of hydrogen with 10% Pd/C (10 mg) and a trace of conc. $H_2SO4$ at rt for 7 h. Filtration over Celite™ afforded 93 mg (92%) of 1-tert-butyloxycarbonyl-1,2,3,4-tetrahydro-4-methylquinoline. Data for 1-tert-butyloxycarbonyl-1,2,3,4-tetrahydro-4-methylquinoline: $^1$H NMR (400 MHz, $CDCl_3$) 7.62 (d, J=8.1, 1H), 7.16 (d, J=7.8, 1H), 7.11 (ddd, J=7.8, 7.8, 1.6, 1H), 7.01 (ddd, J=7.7, 7.5, 1.0, 1H), 3.71 (m, 2H), 2.87 (ddq, J=6.8, 6.8, 6.8, 1H), 2.04 (dddd, J=7.4, 7.4, 7.4, 6.1, 1H), 1.61 (m, 1H), 1.51 (s, 9H), 1.3 (d, J=6.8, 3H).

1,2,3,4-tetrahydro-4-methylquinoline (structure 60A of Scheme XLVIII, where $R^{1-3}$=H, $R^4$=methyl)

This compound was prepared by General Method 12 (EXAMPLE 147) from 1-tert-butyloxycarbonyl-1,2,3,4-tetrahydro-4-methylquinoline (93 mg, 0.353 mmol) to afford 55 mg (95%) of 1,2,3,4-tetrahydro-4-methylquinoline as an oil which was used directly without purification for the next step.

7-Nitro-1,2,3,4-tetrahydro-4-methylquinoline 1,2,3,4-Tetrahydro-4-methylquinoline (55 mg, 0.337 mmol) was dissolved in sulfuric acid (0.5 mL) and the temperature was lowered to 0° C. To this solution 90% fuming nitric acid (15 mL, 0.337 mmol) was added slowly and the mixture stirred at 0° C. for 1 h, then warmed to rt. The reaction mixture was poured onto 1 g of ice and extracted with dichloromethane (2×5 mL). The organic phase was washed with sat. $NaHCO_3$ (1×3 mL) and concentrated in vacuo to a reddish residue that was subjected to chromatography (silica gel, hexanes/ethyl acetate, 8:2) which afforded 36 mg (52%) of 7-nitro-1,2,3,4-tetrahydro-4-methylquinoline. Data for 7-nitro-1,2,3,4-tetrahydro-4-methylquinoline: $^1$H NMR (400 MHz, $CDCl_3$) 7.41 (dd, J=8.3, 2.2, 1H), 7.27 (d, J=2.3, 1H), 7.11 (d, J=8.3, 1H), 4.21 (s, 1H), 3.35 (m, 2H), 2.95 (m, 1H), 1.96 (m, 1H), 1.72 (m, 1H), 1.3 (d, J=7.0, 3H).

1,2,3,4-Tetrahydro-4-methyl-6-trifluoromethyl-8pyridono5,6-g]quinoline Compound 425)

A solution of 7-nitro-1,2,3,4-tetrahydro-4-methylquinoline (36 mg, 0.172 mmol) in ethyl acetate (3 mL) was hydrogenated under an atmosphere of hydrogen with 10% Pd/C (4 mg) at rt for 2 h. Filtration over Celite™ afforded 26 mg (85%) of 7-amino-1,2,3,4-tetrahydro-4-methylquinoline (structure 61A of Scheme XLVIII, where $R^{1-3}$=H, $R^4$=methyl) that was used without further purification for the next step. The title compound was prepared by General Method 13 (EXAMPLE 147) from 7-amino-1,2,3, 4-tetrahydro-4-methylquinoline (26 mg, 0.145 mmol), $ZnCl_2$ (30 mg, 0.218 mmol) and ethyl 4,4,4-trifluoroacetoacetate (21 mL, 0.145 mol) to afford 0.8 mg (2%) of 1,2,3,4-tetrahydro-4-methyl-6-trifluoromethyl-8-pyridono[5,6-g]quinoline (Compound 425). Data for Compound 425: $^1$H NMR (400 MHz, DMSO-$D_6$) 11.65 (bs, 1H), 7.20 (s, 1H), 6.96 (s, 1H), 6.37 (s, 2H), 3.25 (m, 2H), 2.90 (m, 1H), 1.84 (m, 1H), 1.59 (m, 1H), 1.20 (d, J=6.9, 3H).

EXAMPLE 326

1,2-Dihydro-2,2,4-trimethyl-6-methoxymethyl-8-pyridono[5,6-g]quinoline (Compound 426, structure 57 of Scheme XVII, where $R^1$=$R^2$=H, $R^3$=methoxymethyl, X=NH)

To a flame-dried 25-mL rb flask at rt was added ethanol (10 mL) and 7-amino-1,2-dihydro-2,2,4-trimethylquinoline (EXAMPLE 147)(600 mg, 3.5 mmol), and the mixture stirred at rt until the amine had completely dissolved. Methyl-4-methoxyacetoacetate (680 μL, 5.3 mmol, 1.5 equiv) was then added, followed by $ZnCl_2$ (960 mg, 7.0 mmol, 2.0 equiv). The reaction was stirred at rt under $N_2$ for 24 h. The solvent was removed under reduced pressure, and the solid residue was dissolved in EtOAc (10 mL). The organic phase was washed with sat'd. NaHCO3 (adjusted to pH 9 with 3.0M NaOH) (3×5 mL), dried ($N_2SO_4$), and concentrated under reduced pressure. Purification by flash chromatography (silica gel, $CH_2Cl_2$/MeOH, 9:1), afforded 65 mg (7%) of Compound 426 as a dark yellow powder. Data for Compound 426: $R_f$0.42 ($CH_2Cl_2$: MeOH, 9:1); $^1$H NMR (400 MHz, DMSO-$D_6$) 11.24 (s, 1H, 9-H), 7.12 (s, 1H, 5-H), 6.63 (s, 1H, 7-H), 6.26 (s, 1H, 10-H), 6.04 (s, 1H, 3-H ), 5.35 [s, 1H, $(CH_3)_2$CNH], 4.56 (s, 2H, $CH_2$), 3.37 (s, 3H, $OCH_3$), 1.93 (s, 3H, 4-$CH_3$), 1.21 [s, 6H, $C(CH_3)_2$].

EXAMPLE 327

1,2,2,-Trimethyl-1,2,3,4-tetrahydro-6-trifluromethyl-8-pyranono[5,6-g]quinoline (Compound 427, structure 41A of Scheme XLII, where $R^{1-2}=R^6=R^8=H$, $R^{3-4}$=methyl, $R^5$=trifluoromethyl)

This compound was prepared in the manner similar to that described for Compound 416 (EXAMPLE 316) from Compound 412 (EXAMPLE 312) (5 mg) to give Compound 427 (4.2 mg, 93% yield) as a bright yellow solid. Data for Compound 427: $^1$H NMR (400 MHz, CDCl$_3$) 7.19 (s, 1H), 6.49 (s, 1H), 6.36 (s, 1H), 2.91 (s, 3H), 2.78 (t, J=6.5, 2H), 1.31 (s, 6H).

EXAMPLE 328

(R/S)-1,2,3,4-Tetrahydro-4-propyl-6-trifluoromethyl-8-pyranono[5,6-g]quinoline (Compound 428, structure 33A of Scheme XL, where $R^{1-3}$, $R^6$=H, $R^4$=n-propyl, $R^5$=trifluoromethyl). 1-tert-Butoxycarbonyl-4-hydroxy-7-methoxy-4-propylquinoline This compound was prepared in a manner similar to that described for 1-tert-butoxycarbonyl-4-ethyl-4-hydroxy-7-methoxyquinoline (EXAMPLE 314) from 1-tert-butoxycarbonyl-1,2,3,4-tetrahydro-7-methoxy-4-quinolinone (100 mg) to give the desired quinoline (51.2 mg, 40% yield) as an off-white solid. Data for 1-tert-butoxycarbonyl-4-hydroxy-7-methoxy-4-propyl-quinoline: $^1$H NMR (400 MHz, CDCl$_3$) 7.37 (d, J=8.7, 1H), 7.30 (d, J=2.5, 1H), 6.66 (dd, J=8.9, 2.8, 1H), 4.08 (m, 1H), 3.86 (s, 3H), 3.42 (m, 1H), 2.04 (m, 1H), 1.89 (m, 1H), 1.81 (m, 2H), 1.53 (s, 9H(, 1.26 (m, 2H), 0.90 (t, J=7.3,3H).

1-tert-Butoxycarbonyl-7-methoxy-4-propylquinoline

This compound was prepared in a manner similar to that described for 1-tert-butoxycarbonyl-4-ethyl-1,2,3,4-tetrahydro-7-methoxyquinoline (EXAMPLE 314) from 1-tert-butoxycarbonyl-1,2,3,4-tetrahydro-4-hydroxy-7-methoxy-4-propylquinoline (50 mg) to give the desired quinoline (44.3 mg, 94% yield) as a colorless oil. Data for 1-tert-butoxycarbonyl-7-methoxy-4-propylquinoline: $^1$H NMR (400 MHz, CDCl$_3$) 7.27 (d, J=2.5, 1H), 7.01 (d, J=8.6, 1H), 6.59 (dd, J=8.5, 2.5, 1H), 3.78 (s, 3H), 3.73 (m, 1H), 3.58 (m, 1H), 2.70 (m, 1H), 1.94 (m, 1H), 1.71 (m, 1H), 1.63 (m, 1H), 1.53 (s, 9H), 1.40 (m, 3H), 0.93 (t, J=7.2, 3H)

1,2,3,4-Tetrahydro-7-methoxy-4-propylquinoline (structure 32A of Scheme XL, where $R^{1-3}$=H, $R^4$=n-propyl)

This compound was prepared in a manner similar to that described for 4-ethyl-1,2,3,4-tetrahydro-7-methoxyquinoline (EXAMPLE 314) from 1-tert-butoxycarbonyl-1,2,3,4-tetrahydro-7-methoxy-4-propylquinoline (44 mg) to give the desired quinoline (28 mg, 98%) as a colorless oil. Data for 1,2,3,4-tetrahydro-7-methoxy-4-propylquinoline: $^1$H NMR (400 MHz, CDCl$_3$) 6.90 (d, J=8.2, 1H), 6.20 (dd, J=8.4, 2.6, 1H), 6.03 (d, J=2.5, 1H), 3.83 (br s, 1H), 3.72 (s, 3H), 3.28 (m, 2H), 2.68 (m, 1H), 1.89 (m, 1H), 1.75 (m, 1H), 1.60 (m, 1H), 1.46 (m, 3H), 0.94 (t, J=7.1, 3H)

1,2,3,4-Tetrahydro-7-hydroxy-4-propylquinoline

This compound was prepared in a manner similar to that described for 4-ethyl-1,2,3,4-tetrahydro-7-hydroxyquinoline (EXAMPLE 314) from 1,2,3,4-tetrahydro-7-methoxy-4-propylquinoline (28 mg) to give the desired quinoline as a colorless oil, which was used without further purification in the following reaction. Data for 1,2,3,4-tetrahydro-7-hydroxy-4-propylquinoline: $^1$H NMR (400 MHz, CDCl$_3$) 6.84 (d, J=8.2, 1H), 6.10 (dd, J=8.2, 2.3, 1H), 5.97 (d, J=2.2, 1H), 3.78 (br s, 1H), 3.29 (m 1H), 3.21 (m, 1 H), 2.66 (m, 1H), 1.87 (m, 1H), 1.75 (m, 1H), 1.60 (m, 1H), 1.45 (m, 3H), 0.933 (t, J=7.2, 3H).

4-Propyl-1,2,3,4-tetrahydro-6-trifluromethyl-8-pyranono[5,6-g]quinoline (Compound 428)

This compound was prepared in a manner similar to that described for Compound 414 (EXAMPLE 314) from 1,2,3,4-tetrahydro-7-hydroxy-4-propylquinoline (23 mg) to give the Compound 428 (28.4 mg, 61%) as a yellow solid. Data for Compound 428: $^1$H NMR (400 MHz, CDCl$_3$) 7.23 (s, 1H), 6.37 (s, 1H), 6.36 (s, 1H), 4.70 (br s, 1H), 3.40 (m, 2H), 2.81 (m, 1H), 1.88 (m, 2H), 1.47 (m, 3H), 0.963 (t, J=7.2, 3H)

EXAMPLE 329

1,2,3,4-Tetrahydro-2,2,4-trimethyl-6-trifluoromethyl-9-thiopyran-8-ono[5,6-g]quinoline (Compound 429, structure 65A of Scheme XLIX, where $R^{1-2}=R^7=H$, $R^{3-5}$=methyl, $R^6$=trifluoromethyl, X=S)

To a solution of Compound 266 (EXAMPLE 166) (50 mg, 0.15 mmol) in dichloromethane (7 mL) was added triethylsilane (0.23 mL, 1.5 mmol) and TFA (0.25 mL) at rt. After 15 h, the reaction was complete according to TLC. The reaction mixture was quenched with a saturated NaHCO$_3$ solution (10 mL). This solution was extracted with EtOAc (20 mL). The organic layer was washed with water and brine (3×5 mL each), dried (Na$_2$SO$_4$), and concentrated in vacuo to afford the crude product as an orange solid. The crude product was purified by prep TLC (20×20 cm, 1000 μm, 1:1 CH$_2$Cl$_2$:Hex.) to afford 49 mg (99%) of Compound 429 as a yellow solid. Data for Compound 429: $R_f$=0.44 (silica gel, 25% EtOAc:Hex); $^1$H NMR(400 MHz, CDCl$_3$) 7.70 (s, 1H), 6.62 (s, 1H), 6.46 (s, 1H), 4.41 (brs, 1H), 2.95 (ddq, J=12.9, 6.1, 1H), 1.81 (dd, J=12.9, 1.1, 1H), 1.48 (d, J=6.1, 1H), 1.41 (d, J=6.1, 3H), 1.31 (s, 3H), 1.24 (s, 3H); IR (film, NaCl) 1134, 1177, 1200, 1235, 1269, 1368, 1365, 1420, 1451, 1476, 1520, 1634, 3351.

EXAMPLE 330

1,2-Dihydro-1,2,2,4-tetramethyl-6-trifluoromethyl-9-thiopyran-8-ono[5,6-g]quinoline (Compound 430, structure 60 of Scheme XVI, where $R^{1-2}=R^5=H$, $R^3$=trifluoromethyl, Z=S).

To a stirred solution of Compound 266 (EXAMPLE 166) (100 mg, 0.30 mmol) and paraformaldehyde (93 mg, 3.0 mmol) in acetic acid (3 mL) at rt was added portionwise sodium cyanoborohydride (100 mg, 1.50 mmol). The resulting mixture was stirred at rt for 16 h, then carefully poured into 20% aqueous NaOH (10 mL) and ice (10 g) and the pH adjusted to ~7. The mixture was extracted with dichloromethane (25 mL), dried (Na$_2$SO$_4$) and concentrated in vacuo to a fluorescent yellow solid that was subjected to flash column chromatography (silica gel, hexanes/ethyl acetate, 9:1) to give 90 mg (88%) of Compound 430 as a fluorescent yellow solid. Data for Compound 430: $^1$H NMR (400 MHz, CDCl$_3$) 7.48 (s, 1H), 6.62 (s, 1H), 6.45 (s, 1H), 5.40 (s, 1H), 2.89 (s, 3H), 2.10 (s, 3H), 1.39 (s, 6H).

EXAMPLE 331

1,2,3,4-Tetrahydro-1,2,2-trimethyl-6-trifluoromethyl-8-pyridono-[5,6-g]quinoline (Compound 431, structure 41A of Scheme XLII, where $R^{1-2}=R^6=R^8=H$, $R^{3-4}$=methyl, $R^5$=trifluoromethyl X=NH).

To a stirred solution of Compound 417 (EXAMPLE 317) (21 mg, 0.07 mmol) and paraformaldehyde (22 mg, 0.70 mmol) in acetic acid (1 mL) at rt was added portionwise sodium cyanoborohydride (22 mg, 0.35 mmol). The resulting mixture was stirred at rt for 16 h then carefully poured into 20% aqueous NaOH (2 mL) and ice (10 g) and the pH adjusted to ~7. The mixture was extracted with dichloromethane (2×10 mL), dried (Na$_2$SO$_4$) and concentrated in vacuo to a fluorescent yellow solid that was subjected to flash column chromatography (silica gel, hexanes/ethyl acetate, 7:3) to give 16 mg (73%) of Compound 431 as a fluorescent yellow solid. Data for Compound 431: $^1$H NMR (400 MHz, CDCl$_3$) 10.83 (bs, 1H), 7.31 (s, 1H), 6.66 (s, 1H), 6.29 (s, 1H), 2.93 (s, 3H), 2.80 (t, J=6.1,2H), 1.83 (t, J=6.5, 2H), 1.30 (s, 6H).

EXAMPLE 332

1,2,3,4-Tetrahydro-1-methyl-4-propyl-6-trifluoromethyl-8-pyranono[5,6-g]quinoline (Compound 432, structure 34A of Scheme XL, where $R^{1-3}$=$R^6$=$R^8$=H, $R^4$=n-propyl, $R^5$=trifluoromethyl)

This compound was prepared in a manner similar to that described for Compound 415 (EXAMPLE 315) from Compound 428 (EXAMPLE 328) (8.0 mg) to afford 7.9 mg (99%) of Compound 432 as a bright yellow solid. Data for Compound 432: $^1$H NMR (400 MHz, CDCl$_3$) 7.18 (s, 1H), 6.43 (s, 1H), 6.35 (s, 1H), 3.46 (m, 1H), 3.33 (m, 1H), 3.00 (s, 3H), 1.92 (m, 1H), 1.87 (m, 1H), 1.49 (m, 4H), 0.95 (d, J=7.3, 3H).

EXAMPLE 333

1,2,3,4-Tetrahydro-10-hydroxymethyl-2,2,4-trimethyl-6-trifluoromethyl-8-pyridono-[5,6-g]quinoline (Compound 433, structure 67A of Scheme L, where $R^{1-2}$=$R^7$=H, $R^{3-5}$=methyl, $R^6$=trifluoromethyl, X=NH)

To an oven-dried 50-mL round-bottom flask containing Compound 409 (EXAMPLE 309) (125 mg, 0.39 mmol) in 1,4-dioxane (7 mL) was added selenium dioxide (107 mg, 0.96 mmol, 2.50 equiv), and the mixture was heated to reflux for 18 h. Upon cooling to rt, the solvent was removed under reduced pressure and the residue was purified by flash chromatography (silica gel, hexanes/ethyl acetate, 4:1 to 0:1 gradient), affording 15.6 mg (12%) of Compound 433 as a fluorescent yellow solid. Data for Compound 433: $^1$H NMR (400 MHz, CDCl$_3$) 9.32 (br s, 1 H, CONH), 7.44 (s, 1H, 5-H), 6.74 (s, 1H, 7-H), 5.32 [br s, 1H, (CH$_3$)$_2$CNH], 4.57 (d, 1H, J=9.7, OH), 5.02 and 4.93 (ABq, 2H, J$_{AB}$=14.0, CH$_2$OH), 2.85 (ddq, 1H, J=1.29, 12.4, 5.5, 4-H), 1.84 and 1.54 [d of ABq, 2H, J$_{AB}$=13.1, J$_A$=4.3, (3-H$_{eq}$), J$_B$=0 (3-H$_{ax}$)], 1.41 (d, 3H, J=5.5 Hz, 4-CH$_3$), 1.39 and 1.26 [2s, 2×3H, 2-(CH$_3$)$_2$].

EXAMPLE 334

1,2,3,4-Tetrahydro-1,2,2,4-tetramethyl-6-trifluoromethyl-9-thiopyran-8-ono[5,6-g]quinoline (Compound 434, structure 28A of Scheme XXXVIII, where $R^{1-2}$=$R^5$=H, $R^3$=trifluoromethyl, Z=S)

To a solution of Compound 429 (EXAMPLE 329) (10 mg, 0.03 mmol) in acetic acid (5 mL) was added paraformaldehyde (10 mg, 0.3 mmol) and sodium cyanoborohydride (10 mg, 0.15 mmol) under nitrogen with stirring at rt. After 15 h, the reaction was complete according to $^1$H NMR. The reaction was quenched with saturated NaHCO$_3$ (10 mL). This solution was extracted with EtOAc (20 mL). The organic layer was washed with water and brine (3×5 mL each), dried (Na$_2$SO$_4$), and concentrated in vacuo to afford the crude product. The product was purified by prep TLC (5×20 cm, 250 µm, 1:1 CH$_2$Cl$_2$:hexanes) to afford 4.5 mg (44%) of Compound 434 as a yellow solid. Data for compound 434: $^1$H NMR(400 MHz, CDCl$_3$) 7.59 (s, 1H), 6.60 (s, 1H), 6.53 (s, 1H), 2.89 (s, 3H), 2.85 (m, 1H), 1.83 (dd, J=13.2, 4.2, 1H), 1.53 (d, J=13.2, 1H), 1.36 (d, J=6.6, 3H), 1.33 (s, 3H), 1.23 (s, 3H); IR (film, NaCl) 1022, 1066, 1094, 1113, 1134, 1271, 1368, 1464, 1512, 1593, 2926.

EXAMPLE 335

1,2,3,4-Tetrahydro-2,2,9-trimethyl-6-trifluoromethl-8-pyridono-[5,6-g]quinoline (Compound 435, structure 84A of Scheme LVI, where $R^1$=$R^{5-6}$=H, $R^{2-3}$=methyl, $R^4$=trifluoromethyl)

In a 25-mL r.b., a solution of Compound 417 (165 mg, 0.557 mmol) in THF (4 mL) was cooled to 0° C. and treated with 60% NaH in mineral oil (23 mg, 0.58 mmol, 1.0 equivuiv). The reaction mixture was stirred 10 min. To this slurry, iodomethane (35 mL, 0.56 mmol, 1.0 equiv) was added via syringe. The reaction mixture was stirred 12 h, diluted with H$_2$O (20 mL), and extracted with ethyl acetate (3×20 mL). The extracts were washed with brine (1×20 mL), combined, dried (MgSO$_4$), filtered, and concentrated. Purification by silica gel chromatography (CH$_2$Cl$_2$:MeOH, 50:1) afforded 134 mg (78%) of Compound 435 as a pale yellow powder. Data for Compound 435: $^1$H NMR (400 MHz, acetone-d6): 7.35 (s, 1H), 6.56 (s, 1H), 6.51 (s, 1H), 6.09 (br s, 1H), 3.53 (s, 3H), 2.87 (t, J=6.7, 2H), 1.76 (t, J=6.7, 2H), 1.29 (s, 6H).

EXAMPLE 336

(R/S)-1,2,3,4-Tetrahydro-3-methyl-6-trifluoromethyl-8-pyridono-[5,6-g]quinoline (Compound 436, structure 62A of Scheme XL VIII, where $R^{1-2}$=$R^4$=$R^6$=H, $R^3$=methyl, $R^5$=trifluoromethyl)

1-tert-Butyloxycarbonyl-1,2,3,4-tetrahydro-3-methyl-4-quinolinone (structure 69A of Scheme LI, where $R^{1-2}$=H, $R^3$=methyl). To a solution of 1-tert-butyloxycarbonyl-1,2,3,4-tetrahydro-4-quinolinone (structure 68A of Scheme LI, where $R^{1-2}$=H) (EXAMPLE 325) (500 mg, 0.002 mol) in THF (5 mL) at −78° C. was added 2.0M LDA in THF (1.01 mL, 0.002 mol). The reaction mixture was stirred at −78° C. for 15 min and iodomethane (126 mL, 0.002 mol) was added all at once. The temperature was raised to 0° C. and the resulting mixture stirred for 4 h. The reaction was then quenched with sat'd NH$_4$Cl (5 mL), extracted with ethyl acetate (2×10 mL), dried (Na$_2$SO$_4$) and concentrated in vacuo to a solid residue that was subjected to flash column chromatography (silica gel, hexanes/ethyl acetate, 95:5) to give 117 mg (23%) of 1-tert-butyloxycarbonyl-1,2,3,4-tetrahydro-3-methyl-4-quinolinone (structure 69A of Scheme LI, where $R^{1-2}$=H, $R^3$=methyl), 128 mg (23%) of 1-tert-butyloxycarbonyl-1,2,3,4-tetrahydro-3,3-dimethyl-4-quinolinone (structure 70A of Scheme LII, where $R^{1-2}$=H, $R^{3-4}$=methyl) and 200 mg (40%) of recovered starting material. Data for 1-tert-butyloxycarbonyl-1,2,3,4-tetrahydro-3-methyl-4-quinolinone: $^1$H NMR (400 MHz, CDCl$_3$) 7.99 (dd, J=7.9, 1.7, 1H), 7.77 (d, J=8.4, 1H), 7.48 (ddd, J=7.3, 7.3, 1.7, 1H), 7.13 (dd, J=7.4, 1.0, 1H), 4.32 (dd, J=13.4, 4.4, 1H), 3.69 (dd, J=13.3, 9.8, 1H), 2.76 (ddq, J=9.8, 7.0, 4.4, 1H), 1.56 (s, 9H), 1.24 (d, J=7.0, 3H).

1-tert-Butyloxycarbonyl-1,2,3,4-tetrahydro-3-methylquinoline. To a solution of 1-tert-butyloxycarbonyl-1,2,3,4-tetrahydro-3-methyl-4-quinolinone (117 mg, 0.45 mmol) in methanol (2 mL) at 0° C. was added portionwise sodium borohydride (17 mg, 0.45 mmol) and the reaction mixture was stirred at 0° C. for 3 h. The reaction was quenched with of sat'd NH$_4$Cl (2 mL), extracted with ethyl acetate (2×5 mL), dried (Na$_2$SO$_4$) and concentrated in vacuo to give 116 mg (98%) of the alcohol that was used directly without purification for the next step. A solution of the alcohol intermediate (116 mg, 0.44 mmol) in ethyl acetate (3 mL) was hydrogenated under an atmosphere of hydrogen with 10% Pd/C (20 mg) and a trace of conc. $H_2SO_4$ at rt for 16 h. Filtration over Celite™ afforded 104 mg (95%) of 1-tert-butyloxycarbonyl-1,2,3,4-tetrahydro-3-methylquinoline. Data for 1-tert-butyloxycarbonyl-1,2,3,4-tetrahydro-3-methylquinoline: $^1$H NMR (400 MHz, $CDCl_3$) 7.65 (d, J=8.3, 1H), 7.11 (dd, J=7.7, 7.7,1H), 7.04 (d, J=7.2, 1H), 6.96 (dd, J=7.4, 7.4, 1H), 3.97 (ddd, J=12.7, 4.2, 1.0, 1H), 3.09 (dd, J=11.8, 9.8, 1H), 2.86 (dd, J=16.2, 5.3, 1H), 2.40 (dd, J=16.1, 9.6, 1H), 2.03 (m, 1H), 1.52 (s, 9H), 1.05 (d, J=6.7, 3H).

1,2,3,4-tetrahydro-3-methylquinoline (structure 60A of Scheme LI, where $R^{1-2}=R^4=H$, $R^3$=methyl)

This compound was prepared by General Method 12 (EXAMPLE 147) from 1-tert-butyloxycarbonyl-1,2,3,4-tetrahydro-3-methylquinoline (104 mg, 0.42 mmol) to afford 51 mg (83%) of 1,2,3,4-tetrahydro-3-methylquinoline as an oil which was used directly without purification for the next step.

7-Nitro-1,2,3,4-tetrahydro-3-methylquinoline. 1,2,3,4-Tetrahydro-3-methylquinoline (51 mg, 0.35 mmol) was dissolved in sulfuric acid (0.5 mL) and the temperature lowered to 0° C. To this solution 90% fuming nitric acid (15 mL, 0.35 mmol) was added slowly and the mixture stirred at 0° C. for 1 h, then warmed to rt. The reaction mixture was then poured onto 1 g of ice and extracted with dichloromethane (2×5 mL). The organic phase was washed with saturated aqueous $NaHCO_3$ (3 mL) and concentrated in vacuo to a reddish residue that was subjected to chromatography (silica gel, hexanes/ethyl acetate, 85:15) which afforded 8.2 mg (12%) of 7-nitro-1,2,3,4-tetrahydro-3-methylquinoline. Data for 7-nitro-1,2,3,4-tetrahydro-3-methylquinoline: $^1$H NMR (400 MHz, $CDCl_3$) 7.39 (dd, J=8.25, 2.2, 1H), 7.27 (d, J=2.3, 1H), 7.01 (d, J=8.3, 1H), 4.19 (s, 1H), 3.33 (m, 1H), 2.94 (dd, J=10.1, 10.1, 1H), 2.86 (ddd, J=13.8, 4.7, 1.7, 1H), 2.46 (dd, J=16.6, 10.0, 1H), 2.05 (m, 1H), 1.06 (d, J=6.7, 3H).

1,2,3,4-Tetrahydro-3-methyl-6-trifluoromethyl-8-pyridono-[5,6-g]quinoline (Compound 436)

A solution of 7-nitro-1,2,3,4-tetrahydro-3-methylquinoline (8.2 mg, 0.042 mmol) in ethyl acetate (1 mL) was hydrogenated under an atmosphere of hydrogen with 10% Pd/C (4 mg) at rt for 2 h. Filtration over Celite™ afforded 6.2 mg (89%) of 7-amino-1,2,3,4-tetrahydro-3-methylquinoline (structure 61A of Scheme XL VIII, where $R^{1-2}=R^4=H$, $R^3$=methyl) that was used without further purification for the next step. Compound 436 was prepared by General Method 13 (EXAMPLE 147) from 7-amino-1, 2,3,4-tetrahydro-3-methylquinoline (6.2 mg, 0.038 mmol), $ZnCl_2$ (8.0 mg, 0.057 mmol) and ethyl 4,4,4-trifluoroacetoacetate (5.5 mL, 0.038 mol) to afford 5.8 mg (54%) of Compound 436 as a yellow solid. Data for Compound 436: $^1$H NMR (400 MHz, DMSO-$d_6$) 11.80 (bs, 1H), 7.11 (s, 1H), 6.95 (s, 1H), 6.37 (s, 2H), 3.26 (m, 1H), 2.83 (m, 2H), 2.51 (dd, J=15.7, 10.3, 1H), 1.88 (s, 1H), 0.97 (d, J=6.6, 3H).

EXAMPLE 337

1,2,3,4-Tetrahydro-3,3-dimethyl-6-trifluoromethyl-8-pyridono-[5,6-g]quinoline (Compound 437, structure 73A of Scheme LII, where $R^{1-2}=R^5=R^7=H$, $R^{3-4}$=methyl, $R^6$=trifluoromethyl)

1-tert-Butyloxycarbonyl-1,2,3,4-tetrahydro-3,3-dimethyl-4-quinolinone (structure 70A of Scheme LII, where $R^{1-2}=H$, $R^{3-4}$=methyl)

This compound was obtained along with 1-tert-butyloxycarbonyl-1,2,3,4-tetrahydro-3-methyl-4-quinolinone as described above (EXAMPLE 336). Data for 1-tert-butyloxycarbonyl-1,2,3,4-tetrahydro-3,3-dimethyl-4-quinolinone: $^1$H NMR (400 MHz, $CDCl_3$) 8.01 (dd, J=7.9, 1.6, 1H), 7.78 (d, J=8.4, 1H), 7.49 (ddd, J=7.6, 7.6, 1.7, 1H), 7.14 (ddd, J=7.8, 7.8, 1.6, 1H), 3.86 (s, 2H), 1.56 (s, 9H), 1.20 (s, 6H).

1-tert-Butyloxycarbonyl-1,2,3,4-tetrahydro-3,3-dimethylquinoline

To a solution of 1-tert-butyloxycarbonyl-1,2,3,4-tetrahydro-3,3-dimethyl-4-quinolinone (128 mg, 0.47 mmol) in methanol (2 mL) at 0° C. was added portionwise sodium borohydride (18 mg, 0.47 mmol) and the reaction mixture was stirred at 0° C. for 3 h. The reaction mixture was then quenched with sat'd $NH_4Cl$ (2 mL), extracted with ethyl acetate (2×5 mL), dried ($Na_2SO_4$) and concentrated. A solution of this crude material in ethyl acetate (3 mL) was hydrogenated under an atmosphere of hydrogen with 10% Pd/C (20 mg) and a trace of conc. $H_2SO_4$ at rt for 16 h. Filtration over Celite™ afforded 100 mg (84%) of 1-tert-butyloxycarbonyl-1,2,3,4-tetrahydro-3,3-dimethylquinoline. Data for 1-tert-butyloxycarbonyl-1,2,3, 4-tetrahydro-3,3-dimethylquinoline: $^1$H NMR (400 MHz, $CDCl_3$) 7.68 (d, J=8.3, 1H), 7.12 (ddd, J=8.8, 8.8, 1.5, 1H), 7.02 (d, J=7.0, 1H), 6.97 (ddd, J=7.4, 7.4, 1.0, 1H), 3.46 (s, 2H), 2.58 (s, 2H), 1.51 (s, 9H), 1.01 (6H).

1,2,3,4-tetrahydro-3,3-dimethylquinoline (structure 71A of Scheme LII, where $R^{1-2}=R^5=H$, $R^{3-4}$=methyl)

This compound was prepared by General Method 12 (EXAMPLE 147) from 1-tert-butyloxycarbonyl-1,2,3,4-tetrahydro-3,3-dimethylquinoline (100 mg, 0.38 mmol) to afford 51 mg (83%) of 1,2,3,4-tetrahydro-3,3-dimethylquinoline as an oil which was used directly without purification for the next step.

7-Nitro-1,2,3,4-tetrahydro-3,3-dimethylquinoline 1,2,3,4-Tetrahydro-3,3-dimethylquinoline (51 mg, 0.32 mmol) was dissolved in sulfuric acid (0.5 mL) and the temperature lowered to 0° C. To this solution 90% fuming nitric acid (14 mL, 0.32 mmol) was added slowly and the mixture stirred at 0° C. for 1 h, then warmed to rt. The reaction mixture was then poured onto 1 g of ice and extracted with dichloromethane (2×5 mL). The organic phase was washed with saturated aqueous $NaHCO_3$ (3 mL) and concentrated in vacuo to a reddish residue that was subjected to chromatography (silica gel, hexanes/ethyl acetate, 85:15) which afforded 39 mg (58%) of 7-nitro-1,2, 3,4-tetrahydro-3,3-dimethylquinoline. Data for 7-nitro-1,2, 3,4-tetrahydro-3,3-dimethylquinoline: $^1$H NMR (400 MHz, $CDCl_3$) 7.40 (dd, J=8.3, 2.1, 1H), 7.29 (d, J=1.8, 1H), 7.01 (d, J=8.3H, 1H), 4.25 (s, 1H), 2.98 (s, 2H), 2.54 (s, 2H), 1.01 (s, 6H).

1,2,3,4-Tetrahydro-3,3-dimethyl-6-trifluoromethyl-8-pyridono-[5,6-g]quinoline (Compound 437)

A solution of 7-nitro-1,2,3,4-tetrahydro-3,3-dimethylquinoline (39 mg, 0.187 mmol) in ethyl acetate (2 mL) was hydrogenated under an atmosphere of hydrogen with 10% Pd/C (4 mg) at rt for 2 h. Filtration over Celite™ afforded 30 mg (91%) of 7-amino-1,2,3,4-tetrahydro-3,3-dimethylquinoline (structure 72A of Scheme LII, where $R^{1-2}=R^5=H$, $R^{3-4}$=methyl) that was used without further purification in the next step. Compound 437 was prepared by General Method 13 (EXAMPLE 147) from 7-amino-1,2,3, 4-tetrahydro-3,3-dimethylquinoline (30 mg, 0.17 mmol), $ZnCl_2$ (34 mg, 0.25 mmol) and ethyl 4,4,4-trifluoroacetoacetate (25 mL, 0.17 mol) to afford 13 mg (26%) of Compound 437 as a yellow solid. Data for Compound 437: $^1$H NMR (400 MHz, DMSO-d$_6$) 11.71 (bs, 1H), 7.11 (s, 1H), 7.01 (s, 1H), 6.40 (s, 1H), 6.37 (s, 1H), 2.89 (s, 2H), 2.51 (s, 2H), 0.93 (s, 6H).

EXAMPLE 338

(R/S) 1,2,3,4-Tetrahydro-2,2,3-trimethyl-6-trifluoromethyl-8-pyridono-[5,6-g]quinoline (Compound 438, structure 79A of Scheme LII, where $R^1$=$R^5$=$R^7$=H, $R^{2-4}$=methyl, $R^6$=trifluoromethyl).

1-tert-Butoxycarbonyl-1,2,3,4-tetrahydro-2,2-dimethyl-4-quinolinone (structure 76A of Scheme LII, where $R^1$=H, $R^{2-3}$=methyl)

A solution of aniline (19 mL, 0.20 mol), 3-acetoxy-3-methyl-1-butyne (26 g, 0.20 mol), CuCl (1.0 g, 10 mmol) and Et$_3$N (28 mL, 0.20 mol) in THF (120 mL) was heated at reflux for 5 h and was filtered through a pad of Celite™. Removal of solvent and chromatography of the crude mixture (silica gel, EtOAc/hexane, 3/7) afforded 21 g (67%) of 3-methyl-3-phenylamino-1-butyne. Treatment of the aminobutyne with CuCl (0.70 mg, 7.0 mmol) in THF (200 mL) at 70° C. for 16 h followed by chromatography (silica gel, EtOAc/hexane, 3/7) afforded 13 g (60%) of 1,2-dihydro-2,2-dimethylquinoline (structure 75A of Scheme LII, where $R^1$=H, $R^{2-3}$=methyl). Treatment of the quinoline with di-tert-butyl dicarbonate (22 g, 0.10 mol) and DMAP (12 g, 0.10 mol) in THF (100 mL) for 16 h followed by chromatography (silica gel, EtOAc/hexane, 2/8) afforded 15 g (71%) of 1-tert-butoxycarbonyl-1,2-dihydro-2,2-dimethylquinoline. 1-tert-Butoxycarbonyl-1,2-dihydro-2,2-dimethylquinoline (3.0 g, 11 mmol) in THF (30 mL) was treated with 1.0M BH$_3$-THF in THF (29 mL, 29 mmol) at rt for 3 h and was quenched with 3M KOH (20 mL). To the above solution 30% H$_2$O$_2$ (5 mL) was added and the mixture was stirred for 60 min, then 5 mL of water was introduced. The mixture was extracted, washed with brine and concentrated. Chromatography of the crude mixture on a silica gel column using a 10–30% mixture of EtOAc/Hexane as eluents afforded a 2:1 mixture of two isomers (0.87 g, 3.1 mmol), which was oxidized with PCC (2.5 g, 11 mmol) in 60 mL of methylene chloride at rt for 60 min. Removal of solvent and chromatography of the black oil on a silica gel column using a 20% mixture of EtOAc and hexane as solvent afforded 0.58 g (68%) of 1-tert-butoxycarbonyl-1,2,3,4-tetrahydro-2,2-dimethyl-4-quinolinone as a white solid. Data for 1-tert-butoxycarbonyl-1,2,3,4-tetrahydro-2,2-dimethyl-4-quinolinone: $^1$H NMR (400 MHz, CDCl$_3$) 7.93 (d, J=7.8, 1H), 7.42 (t, J=7.8, 1H), 7.31 (d, J=7.8, 1H), 7.02 (t, J=7.8, 1H), 2.73 (s, 2H), 1.56 (s, 9H), 1.49 (s, 6H). 1,2,3,4-tetrahydro-2,2,3-trimethylquinoline (structure 77A of Scheme LII, where $R^1$=$R^5$=H, $R^{2-4}$=methyl)

To a solution of 1-tert-butoxycarbonyl-1,2,3,4-tetrahydro-2,2-dimethyl-4-quinoline (0.10 g, 0.36 mmol) and iodomethane (0.50 mL, 8.0 mmol) in DMF (4 mL) was added NaH (60% in mineral oil, 20 mg, 0.50 mmol) and the resulting mixture was stirred at rt for 2 h. The reaction was quenched with water (5 mL) and was extracted with EtOAc (2×15 mL). Removal of solvent and chromatography of the crude residue on a silica gel column using a 10% mixture of EtOAc and hexane as solvents afforded 90 mg (86%) of 1-tert-butoxycarbonyl-1,2,3,4-tetrahydro-2,2,3-trimethyl-4-quinolinone as a colorless oil. The oil (90 mg, 0.32 mmol) was treated with NaBH$_4$ (50 mg, 1.3 mmol) in methanol (5 mL) for 1 h and the reaction mixture was concentrated. Filtration from the inorganic material through a silica gel pad provided a colorless oil, which was then subjected to hydrogenation over 10% Pd/C (10 mg) in EtOAc (5 mL) under a hydrogen balloon for 15 h. Filtration from the catalyst through a Celite™ pad followed by removal of solvent gave 70 mg (82%) of 1-tert-butoxycarbonyl-1,2,3,4-tetrahydro-2,2,3-trimethylquinoline as a colorless oil. The crude oil (70 mg, 0.26 mmol) was treated with TFA (0.50 mL, 6.5 mmol) in CH$_2$Cl$_2$ for 30 min. and was quenched with 5% NaOH (6 mL). The mixture was extracted with EtOAc (2×15 mL) and was concentrated. Chromatography on silica gel using a 10% mixture of EtOAc and hexane afforded 1,2,3,4-tetrahydro-2,2,3-trimethylquinoline as a colorless oil (40 mg, 89%). Data for 1,2,3,4-tetrahydro-2,2,3-trimethylquinoline: $^1$H NMR (400 MHz, CDCl$_3$) 7.00–6.91 (m, 2H), 6.60 (t, J=7.3, 1H), 6.45 (d, J=7.3, 1H), 3.61 (br s, 1H), 2.74 (dd, J=16.6, 5.3, 1H), 2.47 (dd, J=16.6, 10.3, 1H), 1.82 (m, 1H), 1.20 (s, 3H), 1.05 (s, 3H), 0.97 (d, J=7.2, 3H).

(R/S) 1,2,3,4-Tetrahydro-2,2,3-trimethyl-6-trifluoromethyl-8-pyridono-[5,6-g]quinoline (Compound 438, structure). The quinoline (20 mg, 0.11 mmol) was converted to Compound 438 according to the nitration-hydrogenation-Knorr procedure described above for Compound 436 (EXAMPLE 336) in a 12% yield as a yellow solid (4 mg). Data for Compound 436: $^1$H NMR (400 MHz, CDCl$_3$) 11.46 (s, 1H), 7.35 (s, 1H), 6.66 (s, 1H), 6.31 (s, 1H), 440 (s, 1H), 2.83 (dd, J=16.6, 4.8, 1H), 2.57 (dd, J=16.6, 10.3, 1H), 1.83 (m, 1H), 1.25 (s, 3H), 1.10 (s, 3H), 0.99 (d, J=6.9, 3H).

EXAMPLE 339

(R/S-21,4u)-1,2,3,4-Tetrahydro-2,4-dimethyl-6-trifluoromethyl-8-pyridono-[5,6-g]quinoline (Compound 439, structure 62A of Scheme XL VIII, where $R^1$=$R^3$=$R^6$=H, $R^2$=$R^4$=methyl, $R^5$=trifluoromethyl)

1-tert-Butoxycarbonyl-1,2,3,4-tetrahydro-2-methyl-4-quinolinone

A mixture of aniline (3.0 g, 32 mmol) and crotonic acid (2.0 g, 23 mmol) in toluene (20 mL) was heated at reflux for 18 h. Removal of solvent and chromatography (silica gel, EtOAc/hexane, 9/1) of the crude material afforded 2.5 g (61%) of 3-phenylaminobutanoic acid. The acid was treated with PPA (20 mL) at 110° C. for 6 h and the reaction mixture was poured into ice water (50 mL) and then was neutralized with Na$_2$CO$_3$ to pH 7. Extraction with EtOAc (3×60 mL) followed by chromatography (silica gel, EtOAc/hexane, 4/6) afforded 1.0 g (44%) of 1,2,3,4-tetrahydro-2-methyl-4-quinolinone (structure 59A of Scheme XL VIII, where $R^1$=$R^3$=H, $R^2$=methyl) as a yellow solid. The quinolinone was treated with di-tert-butyl dicarbonate (2.2 g, 10 mmol) and DMAP (0.84 g, 6.8 mmol) in THF (15 mL) for 16 h followed by chromatography (silica gel, EtOAc/hexane, 2/8) to afford 1.1 g (68%) of 1-tert-butoxycarbonyl-1,2,3,4-tetrahydro-2-methyl-4-quinolinone as a yellow oil. Data for 1-tert-butoxycarbonyl-1,2,3,4-tetrahydro-2-methyl-4-quinolinone: $^1$H NMR (400 MHz, CDCl$_3$) 7.99 (d, J=7.5, 1H), 7.78 (d, J=7.5, 1H), 7.50 (t, J=7.5, 1H), 7.12 (t, J=7.5, 1H), 5.10 (m, 1H), 3.04 (dd, J=17.3,5.8, 1H), 2.57 (dd, J=17.3, 1.7, 1H), 1.56 (s, 9H), 1.22 (d, J=6.9, 3H).

(R/S-21,4u)-1,2,3,4-Tetrahydro-2,4-dimethyl-6-trifluoromethyl-8-pyridono-[5,6-g]quinoline (Compound 439)

To a solution of a 3.0M ether solution of MeMgBr (1.0 mL, 3.0 mmol) was added 1-tert-butoxycarbonyl-1,2,3,4-tetrahydro-2-methyl-4-quinolinone (0.13 mg, 0.50 mmol) in THF (6 mL) and the reaction was allowed to stir at rt for 3 h, then was quenched with water (10 mL). Extraction with EtOAc (2×30 mL) followed by chromatography (silica gel, EtOAc/hexane, 3/7) afforded 50 mg (36%) of the adduct, which was treated with 10% Pd/C (10 mg) and one drop of H$_2$SO$_4$ in EtOAc (15 mL) under a hydrogen atmosphere for 16 h. Filtration from the catalyst through Celite™ afforded the crude 1-tert-butoxycarbonyl-1,2,3,4-tetrahydro-2,4-dimethyl-4-quinoline, which was treated with TFA (0.4 mL) in methylene chloride (1 mL) for 30 min. The reaction was neutralized with 5% NaOH to pH 10 and was extracted with EtOAc (2×20 mL). Chromatography (silica gel, EtOAc/hexane, 1/9) afforded 20 mg (69%) of (R/S-2l-4u)-1,2,3,4-tetrahydro-2,4-dimethyl-4-quinoline (structure 60A of Scheme LI, where $R^1=R^3=H$, $R^2=R^4=$methyl) as a colorless oil. The quinoline was converted to the title compound according to the general nitration-hydrogenation-Knorr procedure described above for Compound 436 (EXAMPLE 336) in 14% three step yield as a yellow solid. Data for Compound 439: $^1$H NMR (400 MHz, CDCl$_3$) 11.75 (s, 1H), 7.47 (s, 1H), 6.65 (s, 1H), 6.33 (s, 1H), 4.41 (s, 1H), 3.59 (m, 1H), 2.92 (m, 1H), 1.94 (m, 1H), 1.38 (d, J=6.8, 3H), 1.24 (m, 1H), 1.22 (d, J=6.4, 3H).

EXAMPLE 340

(R/S-21,4u)-4-Ethyl-1,2,3,4-tetrahydro-2-methyl-6-trifluoromethyl-8-pyranono[5,6-g]quinoline (Compound 440, structure 33A of Scheme XL, where $R^{1-2}=R^6=H$, $R^3=$methyl, $R^4=$ethyl, $R^5=$trifluoromethyl).

(R/S)-1,2,3,4-Tetrahydro-7-methoxy-2-methyl-4-quinoline

This compound was prepared in a manner similar to that described for 1,2,3,4-tetrahydro-7-methoxy-4-quinolone (EXAMPLE 310) from anisidine and crotonic acid to afford the quinolinone as a brown oil. Data for 1,2,3,4-tetrahydro-7-methoxy-2-methyl-4-quinolinone: $^1$H NMR (400 MHz, CDCl$_3$) 7.78 (d, J=8.7, 1H), 6.33 (dd, J=6.2, 2.2, 1H), 6.08 (d, J=2.1, 1H), 4.27 (br s, 1H), 3.80 (s, 3H), 2.59 (dd, J=16, 3.7, 2H), 2.42 (dd, J=13, 12, 2H), (R/S)-1-tert-Butoxycarbonyl-1,2,3,4-tetrahydro-7-methoxy-2-methyl-4-quinolone (structure 31A of Scheme XL, where $R^{1-2}=H$, $R^3=$methyl)

This compound was prepared in a manner similar to that described for 1-tert-butoxycarbonyl-1,2,3,4-tetrahydro-7-methoxy-4-quinolone (EXAMPLE 310) from 1,2,3,4-tetrahydro-7-methoxy-2-methyl-4-quinolinone (3.26 mg) to give 961 mg (62%) of the desired quinolone as an off-white solid. Data for 1-tert-butoxycarbonyl-1,2,3,4-tetrahydro-7-methoxy-2-methyl-4-quinolone: $^1$H NMR (400 MHz, CDCl$_3$) 7.94 (d, J=8.9, 1H), 7.35 (d, J=2.4, 1H), 6.67 (dd, J=8.7, 2.4, 1H), 5.08 (m, 1H), 3.86 (s, 3H), 2.99 (dd, J=17, 5.8, 1H), 2.48 (dd, J=17, 1.7, 1H), 1.57 (s, 9H), 1.24 (d, J=6.9, 3H).

(R/S)-1-tert-Butoxycarbonyl-4-ethyl-1,2,3,4-tetrahydro-7-methoxy-2-methylquinoline (structure 32A of Scheme XL, where $R^{1-2}=H$, $R^3=$methyl, $R^4=$ethyl). This compound was prepared in a manner similar to that described for 1-tert-butoxycarbonyl-4-ethyl-1,2,3,4-tetrahydro-7-methoxy-4-quinolone (EXAMPLE 314) from 1-tert-butoxycarbonyl-1,2,3,4-tetrahydro-7-methoxy-2-methyl-4-quinolone (100 mg) to give the desired quinoline (34 mg, 30%) as a mixture of diastereomers. Data for 1-tert-butoxycarbonyl-4-ethyl-1,2,3,4-tetrahydro-7-methoxy-2-methylquinoline: $^1$H NMR (400 MHz, CDCl$_3$) 7.05 (d, J=8.6, 1H), 6.97 (d, J=2.5, 1H), 6.66 (dd, J=8.5, 2.5, 1H), 4.38 (m, 1H), 3.78 (s, 3H), 2.39 (m, 1H), 2.28 (m, 1H), 2.04 (m, 2H), 1.55 (m, 1H), 1.49 (s, 9H), 1.14 (d, J=6.2, 3H), 1.08 (t, J=7.4, 3H).

(R/S)-4-Ethyl-1,2,3,4-tetrahydro-7-hydroxy-2-methylquinoline

This compound was prepared in a manner similar to that described for 4-ethyl-1,2,3,4-tetrahydro-7-hydroxyquinoline (EXAMPLE 314) from 1-tert-butoxycarbonyl-4-ethyl-1,2,3,4-tetrahydro-7-methoxy-2-methylquinoline (34 mg) to give the desired quinoline as a colorless oil, which was used without further purification in the following reaction.

(R/S-21,4u)-4-Ethyl-1,2,3,4-tetrahydro-2-methyl-6-trifluoromethyl-8-pyranono[5,6-g]quinoline, (Compound 440)

This compound was prepared in a manner similar to that described for Compound 414 (EXAMPLE 314) to give the desired compound as a mix of diastereomers. Recrystallization of the diastereomeric mixture afforded a sample of Compound 440. Data for Compound 440: $^1$H NMR (400 MHz, CDCl$_3$) 7.38 (s, 1H), 6.37 (s, 1H), 6.35 (s, 1H), 4.43 (br s, 1H), 3.57 (m, 1H), 2.79 (m, 1H), 2.04 (m, 2H), 1.61 (m, 1H), 1.28 (d, J=6.4, 3H), 1.00 (t, J=7.3, 3H).

EXAMPLE 341

(R/S-21,3u)-1,2,3,4-Tetrahydro-2,3-dimethyl-6-trifluoromethyl-8-pyridono-[5,6-g]quinoline (Compound 441, structure 62A of Scheme XL VIII, where $R^1=R^4=R^6=H$, $R^{2-3}=$methyl, $R^5=$trifluoromethyl).

To a solution of 1-tert-butoxycarbonyl-1,2,3,4-tetrahydro-2-methyl-4-quinolinone (EXAMPLE 339) (0.13 mg, 0.50 mmol) and iodomethane (0.50 mL, 8.0 mmol) in DMF (6 mL) was added NaH in a 60% mineral oil (40 mg, 1.0 mmol). The reaction mixture was stirred at rt for 16 h and was quenched by water (10 mL). Extraction of the mixture with EtOAc (2×30 mL) followed by chromatography (silica gel, EtOAc/hexane, 1/9) afforded a mixture of three alkylated products (125 mg, 91%). The above mixture was treated with NaBH$_4$ (38 mg, 1.0 mmol) in methanol (15 mL) for 1 h and the alcohol intermediates were purified by chromatography (silica gel, EtOAc/hexane, 3/7) to afford a mixture of three alcohols (120 mg, 95%). The mixture of alcohol intermediates (120 mg, 0.43 mmol) was treated with 10% Pd/C (20 mg) and one drop of H$_2$SO$_4$ in EtOAc (15 mL) under H$_2$ for 18 h. Filtration through a Celite™ pad provided the reduced products, which were directly treated with TFA (0.5 mL) in methylene chloride (1.0 m) for 1 h. The reaction was quenched with 5% NaOH, brought to pH 10, and was extracted with EtOAc (2×20 mL). Chromatography (silica gel, EtOAc/hexane, 2/8) afforded a mixture of three products (30 mg, 43%), containing (R/S-21,31)-1,2,3,4-tetrahydro-2,3-dimethylquinoline (structure 60A of Scheme LI, where $R^1=R^4=H$, $R^{2-3}=$methyl); (R/S-21,31)-1,2,3,4-tetrahydro-2,3-dimethylquinoline (structure 60A of Scheme LI, where $R^1=R^4=H$, $R^{2-3}=$methyl), and (R/S)- 1,2,3,4-tetrahydro-2,3,3-trimethylquinoline (structure 71A of Scheme LII, where $R^1=R^5=H$, $R^{2-4}=$methyl). The mixture of the quinolines (30 mg, 0.18 mmol) was subjected to the nitration-hydrogenation-Knorr procedure described above for Compound 436 (EXAMPLE 336) to afford a mixture of Compound 441, 442, and 443, which was purified by HPLC (10 mm×25 cm ODC column, 80% MeOH/20% H$_2$O, 3.0 mL/min.). Data for Compound 441: $^1$H NMR (400 MHz, acetone-d$_6$) 10.68 (s, 1H), 7.25 (s, 1H), 6.48 (s, 1H), 6.41 (s, 1H), 6.09 (s, 1H), 3.13 (m, 1H), 2.80 (dd, J=15.9, 4.3, 1H), 2.53 (dd, J=15.9, 12.0, 1H), 1.61 (m, 1H), 1.24 (d, J=6.3, 3H), 1.04 (d, J=6.5, 3H).

EXAMPLE 342

(R/S-21,31)-1,2,3,4-Tetrahydro-2,3-dimethyl-6-trifluoromethyl-8-pyridono-[5,6-g]quinoline (Compound 441, structure 62A of Scheme XL VIII, where $R^1=R^4=R^6=H$, $R^{2-3}=$methyl, $R^5=$trifluoromethyl)

Compound 442 was obtained along with Compounds 441 and 443 as described above (EXAMPLE 341). Data for Compound 442: $^1$H NMR (400 MHz, acetone-d$_6$) 10.80 (s, 1H), 7.28 (s, 1H), 6.49 (s, 1H), 6.48 (s, 1H), 6.15 (s, 1H), 3.62 (m, 1H), 2.91 (m, 1H), 2.62 (dd, J=16.3, 6.5, 1H), 2.07 (m, 1H), 1.15 (d, J=6.5, 3H), 0.93 (d, J=6.8, 3H).

EXAMPLE 343

(R/S)-1,2,3,4-Tetrahydro-2,3,3-trimethyl-6-trifluoromethyl-8-pyridono-[5,6-g]quinoline (Compound 443, structure 73A of Scheme LII, where $R^1=R^5=R^7=H$, $R^{2-4}$=methyl, $R^6$=trifluoromethyl)

Compound 443 was obtained along with Compounds 441 and 442 as described above (EXAMPLE 341). Data for Compound 443: $^1$H NMR (400 MHz, acetone-d$_6$) 10.58 (s, 1H), 7.23 (s, 1H), 6.50 (s, 1H), 6.41 (s, 1H), 6.08 (s, 1H), 3.28 (m, 1H), 2.65 (d, J=15.8, 1H), 2.53 (d, J=15.8, 1H), 1.15 (d, J=6.6, 3H), 1.03 (s, 3H), 0.84 (s, 3H).

EXAMPLE 344

(R/S)-1,2,3,4-Tetrahydro-2-methyl-6-trifluoromethyl-8-pyridono-[5,6-g]quinoline (Compound 444, structure 53A of Scheme XL VI, where $R^{1-2}=R^5$=H, $R^3$=methyl, $R^4$=trifluoromethyl)

1,2,3,4-tetrahydro-2-methylquinoline (0.15 g, 1.0 mmol) was converted to Compound 444 according to the nitration-hydrogenation-Knorr procedure described for Compound 436 (EXAMPLE 336) to afford 35 mg(13%) of Compound 444 as a yellow solid. Data for Compound 444: $^1$H NMR (400 MHz, acetone-d$_6$) 10.83 (s, 1H), 7.29 (s, 1H), 6.55 (s, 1H), 6.50 (s, 1H), 6.17 (s, 1H), 3.57 (m, 1H), 2.91–2.82 (m, 2H), 2.03 (m, 1H), 1.54 (m, 1H), 1.25 (d, J=6.4, 3H).

EXAMPLE 345

(R/S)-4-Ethyl-1,2,3,4-tetrahydro-6-trifluoromethyl-8-pyridonoo[5,6-g]quinlone (Compound 445, structure 62A of Scheme XL VIII where $R^{1-3}=R^6$=H $R^4$=ethyl, $R^5$=trifluorometh1)

(R/S)-1-tert-Butyloxycarbonyl-4-ethyl-1,2,3,4-tetrahydro-4-hydroxyquinoline

To a flame-dried 25-mL rb flask containing ethylmagnesium bromide (4.0 mL of a 3.0M solution in Et$_2$O, 12.0 mmol, 3.0 equiv), at −10° C. was added dropwise a solution of 1-tert-butyloxycarbonyl-1,2,3,4-tetrahydro-4-quinolone (1.0 g, 4.0 mmol) in Et$_2$O (4 mL). The reaction mixture was stirred at −10° C. for 15 min, then allowed to warm to rt over 10 min. A 1.0M solution of NaHSO$_4$ (10 mL) was then rapidly added. The resulting biphasic mixture was extracted with EtOAc (3×10 mL), and the combined organic extracts were dried (Na$_2$SO$_4$) and concentrated under reduced pressure. The residue was purified by flash chromatography (silica gel, hexanes/EtOAc, 4:1), affording 800 mg (71%) of the desired product as a clear yellow oil (R$_f$0.14, hexanes/ EtOAc, 4:1). Data for 1-tert-butoxycarbonyl-4-ethyl-1,2,3, 4-tetrahydro-4-hydroxyquinoline: $^1$H NMR (400 MHz, CDCl$_3$) 7.68 (d, 1H, J=8.4, 8-H), 7.47 (dd, 1H, J=7.9, 1.7, 5-H), 7.21 (ddd, 1H, J=7.4, 7.4, 1.6, 6-H), 7.09 (ddd, 1H, J=7.8, 7.8, 1.1, 7-H), 4.03 (ddd, 1H, J=12.9, 7.1, 4.7, 2-H), 3.47 (ddd, 1H, J=13.1, 8.6, 4.3, 2-H), 2.11 (ddd, 1H, J=13.5, 8.6, 4.8, 3-H), 1.86 (m, 3H, 3-H, CH$_2$CH$_3$), 1.52 [s, 9H, C(CH$_3$)$_3$], 0.89 (t, 3H, J=7.5, CH$_3$).

(R/S)-4-Ethyl-1,2,3,4-tetrahydroquinoline (structure 60A of Scheme XL VIII, where $R^{1-3}$=H, $R^4$=ethyl)

To a flame-dried 100-mL rb flask containing 1-tert-butyloxycarbonyl-4-ethyl-1,2,3,4-tetrahydro-4-hydroxyquinoline (800 mg, 2.88 mmol) in a 1:1 solution of EtOAc/EtOH (20 mL) at rt was added 10% Pd/C (approx. 1 mol %). After evacuation and flushing of the vessel three times with nitrogen, one drop of trifluoroacetic acid was added, the vessel evacuated once more, and the mixture stirred under an atmosphere of hydrogen for 16 h. The reaction mixture was then filtered, and concentrated under reduced pressure. The residue was transferred to a 25-mL rb flask with CH$_2$Cl$_2$ (3 mL) and stirred at rt. TFA (1.2 mL) was added and the reaction was vented and stirred for 2 h at rt. A solution of sat'd. NaHCO$_3$ (adjusted to pH 9 with 3.0M NaOH) was added until the aqueous phase was approximately pH 9. The resulting aqueous phase was extracted with CH$_2$Cl$_2$ (3×10 mL), and the combined organic extracts were dried (Na$_2$SO$_4$), and concentrated under reduced pressure to yield 351 mg (71%) of a colorless oil, which turned blue on exposure to air (R$_f$0.40, hexanes/EtOAc, 2:1). Data for (R/S)-4-ethyl-1,2,3,4-tetrahydroquinoline: $^1$H NMR (400 MHz, CDCl$_3$) 7.02 (d, 1H, J=7.6, 8-H), 6.96 (ddd, 1H, J=7.7, 7.7, 1.3, 7-H), 6.61 (ddd, 1H, J=8.2, 8.2, 1.0, 6-H), 6.47 (d, 1H, J=7.9, 5-H), 3.83 (br s, 1H, CH$_2$NH ), 3.31 (ddd, 1H, J=11.3, 11.3, 3.6, 2-H), 3.25 (ddd, 1H, J=9.7, 9.7, 4.8, 2-H), 2.65 (dddd, 1H, J=10.1, 5.1, 5.1, 5.1, 4-H), 1.92 (dddd, 1H, J=9.6, 4.7, 4.7, 4.7, 3-H), 1.82 (m, 1H, 3-H), 1.74 (m, 1H, CH$_2$CH$_3$), 0.98 (t, 3H, J=7.4, CH$_3$).

(R/S)-7-Amino-4-ethyl-1,2,3,4-tetrahydroquinoline (structure 61A of Scheme XL VIII where $R^{1-3}$=H, $R^4$=ethyl A 25-mL rb flask containing (R/S)-4-ethyl-1,2,3,4-tetrahydroquinoline (340 mg, 2.1 mmol) was cooled to −10° C., and conc. H$_2$SO$_4$ (5 mL) was added slowly. The resulting solution was warmed to rt to effect complete dissolution of the quinoline, then cooled again to −10° C. and stirred vigorously. Fuming HNO$_3$ (85 µL) was added dropwise, slowly, and the reaction mixture turned dark red. After 10 min, the reaction mixture was poured onto cracked ice and diluted with water (5 mL). Sat'd NaHCO$_3$ (80 mL) was added, and the pH was adjusted to pH 9 with 3.0M NaOH. This aqueous phase was extracted with EtOAc (3×75 mL), and the combined extracts were dried (Na$_2$SO$_4$),and concentrated under reduced pressure to yield a dark red oil. This crude material was placed into a 250-mL rb flask with 1:1 EtOAc/EtOH (40 mL) and 10% Pd on C (approx. 1 mol %). The vessel was evacuated and flushed with nitrogen three times, then stirred under an atmosphere of hydrogen for 16 h, filtered, and concentrated under reduced pressure to yield a yellow oil, which was purified by flash chromatography (silica gel, CH$_2$Cl$_2$/methanol, 9:1), affording 210 mg (57%) of the desired product as a dark yellow oil (R$_f$0.50, CH$_2$Cl$_2$/ MeOH, 9:1). Data for (R/S)-7-amino-4-ethyl-1,2,3,4-tetrahydroquinoline: $^1$H NMR (400 MHz, CDCl$_3$) 6.81 (d, 1H, J=8.1, 5-H), 6.02 (dd, 1H, J=8.0, 2.2, 6-H), 5.84 (d, 1H, J=2.3, 8-H), 3.48 (s, 2H, NH$_2$), 3.27 (ddd, 1H, J=11.1, 11.1, 3.5, 2-H), 3.20 (ddd, 1H, J=9.8, 5.3, 4.5, 2-H), 2.55 (dddd, 1H, J=10.2, 5.2, 5.2, 5.2, 4H), 1.90 (dddd, 1H, J=9.6, 9.6, 9.6, 4.7, 3-H), 1.72 (m, 2H, 3-H, CH$_2$CH$_3$), 1.48 (m, 1H, CH$_2$CH$_3$), 0.96 (t, 3H, J=7.4, CH$_3$), (R/S)4-Ethyl-1,2,3,4-tetrahydro-6-trifluoromethyl-8-pyridono [5,6-g]quinoline (Componud 445)

To a flame-dried 100-mL rb flask containing 7-amino-4-ethyl-1,2,3,4-tetrahydroquinoline (210 mg, 1.19 mmol), in ethanol (20 mL), at rt, was added ethyl-4,4,4-trifluoroacetoacetate (190 µL, 1.31 mmol, 1.1 equiv) followed by ZnCl$_2$ (244 mg, 1.79 mmol, 1.5 equiv). The reaction mixture was heated to reflux for 6 h, at which point all starting material had been consumed (by TLC analysis). The reaction mixture was cooled to rt, and the solvent removed under reduced pressure. Dichloromethane (20 mL) was added and the organic phase washed with sat'd NaHCO$_3$ (2×10 mL) and brine (1×10 mL), then dried (Na$_2$SO$_4$), and concentrated under reduced presure. This crude product was purified by flash chromatography (silica gel, CH$_2$Cl$_2$/MeOH, 15:1), affording 24.4 mg (7%) of the desired product as a yellow solid. Data for Compound 445: Rf 0.37, (CH$_2$Cl$_2$/MeOH, 9:1); $^1$H NMR (400 MHz, CD$_3$OD) 7.31 (s, 1H, 5-H), 6.47 (s, 1H, 7-H), 6.37 (s, 1H, 10-H), 3.34 (m, 2H, 2-H), 2.70 (m, 1H), 1.88 (m, 2H, 3-H), 1.62 (m, 2H, CH$_2$CH$_3$), 1.00 (t, 3H, J=7.5, CH$_3$).

EXAMPLE 346

(R/S-21,3u)-1,2,3,4-Tetrahydro-2,3,9-trimethyl-6-trifluoromethyl-8-pyridono[5,6-g]quinoline (Compound 446, structure 81A of Scheme LIII, where R$^1$=R$^4$=R$^6$=R$^8$=H, R$^{2-}$=methyl, R$^5$=trifluoromethyl)

To a solution of Compound 441 (3.5 mg, 0.012 mmol) and iodomethane (0.10 mL, 1.6 mmol) in THF (2.0 mL) was added NaH as a 60% in mineral oil (10 mg, 0.25 mmol) and the reaction was stirred at rt for 1 h, then, was quenched by water (10 mL). Extraction with EtOAc (2×15 mL) and chromatography (silica gel, EtOAc/hexane, 1/1) afforded 3.0 mg (81%) of Compound 446 as a yellowish solid. Data for Compound 446: $^1$H NMR (400 MHz, CDCl$_3$) 7.36 (s, 1H), 6.72 (s, 1H), 6.32 (s, 1H), 4.40 (s, 1H), 3.61 (s, 3H), 3.14 (m, 1H), 2.83 (dd, J=16.0, 4.4, 1H), 2.54 (dd, J=16.0, 11.0, 1H), 1.63 (m, 1H), 1.26 (d, J=6.3, 3H), 1.06 (d, J -6.6, 3H).

EXAMPLE 347

(R/S)-1,2,3,4-Tetrahdro-4-propyl-6-trifluoromethyl-8-pyridono[5,6-quinoline (Compound 447, structure 62A of Scheme XL VIII, where R$^{1-3}$=R$^6$=H, R$^4$=n-propyl, R$^5$-trifluoromethyl) 1-tert-Butyloxycarbonyl-1,2,3,4-tetrahydro-4-hydroxy-4-propylquinoline This compound was prepared from 1-tert-butyloxycarbamoyl-1,2,3,4-tetrahydro-4-quinolone (1.00 g, 4.00 mmol) in the manner previously described for 1-tert-butyloxycarbamoyl-4-ethyl-1,2,3,4-tetrahydro-4-hydroxyquinoline (EXAMPLE 345), affording 567 mg (48%) of the tertiary alcohol as a yellow oil (Rf 0.22, hexanes/EtOAc, 4:1). Data for 1-tert-butyloxycarbonyl-1,2,3,4-tetrahydro-4-hydroxy-4-propylquinoline: $^1$H NMR (400 MHz, CDCl$_3$) 7.67 (d, 1H, J=8.2, 8-H), 7.48 (dd, 1H, J=7.9, 1.7, 5-H), 7.20 (ddd, 1H, J=8.6, 8.6, 1.4, 6-H), 7.08 (ddd, 1H, J=7.6, 7.6, 1.1, 7-H), 4.03 (ddd, 1H, J=12.8, 7.1, 4.8, 2-H), 3.46 (ddd, 1H, J=13.0, 8.5, 4.4, 2-H), 2.11 (ddd, 1H, J=13.5, 8.5, 4.8, 3-H), 1.89 (ddd, 1H, J=13.6, 7.2, 4.4, 3-H), 1.78 (m, 2H, CH$_2$C$_2$H$_5$), 1.52 (s, 9H, C(CH$_3$)$_3$], 1.32 (m, 2H, CH$_2$CH$_3$), 0.90 (t, 3H, J=7.3, CH$_2$CH$_3$).

(R/S)-1,2,3,4-Tetrahydro-4-propylquinoline (structure 60A of Scheme XL VIII where R$^{1-3}$=H, R$^4$-n-propyl)

This compound was prepared from 1-tert-butyloxycarbonyl-1,2,3,4-tetrahydro-4-hydroxy-4-propylquinoline (550 mg, 1.89 mmol) in the manner previously described for 4-ethyl-1,2,3,4-tetrahydroquinoline (EXAMPLE 345), affording 229 mg (66%) of the desired tetrahydroquinoline as a yellow oil (Rf 0.10, hexanes/EtOAc, 2:1). Data for (R/S)-1,2,3,4-tetrahydro-4-propylquinoline: $^1$H NMR (400 MHz, CDCl$_3$) 7.07 (d, 1H, J=7.6, 5-H), 7.02 (ddd, 1H, J=7.9, 7.9, 1.1, 7-H), 6.77 (dd, 1H, J=7.5, 7.4, 6-H), 6.67 (d, 1H, J=7.9, 8H), 6.25 (br s, 1H, NH), 3.37 (ddd, 1H, J=11.5, 11.5, 3.5, 2-H), 3.30 (m, 1H, 2-H), 2.78 (dddd, 1H, J=10.0, 5.0, 5.0, 5.0, 4-H), 1.99 and 1.84 (2×m, 2×1H, 3-H), 1.68 (m, 1H, CH$_2$CH$_2$CH$_3$), 1.47 (m, 3H, CH$_2$CH$_2$CH$_3$), 0.95 (t, 3H, J=7.3, CH$_3$).

(R/S)-7-Amino-1,2,3,4-tetrahydro-4-propylquinoline (structure 61A of Scheme XL VIII, where R$^{1-3}$=H, R$^4$=n-propyl)

This compound was prepared from (R/S)-1,2,3,4-tetrahydro-4-propylquinoline (220 mg, 0.78 mmol) in the manner previously described for 7-amino-4-ethyl-1,2,3,4-tetrahydroquinoline (EXAMPLE 345), affording 114 mg (77%) of the product as a colorless oil (Rf 0.10, hexanes/EtOAc, 2:1). Data for (R/S)-7-amino-1,2,3,4-tetrahydro-4-propylquinoline: $^1$H NMR (400 MHz, CDCl$_3$) 6.80 (d, 1H, J=8.0, 5-H), 6.01 (dd, 1H, J=8.0, 2.3, 6-H), 5.83 (d, 1H, J=2.2, 8-H), 3.74 (br s, 1H, NH), 3.41 (br s, 2H, NH$_2$), 3.28 (ddd, 1H, J=11.0, 11.0, 3.3, 2-H), 3.19 (ddd, 1H, J=9.7, 4.7, 4.7, 2-H), 2.65 (dddd, 1H, J=5.1, 5.1 5.1, 5.1, 4-H), 1.89 (dddd, 1H, J=9.7, 9.7, 9.7, 4.5, 3-H), 1.73 (dddd, 1H, J=8.6, 8.6, 4.8 4.8, 3-H), 1.61 (m, 1H, CH$_2$CH$_2$CH$_3$), 1.40 (m, 3H, CH$_2$CH$_2$CH$_3$), 0.93 (t, 3H, J=7.0, CH$_3$).

(R/S)-1,2,3,4-Tetrahydro-4-0propyl-6-trifluoromethyl-8-pyridono[5,6-g]quinoline (Compound 447)

This compound was prepared from 7-amino-1,2,3,4-tetrahydro-4-propylquinoline (110 mg, 0.58 mmol) in the manner previously described for Compound 445 (EXAMPLE 345), affording 8.9 mg (5%) of the desired product as a yellow powder (Rf0.44, CH$_2$Cl$_2$/MeOH, 9:1). $^1$H NMR (400 MHz, CDCl$_3$) 7.34 (s, 1H, 5-H), 6.65 (s, 1H, 7-H), 6.40 (s, 1H, 10-H), 4.65 [br, s, 1H, (CH$_3$)$_2$CNH)], 3.42 (ddd, 1H, J=11.2, 11.2, 4.0, 2-H), 3.34 (ddd, 1H, J=7.9, 3.8, 3.8, 2-H), 2.82 (m, 1H, 4-H), 1.88 (m, 2H, 3-H), 1.52 (m, 4H, CH$_2$CH$_2$CH$_3$), 0.96 (t, 3H, J=7.1, CH$_3$).

EXAMPLE 348

(R/S)-3-Ethyl-1,2,3,4-tetrahydro-2,2-dimethyl-6-trifluoromethyl-8-pyridono[5,6-g]quinoline (Compound 448, structure 79A of Scheme LIII, where R$^1$=R$^5$=R$^7$=H, R$^{2-3}$=methyl, R$^4$=ethyl, R$^6$=trifluoromethyl)

(R/S)-3-Ethyl-1,2,3,4-tetrahdro-2,2-dimethylquinoline (structure 77A of Scheme LIII, where R$^1$=R$^5$=H, R$^{2-3}$= methyl, R$^4$=ethyl To a solution of 1-tert-butoxycarbonyl-1,2,3,4-tetrahydro-2,2-dimethyl-4-quinolinone (EXAMPLE 325) (0.10 g, 0.36 mmol) and iodoethane (0.50 mL, 6.3 mmol) in DMF (5 mL) was added NaH (60% in mineral oil, 40 mg, 1.0 mmol) and the resulting mixture was stirred at rt for 15 h. The reaction was quenched with water (5 mL) and was extracted with EtOAc (2×15 mL). Removal of solvent and chromatography of the crude residue on a silica gel column using a 10% mixture of EtOAc and hexane as solvents afforded a mixture of products, which was treated with TFA (0.50 mL) in methylene chloride (1.0 mL) for 3 h. The reaction was neutralized to pH 10 by 5% NaOH and was extracted with EtOAc (2×20 mL). Chromatography (silica gel, EtOAc/hexane, 3/7) afforded 30 mg (41%) of (R/S)-3-ethyl-1,2,3,4-tetrahydro-2,2-dimethyl-4-quinolinone (30 mg, 0.15 mmol) as a colorless oil. The quinolinone (30 mg, 0.15 mmol) was treated with Et$_3$SiH (1.0 mL) and BF$_3$-OEt$_2$ (0.05 mL, 0.4 mmol) in CH$_2$Cl$_2$ (1.0 mL) at 100° C. for 15 h in a sealed tube. Purification of the crude product by chromatography (silica gel, EtOAc/hexane, 1/9) afforded 20 mg (71%) of (R/S)-3-ethyl-1,2,3,4-tetrahydro-2,2-dimethylquinoline. Data for (R/S)-3-ethyl-1,2,3,4-tetrahydro-2,2-dimethylquinoline: $^1$H NMR (400 MHz, CDCl$_3$) 6.98 (d, J=7.5, 1H), 6.96 (t, J=7.5, 1H), 6.61 (t, J=7.5, 1H), 6.44(d, J=7.5, 1H), 3.60 (s, 1H), 2.90 (dd, J=16.7, 5.2, 1H), 2.41 (dd, J=16.7, 10.7, 1H), 1.68 (m, 1H), 1.52 (m, 1H), 1.23 (m, 1H), 1.22 (s, 3H), 1.05 (s, 3H).

(R/S)-3-Ethyl-1,2,3,4-tetrahydro-2,2-dimethyl-6-trifluoromethyl-8-pyridono[5,6-g]quinoline (Compound 448)

The quinoline prepared above (20 mg) was converted to Compound 448 according to the nitration-hydrogenation-Knorr procedure described for Compound 436 (EXAMPLE 336) to afford 2.0 mg(13%) of Compound 448 as a yellow solid. Data for Compound 448: $^1$H NMR (400 MHz, acetone-$d_6$) 10.65 (s, 1H), 7.31 (s, 1H), 6.47 (s, 1H), 6.41 (s, 1H), 6.06 (s, 1H), 3.01 (dd, J=16.6, 4.8, 1H), 2.53 (dd, J=16.6, 11.0, 1H), 1.72 (m, 1H), 1.53 (m, 1H), 1.30 (s, 1H), 1.12 (s, 3H), 1.10–1.00 (m, 4H).

EXAMPLE 349

(R/S)-1,2,3,4-Tetrahydro-2,2-dimethyl-6-trifluoromethyl-3-propyl-8-pyridono[5,6-g]quinoline (Compound 449, structure 79A of Scheme LIII, where $R^1=R^5=R^7=H$, $R^{2-3}=$methyl, $R^4$=n-propyl, $R^6$=trifluoromethyl))

(R/S)-1,2,3,4-Tetrahydro-2,2-dimethyl-4-propylquinoline (structure 77A of Scheme LIII, where $R^1=R^5=H$, $R^{2-3}=$methyl, $R^4$=n-propyl)

This compound was prepared in a manner similar to that described for (R/S)-3-ethyl-1,2,3,4-tetrahydro-2,2-dimethylquinoline (EXAMPLE 348) but using iodopropane in place of iodoethane. (R/S)-1,2,3,4-Tetrahydro-2,2-dimethyl-4-propylquinoline was obtained in 16% overall yield as a colorless oil. Data for (R/S)-1,2,3,4-tetrahydro-2,2-dimethyl-4-propylquinoline: $^1$H NMR (400 MHz, CDCl$_3$) 6.98 (d, J=7.4, 1H), 6.96 (t, J=7.4, 1H), 6.61 (t, J=7.4, 1H), 6.45 (d, J=7.4, 1H), 3.60 (brs, 1H), 2.87 (dd, J=16.6, 5.2, 1H), 2.42 (dd, J=16.6, 10.7, 1H), 1.66–1.49 (m, 3H), 1.40–1.25 (m, 2H), 1.21 (s, 3H), 1.05 (s, 3H), 0.92 (t, J=7.1, 3H).

(R/S)-1,2,3,4-Tetrahydro-2,2-dimethyl-6-trifluoromethyl-3-propyl-8-pyridono[5,6-g]quinoline (Compound 449)

Compound 449 was prepared in manner similar to that described for Compound 448 (EXAMPLE 348), to afford Compound 449 in a 32% overall yield. Data for Compound 449: $^1$H NMR (400 MHz, CDCl$_3$) 11.00 (s, 1H), 7.32 (s, 1H), 6.61 (s, 1H), 6.42 (s, 1H), 4.60 (brs, 1H), 2.90 (dd, J=16.6, 4.4, 1H), 2.45 (dd, J=16.6, 11.3, 1H), 1.70–1.42 (m, 3H), 1.36–1.24 (m, 2H), 1.18 (s, 3H), 1.02 (s, 3H), 0.93 (t, J=6.7, 3H).

EXAMPLE 350

1-Methyl-5-trifluoromethyl-7-pyridono[5,6-f]indoline (Compound 450, structure 83A of Scheme LV, where $R^{1-3}=R^5=H$, $R^4$=trifluoromethyl, $R^6$=methyl)

Compound 419 (10 mg, 0.0393 mmol) and paraformaldehyde (11 mg, 0.0393 mmol) were dissolved in glacial acetic acid (2.5 mL) and stirred for 10 min at rt. NaBH$_3$CN (13 mg, 0.197 mmol) was added in one portion and allowed to stir at rt for 15 h. The reaction mixture was poured over ice and made basic with 10% NaOH. The aqueous layer was extracted with EtOAc (3×50 mL), dried (Na$_2$SO$_4$), filtered, and concentrated. The crude material was dissolved in 5% MeOH/CHCl$_3$ (0.5 mL) and loaded onto a 1000 μm reverse phase TLC plate (Whatman PLKC18F Silica Gel 150 Å). The plate was eluted with 80% MeOH/H$_2$O to afford 5.8 mg (55%) of Compound 450 as a light yellow solid. Data for Compound 450: $^1$H NMR (400 MHz, acetone-$d_6$) 7.29 (d, J=1.6, 1H), 6.54 (s, 1H), 6.10 (s, 1H), 3.50 (t, J=8.1, 2H), 3.01 (t, J=8.0, 2H), 2.83 (s, 3H).

EXAMPLE 351

6-(5-Cyano-2-thienyl)-1,2-dihydro-2,2,4-trimethylquinoline (Compound 451, structure 4 of Scheme II, where $R^1$=5-cyano-2-thienyl)

To a solution of 1-tert-butyloxycarbonyl-6-(5-formyl-2-thienyl)-1,2-dihydro-2,2,4-trimethylquinoline (12 mg, 0.03 mmol) in acetonitrile/water (10 ml/0.5 ml) was added hydroxylamine-O-sulphonic acid (5 mg, 0.04 mmol). The reaction mixture was heated to 65° C. for 1 h. The reaction was quenched with 10% NaOH (5 mL) and extracted with EtOAc (10 mL). The organic layer was washed with water and brine (3×5 mL each), dried (Na$_2$SO$_4$), and concentrated in vacuo to afford the crude product as a yellow oil. The crude product was purified by prep. TLC (20×20 cm, 250 μm, 25% EtOAc:hexane) to afford 5 mg (40%) of 1-tert-butyloxycarbonyl-6-(5-cyano-2-thienyl)-1,2-dihydro-2,2,4-trimethylquinoline as a yellow oil. This product was dissolved in CH$_2$Cl$_2$ (5 mL) and treated with TFA (0.1 ml) at rt with stirring. After 2 h, the reaction was quenched with 10% NaOH (5 mL). The organic layer was washed with water and brine (3×5 mL each), dried (Na$_2$SO$_4$) and concentrated in vacuo to afford the crude product as a yellow oil. The crude product was purified by prep. TLC (20×20 cm, 250 μm, 25% EtOAc:hexane) to afford 2 mg (60%) of Compound 451 as a yellow oil. Data for Compound 451: Rf 0.3 (silica gel, 25% EtOAc:Hex); $^1$H NMR(400 MHz, CDCl$_3$) 7.52 (d, J=4.0, 1H), 7.23 (s, 1H), 7.22 (d, J=7.4, 1H), 7.07 (d, J=4.0, 1H), 6.43 (d, J=7.4, 1H), 5.38 (s, 1H), 2.02 (s, 3H), 1.31 (s, 6H).

EXAMPLE 352

6-(5-Cyano-3-thienyl-1,2-dihydro-2,2,4-trimethylquinoline (Compound 452, structure 4 of Scheme II, where $R^1$=5-cyano-3-thienyl)

4-Bromo-2-cyanothiophene

To a solution of 4-bromo-2-thiophenecarboxaldehyde (1.0 g, 5.2 mmol, Aldrich) in acetonitrile/water (20 mL/2 mL) was added hyroxylamine-O-sulfonic acid (2.4 g, 21.2 mmol, Aldrich). The dark solution was heated to 65° C. with stirring. After 8 h, the reaction was quenched with 10% NaOH (10 mL). The solution was extracted with EtOAc (30 mL). The organic layer was washed with water and brine (3×10 mL each), dried (Na$_2$SO$_4$), and concentrated in vacuo to afford the crude product as a tan solid. The crude product was purified by silica flash chromatography (5–25% EtOAc:hexane) to afford 0.50 g (51%) of 4-bromo-2-cyanothiophene as a white solid. Data for 4-bromo-2-cyanothiophene: Rf 0.49 (silica, 25% EtOAc:hex.); $^1$H NMR(400 MHz, CDCl$_3$) 7.54 (s, 1H), 7.50 (s, 1H).

6-(5-Cyano-3-thienyl)-1,2-dihydro-2,2,4-trimethylquinoline (Compound 452)

This compound was prepared by General Method 2 from compound 9 (200 mg, 0.63 mmol) and 4-bromo-2-cyanothiophene (0.50 g, 2.65 mmol). The crude product was purified by prep. TLC (20×20 cm, 1000 μm, 25% ETOAc:Hexane) to afford 160 mg (91%) of Compound 452 as a yellow oil. Data for Compound 452: Rf0.50 (silica gel, 25% EtOAc:hex); $^1$H NMR (400 MHz, CDCl$_3$) 7.79 (s, 1H), 7.46 (s, 1H), 7.20 (s, 1H), 7.16 (d, J=8.3, 1H), 6.46 (d, J=8.3, 1H), 5.37 (s, 1H), 2.03 (s, 3H), 1.31 (s, 6H); IR(film, NaCl) 1159, 1381, 1402, 1449, 1476, 1499, 1609, 1653, 2216, 2915, 3294, 3584.

EXAMPLE 353

6-(3-Formylphenyl)-1,2-dihydro-2,2,4-trimethylquinoline (Compound 453, structure 4 of Scheme II, where $R^1$=3-formylphenyl)

This compound was prepared by General Method 2 from Compound 9 (50 mg, 0.158 mmol) and 2-(3-bromophenyl)-1,3-dioxolane (171 mg, 0.788 mmol). Purification by flash chromatography on silica gel (20 g) using 5% EtOAc:hexanes afforded 21 mg (48%) of Compound 453 as a yellow oil. Data for Compound 453: $^1$H NMR (400 MHz, acetone-$d_6$) 10.09 (s, 1H), 8.11 (d, J=1.4, 1H), 7.90 (d, J=7.2, 1H), 7.77 (d, J=7.5, 1H), 7.59 (t, J=7.6, 1H), 7.40 (d, J=2.2, 1H), 7.33 (dd, J=8.4, 2.2, 1H), 6.61 (d, J=8.2, 1H), 5.40 (s, 1H), 5.38 (bs, 1H), 1.29 (s, 9H).

EXAMPLE 354

1,2-Dihydro-2,2,4-trimethyl-6-[3-(methylsulfonyl)phenyl] quinoline (Compound 454, structure 4 of Scheme II, where $R^1$=3-(methylsulfonyl)phenyl)

3-Bromophenyl(methyl)sulfone

In a 50 mL r.b flask, m-CPBA (623 mg, 2.166 mmol, 60%) was suspended in $CH_2Cl_2$ (20 mL) and cooled to –20° C. 3-Bromothioanisole (200 mg, 0.985 mmol) in $CH_2Cl_2$ (1 mL) was added to the slurry and allowed to warm to rt for 2 h. The reaction was quenched with $H_2O$ and the aqueous layer was extracted with $CH_2C_2$ (3×50 mL). The combined organics were washed with brine (25 mL), dried ($Na_2SO_4$), filtered, and concentrated onto Celite™. The material was purified by flash chromatography on silica gel (40 g) using 30% EtOAc/hexanes as eluent to afford 229 mg (99%) of the sulfone as a tan solid. Data for 3-bromophenyl(methyl) sulfone: $^1$H NMR (400 MHz, $CDCl_3$) 8.10 (t, J=1.6, 1H), 7.88 (d, J=7.9, 1H), 7.79 (d, J=8.0, 1H), 7.46 (t, J=7.9, 1H), 3.07 (s, 3H).

1,2-Dihydro-2,2,4-trimethyl6-[3-(methylsulfonyl)phenyl] quinoline (Compound 454)

This compound was prepared by a modification of General Method 2 as follows. A flask was charged with Compound 9 (123 mg, 0.388 mmol), the sulfone (83 mg, 0.353 mmol), $Pd(OAc)_2$ (4 mg, 0.018 mmol), triphenylphosphine (18.5 mg, 0.071 mmol), and $K_3PO_4$ (112.4 mg, 0.530 mmol). The flask was flushed with $N_2$ for 5 min and then 5 mL of DMF (anhydrous) was added. The resulting reaction mixture was heated to 100° C. for 15 h. The reaction was allowed to cool to rt and was quenched with $H_2O$ (20 mL). The aqueous layer was extracted with EtOAc (3×100 mL). The combined organics were washed with $H_2O$ (3×50 mL) and brine (30 mL), dried ($Na_2SO_4$), filtered and concentrated. The resulting material was dissolved in dimethylsulfide (0.5 mL), and cooled to 0° C. This solution was treated with trifluoroacetic acid (0.5 mL) and allowed to stir at 0° C. for 1 h. The reaction was quenched with $H_2O$ (2 mL) followed by a slow addition of $NaHCO_3$ (sat) until neutralized. The aqueous was extracted with EtOAc (2×30 mL). The combined organics were washed with brine (10 mL), dried ($Na_2SO_4$), filtered and concentrated onto Celite™. The material was purified by flash chromatography on silica gel (30 g) using 25% EtOAc/hexanes as eluent to give 15 mg (12% overall) of Compound 454 as a light yellow film. Data for Compound 454: $^1$H NMR (400 MHz, acetone-$d_6$) 8.08 (t, J=1.8, 1H), 7.91 (dd, J=6.7, 1.5, 1H), 7.78 (dd, J=6.5, 1.6, 1H), 7.64 (t, J=7.8, 1H), 7.39 (d, J=2.1, 1H), 7.33 (dd, J=8.1, 2.0, 1H), 6.61 (d, J=8.1, 1H), 5.43 (bs, 1H), 5.41 (s, 1H), 3.16 (s, 3H), 2.09 (s, 3H), 1.3 (s, 6H).

EXAMPLE 355

(R/S)-6-(3-Cyano-5-fluorophenyl)-1,2,3,4-Tetrahydro-2,2, 4-trimethylquinoline (Compound 455, structure 5 of Scheme I, where $R^1$=3-cyano-5-fluorophenyl)

A 25 mL r.b. flask was charged with Compound 271 (EXAMPLE 171) (145.0 mg, 0.50 mmol), ethyl acetate (1 mL) and 10% Pd/C (10 mg). The flask was fitted with a septum and the system was flushed with nitrogen. A balloon filled with hydrogen gas was inserted into the reaction flask and the reaction was allowed to progress at rt for 2 h. The crude reaction mixture was filtered through a plug of Celite™. The crude mixture was purified by reverse phase semi-preparatory HPLC (70% methanol/water-with trace triethyl amine; retention time 29 min.) yielding 50.0 mg (34%) of Compound 455. Data for Compound 455: $^1$H NMR (400 MHz, acetone-$d_6$) 7.81 (dt, J=2.9, 1.5, 1H), 7.65 (ddt, J=8.9, 3.7, 2.3, 1H), 7.55 (s, 1H), 7.37 (dd, J=9.7, 1.1, 1H), 7.32 (dd, J=8.6, 1.2, 1H), 6.59 (d, J=8.4, 1H), 5.25 (br s, 1H), 2.95 (m, 1H), 1.80 (ddd, J=8.0, 5.4, 1.5, 1H), 1.40 (m, 4H), 1.25 (s, 3H), 1.19 (s, 3H).

EXAMPLE 356

(R/S)-9-Chloro-1,2-dihydro-2,2,4-trimethyl-5-phenyl-5H-chromeno[3,4-f]quinoline (Compound 456, structure 42 of Scheme XI where R=phenyl $R^1$=H, $R^2$=Cl)

This compound was prepared by General Method 5 (Example 60) from Compound 209 (75 mg, 0.230 mmol) and phenyl magnesium bromide (1.84 mL, 1.84 mmol) to afford 61 mg (68%) of Compound 456 as a clear film. Data for Compound 456: $^1$H NMR (400 MHz, acetone-$d_6$) 7.58 (d, J=2.3, 1H), 7.56 (s, 1H), 7.22 (m, 4H), 7.19 (m, 1H), 6.94 (dd, J=8.5, 2.5, 2H), 6.83 (d, J=8.5, 1H), 6.76 (d, J=8.5, 1H), 5.63 (br s, 1H), 5.46 (d, J=8.5, 1H), 1.98 (s, 3H), 1.26 (s, 3H), 1.24 (s, 3H).

EXAMPLE 357

(R/S)-5-Butyl-1,2-dihydro-2,2,4,9-tetramethyl-5H-chromeno[3,4-f]quinoline (Compound 457, structure 42of Scheme XI where R=n-butyl, $R^1$=H, $R^2$=methyl)

This compound was prepared by General Method 5 (EXAMPLE 60) from Compound 316 (EXAMPLE 216) (44 mg, 0.14 mmol) and n-BuLi (2.5M in hexanes, 0.30 mL, 0.75 mmol, 5.2 equivuiv) to afford 12 mg (24%) of Compound 457 as a pale yellow glass. Data for Compound 457: $^1$H NMR (400 MHz, acetone-$d_6$): 7.48 (s, 1H), 7.45 (d, J=8.2, 1H), 6.91 (d, J=6.6, 1H), 6.76 (d, J=8.0, 1H), 6.67 (d, J=8.2, 1H), 5.80 (dd, J=7.9, 3.3, 1H), 5.51 (s, 1H), 5.36 (br s, 1H), 2.81 (s, 3H), 2.78 (s, 3H), 1.75 (m, 1H), 1.55–1.35 (m, 3H), 1.30–1.20 (m, 2H), 1.27 (s, 3H), 1.18 (s, 3H), 0.84 (t, J=7.3, 3H).

Steroid Receptor Activity

Utilizing the "cis-trans" or "co-transfection" assay described by Evans et al., Science, 240:889–95 (May 13, 1988), the disclosure of which is herein incorporated by reference, the compounds of the present invention were tested and found to have strong, specific activity as both agonists, partial agonists and antagonists of PR, AR, ER, GR and MR. This assay is described in further detail in U.S. Pat. Nos. 4,981,784 and 5,071,773, the disclosures of which are incorporated herein by reference.

The co-transfection assay provides a method for identifying functional agonists and partial agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., progesterone for PR) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of selected steroid receptor modulator compounds of the present invention were evaluated utilizing the co-transfection assay, and in standard IR binding assays, according to the following illustrative Examples.

EXAMPLE 358

Co-transfection assay

CV-1 cells (African green monkey kidney fribroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine PR agonist and antagonist activity of the compounds of the present invention, the CV-1 cells were transiently transfected by calcium phosphate coprecipitation according to the procedure of Berger et al., 41 *J. Steroid Biochem. Mol. Biol.*, 733 (1992) with the following plasmids: pSVhPR-B (5 ng/well), MTV-LUC reporter (100 ng/well), pRS-β-Gal (50 ng/well) and filler DNA (pGEM; 45 ng/well). The receptor plasmid, pSVhPR-B, contains the human PR-B under constitutive control of the SV-40 promoter, and is more fully described in E. Vegeto et al., "The mechanism of RU 486 antagonism is dependent on the conformation of the carboxy-terminal tail of the human progesterone receptor", 69 *Cell*, 703 (1992), the disclosure of which is herein incorporated by reference. Similarly, the AR, ER, GR and MR agonist and antagonist activity of the compounds of the present invention were determined according to the same procedure described herein, except that the plasmids pRShAR, pRShER, pRShGR and pRShMR were substituted for the plasmid pSVhPR-B described above. Each of these plasmids are more fully described in J. A. Simental et al., "Transcriptional activation and nuclear targeting signals of the human androgen receptor", 266 *J. Biol. Chem.*, 510 (1991) (pRShAR), M. T. Tzukerman et al., "Human estrogen receptor transactivational capacity is determined by both cellular and promoter context and mediated by two functionally distinct intramolecular regions", 8 *Mol. Endocrinol*, 21 (1994) (pRShER), V. Giguere et al., "Functional domains of the human glucocorticoid receptor", 46 *Cell*, 645 (1986) (pRShGR), and J. L. Arriza et al., "Cloning of human mineralocorticoid receptor complementary DNA: structural and functional kinship with glucocorticoid receptor", 237 *Science*, 268 (1987) (pRShMR), the disclosures of which are herein incorporated by reference.

The reporter plasmid, MTV-LUC, contains the cDNA for firefly luciferase (LUC) under control of the mouse mammary tumor virus (MTV) long terminal repeat, a conditional promoter containing a progesterone response element. This plasmid is more fully described in Berger et al. supra. In addition, for ER agonist and antagonist determinations, the reporter plasmid MTV-ERE5-LUC, which contains LUC under control of the mouse mammary tumor virus (MTV) long terminal repeat in which the glucocorticoid response elements have been deleted and replaced with five copies of a 33-base pair ERE as described in Tzukerman et al., supra, was substituted for the MTV-LUC plasmid described herein. pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11 beta,17 beta)-11-[4-(dimethylamino)phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl]pronanamide; Schering-Plough) as an AR antagonist; estradiol (Sigma) as an ER agonist and ICI 164,384 (N-butyl-3,17-dihydroxy-N-methyl-(7-alpha,17-beta)-estra-1,3,5 (10)-triene-7-undecanamide; ICI Americas) as an ER antagonist; dexamethasone (Sigma) as a GR agonist and RU486 as a GR antagonist; and aldosterone (Sigma) as a MR agonist and spirolactone ((7-alpha-[acetylthio]-17-alpha-hydroxy-3-oxopregn-4-ene-21-carboxylic acid gamma-lactone; Sigma) as an MR antagonist) and/or the modulator compounds of the present invention in concentrations ranging from $10^{-12}$ to $10^{-5}$M were added to the cells. Three to four replicates were used for each sample. Transfections and subsequivuent procedures were performed on a Biomek 1000 automated laboratory work station.

After 40 hours, the cells were washed with PBS, lysed with a Triton X-100-based buffer and assayed for LUC and B-Gal activities using a luminometer or spectrophotometer, respectively. For each replicate, the normalized response (NR) was calculated as:

LUC response/β-Gal rate where

β-Gal rate=β-Gal·1×$10^{-5}$/β-Gal incubation time.

The mean and standard error of the mean (SEM) of the NR were calculated. Data was plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of progesterone as a PR agonist, DHT as an AR agonist, estradiol as an ER agonist, dexamethasone as a GR agonist, or aldosterone as an MR agonist at the $EC_{50}$ concentration. The concentration of test compound that inhibited 50% of LUC expression induced by the reference agonist was quantified ($IC_{50}$). In addition, the efficacy of antagonists was determined as a function (%) of maximal inhibition.

IR Binding assay

PR and GR Binding

In addition, the binding of the compounds of the present invention to the steroid receptors was also investigated according to the following methodology for PR and GR. PR and GR proteins were prepared from Baculovirus extracts by incorporating the appropriate cDNAs for human progesterone receptor A form (PR-A; P. Kastner et al., 9 EMBO, 1603 (1990), the disclosure of which is herein incorporated by reference) and human glucocorticoid receptor alpha (GRα) into appropriate baculovirus the expression plasmids as described in E. A. Allegretto et al., 268 J. Biol. Chem., 26625 (1993); G. Srinivasan and B. Thompson, 4 Mol. Endo., 209 (1990); and D. R. O'Reilly et al., In, "Baculovirus Expression Vectors", D. R. O'Reilly et al., eds., W. H. Freeman, New York, N.Y., pp. 139–179 (1992), the disclosures of which are herein incorporated by reference. Assay buffers consisted of the following: PR, 10% glycerol, 10 mM Tris, 1 mM EDTA, 12 mM monothioglycerol (MTG) and 1 mM PMSF, pH=7.5 @ 4° C.; GR, 10% glycerol, 25 mM sodium phosphate, 10 mM KF, 2 mM DTT, 0.25 mM CHAPS, and 20 mM sodium molybdate, pH=7.5.

The PR and GR steroid receptor binding assays were performed in the same manner. The final assay volume was 500 μL for PR and 250 μL for GR, and contained ~5 μg of extract protein for PR and ~50 mg for GR, as well as 2–4 nM of the appropriate [$^3$H] steroid (e.g. [$^3$H] progesterone and [$^3$H] dexamethasone, respectively) and varying concentrations of competing ligand at concentrations that ranged from $0-10^{-5}$ M. Incubations were carried out at 4° C. for 16 hours.

Non-specific binding was defined as that binding remaining in the presence of 500 nM of the appropriate unlabelled steroid. At the end of the incubation period, bound from free ligand were separated by either charcoal (PR) or hydroxylapatite (GR). The amount of bound tritiated hormone was determined by liquid scintillation counting of an aliquot (700 mL) of the supernatant fluid or the hydroxylapatite pellet.

AR Binding

For the whole cell binding assay, COS-1 cells in 96-well microtiter plates containing DMEM-10% FBS were transfected as described above with the following plasmid DNA: pRShAR (2 ng/well), pRS-β-Gal (50 ng/well) and pGEM (48 ng/well). Six hours after transfection, media was removed, the cells were washed with PBS and fresh media was added. The next day, the media was changed to DMEM-serum free to remove any endogenous ligand that might be complexed with the receptor in the cells.

After 24 hours in serum-free media, either a saturation analysis to determine the $K_d$ for tritiated dihydrotestosterone ($^3$H-DHT) on human AR or a competitive binding assay to evaluate the ability of test compounds to compete with $^3$H-DHT for AR was performed. For the saturation analysis, media (DMEM-0.2% CA-FBS) containing $^3$H-DHT (in concentrations ranging from 12 nM to 0.24 nM) in the absence (total binding) or presence (non-specific binding) of a 100-fold molar excess of unlabeled DHT were added to the cells. For the competitive binding assay, media containing 1 nM $^3$H-DHT and test compounds in concentrations ranging from $10^{-10}$ to $10^{-6}$M were added to the cells. Three replicates were used for each sample. After three hours at 37° C., an aliquot of the total binding media at each concentration of $^3$H-DHT was removed to estimate the amount of free $^3$H-DHT. The remaining media was removed, the cells were washed three times with PBS to remove unbound ligand, and cells were lysed with a Triton X-100-based buffer. The lysates were assayed for amount of bound $^3$H-DHT and β-Gal activity using a scintillation counter or spectrophotometer, respectively.

For the saturation analyses, the difference between the total binding and the nonspecific binding, normalized by the β-Gal rate, was defined as specific binding. The specific binding was evaluated by Scatchard analysis to determine the $K_d$ for $^3$H-DHT. See e.g. D. Rodbard, "Mathematics and statistics of ligand assays: an illustrated guide" In: J. Langon and J. J. Clapp, eds., Ligand Assay, Masson Publishing U.S.A., Inc., New York, pp. 45–99, (1981), the disclosure of which is herein incorporated by reference. For the competition studies, the data was plotted as the mount of $^3$H-DHT (% of control in the absence of test compound) remaining over the range of the dose-response curve for a given compound. The concentration of test compound that inhibited 50% of the amount of $^3$H-DHT bound in the absence of competing ligand was quantified ($IC_{50}$) after log-logit transformation. The $K_i$ values were determined by application of the Cheng-Prusoff equivuation to the $IC_{50}$ values, where:

$$K_i = \frac{IC_{50}}{(1 + [^3H-DHT])/K_d \text{ for } ^3H-DHT}$$

To date, binding assays have not been performed utilizing ER or MR proteins.

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prusoff equivuation to the $IC_{50}$ values, the labeled ligand concentration and the $K_d$ of the labeled ligand.

The agonist, antagonist and binding activity assay results of selected steroid receptor modulator compounds of present invention and the standard reference compounds on PR, AR, ER, GR and MR, as well as the cross-reactivity of selected compounds on all of these receptors, are shown in Tables 1–5 below. Efficacy is reported as the percent maximal response observed for each compound relative to the reference agonist and antagonist compounds indicated above. Also reported in Tables 1–5 for each compound is its antagonist potency or $IC_{50}$ (which is the concentration (nM), required to reduce the maximal response by 50%), its agonist potency or $EC_{50}$ (nM). PR, AR and GR protein binding activity ($K_i$ in nM) is shown in Tables 1–2 and 4.

TABLE 1

Agonist, antagonist and binding activity of selected steroid receptor modulator compounds of present invention and the reference agonist compound, Progesterone (Prog), and reference antagonist compound, mifepristone (RU486), on PR.

| Cmpd No. | PR Agonist CV-1 Cells | | PR Antagonist CV-1 Cells | | PR Binding |
|---|---|---|---|---|---|
| | Efficacy (%) | Potency (nM) | Efficacy (%) | Potency (nM) | $k_i$ (nM) |
| 103 | na | na | 91 | 780 | 372 |
| 104 | 39 | 2,750 | 71 | 120 | 82 |
| 109 | na | na | 87 | 138 | 23 |
| 116 | nt | nt | 85 | 549 | 38 |
| 117 | na | na | 68 | 462 | na |

TABLE 1-continued

Agonist, antagonist and binding activity of selected steroid receptor modulator compounds of present invention and the reference agonist compound, Progesterone (Prog), and reference antagonist compound, mifepristone (RU486), on PR.

| Cmpd No. | PR Agonist CV-1 Cells Efficacy (%) | PR Agonist CV-1 Cells Potency (nM) | PR Antagonist CV-1 Cells Efficacy (%) | PR Antagonist CV-1 Cells Potency (nM) | PR Binding $k_i$ (nM) |
|---|---|---|---|---|---|
| 124 | 74 | 1,600 | 36 | 10 | 4 |
| 126 | 124 | 2,400 | 58 | 145 | 11 |
| 132 | 22 | 6,400 | 76 | 80 | 31 |
| 150 | 24 | 3,200 | 91 | 24 | 17 |
| 152 | na | na | 82 | 130 | 53 |
| 161 | 47 | 203 | 75 | 209 | 3 |
| 163 | 77 | 15 | 45 | 3,617 | 1 |
| 191 | 26 | 9 | 74 | 150 | 1 |
| 195 | 89 | 13 | na | na | 3 |
| 210 | 72 | 16 | na | na | 3 |
| 220 | 147 | 33 | na | na | 1 |
| 221 | 105 | 117 | na | na | 4 |
| 228 | 114 | 40 | na | na | 3 |
| 271 | na | na | 78 | 32 | 10 |
| 286 | na | na | 84 | 155 | 61 |
| 291 | na | na | 79 | 46 | 4 |
| 310 | na | na | 70 | 260 | 7 |
| 313 | 26 | 300 | 94 | 140 | 87 |
| 328 | 86 | 2200 | 65 | 26 | 7 |
| 331 | na | na | 88 | 210 | 273 |
| 332 | 138 | 3 | na | na | 0.4 |
| 368 | 183 | 43 | na | na | 4 |
| 374 | 231 | 4 | na | na | 0.5 |
| 377 | 101 | 550 | na | na | 20 |
| 379 | na | na | 87 | 350 | 25 |
| 381 | 81 | 58 | na | na | 18 |
| 385 | 27 | 82 | 45 | 2300 | 31 |
| 389 | 133 | 17 | na | na | 4 |
| 391 | na | na | 65 | 120 | 187 |
| 400 | na | na | 68 | 370 | 14 |
| 401 | 43 | 600 | na | na | 150 |
| 452 | 119 | 2400 | 70 | 24 | 17 |
| 455 | na | na | 76 | 35 | 10 |
| Prog | 100 | 4 | na | na | 3 |
| RU486 | na | na | 96 | 0.1 | 0.8 | na = not active (i.e. efficacy of <20 and potency of >10,000)
nt = not tested

TABLE 2

Agonist, antagonist and binding activity of selected steroid receptor modulator compounds of present invention and the reference agonist compound, dihydrotestosterone (DHT), and reference antagonist compound, 2-hydroxyflutamide (Flut), on AR.

| Cmpd No. | AR Agonist CV-1 Cells Efficacy (%) | AR Agonist CV-1 Cells Potency (nM) | AR Antagonist CV-1 Cells Efficacy (%) | AR Antagonist CV-1 Cells Potency (nM) | AR Binding $K_i$ (nM) |
|---|---|---|---|---|---|
| 238* | 96 | 10 | na | na | 44 |
| 247 | 23 | 2,400 | 69 | 34 | 864 |
| 255 | na | na | 82 | 25 | 675 |
| 256 | na | na | 91 | 62 | 4,500 |
| 260 | na | na | 53 | 24 | 435 |
| 265 | na | na | 78 | 56 | 23 |
| 405 | na | na | 89 | 77 | 6 |
| 414 | 118 | 1 | na | na | 0.3 |
| 416 | 88 | 340 | 24 | 5009 | 388 |
| 417 | na | na | 74 | 21 | 23 |
| 418 | na | na | 63 | 200 | 1000 |
| 419 | 29 | 1800 | 74 | 46 | 60 |
| 420 | 40 | 2100 | 80 | 32 | 346 |
| 437 | na | na | 72 | 13 | 38 |

TABLE 2-continued

Agonist, antagonist and binding activity of selected steroid receptor modulator compounds of present invention and the reference agonist compound, dihydrotestosterone (DHT), and reference antagonist compound, 2-hydroxyflutamide (Flut), on AR.

| Cmpd No. | AR Agonist CV-1 Cells Efficacy (%) | AR Agonist CV-1 Cells Potency (nM) | AR Antagonist CV-1 Cells Efficacy (%) | AR Antagonist CV-1 Cells Potency (nM) | AR Binding $K_i$ (nM) |
|---|---|---|---|---|---|
| 445 | 74 | 7 | 32 | 8450 | 13 |
| DHT | 100 | 6 | na | na | 2 |
| Flut | na | na | 87 | 26 | 2085 | na = not active (i.e. efficacy of <20 and potency of >10,000)
*profiles as an AR antagonist in vivo

TABLE 3

Agonist, antagonist and binding activity of selected steroid receptor modulator compounds of present invention and the reference agonist compound, Estrogen (Estr), and reference antagonist compound, ICI 164,384 (ICI 164), on ER.

| Cmpd No. | ER Agonist CV-1 Cells Efficacy (%) | ER Agonist CV-1 Cells Potency (nM) | ER Antagonist CV-1 Cells Efficacy (%) | ER Antagonist CV-1 Cells Potency (nM) |
|---|---|---|---|---|
| 161 | nt | nt | 86 | 505 |
| 170 | nt | nt | 78 | 580 |
| 191 | nt | nt | 93 | 330 |
| 192 | na | na | 80 | 195 |
| 194 | nt | nt | 94 | 390 |
| 195 | 90 | 1900 | 68 | 4406 |
| Estr | 100 | 7 | na | na |
| ICI 164 | na | na | 99 | 43 | na = not active (i.e. efficacy of <20 and potency of >10,000)
nt = not tested

TABLE 4

Antagonist and binding activity of selected steroid receptor modulator compounds of present invention and the reference antagonist compounds, RU486 and Spironolactone (Spir), on GR and MR, respectively.

| Cmpd No. | GR Antagonist CV-1 Cells Efficacy (%) | GR Antagonist CV-1 Cells Potency (nM) | MR Antagonist CV-1 Cells Efficacy (%) | MR Antagonist CV-1 Cells Potency (nM) | GR Binding $K_i$ (nM) |
|---|---|---|---|---|---|
| 161 | 97 | 600 | 58 | 1000 | 137 |
| 167 | 96 | 855 | 61 | 2000 | 21 |
| 170 | 94 | 1550 | 84 | 410 | 47 |
| 192 | 81 | 280 | 70 | 320 | 214 |
| 195 | 96 | 590 | 47 | 1900 | 26 |
| RU486 | 100 | 1 | 77 | 1100 | 0.4 |
| Spir | 80 | 2000 | 96 | 25 | nt | nt - not tested

TABLE 5

Overall agonist and antagonist potency of selected steroid receptor modulator compounds of present invention and the reference agonist and antagonist compounds shown in Tables 1–4 on PR, AR, ER, GR and MR.

| Cmpd No. | PR Potency Agon (nM) | PR Potency An-tag (nM) | AR Potency Agon (nM) | AR Potency An-tag (nM) | ER Potency Agon (nM) | ER Potency An-tag (nM) | GR Potency Antag (nM) | MR Potency Antag (nM) |
|---|---|---|---|---|---|---|---|---|
| 124 | 1600 | 10 | nt | 1500 | 2100 | na | na | na |
| 150 | 3200 | 24 | nt | 140 | nt | na | 2700 | 1900 |
| 163 | 15 | 3617 | nt | 1550 | na | 2150 | 1330 | 1450 |
| 170 | 73 | 145 | nt | 290 | nt | 580 | 1550 | 410 |
| 191 | 9 | 150 | nt | 520 | nt | 330 | nt | nt |
| 192 | na | 89 | nt | 79 | nt | 195 | 280 | 320 |
| 195 | 13 | na | nt | 470 | 1900 | 4406 | 590 | 1900 |
| 255 | na | 3050 | na | 25 | na | na | na | na |
| 260 | na | 230 | na | 24 | nt | nt | nt | nt |
| Prog | 4 | na | 1300 | na | na | na | na | nt |
| RU486 | na | 0.1 | na | 12 | na | 1500 | 0.7 | 1100 |
| DHT | na | 1800 | 6 | na | 1700 | na | na | nt |
| Flut | na | 1900 | na | 26 | na | na | na | na |
| Estr | nt | nt | na | na | 7 | na | na | nt |
| ICI 164 | na | na | na | na | na | 160 | na | na |
| Spir | nt | 268 | nt | nt | na | na | 2000 | 25 | na = not active (i.e., efficacy of >20 and potency of >10,000)
nt = not tested

As can be seen in the Tables, Compounds 163, 191, 332 and 374 are highly selective PR agonists, while Compounds 124, 150, 328 and 455 are highly selective PR antagonists. Importantly, these PR antagonist Compounds show very little or no cross reactivity on GR, or any of the other tested steroid receptors. In contrast, the known PR antagonist, RU486, shows strong cross reactivity on both GR and AR, showing essentially equivual potency as both a PR and GR antagonist. Thus RU486 may not be generally useful for long-term, chronic administration due to this undesirable GR cross reactivity. Furthermore, Compounds 255, 260, 417 and 437 of the present invention shown equivual or better activity as AR antagonists than the known antagonist compound 2-OH-flutamide.

EXAMPLE 359

The effectiveness of selected compounds of the present invention as PR agonists was investigated in the well recognized uterine wet weight assay, as described in G. J. Marcus, "Mitosis in the rat uterus during the estrous cycle, early pregnancy and early pseudopregnancy", 10 Biol. Reprod., 447 (1974), S. Sakamoto et al., "Effects of estrogen and progesterone on thymidine kinase activity in the immature rat uterus", 145 Am. J. Obstet. Gynecol., 711 (1983), and C. W. Emmens and R. I. Dorfman, "Estrogens" (Ch. 2) and "Antiestrogens" (Ch. 3). in Methods in Hormone Research, ed. R. I. Dorfman, Academic Press, New York, N.Y., pp101–130 (1969), the disclosures of which are herein incorporated by reference. Four to five week old, ovariectomized, Sprague-Dawely rats (Harlan-Sprague-Dawely, Indianapolis, Ind.) were obtained 1 week after surgery and allowed to acclimate for an additional week after shipment. Compound 163, Compound 210, medroxyprogesterone acetate (MPA) (Sigma, St. Louis, Mo.) a synthetic progesterone agonist, and estrone (E1) (Sigma, St. Louis, Mo.) a synthetic estrogen agonist, were fully dissolved in purified sesame oil (Croda, Parsippany, N.J.). Animals were randomized into treatment groups (4 rats/group) and administered Compound 163, Compound 210, or MPA (0.3, 1.0 or 3.0 mg/rat, 0.5 mL volumes, oral, once a day for three days in the presence of estrone (10 µg/day, subcutaneous). Additional control groups of rats were administered estrone or vehicle (i.e. sesame oil) alone. Animals were sacrificed on the fourth day of the experiment. Upon necropsy, uterine wet weights were obtained, and are reported in Table 6 below.

TABLE 6

Mean uterine wet weights in presence of estrone (10 µg), MPA, a recognized PR agonist, and Compounds 163 and 210 of the present invention.

| Group | E1 (µg) | MPA (mg) | Cmpd 163 (mg) | Cmpd 210 (mg) | Mean Uterine Wet Weight (mg) |
|---|---|---|---|---|---|
| Control | none | none | none | none | 45 |
| 1 | 10 | none | none | none | 205 |
| 2 | 10 | 0.3 | none | none | 140 |
| 3 | 10 | 1.0 | none | none | 130 |
| 4 | 10 | 3.0 | none | none | 130 |
| 5 | 10 | none | 3.0 | none | 125 |
| 6 | 10 | none | none | 0.3 | 110 |
| 7 | 10 | none | none | 1.0 | 100 |
| 8 | 10 | none | none | 3.0 | 100 |

As can be seen in Table 6, estrone alone increased uterine wet weight 4-fold over control treated animals. MPA co-administered with estrone significantly decreased the uterine wet weight at doses of 0.3 mg, 1.0 mg, and 3.0 mg/rat. Compound 163 at a dosage of 3 mg/rat, decreased by approximately half, the mean uterine wet weight, as did Compound 210 at doses of 0.3 mg, 1.0 mg, and 3.0 mg/rat.

EXAMPLE 360

The activity of Compound 150 of the present invention as a PR antagonist was measured via an implantation assay, a recognized test of antiprogestin activity, as described in F. H. Bronson, et al., "Reproduction", In Biology of the Laboratory Mouse, 2nd ed., pp 187–204, McGraw Hill, New York, N.Y. (1966), the disclosure of which is herein incorporated by reference. Virgin female mice (ICR strain) were caged with fertile males of the same strain overnight and examined the next morning for vaginal plugs (Day 1 of pregnancy). Mating was assumed to have taken place at 02.00 h, time 0.

The animals were treated orally with a known amount of the antiprogestin, mifepristone (RU486) or Compound 150 daily between days 2 and 4 of pregnancy. Compound 150 was dissolved in sesame oil (50 mg/mL) and kept at room temperature before use. RU486 was first dissolved in 100% ethanol and diluted to a concentration of 10 mg/mL with sesame oil. Control animals received an equivuivalent volume of the control vehicle, sesame oil, alone.

The animals were sacrificed, and autopsies were carried out at Day 8 of pregnancy, and numbers of implantation sites counted and recorded, and are shown in Table 7 below. Each group consisted of between 5 and 7 animals.

TABLE 7

Percent pregnancy rate in mice in the presence of RU486 (mifepristone), a recognized PR antagonist, and Compound 150 of the present invention.

| Group | RU486 (mg/day) | Cmpd 150 (mg/day) | Percent Pregnancy Rate |
|---|---|---|---|
| Control | none | none | 100 |
| 1 | 1.0 | none | 0 |
| 2 | none | 2.5 | 50 |
| 3 | none | 5.0 | 0 |

As can be seen from Table 7, the control group of mice exhibited a pregnancy rate of one hundred. Administration of 1.0 mg/day of RU486 resulted in a pregnancy rate of zero, while administration of Compound 150 at 2.5 mg/day and 5.0 mg/day resulted in pregnancy rates of 50 and 0, respectively. In addition, the above noted effect on pregnancy rate of Compound 150 was reversed to the control level by the simultaneous injection of the known PR agonist Compound R5020 (promegestone; (17β)-17-methyl-17-(1-oxopropyl) estra-4,9-dien-3-one; New England Nuclear, Boston, Mass.) at a dose of 1.0 mg per day.

EXAMPLE 361

The activity of selected compounds of the present invention as AR antagonists was investigated in an immature castrated male rat model, a recognized test of the antiandrogen activity of a given compound, as described in L. G. Hershberger et al., 83 *Proc. Soc. Exptl. Biol. Med.*, 175 (1953); P. C. Walsh and R. F. Gittes, "Inhibition of extratesticular stimuli to prostatic growth in the castrated rat by anti androgens", 86 *Endocrinology*, 624 (1970); and B. J. Furr et al., "ICI 176,334: A novel non-steroidal, peripherally selective antiandrogen", 113 *J. Endocrinol.*, R7–9 (1987), the disclosures of which are herein incorporated by reference.

The basis of this assay is the fact that the male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone (DHT), within the prostate by 5α-reductase. Adrenal androgens also contribute about 20% of total DHT in the rat prostate, and about 40% of that in 65-year-old men. F. Labrie et al., 16 *Clin. Invest. Med.*, 475–492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostatic tissue. M. C. Luke and D. S. Coffey, "The Physiology of Reproduction" ed. by E. Knobil and J. D. Neill, 1, 1435–1487 (1994). Since the male sex organs are the tissues most responsive to modulation of androgen activity, this model is used to determine the androgen-dependent growth of the sex accessory organs in immature castrated rats.

Male immature rats (60–70 g, 23–25-day-old, Sprague-Dawley, Harlan) were castrated under metofane anesthesia. Five days after surgery, animals groups were dosed for 3 days as follows:

(1) control vehicle (2) Testosterone Propionate (TP)(0.1 mg/rat/day, sub cutaneous)

(3) TP plus flutamide, a recognized antiandrogen, as a reference compound, and/or a compound of the present invention (different doses, oral administration, daily) to demonstrate antagonist activity, or (4) a compound of the present invention alone (different doses, oral administration daily) to demonstrate agonist activity At the end of the 3-day treatment, the animals were sacrificed, and the ventral prostates (VP) and seminal vesicles (SV) were collected and weighed. To compare data from different experiments, the sexual organ weights were first standardized as mg per 100 g of body weight, and the increase in organ weight induced by TP was considered as the maximum increase (100%). Super-anova (one factor) was used for statistical analysis.

The gain and loss of sexual organ weights reflect the changes of cell number (DNA content) and cell mass (protein content), depending upon the serum androgen concentration. See Y. Okuda et al., 145 *J Urol.*, 188–191 (1991), the disclosure of which is herein incorporated by reference. Therefore, measurement of organ wet weights is sufficient to indicate the bioactivity of androgens and androgen antagonists. In immature castrated rats, replacement of exogenous androgens increased the weights of the ventral prostate (VP) and the seminal vesicles (SV) in a dose-dependent manner as shown in Table 8.

TABLE 8

TP-Induced Ventral Prostate and Seminal Vesicle Growth in castrated immature rats, with oral dosing once daily, for 3 days.

| Treatment (mg TP) | VP (wet wt) | % VP growth | SV (wet wt) | % SV growth |
|---|---|---|---|---|
| 0 | 10.5 ± 1.0 | 100 | 7.5 ± 0.6 | 100 |
| 0.01 | 15.4 ± 0.6 | 146.5 | 12.3 ± 0.8 | 165.1 |
| 0.03 | 23.5 ± 1.3 | 224.1 | 27.5 ± 0.8 | 369.5 |
| 0.1 | 35.3 ± 2.1 | 337.0 | 42.0 ± 2.0 | 563.8 |
| 0.3 | 43.6 ± 1.1 | 415.9 | 45.9 ± 1.9 | 616.1 |
| 1 | 44.8 ± 3.7 | 427.4 | 51.0 ± 5.4 | 684.6 |

The maximum increase in organ wet weights was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weights of VP and SV also correlated with the increase in the serum T and DHT concentrations. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

In this immature castrated rat model, a known AR antagonist (flutamide) was also administered simultaneously with 0.1 mg of TP ($ED_{80}$), inhibiting the testosterone-mediated increases in the weights of VP and SV in a dose-dependent manner as shown in Table 9. The antagonist effects were similar when dosing orally or subcutaneously. Compounds 255 and 261 also exhibited AR antagonist activity by suppressing the testosterone-mediated increases in the weights of the VP and SV, as summarized in Table 9.

TABLE 9

Inhibition of TP-Induced Ventral Prostate and Seminal Vesicle Growth in castrated immature rats at oral dosing, once daily, for 3 days of flutamide (flut), Compound 255 or Compound 261.

| Treatment | VP (wet wt) | VP wt (% of TP (0.1) control) | SV (wet wt) | SV wt (% of TP (0.1) control) |
|---|---|---|---|---|
| Control | 9.8 ± 1.2 | 36.2 | 9.9 ± 0.9 | 21.7 |
| TP (0.1) | 25.5 ± 1.2 | 100 | 33.6 ± 4.0 | 100 |
| TP + flut (1.0) | 12.4 ± 1.1 | 49.9 | 8.5 ± 0.6 | 30.3 |
| TP + flut (3.0) | 9.5 ± 0.4 | 37.4 | 9.8 ± 0.5 | 29.3 |
| TP + 255 (0.3) | 22.1 ± 0.7 | 86.4 | 29.8 ± 2.5 | 88.7 |
| TP + 255 (1.0) | 20.0 ± 4.5 | 78.2 | 24.8 ± 9.0 | 73.9 |
| TP + 255 (3.0) | 17.3 ± 1.2 | 67.7 | 20.4 ± 1.2 | 60.6 |
| TP + 261 (1.0) | 21.0 ± 1.7 | 84.4 | 23.8 ± 1.8 | 85.0 |
| TP + 261 (3.0) | 16.7 ± 1.0 | 67.1 | 20.8 ± 1.3 | 74.2 |

Pharmacological and Other Applications

As will be discernible to those skilled in the art, the non-steroid modulator compounds of the present invention can be readily utilized in pharmacological applications where PR, AR, ER, GR and/or MR antagonist or agonist activity is desired, and where it is desired to minimize cross reactivities with other steroid receptor related IRs. In vivo applications of the invention include administration of the disclosed compounds to mammalian subjects, and in particular to humans.

The following Example provides illustrative pharmaceutical composition formulations:

EXAMPLE 362

Hard gelatin capsules are prepared using the following ingredients:

|  | Quantity (mg/capsule) |
|---|---|
| COMPOUND 191 | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

|  | Quantity (mg/tablet) |
|---|---|
| COMPOUND 191 | 140 |
| Cellulose, microcrystalline | 200 |
| Silicon dioxide, fumed | 10 |
| Stearic acid | 10 |
| Total | 360 mg |

The components are blended and compressed to form tablets each weighing 665 mg.

Tablets, each containing 60 mg of active ingredient, are made as follows:

|  | Quantity (mg/tablet) |
|---|---|
| COMPOUND 191 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

Suppositories, each containing 225 mg of active ingredient, may be made as follows:

|  |  |
|---|---|
| COMPOUND 191 | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

|  |  |
|---|---|
| COMPOUND 191 | 100 mg |
| Isotonic saline | 1,000 mL |
| Glycerol | 100 mL |

The compound is dissolved in the glycerol and then the solution is slowly diluted with isotonic saline. The solution of the above ingredients is then administered intravenously at a rate of 1 mL per minute to a patient.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A compound of the formula:

(III)

wherein:

$R^2$ is hydrogen, a $C_1$–$C_4$ alkyl or perfluoroalkyl, aryl, heteroaryl or optionally substituted allyl, arylmethyl, alkynyl or alkenyl;

$R^3$ is hydrogen, a $C_1$–$C_4$ alkyl or perfluoroalkyl, hydroxymethyl, aryl, heteroaryl or optionally substituted allyl, arylmethyl, alkynyl or alkenyl;

$R^4$ is hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$ has the definition given above, $R^7$ is hydrogen, a $C_1$–$C_4$ alkyl or perfluoroalkyl, aryl, heteroaryl, optionally substituted allyl or arylmethyl, $OR^8$ or $NHR^8$, where $R^8$ is hydrogen, a $C_1$–$C_6$ alkyl or perfluoroalkyl, aryl, heteroaryl, optionally substituted allyl or arylmethyl, $SO_2R^2$ or $S(O)R^2$;

$R^9$ and $R^{10}$ each independently are hydrogen, a $C_1$–$C_6$ alkyl or perfluoroalkyl, aryl, heteroaryl or optionally substituted allyl, arylmethyl, alkynyl or alkenyl, or $R^9$ and $R^{10}$ taken together can form a three- to seven-membered ring optionally substituted with hydrogen, F, $OR^2$, or $NR^2R^7$, where $R^2$ and $R^7$ have the definitions given above;

$R^{11}$ through $R^{14}$ each independently are hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$, $R^7$ and $R^8$ have the definitions given above;

W is O, NH, $NR^7$, $CH_2$, CHOH, C=O, OC=O, O=CO, $NR^7$C=O, NHC=O, O=$CNR^7$, O=CNH, SC=O, O=CS, or CHOCOR$^7$, where $R^7$ has the definition given above, except that when W is NH, $CH_2$ or O in the compounds of formula III, then $R^{11}$ through $R^{14}$ and $R^4$ cannot all be hydrogen when $R^3$, $R^9$ and $R^{10}$ are all $CH_3$, nor can they be a single F, Cl or Br substituent with the remaining substituents all being hydrogen when $R^3$, $R^9$ and $R^{10}$ are all $CH_3$, nor can R3 through $R^4$ and $R^9$ through $R^{14}$ all be hydrogen, or all be hydrogen and a single methyl, when W=O; and the dotted lines in the structures depict optional double bonds.

2. A compound according to claim 1, wherein in a co-transfection assay the compound is a progesterone receptor agonist.

3. A compound according to claim 1, wherein in a co-transfection assay the compound is a progesterone receptor partial agonist.

4. A compound according to claim 1, wherein in a co-transfection assay the compound is a progesterone receptor antagonist.

5. A compound according to claim 1, wherein the compound is a progesterone receptor antagonist selected from the group consisting of 8-Bromo-1,2-dihydro-2,2,4-trimethylindeno[1,2-g]quinoline (Compound 117); 1,2-Dihydro-2,2,4-trimethylbenzo[b]furano[3,2,g]quinoline (Compound 118); 9-Fluoro-1,2-dihydro-2,2,4-trimethylindeno[1,2-g]quinoline (Compound 121); 1,2-Dihydro-9-hydroxylmethyl-2,2,4-trimethylindeno[1,2-g]quinoline (Compound 122); 8-Chloro-1,2-dihydro-2,2,4-trimethylindeno[1,2-g]quinoline (Compound 123); 8-Fluoro-1,2-dihydro-2,2,4-trimethylindeno[1,2-g]quinoline (Compound 124); 8-Acetyl-1,2-dihydro-2,2,4-trimethylindeno[1,2-g]quinoline (Compound 125); 6-Fluoro-1,2-dihydro-2,2,4-trimethylindeno[1,2-g]quinoline (Compound 126); 1,2-Dihydro-2,2,4-trimethyl-8-nitroindeno[1,2-g]quinoline (Compound 129); 6,9-Difluoro-1,2-dihydro-2,2,4-trimethylindeno[1,2-g]quinoline (Compound 130); 7,9-Difluoro-1,2-dihydro-10-hydroxy-2,2,4-trimethylindeno[1,2-g]quinoline (Compound 133); 7,9-Difluoro-1,2-dihydro-2,2,4-trimethyl-10-oxoindeno[1,2-g]quinoline (Compound 135); 8-Fluoro-1,2-dihydro-10-hydroxy-2,2,4-trimethylindeno[1,2-g]quinoline (Compound 136); 8-Fluoro-1,2-dihydro-2,2,4-trimethyl-10-oxoindeno[1,2-g]quinoline (Compound 137); 7-Fluoro-1,2-dihydro-2,2,4-trimethyl-8-nitroindeno[1,2-g]quinoline (Compound 138); 5-Chloro-1,2-dihydro-10-hydroxy-2,2,4-trimethylindeno[1,2-g]quinoline (Compound 139); 6-Fluoro-1,2-dihydro-2,2,4-trimethyl-10-oxoindeno[1,2-g]quinoline (Compound 140); 6-Fluoro-1,2-dihydro-10-hydroxy-2,2,4-trimethylindeno[1,2-g]quinoline (Compound 141); 5,8-Difluoro-1,2-dihydro-2,2,4-trimethyl-10-(trifluoroacetoxy)indeno[1,2-g]quinoline (Compound 142); 1,2-Dihydro-2,2,4-trimethylindolo[3,2-g]quinoline (Compound 144); 5,8-Difluoro-1,2-dihydro-2,2,4-trimethylindeno[1,2-g]quinoline (Compound 157); and 8-Cyano-1,2-dihydro-2,2,4-trimethylindeno[3,2-e]quinoline (Compound 270).

6. A pharmaceutical composition comprising a compound of claim 1 and a pharmaceutically acceptable carrier.

7. A pharmaceutical composition according to claim 6, wherein the composition is formulated for oral, topical, intravenous, suppository or parental administration.

8. A pharmaceutical composition according to claim 6, wherein the compound is administered to a patient as a dosage unit at from about 1 μg/kg of body weight to about 500 mg/kg of body weight.

9. A pharmaceutical composition according to claim 6, wherein the compound is administered to a patient as a dosage unit at from about 10 μg/kg of body weight to about 250 mg/kg of body weight.

10. A pharmaceutical composition according to claim 6, wherein the compound is administered to a patient as a dosage unit at from about 20 μg/kg of body weight to about 100 mg/kg of body weight.

11. A pharmaceutical composition according to claim 6, wherein the composition is effective in female hormone replacement, modulating human fertility, treating dysfunctional uterine bleeding, treating endometriosis, treating leiomyomas, treating osteoporosis, treating cancer of the breast, treating cancer of the ovaries or treating endometrial cancer.

12. A method of affecting progesterone receptor activity comprising the in vivo administration of a compound according to claim 1.

13. A method of modulating a process mediated by progesterone receptor comprising administering to a patient an effective amount of a compound according to claim 1.

14. A pharmaceutical composition which modulates progesterone receptor activity comprising an effective amount of a progesterone receptor modulating compound of the formula:

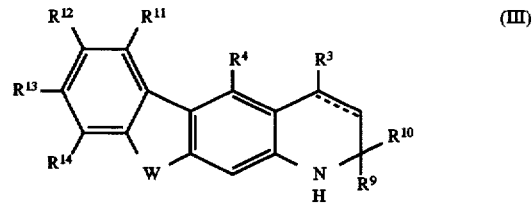

(III)

wherein:

$R^2$ is hydrogen, a $C_1$–$C_4$ alkyl or perfluoroalkyl, aryl, heteroaryl or optionally substituted allyl, arylmethyl, alkynyl or alkenyl;

$R^3$ is hydrogen, a $C_1$–$C_4$ alkyl or perfluoroalkyl, hydroxymethyl, aryl, heteroaryl or optionally substituted allyl, arylmethyl, alkynyl or alkenyl;

$R^4$ is hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalky, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$ has the definition given above, $R^7$ is hydrogen, a $C_1$–$C_4$ alkyl or perfluoroalkyl, aryl, heteroaryl, optionally substituted allyl or arylmethyl, $OR^8$ or $NHR^8$, where $R^8$ is hydrogen, a $C_1$–$C_6$ alkyl or perfluoroalkyl, aryl, heteroaryl, optionally substituted allyl or arylmethyl, $SO_2R^2$ or $S(O)R^2$;

$R^9$ and $R^{10}$ each independently are hydrogen, a $C_1$–$C_6$ alkyl or perfluoroalkyl, aryl, heteroaryl or optionally substituted allyl, arylmethyl, alkynyl or alkenyl, or $R^9$ and $R^{10}$ taken together can form a three- to seven-membered ring optionally substituted with hydrogen, F, $OR^2$, or $NR^2R^7$, where $R^2$ and $R^7$ have the definitions given above;

$R^{11}$ through $R^{14}$ each independently are hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$, $R^7$ and $R^8$ have the definitions given above;

W is O, NH, $NR^7$, $CH_2$, CHOH, C=O, OC=O, O=CO, $NR^7C$=O, NHC=O, O=$CNR^7$, O=CNH, SC=O, O=CS, or $CHOCOR^7$, where $R^7$ has the definition given above, except that when W is NH, $CH_2$ or O in the compounds of formula III, then $R^{11}$ through $R^{14}$ and $R^4$ cannot all be hydrogen when $R^3$, $R^9$ and $R^{10}$ are all $CH_3$, nor can they be a single F, Cl or Br substituent with the remaining substituents all being hydrogen when $R^3$, $R^9$ and $R^{10}$ are all $CH_3$, nor can R3 through $R^4$ and $R^9$ through $R^{14}$ all be hydrogen, or all be hydrogen and a single methyl, when W=O;

the dotted lines in the structures depict optional double bonds; and a pharmaceutically acceptable carrier.

15. A composition comprising an agonistically effective amount of a progesterone receptor agonist compound according to claim 14.

16. A composition comprising an partially agonistically effective amount of a progesterone receptor partial agonist compound according to claim 14.

17. A composition comprising an antagonistically effective amount of a progesterone receptor antagonist compound according to claim 14.

18. A composition according to claim 14, wherein the composition is formulated for oral, topical, intravenous, suppository or parental administration.

19. A composition according to claim 14, wherein the compound is administered to a patient as a dosage unit at from about 1 μg/kg of body weight to about 500 mg/kg of body weight.

20. A composition according to claim 14, wherein the compound is administered to a patient as a dosage unit at from about 10 μg/kg of body weight to about 250 mg/kg of body weight.

21. A composition according to claim 14, wherein the compound is administered to a patient as a dosage unit at from about 20 μg/kg of body weight to about 100 mg/kg of body weight.

22. A composition according to claim 14, wherein the composition is effective in female hormone replacement, modulating human fertility, treating dysfunctional uterine bleeding, treating endometriosis, treating leiomyomas, treating osteoporosis, treating cancer of the breast, treating cancer of the ovaries or treating endometrial cancer.

23. A method of treating a patient requiring progesterone receptor therapy comprising administering to a patient an effective amount of a progesterone receptor modulating compound having the formula:

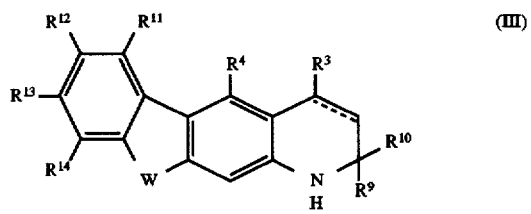

(III)

wherein:

$R^2$ is hydrogen, a $C_1$–$C_4$ alkyl or perfluoroalkyl, aryl, heteroaryl or optionally substituted allyl, arylmethyl, alkynyl or alkenyl;

$R^3$ is hydrogen, a $C_1$–$C_4$ alkyl or perfluoroalkyl, hydroxymethyl, aryl, heteroaryl or optionally substituted allyl, arylmethyl, alkynyl or alkenyl;

$R^4$ is hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$ has the definition given above, $R^7$ is hydrogen, a $C_1$–$C_4$ alkyl or perfluoroalkyl, aryl, heteroaryl, optionally substituted allyl or arylmethyl, $OR^8$ or $NHR^8$, where $R^8$ is hydrogen, a $C_1$–$C_6$ alkyl or perfluoroalkyl, aryl, heteroaryl or optionally substituted allyl, arylmethyl, $SO_2R^2$ or $S(O)R^2$;

$R^9$ and $R^{10}$ each independently are hydrogen, a $C_1$–$C_6$ alkyl or perfluoroalkyl, aryl, heteroaryl or optionally substituted allyl, arylmethyl, alkynyl or alkenyl, or $R^9$ and $R^{10}$ taken together can form a three- to seven-membered ring optionally substituted with hydrogen, F, $OR^2$, or $NR^2R^7$, where $R^2$ and $R^7$ have the definitions given above;

$R^{11}$ through $R^{14}$ each independently are hydrogen, F, Cl, Br, I, $NO_2$, $CO_2H$, $CO_2R^2$, $COR^2$, CN, $CF_3$, $CH_2OH$, a $C_1$–$C_4$ alkyl or perfluoroalkyl, $OR^2$, $SR^2$, $S(O)R^2$, $SO_2R^2$, $SO_3H$, $S(NR^2R^7)R^2$, $S(O)(NR^2R^7)R^2$, $NR^2R^7$, aryl, heteroaryl or optionally substituted allyl, arylmethyl, alkynyl or alkenyl, where $R^2$, $R^7$ and $R^8$ have the definitions given above;

W is O, NH, $NR^7$, $CH_2$, CHOH, C=O, OC=O, O=CO, $NR^7C$=O, NHC=O, O=$CNR^7$, O=CNH, SC=O, O=CS, or $CHOCOR^7$, where $R^7$ has the definition given above; and the dotted Lines in the structures depict optional double bonds.

24. A method of treating a patient according to claim 23, wherein the progesterone receptor modulating compound is a progesterone receptor agonist.

25. A method of treating a patient according to claim 23, wherein the progesterone receptor modulating compound is a progesterone receptor partial agonist.

26. A method of treating a patient according to claim 23, wherein the progesterone receptor modulating compound is a progesterone receptor antagonist.

27. A method of treating a patient according to claim 23, wherein the compound is effective in female hormone replacement, modulating human fertility, treating dysfunctional uterine bleeding, treating endometriosis, treating leiomyomas, treating osteoporosis, uncaring cancer of the breast, treating cancer of the ovaries or treating endormetrial cancer.

* * * * *